US008278085B2

(12) United States Patent
Trotta et al.

(10) Patent No.: US 8,278,085 B2
(45) Date of Patent: Oct. 2, 2012

(54) RNA PROCESSING PROTEIN COMPLEXES AND USES THEREOF

(75) Inventors: Christopher R. Trotta, Somerset, NJ (US); Sergey Paushkin, Belle Mead, NJ (US)

(73) Assignee: PTC Therapeutics, Inc., South Plainfield, NJ (US)

(*) Notice: Subject to any disclaimer, the term of this patent is extended or adjusted under 35 U.S.C. 154(b) by 466 days.

(21) Appl. No.: 12/317,899

(22) Filed: Dec. 30, 2008

(65) Prior Publication Data

US 2010/0136710 A1 Jun. 3, 2010

Related U.S. Application Data

(63) Continuation of application No. 10/884,695, filed on Jul. 2, 2004, now abandoned.

(60) Provisional application No. 60/484,615, filed on Jul. 2, 2003.

(51) Int. Cl.
*C07K 14/00* (2006.01)
*C12N 9/16* (2006.01)
*C12P 21/00* (2006.01)
*C12Q 1/44* (2006.01)

(52) U.S. Cl. .......... 435/196; 435/69.1; 435/19; 530/350

(58) Field of Classification Search .................. 435/196, 435/69.1, 19; 530/412, 350
See application file for complete search history.

(56) References Cited

U.S. PATENT DOCUMENTS

| | | | |
|---|---|---|---|
| 4,987,071 A | 1/1991 | Cech et al. |
| 5,093,246 A | 3/1992 | Cech et al. |
| 5,310,664 A | 5/1994 | Butow et al. |
| 5,354,855 A | 10/1994 | Cech et al. |
| 5,439,797 A | 8/1995 | Tsien et al. |
| 5,591,610 A | 1/1997 | Cech et al. |
| 5,726,195 A | 3/1998 | Hill et al. |
| 5,776,738 A | 7/1998 | Dell'Orco, Sr. |
| 5,939,288 A | 8/1999 | Thornburg |
| 5,994,124 A | 11/1999 | Bozzoni |
| 6,025,167 A | 2/2000 | Cech et al. |
| 6,180,399 B1 | 1/2001 | Cech et al. |
| 6,214,563 B1 | 4/2001 | Negulescu et al. |
| 6,221,587 B1 | 4/2001 | Ecker et al. |
| 6,221,612 B1 | 4/2001 | Knapp et al. |
| 6,232,070 B1 | 5/2001 | Shuman |
| 6,446,032 B1 | 9/2002 | Schimmel |
| 6,503,713 B1 | 1/2003 | Rana et al. |
| 6,583,309 B1 | 6/2003 | Rana et al. |
| 6,875,736 B2 | 4/2005 | Rana et al. |
| 2004/0023239 A1 | 2/2004 | Tocchini-Valentini et al. |
| 2004/0219545 A1 | 11/2004 | Rando et al. |
| 2005/0053985 A1 | 3/2005 | Trotta |
| 2005/0142545 A1 | 6/2005 | Conn et al. |
| 2005/0221368 A1 | 10/2005 | Rana et al. |
| 2006/0194234 A1 | 8/2006 | Conn et al. |
| 2006/0228730 A1 | 10/2006 | Rando et al. |
| 2006/0269923 A1 | 11/2006 | Trotta |
| 2007/0020630 A1 | 1/2007 | Trotta |
| 2007/0178456 A1 | 8/2007 | Trotta |

FOREIGN PATENT DOCUMENTS

| | | |
|---|---|---|
| CA | 1340280 | 12/1998 |
| CN | 1328156 | 12/2001 |
| DE | 3436818 | 4/1989 |
| EP | 0177827 B1 | 11/1993 |
| WO | WO 91/09942 | 7/1991 |
| WO | WO 98/49274 | 11/1998 |
| WO | WO 99/20795 | 4/1999 |
| WO | WO 00/67580 | 11/2000 |
| WO | WO 01/12820 | 2/2001 |
| WO | WO 01/25486 | 4/2001 |
| WO | WO 01/53455 | 7/2001 |
| WO | WO 01/92463 | 12/2001 |
| WO | WO 02/40685 | 5/2002 |
| WO | WO 02/42326 | 5/2002 |
| WO | WO 02/083837 | 10/2002 |
| WO | WO 02/083953 | 10/2002 |
| WO | WO 2004/001010 | 12/2003 |
| WO | WO 2004/087069 | 10/2004 |
| WO | WO 2004/087070 | 10/2004 |
| WO | WO 2004/087884 | 10/2004 |
| WO | WO 2005/003316 | 1/2005 |

OTHER PUBLICATIONS

Ausubel, F., Current Protocols in Molecular Biology, Hybridization Analysis of DNA Blots, pp. 2.10.8-2.10.11.*
Abelson et al.,1998, "tRNA splicing." Journal of Biological Chemistry 273(21):12685-12688.
Adams et al., 1991, "Fluorescence ratio imaging of cyclic AMP in single cells." Nature 349:694-697.
Baldi et al., 1992, "Participation of the intron in the reaction catalyzed by the Xenopus tRNA splicing endonuclease." Science 255:1404-1408.
Barbino & Kelller, 1999, "Last but not least: regulated poly(A) tail formation." Cell 99(1):9-11.
Belford et al., 1993, "Multiple nucleotide cofactor use by yeast ligase in tRNA splicing. Evidence for independent ATP- and GTP-binding sites" J. Biol. Chem. 268(4):2444-2450.
Belfort, M., & Weiner, A., 1997, "Another bridge between kingdoms: tRNA splicing in archaea and eukaryotes." Cell 89(7):1003-1006.

(Continued)

*Primary Examiner* — Delia Ramirez
(74) *Attorney, Agent, or Firm* — Jones Day

(57) ABSTRACT

The invention provides human protein complexes with endonuclease activity, including tRNA splicing endonuclease activity and 3' end pre-mRNA endonuclease activity, and pre-ribosomal RNA cleavage activity. The invention also provides a splice variant of human Sen2, and human protein complexes comprising the variant. The invention provides human protein complexes with pre-ribosomal RNA cleavage activity. The invention also provides antibodies that immunospecifically bind to a complex described herein or a component thereof, and uses of such antibodies. The present invention also provides methods of preparing and purifying the complexes and uses of the complexes inter alia, in screening, diagnosis, and therapy. The present invention further provides methods of identifying a compound that modulates the expression of a component of a complex described herein, the formation of a complex described herein or the activity of a complex described herein, and methods of preventing, treating, managing or ameliorating a disorder, such as a proliferative disorder, or a symptom thereof utilizing such a compound.

15 Claims, 33 Drawing Sheets

OTHER PUBLICATIONS

Figure 1:
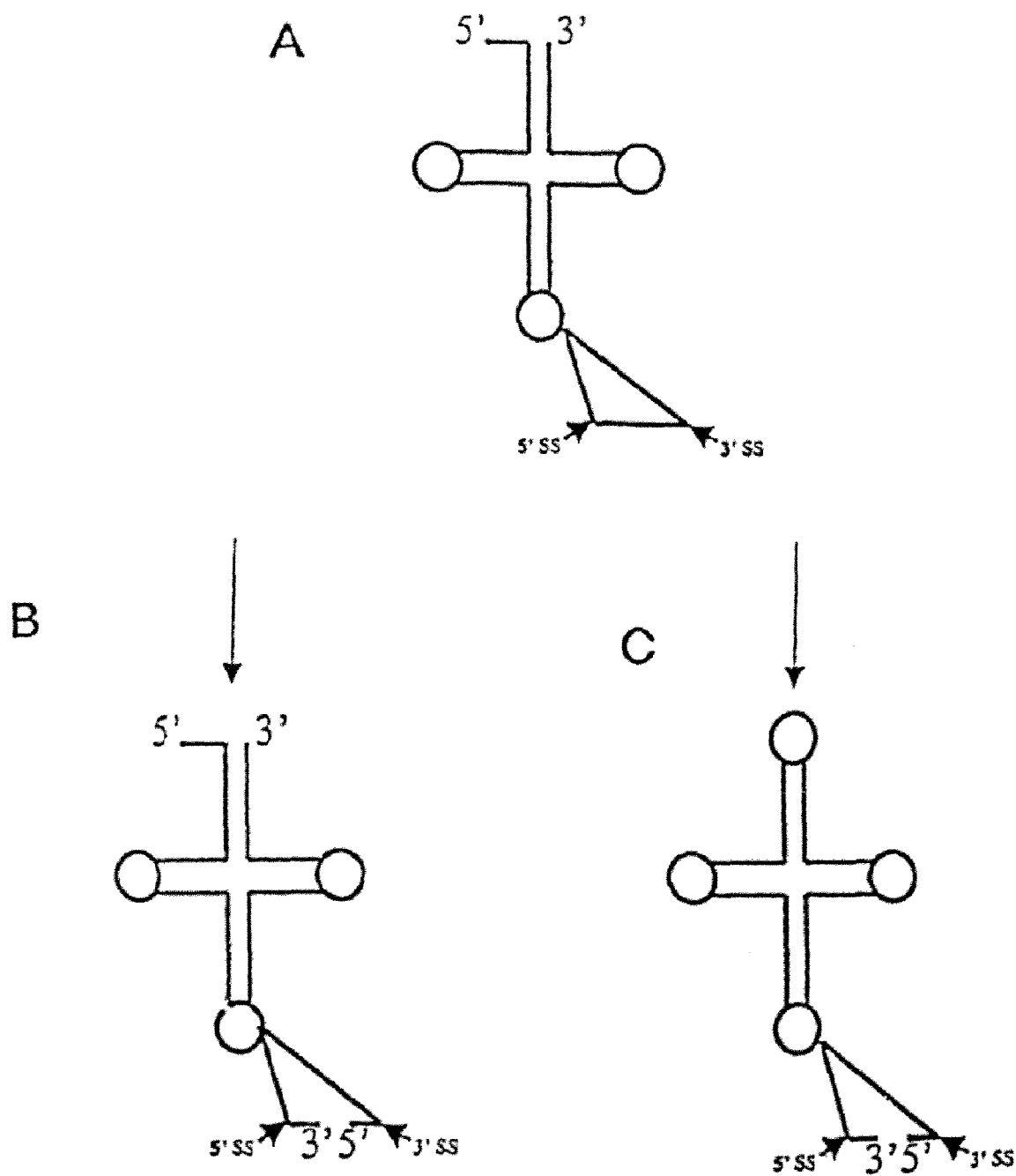

Bjork, G., 1995, "Biosynthesis and Function of Modified Nucleosides, in tRNA: Structure, Biosynthesis and Function." D. Soli & U. RajBhandary (eds.), American Society for Microbiology, Washington DC: pp. 165-205.

Branden et al., 1991, Chapter 16: Prediction, Engineering, and Design of Protein Structures *in* Introduction to Protein Structure, Garland Publishing, Inc., p. 247.

Brown, 1993 "Hybridization Analysis of DNA blots" Curr. Prot. In Molec. Biol. 2.10-2.10.11.

Bujnicki, J.M., & Rychlewski, L., 2000, "Prediction of a common fold for all four subunits of the yeast tRNA splicing endonuclease: implications for the evolution of the EndA/Sen family." FEBS Lett 486: 328-329.

Buvoli et al, 2000, "Suppression of nonsense mutations in cell culture and mice by multimerized suppressor tRNA genes" Molecular and Cellular Biology 20(9):3116-3124.

Calvo, O., and Manley, J.L., 2003, "Strange bedfellows: polyadenylation factors at the promoter." Genes Dev 17(11):1321-1327.

Choi and Dreyfuss, 1984, "Monoclonal antibody characterization of the C proteins of heterogeneous nuclear ribonucleoprotein complexes in vertebrate cells." J. Cell. Biol. 99(6):1997-2004.

Culver et al., 1997, "A 2'-phosphotransferase implicated in tRNA splicing is essential in *Saccharomyces cerevisiae*." J Biol Chem 272:13203-13210.

De Vries, H. et al., 2000, "Human pre-mRNA cleavage factor II(m) contains homologs of yeast proteins and bridges two other cleavage factors." EMBO J 19:5895-5904.

Deutscher, M.P. , 1995 "tRNA Processing Nucleases, in tRNA:Structure, Biosynthesis and Function." D. Soll and U. RjaBhandary (eds.), American Society for Microbiology, Washington DC: pp. 51-65.

Diener & Moore, 1998, "Solution Structure of a Substrate for the Archael Pre-tRNA Splicing Endonucleases: The Bulge-Helix-Bulge Motif." Mol. Cell. 1:883-894.

Fabbri, S et al., 1998, "Conservation of substrate recognition mechanisms by tRNA splicing endonucleases." Science 280, 284-286.

Frank & Pace, 1998, "Ribonuclease P: unity and diversity in a tRNA processing ribozyme." Annu Rev Biochem 67, 153-180.

Fruscoloni et al., 2001, "Cleavage of non-tRNA substrates by eukaryal tRNA splicing endonucleases." EMBO Rep 2(3):217-221.

Gandini-Attardi, et al., 1990, "Transfer RNA splicing endonuclease from *Xenopus laevis*." Methods Enzymol 181:510-517.

Gomes et al., 1997, "RNA splicing ligase activity in the archaeon *Haloferax volcanii*" Biochem & Biophys. Res. Comm. 237:588-94.

Greer et al., 1982, "Mechanism of action of a yeast RNA ligase in tRNA splicing" Cell 32:537-546.

Greer et al., 1987, "Substrate recognition and identification of splice sites by the tRNA-splicing endonuclease and ligase from *Saccharomyces cerevisiae*." Mol. & Cell. Biol. 7(1): 76-84.

Greer., 1986, "Assembly of tRNA Splicing Complex: Evidence for Concerted Excision and Joining Steps in Splicing In Vitro." Mol. and Cellular. Bio., 6(2):635-644.

Hirose and Manley, 2000, "RNA polymerase II and the integration of nuclear events." Genes Dev., 14(12):1415-1429.

Hopper, A.K., and Phizicky, E.M., 2003, "tRNA transfers to the limelight." Genes Dev 17(2):162-180.

Huh, et al., 2003, "Global analysis of protein localization in budding yeast." Nature 425:686-691.

Hyde-Deruyscher et al., 2000, "Detection of Small-Molecule Enzyme Inhibitors with Peptides Isolated from Phage-Displayed Combinatorial Peptide Libraries." Chem. & Biol. 7:17-25.

Ikemura, 1985, "Codon Usage and tRNA Content in Unicellular and Multicellular Organisms." Mol. Biol. Evol., 2(1):13-34.

Ikemura, T. and Okeki, H., 1983, "Codon usage and transfer RNA contents: organism-specific codon-choice patterns in reference to the isoacceptor contents." Cold Spring Harbor Symp. Quant. Biol. 47:1087-1097.

Jacobson et al., 1997, "Nuclear domains of the RNA subunit of RNase P." J Cell Sci. 110 ( Pt 7):829-837.

Kleman-Leyer et al., 1997, "Properties of *H. volcanii* tRNA Intron Endonuclease Reveal a Relationship between the Archaeal and Eucaryal tRNA Intron Processing Systems." Cell., 89:839-847.

Laski, F.A. et al., 1983, "Characterization of tRNA precursor splicing in mammalian extracts." J Biol. Chem. 258(19)11974-11980.

Li & Abelson, 2000, "Crystal Structure of a Dimeric Archaeal Splicing Endonuclease." J. Mol. Biol. 302:639-648.

Li et al., 1998, "Crystal structure and evolution of a transfer RNA splicing enzyme" Science 280(5361):279-284.

Lykke-Andersen, J. & Garrett, R.A., 1997, "RNA-protein interactions of an archaeal homotetrameric splicing endoribonuclease with an exceptional evolutionary history." EMBO J 16(20):6290-6300.

Miao et al.;, 1993, "Yeast tRNA-splicing endonuclease cleaves precurson tRNA in a random pathway." J. Biol. Chem. 268(1): 672-677.

Minvielle-Sebastia, L. & Keller, W., 1999, "mRNA polyadenylation and its coupling to other RNA processing reactions and to transcription." Curr. Opin. Cell. Biol. 11:352-357.

O'Connor, J.P., & Peebles, C.L., 1992, "PTA1, an essential gene of *Saccharomyces cerevisiae* affecting pre-tRNA processing." Mol Cell Biol 12:3843-3856.

Otsuka, et al., 1981, "Ribonuclease 'Xlaf' an activity from *Xenopus laevis* oocytes that excises intervening sequences from yeast transfer ribonucleic acid precursors." Mol Cell Biol 1:269-280.

Park & Bhandary, 1998, "Tetracycline-regulated suppression of amber codons in mammalian cells." Mol. & Cell. Biol. 18:4418-4425.

Paushkin et al., 2004, "Identification of a human endonuclease complex reveals a link between tRNA splicing and pre-mRNA 3' End Formation." Cell, 117:311-321.

Phizicky et al., 1986, "*Saccharomyces cerevisiae* tRNA ligase. Purification of the protein and isolation of the structural gene" J. of Biol. Chem. 261(6):2978-2986.

Phizicky et al., 1992, "Yeast tRNA Ligase Mutants are Nonviable and Accumulate tRNA Splicing Intermediates." J. Biol. Chem. 267(7):4577-4582.

Preker et al., 1997, "A multisubunit 3'-end processing factor from yeast containing poly(A) polymerase and homologues of the subunits of mammalian cleavage and polyadenylation specificity factor." EMBO J 16:4727-4737.

Proudfoot, 2000, "Connecting transcription to messenger RNA processing." Trends Biochem Sci. Jun. 2000;25(6):290-293.

Qin & Pyle, 1999, "Site-specific labeling of RNA with fluorophores and other structural probes." Methods 18 (1):60-70.

Rauhut et al., 1990, "Yeast tRNA-splicing endonuclease is a heterotrimeric enzyme." J Biol. Chem. 265(30): 18180-18184.

Reyes & Abelson 1988, "Substrate Recognition and Splice Site Determination in Yeast tRNA Splicing." Cell, 55:719-730.

Reyes et al., 1987, "A synthetic substrate for tRNA splicing." Analyt. Biochem. 166(1):90-106.

Sarkar & Hopper, 1998, "tRNA Nuclear Export in *Saccharomyces cerevisiae*: In Situ Hybridization Analysis." Mol. Biol. of the Cell., 9:3041-3055.

Saxena et al., 1992, "Angiogenin is a Cytotoxic, tRNA-specific Ribonuclease in the RNase A Superfamily." J. of Biol. Chem. 267(30):21982-21986.

Seffernick et al., 2001, "Melamine deaminase and atrazine chlorohydrolase: 98 percent identical but functionally different." J Bacteriol 183(8):2405-2410.

Sood et al., 2001, "Cloning and characterization of 13 novel transcripts and the human RGS8 gene from the 1q25 region encompassing the hereditary prostate cancer (HPC1) locus." Genomics 73:211-222.

Standring et al., 1981, "Yeast tRNA3Leu gene transcribed and spliced in a HeLa cell extract." Proc. Natl. Acad. Sci. USA 78(10):5963-5967.

Takagaki et al., 2000, "Complex protein interactions within the human polyadenylation machinery identify a novel component." Mol. Cell. Biol. 20:1515-1525.

Takaku et al., 2003, "A candidate prostate cancer susceptibility gene encodes tRNA 3' processing endoribonuclease." Nucleic Acids Res 31(9):2272-2278.

Trotta et al., 1997, "The yeast tRNA splicing endonuclease: a tetrameric enzyme with two active site subunits homologous to the archaeal tRNA endonucleases." Cell 89:849-858.

Trotta, C.R. and Abelson, J.N., 1999, "tRNA Splicing: An RNA World Add-On or an Ancient Reaction? in RNA World II" Tom Cech, Ray Gesteland and John Atkins (eds.), Cold Spring Harbor Laboratory Press, 561-584.

Trotta., 1999, "The Composition, Function and Evolution of the tRNA Splicing Endonuclease." Thesis, California Institute of Technology, pp. 1-147.

Tsien et al., 1993, "FRET for studying intracellular signaling." Trends in Cell. Bio. 3(7): 242-245.

Vaughn et al., 2002, "Methonine In and Out of Proteins: Targets for Drug Design." Cuff. Med. Chem. 9(3):385-409.

Volarevic et al., 2000, "Proliferation, But not Growth Blocked by Conditional Deletion of 40S Ribosomal Protein S6." Science 288:2045-2047.

Wahle & Ruegsegger, 1999, "3'-End processing of pre-mRNA in eukaryotes." FEMS Micro Rev., 23(3):277-295.

Wallace et al., 1999, "Two distinct forms of the 64,000 Mr protein of the cleavage stimulation factor are expressed in mouse male germ cells." Proc. Natl. Acad. Sci. 96(12):6763-6768.

Wang et at., 1990, "Substrate Masking: Binding of RNA by EGTA-Inactivated Micrococcal Nuclease Resutls in Artifactual Inhibition of RNA Processing Reactions." Nuc. Acids Res. 18(22):6625-6626.

Winter et al., 2000, "RNA polymerase III transcription factor TFIIIC2 is overexpressed in ovarian tumors." Proc. Natl. Acad. Sci., 97(23):12619-12624.

Witkowski, 1999, "Converstion of β-ketaoacyl Synthase to Malonyl Decarboxylase by Replacement of the Active-site Cysteine and Glutamine." Biochemistry, 38:11643-11650.

Xiao et at., 2002, "Eukaryotic ribonuclease P: a plurality of ribonucleoprotein enzymes." Annu Rev Biochem 71, 165-189.

Xu et al., 1990, "Purification of yeast transfer RNA ligase." Meth. in Enzymol. 181:463-471.

Yoshihisa et al., 2003, "Possibility of cytoplasmic pre-tRNA splicing: the yeast tRNA splicing endonuclease mainly localizes on the mitochondria." Mol Biol Cell 14(8):3266-3279.

Zhang et al., 1997, "Gene Expression Profiles in Normal and Cancer Cells." Science 276:1268-1272.

Zhao, 1999 "Formation of mRNA 3' ends in eukaryotes: mechanism, regulation, and interrelationships with other steps in mRNA synthesis." Microbiol. Mol. Biol. Rev. 63:405-445.

Zillman et al,, 1991, "Conserved mechanism for tRNA splicing in eukaryotes." Mol. & Cell. Biol. 11(11):5410-5416.

GENBANK Accesion No. AAH19582, "TRNA splicing" dated Jan. 3, 2002.

GENBANK Accession No. BC019582, "*Homo sapiens* TRNA" dated Jan. 3, 2002.

GENBANK Accession No. CAA19575, "tRNA-splicing endonuclease subunit Sen34 [*Schizosaccharomyces pombe*]," dated Jun. 30, 2009.

GENBANK Accession No. CAA21061, "tRNA-splicing endonuclease subunit Sen54 (predicted) [*Schizosaccharomyces pombe*]," dated Jun. 30, 2009.

GENBANKK Accession No. CAD27500, "tRNA-splicing endonuclease subunit Sen2 [*Schizosaccharomyces pombe*]," dated Jun. 30, 2009.

GENBANK Accession No. CAE46913; "tRNA-splicing endonuclease subunit Sen15 [*Schizosaccharomyces pombe*]," dated Jun. 30, 2009.

GENBANK: Accession No. NP_079541; "tRNA splicing endonuclease 2 homolog [*Homo sapiens*]," dated Mar. 2, 2006.

GENBANK: Accession No. NT_005927.12; "*Homo sapiens* chromosome 3 reference genomic contig," dated Aug. 1, 2002.

GENBANK: Accession No. NT_011225.9; "*Homo sapiens* chromosome 19 reference genomic contig," dated Aug. 1, 2002.

GENBANK: Accession No. XP_085899; "similar to LENG5 protein [*Homo sapiens*]," dated Aug. 1, 2002.

Spingola et al., 1999. Genome-wide bioinformatic and molecular analysis of introns in *Saccharomyces cerevisiae*, RNA, 5:221-234.

Herrenknecht, 1988, "Pre t-RNA splicing in a nuclear extract from human leukemia cells: separation of endonuclease and ligase activities." Nuc. Acids Res. 16:7713-7714.

Kaminska, 2002, "The isoprenoid biosynthetic pathway in *Saccharomyces cerevisiae* is affected in a mafl-1 mutant with altered tRNA synthesis." FEMS Yeast Res. 2:31-37.

Lucas et al., 2000, "Yeast Sequencing Report: Sequence analysis of two cosmids from the right arm of the *Schizosaccharomyces pombechromosome* II." Yeast 16:299-306.

Marras, 2002, "Efficiences of Fluoresence Resonance Energy transfer and contact-mediated quenching in oligonucelotide probes." Nucleic Acids Res. 30:1-8.

Spaltmann et al., 1999, "Computer-aided target selection—prioritizing targets for antifungal drug discovery." DDT, 4(1):17-26.

Stryer, 1999, Chapter 5: Flow of Genetic Information, p. 96-97; Chapter 33: RNA Synthesis and Splicing, p. 860-864, Chapter 34: Protein Synthesis, p. 875-880; *in* Biochemistry, 4$^{th}$ edition, W.H. Freeman and Co., New York.

Yeast Accession No. YLR105C; SEN2: http://www.yeastgenome.org/, dated Mar. 8, 2006.

Yeast Accession No. YAR008w; SEN34 http://www.yeastgenome.org/, dated Mar. 8, 2006.

Yeast Accession No. YMR059w; SEN 15 http://www.yeastgenome.org/ dated Mar. 8, 2006.

Yeast Accession No. YPL083c; SEN54 "http://www.yeastgenome.org/," dated Mar. 8, 2006.

Preliminary Amendment, dated Sep. 27, 2005, for U.S. Appl. No. 10/551,304, filed May 18, 2006.

Requirement for Restriction/Election, dated Jan. 16, 2008, for U.S. Appl. No. 10/551,304, filed May 18, 2006.

Response to Requirement for Restriction/Election, dated Jul. 15, 2008, for U.S. Appl. No. 10/551,304, filed May 18, 2006.

Requirement for Restriction/Election, dated Nov. 25, 2008, for U.S. Appl. No. 10/551,304, filed May 18, 2006.

Response to Requirement for Restriction/Election, dated Dec. 23, 2008, for U.S. Appl. No. 10/551,304, filed May 18, 2006.

Non-Final Rejection, dated Mar. 17, 2009, for U.S. Appl. No. 10/551,304, filed May 18, 2006.

Response to Non-Final Rejection, dated Aug. 17, 2009, for U.S. Appl. No. 10/551,304, filed May 18, 2006.

Response to Office Communication Regarding Sequence Disclosure and Preliminary Amendment dated Feb. 28, 2006, for U.S. Appl. No. 10/884,695, filed Jul. 2, 2004.

Requirement Restriction/Election dated Jun. 13, 2006 for U.S. Appl. No. 10/884,695, filed Jul. 2, 2004.

Response to Requirement for Restriction/Election and Preliminary Amendment dated Oct. 13, 2006 for U.S. Appl. No. 10/884,695, filed Jul. 2, 2004.

Non-Final Rejection, dated Dec. 21, 2006, for U.S. Appl. No. 10/884,695, filed Jul. 2, 2004.

Amendment after non-final rejection, dated Apr. 17, 2007, for U.S. Appl. No. 10/884,695, filed Jul. 2, 2004.

Non-Final Rejection, dated Jul. 13, 2007, for U.S. Appl. No. 10/884,695, filed Jul. 2, 2004.

Amendment after non-final rejection, dated Nov. 13, 2007, for U.S. Appl. No. 10/884,695, filed Jul. 2, 2004.

Non-Final Rejection, dated Feb. 5, 2008, for U.S. Appl. No. 10/884,695, filed Jul. 2, 2004.

Amendment after non-final rejection, dated Aug. 5, 2008, for U.S. Appl. No. 10/884,695, filed Jul. 2, 2004.

Detailed Action, dated Dec. 1, 2008, for U.S. Appl. No. 10/884,695, filed Jul. 2, 2004.

Notice of Abandonment, dated Jun. 4, 2009, for U.S. Appl. No. 10/884,695, filed Jul. 2, 2004.

Requirement for Restriction/Election, dated Sep. 8, 2008, for U.S. Appl. No. 10/551,300, filed Nov. 29, 2006.

Response to Restriction Requirement and Preliminary Amendment, dated Nov. 10, 2008, for U.S. Appl. No. 10/551,300, filed Nov. 29, 2006.

Notice of Non-compliant, dated Feb. 4, 2009, for U.S. Appl. No. 10/551,300, filed Nov. 29, 2006.

Response to Notice of Non-compliant, dated Mar. 2, 2009, for U.S. Appl. No. 10/551,300, filed Nov. 29, 2006.

Non-Final Rejection, dated, May 22, 2009, for U.S. Appl. 10/551,300, filed Nov. 29, 2006.

Response to Non-Final Rejection, dated Aug. 19, 2009, for U.S. Appl. No. 10/551,300, filed Nov. 29, 2006.
Preliminary Amendment dated Sep. 27, 2005, for PCT/US2004/009572—U.S. Appl. No. 10/551,301, filed Jul. 12, 2006.
Preliminary Amendment dated Aug. 4, 2008, for U.S. Appl. No. 10/551,301, filed Jul. 12, 2006.
Requirement for Restriction/Election, dated Jan. 16, 2009, for U.S. Appl. No. 10/551,301, filed Jul. 12, 2006.
Response to requirement for Restriction/Election, dated Feb. 17, 2009, for U.S. Appl. No. 10/551,301, filed Jul. 12, 2006.
Non-Final Rejection, dated May 12, 2009, for U.S. Appl. No. 10/551,301, filed Jul. 12, 2006.
International Search Report, dated Jun. 22, 2005 of PCT/US2004/009572, filed Mar. 26, 2004.
Written Opinion, dated Jun. 22, 2005 of PCT/US2004/009572, filed Mar. 26, 2004.
International Preliminary Report on Patentability, dated Nov. 11, 2005 of PCT/US2004/009572, filed Mar. 26, 2004.
European Search Report, dated Jul. 23, 2007 of EP 1 613 158 published Jan. 11, 2006.
International Search Report, dated Jan. 27, 2005 of PCT/US2004/009590, filed Mar. 26, 2004.
Written Opinion, dated Jan. 27, 2005 of PCT/US2004/009590, filed Mar. 26, 2004.
International Preliminary Report on Patentability, dated Jun. 16, 2005 of PCT/US2004/009590, filed Mar. 26, 2004.
European Search Report, dated Jul. 23, 2007 of EP 1 613 160 published Jan. 11, 2006.
International Search Report, dated Apr. 24, 2007 of PCT/US2004/021334, filed Jul. 2, 2004.
Written Opinion, dated Apr. 24, 2007 of PCT/US2004/021334, filed Jul. 2, 2004.
International Preliminary Report on Patentability, Dec. 4, 2007 of PCT/US2004/021334, filed Jul. 2, 2004.
Supplementary European Search Report, dated May 8, 2009 of EP 1 649 002 published Apr. 26, 2006.
International Search Report, dated Jun. 9, 2005 of PCT/US2004/009574, filed Mar. 26, 2004.
Written Opinion, dated Jun. 9, 2005 of PCT/US2004/009574, filed Mar. 26, 2004.
International Preliminary Report on Patentability, dated Nov. 11, 2005 of PCT/US2004/009574, filed Mar. 26, 2004.
European Search Report, dated Jul. 3, 2007 of EP 1 613 159 published Jan. 11, 2006.
GENBANK Accession No. M32336, "S.cerevisiae tRNA splicing endonuclease beta-subunit (SEN2) gene, complete cds," dated Aug. 6, 1997.
European communication from the examining division, dated Jul. 6, 2007, of EP 1 649 002, published Apr. 26, 2006.
Reply to European communication, dated Aug. 13, 2007, of EP 1 649 002, published Apr. 26, 2006.
European communication regarding deficiencies in sequence listing from the examining division, dated Sep. 27, 2007, of EP 1 649 002, published Apr. 26, 2006.
Reply to European communication to remedy deficiencies in sequence listing, dated Oct. 12, 2007, of EP 1 649 002, published Apr. 26, 2006.
European communication regarding transmission of Supplementary European Search Report from the examining division, dated May 8, 2009, of EP 1 649 002, published Apr. 26, 2006.
European communication from the examining division, dated May 26, 2009, of EP 1 649 002, published Apr. 26, 2006.
Reply to European communication from the examining division, dated Jul. 7, 2009, of EP 1 649 002, published Apr. 26, 2006.
Response to Non-Final Rejection, dated Sep. 10, 2009, for U.S. Appl. No. 10/551,301 filed Jul. 12, 2006.
Final Rejection, dated Nov. 12, 2009, for U.S. Appl. No. 10/551,304, filed May 18, 2006.
Final Rejection, dated Dec. 2, 2009, for U.S. Appl. No. 10/551,300 filed Nov. 29, 2006.
Final Rejection, dated Dec. 9, 2009, for U.S. Appl. No. 10/551,301 filed Jul. 12, 2006.
Kohrer et al., 1990, "A yeast tRNA precursor containing a pre-mRNA intron is spliced via the pre-mRNA splicing mechanism", EMBO J, 9(3):705-9.
Response to Final Rejection, dated Nov. 12, 2009, for U.S. Appl. No. 10/551,304, filed Apr. 12, 2010.
GENBANK Accession No. BC021975.2, "Homo sapiens tRNA splicing endonuclease 2 homolog (S. cerevisiae), mRNA," dated Aug. 18, 2006.
Notice of Abandonment, dated Jun. 22, 2010, for U.S. Appl. No. 10/551,301, filed Jul. 12, 2006.
Notice of Abandonment, dated Jun. 23, 2010, for U.S. Appl. No. 10/551,300, filed Nov. 29, 2006.
Notice of Allowance, dated Jun. 23, 2010, for U.S. Appl. No. 10/551,300, filed May 18, 2006.
European communication from the examining division, dated Sep. 1, 2011. of EP 1 649 002, published Apr. 26, 2006.
European Response to communication, dated Mar. 12, 2012, of EP 1 649 002, published Apr. 26, 2006.

* cited by examiner

Sequence alignment of human and
yeast tRNA splicing endonuclease Sen2 subunits

```
                        1                                                        50
Hs Sen2p            MAEAVPHAPK RKRHVYETYE SPLPIPPCQD HGPLREFKIF RADMIKHVI
Hs Sen2 var.        MAEAVPHAPK RKRHVYETYE SPLPIPPCQD HGPLREFKIF RADMIKHVI
Sc Sen2p            ---------- ---------- ---------- ---------- ---------

51                                                       100
Hs Sen2p            VRHAEDIEQL YGRGYGKGI LSRSRSFFI SDPKLVANWK DWCTKMPI..
Hs Sen2 var.        VRHAEDIEQL YGRGYGKGI LSRSRSFFI SDPKLVANWK DWCTKMPI..
Sc Sen2p            ---------- ---------- ---------- -HSKEVWQK RYKYPLPIKP 101                                                      150
Hs Sen2p            ...ITSKHYQ HSVDMAAELM BRGQQDESTV RRIILKDYTKP LE.KPPVKRH
Hs Sen2 var.        ...ITSKHYQ HSVDMAAELM BRGQQDESTV RRIILKDYTKP LE.KPPVKRH
Sc Sen2p            VDDLPELILH MPLSMLYMAY RLYYKSTWALM DKVHVDFIGD TTLHITVQ..

151                                                      200
Hs Sen2p            EEAQVHDKLN SGWSIMDEST AGGERSVVR GDSGKSGGVG DPREPLGKLQ
Hs Sen2 var.        EEAQVHDKLN SGWSEMDEST AGGERSVVR GDSGKSGGVG DPREPLGKLQ
Sc Sen2p            DDKDMYLMR KGPYGT..GQ FSREEFYMRA KTEARLGLFD TPLHHEGCYK 201                                                      250
Hs Sen2p            KSSCHPTTE SPEKSVR.ED ASPLPHVCCC KQDALILQRG LHHEDSQHI
Sen2_variant        KSSCHPTTE SPEKSVR.ED ASPLPHVCCC KQDALILQRG LHHEDSQHI
Sc Sen2p            SMTETEWTLE KYTQQRLQB LEFKKERAKL ERELLELRKK GKHID.EEHI 251                                                      300
Hs Sen2p            GLLHRGDRGP DHEVLVLEEA RCAMSEHEAA PMEELWQRNR LICRHPYRI
Hs Sen2 var.        GLLHRGDRGP DHEVLVLEEA RCAMSEHEAA PMEELWQRHR LICRHPYRI
Sc Sen2p            LLEKDRESLP KPYLAGTHSV GIVAQCODIS KSHLHDEDKN LLDHHGDLLP 301                                                      350
Hs Sen2p            PKYLQLSLEE APFLVYALGC LSIYYEREPL TIVKLMKAFT VVQCFFRITY
Hs Sen2 var.        PKYLQLSLEE ---------- ....REPL TIVKLMKAFT VVQCFFRITY
Sc Sen2p            LESLREAFVE ARFLATFALPV LDISPACLMQ KLFQTDANYK DIH.SFVRSY 351                                                      400
Hs Sen2p            MATHYPLSKG WPKVGLAYG TDLLLYRKGP PFYHASYSVI IELVDDHPEG
Hs Sen2 var.        MATHYPLSKG WPKVGLAYG TDLLLYRKGP PFYHASYEVI IELVDDHPEG
Sc Sen2p            VITHHYSHQ MCYRSGIHFG CDVLLYTRGP FYGHAETCV. ..MGLDK...

401                                                      450
Hs Sen2p            SLRRPLSWKS LAALSRWSVH VSKELMLCYL IKPSTWTD.. ....KEMESPE
Hs Sen2 var.        SLRRPLSWKS LAALSRWSVH VEKELMLCYL ERSTMTD... ....KEMESPE
Sc Sen2p            DVSKDYTWYS ...STARWGI ARKETVLCYV EDLISEQEAI ALMKSHMPTK 451                       477
Hs Sen2p            CMRRIKVQEV ILSEHVSSHE RSDQDDL
Hs Sen2 var.        CMRRIKVQEV ILSEHVSSHE RSDQDDL
Sc Sen2p            LPHSFYGEY LKEHHVPGRI SD-----
```

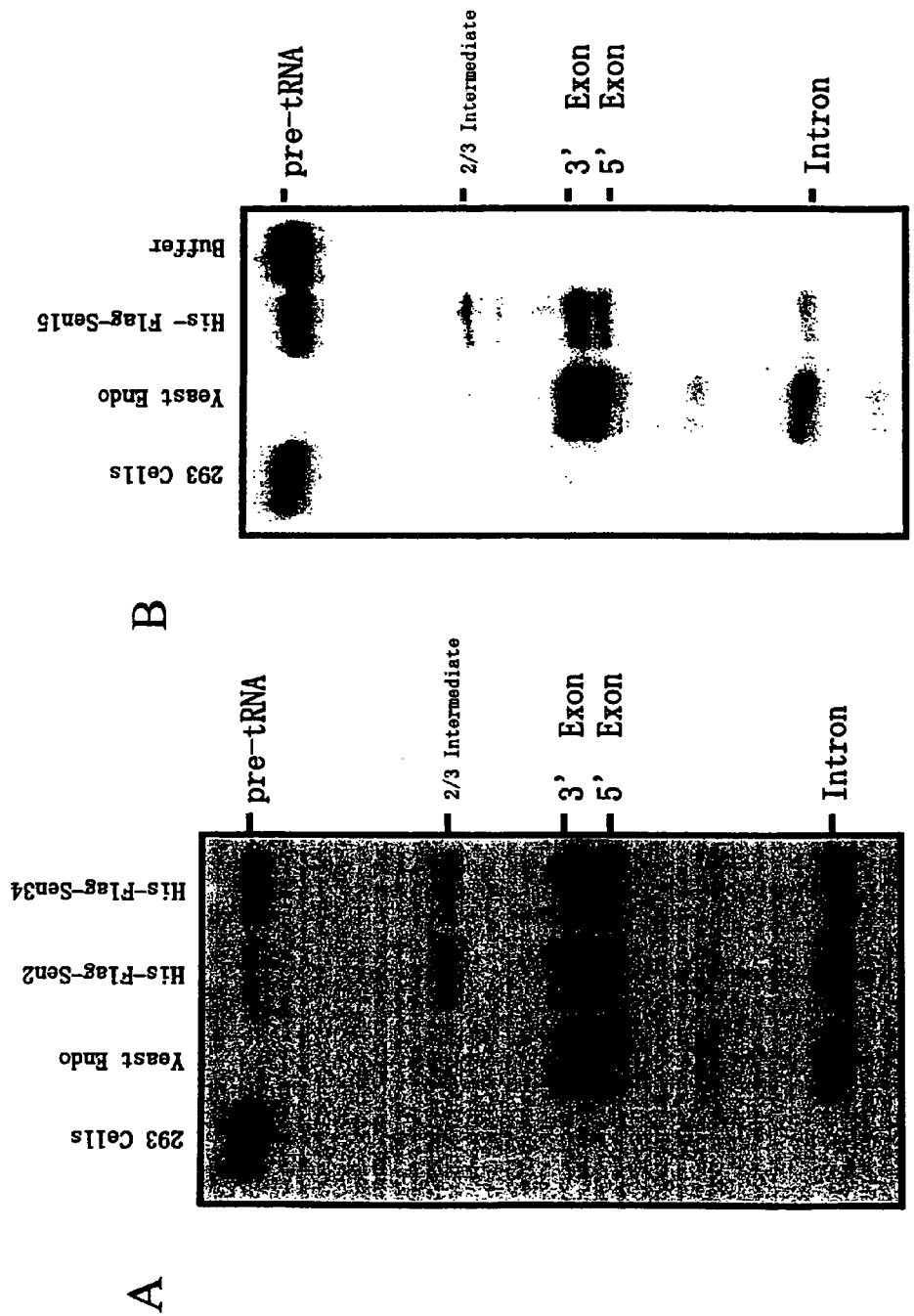
Fig. 10 A-B

Fig. 10C

Human tRNA Splicing Endonuclease Active Site Subunits are Localized in the Nucleus
Myc – Hs Sen2p
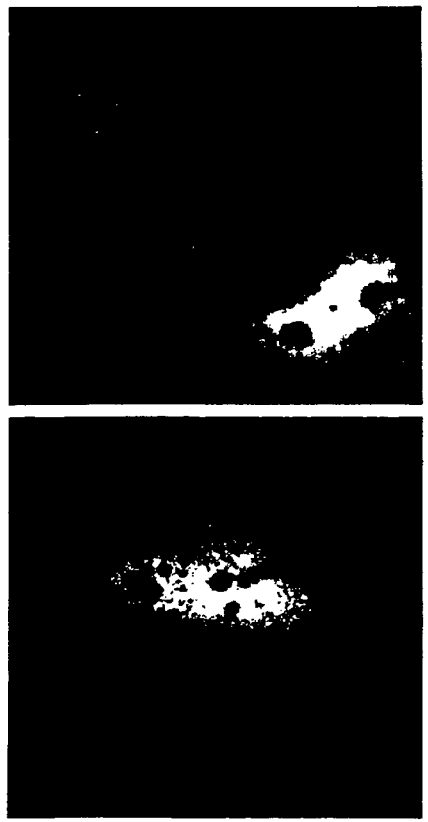
GFP – Hs Sen34p
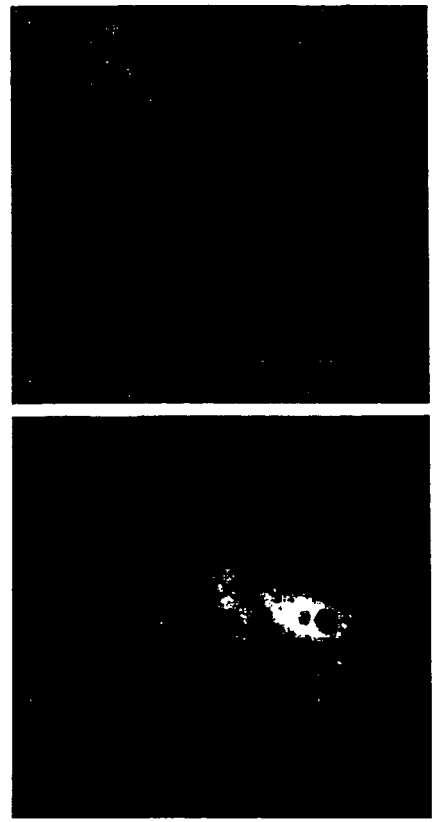
Fig. 11

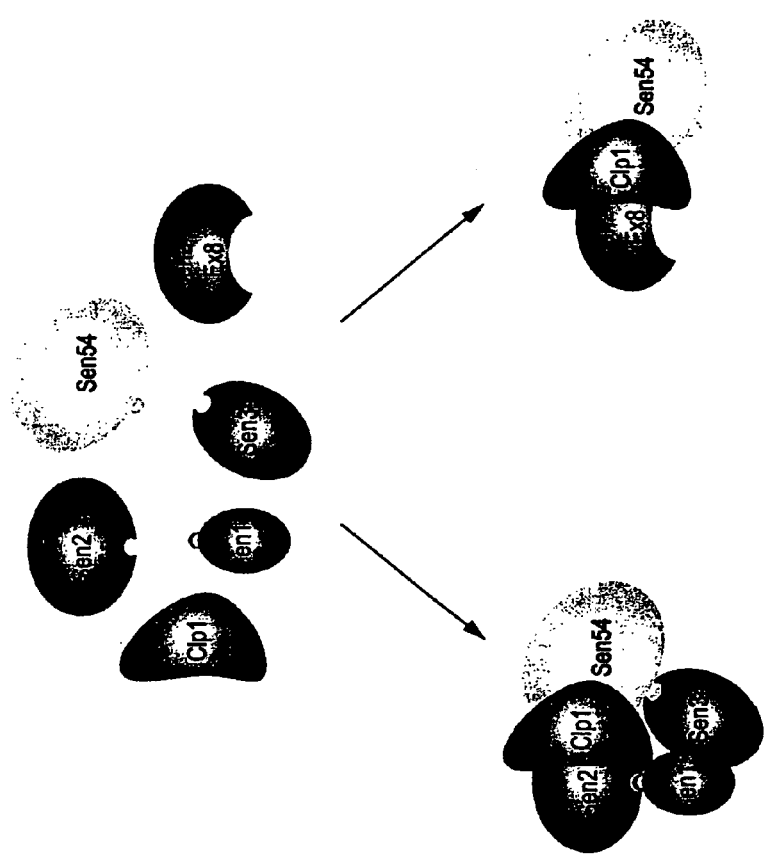

Sen2 Nucleic Acid:

```
   1 gggcgaggaa agcgcggccc tttccgagtt tggtgttttg cagcgaaagg aaatctcgct
  61 cttccgaaag tcctccaggg cgagagagga aagggcctag gtactgtgct ggggtcgcac
 121 agccggccga dacagtgccg ggacggggag ccaggcttcc gagtgcgccc ggtcactgac
 181 tcctccgcgc tttcctcgtg cgcctgcagc ccttggttct tggaaacgcc ggcgccttgt
 241 tcagggctgg tggggctggg gcgcaaggtg cagctgacaa tgcccgagag gagccgcagc
 301 ctctggtgga gttcggtcgg gtgtgggggt agtcaaggaa agaagcaaag gaatacctc
 361 ctctgaaaaa tggcagaagc agttttccat gccccaaaga ggaaaagaag agtgtatgag
 421 acttacgagt ctccattgcc aatccctttt ggtcaggacc atggtcctct gaaagaattc
 481 aagatattcc gtgctgaaat gattaacaac aatgtgattg tgaggaatgc ggaggacatt
 541 gagcagctct atgggaaagg ttattttgga aaaggtattc tttcaagaag ccgtccaagc
 601 ttcacaattt cagatcctaa actggttgct aaatggaaag atatgaagac aaacatgcct
 661 atcatcacat caaagaggta tcagcatagt gttgagtggg cagcagagct gatgcgtaga
 721 cagggcagg atgagagtac agtgcgcaga atcctcaagg attacgaa accgcttgag
 781 catcctcctg tgaaaaggaa tgaagaggct caagtgcatg acaagcttaa ctctggaatg
 841 gtttccaaca tggaaggcac agcaggggga gagagaccttt ctgtggtaaa cggggactct
 901 ggaaagtcag gtggtgtggg tgatccccgt gagccattag gctgcctgca ggagggctct
 961 ggctgccacc caacaacaga gagctttgag aaaagcgtgc gagaggatgc ctcacctctg
1021 ccccatgtct gttgctgcaa acaagatgct ctcatcctcc agcgtggcct tcatcatgaa
1081 gacggcagcc agcacatcgg cctcctgcat cctggggaca gagggcctga ccatgagtac
1141 gtgctggtcg aggaagcgga gtgtgccatg agcgagaggg aggctgcccc aaatgaggaa
1201 ttggtgcaaa gaacaggtt aatatgcaga agaaatccat ataggatctt tgagtatttg
1261 caactcagcc tagaagaggc cttttttcttg gtctatgctc tgggatgttt aagtatttac
1321 tatgagaagg agcctttaac gatagtgaag ctctggaaag ctttcactgt agttcagccc
1381 acgttcagaa ccacctacat ggcctaccat tactttcgaa gcaagggctg ggtgcccaaa
1441 gtgggactca agtacgggac agatttactg ctatatcgga aaggccctcc attttaccat
1501 gcaagttatt ctgtcattat cgagctagtt gatgaccatt ttgaaggctc tctccgcagg
1561 cctctcagtt ggaagtccct ggctgccttg agcagagttt ccgttaatgt ctctaaggaa
1621 cttatgctgt gctatttgat taaaccctct actatgactg acaaggaaat ggagtcacca
1681 gaatgtatga aaaggattaa agttcaggag gtgattctga gtcgatgggt ttcttcacga
1741 gagaggagtg accaagacga tcttttaacaa ttcaacctca aatttctaat ttcaccaaca
1801 actatttatt gagggctagg taaaaagttc ttttttgttgt aatcgtccat taattcataa
1861 gtttttaaagg gcatggtgct cccagcacca gaaaactatc agtgttttta aagataaatt
1921 acacaaggga ggagaaagat ccctgtgcta ggacaacaga ttctatactt gcgttggcct
1981 ctaactcccc catccagagc ctcctgcctc tggcgtcagt ttttttccctc atccactcac
2041 tggggagatt ggactagagg agtcctgaga ggacacttcc aacaagagac atttattctc
2101 tgattttacc tgaaaatggt agtagtttac atttatacag tacagtttat gaagcacttt
2161 catacgcagg catctcttgt tacctacatc taagctgttc ccgaaagagt gttacagaac
2221 acaacagtat tgtacaatat tcgataagca tatcttcact gcacttgtta taaaaatgag
2281 tggtgaaata atgtttggag acataatgaa agcgattaac atttggcaaa atataataaa
2341 gcctttttgt aattggtgaa aaaaaaaaaa aaa
```

Sen2 Amino Acid:

```
  1 maeavfhapk rkrrvyetye splpipfgqd hgplkefkif raeminnnvi vrnaedieql
 61 ygkgyfgkgi lsrsrpsfti sdpklvakwk dmktnmpiit skryqhsvew aaelmrrqgq
121 destvrrilk dytkplehpp vkrneeaqvh dklnsgmvsn megtaggerp svvngdsgks
181 ggvgdprepl gclqegsgch pttesfeksv redasplphv ccckqdalil qrglhhedgs
241 qhigllhpgd rgpdheyvlv eeaecamser eaapneelvq rnrlicrrnp yrifeylqls
301 leeafflvya lgclsiyyek epltivklwk aftvvqptfr ttymayhyfr skgwvpkvgl
361 kygtdlllyr kgppfyhasy sviielvddh fegslrrpls wkslaalsrv svnvskelml
421 cylikpstmt dkemespecm krikvqevil srwvssrers dqddl
```

Fig. 20

Sen2deltaEx8 Nucleic Acid:

```
atggcagaag cagttttcca tgccccaaag aggaaaagaa gagtgtatga gacttacgag      60
tctccattgc caatcccttt tggtcaggac catggtcctc tgaaagaatt caagatattc     120
cgtgctgaaa tgattaacaa caatgtgatt gtgaggaatg cggaggacat tgagcagctc     180
tatgggaaag gttattttgg aaaaggtatt ctttcaagaa gccgtccaag cttcacaatt     240
tcagatccta aactggttgc taaatggaaa gatatgaaga caaacatgcc tatcatcaca     300
tcaaagaggt atcagcatag tgttgagtgg gcagcagagc tgatgcgtag acaggggcag     360
gatgagagta cagtgcgcag aatcctcaag gattacacga accgcttga gcatcctcct      420
gtgaaaagga atgaagaggc tcaagtgcat gacaagctta actctggaat ggtttccaac     480
atggaaggca cagcaggggg agagagacct tctgtggtaa acggggactc tggaaagtca     540
ggtggtgtgg gtgatcccg tgagccatta ggctgcctgc aggagggctc tggctgccac      600
ccaacaacag agagctttga gaaaagcgtg cgagaggatg cctcacctct gcccatgtc      660
tgttgctgca aacaagatgc tctcatcctc cagcgtggcc tcatcatga agacggcagc      720
cagcacatcg gcctcctgca tcctggggac agagggcctg accatgagta cgtgctggtc     780
gaggaagcgg agtgtgccat gagcgagagg aggctgccc caaatgagga attggtgcaa      840
agaaacaggt taatatgcag aagaaatcca tataggatct ttgagtattt gcaactcagc     900
ctagaagagg agcctttaac gatagtgaag ctctggaaag ctttcactgt agttcagccc     960
acgttcagaa ccacctacat ggcctaccat tactttcaga gcaagggctg ggtgcccaaa    1020
gtgggactca agtacgggac agatttactg ctatatcgga aaggccctcc attttaccat   1080
gcaagttatt ctgtcattat cgagctagtt gatgaccatt ttgaaggctc tctccgcagg   1140
cctctcagtt ggaagtccct ggctgccttg agcagagttt ccgttaatgt ctctaaggaa   1200
cttatgctgt gctatttgat taaaccctct actatgactg acaaggaaat ggagtcacca   1260
gaatgtatga aaaggattaa agttcaggag gtgattctga gtcgatgggt ttcttcacga   1320
          gagaggagtg accaagacga tctttaa                              1347
```

Sen2deltaEx8 Amino Acid:

```
  1 maeavfhapk rkrrvyetye splpipfgqd hgplkefkif raeminnnvi vrnaedieql
 61 ygkgyfgkgi lsrsrpsfti sdpklvakwk dmktnmpiit skryqhsvew aaelmrrqgq
121 destvrrilk dytkplehpp vkrneeaqvh dklnsgmvsn megtaggerp svvngdsgks
181 ggvgdprepl gclqegsgch pttesfeksv redasplphv ccckqdalil qrglhhedgs
241 qhigllhpgd rgpdheyvlv eeaecamser eaapneelvq rnrlicrrnp yrifeylqls
301 lee******* ********** epltivklwk aftvvqptfr ttymayhyfr skgwvpkvgl
361 kygtdllllyr kgppfyhasy sviielvddh fegslrrpls wkslaalsrv svnvskelml
421 cylikpstmt dkemespecm krikvqevil srwvssrers dqddl
```

*Denotes deleted amino acid between Sen2deltaEx8 and Sen2

Fig. 21

Sen15 Nucleic Acid:

```
   1 agcgtggggt gcgggtcgtg gtgcaccacg ggagcgccgc accggccggc atggaggagc
  61 gcggcgattc cgagccgacc cccggctgca gcggcctggg tccgggcggt gttcgcggct
 121 ttggcgacgg cggtggagct ccttcgtggg cccctgagga cgcctggatg ggcactcacc
 181 ctaagtatct agaaatgatg gaattagata taggagatgc cacccaagtt tatgtagcgt
 241 tcttggttta cctggacctc atggaaagca aaagctggca tgaagtaaac tgtgtaggat
 301 taccagaact ccagctcatc tgccttgttg gtactgagat agaaggggag gggttacaga
 361 ctgtggtgcc tacccccatc actgcttccc tcagccataa caggataagg gagatcttga
 421 aggcatctcg aaagttgcaa ggtgatccag atttgccgat gtcttttact ttggccatag
 481 tggagtctga ttctacaata gtctattata aacttactga tggatttatg ctgccagacc
 541 ctcagaatat ttctcttaga agatgacatc catgtttcct gatgcttgtt ttattcatac
 601 aagattggat ttgagaccca tcagactgct tcatctttta tctcagaaat agggttgacg
 661 tacatagtga gggttgactt ccccattcca taaggttttc attctgaaga gtaaaacttc
 721 cccaggtaga agactttctc cttcttaaaa aatatagggt gatttcttta aaactttgtt
 781 atctagagac agtttaatta cagttatata caggtttatg cctaggatgt attcagatgg
 841 gtgggacctg tgtgctgctt ttgtcatccc acactcaaag ttgtctcttt gtttcttgct
 901 gccactgcca gctcattgtt gagactgcca tttctttctc ttactcagct ctccccagtg
 961 ccttttggcc actgcagcta ccgtagaatg gcattttata tgtaccttgt cacccacttc
1021 tgtttacttt ttcctctcca gtaaaaagta aagatttct tcaattggt cttcccattg
1081 cagttactgt tatttctctt ttttggttaa ctttaaatca aaactcaaaa tatgttcatc
1141 cagagtgtgt cttaagtaac ttacgtgtct taagtaacag ggaccagaga catgttacct
1201 acaagagttc tgggctatcc ttttcattct tatcacatat catagcttga atattacaac
1261 agtgtgggag agaatcaacc gtaaaaatgt cttcattaat tagacccagt tattccactt
1321 ttgttaatgt ctctcaaatt gtacaaagta taaaaaatta tatgcacaaa gatgttccaa
1381 gtgacattac ttttagtagc ccaaattata aaccacttta agtttgggg taaagattgg
1441 caaacttttt ctataaaggg ccagaaagta actatttag gtttttaaac ctactgtctc
1501 tgtcataact tgtcaacact gctgtatgaa gcacaaaagc agccatagac aatacataaa
1561 caatacgggc gtggctttgt tccagtaaaa ctttgtttac aaatgtggtg ccatagtttg
1621 tcatccctgg gtctaggaaa tagtcaataa acagatatat acaaatgata cataatgtac
1681 ttattaaaaa ttagtaatga atattattaa aaacatgaaa atattacctt aagtaaaaat
1741 tgcaagacgg aaaagtgtat aagtgggtgt aatcatggct gaaataacag accaagcata
1801 tgataaaaag ataacaaagt aaatcaaatt actaactggt tatagtggga taggaggcag
1861 aaaatggatg actttgtctt ttctcaatgt ttttatttgt attttataat aaaaatgttt
1921 taaaattaaa aaaaaaaaaa aaa
```

Sen15 Amino Acid:

```
  1 meergdsept pgcsglgpgg vrgfgdggga pswapedawm gthpkylemm eldigdatqv
 61 yvaflvyldl meskswhevn cvglpelqli clvgteiege glqtvvptpi taslshnrir
121 eilkasrklq gdpdlpmsft laivesdsti vyykltdgfm lpdpqnislr r
```

Fig. 22

Sen34 Nucleic Acid:

```
   1 cacctcgact gcgaattact gtttatgagg tgactcgctg gttctatcgg tggacagtgg
  61 gacattctga agggaggcaa ggaggcggac tgagcgctcc caattgggga ggatgctggt
 121 ggtggaggtg gcgaacggcc gctccctggt gtggggagcc gaggcggtgc aggccctccg
 181 ggagcgcctg ggtgtggggg gccgcacggt aggcgccctg ccccgcgggc ccgccagaa
 241 ctcgcgcctg ggcctcccgc tgctgctgat gcccgaagag gcgcggctct tggccgagat
 301 cggcgccgtg actctggtca gcgccccgcg tccagactct cggcaccaca gcctggccct
 361 gacatccttc aagcgccagc aagaggagag cttccaggag cagagcgcct ggcagctga
 421 ggcccgggag accgtcgtc aggaggtcct ggagaagatt acggagggcc aggctgctaa
 481 gaagcagaaa ctagaacagg cttcagggc cagctcaagc caggaggccg gctcgagcca
 541 ggctgccaaa gaggatgaga ccagtgatgg ccaggcttcg ggagagcagg aggaagctgg
 601 cccctcgtct tcccaagcag gaccctcaaa tggggtagcc cccttgccca gatctgctct
 661 ccttgtccag ctggccactg ccaggcctcg accggtcaag gccaggcccc tggactggcg
 721 tgtccagtct aaagactggc cccacgccgg ccgccctgcc cacgagctgc gctacagtat
 781 ctacagagac ctgtgggagc gaggcttctt cctcagtgcg gctggcaagt cggaggtga
 841 cttcctggtc tatcctggtg acccctccg cttccacgcc cattatatcg ctcagtgctg
 901 ggcccctgag gacacctccc actccaagac ctggttgctg ctgggcgcct ggaaccagc
 961 gtcagaaaga ccctgctcct ctgttctccg cagcctgatg gtaaggtggt ctacacctcc
1021 ctgcaatggg ccagcctgca gtaactcca gagacctagg ggatgtggct gtgtcggcag
1081 caagagcctt tctggatgtt cccagctct tctctgggag tctagaacat cctcctacct
1141 ttctccgcgg ttagttttg attccaggtt ttcgaacact acatcttttt tatgttcttc
1201 cttgtttcaa agcacttatt ggctgtgttt ttgtagttac ctattttcac actgtgagct
1261 tcccgagaat ggggcctggg tttgattcat ctgtttccta cagggtttaa gtctcaggag
1321 gtctcaataa acttggtata taaatgttaa aaaaaaaaaa aaaa
```

Sen34 Amino Acid:

```
   1 mlvvevangr slvwgaeavq alrerlgvgg rtvgalprgp rqnsrlglpl llmpeearll
  61 aeigavtlvs aprpdsrhhs laltsfkrqq eesfqeqsal aaearetrrq evlekitegq
 121 aakkqkleqa sgasssqeag ssqaakedet sdgqasgeqe eagpsssqag psngvaplpr
 181 sallvqlata rprpvkarpl dwrvqskdwp hagrpahelr ysiyrdlwer gfflsaagkf
 241 ggdflvypgd plrfhahyia qcwapedtsh sktwlllgal epaserpcss vlrslmvrws
 301 tppcngpacs elqrprgcgc vgskslsgcs pallwesrts sylsprlvfd srfsnttsfl
 361 csslfqstyw lcfcsylfsh celpengawv
```

Fig. 23

Sen54 Nucleic Acid:

```
   1 gcggcgcgcg cagcggcagg cggcggcggg atggagcccg agcccgagcc cgcggccgtg
  61 gaggttcccg cggggcgcgt gctcagcgcc cgggagctct tcgccgcccg ctcgcggtcg
 121 cagaagctgc cccagcgctc gcatggcccc aaggactttc tgcccgacgg ctcggcagct
 181 caggccgagc ggctgcgccg gtgccgggaa gagctctggc agctgctggc agagcagcgc
 241 gtggagcgcc tgggcagctt ggtggctgcc gagtggaggc cagaagaggg cttcgtggag
 301 ttgaagtctc ccgcgggcaa attctggcag accatgggct tctcagagca gggccggcag
 361 cgccttcacc cggaagaggc cttgtatctt ctggagtgtg gctccatcca cctcttccac
 421 caagacctgc cactgtctat ccaggaagct taccagctgc tgctgaccga ccacactgtg
 481 accttcctgc agtaccaggt cttcagccac ctgaagaggt tgggttatgt ggttcgacga
 541 ttccaaccaa gctctgtcct gtccccgtat gagaggcagc ttaacctgga tgccagcgtg
 601 cagcacttgg aggatggaga tggcaagaga aagaggagca gctccagccc tcggtccatt
 661 aataagaagg ccaaggccct ggacaactcc ctgcaaccca agagtctggc agcctccagc
 721 ccacctccct gcagccagcc cagccaatgc cagaggaga aacccagga gtcaagcccc
 781 atgaagggcc aggggggccc ctttcagctt ctggggtccc tgggccccag ccctggcccg
 841 gccagggagg gggtggggtg cagctgggag agtggcagag ccgagaacgg agtcacggga
 901 gccggtaagc ggcgctggaa cttcgagcag atctccttcc caacatggc ttcagacagc
 961 cgccacaccc ttctgcgcgc cccagcccca gagctgctcc cggccaacgt ggctgggcgg
1021 gagacagacg ctgagtcctg gtgccagaag ctgaaccagc gcaaggagaa gctctccagg
1081 cgggaacggg agcaccacgc ggaggccgcg cagttccagg aagatgtcaa cgccgatccc
1141 gaggtgcagc ggtgctccag ctggcgggag tacaaggagc tgctgcagcg gcggcaggtg
1201 cagaggagcc agcgccgggc ccctcacctg tggggccagc ccgtcacccc gctgctgagt
1261 cctggccagg ccagctcccc agccgtggtc cttcagcata tctctgtgct gcagacaaca
1321 caccttcctg atggaggtgc ccggctgttg gagaagtctg ggggcttgga aatcatcttt
1381 gatgtttacc aggccgacgc tgtggccaca ttccgaaaga ataaccctgg caaacccat
1441 gcccggatgt gcattagtgg atttgatgag cctgtcccag acctctgcag cctcaagcgg
1501 ttgtcttacc agagtgggga tgtccctctg atctttgccc tggtggatca tggtgacatc
1561 tccttctaca gcttcaggga cttcacgttg ccccaggatg tggggcactg acctcacagc
1621 tctgcagagg atggagcttg ctccggggga ccgggactgt ctgttctcag ggaccatctc
1681 ggctgcctcc tgtacccaga ctctaacctg tagcttcaga ggccagtctg gccttggcc
1741 ctgggtgtct gatactcaca gagtgaaact gtgaccctct cccttccctg ctgccttgca
1801 gtgaccctc tggaactcag gactcgattt taaggaccca ggaggtgggg cagaagagag
1861 gactgtgtgc ctttaacgag agggtgcctg cttcgtgcta taaagccaaa gccattaaaa
1921 atagatttct tt
```

Sen54 Amino Acid:

```
   1 mepepepaav evpagrvlsa relfaarsrs qklpqrshgp kdflpdgsaa qaerlrrcre
  61 elwqllaeqr verlgslvaa ewrpeegfve lkspagkfwq tmgfseqgrq rlhpeealyl
 121 lecgsihlfh qdlplsiqea yqllltdhtv tflqyqvfsh lkrlgyvvrr fqpssvlspy
 181 erqlnldasv qhledgdgkr krssssprsi nkkakaldns lqpkslaass pppcsqpsqc
 241 peekpqessp mkgpggpfql lgslgpspgp aregvgcswe sgraengvtg agkrrwnfeq
 301 isfpnmasds rhtllrapap ellpanvagr etdaeswcqk lnqrkeklsr rerehaeaa
 361 qfqedvnadp evqrcsswre ykellqrrqv qrsqrraphl wgqpvtplls pgqasspavv
 421 lqhisvlqtt hlpdggarll eksggleiif dvyqadavat frknnpgkpy armcisgfde
 481 pvpdlcslkr lsyqsgdvpl ifalvdhgdi sfysfrdftl pqdvgh
```

Fig. 24 hClp1 Nucleic Acid:

```
   1 atgactgact tgtagctgga agaaatcatc ggatttttat tcttttatta aagaaaaaaa
  61 atttgaaatg ccttccatgt gccaagcact gtgtcaggtg ggagatgaca gcttggtgaa
 121 acctctgtca ggctgtcttc ctccgctttc tctatccctg ggtttccccc tgcctaaaaa
 181 ggatttttgtg cttcgtggct tgtccaggca agcaggccgt cgcgggacct agaccgagac
 241 agtgagtctc tctttctccc gggcctccct tctgtttcct gggctgcagg ggagcaggaa
 301 atctggggcg agattcccgc cgcggacgcg cactgccgaa gcctggtccc tcgacctgtc
 361 cctgcccagc gcggggcgc aaccgccacg cctcctcacc cctccctccg gctgcacgaa
 421 taatgacaac agccgcccct cccacctttg gcgtcacgtt caaaacaatc ctttgactac
 481 aactcccaga aggccgagcg gcttagcgag tgcacccgct ctcggctgct ccggcaaact
 541 acacatccca aagggcagcg ccgaccgcgt gtcctttcac agcaaagtgc ggaactgcgt
 601 ttgtttccgg cgtgggtccg ggcaagaacc gcttgtagtt tggtttaaat tctgcacggg
 661 aggaccttct gagtttacct gttgggctcc tggctgcgca ggcacagcag ctacacagaa
 721 gagatgggag aagaggctaa tgatgacaag aagccaacca ctaaatttga actagagcga
 781 gaaacagaac ttcgctttga ggtggaggca tctcagtcag ttcagttgga gttgttgact
 841 ggcatgcag agatctttgg cacagagctg acccgaaaca agaaattcac ctttgatgct
 901 ggtgccaagg tggctgtttt cacttggcat ggctgttctg tgcaactgag cggccgcact
 961 gaggtggctt atgtctccaa ggacactcct atgttgcttt acctcaacac tcacacagcc
1021 ttggaacaga tgcggaggca agcggaaaag gaagaagagc gaggtccccg agtgatggta
1081 gtgggcccca ctgatgtggg caagtctaca gtgtgtcgcc ttctgctcaa ctacgcagtg
1141 cgtttgggcc gccgtccac ttatgtggag ctggatgtgg gccagggttc tgtgtccatc
1201 cctggtacca tggggggccct ctacatcgag cggcctgcag atgtcgaaga gggtttctct
1261 atccaggccc ctctggtgta tcattttggt tccaccactc ctggcactaa catcaagctt
1321 tataataaga ttacatctcg tttagcagat gtgttcaacc aaaggtgtga ggtgaaccga
1381 agggcatctg tgagtggctg tgtcattaac acctgtggct gggtcaaggg ctctggttac
1441 caggctctgg tgcatgcagc ctcagctttt gaggtggatg tcgttgttgt tctggatcaa
1501 gaacgactgt acaatgaact gaaacgggac ctcccccact tgtacgcac tgtgctgctc
1561 cctaaatctg ggggtgtggt ggagcgctcc aaggacttcc ggcgggaatg tagggatgag
1621 cgtatccgtg agtattttta tggattccga ggctgtttct atcccatgc cttcaatgtc
1681 aaatttcag atgtgaaaat ctacaaagtt gggcaccca catcccaga ctcctgttta
1741 cctttgggca tgtctcaaga ggataatcag ctcaagctag tacctgtcac tcctgggcga
1801 gatatggtgc accacctact gagtgttagc actgccgagg gtacagagga aacctgtcc
1861 gagacaagtg tagctggctt cattgtggtg accagtgtgg acctggagca tcaggtgttt
1921 actgttctgt ctccagcccc tcgcccactg cctaagaact tccttctcat catggatatc
1981 cggttcatgg atctgaagta gagatcagca ggaagccttg ctgcctggga catagagatc
2041 atctggccac ccctagaggc agatgggctg agataaaaga ctgttgggc cacctgacca
2101 gtaaactgtg gactagtaga agttcatat tctacctcta aaaacaggta gtggtaacct
2161 gactcttcta atcttgaacc aaaaggaaaa ccatgagact gtaattggtt tcttagacca
2221 cctaagatgc cactttgaat tctctaagac cctggagaat tgcatttctt tcactgtgct
2281 actatgtggt ttttaaaaaa tcaatgcttt atattccata tgtggttctt acccatttat
2341 catggatgaa agtgtgaatt agagggactc cttccaataa agttcaaact gaaaaaaaat
2401 cattttaata aatattttg ccatatcata aaaaaaa
``` hClp1 Amino Acid:

```
   1 mgeeanddkk pttkfelere telrfeveas qsvqlelltg maeifgtelt rnkkftfdag
  61 akvavftwhg csvqlsgrte vayvskdtpm llylnthtal eqmrrqaeke eergprvmvv
 121 gptdvgkstv crlllnyavr lgrrptyvel dvgqgsvsip gtmgalyier padveegfsi
 181 qaplvyhfgs ttpgtnikly nkitsrladv fnqrcevnrr asvsgcvint cgwvkgsgyq
 241 alvhaasafe vdvvvvldqe rlynelkrdl phfvrtvllp ksggvversk dfrrecrder
 301 ireyfygfrg cfyphafnvk fsdvkiykvg aptipdsclp lgmsqednql klvpvtpgrd
 361 mvhhllsvst aegteenlse tsvagfivvt svdlehqvft vlspaprplp knfllimdir
 421 fmdlk
```

Fig. 25

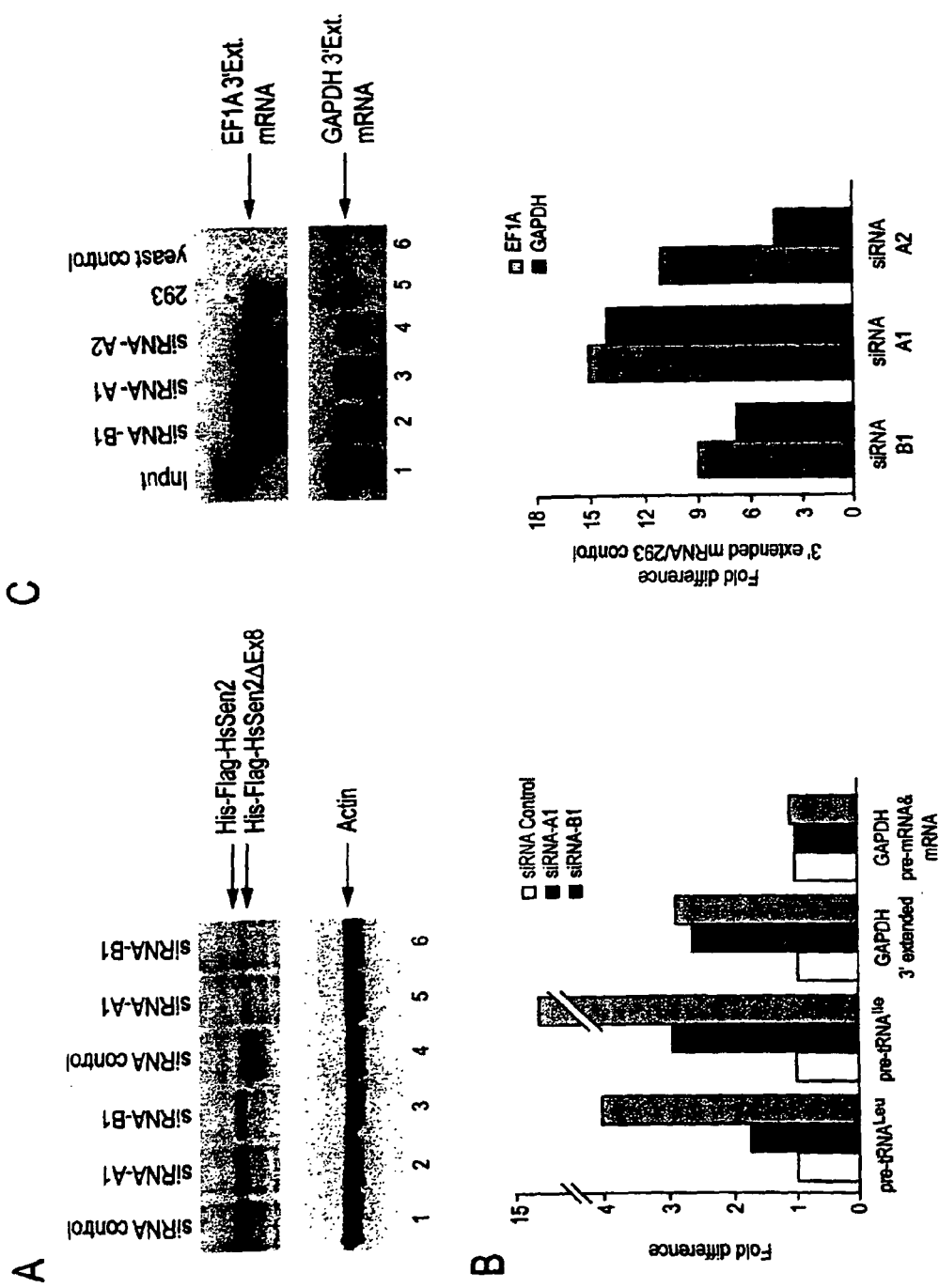
Fig. 30A-C

RNA PROCESSING PROTEIN COMPLEXES AND USES THEREOF

RELATED APPLICATION

This application is a continuation of U.S. patent application Ser. No. 10/884,695, filed Jul. 2, 2004, now abandoned, which claims the benefit of U.S. Provisional Application Ser. No. 60/484,615, filed Jul. 2, 2003, both of which are incorporated by reference herein in their entireties.

1. INTRODUCTION

The invention provides human protein complexes with endonuclease activity. In particular, the invention provides human protein complexes with tRNA splicing endonuclease activity and/or 3' end pre-mRNA endonuclease activity. The invention also provides a splice variant of human Sen2, namely human Sen2deltaEx8, and human protein complexes comprising human Sen2deltaEx8. The human Sen2deltaEx8 complexes have RNA-nucleolytic activity. The invention also provides human protein complexes with pre-ribosomal RNA cleavage activity. The invention also provides antibodies that immunospecifically bind to a complex described herein or a component thereof, and methods of diagnosing, preventing, treating, managing or ameliorating a disorder utilizing such antibodies. The present invention also provides methods utilizing the complexes described herein, inter alia, in screening, diagnosis, and therapy. The invention further provides methods of preparing and purifying the complexes. The present invention further provides methods of identifying a compound that modulates the expression of a component of a complex described herein, the formation of a complex described herein or the activity of a complex described herein, and methods of preventing, treating, managing or ameliorating a disorder, such as a proliferative disorder, or a symptom thereof utilizing a compound identified in accordance with the methods.

2. BACKGROUND OF THE INVENTION

2.1 tRNA Production

Maturation and maintenance of tRNA within eucaryal cells requires several processing events including 5' and 3' end-trimming, modification of specific bases and in some cases, intron removal. The enzymes for these various steps in processing have been characterized in the yeast, archaeal, mammalian and bacterial systems (Deutscher, M. P. tRNA Processing Nucleases, in tRNA:Structure, Biosynthesis and Function, D. Soll and U. RjaBhandary (eds.), American Society for Microbiology, Washington D.C., (1995), pp. 51-65). 5' end trimming requires the activity of Rnase P and 3' end trimming requires the function of various endo- and exonucleases. Modification occurs through interaction of tRNA with various modification enzymes. Most tRNAs contain a number of global as well as, species-specific modifications (Bjork, G. Biosynthesis and Function of Modified Nucleosides, in tRNA: Structure, Biosynthesis and Function, D. Soll and U. RajBhandary (eds.), American Society for Microbiology, Washington D.C., (1995), pp. 165-205). In archaea and eucarya, several isoaccepting groups of tRNA contain intervening sequences ranging in size from 14-105 nucleotides (Trotta, C. R. and Abelson, J. N. tRNA Splicing: An RNA World Add-On or an Ancient Reaction? In RNA World II, Tom Cech, Ray Gesteland and John Atkins (eds.), Cold Spring Harbor Laboratory Press (1999) and Abelson et al., 1998, Journal of Biological Chemistry 273:12685-12688).

Removal of the intron requires the activity of 3 enzymes. In the first step, the tRNA is recognized and cleaved at the 5' and 3' junction by the tRNA splicing endonuclease. The archaeal and eucaryal tRNA endonuclease are evolutionary conserved enzymes and contain a similar active site to achieve cleavage at the 5' and 3' splice sites. However, they have diverged to recognize the tRNA substrate in a different manner. The archaeal enzyme recognizes a conserved intronic structure known as the bulge-helix-bulge. This structure is comprised of two 3-nucleotide bulges separated by a 4-nucleotide helix. Cleavage occurs within each bulge to release the intron. The eucaryal endonuclease recognizes the tRNA substrate in a mature domain dependent fashion, measuring a set distance from the mature domain to the 5' and 3' splice sites (Reyes et al., 1988, Cell 55:719-730). It has recently been demonstrated, however, that the eucaryal enzyme requires a bulge at each splice site and that the enzyme has actually retained the ability to recognize tRNA by an intron-dependent recognition mechanism identical to that of the archaeal endonuclease (Fruscoloni et al., 2001, EMBO Rep 2:217-221). Once cleaved, the tRNA half molecules are ligated by the action of a unique tRNA splicing ligase (Trotta, C. R. and Abelson, J. N. tRNA Splicing: An RNA World Add-On or an Ancient Reaction? In RNA World II, Tom Cech, Ray Gesteland and John Atkins (eds.), Cold Spring Harbor Laboratory Press (1999) and Abelson et al., 1998, Journal of Biological Chemistry 273:12685-12688). In yeast, the product of ligation is a tRNA with a phosphate at the splice junction. Removal of the phosphate is carried out by a tRNA 2'-phosphotransferase to yield a mature tRNA product (Trotta, C. R. and Abelson, J. N. tRNA Splicing: An RNA World Add-On or an Ancient Reaction? In RNA World II, Tom Cech, Ray Gesteland and John Atkins (eds.), Cold Spring Harbor Laboratory Press (1999) and Abelson et al., 1998, Journal of Biological Chemistry 273:12685-12688).

tRNA is an important component in the translational machinery and is quite stable compared to various other protein-based components (elongation factors, amino-acyl synthetases, etc.). tRNA molecules have very long half-lives. Furthermore, like rRNA and ribosomes, tRNA is present in excess within the cytoplasm of actively growing cells (Ikemura, T. and Okeki, H., 1983, Cold Spring Harbor Symp. Quant. Biol. 47:1087-1097). Thus, specific targeting of tRNA molecules allows a selective inhibition of uncontrolled cell proliferation and not cell growth.

2.2 Pre-mRNA Cleavage

Several processing steps are required before eukaryotic mRNA precursors (pre-mRNAs) are exported to the cytoplasm. Pre-mRNA processing includes capping of the 5' end, splicing, and the generation of a new 3' end by endonucleolytic cleavage and polyadenylation. Transcription, capping, splicing and 3' end processing of pre-mRNAs are coupled processes in vivo (reviewed in Barabino and Kelly, 1999, Cell, 99, 9-11; Minvielle-Sebastia and Keller, 1999, Curr. Opin. Cell Biol., 11, 352-357; Zhoa et al., 1999, Microbiol. Mol. Biol. Rev., 63, 405-445; Hirose and Manley, 2000, Genes Dev., 14, 1415-1429; and Proudfoot, 2000, Trends Biochem. Sci., 25, 290-293).

The 3' end of the pre-mRNAs are generated in a two-step reaction. The pre-mRNA is first cleaved endonucleolytically and the upstream cleavage fragment is subsequently polyadenylated and the downstream cleavage product is subsequently degraded. Six trans-acting factors are required for the in vitro reconstitution of mammalian 3' end processing, namely CPSF, CstF, CF $I_m$, CFII$_m$, PAP, PABP2 (reviewed in Wahle and Ruegsegger, 1999, FEMS Micro Rev., 23, 277-295; and Zhoa et al., 1999, Micoboil. Mol. Biol. Rev., 63, 405-445).

Cleavage and polyadenylation specificity factor (CPSF) and cleave stimulation factor (CstF) recognize the hexanucleotide AAUAAA upstream and a G/U-rich sequence element downstream of the cleavage site, respectively. In addition, the cleavage complex contains cleavage factors $I_m$ (CF $I_m$) and $II_m$ (CF $II_m$) and poly(A) polymerase (PAP). After the first step, CstF, CF $I_m$ and CF $II_m$ are released together with the downstream cleavage fragment. CPSF remains bound to the upstream cleavage product and tethers PAP to the RNA. PAP is the enzyme responsible for the addition of the poly(A) tail in a processing reaction that also requires both CPSF and poly(A)-binding protein II (PABP2).

2.3 Cancer and Neoplastic Disease

Cancer is the second leading cause of death in the United States. The American Cancer Society estimated that in 2001, there would be 1.3 million new cases of cancer and that cancer will cause 550,000 deaths. Overall rates have declined by 1% per year during the 1990s. There are 9 million Americans alive who have ever had cancer. NIH estimates the direct medical costs of cancer as $60 billion.

Currently, cancer therapy involves surgery, chemotherapy and/or radiation treatment to eradicate neoplastic cells in a patient (see, for example, Stockdale, 1998, "Principles of Cancer Patient Management", in *Scientific American: Medicine*, vol. 3, Rubenstein and Federman, eds., Chapter 12, Section IV). All of these approaches pose significant drawbacks for the patient. Surgery, for example, can be contraindicated due to the health of the patient or can be unacceptable to the patient. Additionally, surgery might not completely remove the neoplastic tissue. Radiation therapy is effective only when the irradiated neoplastic tissue exhibits a higher sensitivity to radiation than normal tissue, and radiation therapy can also often elicit serious side effects. (Id.) With respect to chemotherapy, there are a variety of chemotherapeutic agents available for treatment of neoplastic disease. However, despite the availability of a variety of chemotherapeutic agents, traditional chemotherapy has many drawbacks (see, for example, Stockdale, 1998, "Principles Of Cancer Patient Management" in *Scientific American Medicine*, vol. 3, Rubenstein and Federman, eds., ch. 12, sect. 10). Almost all chemotherapeutic agents are toxic, and chemotherapy can cause significant, and often dangerous, side effects, including severe nausea, bone marrow depression, immunosuppression, etc. Additionally, many tumor cells are resistant or develop resistance to chemotherapeutic agents through multidrug resistance.

Therefore, there is a significant need in the art for novel compounds and compositions, and methods that are useful for treating cancer or neoplastic disease with reduced or without the aforementioned side effects. Further, there is a need for cancer treatments that provide cancer-cell-specific therapies with increased specificity and decreased toxicity.

Citation of any reference herein is not to be construed as an admission of its availability as prior art.

3. SUMMARY OF THE INVENTION

The invention provides complexes involved in the processing of RNA. In particular the invention provides complexes with RNA-nucleolytic activity that are involved in pre-tRNA splicing, 3' end pre-mRNA endonuclease activity, pre-tRNA cleavage activity, and/or the pre-ribosomal RNA cleavage activity. More specifically, the invention provides a purified complex with RNA-nucleolytic activity comprising two or more or any combination of the following (i) human Sen2 or a functionally active derivative or a functionally active fragment thereof; (ii) human Sen 15 or a functionally active derivative or a functionally active fragment thereof; (iii) human Sen34 or a functionally active derivative or a functionally active fragment thereof; and (iv) human Sen54 or a functionally active derivative or a functionally active fragment thereof.

The invention provides a purified protein complex with endonuclease activity comprising: (i) human Sen2 or a functionally active derivative or a functionally active fragment thereof; (ii) human Sen 15 or a functionally active derivative or a functionally active fragment thereof; (iii) human Sen34 or a functionally active derivative or a functionally active fragment thereof; and (iv) human Sen54 or a functionally active derivative or a functionally active fragment thereof. In a specific embodiment, the protein complex has tRNA splicing endonuclease activity. In another embodiment, the protein complex has 3' end pre-mRNA endonuclease activity. In yet another embodiment, the protein complex has tRNA splicing endonuclease activity and 3' end pre-mRNA endonuclease activity.

In a specific embodiment, the invention provides a purified complex with endonuclease activity comprising: (i) human Sen2 (ACCESSION NO.: NP_079541; FIG. 20 (SEQ ID NO: 2)), or a protein encoded by a nucleic acid that hybridizes to the human Sen2 encoding nucleic acid (ACCESSION NO.: NM_025265; FIG. 20 (SEQ ID NO: 1)) or its complement under high stringency conditions; (ii) human Sen15 (ACCESSION NO.:NP_443197; FIG. 22 (SEQ ID NO: 4)), or a protein encoded by a nucleic acid that hybridizes to the human Sen15 encoding nucleic acid (ACCESSION NO.: NM_052965; FIG. 22 (SEQ ID NO: 3)) or its complement under high stringency conditions; (iii) human Sen34 (ACCESSION NO.:NP_076980; FIG. 23 (SEQ ID NO: 6)), or a protein encoded by a nucleic acid that hybridizes to the human Sen34 encoding nucleic acid (ACCESSION NO.: NM_024075; FIG. 23 (SEQ ID NO: 5)) or its complement under high stringency conditions; and (iv) Sen54 (ACCESSION NO.:XP_208944; FIG. 24 (SEQ ID NO: 8)), or a protein encoded by a nucleic acid that hybridizes to the human Sen54 encoding nucleic acid (ACCESSION NO.: XM_208944; FIG. 24 (SEQ ID NO: 7)) or its complement under high stringency conditions. In accordance with this embodiment, the complex has tRNA splicing endonuclease activity and/or 3' end pre-mRNA endonuclease activity.

The invention also provides a purified protein complex with endonuclease activity comprising: (i) human Sen2 or a functionally active derivative or a functionally active fragment thereof; (ii) human Sen 15 or a functionally active derivative or a functionally active fragment thereof; (iii) human Sen34 or a functionally active derivative or a functionally active fragment thereof; (iv) human Sen54 or a functionally active derivative or a functionally active fragment thereof; and (v) human Clp1 or a functionally active derivative or a functionally active fragment thereof. In a specific embodiment, the protein complex has tRNA splicing endonuclease activity. In another embodiment, the protein complex has 3' end pre-mRNA endonuclease activity. In yet another embodiment, the protein complex has tRNA splicing endonuclease activity and 3' end pre-mRNA endonuclease activity.

In a specific embodiment, the invention provides a purified complex with endonuclease activity comprising: (i) human Sen2 (ACCESSION NO.: NP_079541; FIG. 20 (SEQ ID NO: 2)), or a protein encoded by a nucleic acid that hybridizes to the human Sen2 encoding nucleic acid (ACCESSION NO.: NM_025265; FIG. 20 (SEQ ID NO: 1)) or its complement under high stringency conditions; (ii) human Sen15 (ACCESSION NO.:NP_443197; FIG. 22 (SEQ ID NO: 4)), or a protein encoded by a nucleic acid that hybridizes to the human Sen15 encoding nucleic acid (ACCESSION NO.: NM_052965; FIG. 22 (SEQ ID NO: 3)) or its complement under high stringency conditions; (iii) human Sen34 (ACCESSION NO.:NP_076980; FIG. 23 (SEQ ID NO: 6)), or a protein encoded by a nucleic acid that hybridizes to the human Sen34 encoding nucleic acid (ACCESSION NO.: NM_024075; FIG. 23 (SEQ ID NO: 5)) or its complement under high stringency conditions; (iv) Sen54 (ACCESSION NO.:XP_208944; FIG. 24 (SEQ ID NO: 8)), or a protein encoded by a nucleic acid that hybridizes to the human Sen54 encoding nucleic acid (ACCESSION NO.:XM_208944; FIG. 24 (SEQ ID NO: 7)) or its complement under high stringency conditions; and (v) human Clp1 (ACCESSION NO.:NP_006822; FIG. 25 (SEQ ID NO: 10)) or a protein encoded by a nucleic acid that hybridizes to the human Clp1 encoding nucleic acid (ACCESSION NO.: NM_006831; FIG. 25 (SEQ ID NO: 9)) or its complement under high stringency conditions. In accordance with this embodiment, the complex has tRNA splicing endonuclease activity and/or 3' end pre-mRNA endonuclease activity.

The invention provides a purified protein complex with endonuclease activity comprising: (i) human Sen2 or a functionally active derivative or a functionally active fragment thereof; (ii) human Sen 15 or a functionally active derivative or a functionally active fragment thereof; (iii) human Sen34 or a functionally active derivative or a functionally active fragment thereof; (iv) human Sen54 or a functionally active derivative or a functionally active fragment thereof; (v) human Clp1 (ACCESSION NO.:NP_006822; FIG. 25 (SEQ ID NO: 10)) or a functionally active derivative or a functionally active fragment thereof; (vi) human Cleavage-Polyadenylation Specificity Factor ("CPSF") or a functionally active derivative or a functionally active fragment thereof; (vii) human Cleavage Factor $I_m$ ("CF $I_m$") or a functionally active derivative or a functionally active fragment thereof; (viii) human Cleavage Factor $II_m$ ("CF $II_m$") or a functionally active derivative or a functionally active fragment thereof; and (ix) human Cleavage Stimulation Factor ("CSF") or a functionally active derivative or a functionally active fragment thereof. In a specific embodiment, the protein complex has tRNA splicing endonuclease activity. In another embodiment, the protein complex has 3' end pre-mRNA endonuclease activity. In yet another embodiment, the protein complex has tRNA splicing endonuclease activity and 3' end pre-mRNA endonuclease activity.

In one embodiment, the invention provides a purified complex with endonuclease activity comprising: (i) human Sen2 (ACCESSION NO.: NP_079541; FIG. 20 (SEQ ID NO: 2)), or a protein encoded by a nucleic acid that hybridizes to the human Sen2 encoding nucleic acid (ACCESSION NO.: NM_025265; FIG. 20 (SEQ ID NO: 1)) or its complement under high stringency conditions; (ii) human Sen15 (ACCESSION NO.:NP_443197; FIG. 22 (SEQ ID NO: 4)), or a protein encoded by a nucleic acid that hybridizes to the human Sen15 encoding nucleic acid (ACCESSION NO.: NM_052965; FIG. 22 (SEQ ID NO: 3)) or its complement under high stringency conditions; (iii) human Sen34 (ACCESSION NO.:NP_076980; FIG. 23 (SEQ ID NO: 6)), or a protein encoded by a nucleic acid that hybridizes to the human Sen34 encoding nucleic acid (ACCESSION NO.: NM_024075; FIG. 23 (SEQ ID NO: 5)) or its complement under high stringency conditions; (iv) Sen54 (ACCESSION NO.:XP_208944; FIG. 24 (SEQ ID NO: 8)), or a protein encoded by a nucleic acid that hybridizes to the human Sen54 encoding nucleic acid (ACCESSION NO.:XM_208944; FIG. 24 (SEQ ID NO: 7)) or its complement under high stringency conditions; and (v) human Clp1 (ACCESSION NO.:NP_006822; FIG. 25 (SEQ ID NO: 10)) or a protein encoded by a nucleic acid that hybridizes to the human Clp1 encoding nucleic acid (ACCESSION NO.: NM_006831; FIG. 25 (SEQ ID NO: 9)) or its complement under high stringency conditions; (vi) human Cleavage-Polyadenylation Specificity Factor ("CPSF") or proteins encoded by a nucleic acids that hybridize to human CPSF encoding nucleic acids or their complement under high stringency conditions; (vii) human Cleavage Factor $I_m$ ("CF $I_m$") or proteins encoded by nucleic acids that hybridize to human $CFI_m$ encoding nucleic acids or their complement under high stringency conditions; (viii) human Cleavage Factor $II_m$ ("CF $II_m$") or proteins encoded by nucleic acids that hybridize to human $CFII_m$ encoding nucleic acids or their complement under high stringency conditions; and (ix) human Cleavage Stimulation Factor ("CSF") or proteins encoded by nucleic acids that hybridize to human CstF encoding nucleic acids or their complement under high stringency conditions. In accordance with this embodiment, the complex has tRNA splicing endonuclease activity and/or 3' end pre-mRNA endonuclease activity.

The invention provides a purified protein complex with endonuclease activity comprising: (i) human CPSF160 or a functionally active derivative or a functionally active fragment thereof; (ii) human CPSF30 or a functionally active derivative or a functionally active fragment thereof; (iii) human CstF64 or a functionally active derivative or a functionally active fragment thereof; (iv) human symplekin or a functionally active derivative or a functionally active fragment thereof; (v) human Sen2 or a functionally active derivative or a functionally active fragment thereof; (vi) human Sen15 or a functionally active derivative or a functionally active fragment thereof; (vii) human Sen34 or a functionally active derivative or a functionally active fragment thereof; and (viii) human Sen54 or a functionally active derivative or a functionally active fragment thereof. In certain, more specific embodiments, the complex does not comprise PAP (poly (A) polymerase) and Sm proteins (small nuclear ribonucleoprotein). In a specific embodiment, the protein complex has tRNA splicing endonuclease activity. In another embodiment, the protein complex has 3' end pre-mRNA endonuclease activity. In yet another embodiment, the protein complex has tRNA splicing endonuclease activity and 3' end pre-mRNA endonuclease activity. In accordance with this embodiment, the complex has tRNA splicing endonuclease activity and/or 3' end pre-mRNA endonuclease activity.

The invention provides a purified protein complex with endonuclease activity comprising: (i) human CPSF160 or a protein encoded by a nucleic acid that hybridizes to human CPSF160 encoding nucleic acid or its complement under high stringency conditions; (ii) human CPSF30 or a protein encoded by a nucleic acid that hybridizes to human CPSF30 encoding nucleic acid or its complement under high stringency conditions; (iii) human CstF64 or a protein encoded by a nucleic acid that hybridizes to human CstF64 encoding nucleic acid or its complement under high stringency conditions; (iv) human symplekin or a protein encoded by a nucleic acid that hybridizes to human symplekin encoding nucleic acid or its complement under high stringency conditions; (v) human Sen2 or a protein encoded by a nucleic acid that hybridizes to human Sen2 encoding nucleic acid or its complement under high stringency conditions; (vi) human Sen15 or a protein encoded by a nucleic acid that hybridizes to human Sen15 encoding nucleic acid or its complement under high stringency conditions; (vii) human Sen34 or a protein encoded by a nucleic acid that hybridizes to human Sen34 encoding nucleic acid or its complement under high stringency conditions; and (viii) human Sen54 or a protein encoded by a nucleic acid that hybridizes to human Sen54 encoding nucleic acid or its complement under high stringency conditions. In certain, more specific embodiments, the complex does not comprise PAP (poly(A) polymerase) and Sm proteins (small nuclear ribonucleoprotein). In a specific embodiment, the protein complex has tRNA splicing endonuclease activity. In another embodiment, the protein complex has 3' end pre-mRNA endonuclease activity. In yet another embodiment, the protein complex has tRNA splicing endonuclease activity and 3' end pre-mRNA endonuclease activity. In accordance with this embodiment, the complex has tRNA splicing endonuclease activity and/or 3' end pre-mRNA endonuclease activity.

The invention provides a splice variant of human Sen2, namely human Sen2deltaEx8. In particular, the invention provides nucleic acid sequences encoding human Sen2deltaEx8 or a functionally active fragment or a functionally active derivative thereof, and amino acid sequences coding human Sen2deltaEx8 or a functionally active fragment or a functionally active derivative thereof. In a specific embodiment, the invention provides a nucleic acid sequence that hybridizes under stringent conditions to a nucleic acid sequence encoding Sen2ΔEx8 over the entire length of the nucleic acid sequence encoding Sen2ΔEx8. Preferably, such a nucleic acid sequence encodes a protein having Sen2ΔEx8 activity (such as the ability to form a complex with Clp1 and Sen54). In another embodiment, the invention provides nucleic acid sequences that encode a protein having an amino acid sequence that is at least 90%, preferably at least 95%, at least 98%, at least 99%, at least 99.5%, at least 99.8% or at least 99.9% identical to the amino acid sequence of SEQ ID NO:12, wherein the protein is different from Sen2 (ACCESSION NO.: NP_079541; FIG. 20 (SEQ ID NO: 2)). Preferably, such a protein has Sen2ΔEx8 activity. In another embodiment, the invention provides a nucleic acid sequence comprising the nucleic acid sequence of SEQ ID NO:11. The invention further provides vectors comprising a nucleic acid sequence encoding human Sen2ΔEx8 and host cells comprising the vector. The invention further provides host cells comprising a nucleic acid encoding human Sen2ΔEx8.

The invention provides a purified protein, wherein the protein consists essentially of the amino acid sequence of SEQ ID NO:12 or an amino acid sequence that is at least 90%, preferably at least 95%, at least 98%, at least 99%, at least 99.5%, at least 99.8% or at least 99.9% identical to the amino acid sequence of SEQ ID NO:12. The invention further provides antibodies or fragments thereof that immunospecifically bind to human Sen2ΔEx8 but do not bind to Sen2. In particular, the invention provides an antibody or fragment thereof that immunospecifically binds to the unique region of Sen2ΔEx8 that is created by the deletion of Exon 8 from the Sen2 protein.

The invention also provides purified protein complexes comprising human Sen2deltaEx8. In particular, the invention provides purified protein complexes comprising human Sen2deltaEx8 or a functionally active derivative or a functionally active fragment thereof and one or more, or any combination of the following (i) human Sen54 or a functionally active derivative or a functionally active fragment thereof (ii) human Sen15 or a functionally active derivative or a functionally active fragment thereof and (iii) human Sen34 or a functionally active derivative or a functionally active fragment thereof.

The Sen2deltaEx8 complexes have RNA-nucleolytic activity. In a specific embodiment, Sen2deltaEx8 complexes have pre-tRNA cleavage activity and/or 3' end pre-mRNA endonuclease activity. The invention provides a purified human Sen2deltaEx8 complex comprising: (i) human Sen2deltaEx8 or a functionally active derivative thereof and (ii) human Sen54 or a functionally active derivative or a functionally active fragment thereof. The invention also provides a human Sen2deltaEx8 complex comprising: (i) human Sen2deltaEx8 or a functionally active derivative thereof; (ii) human Sen54 or a functionally active derivative or a functionally active fragment thereof; (iii) human Sen15 or a functionally active derivative or a functionally active fragment thereof; and (iv) human Sen34 or a functionally active derivative or a functionally active fragment thereof. In a specific embodiment, the complex has RNA-nucleolytic activity. In a specific embodiment, the complex has tRNA endonuclease activity. In a specific embodiment, the complex has 3' end mRNA processing activity. These human Sen2deltaEx8 complexes cleave tRNA at multiple sites and are useful in mapping RNA structure and 3' end pre-mRNA endonuclease processing. In certain embodiments, the fidelity and accuracy of the tRNA cleavage activity of a Sen2deltaEx8 comprising complex is reduced compared to the tRNA cleavage activity of full length Sen2 comprising complexes.

In a specific embodiment, the invention provides a purified human Sen2deltaEx8 complex comprising: (i) human Sen2deltaEx8 (, SEQ ID NO:12), or a functionally active fragment thereof or a protein encoded by a nucleic acid that hybridizes to the human Sen2deltaEx8 encoding nucleic acid (SEQ ID NO:11) or its complement under high stringency conditions; and (ii) human Sen15 (ACCESSION NO.:NP_443197; FIG. 22 (SEQ ID NO: 4)), or a protein encoded by a nucleic acid that hybridizes to the human Sen15 encoding nucleic acid (ACCESSION NO.:NM_052965; FIG. 22 (SEQ ID NO: 3)) or its complement under high stringency conditions. In another embodiment, the invention provides a purified human Sen2deltaEx8 complex comprising: (i) human Sen2deltaEx8 (SEQ ID NO:12), or a protein encoded by a nucleic acid that hybridizes to the human Sen2deltaEx8 encoding nucleic acid (SEQ ID NO:11) or its complement under high stringency conditions; (ii) human Sen15 (ACCESSION NO.:NP_443197; FIG. 22 (SEQ ID NO: 4)), or a protein encoded by a nucleic acid that hybridizes to the human Sen15 encoding nucleic acid (ACCESSION NO.: NM_052965; FIG. 22 (SEQ ID NO: 3)) or its complement under high stringency conditions; (iii) human Sen34 (ACCESSION NO.:NP_076980; FIG. 23 (SEQ ID NO: 6)), or a protein encoded by a nucleic acid that hybridizes to the human Sen34 encoding nucleic acid (ACCESSION NO.: NM_024075; FIG. 23 (SEQ ID NO: 5)) or its complement under high stringency conditions; and (iv) Sen54 (ACCESSION NO.:XP_208944; FIG. 24 (SEQ ID NO: 8)), or a protein encoded by a nucleic acid that hybridizes to the human Sen54 encoding nucleic acid (ACCESSION NO.: XM_208944; FIG. 24 (SEQ ID NO: 7)) or its complement under high stringency conditions.

In certain embodiments, the invention provides a purified human Sen2deltaEx8 complex comprising: (i) human Sen2deltaEx8; and (ii) human Sen34. In certain embodiments, the invention provides a purified human Sen2deltaEx8 complex comprising: (i) human Sen2deltaEx8; (ii) human Sen15; and (iii) human Sen34. In certain embodiments, the invention provides a purified human Sen2deltaEx8 complex comprising: (i) Sen2deltaEx8; and (ii) Sen54.

In accordance with these embodiments, the human Sen2deltaEx8 complex has RNA-nucleolytic activity. In a particular embodiment, the human Sen2deltaEx8 complex cleaves tRNA at multiple sites. These human Sen2deltaEx8 complexes are useful in mapping RNA structure and 3′ endonuclease processing. In certain embodiments, the fidelity and accuracy of the tRNA cleavage activity of a Sen2deltaEx8 comprising complex is reduced compared to the tRNA cleavage activity of full length Sen2 comprising complexes.

In certain embodiments, the invention provides a purified human Sen2deltaEx8 complex comprising: (i) human Sen2deltaEx8 or a protein encoded by a nucleic acid that hybridizes to the human Sen2deltaEx8 encoding nucleic acid; and (ii) human Sen34 or a protein encoded by a nucleic acid that hybridizes to the human Sen34 encoding nucleic acid. In certain embodiments, the invention provides a purified human Sen2deltaEx8 complex comprising: (i) human Sen2deltaEx8 or a protein encoded by a nucleic acid that hybridizes to the human Sen2deltaEx8 encoding nucleic acid; (ii) human Sen15 or a protein encoded by a nucleic acid that hybridizes to the human Sen15 encoding nucleic acid; and (iii) human Sen34 or a protein encoded by a nucleic acid that hybridizes to the human Sen34 encoding nucleic acid. In certain embodiments, the invention provides a purified human Sen2deltaEx8 complex comprising: (i) Sen2deltaEx8 or a protein encoded by a nucleic acid that hybridizes to the human Sen2deltaEx8 encoding nucleic acid; and (ii) Sen54 or a protein encoded by a nucleic acid that hybridizes to the human Sen54 encoding nucleic acid.

The invention provides a purified human Sen2deltaEx8 complex with 3′ end pre-mRNA endonuclease activity comprising: (i) human Sen2deltaEx8 or a functionally active derivative thereof; (ii) human Sen54 or a functionally active derivative or a functionally active fragment thereof; (iii) human Sen15 or a functionally active derivative or a functionally active fragment thereof; (iv) human Sen34 or a functionally active derivative or a functionally active fragment thereof; and (v) human Clp1 (ACCESSION NO.:NP__006822; FIG. 25 (SEQ ID NO: 10)) or a functionally active derivative or a functionally active fragment thereof. In certain embodiments, the complex may further comprise: (i) human CPSF160 or a functionally active derivative or a functionally active fragment thereof; (ii) human CPSF30 or a functionally active derivative or a functionally active fragment thereof; (iii) human CstF64 or a functionally active derivative or a functionally active fragment thereof; and/or (iv) human symplekin or a functionally active derivative or a functionally active fragment. The invention also provides a purified human Sen2deltaEx8 complex with 3′ end pre-mRNA endonuclease activity comprising: (i) human Sen2deltaEx8 or a functionally active derivative thereof; (ii) human Sen54 or a functionally active derivative or a functionally active fragment thereof; (iii) human Sen15 or a functionally active derivative or a functionally active fragment thereof; (iv) human Sen34 or a functionally active derivative or a functionally active fragment thereof; (v) human Clp1 (ACCESSION NO.:NP__006822; FIG. 25 (SEQ ID NO: 10)) or a functionally active derivative or a functionally active fragment thereof; (vi) human CSPF or a functionally active derivative or a functionally active fragment thereof; (vii) human $CFI_m$ or a functionally active derivative or a functionally active fragment thereof; (viii) human $CFII_m$. or a functionally active derivative or a functionally active fragment thereof; and (ix) human CstF or a functionally active derivative or a functionally active fragment thereof.

In a specific embodiment, the invention provides a purified human Sen2deltaEx8 complex with 3′ end pre-mRNA endonuclease activity comprising: (i) human Sen2deltaEx8 (SEQ ID NO:12), or a protein encoded by a nucleic acid that hybridizes to the human Sen2deltaEx8 encoding nucleic acid (SEQ ID NO:11) or its complement under high stringency conditions; (ii) human Sen54 (ACCESSION NO.:XP__208944; FIG. 24 (SEQ ID NO: 8)), or a protein encoded by a nucleic acid that hybridizes to the human Sen54 encoding nucleic acid (ACCESSION NO.:XM__208944; FIG. 24 (SEQ ID NO: 7)) or its complement under high stringency conditions; (iii) human Sen15 (ACCESSION NO.:NP__443197; FIG. 22 (SEQ ID NO: 4)), or a protein encoded by a nucleic acid that hybridizes to the human Sen15 encoding nucleic acid (ACCESSION NO.:NM__052965; FIG. 22 (SEQ ID NO: 3)) or its complement under high stringency conditions; (iv) human Sen34 (ACCESSION NO.:NP__076980; FIG. 23 (SEQ ID NO: 6)), or a protein encoded by a nucleic acid that hybridizes to the human Sen34 encoding nucleic acid (ACCESSION NO.:NM__024075; FIG. 23 (SEQ ID NO: 5)) or its complement under high stringency conditions; and (v) human Clp1 (ACCESSION NO.:NP__006822; FIG. 25 (SEQ ID NO: 10)) or a protein encoded by a nucleic acid that hybridizes to the human Clp1 encoding nucleic acid (ACCESSION NO.: NM__006831 (SEQ ID NO: 83); FIG. 25 (SEQ ID NO: 9)) or its complement under high stringency conditions.

In certain embodiments, the complex may further comprise: (i) human CPSF160 or a protein encoded by a nucleic acid that hybridizes to the human CPSF160 encoding nucleic acid; (ii) human CPSF30 or a protein encoded by a nucleic acid that hybridizes to the human CPSF30 encoding nucleic acid; (iii) human CstF64 or a protein encoded by a nucleic acid that hybridizes to the human CstF64 encoding nucleic acid; and/or (iv) human symplekin or a protein encoded by a nucleic acid that hybridizes to the human symplekin encoding nucleic acid.

In another embodiment, the invention provides a purified human Sen2deltaEx8 complex with 3′ end pre-mRNA endonuclease activity comprising: (i) human Sen2deltaEx8 (SEQ ID NO:12), or a protein encoded by a nucleic acid that hybridizes to the human Sen2deltaEx8 encoding nucleic acid (SEQ ID NO: 11) or its complement under high stringency conditions; (ii) human Sen54 (ACCESSION NO.:XP__208944; FIG. 24 (SEQ ID NO: 8)), or a protein encoded by a nucleic acid that hybridizes to the human Sen54 encoding nucleic acid (ACCESSION NO.:XM__208944; FIG. 24 (SEQ ID NO: 7)) or its complement under high stringency conditions; (iii) human Sen15 (ACCESSION NO.:NP__443197; FIG. 22 (SEQ ID NO: 4)), or a protein encoded by a nucleic acid that hybridizes to the human Sen15 encoding nucleic acid (ACCESSION NO.:NM__052965; FIG. 22 (SEQ ID NO: 3)) or its complement under high stringency conditions; (iv) human Sen34 (ACCESSION NO.:NP__076980; FIG. 23 (SEQ ID NO: 6)), or a protein encoded by a nucleic acid that hybridizes to the human Sen34 encoding nucleic acid (ACCESSION NO.:NM__024075; FIG. 23 (SEQ ID NO: 5)) or its complement under high stringency conditions; (v) human Clp1 (ACCESSION NO.:NP__006822; FIG. 25 (SEQ ID NO: 10)) or a protein encoded by a nucleic acid that hybridizes to the human Clp1 encoding nucleic acid (ACCESSION NO.: NM__006831; FIG. 25 (SEQ ID NO: 9)) or its complement under high stringency conditions; (vi) a human CPSF, or a protein encoded by a nucleic acid that hybridizes to the human CPSF encoding nucleic acid or its complement under high stringency conditions; (vii) a human $CFI_m$, or a protein encoded by a nucleic acid that hybridizes to the human $CFI_m$ encoding nucleic acid or its complement under high stringency conditions; (viii) a human $CFII_m$, or a protein encoded by a nucleic acid that hybridizes to the human $CFII_m$ encoding nucleic acid or its complement under high stringency conditions; and (ix) human CSF, or a protein encoded by a nucleic acid that hybridizes to the human CstF encoding nucleic acid or its complement under high stringency conditions.

The invention provides a purified human Sen2deltaEx8 complex with 3' end pre-mRNA endonuclease activity comprising: (i) human Sen2deltaEx8 or a functionally active derivative thereof; (ii) human Sen54 or a functionally active derivative or a functionally active fragment thereof; and (iii) human Clp1 (ACCESSION NO.:NP_006822; FIG. 25 (SEQ ID NO: 10)) or a functionally active derivative or a functionally active fragment thereof, and optionally one or more, or any combination of the following: (i) human CPSF or a functionally active derivative or a functionally active fragment thereof; (ii) human $CFI_m$ or a functionally active derivative or a functionally active fragment thereof; (iii) human $CFII_m$ or a functionally active derivative or a functionally active fragment thereof; and (iv) human CstF or a functionally active derivative or a functionally active fragment thereof. In a specific embodiment, the invention provides a purified Sen2deltaEx8 complex with 3' end pre-mRNA endonuclease activity comprising: (i) human Sen2deltaEx8 (SEQ ID NO:12), or a protein encoded by a nucleic acid that hybridizes to the human Sen2deltaEx8 encoding nucleic acid (SEQ ID NO:11) or its complement under high stringency conditions; (ii) human Sen54 (ACCESSION NO.:XP_208944; FIG. 24 (SEQ ID NO: 8)), or a protein encoded by a nucleic acid that hybridizes to the human Sen54 encoding nucleic acid (ACCESSION NO.:XM_208944; FIG. 24 (SEQ ID NO: 7)) or its complement under high stringency conditions; and (iii) human Clp1 (ACCESSION NO.:NP_006822; FIG. 25 (SEQ ID NO: 10)) or a protein encoded by a nucleic acid that hybridizes to the human Clp1 encoding nucleic acid (ACCESSION NO.: NM_006831; FIG. 25 (SEQ ID NO: 9)) or its complement under high stringency conditions. In certain embodiments, the complex may further comprise: (i) human CPSF160 or a protein encoded by a nucleic acid that hybridizes to the human CPSF160 encoding nucleic acid; (ii) human CPSF30 or a protein encoded by a nucleic acid that hybridizes to the human CPSF30 encoding nucleic acid; (iii) human CstF64 or a protein encoded by a nucleic acid that hybridizes to the human CstF64 encoding nucleic acid; and/or (iv) human symplekin or a protein encoded by a nucleic acid that hybridizes to the human symplekin encoding nucleic acid. In another embodiment, the invention provides a purified Sen2deltaEx8 complex with 3' end pre-mRNA endonuclease activity comprising: (i) human Sen2deltaEx8 (SEQ ID NO:12), or a protein encoded by a nucleic acid that hybridizes to the human Sen2deltaEx8 encoding nucleic acid (SEQ ID NO:11) or its complement under high stringency conditions; (ii) human Sen54 (ACCESSION NO.:XP_208944; FIG. 24 (SEQ ID NO: 8)), or a protein encoded by a nucleic acid that hybridizes to the human Sen54 encoding nucleic acid (ACCESSION NO.:XM_208944; FIG. 24 (SEQ ID NO: 7)) or its complement under high stringency conditions; (iii) human Clp1 (ACCESSION NO.:NP_006822; FIG. 25 (SEQ ID NO: 10)) or a protein encoded by a nucleic acid that hybridizes to the human Clp1 encoding nucleic acid (ACCESSION NO.: NM_006831; FIG. 25 (SEQ ID NO: 9)) or its complement under high stringency conditions; (iv) human CPSF or a protein encoded by a nucleic acid that hybridizes to the human CPSF or its complement under high stringency conditions; (v) human $CFI_m$ or a protein encoded by a nucleic acid that hybridizes to the human $CFI_m$ encoding nucleic acid or its complement under high stringency conditions; (vi) human $CF II_m$ or a protein encoded by a nucleic acid that hybridizes to the human $CFII_m$ encoding nucleic acid or its complement under high stringency conditions; and (vii) human CstF or a protein encoded by a nucleic acid that hybridizes to the human CstF encoding nucleic acid or its complement under high stringency conditions.

The invention also provides protein complexes with pre-ribosomal RNA cleavage activity. In particular, the invention provides a protein complex with pre-ribosomal RNA cleavage activity comprising: (i) human Sen15 or a functionally active derivative or a functionally active fragment thereof; and (ii) human Sen34 or a functionally active derivative or a functionally active fragment thereof. More specifically, the invention provides a protein complex with pre-ribosomal RNA cleavage activity comprising: (i) human Sen15 (ACCESSION NO.:NP_443197; FIG. 22 (SEQ ID NO: 4)), or a protein encoded by a nucleic acid that hybridizes to the human Sen15 encoding nucleic acid (ACCESSION NO.: NM_052965; FIG. 22 (SEQ ID NO: 3)) or its complement under high stringency conditions; and (ii) human Sen34 (ACCESSION NO.:NP_076980; FIG. 23 (SEQ ID NO: 6)), or a protein encoded by a nucleic acid that hybridizes to the human Sen34 encoding nucleic acid (ACCESSION NO.: NM_024075; FIG. 23 (SEQ ID NO: 5)) or its complement under high stringency conditions. This protein complex may be used in the biogenesis of different ribosomal RNAs. For example, the production of 28S, 18S, 5.5S and 5S ribosomal RNA may be altered by modulating this protein complex.

In certain embodiments, at least two protein components, at least three protein components, at least four protein components or at least five protein components of a complex of the invention are covalently linked to each other, e.g., as fusion proteins. In certain other embodiments, a complex of the invention comprises at least two protein components, at least three protein components, at least four protein components or at least five protein components that are non-covalently linked to each other. In yet other embodiments, a complex of the invention comprises a combination of covalently linked and non-covalently linked protein components. In certain other embodiments, a protein component of a complex of the invention is fused to a heterologous amino acid sequence, i.e., an amino acid sequence different from the protein. Further, the complexes of the invention may comprise at least one, preferably at least two functionally active fragments of protein components of the complex. The complexes of the invention may comprise at least three, at least four or at least five functionally active fragments of protein components of the complex. The complexes of the invention may comprise at least one, preferably at least two or at least three, at least four or at least five functionally active derivatives of the protein components of the complex. In one embodiment, such functionally active derivatives are fusion proteins. In accordance with this embodiment, such fusion proteins may comprise a heterologous sequence, i.e., an amino acid sequence different from the amino acid sequence of the protein component.

The invention provides methods for purifying a complex of the invention. In particular, the invention provides a method for purifying a complex of the invention, the method comprising: preparing a cell extract or a nuclear extract from a cell, wherein the cell expresses all of the protein components of the complex and wherein at least one of the protein components is fused to a peptide tag; and purifying the complex by virtue of the peptide tag.

The invention provides antibodies or fragments thereof that immunospecifically bind to a complex of the invention. In a specific embodiment, the invention provides an antibody or a fragment thereof that immunospecifically binds to a complex of the invention with higher affinity than to each individual component of the complex in an immunoassay well-known to one of skill in the art or described herein. In another embodiment, the invention provides an antibody or a fragment thereof that immunospecifically binds to a complex of the invention, but does not bind to each individual component of the complex in an immunoassay well-known to one of skill in the art or described herein. The invention also provides a method for generating an antibody or a fragment thereof that immunospecifically binds to a complex of the invention comprising immunizing a subject with the complex of the invention.

The invention also provides antibodies or fragments thereof that immunospecifically bind to one of the following components of a complex of the invention: (i) human Sen2 or a functionally active derivative or a functionally active fragment thereof; (ii) human Sen2deltaEx8 or a functionally active derivative or a functionally active fragment thereof; (iii) human Sen15 or a functionally active derivative or a functionally active fragment thereof; (iv) human Sen34 or a functionally active derivative or a functionally active fragment thereof; and (v) human Sen54 or a functionally active derivative or a functionally active fragment thereof. Preferably, the antibodies or fragments thereof are not known. The invention also provides a method for generating an antibody or a fragment thereof that immunospecifically binds to a component of a complex of the invention comprising immunizing a subject with the component.

In a specific embodiment, the invention provides an antibody or a fragment thereof that immunospecifically binds to human Sen2deltaEx8 with higher affinity than human Sen2 in an immunoassay well-known to one of skill in the art or described herein. In another embodiment, the invention provides an antibody or a fragment thereof that immunospecifically binds to human Sen2deltaEx8, but does not bind to human Sen2 in an immunoassay well-known to one of skill in the art or described herein.

The invention provides methods of identifying compounds that modulate the expression (at the RNA and/or protein level) of one or more of the following components of a complex of the invention: (i) human Sen2 or a functionally active derivative or a functionally active fragment thereof; (ii) human Sen2deltaEx8 or a functionally active derivative or a functionally active fragment thereof; (iii) human Sen15 or a functionally active derivative or a functionally active fragment thereof; (iv) human Sen34 or a functionally active derivative or a functionally active fragment thereof; and/or (v) human Sen54 or a functionally active derivative or a functionally active fragment thereof. Techniques for measuring expression of proteins are well-known to one of skill in the art and include, e.g., immunoassays for protein expression levels, and RT-PCR or Northern blots for RNA expression levels.

The invention provides screening assays to identify compounds that modulate the formation of a complex of the invention. In particular, the invention provides a method of identifying a compound that modulates the formation of a complex of the invention, the method comprising: contacting a cell with a compound, wherein the cell comprises all of the components of the complex the invention; and measuring the amount of the complex of the invention formed in the cell. The method may further comprise isolating the complex of the invention from the cell. The amount of complex can be measured by any method well-known to one of skill in the art for measuring complex formation or by any method described herein (such as, e.g., FRET). In a specific embodiment, the invention provides a method of identifying a compound that modulates the formation of a complex, the method comprising: contacting a cell comprising all of the components of the complex with a compound, wherein the cell has been engineered to express one, two, three, four or more of the components of the complex; and measuring the amount of the complex formed in the cell. In accordance with this embodiment, the cell may be any non-human cell or a human cell deficient in one or more components of the complex.

The invention provides a method of identifying a compound that modulates the formation of a complex, the method comprising the following steps: (a) incubating the components of a complex of the invention in the presence of a compound under conditions conducive to formation of a complex comprising the proteins; and (b) measuring the amount of the complex, wherein a difference in the amount of the complex measured in step (b) relative to the amount of the complex measured in the absence of the compound or in the presence of an appropriate control (e.g., a negative control such as phosphate buffered saline) or a predetermined reference range indicates that the compound modulates the formation of the complex. Techniques for measuring complex formation are well-known in the art or described herein.

The invention provides methods for identifying compounds that modulate the endonucleolytic activity of a complex of the invention. The invention provides cell-based and cell-free assays for identifying compounds that modulate human tRNA splicing endonuclease activity and/or human 3' end pre-mRNA splicing endonuclease activity. In one embodiment, the invention provides a method for identifying compounds that modulate the endonucleolytic activity of a complex of the invention, the method comprising: (a) contacting a compound or a member of a library of compounds with a cell containing or engineered to contain the components of the human complex and a substrate for the complex; and (b) detecting the level of endonucleolytic activity by measuring either the decrease in substrate or the increase in product of the endonuclease reaction. In another embodiment, the invention provides a method for identifying compounds that modulate the endonucleolytic activity of a complex of the invention, the method comprising: (a) incubating a complex of the invention with an endonuclease substrate and with a compound or a member of a library of compounds; and (b) detecting the level of endonuclease activity by measuring either the decrease in substrate or the increase in product of the endonuclease reaction.

In a particular embodiment, the invention provides a method for identifying a compound that modulates human tRNA splicing endonuclease activity, the method comprising: contacting a compound or a member of a library of compounds with a complex of the invention with human tRNA splicing endonuclease activity and a nucleic acid (e.g., RNA or DNA) comprising a reporter gene under conditions that allow transcription and translation of the reporter gene (e.g., cell-free or cell-based assays), wherein the reporter gene comprises a tRNA intron; and detecting the expression of said reporter gene (i.e., production of processed reporter gene mRNA resulting from tRNA splicing endonuclease activity, the protein product of the reporter gene, and/or activity of the reporter gene product), wherein a compound that modulates tRNA splicing endonuclease activity is identified if the expression of said reporter gene in the presence of the compound is altered relative to the expression of said reporter gene in the absence of said compound or the presence of an appropriate control or a predetermined reference range. A decrease in reporter gene expression relative to a previously determined reference range, or to the expression in the absence of the compound or the presence of an appropriate control (e.g., a negative control) in such reporter-gene based assays indicates that a particular compound reduces or inhibits the activity of a human tRNA splicing endonuclease (e.g., the recognition or cleavage of a tRNA intron). In contrast, an increase in reporter gene expression relative to a previously determined reference range, or to the expression in the absence of the compound or the presence of an appropriate control (e.g., a negative control) in such reporter-gene based assays indicates that a particular compound enhances the activity of a human tRNA splicing endonuclease. In a specific embodiment, the TNT® Coupled Reticulocyte Lysate Systems is used in accordance with the method (Promega, Madison Wis.). In other specific embodiments, a cell extract is used to provide the factors required for transcription and translation of the reporter gene. In even other specific embodiments, a compound and the tRNA splicing endonuclease are introduced into a cell (e.g., by transforming a cell with nucleic acids encoding the complex components, preferably under the control of a heterologous promoter). In accordance with this embodiment of the invention, the recombinant components of a complex of the invention can be expressed in the cell either individually or as a fusion complex. In a preferred embodiment, the human complex is introduced or expressed in a non-human cell.

The invention further provides a method for identifying a compound that modulate human tRNA splicing endonuclease activity, said method comprising: (a) expressing a nucleic acid comprising a reporter gene in a cell, wherein the reporter gene comprises a tRNA intron; (b) contacting said cell with a compound or a member of a library of compounds; and (c) detecting the expression of said reporter gene, wherein a compound that modulates tRNA splicing endonuclease activity is identified if the expression of said reporter gene in the presence of a compound is altered relative to a previously determined reference range, or the expression of said reporter gene in the absence of the compound or the presence of an appropriate control (e.g., a negative control). In particular, an increase in expression of the reporter gene compared to a control indicates that the compound increases human tRNA splicing endonuclease activity. In contrast, a decrease in expression of the reporter gene compared to a control indicates that the compound decreases human tRNA splicing endonuclease activity.

In another embodiment, the invention provides a method for identifying a compound that modulates human tRNA splicing endonuclease activity, said method comprising: (a) contacting a member of a library of compounds with a cell containing a nucleic acid comprising a reporter gene, wherein the reporter gene comprises a tRNA intron; and (b) detecting the expression of said reporter gene, wherein a compound that modulates tRNA splicing endonuclease activity is identified if the expression of said reporter gene in the presence of a compound is altered relative to a previously determined reference range, or the expression of said reporter gene in the absence of said compound or the presence of an appropriate control (e.g., a negative control). In particular, an increase in expression of the reporter gene compared to a control indicates that the compound increases human tRNA splicing endonuclease activity. In contrast, a decrease in expression of the reporter gene compared to a control indicates that the compound decreases human tRNA splicing endonuclease activity.

In another embodiment, the invention provides a method for identifying a compound that modulates human tRNA splicing endonuclease activity, the method comprising: contacting a complex of the invention with tRNA splicing endonuclease activity with a substrate of a tRNA splicing endonuclease and a compound or a member of a library of compounds, wherein the substrate is labeled at the 5' end with a fluorophore and at the 3' end with a quencher or, alternatively, the substrate is labeled at the 5' end with a quencher and at the 3' end with a fluorophore; and measuring the activity of the tRNA splicing endonuclease by measuring the change in fluorescence, wherein a compound that modulates tRNA splicing activity is identified if a fluorescent signal is altered in the presence of the compound relative to the signal in the absence of the compound or the presence of an appropriate control. The tRNA splicing endonuclease in the cell-free extract will cleave the substrate and result in the production of a detectable fluorescent signal. A compound that inhibits or reduces the activity of the tRNA splicing endonuclease will inhibit or reduce the cleavage of the substrate and thus, inhibit or reduce the production of a detectable fluorescent signal relative to a negative control (e.g., PBS). A compound that enhances the activity of the tRNA splicing endonuclease will enhance the cleavage of the substrate and thus, increase the production of a detectable signal relative to a negative control (e.g., PBS).

In another embodiment, the invention provides a method for identifying a compound that modulates human tRNA splicing endonuclease activity, the method comprising: contacting a complex of the invention with tRNA splicing endonuclease activity with a substrate of a tRNA splicing endonuclease and a compound or a member of a library of compounds, wherein said substrate is labeled at the 5' end with a fluorescent donor moiety and labeled at the 3' end with a fluorescent acceptor moiety or, alternatively, the substrate is labeled at the 5' end with a fluorescent acceptor moiety and at the 3' end with a fluorescent donor moiety; and measuring the activity of the tRNA splicing endonuclease, wherein a compound that modulates tRNA splicing endonuclease activity is identified if the fluorescence emission of the fluorescent acceptor moiety at the wavelength of the fluorescent donor moiety in the presence of the compound is altered relative to the absence of the compound or the presence of an appropriate control (e.g., a negative control such as PBS) or a predetermined reference range. The tRNA splicing endonuclease will cleave the substrate and result in a decrease in the fluorescence emission by the fluorescent donor moiety and fluorescent acceptor moiety at the wavelength of the fluorescent donor moiety. A compound that inhibits or reduces the activity of the human tRNA splicing endonuclease will inhibit or reduce cleavage of the substrate and thus, increase the fluorescence emission of the fluorescent acceptor moiety at the wavelength of the fluorescent donor moiety. A compound that enhances the activity of the human tRNA splicing endonuclease will enhance the cleavage of the substrate and thus, reduce the fluorescence emission of the fluorescent acceptor moiety at the wavelength of the fluorescent donor moiety.

In another embodiment, the invention provides a method for identifying a compound that modulates human 3' end pre-mRNA endonuclease activity, the method comprising: contacting a compound or a member of a library of compounds with a complex of the invention with human 3' end pre-mRNA endonuclease activity and a nucleic acid comprising a 3' end cleavage reporter gene, wherein the reporter gene is located 3' of the cleavage site under conditions that allow transcription and translation of the reporter gene (e.g., cell-free or cell based assays); and detecting the expression of said reporter gene (i.e., production of processed mRNA resulting from the 3' end pre-mRNA endonuclease activity cleaving 5' of the reporter gene, amount of the reporter gene product or activity of the reporter gene product), wherein a compound that modulates 3' end pre-mRNA endonuclease activity is identified if the expression of said reporter gene in the presence of a compound is altered relative to the expression of said reporter gene in the absence of said compound or the presence of an appropriate control (e.g., a negative control such as PBS) or to a predetermined reference range. In accordance with this embodiment, all factors required for the expression of the reporter gene are also provided. In a specific embodiment, the TNT® Coupled Reticulocyte Lysate Systems is used (Promega, Madison Wis.). In other specific embodiments, a cell extract is used to provide the factors required for transcription and translation of the reporter gene. In even other specific embodiments, the complex and the 3' end pre-mRNA endonuclease are introduced into a cell. In particular, an increase in reporter gene expression relative to a previously determined reference range, or to the expression in the absence of the compound or the presence of an appropriate control (e.g., a negative control) in such reporter-gene based assays indicates that a particular compound reduces or inhibits the activity of a 3' end pre-mRNA endonuclease (e.g., the recognition or cleavage of a substrate). In contrast, a decrease in reporter gene expression relative to a previously determined reference range, or to the expression in the absence of the compound or the presence of an appropriate control (e.g., a negative control) in such reporter-gene based assays indicates that a particular compound enhances the activity of a human 3' end pre-mRNA endonuclease.

In another embodiment, the invention provides a method of identifying a compound that inhibits or reduces human 3' end pre-mRNA endonuclease activity, the method comprising: contacting a complex of the invention with human 3' end pre-mRNA endonuclease activity with a substrate of a 3' end pre-mRNA endonuclease and a compound or a member of a library of compounds, wherein the substrate is labeled at the 5' end with a fluorophore and at the 3' end with a quencher or, alternatively, the substrate is labeled at the 5' end with a quencher and at the 3' end with a fluorophore; and measuring the activity of the 3' end pre-mRNA endonuclease; wherein a compound that modulates 3' end pre-mRNA endonuclease activity is identified if a fluorescent signal is altered in the presence of the compound relative to the absence of the compound or the presence of an appropriate control (e.g., a negative control such as PBS), or to a predetermined reference range. A compound that inhibits or reduces the activity of the human 3' end pre-mRNA endonuclease will inhibit or reduce cleavage of the substrate and thus, decrease the production of a detectable fluorescent signal relative to a control. A compound that enhances the activity of the human 3' end pre-mRNA endonuclease will enhance the cleavage of the substrate and thus, increase the production of a detectable fluorescent signal relative to a control.

In another embodiment, the invention provides a method of identifying a compound that inhibits or reduces human 3' end pre-mRNA endonuclease activity, the method comprising: contacting a complex of the invention with human 3' end pre-mRNA endonuclease activity with a substrate of 3' end pre-mRNA endonuclease and a compound or a member of a library of compounds, wherein said substrate is labeled at the 5' end with a fluorescent donor moiety and labeled at the 3' end with a fluorescent acceptor moiety or, alternatively, the substrate is labeled at the 5' end with a fluorescent acceptor moiety and at the 3' end with a fluorescent donor moiety; and measuring the activity of the 3' mRNA endonuclease, wherein a compound that modulates 3' end pre-mRNA endonuclease activity is identified if the fluorescence emission of the fluorescent acceptor moiety at the wavelength of the fluorescent donor moiety in the presence of the compound is altered in the presence of the compound relative to the absence of the compound or the presence of an appropriate control (e.g., a negative control such as PBS), or to a predetermined reference range. A compound that inhibits or reduces the activity of the human 3' end pre-mRNA endonuclease will inhibit or reduce cleavage of the substrate and thus, increase the fluorescence emission of the fluorescent acceptor moiety at the wavelength of the fluorescent donor moiety relative to a control. A compound that enhances the activity of the human 3' end pre-mRNA endonuclease will enhance the cleavage of the substrate and thus, reduce the fluorescence emission of the fluorescent acceptor moiety at the wavelength of the fluorescent donor moiety.

In certain embodiments, RT-PCR, such as, but not limited to a quantitative RT-PCR assay as described in section 5.2, can be used to measure the effect of a compound on 3' end pre-mRNA processing; the modification of any expressed gene, e.g., GAPDH and EFIA, can be used.

The present invention further provides methods for identifying compounds that modulate the pre-tRNA cleavage activity and/or pre-ribosomal RNA cleavage activity of a complex of the invention. Techniques well-known to one of skill in the art or described herein may be used to measure the ability of a compound to modulate the pre-tRNA cleavage activity and/or pre-ribosomal RNA cleavage activity of a complex of the invention. For example, the ability of a compound to modulate the pre-tRNA cleavage activity of a complex of the invention may be determined by comparing the level of tRNA fragments produced from a tRNA in the presence of the compound relative to the level of tRNA fragments produced from the same tRNA in the absence of the compound or the presence of an appropriate control (e.g., a negative control such as PBS), wherein a change in the levels indicates that the compound modulates the pre-tRNA cleavage activity of the complex. The ability of a compound to modulate the pre-ribosomal RNA cleavage activity of a complex of the invention may be determined by, e.g., comparing the level of specific ribosomal RNAs (e.g., 28S, 18S, 5.8S and/or 5S) produced from a pre-ribosomal RNA in the presence of the compound relative to the level of the ribosomal RNA produced from the same pre-ribosomal RNA in the absence of the compound or the presence of an appropriate control (e.g., a negative control such as PBS), wherein a change in the levels indicates that the compound modulates the pre-ribosomal RNA cleavage activity of the complex. In certain embodiments, the methods for identifying compounds that modulate the pre-tRNA cleavage activity and/or pre-ribosomal RNA cleavage activity of a complex of the invention are cell-based assays. In other embodiments, the methods for identifying compounds that modulate the pre-tRNA cleavage activity and/or pre-ribosomal RNA cleavage activity of a complex of the invention are cell-free assays.

A compound identified in the assays described herein that modulates the expression of a component of a complex of the invention, the formation of a complex of the invention, the RNA-nucleolytic activity of a complex of the invention (e.g., the pre-tRNA splicing endonuclease activity, the 3' end pre-mRNA endonuclease activity, the pre-tRNA cleavage activity of a complex of the invention, and/or the pre-ribosomal RNA cleavage activity of a complex of the invention) may be tested in in vitro assays (e.g., cell-based assays or cell-free assays) and/or in vivo assays well-known to one of skill in the art or described herein for the effect of the compound a disorder described herein (e.g., a proliferative disorder or a disorder characterized by, associated with or caused by abnormal RNA-nucleolytic activity) or on cells from a patient with a particular disorder.

In a specific embodiment, a compound identified in the assays described herein that inhibits or reduces the expression of a component of a complex of the invention, the formation of a complex of the invention, the RNA-nucleolytic activity of a complex of the invention (e.g., the pre-tRNA splicing endonuclease activity, the 3' end pre-mRNA endonuclease activity, the pre-tRNA cleavage activity of a complex of the invention, and/or the pre-ribosomal RNA cleavage activity of a complex of the invention) may be tested in in vitro assays (e.g., cell-based assays or cell-free assays) and/or in vivo assays well-known to one of skill in the art or described herein for the antiproliferative effect of the compound on hyperproliferative cells versus normal cells. In another embodiment, a compound identified in the assays described herein that inhibits or reduces the expression of a component of a complex of the invention, the formation of a complex of the invention, the RNA-nucleolytic activity of a complex of the invention (e.g., the pre-tRNA splicing endonuclease activity, the 3' end pre-mRNA endonuclease activity, the pre-tRNA cleavage activity of a complex of the invention, and/or the pre-ribosomal RNA cleavage activity of a complex of the invention) may be tested in an animal model for cancer to determine the efficacy of the compound in the prevention, treatment or amelioration of cancer or a symptom thereof. In yet another embodiment, a compound identified in assays described herein that enhances the expression of a component of a complex of the invention, the formation of a complex of the invention, the RNA-nucleolytic activity of a complex of the invention (e.g., the pre-tRNA splicing endonuclease activity, the 3' end pre-mRNA endonuclease activity, the pre-tRNA cleavage activity of a complex of the invention, and/or the pre-ribosomal RNA cleavage activity of a complex of the invention) may be tested for its effect on wound healing.

In a specific embodiment, a compound identified in the assays described herein can be used to assess the function of a complex of the invention or a component of a complex of the invention in different cellular contexts and/or under different biological conditions. For example, cells obtained from different pathological tissues can be contacted with a compound identified in the assays of the invention to test the function of a complex of the invention in such cells.

In even other embodiments, a compound identified in the assays of the invention can be used to modulate expression of a recombinant protein in a cell. For example, a compound that increases the function of human tRNA splicing endonuclease and/or 3' end pre-mRNA endonuclease can be used to enhance the expression of a recombinant protein in a cell.

The structure of the compounds identified in the assays described herein that modulate the expression of a component of a complex of the invention, the formation of a complex of the invention, the nucleolytic activity of a complex of the invention (e.g., the pre-tRNA splicing endonuclease activity, the 3' end pre-mRNA endonuclease activity, the pre-tRNA cleavage activity of a complex of the invention, and/or the pre-ribosomal RNA cleavage activity of a complex of the invention) can be determined utilizing assays well-known to one of skill in the art or described herein. The methods used will depend, in part, on the nature of the library screened. For example, assays or microarrays of compounds, each having an address or identifier, may be deconvoluted, e.g., by cross-referencing the positive sample to an original compound list that was applied to the individual test assays. Alternatively, the structure of the compounds identified herein may be determined using mass spectrometry, nuclear magnetic resonance ("NMR"), circular dichroism, X ray crystallography, or vibrational spectroscopy.

The invention encompasses the use of the compounds that inhibit or reduce the expression of a component of a complex of the invention, the formation of a complex of the invention, the RNA-nucleolytic activity of a complex of the invention (the pre-tRNA splicing endonuclease activity, the 3' end pre-mRNA endonuclease activity, the pre-tRNA cleavage activity of a complex of the invention, and/or the pre-ribosomal RNA cleavage activity of a complex of the invention) for treatment, management or amelioration of a proliferative disorder or a symptom thereof, or a disorder characterized by, associated with or caused by increased RNA-nucleolytic activity (e.g., the pre-tRNA splicing endonuclease activity, the 3' end pre-mRNA endonuclease activity, the pre-tRNA cleavage activity of a complex of the invention, and/or the pre-ribosomal RNA cleavage activity of a complex of the invention) or a symptom thereof. The invention also encompasses the use of compounds that stimulate or enhance the expression of a component of a complex of the invention, the formation of a complex of the invention, the RNA-nucleolytic activity of a complex of the invention (the pre-tRNA splicing endonuclease activity, the 3' end pre-mRNA endonuclease activity, the pre-tRNA cleavage activity of a complex of the invention, and/or the pre-ribosomal RNA cleavage activity of a complex of the invention) for treatment, management or amelioration of a disorder characterized by, associated with or caused by decreased RNA-nucleolytic activity (e.g., the pre-tRNA splicing endonuclease activity, the 3' end pre-mRNA endonuclease activity, the pre-tRNA cleavage activity of a complex of the invention, and/or the pre-ribosomal RNA cleavage activity of a complex of the invention) or a symptom thereof. The invention also encompasses the use of the compounds that stimulate or enhance the expression of a component of a complex of the invention, the formation of a complex of the invention, the nucleolytic activity of a complex of the invention, (e.g., the pre-tRNA splicing endonuclease activity, the 3' end pre-mRNA endonuclease activity, the pre-tRNA cleavage activity of a complex of the invention, and/or the pre-ribosomal RNA cleavage activity of a complex of the invention) for augmenting wound healing in a subject.

The invention provides compositions comprising a carrier and one of the following or a combination of two or more of the following: (i) a component of a complex of the invention; (ii) a complex of the invention, (iii) an antibody or a fragment thereof that immunospecifically binds to a component of a complex of the invention, or a complex of the invention, (iv) a compound that modulates the expression of a component of a complex of the invention, (v) a compound that modulates the formation of a complex of the invention, (vi) a compound that modulates the endonuclease activity (e.g., tRNA splicing endonuclease activity and/or 3' end pre-mRNA endonuclease activity) of a complex of the invention, (vii) a compound that modulates the pre-tRNA cleavage activity of a complex of the invention, and/or (viii) a compound that modulates pre-ribosomal RNA cleavage activity of a complex of the invention. The compositions may further comprise one or more other prophylactic or therapeutic agents. In a preferred embodiment, the compositions are pharmaceutical compositions. In accordance with this embodiment, the pharmaceutical compositions are preferably sterile and in suitable form for the intended method of administration or use. The invention encompasses the use of the compositions of the invention in the prevention, treatment, management or amelioration of a disorder described herein or a symptom thereof.

The invention also provides methods for detecting, diagnosing or monitoring a proliferative disorder or a disorder associated with, characterized by or caused by abnormal pre-tRNA processing and/or 3' end pre-mRNA processing utilizing an antibody that immunospecifically binds to a complex of the invention or a component thereof, or a compound identified in accordance with the methods of the invention that specifically binds to a complex of the invention or a component thereof. The invention also provides methods for detecting, diagnosing or monitoring a proliferative disorder or a disorder associated with, characterized by or caused by abnormal pre-tRNA processing and/or 3' end pre-mRNA processing by comparing the RNA-nucleolytic activity of a complex purified from cells or a tissue sample from a subject with such a disorder or suspected of having such disorder to the RNA-nucleolytic activity of a control, e.g., a complex purified from normal, non-cancerous cells or a tissue sample, using an assay well-known to one of skill in the art or described herein. The invention further provides methods for detecting, diagnosing or monitoring a proliferative disorder or a disorder associated with, characterized by or caused by abnormal pre-tRNA processing and/or 3' end pre-mRNA processing by comparing the structure of a complex of the invention purified from cells or a tissue sample from a subject (e.g., a subject with such a disorder or suspected of having such a disorder) to the structure of a control, e.g., a complex of the invention purified from normal, non-cancerous cells or a tissue sample, using an assay well-known to one of skill in the art (e.g., circular dichroism and nuclear magnetic resonance).

The invention also provides a method for modifying protein expression in a cell, the method comprising expressing in the cell at least one component of a complex of the invention. In more specific embodiments, all components of a complex of the invention and/or a fusion complex of the invention are expressed in a cell using recombinant DNA technology. The component or the complex can be expressed using an inducible, a constitutive or a tissue-specific promoter, e.g., a promoter that supports the overexpression of the component or the complex. In certain embodiments, the component of the complex or the fusion complex is mutated to be more active or less active (i.e., has a higher or lower, respectively, complex-forming activity, or has a higher or lower, respectively, RNA-nucleolytic activity) than the wild-type component or complex.

In certain embodiments of the invention, a complex of the invention is used to cleave an mRNA or pre-mRNA molecule containing a pre-mature stop codon. In certain, more specific, embodiments of the invention, a complex of the invention is used to cleave an mRNA or pre-mRNA molecule at or in the vicinity of a pre-mature stop codon. Without being bound by theory, a complex of the invention cleaves an mRNA or a pre-mRNA molecule at or in the vicinity of a pre-mature stop codon. In certain embodiments, the complex of the invention cleaves an mRNA or a pre-mRNA molecule within 500, 400, 300, 200, 100 or 50 nucleotides of the pre-mature stop codon. In certain embodiments, the complex of the invention cleaves an mRNA or a pre-mRNA molecule within 1 to 50, 1 to 100, 1 to 250, 1 to 500, 10 to 50, 10 to 100, 25 to 100, 50 to 100, 50 to 250, 50 to 500, 100 to 500, or 250 to 500 nucleotides of the pre-mature stop codon.

In certain embodiments of the invention, a complex of the invention is used to identify pre-mature stop codons in an mRNA or pre-mRNA molecule. In certain embodiments, the complex of the invention cleaves an mRNA or a pre-mRNA molecule within 500, 400, 300, 200, 100 or 50 nucleotides of the pre-mature stop codon. In certain embodiments, the complex of the invention cleaves an mRNA or a pre-mRNA molecule within 1 to 50, 1 to 100, 1 to 250, 1 to 500, 10 to 50, 10 to 100, 25 to 100, 50 to 100, 50 to 250, 50 to 500, 100 to 500, or 250 to 500 nucleotides of the pre-mature stop codon.

To identify the pre-mature stop codon, an mRNA or pre-mRNA of interest is incubated with a complex of the invention under conditions conducive to cleavage of the mRNA or pre-mRNA by the complex. Once cleavage occurred, the cleavage products are analyzed to determine the location of the cleavage site. The location of the cleavage site can be determined by any method known to the skilled artisan, such as, but not limited to Northern blot analysis.

In certain embodiments, the complexes of the invention can be used to identify modulators of cleavage of pre-mature stop codons by a complex of the invention. In certain embodiments, a complex of the invention is incubated with an mRNA or pre-mRNA of interest under conditions conducive to cleavage of the mRNA or pre-mRNA by the complex in the presence of a compound, wherein the mRNA or pre-mRNA is known to have a pre-mature stop codon. If the compound increases the amount of cleavage product generated, the compound is identified as an activator of the pre-mature stop codon cleavage activity of a complex of the invention. If the compound decreases the amount of cleavage product generated, the compound is identified as an inhibitor of the pre-mature stop codon cleavage activity of a complex of the invention.

A method of identifying a compound that modulates the stability of a complex, wherein the method comprises the following steps (a) incubating a complex of the invention in the presence of a compound under conditions conducive to maintaining the complex; and (b) determining the amount of the complex, wherein a difference in the amount of the complex determined in step (b) relative to the amount of the complex determined in the absence of the compound indicates that the compound modulates the stability of the complex.

The invention provides a method of identifying a therapeutic agent for the treatment or prevention of cancer, or amelioration of a symptom thereof, said method comprising: contacting a member of a library of compounds with a cell; measuring the amount of a complex of the invention formed in the cell; wherein if a compound that reduces the amount of the complex relative to the amount of the complex in the absence of said compound, then contacting the compound with a cancer cell or a neoplastic cell and detecting the proliferation of said cancer cell or neoplastic cell, so that if the compound reduces or inhibits the proliferation of the cancer cell or neoplastic cell, the compound is identified as an antiproliferative compound. The invention further provides a method of identifying a therapeutic agent for the treatment or prevention of cancer, or amelioration of a symptom thereof, said method comprising: contacting a member of a library of compounds with a complex of the invention and a nucleic acid comprising a reporter gene, wherein the reporter gene comprises a tRNA intron and wherein all factors required for gene expression are present; and detecting the expression of said reporter gene; wherein if a compound reduces the expression of the reporter gene relative to the expression of the reporter gene in the absence of said compound, then contacting the compound with a cancer cell or a neoplastic cell and detecting the proliferation of said cancer cell or neoplastic cell, so that if the compound reduces or inhibits the proliferation of the cancer cell or neoplastic cell, the compound is identified as an antiproliferative compound. The invention further provides a method of identifying a therapeutic agent for the treatment or prevention of cancer, or amelioration of a symptom thereof, said method comprising: contacting a member of a library of compounds with a complex of the invention and a nucleic acid comprising a reporter gene and a 3' end pre-mRNA cleavage site, wherein the reporter gene is located 3' of the 3' end pre-mRNA cleavage site and wherein all factors required for gene expression are present; and detecting the expression of said reporter gene; wherein if a compound reduces the expression of the reporter gene relative to the expression of the reporter gene in the absence of said compound, then contacting the compound with a cancer cell or a neoplastic cell and detecting the proliferation of said cancer cell or neoplastic cell, so that if the compound reduces or inhibits the proliferation of the cancer cell or neoplastic cell, the compound is identified as an antiproliferative compound. The method may further comprise testing said compound in an animal model for cancer, wherein said testing comprises administering said compound to said animal model and verifying that the compound is effective in reducing the proliferation or spread of cancer cells in said animal model. The method may further comprise determining the cytotoxic activity of the compound. The method may further comprise determining the cytostatic activity of the compound.

3.1 TERMINOLOGY

As used herein, the terms "antibody" and "antibodies" refer to monoclonal antibodies, multispecific antibodies, human antibodies, humanized antibodies, camelised antibodies, chimeric antibodies, single-chain Fvs (scFv), single chain antibodies, single domain antibodies, Fab fragments, F(ab) fragments, disulfide-linked Fvs (sdFv), and anti-idiotypic (anti-Id) antibodies, and epitope-binding fragments of any of the above. In particular, antibodies include immunoglobulin molecules and immunologically active fragments of immunoglobulin molecules, i.e., molecules that contain an antigen binding site. Immunoglobulin molecules can be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass.

As used herein, the term "compound" refers to any agent or complex that is being tested for its ability to modulate the RNA-nucleolytic activity of a complex of the invention (e.g., the pre-tRNA splicing endonuclease activity, the 3' end pre-mRNA endonuclease activity, the pre-tRNA cleavage activity of a complex of the invention, and/or the pre-ribosomal RNA cleavage activity of a complex of the invention), has been identified as modulating RNA-nucleolytic activity of a complex of the invention, has been identified as modulating the formation of a complex of the invention, or has been identified as modulating the expression of a component of a complex of the invention. The term "compound" includes, but is not limited to, small molecules, antibodies and fragments thereof, and double-stranded and single-stranded nucleic acids. The RNA-nucleolytic activity of a complex of the invention can be, inter alia, tRNA splicing endonuclease, 3' end pre-mRNA cleavage endonuclease, pre-tRNA cleavage, or rRNA cleavage.

As used herein, the term "derivative" in the context of proteinaceous agent (e.g., proteins, polypeptides, peptides, and antibodies) refers to a proteinaceous agent that comprises an amino acid sequence which has been altered by the introduction of amino acid residue substitutions, deletions, and/or additions. The term "derivative" as used herein also refers to a proteinaceous agent which has been modified, i.e., by the covalent attachment of any type of molecule to the proteinaceous agent. For example, but not by way of limitation, an antibody may be modified, e.g., by glycosylation, acetylation, pegylation, phosphorylation, amidation, derivatization by known protecting/blocking groups, proteolytic cleavage, linkage to a cellular ligand or other protein, etc. A derivative of a proteinaceous agent may be produced by chemical modifications using techniques known to those of skill in the art, including, but not limited to specific chemical cleavage, acetylation, formylation, metabolic synthesis in the presence of tunicamycin, etc. Further, a derivative of a proteinaceous agent may contain one or more non-classical amino acids. A derivative of a proteinaceous agent possesses a similar or identical function as the proteinaceous agent from which it was derived, e.g., participates in a complex with RNA-nucleolytic activity. The term "derivative" in the context of a proteinaceous agent also refers to a proteinaceous agent that possesses a similar or identical function as a second proteinaceous agent (i.e., the proteinaceaous agent from which the derivative was derived) but does not necessarily comprise a similar or identical amino acid sequence of the second proteinaceous agent, or possess a similar or identical structure of the second proteinaceous agent. A proteinaceous agent that has a similar amino acid sequence refers to a second proteinaceous agent that satisfies at least one of the following: (a) a proteinaceous agent having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the amino acid sequence of a second proteinaceous agent; (b) a proteinaceous agent encoded by a nucleotide sequence that hybridizes under stringent conditions to a nucleotide sequence encoding a second proteinaceous agent of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino acid residues, at least 70 contiguous amino acid residues, at least 80 contiguous amino acid residues, at least 90 contiguous amino acid residues, at least 100 contiguous amino acid residues, at least 125 contiguous amino acid residues, or at least 150 contiguous amino acid residues; and (c) a proteinaceous agent encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the nucleotide sequence encoding a second proteinaceous agent. A proteinaceous agent with similar structure to a second proteinaceous agent refers to a proteinaceous agent that has a similar secondary, tertiary or quaternary structure to the second proteinaceous agent. The structure of a proteinaceous agent can be determined by methods known to those skilled in the art, including but not limited to, peptide sequencing, X-ray crystallography, nuclear magnetic resonance, circular dichroism, and crystallographic electron microscopy. In a specific embodiment, a derivative is a functionally active derivative.

To determine the percent identity of the amino acid sequence of a derivative to the amino acid sequence of the proteinaceaous agent from which the derivative is derived or to compare the nucleic acid sequences encoding the derivative and the proteinaceaous agent from which the derivative is derived, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions×100%). In one embodiment, the two sequences are the same length. The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A.

87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present invention. BLAST protein searches can be performed with the XBLAST program parameters set, e.g., to score-50, wordlength=3 to obtain amino acid sequences homologous to a protein molecule of the present invention. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). Another preferred, non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

As used herein, the terms "disorder" and "disease" are to refer to a condition in a subject (e.g., a proliferative disorder or a disorder characterized by, associated with or caused by abnormal RNA-nucleolytic activity).

As used herein, the term "effective amount" in the context of a proliferative disorder refers to the amount of a therapy (e.g., a compound, a complex of the invention, a component of a complex of the invention, a nucleic acid encoding a component of a complex of the invention, a nucleic acid that inhibits the expression of a component of a complex of the invention, an antibody or a fragment thereof that immunospecifically binds to a complex of the invention, or an antibody or a fragment thereof that immunospecifically binds to a component of a complex of the invention), which is sufficient to reduce or ameliorate the progression, severity and/or duration of a proliferative disorder or one or more symptoms thereof, prevent the development, recurrence or onset of a proliferative disorder or one or more symptoms thereof, prevent the advancement of a proliferative disorder or one or more symptoms thereof, or enhance or improve the therapeutic(s) effect(s) of another therapy. An "effective amount" in the context of a disorder characterized by, associated with or caused by abnormal RNA-nucleolytic activity refers to the amount of a therapy (e.g., a compound, a complex of the invention, a component of a complex of the invention, a nucleic acid encoding a component of a complex of the invention, a nucleic acid that inhibits the expression of a component of a complex of the invention, an antibody or a fragment thereof that immunospecifically binds to a complex of the invention, or an antibody or a fragment thereof that immunospecifically binds to a component of a complex of the invention), which is sufficient to reduce or ameliorate the progression, severity and/or duration of a disorder characterized by, associated with or caused by abnormal RNA-nucleolytic activity or one or more symptoms thereof, prevent the development, recurrence or onset of a disorder characterized by, associated with or caused by abnormal RNA-nucleolytic activity or one or more symptoms thereof, prevent the advancement of a disorder characterized by, associated with or caused by abnormal RNA-nucleolytic activity or one or more symptoms thereof, or enhance or improve the therapeutic(s) effect(s) of another therapy. As used herein, the term "effective amount" in the context of wound healing refers to the amount of a therapy (e.g., a compound, a complex of the invention, a component of a complex of the invention, a nucleic acid encoding a component of a complex of the invention, a nucleic acid that inhibits the expression of a component of a complex of the invention, an antibody or a fragment thereof that immunospecifically binds to a complex of the invention, or an antibody or a fragment thereof that immunospecifically binds to a component of a complex of the invention), which is sufficient to reduce or ameliorate the progression, severity and/or duration of a wound (e.g., a wound caused by an injury) or one or more symptoms thereof, prevent the development, recurrence or onset of a wound, a condition associated with a wound, or one or more symptoms thereof, prevent the advancement of a condition associated with a wound or one or more symptoms thereof, or enhance or improve the therapeutic(s) effect(s) of another therapy.

As used herein, the term "fluorescent acceptor moiety" refers to a fluorescent compound that absorbs energy from a fluorescent donor moiety and re-emits the transferred energy as fluorescence. Examples of fluorescent acceptor moieties include, but are not limited to, coumarins and related fluorophores, xanthenes (e.g., fluoresceins, rhodols, and rhodamines), resorufins, cyanines, difluoroboradiazindacenes and phthalocyanines.

As used herein, the term "fluorescent donor moiety" refers to a fluorescent compound that can absorb energy and is capable of transferring the energy to an acceptor, such as another fluorescent compound. Examples of fluorescent donor moieties include, but are not limited to, coumarins and related dyes, xanthene dyes (e.g., fluoresceins, rhodols and rhodamines), resorufins, cyanine dyes, bimanes, acridines, isoindoles, dansyl dyes, aminophthalic hydrazides (e.g., luminol and isoluminol derivatives), aminophthalimides, aminonaphthalimides, aminobenzofurans, aminoquinolines, dicyanohydroquinones, fluorescent europium, terbium complexes and related compounds.

As used herein, the term "fluorophore" refers to a chromophore that fluoresces.

As used herein, the term "fragment" refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of another polypeptide or protein. In a specific embodiment, a fragment of a protein or polypeptide retains at least one function of the protein or polypeptide.

As used herein, the term "functionally active derivative" in the context of proteinaceous agent is a derivative of a proteinaceous agent that retains at least one function of the polypeptide or protein from which the derivative is derived. In a specific embodiment, a functionally active derivative retains at least two, three, four, or five functions of the protein or polypeptide from which the derivative is derived. In a specific embodiment, the functionally active derivative retains the ability of the protein from which it is derived to bind to a specific third protein or form a specific complex with RNA-nucleolytic activity, e.g., a complex of the invention. In another specific embodiment, the functionally active derivative retains the RNA-nucleolytic activity of protein from which the derivative is derived.

As used herein, the term "functionally active fragment" refers to a fragment of a polypeptide or protein that retains at least one function of the second, different polypeptide or protein. In a specific embodiment, a fragment of a polypeptide or protein retains at least two, three, four, or five functions of the protein or polypeptide. In a specific embodiment, the functionally active fragment retains the ability of the second protein to bind to a specific third protein or form a specific complex. In another specific embodiment, the functionally active fragment retains the RNA-nucleolytic activity of the second protein.

As used herein, the term "fusion complex" means a protein complex, wherein the protein components of the complex are linked to each other via a peptide bond or other covalent linkage.

As used herein, the term "fusion protein" refers to a polypeptide or protein that comprises an amino acid sequence of a first protein or polypeptide or functional fragment, analog or derivative thereof, and an amino acid sequence of a heterologous protein, polypeptide, or peptide (i.e., a second protein or polypeptide or fragment, analog or derivative thereof different than the first protein or fragment, analog or derivative thereof). In other words, a fusion protein comprises an amino acid sequence of a first protein, polypeptide or peptide and an amino acid sequence that is not normally associated with or a part of the first protein.

As used herein, the term "host cell" includes a particular subject cell transfected or transformed with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

As used herein, the term "hybridizes under stringent conditions" describes conditions for hybridization and washing under which nucleotide sequences at least 30% (preferably, 35%, 40%, 45%, 50%, 55%, 60%, 65%, 70%, 75%, 80%, 85%, 90%, 95%, 98%, 99% or 99.5%) identical to each other typically remain hybridized to each other. Such stringent conditions are known to those skilled in the art and can be found in *Current Protocols in Molecular Biology*, John Wiley & Sons, N.Y. (1989), 6.3.1-6.3.6. In one, non-limiting example stringent hybridization conditions are hybridization at 6× sodium chloride/sodium citrate (SSC) at about 45° C., followed by one or more washes in 0.1×SSC, 0.2% SDS at about 68 C. In a preferred, non-limiting example stringent hybridization conditions are hybridization in 6×SSC at about 45° C., followed by one or more washes in 0.2×SSC, 0.1% SDS at 50-65° C. (i.e., one or more washes at 50° C., 55° C., 60° C. or 65° C.). It is understood that the nucleic acids of the invention do not include nucleic acid molecules that hybridize under these conditions solely to a nucleotide sequence consisting of only A or T nucleotides. In a specific embodiment, high stringency conditions comprise hybridization in a buffer consisting of 6×SSC, 50 mM Tris-HCl (pH=7.5), 1 mM EDTA, 0.02% PVP, 0.02% Ficoll, 0.02% BSA and 100 µg/ml denatured salmon sperm DNA, for 48 hours at 65° C., washing in a buffer consisting of 2×SSC, 0.01% PVP, 0.01% Ficoll and 0.01% BSA, for 45 minutes at 37° C., and washing in a buffer consisting of 0.1×SSC, for 45 minutes at 50° C. For an exemplary method for determining stringency conditions, see section 4.3.1.

As used herein, the term "immunospecifically binds" and analogous terms refer to peptides, polypeptides, proteins, fusion proteins and antibodies or fragments thereof that specifically bind to an antigen or a fragment and do not specifically bind to other antigens (e.g., as determined via standard immunoassays, such as, but not limited to, an ELISA). A peptide, polypeptide, protein, or antibody that immunospecifically binds to an antigen may bind to other peptides, polypeptides, or proteins with lower affinity as determined by, e.g., immunoassays, BIAcore, or other assays known in the art. Antibodies or fragments that immunospecifically bind to an antigen may be cross-reactive with related antigens. Preferably, antibodies or fragments that immunospecifically bind to an antigen do not cross-react with other antigens.

As used herein, the term "in combination" refers to the use of more than one therapy (e.g., prophylactic and/or therapeutic agents). The use of the term "in combination" does not restrict the order in which therapies (e.g., prophylactic and/or therapeutic agents) are administered to a subject with a disorder. A first therapy (e.g., a prophylactic or therapeutic agent such as a compound identified in accordance with the methods of the invention) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent such as a chemotherapeutic agent or a TNF-α antagonist) to a subject with a disorder.

As used herein, the term "library" refers to a plurality of compounds. A library can be a combinatorial library, e.g., a collection of compounds synthesized using combinatorial chemistry techniques, or a collection of unique chemicals of low molecular weight (less than 1000 daltons) that each occupy a unique three-dimensional space. In a specific embodiment, a library is composed of at least 50; 100; 150; 200; 250; 500; 750; 1,000; 1,250; 1,500; 1,750; 2,000; 2,500; 5,000; 7,500; 10,000; 20,000; 30,000; 40,000; or at least 50,000 different compounds. In a specific embodiment, a library is composed of at most 50; 100; 150; 200; 250; 500; 750; 1,000; 1,250; 1,500; 1,750; 2,000; 2,500; 5,000; 7,500; 10,000; 20,000; 30,000; 40,000; or at most 50,000 different compounds. In a specific embodiment, a library is composed of between 10 and 100; 10 and 150; 100 and 200; 100 and 250; 100 and 500; 100 and 750; 500 and 1,000; 500 and 1,250; 500 and 1,500; 500 and 1,750; 1,000 and 2,000; 1,000 and 2,500; 2,000 and 5,000; 2,000 and 7,500; 2,000 and 10,000; 5,000 and 20,000; 10,000 and 30,000; 10,000 and 40,000; between 20,000 and 50,000 different compounds.

As used herein, the terms "manage", "managing" and "management" refer to the beneficial effects that a subject derives from a therapy (e.g., administration of a prophylactic or therapeutic agent) which does not result in a cure of the disorder. In certain embodiments, a subject is administered one or more therapies to "manage" a disease or disorder so as to prevent the progression or worsening of the disease or disorder.

As used herein, the terms "non-responsive" and refractory" describe patients treated with a currently available therapy (e.g., prophylactic or therapeutic agent) for a disorder (e.g., cancer), which is not clinically adequate to relieve the disorder or one or more symptoms associated with such disorder. Typically, such patients suffer from severe, persistently active disease and require additional therapy to ameliorate the symptoms associated with their disorder.

As used herein, the term "ORF" refers to the open reading frame of a mRNA, i.e., the region of the mRNA that is translated into protein.

As used herein, the phrase "pharmaceutically acceptable salt(s)," includes, but is not limited to, salts of acidic or basic groups that may be present in compounds identified using the methods of the present invention. Compounds that are basic in nature are capable of forming a wide variety of salts with various inorganic and organic acids. The acids that can be used to prepare pharmaceutically acceptable acid addition salts of such basic compounds are those that form non-toxic acid addition salts, i.e., salts containing pharmacologically acceptable anions, including but not limited to sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds that include an amino moiety may form pharmaceutically acceptable salts with various amino acids, in addition to the acids mentioned above. Compounds that are acidic in nature are capable of forming base salts with various pharmacologically acceptable cations. Examples of such salts include alkali metal or alkaline earth metal salts and, particularly, calcium, magnesium, sodium lithium, zinc, potassium, and iron salts.

As used herein, the terms "prevent", "preventing" and "prevention" refer to the prevention of the development, recurrence or onset of a disorder or one or more symptoms thereof resulting from the administration of a therapy or the administration of a combination of therapies.

As used herein, the term "previously determined reference range" refers to a reference range for the readout of a particular assay. In a specific embodiment, the term refers to a reference range for the expression and/or the activity of a reporter gene by a particular cell or in a particular cell-free extract. Each laboratory will establish its own reference range for each particular assay, each cell type and each cell-free extract. In a preferred embodiment, at least one positive control and at least one negative control are included in each batch of compounds analyzed.

As used herein, the terms "prophylactic agent" and "prophylactic agents" refer to any agent(s) which can be used in the prevention of a disorder. In certain embodiments, the term "prophylactic agent" refers to a compound identified in the screening assays described herein, a complex of the invention, an antibody or a fragment thereof that immunospecifically binds to a complex of the invention, Sen2ΔEx8 protein, a nucleic acid encoding Sen2ΔEx8, an antibody or a fragment thereof that immunospecifically binds to Sen2ΔEx8, a component of a complex of the invention or a nucleic acid encoding a component of a complex of the invention or a nucleic acid that prevents or reduces the expression of a component of a complex of the invention (e.g., an antisense nucleic acid or using RNAi). In certain other embodiments, the term "prophylactic agent" refers to an agent other than a compound identified in the screening assays described herein, a complex of the invention, an antibody or a fragment thereof that immunospecifically binds to a complex of the invention, Sen2ΔEx8 protein, a nucleic acid encoding Sen2ΔEx8, an antibody or a fragment thereof that immunospecifically binds to Sen2ΔEx8, a component of a complex of the invention or a nucleic acid encoding a component of a complex of the invention or a nucleic acid that prevents or reduces the expression of a component of a complex of the invention (e.g., an antisense nucleic acid or using RNAi), which is known to be useful for, or has been or is currently being used to prevent or impede the onset, development and/or progression of a disorder or one or more symptoms thereof. A "prophylactic agent" in the context of a disorder characterized by, associated with or caused by abnormal RNA-nucleolytic activity refers to the amount of a compound, a complex of the invention, a component of a complex of the invention, a nucleic acid encoding a component of a complex of the invention, a nucleic acid that inhibits the expression of a component of a complex of the invention, an antibody or a fragment thereof that immunospecifically binds to a complex of the invention, or an antibody or a fragment thereof that immunospecifically binds to a component of a complex of the invention, which can prevent or reduce the risk of a disorder characterized by, associated with or caused by abnormal RNA-nucleolytic activity or one or more symptoms thereof. As used herein, the term "prophylactic agent" in the context of wound healing refers to a compound, a complex of the invention, a component of a complex of the invention, a nucleic acid encoding a component of a complex of the invention, a nucleic acid that inhibits the expression of a component of a complex of the invention, an antibody or a fragment thereof that immunospecifically binds to a complex of the invention, or an antibody or a fragment thereof that immunospecifically binds to a component of a complex of the invention, which can prevent the development, recurrence or onset of a wound, a condition associated with a wound, or one or more symptoms thereof, prevent the advancement of a condition associated with a wound or one or more symptoms thereof, or enhance or improve the therapeutic(s) effect(s) of another therapy.

As used herein, the phrase "prophylactically effective amount" refers to the amount of a therapy (e.g., a prophylactic agent, such as a compound identified by the methods of the invention, a complex of the invention, a component of a complex of the invention, a nucleic acid encoding a component of a complex of the invention, a nucleic acid that inhibits the expression of a component of a complex of the invention, an antibody or a fragment thereof that immunospecifically binds to a complex of the invention, or an antibody or a fragment thereof that immunospecifically binds to a component of a complex of the invention) which is sufficient to result in the prevention of the development, recurrence or onset of a disorder or one or more symptoms thereof.

As used herein, the term "purified" in the context of a compound other than a proteinaceous agent or a nucleic acid, e.g., a compound identified in accordance with the method of the invention, refers to a compound that is substantially free of chemical precursors or other chemicals when chemically synthesized. In a specific embodiment, the compound is 60%, preferably 65%, 70%, 75%, 80%, 85%, 90%, or 99% free of other, different compounds. In a preferred embodiment, a compound identified in accordance with the methods of the invention is purified.

Specifically, the term "purified," in the context of a proteinaceous agent (e.g., a peptide, polypeptide, or protein, such as a tRNA splicing endonuclease or subunit thereof) refers to a proteinaceous agent which is substantially free of cellular material or contaminating proteins from the cell or tissue source from which it is derived, or substantially free of chemical precursors or other chemicals when chemically synthesized. The language "substantially free of cellular material" includes preparations of a proteinaceous agent in which the proteinaceous agent is separated from cellular components of the cells from which it is purified or recombinantly produced. Thus, a proteinaceous agent or an agent that is substantially free of cellular material includes preparations of a proteinaceous agent having less than about 30%, 20%, 10%, or 5% (by dry weight) of heterologous protein, polypeptide, peptide, or antibody (also referred to as a "contaminating protein"). When the proteinaceous agent is recombinantly produced, it is also preferably substantially free of culture medium, i.e., culture medium represents less than about 20%, 10%, or 5% of the volume of the protein preparation. When the proteinaceous agent is produced by chemical synthesis, it is preferably substantially free of chemical precursors or other chemicals, i.e., it is separated from chemical precursors or other chemicals which are involved in the synthesis of the proteinaceous agent. Accordingly, such preparations of a proteinaceous agent have less than about 30%, 20%, 10%, 5% (by dry weight) of chemical precursors or compounds other than the proteinaceous agent of interest. Preferably, proteinaceous agents disclosed herein are purified.

As used herein, the term "purified" in the context of nucleic acid molecules refers to a nucleic acid molecule which is separated from other nucleic acid molecules which are present in the natural source of the nucleic acid molecule. Moreover, a "purified" nucleic acid molecule, such as a cDNA molecule, is preferably substantially free of other cellular material, or culture medium when produced by recombinant techniques, or substantially free of chemical precursors or other chemicals when chemically synthesized. In a specific embodiment, nucleic acid molecules are purified. In a preferred embodiment, a nucleic acid molecule encoding a component of a complex of the invention is purified.

As used herein, the term "quencher" refers to a molecule or a part of a compound that is capable of reducing the emission from a fluorescent moiety. Such reduction includes reducing the light after the time when a photon is normally emitted from a fluorescent moiety.

As used herein, "RNA-nucleolytic activity" refers to, but is not limited to, pre-tRNA splicing activity, 3' end pre-mRNA endonuclease activity, pre-tRNA cleavage activity and pre-ribosomal RNA cleavage activity.

As used herein, the term "small molecules" and analogous terms include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, organic or inorganic compounds having a molecular weight less than about 100 grams per mole, and salts, esters, and other pharmaceutically acceptable forms of such compounds. Salts, esters, and other pharmaceutically acceptable forms of such compounds are also encompassed.

As used herein, the term "specifically binds" and analogous terms in the context of compounds identified in accordance with the invention refers to refer compounds identified in accordance with the invention that bind to a complex of the invention or a protein component of a complex of the invention or a fragment of a protein component of a complex of the invention and do not bind to, or bind with lower affinity to, other complexes, proteins or polypeptides. The binding affinity can be determined by, e.g., immunoassays, BIAcore, or other assays known in the art. Compounds that specifically bind to a complex of the invention or a protein component of a complex of the invention or a fragment of a protein component of a complex of the invention may be cross-reactive with related proteins or polypeptides. Preferably, compounds that specifically bind to a complex of the invention or a protein component of a complex of the invention or a fragment of a protein component of a complex of the invention are not cross-reactive with related proteins or polypeptides.

As used herein, the terms "subject" and "patient" are used interchangeably herein. The terms "subject" and "subjects" refer to an animal, preferably a mammal including a non-primate (e.g., a cow, pig, horse, cat, dog, rat, and mouse) and a primate (e.g., a chimpanzee, a monkey such as a cynomolgous monkey, and a human), and more preferably a human. In one embodiment, the subject is refractory or non-responsive to current therapies for a proliferative disorder. In another embodiment, the subject is a farm animal (e.g., a horse, a cow, a pig, etc.) or a pet (e.g., a dog or a cat). In a preferred embodiment, the subject is a human.

As used herein, the phrase "a substrate for a human tRNA splicing endonuclease" refers to any nucleotide sequence recognized and excised by a human tRNA splicing endonuclease. For example, a nucleotide sequence comprising a bulge-helix-bulge structure or a mature domain of a precursor tRNA may be utilized as a substrate for a human tRNA splicing endonuclease in an assay described herein. A nucleotide sequence recognized and excised by a human tRNA splicing endonuclease may comprise 10 nucleotides, 15 nucleotides, 20 nucleotides, 25 nucleotides, 25 nucleotides, 30 nucleotides, 40 nucleotides, 45 nucleotides, 50 nucleotides, 55 nucleotides, 60 nucleotides, 65 nucleotides, 75 nucleotides, 100 nucleotides, 125 nucleotides, 150 nucleotides, or more. In a specific embodiment, the substrates for a tRNA splicing endonuclease utilized in the assays described herein comprise a tRNA intron. The substrate may comprise a mature domain or a bulge-helix-bulge conformation. In a preferred embodiment, the substrate comprises a mature domain of a precursor tRNA.

A substrate for a human tRNA endonuclease may be produced by any method well-known to one of skill in the art. For example, the substrate may be chemically synthesized using phosphoramidite or other solution or solid-phase methods. Detailed descriptions of the chemistry used to form polynucleotides by the phosphoramidite method are well known (see, e.g., Caruthers et al., U.S. Pat. Nos. 4,458,066 and 4,415,732; Caruthers et al., 1982, Genetic Engineering 4:1-17; *Users Manual Model* 392 and 394 *Polynucleotide Synthesizers*, 1990, pages 6-1 through 6-22, Applied Biosystems, Part No. 901237; Ojwang, et al., 1997, Biochemistry, 36:6033-6045). After synthesis, the substrate can be purified using standard techniques known to those skilled in the art (see Hwang et al., 1999, Proc. Natl. Acad. Sci. USA 96(23): 12997-13002 and references cited therein). Depending on the length of the substrate and the method of its synthesis, such purification techniques include, but are not limited to, reverse-phase high-performance liquid chromatography ("reverse-phase HPLC"), fast performance liquid chromatography ("FPLC"), and gel purification. In a specific embodiment, the substrates depicted in FIG. 1 are utilized in the assays described herein.

To generate the hybridized tRNA substrate depicted in FIG. 1, both strands of the hybridized substrate are transcribed separately and the two strands are subsequently hybridized by heating and cooling. For synthesis of the circularly permuted *tRNA* substrate, the RNA is transcribed from the 5' end in the intron (see FIG. 1C) to the 3' end in the intron.

As used herein, the phrase "a substrate for a human 3' end pre-mRNA endonuclease" refers to any nucleotide sequence recognized and excised by a human 3' end pre-mRNA endonuclease. For example, a nucleotide sequence comprising a hexanucleotide with the sequence AAUAAA upstream and a G/U-rich sequence element downstream of the cleavage site may be utilized as a substrate for 3' end pre-mRNA endonuclease in an assay described herein. A nucleotide sequence recognized and excised by a 3' end pre-mRNA endonuclease may comprise 10 nucleotides, 15 nucleotides, 20 nucleotides, 25 nucleotides, 25 nucleotides, 30 nucleotides, 40 nucleotides, 45 nucleotides, 50 nucleotides, 55 nucleotides, 60 nucleotides, 65 nucleotides, 75 nucleotides, 100 nucleotides, 125 nucleotides, 150 nucleotides, or more. In a specific embodiment, the substrates for 3' end pre-mRNA endonuclease utilized in the assays described herein comprise a cleavage and polyadenylation site.

As used herein, the term "synergistic" refers to a combination of a compound identified using one of the methods described herein (i.e., that modulates the activity of a complex of the invention), a complex of the invention, a component of a complex of the invention, an antibody or a fragment thereof that immunospecifically binds to a complex of the invention, an antibody or a fragment thereof that immunospecifically binds to a component of a complex of the invention, or a nucleic acid encoding a component of a complex of the invention, and another therapy (e.g., agent) which has been or is currently being used to prevent, treat, manage or ameliorate a disorder or a symptom thereof, which is more effective than the additive effects of the therapies. A synergistic effect of a combination of therapies (e.g., prophylactic or therapeutic agents) permits the use of lower dosages of one or more of the therapies and/or less frequent administration of said therapies to a subject with a disorder. The ability to utilize lower dosages of a therapy (e.g., a prophylactic or therapeutic agent) and/or to administer said therapy less frequently reduces the toxicity associated with the administration of said agent to a subject without reducing the efficacy of said therapies in the prevention, treatment, management or amelioration of a disorder or a symptom thereof. In addition, a synergistic effect can result in improved efficacy of therapies (e.g., agents) in the prevention, treatment, management or amelioration of a disorder or a symptom thereof. Finally, a synergistic effect of a combination of therapies (e.g., prophylactic or therapeutic agents) may avoid or reduce adverse or unwanted side effects associated with the use of either therapy alone.

As used herein, the terms "therapeutic agent" and "therapeutic agents" refer to any agent(s) which can be used in the prevention, treatment, management or amelioration of a disorder or a symptom thereof. In certain embodiments, the term "therapeutic agent" refers to a compound identified in the screening assays described herein, a complex of the invention, a component of a complex of the invention, an antibody or a fragment thereof that immunospecifically binds to a complex of the invention, an antibody or a fragment thereof that immunospecifically binds to a component of a complex of the invention, or a nucleic acid encoding a component of a complex of the invention or anti-sense or RNAi nucleic acid. In other embodiments, the term "therapeutic agent" refers to an agent other than a compound identified in the screening assays described herein which is known to be useful for, or has been or is currently being used to prevent, treat, manage or ameliorate a disorder or one or more symptoms thereof.

As used herein, the term "therapeutically effective amount" refers to that amount of a therapy (e.g., a therapeutic agent) sufficient to result in the amelioration of one or more symptoms of a disorder, prevent advancement of a disorder, cause regression of the disorder, or to enhance or improve the therapeutic effect(s) of another therapy (e.g., therapeutic agent). In a specific embodiment, with respect to the treatment of cancer, a therapeutically effective amount refers to the amount of a therapy (e.g., a therapeutic agent) that inhibits or reduces the proliferation of cancerous cells, inhibits or reduces the spread of tumor cells (metastasis), inhibits or reduces the onset, development or progression of one or more symptoms associated with cancer, or reduces the size of a tumor. Preferably, a therapeutically effective of a therapy (e.g., a therapeutic agent) reduces the proliferation of cancerous cells or the size of a tumor by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% relative to a control such as phosphate buffered saline ("PBS"). A "therapeutically effective amount" in the context of a disorder characterized by, associated with or caused by abnormal RNA-nucleolytic activity refers to the amount of a compound, a complex of the invention, a component of a complex of the invention, a nucleic acid encoding a component of a complex of the invention, a nucleic acid that inhibits the expression of a component of a complex of the invention, an antibody or a fragment thereof that immunospecifically binds to a complex of the invention, or an antibody or a fragment thereof that immunospecifically binds to a component of a complex of the invention, which is sufficient to reduce or ameliorate the progression, severity and/or duration of a disorder characterized by, associated with or caused by abnormal RNA-nucleolytic activity or one or more symptoms thereof, prevent the development, recurrence or onset of a disorder characterized by, associated with or caused by abnormal RNA-nucleolytic activity or one or more symptoms thereof, prevent the advancement of a disorder characterized by, associated with or caused by abnormal RNA-nucleolytic activity or one or more symptoms thereof, or enhance or improve the therapeutic(s) effect(s) of another therapy. As used herein, the term "therapeutically effective amount" in the context of wound healing refers to the amount of a compound, a complex of the invention, a component of a complex of the invention, a nucleic acid encoding a component of a complex of the invention, a nucleic acid that inhibits the expression of a component of a complex of the invention, an antibody or a fragment thereof that immunospecifically binds to a complex of the invention, or an antibody or a fragment thereof that immunospecifically binds to a component of a complex of the invention, which is sufficient to reduce or ameliorate the progression, severity and/or duration of a wound (e.g., a wound caused by an injury) or one or more symptoms thereof, prevent the development, recurrence or onset of a wound, a condition associated with a wound, or one or more symptoms thereof, prevent the advancement of a condition associated with a wound or one or more symptoms thereof, or enhance or improve the therapeutic(s) effect(s) of another therapy.

As used herein, the terms "treat", "treatment" and "treating" refer to the reduction or amelioration of the progression, severity and/or duration of a disorder or one or more symptoms thereof resulting from the administration of one or more therapies (e.g., compounds identified in accordance the methods of the invention, a complex of the invention, a component of a complex of the invention, an antibody or a fragment thereof that immunospecifically binds to a complex of the invention, an antibody or a fragment thereof that immunospecifically binds to a component of a complex of the invention, or a nucleic acid encoding a component of a complex of the invention, or a combination thereof and another therapy). In specific embodiments, such terms refer to the inhibition or reduction in the proliferation of cancerous cells, the inhibition or reduction the spread of tumor cells (metastasis), the inhibition or reduction in the onset, development or progression of one or more symptoms associated with cancer, or the reduction in the size of a tumor.

As used herein, the term "tRNA intron" refers to any nucleotide sequence recognized and excised by a human tRNA splicing endonuclease. In particular, the term "tRNA intron" refers to an intron typically found in a precursor tRNA.

As used herein, the term "tRNA splicing endonuclease" refers to the enzyme that is responsible for the recognition of the splice sites contained in precursor tRNA and the cleavage of the introns present in precursor tRNA. The archaeal tRNA splicing endonuclease recognizes the bulge-helix-bulge motif in archaeal precursor tRNA. The eukaryotic tRNA splicing endonuclease recognizes the splice sites contained in precursor tRNA by measuring the distance from the mature domain to the splice sites. The eukaryotic tRNA splicing endonuclease also has the capacity to recognize a bulge-helix-bulge motif contained in precursor tRNA. The yeast tRNA endonuclease is a heterotetramer comprising subunits having the molecular masses of 54 kDa (SEN54), 44 kDa (SEN2), 34 kDa (SEN 34), and 15 kDa (SEN 15). The human homologs of these factors and their GenBank accession numbers are set forth in Table 1.

As used herein, the terms "therapy" and "therapies" refer to any method, protocol and/or agent that can be used in the prevention, treatment, management or amelioration of a disease or disorder (e.g., a proliferative disorder or a condition associated with wound healing) or one or more symptoms thereof. In certain embodiments, such terms refer to chemotherapy, radiation therapy, surgery, supportive therapy and/or other therapies useful in the prevention, treatment, management or amelioration of a disease or disorder (e.g., a proliferative disorder or a condition associated with wound healing) or one or more symptoms thereof known to skilled medical personnel.

| Abbreviations | |
|---|---|
| CPSF | Cleavage-Polyadenylation Specificity Factor |
| $CFI_m$ | Cleavage Factor $I_m$ |
| $CFII_m$ | Cleavage Factor $II_m$ |
| CstF or CSTF | Cleavage Stimulation Factor |
| HTS | High Throughput Screen |
| FP | fluorescence polarization |
| FRET | Fluorescence Resonance Energy Transfer |
| HPLC | high-performance liquid chromatography |
| FPLC | fast performance liquid chromatography |
| FACS | Fluorescence activated cell sorter |

3.2 BRIEF DESCRIPTION OF THE DRAWINGS

FIG. 1: Substrates for HTS Fluorescent screening. The endogenous tRNA is shown in panel A; the hybridized tRNA substrate is shown in panel B; and the circularly permuted tRNA substrate is shown in panel C. The 5' ss designates the 5' splice site and 3' ss designates the 3' splice site.

Figure 2:
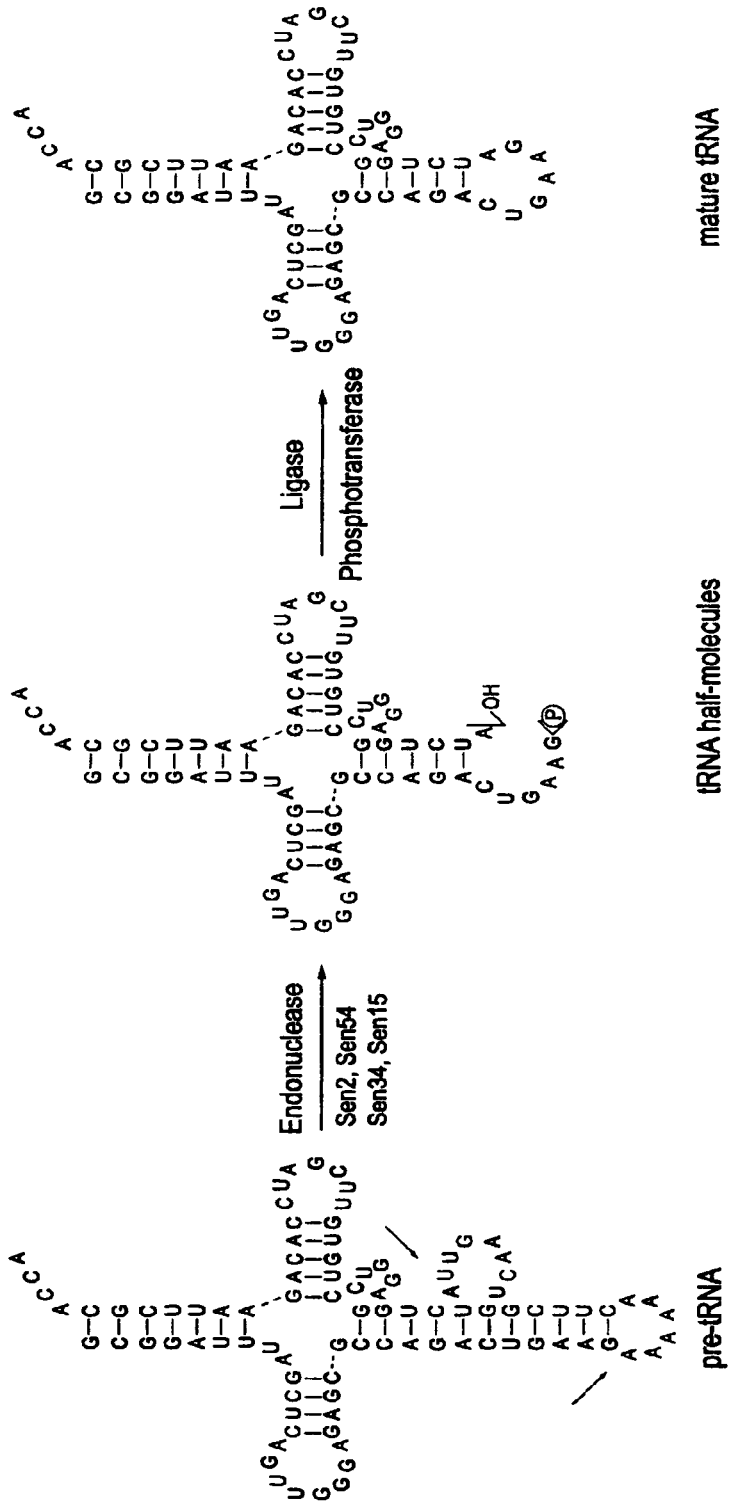

FIG. 2: Schematic representation of removal of introns from pre-tRNA in yeast. In yeast tRNA intron removal requires the function of three enzymes. In the first step a tRNA endonuclease recognizes and cleaves the precursor tRNA at the 5' and 3' splice sites. This enzyme is a heterotetramer composed of the Sen54, Sen2, Sen34 and Sen15 proteins. The product 5' and 3' exons are ligated by a tRNA ligase through a series of enzymatic steps which ultimately leads to joining of the two exons with a 2' phosphate at the splice junction. This unusual tRNA intermediate is then processed by a 2' phosphotransferase which transfers the 2' phosphate to an NAD acceptor yielding a mature tRNA.

Figure 3:
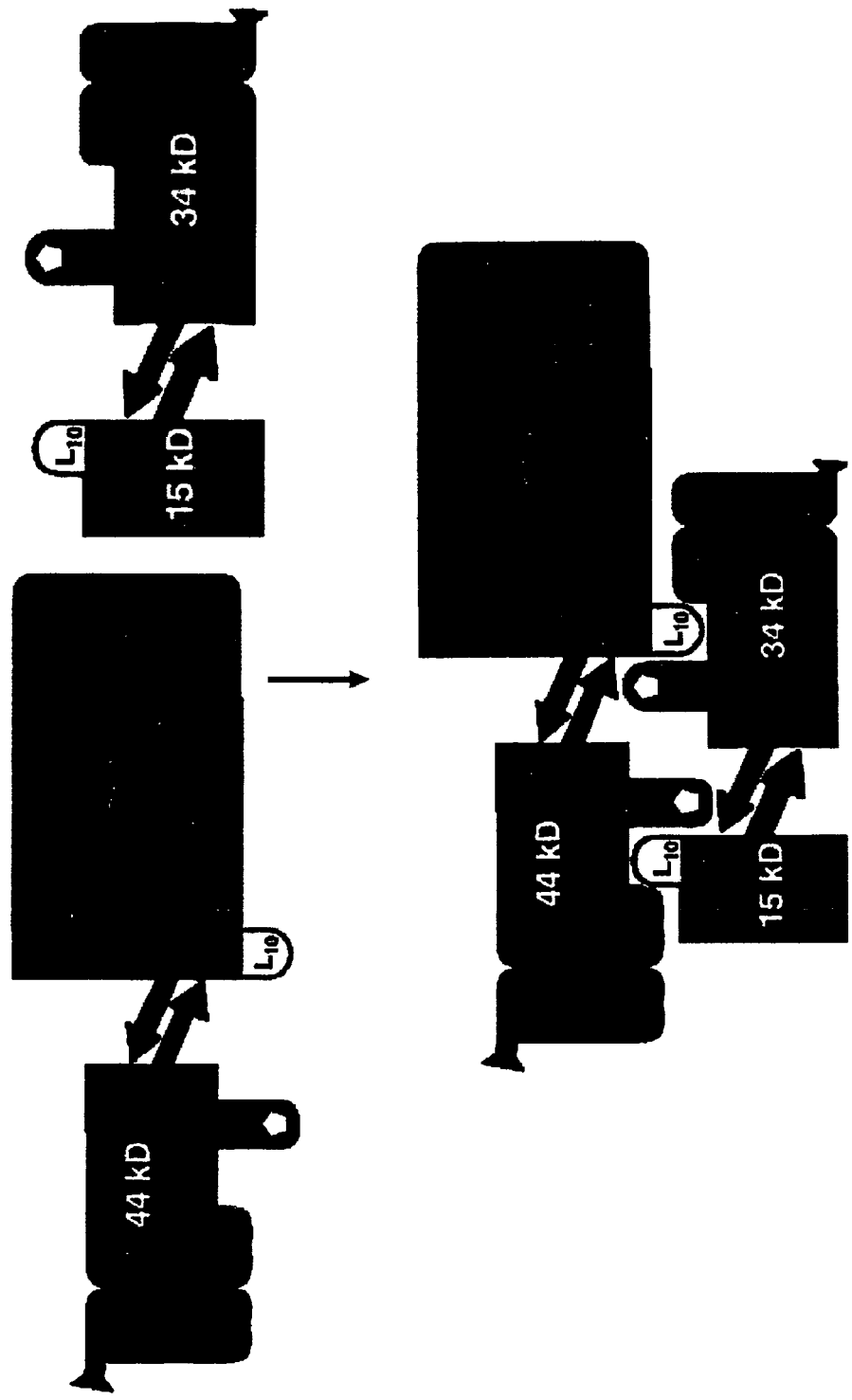

FIG. 3: Schematic Representation of Yeast tRNA Splicing Holoenzyme. Through structural Studies with the Archaeal enzyme and subsequent two-hybrid interaction experiments with the yeast subunits, a model for the interaction of the four subunits of the yeast tRNA endonuclease was proposed (Li et al., 1998 Science 280, 279-284). Dimerization of heterologous subunits Sen54 and Sen15 with active site subunits Sen2 and Sen34 respectively is achieved by the interaction of a conserved Beta sheet at the C-terminus each subunit. The active site containing dimers are then brought together through interaction of the conserved charged Loop L10 with a basic groove formed between the N and Cterminal domains in the two active site containing subunits.

Figure 4:
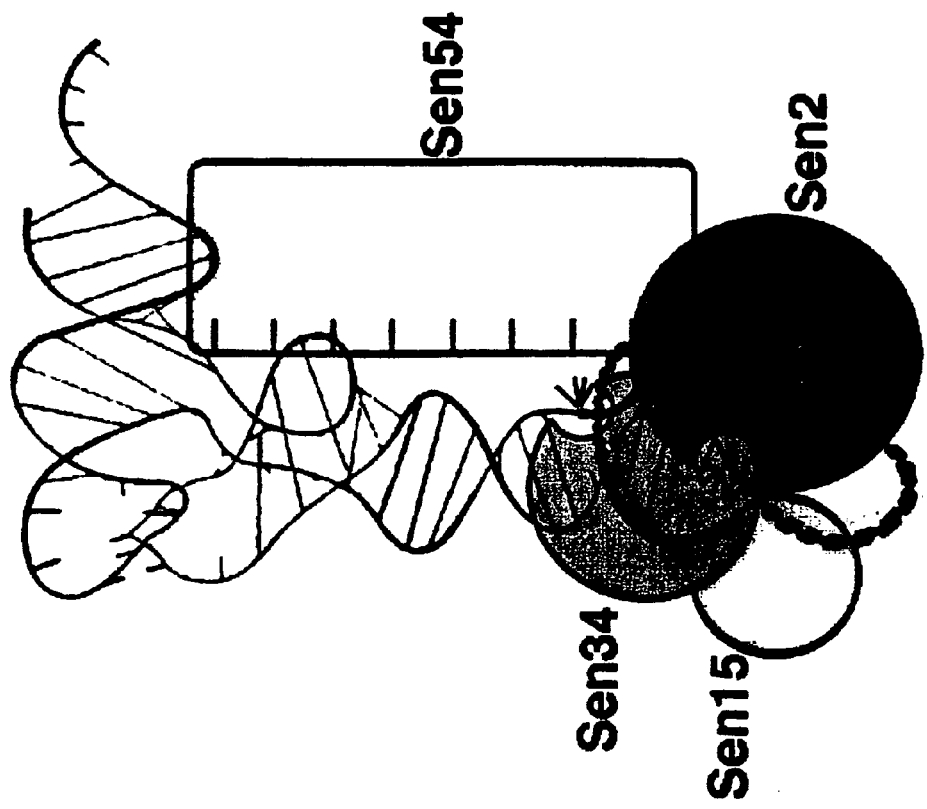

FIG. 4: Model for Cleavage of tRNA by the Yeast tRNA Endonuclease. Cleavage of tRNA occurs through catalysis of the 5' splice site by the active site contained in the Sen2 subunit and the 3' splice site by Sen34.

FIG. 5: Amino Acid Sequence Alignment of human (Hs) Sen2 (SEQ ID NO: 38) and HsSen2 var. (SEQ ID NO: 39) and the yeast *Saccaromyces* cerevisiae (ScSen2p (SEQ ID NO: 40)) tRNA splicing endonuclease Sen2 subunit. The boxed amino acid residues indicate the YRGGY (SEQ ID NO: 56) active site motif, the circled amino acid residue indicates the active site histidine, and the underlined amino acid residues indicate the yeast putative transmembrane domain.

FIGS. 6A,B. Sequence conservation between human and yeast tRNA endonuclease active site subunits Sen2 and Sen34. A. Comparison of Sen2 amino acid sequences in *Saccaromyces* cerevisiae (ScSen2 (SEQ ID NO: 41)), Schizosaccaromyces pombe (SpSen2 (SEQ ID NO: 42)) and *H. sapiens* (HsSen2 (SEQ ID NO: 57)). B. Comparison of Sen34 amino acid sequences in *S. cerevisiae* (ScSen34 (SEQ ID NO: 43)), *S. pombe* (SpSen34 (SEQ ID NO: 44)) and *H. sapiens* (HsSen34 (SEQ ID NO: 58)).

FIGS. 7A,B. Sequence conservation between human and yeast tRNA endonuclease subunits Sen15 and Sen54. A. Comparison of Sen54 amino acid sequences in *S. cerevisiae* (ScSen54 (SEQ ID NO: 45)), *S. pombe* (SpSen54 (SEQ ID NO: 44)) and *H. sapiens* (HsSen54 (SEQ ID NO: 57)). B. Comparison of Sen15 amino acid sequences in *S. cerevisiae* (ScSen15 (SEQ ID NO: 47)), *S. pombe* (SpSen15 (SEQ ID NO: 48)) and *H. sapiens* (HsSen15 (SEQ ID NO: 4)).

Figure 8:
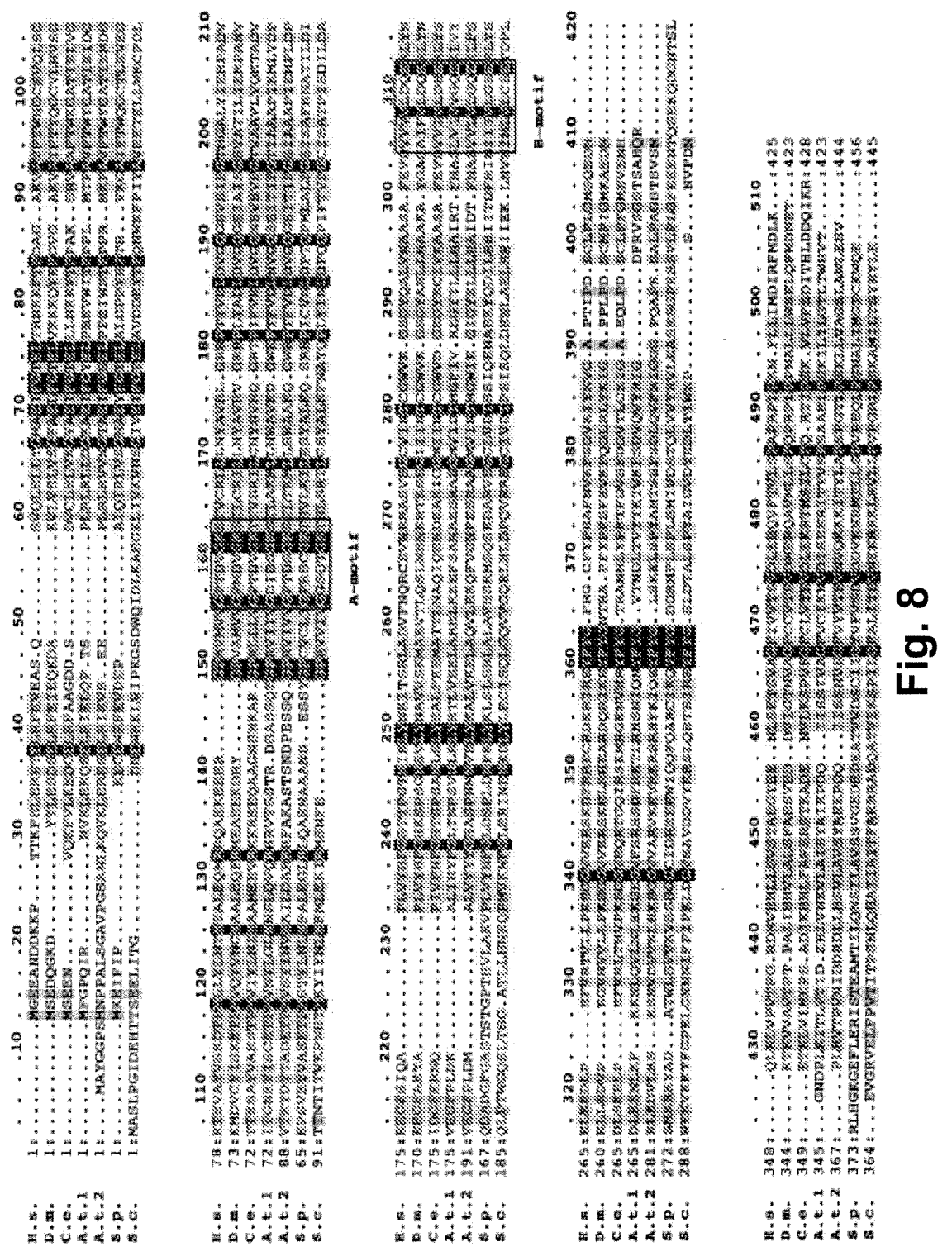

FIG. 8. Protein sequence alignment of Clp1 from different species (SEQ ID NOS: 10 and SEQ ID NOS: 49-54). hC1p1 is evolutionarily conserved and has an ATP/GTP-binding motif. The alignment of *H. sapiens* (tr: ☐92989, SEQ ID NO: 10), *D. melanogaster* (tr: Q9V6Q1, SEQ ID NO: 49), *C. elegans* (sp: P52874, SEQ ID NO: 50), *A. thaliana* 1 (gb: AB010077, SEQ ID NO: 51), *A. thaliana* 2 (tr: QSR06, SEQ ID NO: 52), *S. pombe* (tr: Q10299, SEQ ID NO: 53) and *S. cerevisiae* (tr: ☐08685, SEQ ID NO: 54) Clp1p sequences was generated with clustalx. The black and gray boxes indicate identical and similar residues, respectively. The conserved Walker A motif with the consensus sequence -A/G-X-X-X-X-G-K-S/T- and the B motif are indicated.

Figure 9:
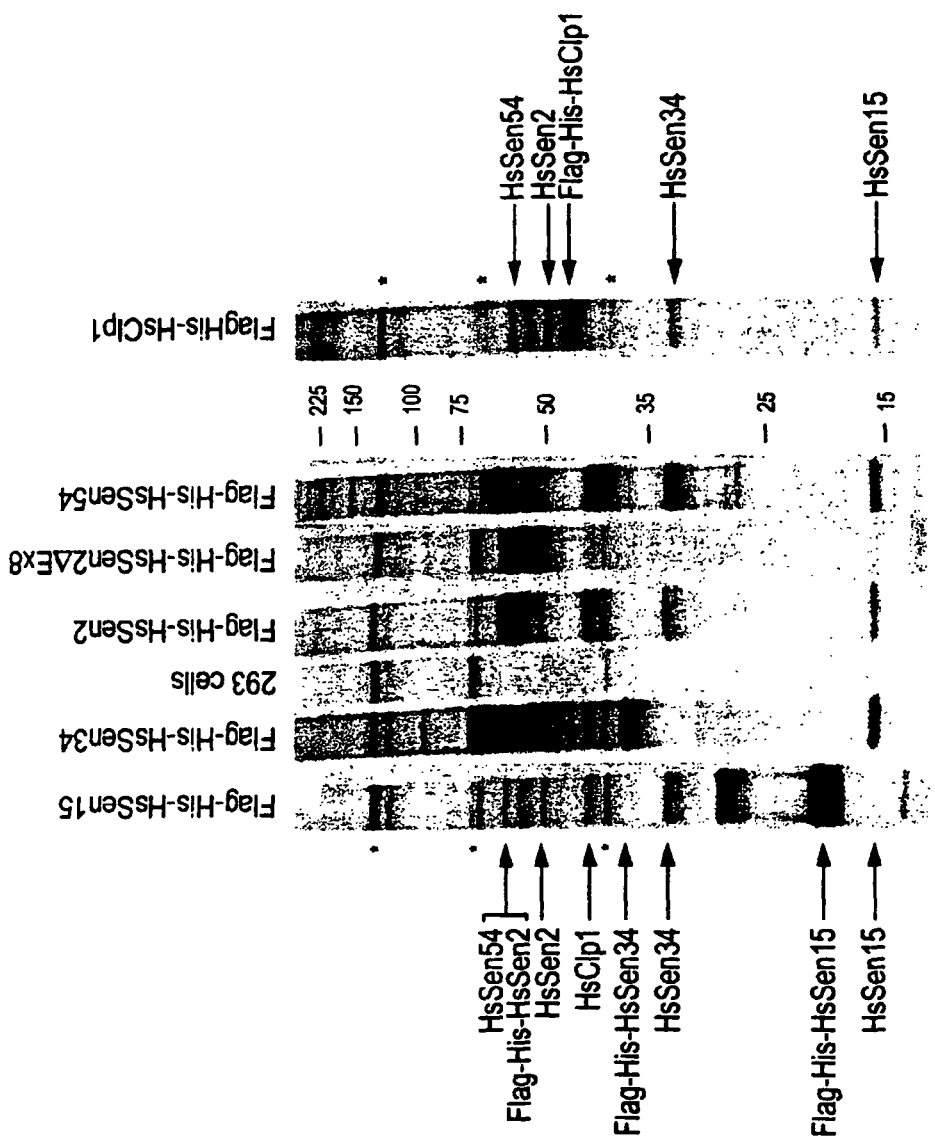

FIG. 9. Identification of components of the tRNA splicing endonuclease complex. His-Flag-Sen2 or His-Flag-Sen34 or His-Flag-Sen15 or His-Flag-Clp1 or His-Flag-Sen54 or His-Flag-Sen2deltaEx8 proteins were purified as described in Example 5.1.2. Proteins co-purified with His-Flag-Sen2, His-Flag-34, His-Flag-Sen15, His-Flag-Clp1, His-Flag-Sen54, His-Flag-Sen2deltaEx8 were analyzed by SDS-PAGE followed by a silver staining Sen2, Sen34, Sen15, Sen54 and Clp1 are identified as components of the tRNA splicing complex. Extracts from untransfected 293 cells were used as a negative control.

FIGS. 10A,B Purification of cell extract fractions containing tRNA splicing endonuclease activity. His-Flag-Sen2, His-Flag-Sen34 and His-Flag-Sen15 proteins were purified as described in Example 5.1.2. Extracts from untransfected 293 cells were used as a negative control. Yeast endonuclease was used as a positive control for endonuclease activity. A. Fractions co-purifiying with His-Flag-Sen2 or His-Flag-Sen34 show endonuclease activity, cleaving labeled tRNA at intron/exon borders. B. Fractions co-purifiying with His-Flag-Sen15 show endonuclease activity, cleaving labeled tRNA at intron/exon borders. C. Proteins co-purified with Flag-His-HsClp1 have pre-tRNA endonuclease activity.

FIG. 11. Human tRNA Splicing endonuclease active site subunits are localized in the nucleus. Myc-Sen2 (top panel) and GFP-Sen34 (bottom panel) vectors were transiently transfected into Hela cells and visualized by immunofluorescence.

Figure 12:
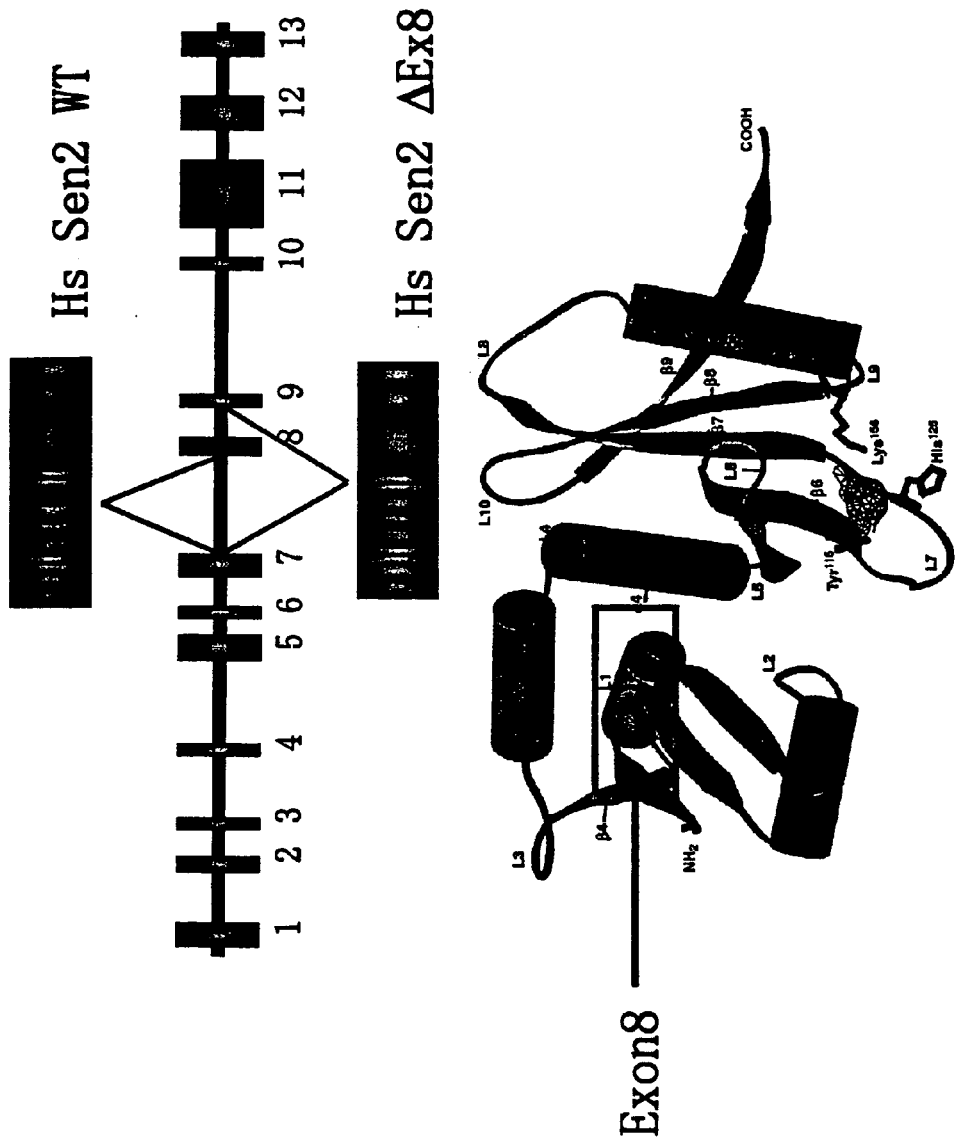

FIG. 12. Endonuclease active site subunit Sen2p is alternatively spliced into two distinct forms. Sen2p WT contains all 13 Sen2p exons, while the splice variant Sen2deltaEx8 (also designated as Sen2ΔEx8) contains all exons except Exon 8. An alignment of the active site of the archael endonuclease to the human Sen2delta Exon8 subunit suggests that the amino acid sequence of Exon8 corresponds exactly to a conserved Alpha helix of the archaeal endonuclease. The alpha helix serves to orient the N-terminal and C-terminal domains of the active site subunit, forming the basic groove to which Loop L10 from the heterologous Sen15 subunit is proposed to interact.

Figure 13:
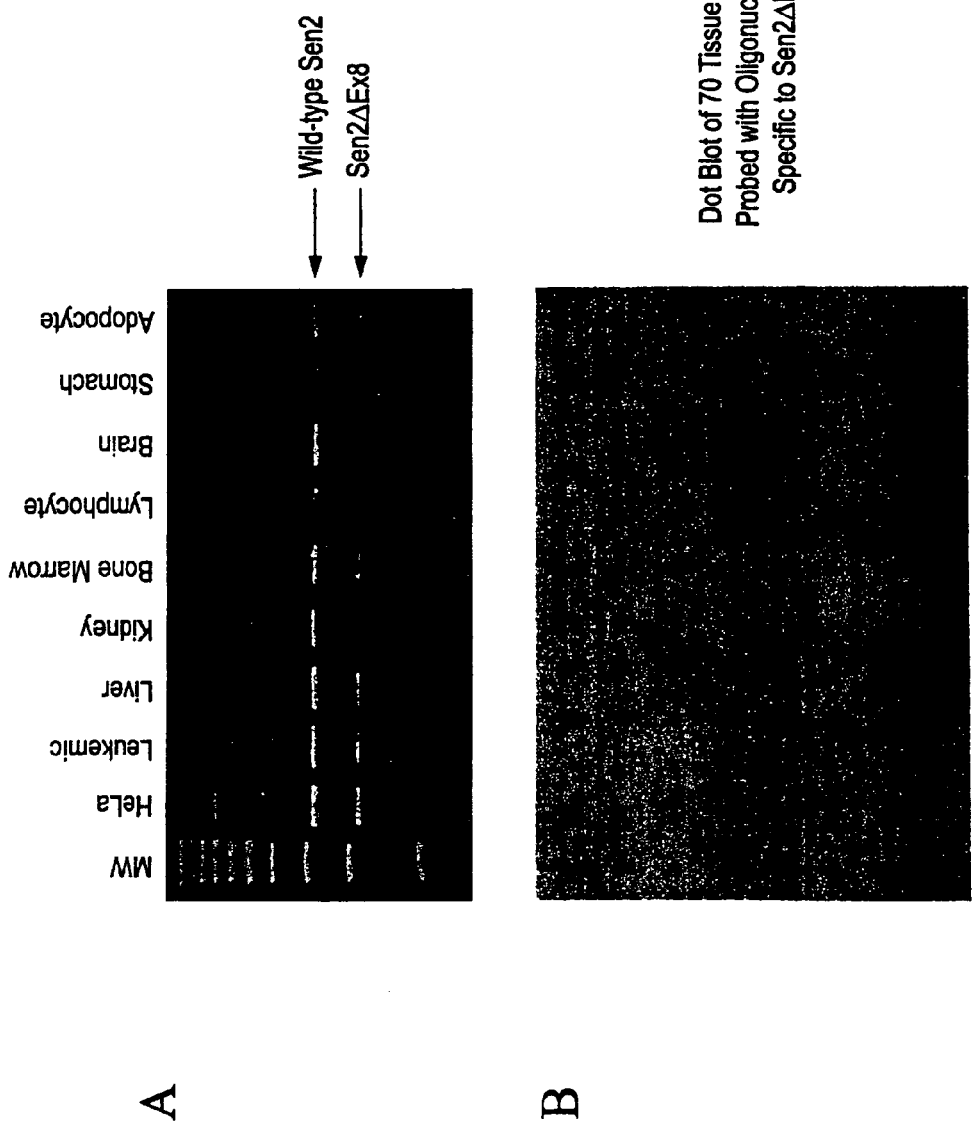

FIG. 13 A,B. Alternatively spliced endonuclease subunit Sen2ΔEx8 is expressed in many human tissues. A. PCR analysis of the expression of Wild-type Sen2 and splice variant Sen2ΔEx8 in HeLa cells as well as leukemic, liver, kidney, bone marrow, lymphocyte, brain, stomach, and adipocyte tissues as described in Example 5.2.3. B. Northern blot analysis of 70 tissue types probed with an oligonucleotide specific to Sen2ΔEx8 reveals Sen2ΔEx8 expression in an array of tissues.

Figure 14:
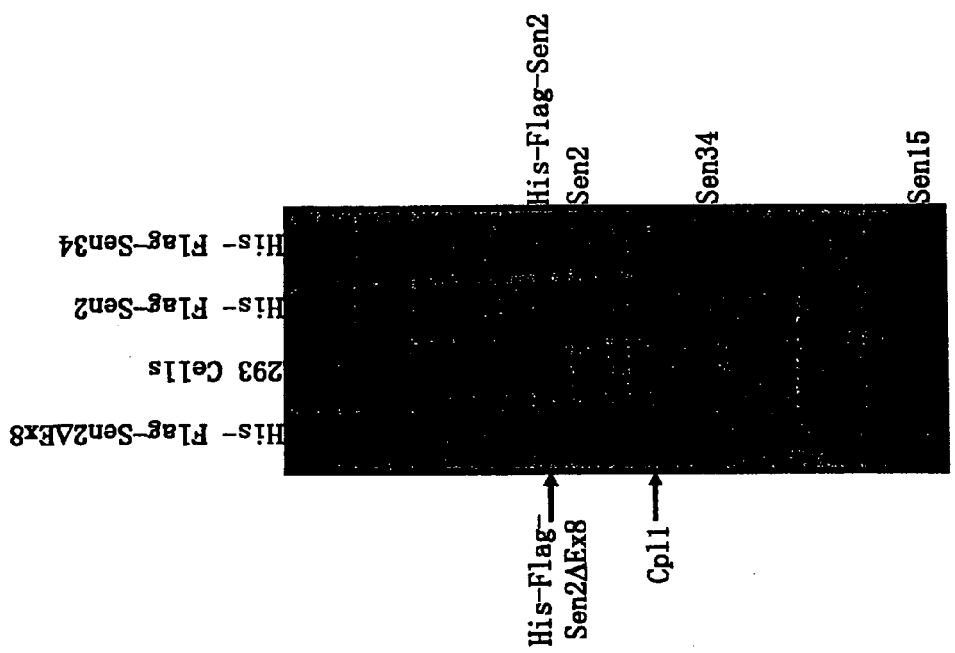

FIG. 14. Sen2ΔEx8 has decreased ability to bind Sen15 and Sen34. His-Flag-Sen2ΔEx8 or His-Flag-Sen34 or His-Flag-Sen2 proteins were purified as described in Example 5.1.2. Extract prerared from 293 cells was used as a negative control. Proteins co-purified with His-Flag-Sen2ΔEx8 or His-Flag-Sen34 or His-Flag-Sen2 were analyzed by SDS-PAGE followed by a silver staining.

Figure 15:
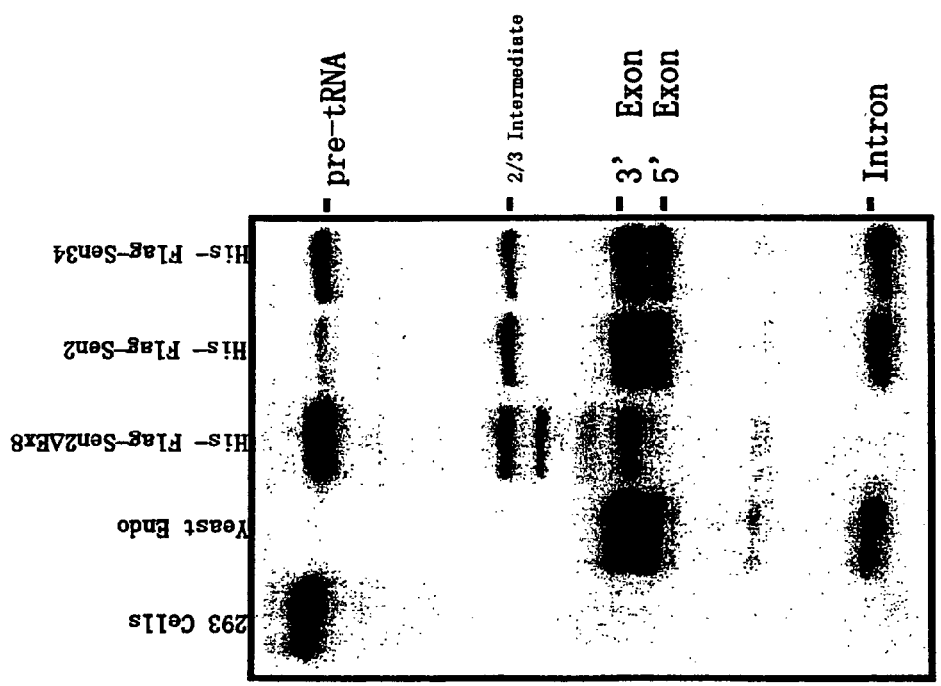

FIG. 15. Endonuclease containing Sen2ΔEx8 is deficient in pre-tRNA cleavage activity. His-Flag-Sen2, His-Flag-Sen34 and His-Flag-Sen2ΔEx8 proteins were purified as described in Example 5.1.2. Extracts from untransfected 293 cells were used as a negative control. Yeast endonuclease was used as a positive control for endonuclease activity. Fractions co-purifiying with His-Flag-Sen2 or His-Flag-Sen34 show endonuclease activity, cleaving labeled tRNA at intron/exon borders, whereas fractions co-purifiying with His-Flag-Sen2ΔEx8 show deficient endonuclease activity.

FIG. 16. A model of assembly of two distinct complexes human endonuclease complexes. The human holoenzyme appears to consist of five subunits and due to the presence of conserved interaction elements the enzyme can heterotetramerize in a manner analogous to the yeast tRNA splicing endonuclease. Sen2ΔEx8 can dimerize with Sen54 protein, but is unable to form a stable interaction with the Sen34, Sen15. This purified enzyme is able to cleave pre-tRNA in vitro, but in an aberrant fashion. Thus it suggests that in vivo this enzyme may function to process other types of RNA substrates such as pre-mRNA.

Figure 17A:
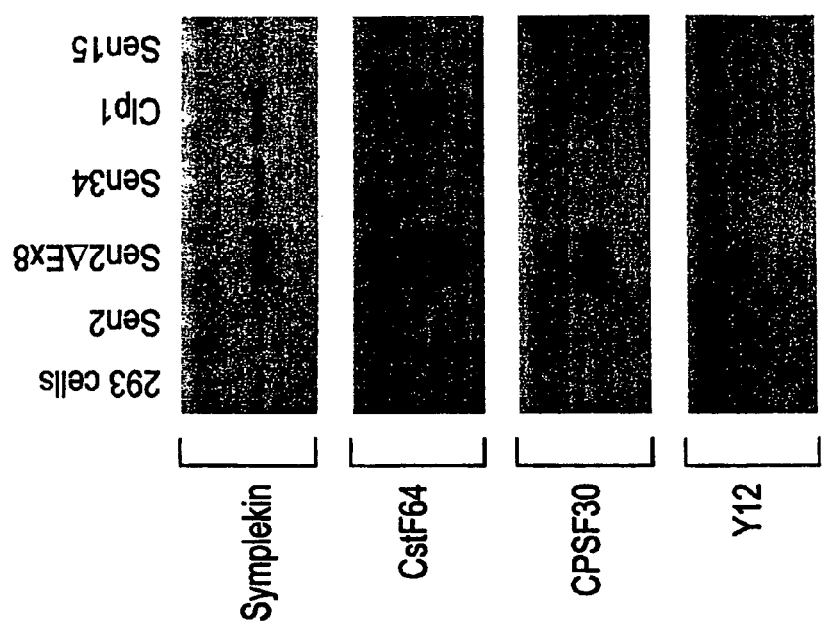
Figure 17B:
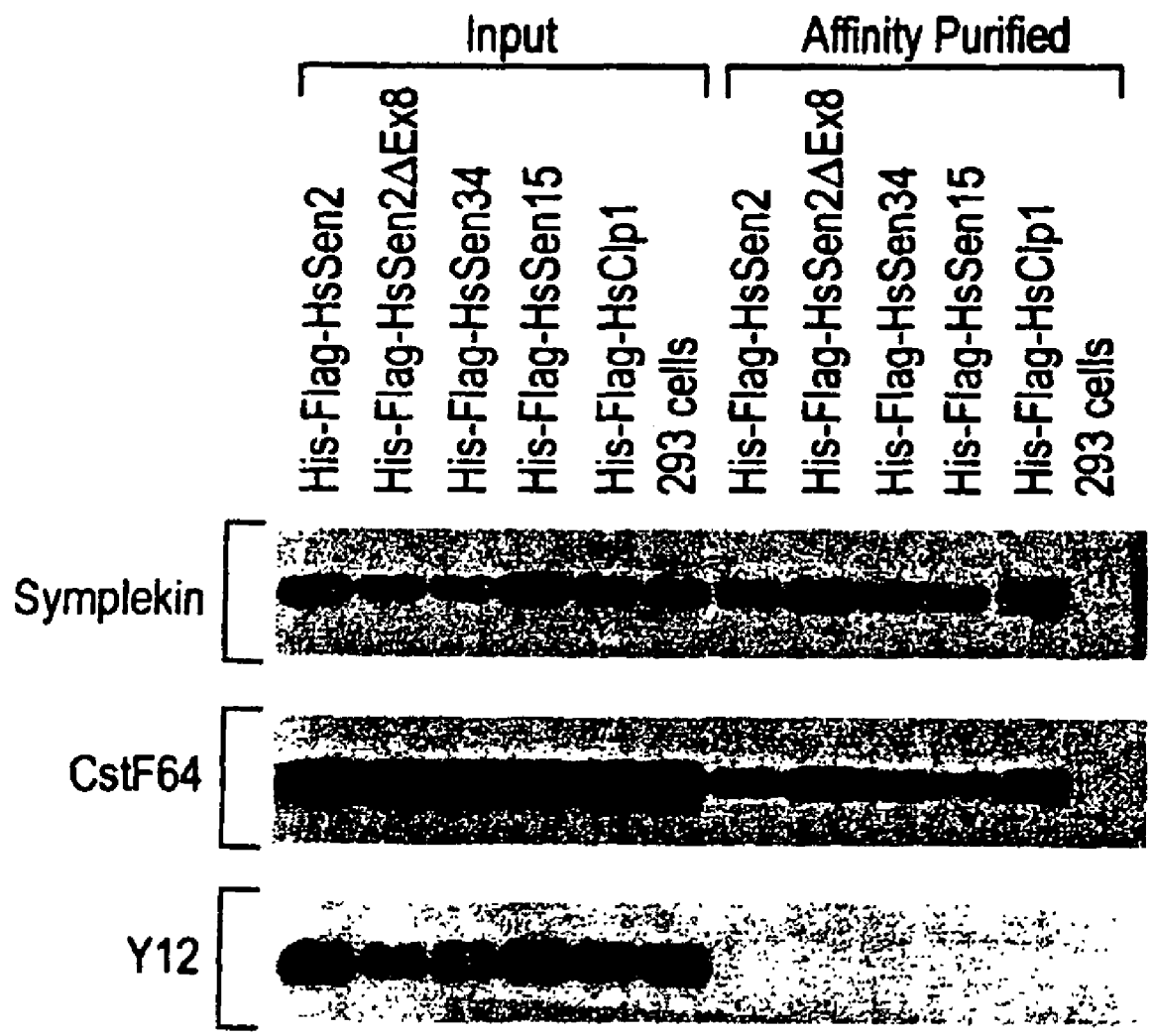

FIG. 17. (A) The human endonuclease complexes are associated with pre-mRNA 3' end processing factors. Proteins co-purified with His-Flag-Sen2, His-Flag-Sen2ΔEx8, His-Flag-Sen34, His-Flag-Clp1, His-Flag-Sen15 were analyzed by SDS-PAGE followed by a western blotting with antibodies against the components of 3' end pre-mRNA processing complex, such as CPSF30, Symplekin, CstF64. Y12 antibody that recognizes pre-mRNA splicing SmB/B' proteins was used a a negative control. His-Flag-Sen2ΔEx8 is strongly associated with CPSF30, Symplekin, CstF64 suggesting that Flag-Sen2ΔEx8 is largely involved in pre-mRNA processing. (B) Proteins co-purified with His-Flag-HsSen2, His-Flag-HsSen2ΔEx8, His-Flag-HsSen34, His-Flag-HsSen15 and His-Flag-HsClp1 were analyzed by SDS-PAGE followed by Western blotting with antibodies against Symplekin, CstF64. Y12 antibody that recognizes SmB/B' proteins was used a negative control. Note that the antibody directed to Cstf-64 recognizes two isoforms of this protein present in 293 cell line (Wallace et al., 1999, PNAS 96:6763-6768).

Figure 18:
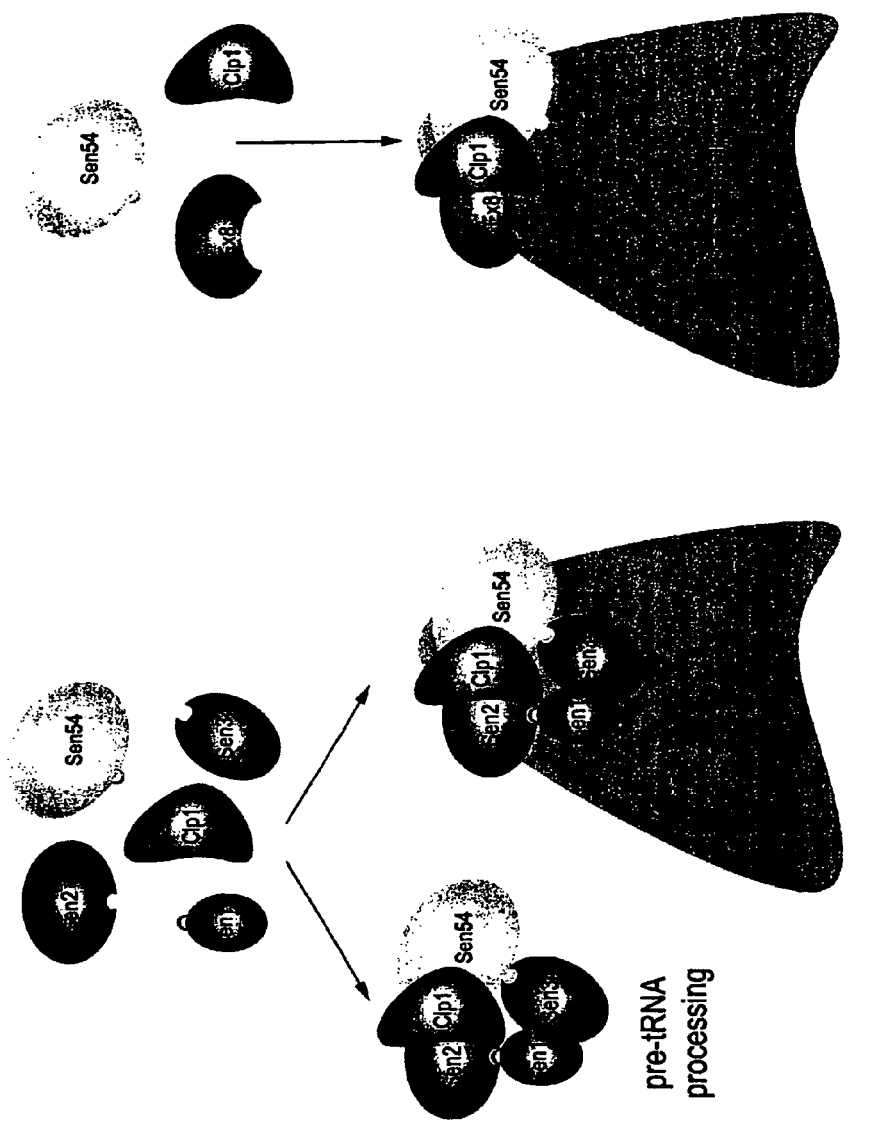

FIG. 18. Human endonucleases process different types of RNAs. The Sen2 protein together with Sen54, Sen34, Sen15, and Clp1 forms a complex that removes introns from pre-tRNA. Since the Clp1 protein also can be a part of another complex that is involved in maturation of pre-mRNA, we propose that all the subunits of the tRNA splicing endonuclease form a complex with the factors responsible for the 3' end processing of pre-mRNA. Sen2ΔEx8 is unable to form a complex with Sen34 and Sen15 and deficient in pre-tRNA cleavage but it is able to interact with Clp1. As a result of this interaction, Sen2ΔEx8 is involved in the 3' end processing of pre-mRNA.

Figure 19:
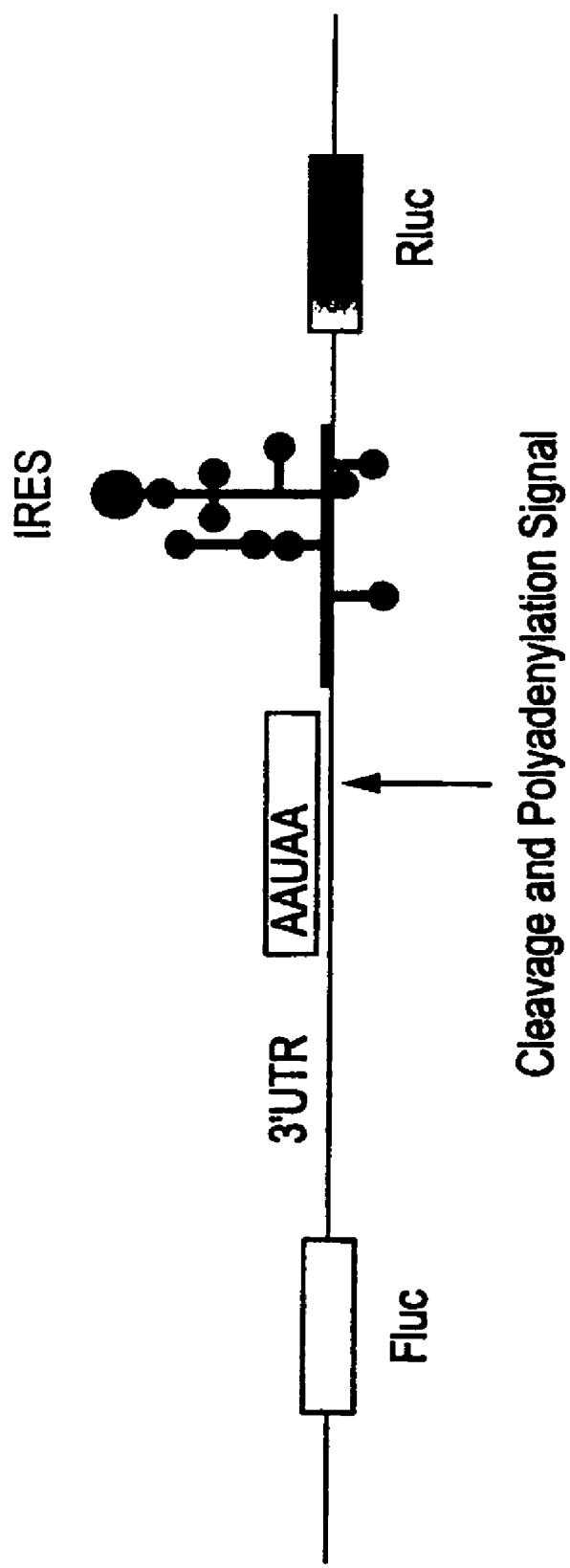

FIG. 19. depicts an exemplary substrate for 3' end pre-mRNA endonuclease. The pre-mRNA molecule is shown as a line. The positions of the 3' end pre-mRNA endonuclease cleavage site and the internal ribosome entry site are indicated. The open reading frames of two reporter genes, firefly (FLuc) or renilla (RLuc) luciferase are shown as boxes.

FIG. 20. shows the nucleic acid sequence (SEQ ID NO: 1) and the amino acid sequence (SEQ ID NO: 2) of human Sen2.

FIG. 21. shows the nucleic acid sequence (SEQ ID NO: 11) and the amino acid sequence (SEQ ID NO: 12) of human Sen2ΔEx8.

FIG. 22. shows the nucleic acid sequence (SEQ ID NO: 3) and the amino acid sequence (SEQ ID NO: 4) of human Sen15.

FIG. 23. shows the nucleic acid sequence (SEQ ID NO: 5) and the amino acid sequence (SEQ ID NO: 6) of human Sen34.

FIG. 24. shows the nucleic acid sequence (7-1938 of SEQ ID NO: 7) and the amino acid sequence (SEQ ID NO:8) of human Sen54.

FIG. 25. shows the nucleic acid sequence (SEQ ID NO: 9) and the amino acid sequence (SEQ ID NO: 10) of human Clp1.

Figure 26:
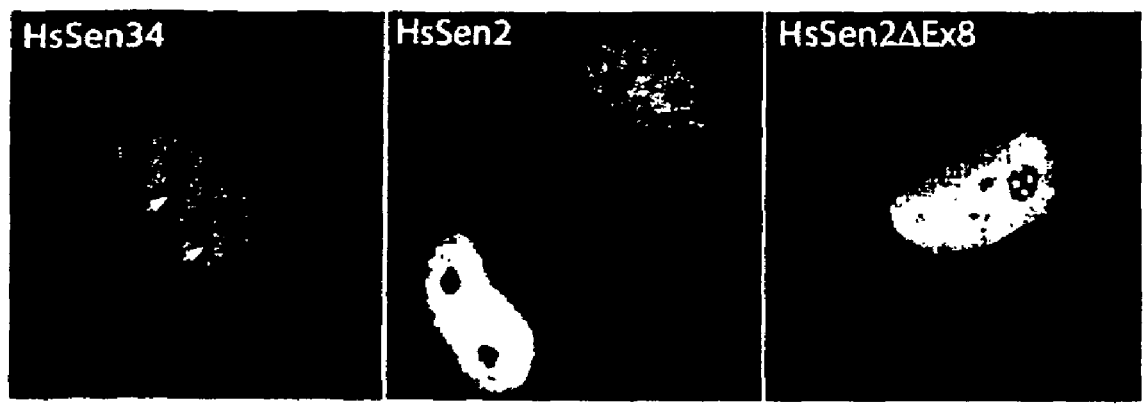

FIG. 26. Localization of the human tRNA splicing endonuclease subunits. HeLa cells were transiently transfected with a vector encoding GFP-HsSen34 (left panel), Myc-HsSen2 (middle panel) or Myc-HsSen2deltaEx8 (right panel) and analyzed by indirect immunofluorescence microscopy using antibody against myc-epitope.

Figure 27:
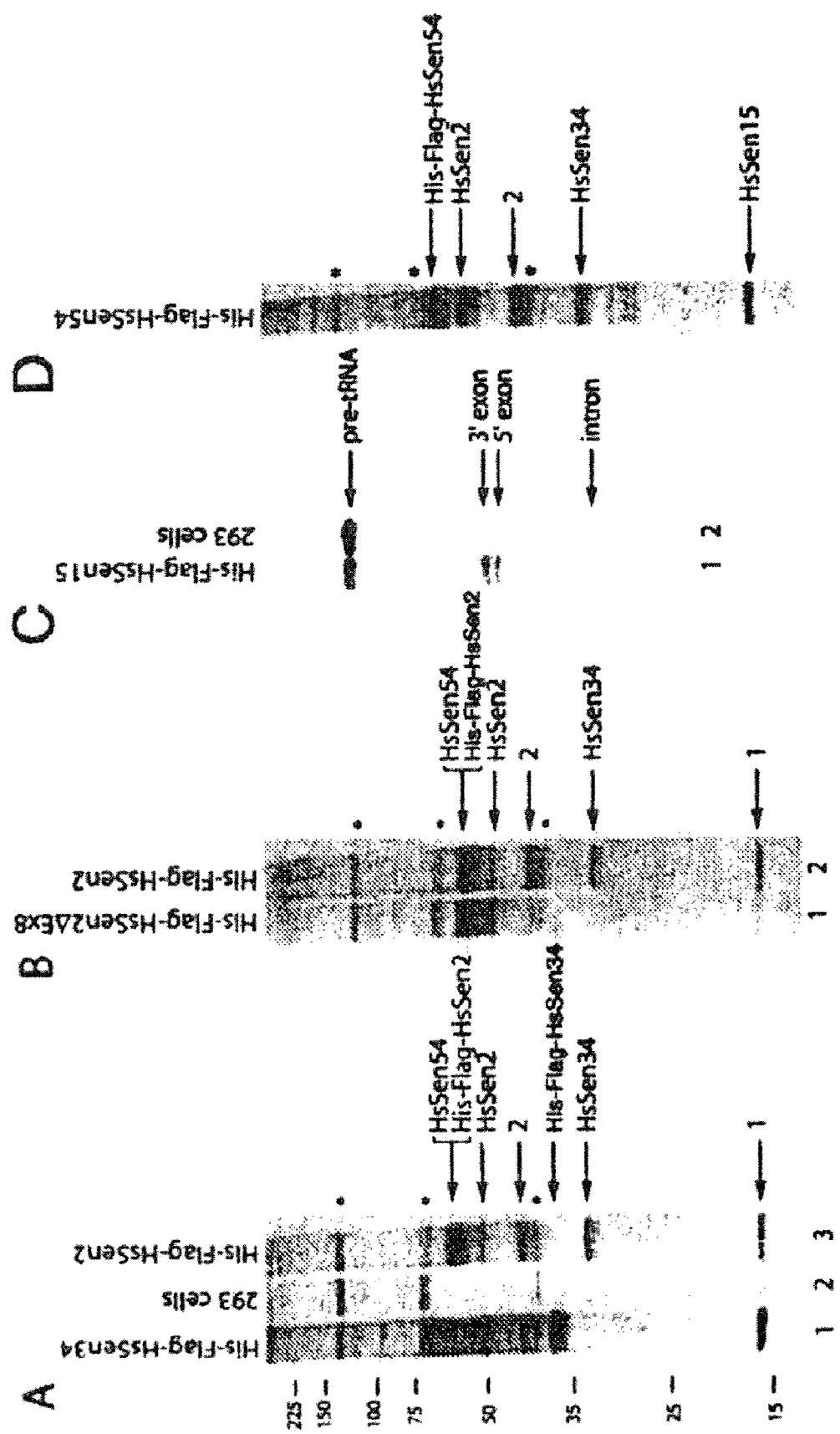

FIG. 27. Identification of components of the human tRNA splicing endonuclease complex. Proteins co-purified with His-Flag-HsSen2 and His-Flag-HsSen34 (A) or with His-Flag-Sen2deltaEx8 and His-Flag-Sen2 (B) were analyzed by SDS-PAGE followed by silver staining. Major bands in panel A, lane 3 and panel B, lane 2, correspond to His-Flag-Sen2 and His-Flag-Sen2deltaEx8, respectively. These bands overlap with endogenous HsSen54. Several bands, marked with asterisks, were detected in the control untransfected 293 purification and thus represent nonspecific contaminants of the purification protocol (Hu et al., 2003). Bands 1 and 2 were identified by protein sequence as HsSen15 and HsClp1, respectively. (C) Cell extract fraction co-purified with His-Flag-HsSen15 was examined for endonuclease activity with labeled pre-tRNA$^{phe}$. Cleavage products were analyzed by denaturing polyacrylamide gel. 293 cell extract was used as a negative control. (D) Proteins co-purified with His-Flag-HsSen54 were analyzed by SDS-PAGE followed by silver staining as described above. We note some additional bands present in HsSen54 purification that are currently under investigation.

Figure 28:
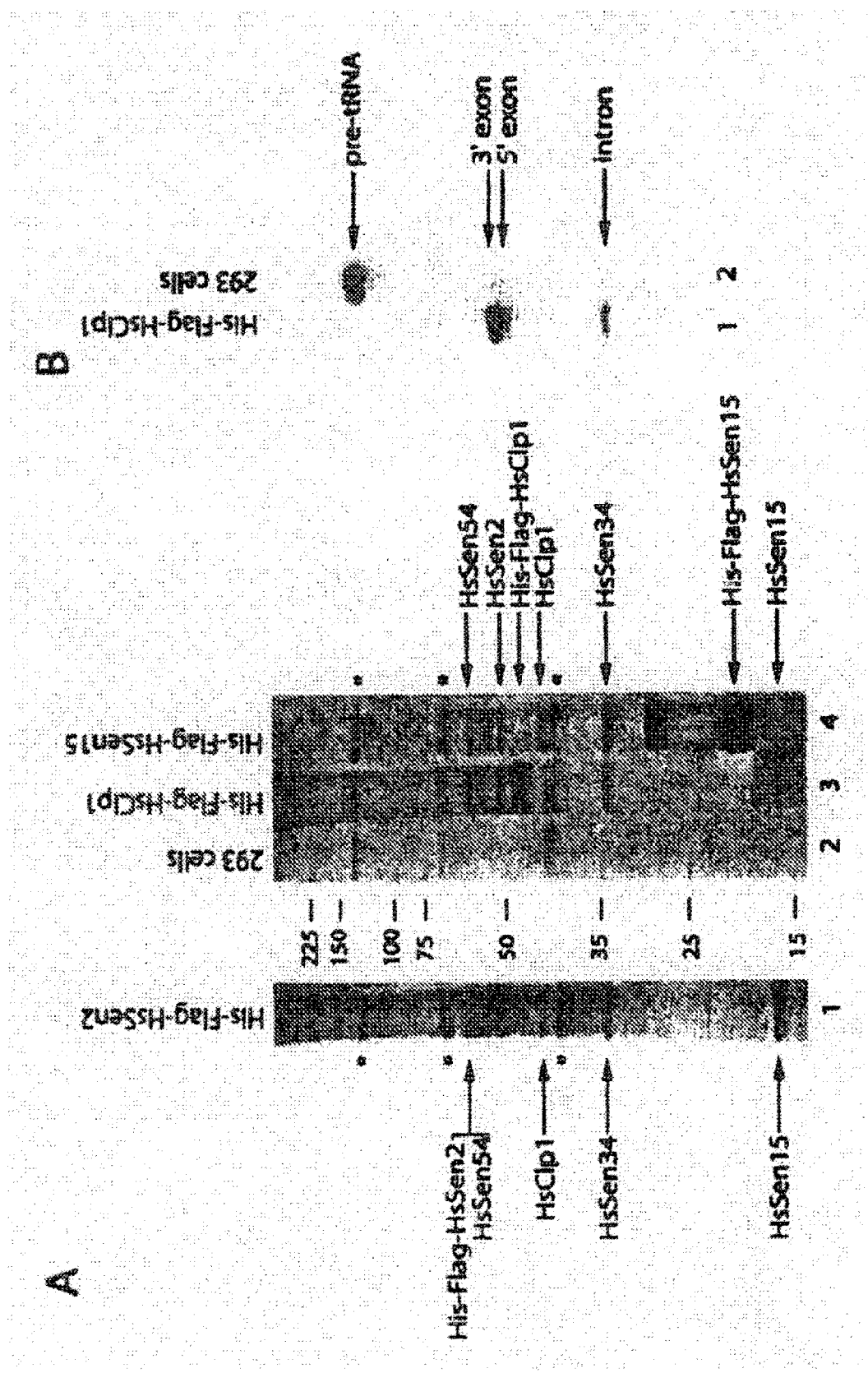

FIG. 28. HsClp1 and HsSen15 are genuine components of the human tRNA splicing endonuclease complex. (A) Proteins that are co-purified with His-Flag-HsSen15 and His-Flag-HsClp1 were analyzed by SDS-PAGE followed by silver staining. Proteins co-purifying with His-Flag-HsSen2 (on the left) are shown for a comparison with His-Flag-HsSen15 and His-Flag-HsClp1. (B) Cell extract fractions co-purified with His-Flag-HsSen15 were examined for endonuclease activity with labeled pre-tRNA$^{Phe}$. Cleavage products were analyzed by denaturing polyacrylamide gel. 293 cell extract was used as a negative control.

Figure 29:
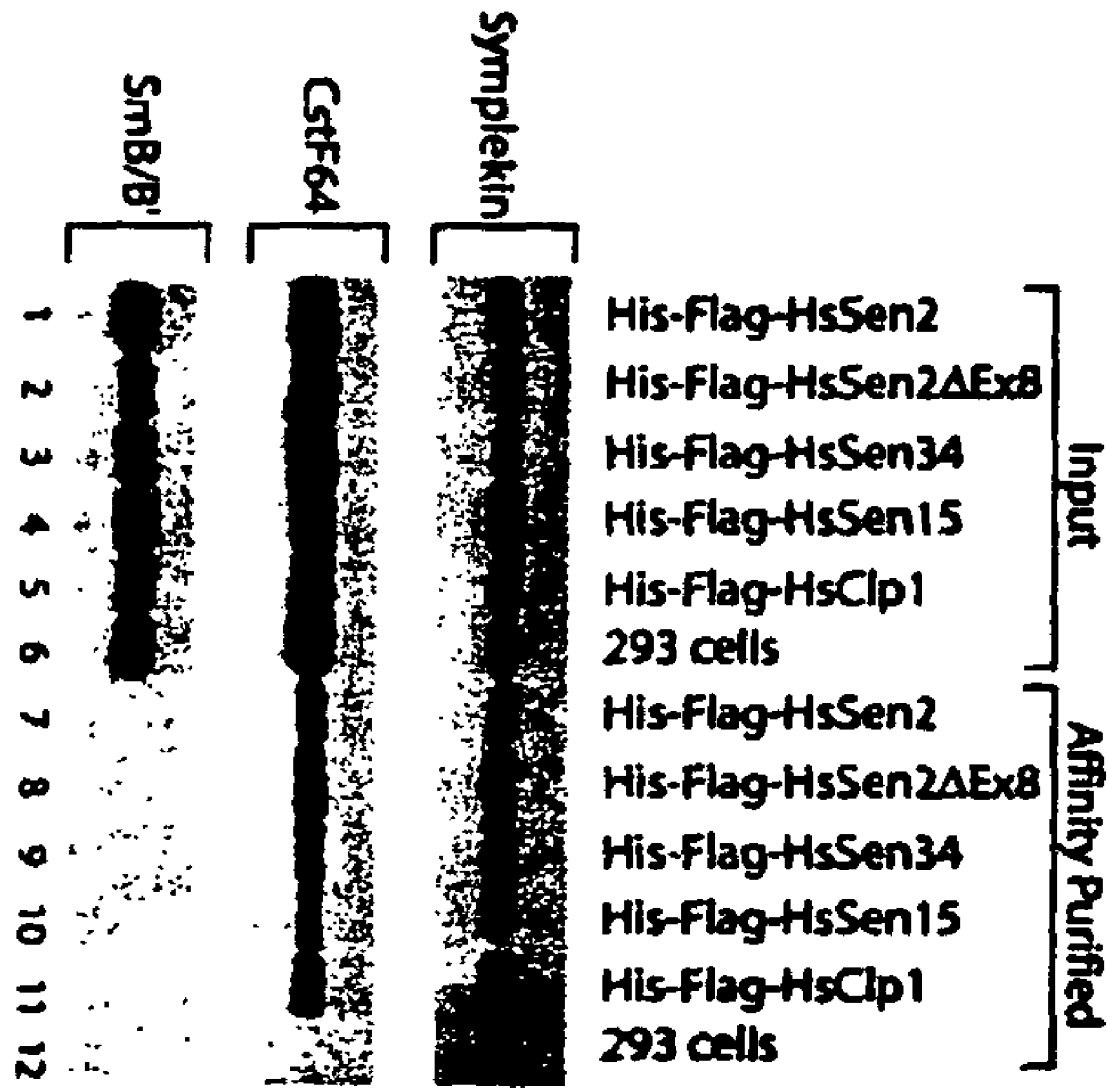

FIG. 29. The human endonuclease is associated with factors essential for pre-mRNA 3'-end processing. Proteins co-purified with His-Flag-HsSen2, His-Flag-HsSen2deltaEx8, His-Flag-HsSen34, His-Flag-HsSen15 and His-Flag-HsClp1 were analyzed by SDS-PAGE followed by Western blotting with antibodies against Symplekin, CstF64. Y12 antibody that recognizes SmB/B' proteins was used a negative control. We note that our antibody to Cstf-64 recognizes two isoforms of this protein present in 293 cell line (Wallace et al., 1999).

Figure 30:
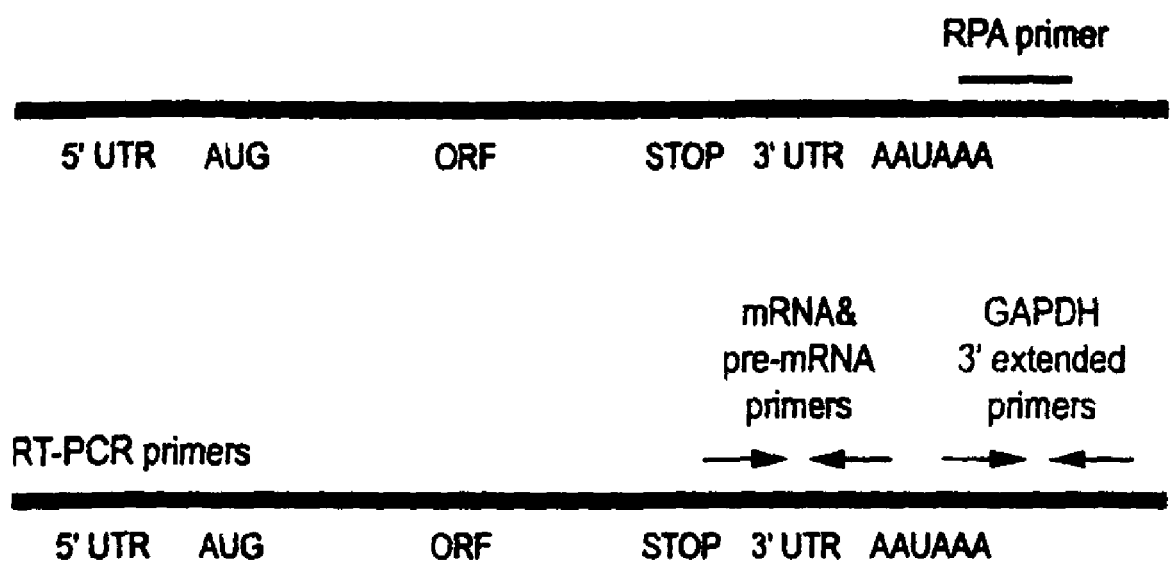

FIG. 30. The human endonuclease is involved in pre-mRNA 3'-end processing. (A) Several 293 cell lines, stably expressing siRNA-A, specific for SEN2 exon 8, or SiRNA-B, specific for SEN2 exon 9, were transfected with either His-Flag-HsSen2 (lanes 1-3) or His-Flag-HsSen2deltaEx8. Total cell extracts were prepared from these cells and analyzed by Western blot analysis with anti-FLAG (top) or anti-actin (bottom) antibodies. (B) Quantative RT-PCR analysis of 293 cells stably expressing siRNA-A or siRNA-B, shown in panel A. White bar corresponds to control siRNA, black bar corresponds to siRNA-A1 and grey bar corresponds to siRNA-B2. (C) (Top) Ribonuclease protection assay of EF1A and GAPDH 3'-extended mRNA. Ten micrograms of yeast total RNA (lane 6), mRNA from 293 cells (lane 5) or 293 stably expressing, siRNA-B1 (lane 2), siRNA-A1 (lane 3) or siRNA-A2 (lane 4) were hybridized to a riboprobe corresponding to the antisense downstream of either the EF1A or GAPDH 3'-end cleavage and polyadenylation site and digested with ribonuclease. Lane 1 represents a 1:250 or 1:100 dilution of the input probe for EF1A or GAPDH, respectively. (Bottom) Measurement of the abundance of 3'-end extended EF1A (grey bars) and GAPDH (black bars) pre-mRNA quantitated by phosphorimager. Data is plotted as fold difference relative to 293 total RNA protected product (lane 5); (D) shows a schematic representation of the primers used with the siRNA experiment.

4. DETAILED DESCRIPTION OF THE INVENTION

The invention provides complexes involved in the processing of RNA. In particular the invention provides complexes with endonuclease activity that are involved in pre-tRNA splicing and/or 3' end pre-mRNA cleavage. More specifically, the invention provides a purified complex with RNA-nucleolytic activity comprising two or more or any combination of the following (i) human Sen2 or a functionally active derivative or a functionally active fragment thereof; (ii) human Sen 15 or a functionally active derivative or a functionally active fragment thereof; (iii) human Sen34 or a functionally active derivative or a functionally active fragment thereof; and (iv) human Sen54 or a functionally active derivative or a functionally active fragment thereof.

The invention provides a purified protein complex with endonuclease activity comprising: (i) human Sen2 or a functionally active derivative or a functionally active fragment thereof; (ii) human Sen 15 or a functionally active derivative or a functionally active fragment thereof; (iii) human Sen34 or a functionally active derivative or a functionally active fragment thereof; and (iv) human Sen54 or a functionally active derivative or a functionally active fragment thereof. In a specific embodiment, the protein complex has tRNA splicing endonuclease activity. In another embodiment, the protein complex has 3' end pre-mRNA endonuclease activity. In yet another embodiment, the protein complex has tRNA splicing endonuclease activity and 3' end pre-mRNA endonuclease activity.

In certain embodiments, a complex of the invention may further comprise: (i) human CPSF160 or a functionally active derivative or a functionally active fragment thereof; (ii) human CPSF30 or a functionally active derivative or a functionally active fragment thereof; (iii) human CstF64 or a functionally active derivative or a functionally active fragment thereof; and/or (iv) human symplekin or a functionally active derivative or a functionally active fragment.

The invention also provides a purified protein complex with endonuclease activity comprising: (i) human Sen2 or a functionally active derivative or a functionally active fragment thereof; (ii) human Sen 15 or a functionally active derivative or a functionally active fragment thereof; (iii) human Sen34 or a functionally active derivative or a functionally active fragment thereof; (iv) human Sen54 or a functionally active derivative or a functionally active fragment thereof; and (v) human Clp1 or a functionally active derivative or a functionally active fragment thereof. In a specific embodiment, the protein complex has tRNA splicing endonuclease activity. In another embodiment, the protein complex has 3' end pre-mRNA endonuclease activity. In yet another embodiment, the protein complex has tRNA splicing endonuclease activity and 3' end pre-mRNA endonuclease activity.

In certain embodiments, a complex of the invention may further comprise: (i) human CPSF160 or a functionally active derivative or a functionally active fragment thereof; (ii) human CPSF30 or a functionally active derivative or a functionally active fragment thereof; (iii) human CstF64 or a functionally active derivative or a functionally active fragment thereof; and/or (iv) human symplekin or a functionally active derivative or a functionally active fragment.

The accession numbers of the amino acid sequences of components of the complexes of the invention and nucleotide sequences encoding such components are set forth in Table 1 below.

The invention provides a purified protein complex with endonuclease activity comprising: (i) human Sen2 or a functionally active derivative or a functionally active fragment thereof; (ii) human Sen 15 or a functionally active derivative or a functionally active fragment thereof; (iii) human Sen34 or a functionally active derivative or a functionally active fragment thereof; (iv) human Sen54 or a functionally active derivative or a functionally active fragment thereof; (v) human Clp1 or a functionally active derivative or a functionally active fragment thereof; (vi) human CPSF or a functionally active derivative or a functionally active fragment thereof; (vii) human $CFI_m$ or a functionally active derivative or a functionally active fragment thereof; (viii) human $CFII_m$ or a functionally active derivative or a functionally active fragment thereof; and (ix) human CstF or a functionally active derivative or a functionally active fragment thereof. In a specific embodiment, the protein complex has tRNA splicing endonuclease activity. In another embodiment, the protein complex has 3' end pre-mRNA endonuclease activity. In yet another embodiment, the protein complex has tRNA splicing endonuclease activity and 3' end pre-mRNA endonuclease activity.

In certain embodiments, a complex of the invention may further comprise: (i) human CPSF160 or a functionally active derivative or a functionally active fragment thereof; (ii) human CPSF30 or a functionally active derivative or a functionally active fragment thereof; (iii) human CstF64 or a functionally active derivative or a functionally active fragment thereof; and/or (iv) human symplekin or a functionally active derivative or a functionally active fragment.

The invention provides a splice variant of human Sen2, namely human Sen2deltaEx8. In particular, the invention provides nucleic acid sequences encoding human Sen2deltaEx8 or a functionally active fragment or a functionally active derivative thereof, and amino acid sequences coding human Sen2deltaEx8 or a functionally active fragment or a functionally active derivative thereof. In a specific embodiment, the invention provides a nucleic acid sequence that hybridizes under stringent conditions to a nucleic acid sequence encoding Sen2ΔEx8 over the entire length of the nucleic acid sequence encoding Sen2ΔEx8. In another embodiment, the invention provides nucleic acid sequences that encode a protein having an amino acid sequence that is at least 90%, preferably at least 95%, at least 98%, at least 99%, at least 99.5%, at least 99.8% or at least 99.9% identical to the amino acid sequence of SEQ ID NO:12, wherein the protein is different from Sen2 (ACCESSION NO.: NP_079541; FIG. 20 (SEQ ID NO: 2)). In another embodiment, the invention provides a nucleic acid sequence comprising the nucleic acid sequence of SEQ ID NO:11. The invention further provides vectors comprising a nucleic acid sequence encoding human Sen2ΔEx8 and host cells comprising the vector. The invention further provides host cells comprising a nucleic acid encoding human Sen2ΔEx8.

The invention provides a purified protein, wherein the protein consists essentially of the amino acid sequence of SEQ ID NO:12 or an amino acid sequence that is at least 90%, preferably at least 95%, at least 98%, at least 99%, at least 99.5%, at least 99.8% or at least 99.9% identical to the amino acid sequence of SEQ ID NO:12. The invention further provides antibodies or fragments thereof that immunospecifically bind to human Sen2ΔEx8 but do not bind to Sen2. In particular the invention provides an antibody or fragment thereof that immunospecifically binds to the unique region of Sen2ΔEx8 that is created by the deletion of Exon 8 from the Sen2 protein.

The invention also provides purified protein complexes comprising human Sen2deltaEx8. The Sen2deltaEx8 complexes have RNA-nucleolytic activity. In a specific embodiment, the Sen2deltaEx8 complexes have pre-tRNA cleavage activity and/or 3' end pre-mRNA endonuclease activity. The invention provides a purified human Sen2deltaEx8 complex comprising: (i) human Sen2deltaEx8 or a functionally active derivative thereof; and (ii) human Sen54 or a functionally active derivative or a functionally active fragment thereof. The invention also provides a human Sen2deltaEx8 complex with comprising: (i) human Sen2deltaEx8 or a functionally active derivative thereof; (ii) human Sen54 or a functionally active derivative or a functionally active fragment thereof; (iii) human Sen15 or a functionally active derivative or a functionally active fragment thereof; and (iv) human Sen34 or a functionally active derivative or a functionally active fragment thereof. In certain embodiments, the Sen2deltaEx8 complex has RNA-nucleolytic activity. In a specific embodiment the Sen2deltaEx8 complex has tRNA endonuclease and/or 3' end mRNA processing activity. In certain embodiments, the fidelity and accuracy of the tRNA cleavage activity of a Sen2deltaEx8 comprising complex is reduced compared to the tRNA cleavage activity of full length Sen2 comprising complexes. In certain embodiments, the complex may further comprise: (i) human CPSF160 or a functionally active derivative or a functionally active fragment thereof; (ii) human CPSF30 or a functionally active derivative or a functionally active fragment thereof; (iii) human CstF64 or a functionally active derivative or a functionally active fragment thereof; and/or (iv) human symplekin or a functionally active derivative or a functionally active fragment. These human Sen2deltaEx8 complexes cleave tRNA at multiple sites and are useful in mapping RNA structure and 3' end endonuclease processing. In certain embodiments, the fidelity and accuracy of the tRNA cleavage activity of a Sen2deltaEx8 comprising complex is reduced compared to the tRNA cleavage activity of full length Sen2 comprising complexes.

The invention provides a purified human Sen2deltaEx8 complex comprising: (i) human Sen2deltaEx8 or a functionally active derivative thereof; (ii) human Sen54 or a functionally active derivative or a functionally active fragment thereof; (iii) human Sen15 or a functionally active derivative or a functionally active fragment thereof; (iv) human Sen34 or a functionally active derivative or a functionally active fragment thereof; and (v) human Clp1 or a functionally active derivative or a functionally active fragment thereof. In certain embodiments, the Sen2deltaEx8 complex has RNA-nucleolytic activity. In a specific embodiment the Sen2deltaEx8 complex has tRNA endonuclease and/or 3' end mRNA processing activity. In certain embodiments, the fidelity and accuracy of the tRNA cleavage activity of a Sen2deltaEx8 comprising complex is reduced compared to the tRNA cleavage activity of full length Sen2 comprising complexes. In certain embodiments, the complex may further comprise: (i) human CPSF160 or a functionally active derivative or a functionally active fragment thereof; (ii) human CPSF30 or a functionally active derivative or a functionally active fragment thereof; (iii) human CstF64 or a functionally active derivative or a functionally active fragment thereof; and/or (iv) human symplekin or a functionally active derivative or a functionally active fragment. The invention also provides a purified human Sen2deltaEx8 complex comprising: (i)

human Sen2deltaEx8 or a functionally active derivative thereof; (ii) human Sen54 or a functionally active derivative or a functionally active fragment thereof; (iii) human Sen15 or a functionally active derivative or a functionally active fragment thereof; (iv) human Sen34 or a functionally active derivative or a functionally active fragment thereof; (v) human Clp1 or a functionally active derivative or a functionally active fragment thereof; (vi) human CSPF or a functionally active derivative or a functionally active fragment thereof; (vii) human $CFI_m$ or a functionally active derivative or a functionally active fragment thereof; (viii) human $CFII_m$. or a functionally active derivative or a functionally active fragment thereof; and (ix) human CstF or a functionally active derivative or a functionally active fragment thereof. The invention also provides a purified human Sen2deltaEx8 complex comprising: (i) human Sen2deltaEx8 or a functionally active derivative thereof; (ii) human Sen54 or a functionally active derivative or a functionally active fragment thereof; and (iii) human Clp1 or a functionally active derivative or a functionally active fragment thereof, and optionally (i) human CPSF or a functionally active derivative or a functionally active fragment thereof; (ii) human $CFI_m$ or a functionally active derivative or a functionally active fragment thereof; (iii) human $CFII_m$ or a functionally active derivative or a functionally active fragment thereof; and (iv) human CstF or a functionally active derivative or a functionally active fragment thereof. In certain embodiments, the complexes of the invention have RNA nucleolytic activity. In certain, more specific embodiments, the complexes have tRNA cleavage activity and/or 3' end pre-mRNA processing activity.

The invention also provides protein complexes with pre-ribosomal RNA cleavage activity. In particular, the invention provides a protein complex with pre-ribosomal RNA cleavage activity comprising: (i) human Sen15 or a functionally active derivative or a functionally active fragment thereof; and (ii) human Sen34 or a functionally active derivative or a functionally active fragment thereof. This protein complex may be used in the biogenesis of different ribosomal RNAs. For example, the production of 28S, 18S, 5.5S and 5S ribosomal RNA may be altered by modulating this protein complex.

The invention provides methods for purifying a complex of the invention. In particular, the invention provides a method for purifying a complex of the invention, the method comprising: preparing a cell extract or a nuclear extract from a cell, wherein the cell expresses all of the protein components of the complex and wherein at least one of the protein components is fused to a peptide tag; and purifying the complex by virtue of the peptide tag.

The invention provides antibodies or fragments thereof that immunospecifically bind to a complex of the invention. In a specific embodiment, the invention provides an antibody or a fragment thereof that immunospecifically binds to a complex of the invention with higher affinity than to each individual component of the complex in an immunoassay well-known to one of skill in the art or described herein. In another embodiment, the invention provides an antibody or a fragment thereof that immunospecifically binds to a complex of the invention, but does not bind to each individual component of the complex in an immunoassay well-known to one of skill in the art or described herein. The invention also provides a method for generating an antibody or a fragment thereof that immunospecifically binds to a complex of the invention comprising immunizing a subject with the complex of the invention.

The invention also provides antibodies or fragments thereof that immunospecifically bind to one of the following components of a complex of the invention: (i) human Sen2 or a functionally active derivative or a functionally active fragment thereof; (ii) human Sen2deltaEx8 or a functionally active derivative or a functionally active fragment thereof; (iii) human Sen15 or a functionally active derivative or a functionally active fragment thereof; (iv) human Sen34 or a functionally active derivative or a functionally active fragment thereof; and (v) human Sen54 or a functionally active derivative or a functionally active fragment thereof. Preferably, the antibodies or fragments thereof are not known. The invention also provides a method for generating an antibody or a fragment thereof that immunospecifically binds to a component of a complex of the invention comprising immunizing a subject with the component.

In a specific embodiment, the invention provides an antibody or a fragment thereof that immunospecifically binds to human Sen2deltaEx8 with higher affinity than human Sen2 in an immunoassay well-known to one of skill in the art or described herein. In another embodiment, the invention provides an antibody or a fragment thereof that immunospecifically binds to human Sen2deltaEx8, but does not bind to human Sen2 in an immunoassay well-known to one of skill in the art or described herein.

The invention provides methods of identifying compounds that modulate the expression (at the RNA and/or protein level) of one or more of the following components of a complex of the invention: (i) human Sen2 or a functionally active derivative or a functionally active fragment thereof; (ii) human Sen2deltaEx8 or a functionally active derivative or a functionally active fragment thereof; (iii) human Sen15 or a functionally active derivative or a functionally active fragment thereof; (iv) human Sen34 or a functionally active derivative or a functionally active fragment thereof; and/or (v) human Sen54 or a functionally active derivative or a functionally active fragment thereof. Techniques for measuring expression of proteins are well-known to one of skill in the art and include, e.g., immunoassays for protein expression levels, and RT-PCR or Northern blots for RNA expression levels.

The invention provides screening assays to identify compounds that modulate the formation of a complex of the invention. In particular, the invention provides methods for identifying compounds that stabilize or promote the formation of a complex of the invention. The invention also provides methods for identifying compounds that destabilize or promote the dissociation of a complex of the invention. Such methods can be cell-based or they can be conducted in a cell-free system.

The present invention also provides methods for identifying compounds that modulate the RNA-nucleolytic activity of a complex of the invention. In particular, the invention provides methods for identifying a compound that modulates the pre-tRNA processing activity and/or 3' end pre-mRNA processing activity of a complex of the invention using assays well-known to one of skill in the art or described herein. For example, reporter gene-based assays, FRET assays and FISH assays may be used to in accordance with the methods of the invention to identify compounds that modulate the RNA-nucleolytic activity of a complex of the invention.

The present invention further provides methods for identifying compounds that modulate the pre-tRNA cleavage activity and/or pre-ribosomal RNA cleavage activity of a complex of the invention. Techniques well-known to one of skill in the art or described herein may be used to measure the ability of a compound to modulate the pre-tRNA cleavage activity and/or pre-ribosomal RNA cleavage activity of a complex of the invention. For example, the ability of a compound to modulate the pre-tRNA cleavage activity of a complex of the invention may be determined by comparing the level of tRNA fragments produced from a tRNA in the presence of the compound relative to the level of tRNA fragments produced from the same tRNA in the absence of the compound or the presence of an appropriate control (e.g., a negative control such as PBS), wherein a change in the levels indicates that the compound modulates the pre-tRNA cleavage activity of the complex. The ability of a compound to modulate the pre-ribosomal RNA cleavage activity of a complex of the invention may be determined by, e.g., comparing the level of specific ribosomal RNAs (e.g., 28S, 18S, 5.8S and/or 5S) produced from a pre-ribosomal RNA in the presence of the compound relative to the level of the ribosomal RNA produced from the same pre-ribosomal RNA in the absence of the compound or the presence of an appropriate control (e.g., a negative control such as PBS), wherein a change in the levels indicates that the compound modulates the pre-ribosomal RNA cleavage activity of the complex.

A compound identified in assays described herein that modulates the expression of a component of a complex of the invention, the formation of a complex of the invention, the RNA-nucleolytic activity of a complex of the invention (e.g., the pre-tRNA splicing endonuclease activity, the 3' end pre-mRNA endonuclease activity, the pre-tRNA cleavage activity of a complex of the invention, and/or the pre-ribosomal RNA cleavage activity of a complex of the invention) may be tested in in vitro assays (e.g., cell-based assays or cell-free assays) or in vivo assays well-known to one of skill in the art or described herein for the effect of the compound a disorder described herein (e.g., a proliferative disorder or a disorder characterized by, associated with or caused by abnormal RNA-nucleolytic activity) or on cells from a patient with a particular disorder.

In a specific embodiment, a compound identified in assays described herein that inhibits or reduces the expression of a component of a complex of the invention, the formation of a complex of the invention, the RNA-nucleolytic activity of a complex of the invention (e.g., the pre-tRNA splicing endonuclease activity, the 3' end pre-mRNA endonuclease activity, the pre-tRNA cleavage activity of a complex of the invention, and/or the pre-ribosomal RNA cleavage activity of a complex of the invention) may be tested in in vitro assays (e.g., cell-based assays or cell-free assays) or in vivo assays well-known to one of skill in the art or described herein for the antiproliferative effect of the compound on hyperproliferative cells versus normal cells. In another embodiment, a compound identified in assays described herein that inhibits or reduces the expression of a component of a complex of the invention, the formation of a complex of the invention, the RNA-nucleolytic activity of a complex of the invention (e.g., the pre-tRNA splicing endonuclease activity, the 3' end pre-mRNA endonuclease activity, the pre-tRNA cleavage activity of a complex of the invention, and/or the pre-ribosomal RNA cleavage activity of a complex of the invention) may be tested in an animal model for cancer to determine the efficacy of the compound in the prevention, treatment or amelioration of cancer or a symptom thereof. In yet another embodiment, a compound identified in assays described herein that enhances the expression of a component of a complex of the invention, the formation of a complex of the invention, the RNA-nucleolytic activity of a complex of the invention (e.g., the pre-tRNA splicing endonuclease activity, the 3' end pre-mRNA endonuclease activity, the pre-tRNA cleavage activity of a complex of the invention, and/or the pre-ribosomal RNA cleavage activity of a complex of the invention) may be tested for its effect on wound healing.

The structure of the compounds identified in the assays described herein that modulate the expression of a component of a complex of the invention, the formation of a complex of the invention, the RNA-nucleolytic activity of a complex of the invention (e.g., the pre-tRNA splicing endonuclease activity, the 3' end pre-mRNA endonuclease activity, the pre-tRNA cleavage activity of a complex of the invention, and/or the pre-ribosomal RNA cleavage activity of a complex of the invention) can be determined utilizing assays well-known to one of skill in the art or described herein. The methods used will depend, in part, on the nature of the library screened. For example, assays or microarrays of compounds, each having an address or identifier, may be deconvoluted, e.g., by cross-referencing the positive sample to an original compound list that was applied to the individual test assays. Alternatively, the structure of the compounds identified herein may be determined using mass spectrometry, nuclear magnetic resonance ("NMR"), circular dichroism, X ray crystallography, or vibrational spectroscopy.

The invention encompasses the use of the compounds that inhibit or reduce the expression of a component of a complex of the invention, the formation of a complex of the invention, the RNA-nucleolytic activity of a complex of the invention, (e.g., the pre-tRNA splicing endonuclease activity, the 3' end pre-mRNA endonuclease activity, the pre-tRNA cleavage activity of a complex of the invention, and/or the pre-ribosomal RNA cleavage activity of a complex of the invention) which were identified in accordance with the methods described herein for the prevention, treatment, management or amelioration of a proliferative disorder or a symptom thereof, or a disorder characterized by, associated with or caused by increased RNA-nucleolytic activity (e.g., the pre-tRNA splicing endonuclease activity, the 3' end pre-mRNA endonuclease activity, the pre-tRNA cleavage activity of a complex of the invention, and/or the pre-ribosomal RNA cleavage activity of a complex of the invention) or a symptom thereof. The invention encompasses the use of the compounds that stimulate or enhance the expression of a component of a complex of the invention, the formation of a complex of the invention, the RNA-nucleolytic activity of a complex of the invention (e.g., the pre-tRNA splicing endonuclease activity, the 3' end pre-mRNA endonuclease activity, the pre-tRNA cleavage activity of a complex of the invention, and/or the pre-ribosomal RNA cleavage activity of a complex of the invention) which were identified in accordance with the methods described herein for the prevention, treatment, management or amelioration of a disorder characterized by, associated with or caused by decreased RNA-nucleolytic activity (e.g., the pre-tRNA splicing endonuclease activity, the 3' end pre-mRNA endonuclease activity, the pre-tRNA cleavage activity of a complex of the invention, and/or the pre-ribosomal RNA cleavage activity of a complex of the invention). The invention also encompasses the use of the compounds that stimulate or enhance the expression of a component of a complex of the invention, the formation of a complex of the invention, the RNA-nucleolytic activity of a complex of the invention, (e.g., the pre-tRNA splicing endonuclease activity, the 3' end pre-mRNA endonuclease activity, the pre-tRNA cleavage activity of a complex of the invention, and/or the pre-ribosomal RNA cleavage activity of a complex of the invention) which were identified in accordance with the methods described herein for augmenting wound healing in a subject.

The invention provides compositions comprising a carrier and one the following or a combination of two or more of the following: (i) a component of the a complex of the invention; (ii) a complex of the invention, (iii) an antibody or a fragment thereof that immunospecifically binds to a component of a complex of the invention, or a complex of the invention, (iv) a compound that modulates the expression of a component of a complex of the invention, (v) a compound that modulates the formation of a complex of the invention, (vi) a compound that modulates the endonuclease activity (e.g., tRNA splicing endonuclease activity and/or 3' end pre-mRNA endonuclease activity) of a complex of the invention, (vii) a compound that modulates the pre-tRNA cleavage activity of a complex of the invention, and/or (viii) a compound that modulates pre-ribosomal RNA cleavage activity of a complex of the invention. The compositions may further comprise one or more other prophylactic or therapeutic agents. In a preferred embodiment, the compositions are pharmaceutical compositions. In accordance with this embodiment, the pharmaceutical compositions are preferably sterile and in suitable form for the intended method of administration or use. The invention encompasses the use of the compositions of the invention in the prevention, treatment, management or amelioration of a disorder described herein or a symptom thereof.

The invention also provides methods for detecting, diagnosing or monitoring a proliferative disorder or a disorder associated with, characterized by or caused by abnormal pre-tRNA processing and/or 3' end pre-mRNA processing utilizing an antibody that immunospecifically binds to a complex of the invention or a component thereof, or a compound identified in accordance with the methods of the invention that specifically binds to a complex of the invention or a component thereof. The invention also provides methods for detecting, diagnosing or monitoring a proliferative disorder or a disorder associated with, characterized by or caused by abnormal pre-tRNA processing and/or 3' end pre-mRNA processing by comparing the RNA-nucleolytic activity of a complex purified from cells or a tissue sample from a subject with such a disorder or suspected of having such disorder to the RNA-nucleolytic activity of a control, e.g., a complex purified from normal, non-cancerous cells or a tissue sample, using an assay well-known to one of skill in the art or described herein. The invention further provides methods for detecting, diagnosing or monitoring a proliferative disorder or a disorder associated with, characterized by or caused by abnormal pre-tRNA processing and/or 3' end pre-mRNA processing by comparing the structure of a complex of the invention purified from cells or a tissue sample from a subject (e.g., a subject with such a disorder or suspected of having such a disorder) to the structure of a control, e.g., a complex of the invention purified from normal, non-cancerous cells or a tissue sample, using an assay well-known to one of skill in the art (e.g., circular circular dichroism and nuclear magnetic resonance).

4.1 Sen2ΔEx8

The invention provides nucleic acids encoding a splice variant of Sen2, termed Sen2ΔEx8 or Sen2deltaEx8. The Sen2ΔEx8 is a splice variant of human Sen2 lacking exon 8 of the genomic DNA sequence for human Sen2. FIG. 2 depicts an amino acid sequence alignment of the amino acid sequences of the two human Sen 2 subunits (i.e., Hs Sen2 and Sen2ΔEx8) and the amino acid sequence of the yeast subunit Sc Sen 2p. The sequence alignment reveals a high degree of similarity in the YRGGY motif, the active site for the 5' splice site of yeast (Sc Sen 2p) and archael (not shown) tRNA splicing endonuclease. Based upon the sequence alignment, human Sen2ΔEx8 lacks the putative transmembrane domain found in the human Sen 2 endonuclease, which may affect the localization of the Sen2ΔEx8 in a human cell.

The invention provides for nucleic acid sequences encoding human Sen2ΔEx8 or functionally active fragments, or functionally active derivatives thereof. In particular, the invention provides a nucleic acid sequence comprising a contiguous nucleotide sequence identical to the nucleotide sequence of SEQ ID NO:11. The invention also provides nucleic acid sequences that are at least 90%, preferably at least 95%, at least 98%, at least 99%, at least 99.5%, or at least 99.8% identical to the nucleotide sequence of SEQ ID NO:11 or a complement thereof. The invention provides nucleic acid sequences which comprise at least 15, preferably at least 20, at least 25, at least 30, at least 35, at least 40, at least 45, at least 50 or more contiguous nucleotides of the nucleotide sequence of nucleotide of SEQ ID NO:11 or a complement thereof, wherein the nucleotide sequence comprises nucleotide 910 to nucleotide 960 of SEQ ID NO:11 or a complement thereof. The invention also provides nucleic acid sequences comprising a contiguous nucleotide sequence that hybridizes under high stringency conditions to the nucleotide sequence of SEQ ID NO:11 or a complement thereof over the entire length of the nucleic acid sequence of SEQ ID NO:11.

The invention provides nucleic acid sequences comprising a contiguous nucleotide sequence that encodes a polypeptide of the amino acid sequence of SEQ ID NO:12. The invention also provides nucleic acid sequences comprising a contiguous nucleotide sequence that encodes a polypeptide of an amino acid sequence that is at least 90%, preferably at least 95%, at least 98%, at least 99%, at least 99.5%, or at least 99.8% identical to the amino acid sequence of SEQ ID NO:12. The invention also provides nucleic acid sequences comprising a nucleotide sequence that encodes a polypeptide comprising at least 10, preferably at least 15, at least 20, or at least 25, at least 30, at least 35, at least 40, at least 45, at least 50, at least 55 or more contiguous amino acids of amino acid sequence of SEQ ID NO:12, wherein the polypeptide contains residues 311 to 327 of SEQ ID NO:12. The invention also provides nucleic acid sequences that hybridize under highly stringent conditions to a nucleic acid sequence encoding the amino acid sequence of SEQ ID NO:12 over the entire length of the nucleic acid sequence encoding the amino acid sequence of SEQ ID NO:12.

The invention provides host cells containing or comprising a nucleic acid sequence encoding Sen2ΔEx8, such as, but not limited to, the nucleic acid of SEQ ID NO:11. The invention also provides a vector comprising a nucleic acid sequence comprising a nucleotide sequence encoding Sen2ΔEx8, such as, but not limited to, the nucleic acid of SEQ ID NO:11. The invention also provide host cells containing or comprising a vector comprising a nucleic acid sequence comprising a nucleotide sequence encoding Sen2ΔEx8, such as, but not limited to, the nucleic acid of SEQ ID NO:11. Techniques well-known to one of skill in the art, such as electroporation, calcium phosphate precipitate and lipsomes, may be used to transfect a host cell with a nucleic acid sequence encoding Sen2ΔEx8 or a functionally active fragment or derivative thereof. See, e.g., Section 4.5.4.1.4 and 4.5.4.1.5, infra, for a description of vectors, transfection techniques and host cells. Techniques well-known to one of skill in the art, such as immunoprecitation using antibodies immunospecific human Sen2ΔEx8 or a functionally active fragment or derivative thereof, may be used to purify human Sen2ΔEx8 or a functionally active fragment or derivative thereof. See Section 4.3, infra, for a description of methods of purify proteinaceous agents such as human Sen2ΔEx8 or a functionally active fragment or derivative thereof.

The invention provides amino acid sequences of human SenAEx8 or functionally active fragments, or functionally active derivatives thereof. In particular, the invention provides a purified protein comprising the amino acid sequence of SEQ ID NO:12. The invention also provides a purified protein that is at least 90%, preferably at least 95%, at least 98%, at least 99%, at least 99.5%, or at least 99.8% identical to the amino acid sequence of SEQ ID NO:12. The invention also provides a purified protein encoded by a nucleotide sequence that hybridizes over its full-length under highly stringent conditions to the nucleotide sequence of SEQ ID NO:11. The invention also provides a purified polypeptide comprising at least 10, preferably at least 15, at least 20, or at least 25, at least 30, at least 35, at least 40, at least 45, at least 50, at least 55 or more contiguous amino acids of amino acid sequence of SEQ ID NO:12, wherein the polypeptide contains residues 311 to 327 of SEQ ID NO:12. The invention also provides a purified protein comprising a contiguous nucleotide sequence that encodes a polypeptide that is at least 90%, preferably at least 95%, at least 98%, at least 99%, at least 99.5%, or at least 99.8% identical to the amino acid sequence of SEQ ID NO:12.

The invention also provides fusion proteins comprising human Sen2ΔEx8 or a functionally active fragment or a functionally active derivative thereof and a heterologous amino acid sequence (i.e., a different amino acid sequence; an amino acid sequence not naturally found in conjunction with the amino acid sequence of human Sen2ΔEx8).

4.2 Complexes of the Invention 4.2.1 tRNA Splicing Endonuclease Complex

The invention provides a purified protein complex with tRNA endonuclease activity comprising two or more of the following: (i) human Sen2 or a functionally active derivative or a functionally active fragment thereof; (ii) human Sen 15 or a functionally active derivative or a functionally active fragment thereof; (iii) human Sen34 or a functionally active derivative or a functionally active fragment thereof; and (iv) human Sen54 or a functionally active derivative or a functionally active fragment thereof.

In particular, the invention provides a purified protein complex with tRNA splicing endonuclease activity comprising: (i) human Sen2 or a functionally active derivative or a functionally active fragment thereof; (ii) human Sen 15 or a functionally active derivative or a functionally active fragment thereof; (iii) human Sen34 or a functionally active derivative or a functionally active fragment thereof; and (iv) human Sen54 or a functionally active derivative or a functionally active fragment thereof. In one embodiment, the invention provides a purified complex with tRNA splicing endonuclease activity comprising: (i) human Sen2 (ACCESSION NO.: NP_079541; FIG. 20 (SEQ ID NO: 2)), or a protein encoded by a nucleic acid that hybridizes to the human Sen2 encoding nucleic acid (ACCESSION NO.: NM_025265; FIG. 20 (SEQ ID NO: 1)) or its complement under high stringency conditions; (ii) human Sen15 (ACCESSION NO.: NP_443197; FIG. 22 (SEQ ID NO: 4)), or a protein encoded by a nucleic acid that hybridizes to the human Sen15 encoding nucleic acid (ACCESSION NO.:NM_052965; FIG. 22 (SEQ ID NO: 3)) or its complement under high stringency conditions; (iii) human Sen34 (ACCESSION NO.:NP_076980; FIG. 23 (SEQ ID NO: 6)), or a protein encoded by a nucleic acid that hybridizes to the human Sen34 encoding nucleic acid (ACCESSION NO.:NM_024075; FIG. 23 (SEQ ID NO: 5)) or its complement under high stringency conditions; and (iv) Sen54 (ACCESSION NO.:XP_208944; FIG. 24 (SEQ ID NO: 8)), or a protein encoded by a nucleic acid that hybridizes to the human Sen54 encoding nucleic acid (ACCESSION NO.:XM_208944; FIG. 24 (SEQ ID NO: 7)) or its complement under high stringency conditions.

In a specific embodiment, the protein complex has 3' end pre-mRNA endonuclease activity. In another embodiment, the protein complex has tRNA splicing endonuclease activity and 3' end pre-mRNA endonuclease activity.

The invention also provides a purified protein complex with tRNA endonuclease activity comprising: (i) human Sen2 or a functionally active derivative or a functionally active fragment thereof; (ii) human Sen 15 or a functionally active derivative or a functionally active fragment thereof; (iii) human Sen34 or a functionally active derivative or a functionally active fragment thereof; (iv) human Sen54 or a functionally active derivative or a functionally active fragment thereof; and (v) human Clp1 or a functionally active derivative or a functionally active fragment thereof.

In certain embodiments, the Sen2deltaEx8 complex has RNA-nucleolytic activity. In a specific embodiment the Sen2deltaEx8 complex has tRNA endonuclease and/or 3' end mRNA processing activity. In certain embodiments, the fidelity and accuracy of the tRNA cleavage activity of a Sen2deltaEx8 comprising complex is reduced compared to the tRNA cleavage activity of full length Sen2 comprising complexes. In certain embodiments, the complex may further comprise: (i) human CPSF160 or a functionally active derivative or a functionally active fragment thereof; (ii) human CPSF30 or a functionally active derivative or a functionally active fragment thereof; (iii) human CstF64 or a functionally active derivative or a functionally active fragment thereof; and/or (iv) human symplekin or a functionally active derivative or a functionally active fragment.

In one embodiment, the invention provides a purified complex with tRNA splicing endonuclease activity comprising: (i) human Sen2 (ACCESSION NO.: NP_079541; FIG. 20 (SEQ ID NO: 2)), or a protein encoded by a nucleic acid that hybridizes to the human Sen2 encoding nucleic acid (ACCESSION NO.: NM_025265; FIG. 20 (SEQ ID NO: 1)) or its complement under high stringency conditions; (ii) human Sen15 (ACCESSION NO.:NP_443197; FIG. 22 (SEQ ID NO: 4)), or a protein encoded by a nucleic acid that hybridizes to the human Sen15 encoding nucleic acid (ACCESSION NO.:NM_052965; FIG. 22 (SEQ ID NO: 3)) or its complement under high stringency conditions; (iii) human Sen34 (ACCESSION NO.:NP_076980; FIG. 23 (SEQ ID NO: 6)), or a protein encoded by a nucleic acid that hybridizes to the human Sen34 encoding nucleic acid (ACCESSION NO.: NM_024075; FIG. 23 (SEQ ID NO: 5)) or its complement under high stringency conditions; (iv) Sen54 (ACCESSION NO.:XP_208944; FIG. 24 (SEQ ID NO: 8)), or a protein encoded by a nucleic acid that hybridizes to the human Sen54 encoding nucleic acid (ACCESSION NO.:XM_208944; FIG. 24 (SEQ ID NO: 7)) or its complement under high stringency conditions; and (v) human Clp1 (ACCESSION NO.:NP_006822; FIG. 25 (SEQ ID NO: 10)) or a protein encoded by a nucleic acid that hybridizes to the human Clp1 encoding nucleic acid (ACCESSION NO.: NM_006831; FIG. 25 (SEQ ID NO: 9)) or its complement under high stringency conditions. In certain embodiments, the Sen2deltaEx8 complex has RNA-nucleolytic activity. In a specific embodiment the Sen2deltaEx8 complex has tRNA endonuclease and/or 3' end mRNA processing activity. In certain embodiments, the fidelity and accuracy of the tRNA cleavage activity of a Sen2deltaEx8 comprising complex is reduced compared to the tRNA cleavage activity of full length Sen2 comprising complexes. In certain embodiments, the complex may further comprise: (i) human CPSF160 or a protein encoded by a nucleic acid that hybridizes under stringent conditions to a CPSF160 encoding nucleic acid; (ii) human CPSF30 or a protein encoded by a nucleic acid that hybridizes under stringent conditions to a CPSF30 encoding nucleic acid; (iii) human CstF64 or a protein encoded by a nucleic acid that hybridizes under stringent conditions to a CstF64 encoding nucleic acid; and/or (iv) human symplekin or a protein encoded by a nucleic acid that hybridizes under stringent conditions to a symplekin encoding nucleic acid. In a specific embodiment, the protein complex has 3' end pre-mRNA endonuclease activity. In another embodiment, the protein complex has tRNA splicing endonuclease activity and 3' end pre-mRNA endonuclease activity.

The invention provides a purified protein complex with tRNA splicing endonuclease activity comprising: (i) human Sen2 or a functionally active derivative or a functionally active fragment thereof; (ii) human Sen 15 or a functionally active derivative or a functionally active fragment thereof; (iii) human Sen34 or a functionally active derivative or a functionally active fragment thereof; (iv) human Sen54 or a functionally active derivative or a functionally active fragment thereof; (v) human Clp1 (ACCESSION NO.:NP_006822; FIG. 25 (SEQ ID NO: 10)) or a functionally active derivative or a functionally active fragment thereof; (vi) human Cleavage-Polyadenylation Specificity Factor ("CPSF") or a functionally active derivative or a functionally active fragment thereof; (vii) human Cleavage Factor I$_m$ ("CFI$_m$") or a functionally active derivative or a functionally active fragment thereof; (viii) human Cleavage Factor II$_m$ ("CFII$_m$") or a functionally active derivative or a functionally active fragment thereof; and (ix) human Cleavage Stimulation Factor ("CSF") or a functionally active derivative or a functionally active fragment thereof. In a specific embodiment, the protein complex has 3' end pre-mRNA endonuclease activity. In another embodiment, the protein complex has tRNA splicing endonuclease activity and 3' end pre-mRNA endonuclease activity.

CPSF, CstF, CFIm and CFIIm consist of multiple subunits. The accession numbers of the different subunits are set forth in Table 1 below. CPSF, CstF, CFIm and CFIIm can each comprise a different set of subunits. In a specific embodiment, CPSF comprises the 160 kD factor 1 and the 30 kD factor 4. In a more specific embodiment, CPSF comprises the 160 kD factor 1, the 100 kD factor 2, the 73 kD factor 3, and the 30 kD factor 4. In a specific embodiment, CstF comprises the 50 kD subunit 1, the 64 kD subunit 2, and the 77 kD subunit 3. In a more specific embodiment, CstF comprises the 50 kD subunit 1, the 64 kD subunit 2, the 77 kD subunit 3, and symplekin. In a specific embodiment, CFIm comprises the 68 kD subunit and the 25 kD subunit. In a more specific embodiment, CFIm comprises the 68 kD subunit, the 25 kD subunit, the 59 kD subunit, and the 72 kD subunit. In a specific embodiment, CFIIm comprises Clp1. In a more specific embodiment, CFIIm comprises Clp1 and hPcf11. In another more specific embodiment, CFIIm comprises ClpI, the CFIm 25 kD subunit and the CFIm 68 kD subunit. In even another more specific embodiment, CFIIm comprises ClpI, the CFIm 25 kD subunit and the CFIm 68 kD subunit and hpcf11.

Detailed information on Symplekin can be obtained from the homepage of Dr. Keller's laboratory at the biocentre of the University of Basel and in Takagaki, Y. and J. Manley, 2000, Molecular & Cellular Biol 20:1515-1525.

Wahle and Ruegsegger, 1999, *FEMS Micro Rev.*, 23, 277-295 and Zhoa et al., 1999, *Micoboil. Mol. Biol. Rev.*, 63, 405-445 describe factors involved RNA processing, both references are incorporated herein in their entireties.

In certain embodiments, all subunits of CPSF and CstF, respectively, are present in a complex of the invention.

TABLE 1

GenBank Accession Numbers

| NAME | NUCLEOTIDE ACC. NO. | PROTEIN ACC. NO. |
|---|---|---|
| Sen2 | NM_025265 (SEQ ID NO: 1) | NP_079541 (SEQ ID NO: 12) |
| Sen2deltaEx8 | SEQ ID NO: 11 | SEQ ID NO: 12 |
| Sen15 | NM_052965 (SEQ ID NO: 3) AF288394 (SEQ ID NO: 91) | NP_443197 (SEQ ID NO: 4) AAG60614 (SEQ ID NO: 92) |
| Sen34 | NM_024075 (SEQ ID NO: 5) | NP_076980, (SEQ ID NO: 6) XP_085899 (SEQ ID NO: 93) |
| Sen54 | XM_208944 (SEQ ID NO: 7) | XP_208944 (SEQ ID NO: 8) |
| Clp1 | NM_006831 (SEQ ID NO: 9) | NP_006822 (SEQ ID NO: 10) |
| CFII$_m$ subunit hPcf11 | NM_015885 (SEQ ID NO: 59) | NP_056969 (SEQ ID NO: 60) |
| CFII$_m$ subunit Clp1 | NM_006831 (SEQ ID NO: 9) | NP_006822 (SEQ ID NO: 10) |
| CFI$_m$ 25 kD subunit | NM_007006 (SEQ ID NO: 61) AJ001810 (SEQ ID NO: 63) | NP_008937 (SEQ ID NO: 62) CAA05026 (SEQ ID NO: 62) |
| CFI$_m$ 59 kD subunit | NM_024811.2 (SEQ ID NO: 64) AJ275970 (SEQ ID NO: 65) | NP_079087 (SEQ ID NO: 66) CAC81661 (SEQ ID NO: 66) |
| CFI$_m$ 68 kD subunit | NM_007007 (SEQ ID NO: 67) X67337 (SEQ ID NO: 67) | NP_008938 (SEQ ID NO: 68) CAA47752 (SEQ ID NO: 68) |
| CFI$_m$ 72 kD subunit | See, e.g., de Vries et al., 2000, EMBO J. 19: 5895-5904 | |
| CstF50 (50 kD subunit 1) | NM_001324 (SEQ ID NO: 69) | NP_001315 (SEQ ID NO: 70) |
| CstF64 (64 kD subunit 2) | NM_001325 (SEQ ID NO: 71) NM_015235 (SEQ ID NO: 72) | NP_001316 (SEQ ID NO: 73) NP_056050 (SEQ ID NO: 74) |
| CstF77 (77 kD subunit 3) | NM_001326 (SEQ ID NO: 75) | NP_001317 (SEQ ID NO: 76) |
| CstF subunit Symplekin | NM_004819 (SEQ ID NO: 77) | NP_004810 (SEQ ID NO: 78) |
| CPSF160 (160 kD factor 1) | NM_013291 (SEQ ID NO: 79) XM_209402 (SEQ ID NO: 80) | NP_037423 (SEQ ID NO: 81) XP_209402 (SEQ ID NO: 82) |
| CPSF100 (100 kD factor 2) | XM_029311.2 (SEQ ID NO: 83) | XP_029311 (SEQ ID NO: 84) |
| CPSF73 (73 kD factor 3) | NM_016207 (SEQ ID NO: 85) | NP_057291 (SEQ ID NO: 86) |
| CPSF30 (30 kD factor 4) | NM_006693 (SEQ ID NO: 87) XM_292584 (SEQ ID NO: 88) | NP_006684 (SEQ ID NO: 89) XP_292584 (SEQ ID NO: 90) |
| FIP subunit of CPSF | | |
| PFS2 subunit of CPSF | | |

In one embodiment, the invention provides a purified complex with tRNA splicing endonuclease activity comprising: (i) human Sen2 (ACCESSION NO.: NP_079541; FIG. 20 (SEQ ID NO: 2)), or a protein encoded by a nucleic acid that hybridizes to the human Sen2 encoding nucleic acid (ACCESSION NO.: NM_025265; FIG. 20 (SEQ ID NO: 1)) or its complement under high stringency conditions; (ii) human Sen15 (ACCESSION NO.:NP_443197; FIG. 22 (SEQ ID NO: 4)), or a protein encoded by a nucleic acid that hybridizes to the human Sen15 encoding nucleic acid (ACCESSION NO.:NM_052965; FIG. 22 (SEQ ID NO: 3)) or its complement under high stringency conditions; (iii) human Sen34 (ACCESSION NO.:NP_076980; FIG. 23 (SEQ ID NO: 6)), or a protein encoded by a nucleic acid that hybridizes to the human Sen34 encoding nucleic acid (ACCESSION NO.: NM_024075; FIG. 23 (SEQ ID NO: 5)) or its complement under high stringency conditions; (iv) Sen54 (ACCESSION NO.:XP_208944 (SEQ ID NO: 94), SEQ ID NO: 8), or a protein encoded by a nucleic acid that hybridizes to the human Sen54 encoding nucleic acid (ACCESSION NO.: XM_208944; FIG. 24 (SEQ ID NO: 7)) or its complement under high stringency conditions; (v) human Clp1 (ACCESSION NO.:NP_006822; FIG. 25 (SEQ ID NO: 10)) or a protein encoded by a nucleic acid that hybridizes to the human Clp1 encoding nucleic acid (ACCESSION NO.: NM_006831; FIG. 25 (SEQ ID NO: 9)) or its complement under high stringency conditions; (vi) human Cleavage-Polyadenylation Specificity Factor ("CPSF") or a protein encoded by a nucleic acid that hybridizes to the human CPSF or its complement under high stringency conditions; (vii) human Cleavage Factor $I_m$ ("CF $I_m$") or a protein encoded by a nucleic acid that hybridizes to the human $CFI_m$ encoding nucleic acid or its complement under high stringency conditions; (viii) human Cleavage Factor $II_m$ ("CF $II_m$") or a protein encoded by a nucleic acid that hybridizes to the human $CFII_m$ encoding nucleic acid or its complement under high stringency conditions; and (ix) human Cleavage Stimulation Factor ("CSF") or a protein encoded by a nucleic acid that hybridizes to the human CstF encoding nucleic acid or its complement under high stringency conditions. In accordance with this embodiment, the complex may also have 3' end pre-mRNA endonuclease activity.

In certain, more specific embodiments, a complex of the invention is purified.

In certain embodiments, the invention provides complexes that comprise homologs or analogs of the human proteins of the complexes of the invention. Homologs or analogs of the components of a complex of the invention are at least 50%, at least 55%, at least 60%, at least 65%, at least 70%, at least 75%, at least 80%, at least 85%, at least 90%, at least 95%, at least 98%, at least 99% or at least 99.5% identical to a human protein of a complex of the invention. Derivatives can be, e.g., fusion proteins, mutant forms of the protein, or forms of the protein with chemical moieties linked to the protein. A fragment of a component of a complex of the invention is a portion of the protein component that maintains the ability of the component to be physically integrated into the complex.

In certain embodiments, the protein components of a complex of the invention are derived from the same species. In more specific embodiments, the protein components are all derived from human. In another specific embodiment, the protein components are all derived from a mammal.

In certain other embodiments, the protein components of a complex of the invention are derived from a non-human species, such as, but not limited to, cow, pig, horse, cat, dog, rat, mouse, a primate (e.g., a chimpanzee, a monkey such as a cynomolgous monkey). In certain embodiments, one or more components are derived from human and the other components are derived from a mammal other than a human to give rise to chimeric complexes.

4.2.2 3' End pre-mRNA Endonuclease Complex

The invention provides a purified protein complex with 3' end pre-mRNA endonuclease activity comprising two or more of the following: (i) human Sen2 or a functionally active derivative or a functionally active fragment thereof; (ii) human Sen 15 or a functionally active derivative or a functionally active fragment thereof; (iii) human Sen34 or a functionally active derivative or a functionally active fragment thereof; (iv) human Sen54 or a functionally active derivative or a functionally active fragment thereof; (v) human Clp1 (ACCESSION NO.:NP_006822; FIG. 25 (SEQ ID NO: 10)) or a functionally active derivative or a functionally active fragment thereof; (vi) human CPSF160 or a functionally active derivative or a functionally active fragment thereof; (vii) human CPSF30 or a functionally active derivative or a functionally active fragment thereof; (viii) human CstF64 or a functionally active derivative or a functionally active fragment thereof; and/or (ix) human symplekin or a functionally active derivative or a functionally active fragment (x) human CPSF or a functionally active derivative or a functionally active fragment thereof; (xi) human $CFI_m$ or a functionally active derivative or a functionally active fragment thereof; (xii) human $CFII_m$ or a functionally active derivative or a functionally active fragment thereof; and (xiii) human CstF or a functionally active derivative or a functionally active fragment thereof.

In particular, the invention provides a purified protein complex with 3' end pre-mRNA endonuclease activity comprising: (i) human Sen2 or a functionally active derivative or a functionally active fragment thereof; (ii) human Sen 15 or a functionally active derivative or a functionally active fragment thereof; (iii) human Sen34 or a functionally active derivative or a functionally active fragment thereof; (iv) human Sen54 or a functionally active derivative or a functionally active fragment thereof; (v) human Clp1 (ACCESSION NO.:NP_006822; FIG. 25 (SEQ ID NO: 10)) or a functionally active derivative or a functionally active fragment thereof; (vi) human CPSF or a functionally active derivative or a functionally active fragment thereof; (vii) human $CFI_m$ or a functionally active derivative or a functionally active fragment thereof; (viii) human $CFII_m$ or a functionally active derivative or a functionally active fragment thereof; and (ix) human CstF or a functionally active derivative or a functionally active fragment thereof.

In one embodiment, the invention provides a purified complex with 3' end pre-mRNA endonuclease activity comprising: (i) human Sen2 (ACCESSION NO.: NP_079541; FIG. 20 (SEQ ID NO: 2)), or a protein encoded by a nucleic acid that hybridizes to the human Sen2 encoding nucleic acid (ACCESSION NO.: NM_025265; FIG. 20 (SEQ ID NO: 1)) or its complement under high stringency conditions; (ii) human Sen15 (ACCESSION NO.:NP_443197; FIG. 22 (SEQ ID NO: 4)), or a protein encoded by a nucleic acid that hybridizes to the human Sen15 encoding nucleic acid (ACCESSION NO.:NM_052965; FIG. 22 (SEQ ID NO: 3)) or its complement under high stringency conditions; (iii) human Sen34 (ACCESSION NO.:NP_076980; FIG. 23 (SEQ ID NO: 6)), or a protein encoded by a nucleic acid that hybridizes to the human Sen34 encoding nucleic acid (ACCESSION NO.:NM_024075; FIG. 23 (SEQ ID NO: 5)) or its complement under high stringency conditions; (iv) Sen54 (ACCESSION NO.:XP_208944 (SEQ ID NO: 94), SEQ ID NO: 8), or a protein encoded by a nucleic acid that hybridizes to the human Sen54 encoding nucleic acid (ACCESSION NO.: XM_208944; FIG. 24 (SEQ ID NO: 7)) or its complement under high stringency conditions; (v) human Clp1 (ACCESSION NO.:NP_006822; FIG. 25 (SEQ ID NO: 10)) or a protein encoded by a nucleic acid that hybridizes to the human Clp1 encoding nucleic acid (ACCESSION NO.: NM_006831; FIG. 25 (SEQ ID NO: 9)) or its complement under high stringency conditions. In certain embodiments, the Sen2deltaEx8 complex has RNA-nucleolytic activity. In a specific embodiment the Sen2deltaEx8 complex has tRNA endonuclease and/or 3' end mRNA processing activity. In certain embodiments, the fidelity and accuracy of the tRNA cleavage activity of a Sen2deltaEx8 comprising complex is reduced compared to the tRNA cleavage activity of full length Sen2 comprising complexes. In certain embodiments, the complex may further comprise: (i) human CPSF160 or a functionally active derivative or a functionally active fragment thereof; (ii) human CPSF30 or a functionally active derivative or a functionally active fragment thereof; (iii) human CstF64 or a functionally active derivative or a functionally active fragment thereof; and/or (iv) human symplekin or a functionally active derivative or a functionally active fragment. In other embodiments, the complexes further comprise (i) human Cleavage-Polyadenylation Specificity Factor ("CPSF") or proteins encoded by nucleic acids that hybridize to human CPSF encoding nucleic acids or their complements under high stringency conditions; (ii) human Cleavage Factor $I_m$ ("CF $I_m$") or proteins encoded by nucleic acids that hybridize to human $CFI_m$ encoding nucleic acids or their complements under high stringency conditions; (iii) human Cleavage Factor $II_m$ ("CF $II_m$") or proteins encoded by nucleic acids that hybridize to human $CFII_m$ encoding nucleic acids or their complements under high stringency conditions; and (iv) human Cleavage Stimulation Factor ("CSF") or proteins encoded by nucleic acids that hybridize to human CSF encoding nucleic acids or their complements under high stringency conditions.

The invention provides purified protein complexes having 3' end pre-mRNA endonuclease activity and comprising human Sen2deltaEx8. The invention provides a purified protein complex comprising two or more of the following: (i) human Sen2deltaEx8 or a functionally active derivative thereof; (ii) human Sen54 or a functionally active derivative or a functionally active fragment thereof; (iii) human Sen15 or a functionally active derivative or a functionally active fragment thereof; (iv) human Sen34 or a functionally active derivative or a functionally active fragment thereof; and (v) Clp1 or a functionally active derivative or a functionally active fragment thereof. In particular, the invention provides a purified human Sen2deltaEx8 complex with 3' end pre-mRNA endonuclease activity comprising: (i) human Sen2deltaEx8 or a functionally active derivative thereof; and (ii) human Sen54 or a functionally active derivative or a functionally active fragment thereof. The invention also provides a human Sen2deltaEx8 complex with 3' end pre-mRNA endonuclease activity comprising: (i) human Sen2deltaEx8 or a functionally active derivative thereof; (ii) human Sen54 or a functionally active derivative or a functionally active fragment thereof; (iii) human Sen15 or a functionally active derivative or a functionally active fragment thereof; and (iv) human Sen34 or a functionally active derivative or a functionally active fragment thereof. These human Sen2deltaEx8 complexes are useful in mapping RNA structure and 3' end pre-mRNA endonuclease processing.

In a specific embodiment, the invention provides a purified human Sen2deltaEx8 complex with 3' end pre-mRNA endonuclease activity comprising: (i) human Sen2deltaEx8 (SEQ ID NO: 12), or a protein encoded by a nucleic acid that hybridizes to the human Sen2deltaEx8 encoding nucleic acid (SEQ ID NO:11) or its complement under high stringency conditions; and (ii) human Sen15 (ACCESSION NO.:NP_443197; FIG. 22 (SEQ ID NO: 4)), or a protein encoded by a nucleic acid that hybridizes to the human Sen15 encoding nucleic acid (ACCESSION NO.:NM_052965; FIG. 22 (SEQ ID NO: 3)) or its complement under high stringency conditions. In another embodiment, the invention provides a purified human Sen2deltaEx8 complex comprising: (i) human Sen2deltaEx8 (SEQ ID NO:12), or a protein encoded by a nucleic acid that hybridizes to the human Sen2deltaEx8 encoding nucleic acid (SEQ ID NO:11) or its complement under high stringency conditions; (ii) human Sen15 (ACCESSION NO.:NP_443197; FIG. 22 (SEQ ID NO: 4)), or a protein encoded by a nucleic acid that hybridizes to the human Sen15 encoding nucleic acid (ACCESSION NO.: NM_052965; FIG. 22 (SEQ ID NO: 3)) or its complement under high stringency conditions; (iii) human Sen34 (ACCESSION NO.:NP_076980; FIG. 23 (SEQ ID NO: 6)), or a protein encoded by a nucleic acid that hybridizes to the human Sen34 encoding nucleic acid (ACCESSION NO.: NM_024075; FIG. 23 (SEQ ID NO: 5)) or its complement under high stringency conditions; (iv) Sen54 (ACCESSION NO.:XP_208944 (SEQ ID NO: 94), SEQ ID NO: 8), or a protein encoded by a nucleic acid that hybridizes to the human Sen54 encoding nucleic acid (ACCESSION NO.: XM_208944; FIG. 24 (SEQ ID NO: 7)) or its complement under high stringency conditions. In accordance with these embodiments, the human Sen2deltaEx8 complex cleaves tRNA at multiple sites. These human Sen2deltaEx8 complexes are useful in mapping RNA structure and 3' endonuclease processing.

The invention provides a purified human Sen2deltaEx8 complex with 3' end pre-mRNA endonuclease activity comprising: (i) human Sen2deltaEx8 or a functionally active derivative thereof; (ii) human Sen54 or a functionally active derivative or a functionally active fragment thereof; (iii) human Sen15 or a functionally active derivative or a functionally active fragment thereof; (iv) human Sen34 or a functionally active derivative or a functionally active fragment thereof; and (v) human Clp1 (ACCESSION NO.:NP_006822; FIG. 25 (SEQ ID NO: 10)) or a functionally active derivative or a functionally active fragment thereof. In certain embodiments, the Sen2deltaEx8 complex has RNA-nucleolytic activity. In a specific embodiment the Sen2deltaEx8 complex has tRNA endonuclease and/or 3' end mRNA processing activity. In certain embodiments, the fidelity and accuracy of the tRNA cleavage activity of a Sen2deltaEx8 comprising complex is reduced compared to the tRNA cleavage activity of full length Sen2 comprising complexes. In certain embodiments, the complex may further comprise: (i) human CPSF160 or a functionally active derivative or a functionally active fragment thereof; (ii) human CPSF30 or a functionally active derivative or a functionally active fragment thereof; (iii) human CstF64 or a functionally active derivative or a functionally active fragment thereof; and/or (iv) human symplekin or a functionally active derivative or a functionally active fragment.

The invention also provides a purified human Sen2deltaEx8 complex with 3' end pre-mRNA endonuclease activity comprising: (i) human Sen2deltaEx8 or a functionally active derivative thereof; (ii) human Sen54 or a functionally active derivative or a functionally active fragment thereof; (iii) human Sen15 or a functionally active derivative or a functionally active fragment thereof; (iv) human Sen34 or a functionally active derivative or a functionally active fragment thereof; (v) human Clp1 (ACCESSION NO.:NP_006822; FIG. 25 (SEQ ID NO: 10)) or a functionally active derivative or a functionally active fragment thereof; (vi) human CSPF or a functionally active derivative or a functionally active fragment thereof; (vii) human $CFI_m$ or a functionally active derivative or a functionally active fragment thereof (viii) human $CFII_m$. or a functionally active derivative or a functionally active fragment thereof and (ix) human CstF or a functionally active derivative or a functionally active fragment thereof.

In a specific embodiment, the invention provides a purified human Sen2deltaEx8 complex with 3' end pre-mRNA endonuclease activity comprising: (i) human Sen2deltaEx8 (SEQ ID NO:12), or a protein encoded by a nucleic acid that hybridizes to the human Sen2deltaEx8 encoding nucleic acid (SEQ ID NO:11) or its complement under high stringency conditions; (ii) (ii) human Sen54 (ACCESSION NO.:XP_208944; FIG. 24 SEQ ID NO: 8)), or a protein encoded by a nucleic acid that hybridizes to the human Sen54 encoding nucleic acid (ACCESSION NO.:XM_208944; FIG. 24 (SEQ ID NO: 7)) or its complement under high stringency conditions; (iii) human Sen15 (ACCESSION NO.:NP_443197; FIG. 22 (SEQ ID NO: 4)), or a protein encoded by a nucleic acid that hybridizes to the human Sen15 encoding nucleic acid (ACCESSION NO.:NM_052965; FIG. 22 (SEQ ID NO: 3)) or its complement under high stringency conditions; (iv) human Sen34 (ACCESSION NO.:NP_076980; FIG. 23 SEQ ID NO: 6)), or a protein encoded by a nucleic acid that hybridizes to the human Sen34 encoding nucleic acid (ACCESSION NO.:NM_024075; FIG. 23 (SEQ ID NO: 5)) or its complement under high stringency conditions; and (v) human Clp1 (ACCESSION NO.:NP_006822; FIG. 25 (SEQ ID NO: 10)) or a protein encoded by a nucleic acid that hybridizes to the human Clp1 encoding nucleic acid (ACCESSION NO.: NM_006831; FIG. 25 SEQ ID NO: 9) or its complement under high stringency conditions. In certain embodiments, the complex may further comprise: (i) human CPSF160 or a protein encoded by a nucleic acid that hybridizes to the human CPSF160 encoding nucleic acid; (ii) human CPSF30 or a protein encoded by a nucleic acid that hybridizes to the human CPSF30 encoding nucleic acid; (iii) human CstF64 or a protein encoded by a nucleic acid that hybridizes to the human CstF64 encoding nucleic acid; and/or (iv) human symplekin or a protein encoded by a nucleic acid that hybridizes to the human symplekin encoding nucleic acid.

In another embodiment, the invention provides a purified human Sen2deltaEx8 complex with 3' end pre-mRNA endonuclease activity comprising: (i) human Sen2deltaEx8 (SEQ ID NO: 12), or a protein encoded by a nucleic acid that hybridizes to the human Sen2deltaEx8 encoding nucleic acid (SEQ ID NO: 11) or its complement under high stringency conditions; (ii) human Sen54 (ACCESSION NO.:XP_208944; FIG. 24 (SEQ ID NO: 8)), or a protein encoded by a nucleic acid that hybridizes to the human Sen54 encoding nucleic acid (ACCESSION NO.:XM_208944; FIG. 24 (SEQ ID NO: 7)) or its complement under high stringency conditions; (iii) human Sen15 (ACCESSION NO.:NP_443197; FIG. 22 (SEQ ID NO: 4)), or a protein encoded by a nucleic acid that hybridizes to the human Sen15 encoding nucleic acid (ACCESSION NO.:NM_052965; FIG. 22 (SEQ ID NO: 3)) or its complement under high stringency conditions; (iv) human Sen34 (ACCESSION NO.:NP_076980; FIG. 23 (SEQ ID NO: 6)), or a protein encoded by a nucleic acid that hybridizes to the human Sen34 encoding nucleic acid (ACCESSION NO.:NM_024075; FIG. 23 (SEQ ID NO: 5)) or its complement under high stringency conditions; (v) human Clp1 (ACCESSION NO.:NP_006822; FIG. 25 (SEQ ID NO: 10)) or a protein encoded by a nucleic acid that hybridizes to the human Clp1 encoding nucleic acid (ACCESSION NO.: NM 006831; FIG. 25 (SEQ ID NO: 9)) or its complement under high stringency conditions; (vi) a human CPSF (see Table 1 for accession numbers of components), or proteins encoded by nucleic acids that hybridize to the human CPSF encoding nucleic acids or their complements under high stringency conditions; (vii) a human $CFI_m$ (see Table 1 for accession numbers of components), or proteins encoded by nucleic acids that hybridize to the human $CFI_m$ encoding nucleic acids or their complements under high stringency conditions; (viii) a human $CFII_m$ (see Table 1 for accession numbers of components), or proteins encoded by nucleic acids that hybridize to the human $CFII_m$ encoding nucleic acids or their complements under high stringency conditions; and (ix) human CstF (see Table 1 for accession numbers of components), or proteins encoded by nucleic acids that hybridize to the human CstF encoding nucleic acids or their complements under high stringency conditions.

The invention provides a purified human Sen2deltaEx8 complex with 3' end pre-mRNA endonuclease activity comprising: (i) human Sen2deltaEx8 or a functionally active derivative thereof; (ii) human Sen54 or a functionally active derivative or a functionally active fragment thereof; and (iii) human Clp1 (ACCESSION NO.:NP_006822; FIG. 25 (SEQ ID NO: 10)) or a functionally active derivative or a functionally active fragment thereof. In certain embodiments, the Sen2deltaEx8 complex has RNA-nucleolytic activity. In a specific embodiment the Sen2deltaEx8 complex has tRNA endonuclease and/or 3' end mRNA processing activity. In certain embodiments, the fidelity and accuracy of the tRNA cleavage activity of a Sen2deltaEx8 comprising complex is reduced compared to the tRNA cleavage activity of full length Sen2 comprising complexes. In certain embodiments, the complex may further comprise: (i) human CPSF160 or a functionally active derivative or a functionally active fragment thereof; (ii) human CPSF30 or a functionally active derivative or a functionally active fragment thereof; (iii) human CstF64 or a functionally active derivative or a functionally active fragment thereof; and/or (iv) human symplekin or a functionally active derivative or a functionally active fragment.

In other embodiments, the purified complex further comprises (i) human CPSF or a functionally active derivative or a functionally active fragment thereof; (ii) human CFI, or a functionally active derivative or a functionally active fragment thereof; (iii) human $CFII_m$ or a functionally active derivative or a functionally active fragment thereof; and (iv) human CstF or a functionally active derivative or a functionally active fragment thereof.

In a specific embodiment, the invention provides a purified Sen2deltaEx8 complex with 3' end pre-mRNA endonuclease activity comprising: (i) human Sen2deltaEx8 (SEQ ID NO: 12), or a protein encoded by a nucleic acid that hybridizes to the human Sen2deltaEx8 encoding nucleic acid (SEQ ID NO: 11) or its complement under high stringency conditions; (ii) human Sen54 (ACCESSION NO.:XP_208944; FIG. 24 (SEQ ID NO: 8)), or a protein encoded by a nucleic acid that hybridizes to the human Sen54 encoding nucleic acid (ACCESSION NO.:XM_208944; FIG. 24 (SEQ ID NO: 7)) or its complement under high stringency conditions; and (iii) human Clp1 (ACCESSION NO.:NP_006822; FIG. 25 (SEQ ID NO: 10)) or a protein encoded by a nucleic acid that hybridizes to the human Clp1 encoding nucleic acid (ACCESSION NO.: NM_006831; FIG. 25 (SEQ ID NO: 9)) or its complement under high stringency conditions.

In certain embodiments, the Sen2deltaEx8 complex has RNA-nucleolytic activity. In a specific embodiment the Sen2deltaEx8 complex has tRNA endonuclease and/or 3' end mRNA processing activity. In certain embodiments, the fidelity and accuracy of the tRNA cleavage activity of a Sen2deltaEx8 comprising complex is reduced compared to the tRNA cleavage activity of full length Sen2 comprising complexes. In certain embodiments, the complex may further comprise: (i) human CPSF160 or a protein encoded by a nucleic acid that hybridizes under stringent conditions to a CPSF160 encoding nucleic acid; (ii) human CPSF30 or a protein encoded by a nucleic acid that hybridizes under stringent conditions to a CPSF30 encoding nucleic acid; (iii) human CstF64 or a protein encoded by a nucleic acid that hybridizes under stringent conditions to a CstF60 encoding nucleic acid; and/or (iv) human symplekin or a protein encoded by a nucleic acid that hybridizes under stringent conditions to a symplekin encoding nucleic acid.

In another embodiment, the invention provides a purified Sen2deltaEx8 complex with 3' end pre-mRNA endonuclease activity comprising: (i) human Sen2deltaEx8 (SEQ ID NO:12), or a protein encoded by a nucleic acid that hybridizes to the human Sen2deltaEx8 encoding nucleic acid (SEQ ID NO:11) or its complement under high stringency conditions; (ii) human Sen54 (ACCESSION NO.:XP_208944; FIG. 24 (SEQ ID NO: 8)), or a protein encoded by a nucleic acid that hybridizes to the human Sen54 encoding nucleic acid (ACCESSION NO.:XM_208944; FIG. 24 (SEQ ID NO: 7)) or its complement under high stringency conditions; (iii) human Clp1 (ACCESSION NO.:NP_006822; FIG. 25 (SEQ ID NO: 10)) or a protein encoded by a nucleic acid that hybridizes to the human Clp1 encoding nucleic acid (ACCESSION NO.: NM_006831; FIG. 25 (SEQ ID NO: 9)) or its complement under high stringency conditions; (iv) human CPSF or proteins encoded by nucleic acids that hybridize to the human CPSF encoding nucleic acids or their complements under high stringency conditions; (v) human $CFI_m$ or proteins encoded by nucleic acids that hybridize to the human $CFI_m$ encoding nucleic acids or their complements under high stringency conditions; (vi) human $CF\ II_m$ or proteins encoded by nucleic acids that hybridize to the human $CFII_m$ encoding nucleic acids or their complements under high stringency conditions; and (vii) human CstF or proteins encoded by nucleic acids that hybridize to the human CstF encoding nucleic acids or their complements under high stringency conditions.

CPSF, CstF, CFIm and CFIIm consist of multiple subunits. The accession numbers of the different subunits are set forth in Table 1 in section 4.2.1. CPSF, CstF, CFIm and CFIIm can each comprise a different set of subunits. In a specific embodiment, CPSF comprises the 160 kD factor 1 and the 30 kD factor 4. In a more specific embodiment, CPSF comprises the 160 kD factor 1, the 100 kD factor 2, the 73 kD factor 3, and the 30 kD factor 4. In a specific embodiment, CstF comprises the 50 kD subunit 1, the 64 kD subunit 2, and the 77 kD subunit 3. In a more specific embodiment, CstF comprises the 50 kD subunit 1, the 64 kD subunit 2, the 77 kD subunit 3, and symplekin. In a specific embodiment, CFIm comprises the 68 kD subunit and the 25 kD subunit. In a more specific embodiment, CFIm comprises the 68 kD subunit, the 25 kD subunit, the 59 kD subunit, and the 72 kD subunit. In a specific embodiment, CFIIm comprises Clp1. In a more specific embodiment, CFIIm comprises Clp1 and hPcf11. In another more specific embodiment, CFIIm comprises ClpI, the CFIm 25 kD subunit and the CFIm 68 kD subunit. In even another more specific embodiment, CFIIm comprises ClpI, the CFIm 25 kD subunit and the CFIm 68 kD subunit and hpcf11.

Detailed information on Symplekin can be obtained from the homepage of Dr. Keller's laboratory at the biocentre of the University of Basel and in Takagaki, Y. and J. Manley, 2000, Molecular & Cellular Biol 20:1515-1525.

Wahle and Ruegsegger, 1999, *FEMS Micro Rev.*, 23, 277-295 and Zhoa et al., 1999, *Micoboil. Mol. Biol. Rev.*, 63, 405-445 describe factors involved RNA processing, both references are incorporated herein in their entireties.

In certain embodiments, all subunits of CPSF and CstF, respectively, are present in a complex of the invention.

In certain embodiments, the invention provides complexes wherein the components are homologs or analogs of the human components of the protein complexes of the invention. Homologs or analogs of the human components of a complex of the invention are at least 50%, at least 55%, at least 60%, at least 65%, at least 70%, at least 75%, at least 80%, at least 85%, at least 90%, at least 95%, at least 98%, at least 99% or at least 99.5% identical to a human component of a complex of the invention. Derivatives can be, e.g., fusion proteins, mutant forms of the protein, or forms of the protein with chemical moieties linked to the protein. A fragment of a component of a complex of the invention is a portion of the protein component that maintains the ability of the component to be physically integrated into the complex.

In certain embodiments, the protein components of a complex of the invention are derived from the same species. In more specific embodiments, the protein components are all derived from human. In another specific embodiment, the protein components are all derived from a mammal.

In certain other embodiments, the protein components of a complex of the invention are derived from a non-human species, such as, but not limited to, cow, pig, horse, cat, dog, rat, mouse, a primate (e.g., a chimpanzee, a monkey such as a cynomolgous monkey). In certain embodiments, one or more components are derived from human and the other components are derived from a mammal other than a human to give rise to chimeric complexes.

4.2.3 tRNA Cleavage Complex

The invention provides Sen2deltaEx8 complexes with pre-tRNA cleavage activity.

The invention provides a purified protein complex with pre-tRNA cleavage activity comprising two or more of the following: (i) human Sen2deltaEx8 or a functionally active derivative thereof; (ii) human Sen54 or a functionally active derivative or a functionally active fragment thereof; (iii) human Sen15 or a functionally active derivative or a functionally active fragment thereof; (iv) human Sen34 or a functionally active derivative or a functionally active fragment thereof; and (v) Clp1 or a functionally active derivative or a functionally active fragment thereof.

In certain embodiments, the invention provides complexes comprising two or more of the following: (i) human Sen2deltaEx8 (SEQ ID NO: 12), or a protein encoded by a nucleic acid that hybridizes to the human Sen2deltaEx8 encoding nucleic acid (SEQ ID NO: 11) or its complement under high stringency conditions; (ii) human Sen15 (ACCESSION NO.:NP_443197; FIG. 22 (SEQ ID NO: 4)), or a protein encoded by a nucleic acid that hybridizes to the human Sen15 encoding nucleic acid (ACCESSION NO.: NM_052965; FIG. 22 (SEQ ID NO: 3)) or its complement under high stringency conditions; (iii) human Sen34 (ACCESSION NO.:NP_076980; FIG. 23 (SEQ ID NO: 6)), or a protein encoded by a nucleic acid that hybridizes to the human Sen34 encoding nucleic acid (ACCESSION NO.: NM_024075; FIG. 23 (SEQ ID NO: 5)) or its complement under high stringency conditions; and (iv) human Sen54 (ACCESSION NO.:XP_208944; FIG. 24 (SEQ ID NO: 8)), or a protein encoded by a nucleic acid that hybridizes to the human Sen54 encoding nucleic acid (ACCESSION NO.: XM_208944; FIG. 24 (SEQ ID NO: 7)) or its complement under high stringency conditions.

The invention provides a purified human Sen2deltaEx8 complex with pre-tRNA cleavage activity comprising: (i) human Sen2deltaEx8 or a functionally active derivative thereof; and (ii) human Sen54 or a functionally active derivative or a functionally active fragment thereof. The invention also provides a human Sen2deltaEx8 complex with pre-tRNA cleavage activity comprising: (i) human Sen2deltaEx8 or a functionally active derivative thereof; (ii) human Sen54 or a functionally active derivative or a functionally active fragment thereof; (iii) human Sen15 or a functionally active derivative or a functionally active fragment thereof; and (iv) human Sen34 or a functionally active derivative or a functionally active fragment thereof. These human Sen2deltaEx8 complexes cleave tRNA at multiple sites and are useful in mapping RNA structure and 3' end endonuclease processing.

In a specific embodiment, the invention provides a purified human Sen2deltaEx8 complex with pre-tRNA cleavage activity comprising: (i) human Sen2deltaEx8 (SEQ ID NO:12), or a protein encoded by a nucleic acid that hybridizes to the human Sen2deltaEx8 encoding nucleic acid (SEQ ID NO:11) or its complement under high stringency conditions; and (ii) human Sen15 (ACCESSION NO.:NP_443197; FIG. 22 (SEQ ID NO: 4)), or a protein encoded by a nucleic acid that hybridizes to the human Sen15 encoding nucleic acid (ACCESSION NO.:NM_052965; FIG. 22 (SEQ ID NO: 3)) or its complement under high stringency conditions. In another embodiment, the invention provides a purified human Sen2deltaEx8 complex comprising: (i) human Sen2deltaEx8 (SEQ ID NO:12), or a protein encoded by a nucleic acid that hybridizes to the human Sen2deltaEx8 encoding nucleic acid (SEQ ID NO:11) or its complement under high stringency conditions; (ii) human Sen15 (ACCESSION NO.:NP_443197; FIG. 22 (SEQ ID NO: 4)), or a protein encoded by a nucleic acid that hybridizes to the human Sen15 encoding nucleic acid (ACCESSION NO.:NM_052965; FIG. 22 (SEQ ID NO: 3)) or its complement under high stringency conditions; (iii) human Sen34 (ACCESSION NO.:NP_076980; FIG. 23 (SEQ ID NO: 6)), or a protein encoded by a nucleic acid that hybridizes to the human Sen34 encoding nucleic acid (ACCESSION NO.:NM_024075; FIG. 23 (SEQ ID NO: 5)) or its complement under high stringency conditions; and (iv) Sen54 (ACCESSION NO.:XP_208944; FIG. 24 (SEQ ID NO: 8)), or a protein encoded by a nucleic acid that hybridizes to the human Sen54 encoding nucleic acid (ACCESSION NO.:XM_208944; FIG. 24 (SEQ ID NO: 7)) or its complement under high stringency conditions. In certain embodiments, the Sen2deltaEx8 complex has RNA-nucleolytic activity. In a specific embodiment the Sen2deltaEx8 complex has tRNA endonuclease and/or 3' end mRNA processing activity. In certain embodiments, the fidelity and accuracy of the tRNA cleavage activity of a Sen2deltaEx8 comprising complex is reduced compared to the tRNA cleavage activity of full length Sen2 comprising complexes. In certain embodiments, the complex may further comprise: (i) human CPSF160 or a protein encoded by a nucleic acid that hybridizes under stringent conditions to a CPSF160 encoding nucleic acid; (ii) human CPSF30 or a protein encoded by a nucleic acid that hybridizes under stringent conditions to a CPSF30 encoding nucleic acid; (iii) human CstF64 or a protein encoded by a nucleic acid that hybridizes under stringent conditions to a CstF64 encoding nucleic acid; and/or (iv) human symplekin or a protein encoded by a nucleic acid that hybridizes under stringent conditions to a symplekin encoding nucleic acid. In accordance with these embodiments, the human Sen2deltaEx8 complex cleaves tRNA at multiple sites. These human Sen2deltaEx8 complexes are useful in mapping RNA structure and 3' endonuclease processing.

In certain embodiments, the invention provides complexes wherein the components are homologs or analogs of the human components of the protein complexes of the invention. Homologs or analogs of the human components of a complex of the invention are at least 50%, at least 55%, at least 60%, at least 65%, at least 70%, at least 75%, at least 80%, at least 85%, at least 90%, at least 95%, at least 98%, at least 99% or at least 99.5% identical to a human component of a complex of the invention. Derivatives can be, e.g., fusion proteins, mutant forms of the protein, or forms of the protein with chemical moieties linked to the protein. A fragment of a component of a complex of the invention is a portion of the protein component that maintains the ability of the component to be physically integrated into the complex.

4.2.4 Ribosomal RNA Cleavage Complex

The invention also provides protein complexes with pre-ribosomal RNA cleavage activity. In particular, the invention provides a protein complex with pre-ribosomal RNA cleavage activity comprising: (i) human Sen15 or a functionally active derivative or a functionally active fragment thereof and (ii) human Sen34 or a functionally active derivative or a functionally active fragment thereof. This protein complex may be used in the biogenesis of different ribosomal RNAs. For example, the production of 28S, 18S, 5.5S and 5S ribosomal RNA may be altered by modulating this protein complex.

In particular, the invention provides a complex with pre-ribosomal RNA cleavage activity, wherein the complex comprises: human Sen34 (ACCESSION NO.:NP_076980, (SEQ ID NO: 81), SEQ ID NO: 6), or a protein encoded by a nucleic acid that hybridizes to the human Sen34 encoding nucleic acid (ACCESSION NO.:NP_076980; FIG. 23 (SEQ ID NO: 6)), or a protein encoded by a nucleic acid that hybridizes to the human Sen34 encoding nucleic acid (ACCESSION NO.: NM_024075; FIG. 23 (SEQ ID NO: 5)) or its complement under high stringency conditions; and human Sen15 (ACCESSION NO.:NP_443197; FIG. 22 (SEQ ID NO: 4)), or a protein encoded by a nucleic acid that hybridizes to the human Sen15 encoding nucleic acid (ACCESSION NO.: NM_052965; FIG. 22 (SEQ ID NO: 3)) or its complement under high stringency conditions.

In certain embodiments, the invention provides complexes wherein the components are homologs or analogs of the human components of the protein complexes of the invention. Homologs or analogs of the human components of a complex of the invention are at least 50%, at least 55%, at least 60%, at least 65%, at least 70%, at least 75%, at least 80%, at least 85%, at least 90%, at least 95%, at least 98%, at least 99% or at least 99.5% identical to a human component of a complex of the invention. Derivatives can be, e.g., fusion proteins, mutant forms of the protein, or forms of the protein with chemical moieties linked to the protein. A fragment of a component of a complex of the invention is a portion of the protein component that maintains the ability of the component to be physically integrated into the complex.

In certain embodiments, the protein components of a complex of the invention are derived from the same species. In more specific embodiments, the protein components are all derived from human. In another specific embodiment, the protein components are all derived from a mammal.

In certain other embodiments, the protein components of a complex of the invention are derived from a non-human species, such as, but not limited to, cow, pig, horse, cat, dog, rat, mouse, a primate (e.g., a chimpanzee, a monkey such as a cynomolgous monkey). In certain embodiments, one or more components are derived from human and the other components are derived from a mammal other than a human to give rise to chimeric complexes.

4.3 Generation and Purification of Complexes of the Invention

The complexes of the invention can be generated by any method known to the skilled artisan. In certain embodiments, the complexes can be generated by co-expressing the components of the complex in a cell and subsequently purifying the complex. In certain, more specific embodiments, the cell expresses at least one component of the complex by recombinant DNA technology. In other embodiments, the cells normally express the components of the complex. In certain other embodiments, the components of the complex are expressed separately, wherein the components can be expressed using recombinant DNA technology or wherein at least one component is purified from a cell that normally expresses the component. The individual components of the complex are incubated in vitro under conditions conducive to the binding of the components of a complex of the invention to each other to generate a complex of the invention.

If one or more of the components is expressed by recombinant DNA technology, any method known to the skilled artisan can be used to produce the recombinant protein. The nucleic and amino acid sequences of the component proteins of the protein complexes of the present invention are provided herein (see Table 1; and SEQ ID NOs: 1-12), and can be obtained by any method known in the art, e.g., by PCR amplification using synthetic primers hybridizable to the 3' and 5' ends of each sequence, and/or by cloning from a cDNA or genomic library using an oligonucleotide specific for each nucleotide sequence.

The protein components, either alone or in a complex, can be obtained by methods well known in the art for protein purification and recombinant protein expression. For recombinant expression of one or more of the proteins, the nucleic acid containing all or a portion of the nucleotide sequence encoding the protein can be inserted into an appropriate expression vector, i.e., a vector that contains the necessary elements for the transcription and translation of the inserted protein coding sequence. The necessary transcriptional and translational signals can also be supplied by the native promoter of the component protein gene, and/or flanking regions.

A variety of host-vector systems may be utilized to express the protein coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

In a preferred embodiment, a complex of the present invention is obtained by expressing the entire coding sequences of the component proteins in the same cell, either under the control of the same promoter or separate promoters. In yet another embodiment, a derivative, fragment or homolog of a component protein is recombinantly expressed. Preferably the derivative, fragment or homolog of the protein forms a complex with the other components of the complex. In a specific embodiment, the protein components form a complex that binds to an anti-complex antibody.

Any method available in the art can be used for the insertion of DNA fragments into a vector to construct expression vectors containing a chimeric gene consisting of appropriate transcriptional/translational control signals and protein coding sequences. These methods may include in vitro recombinant DNA and synthetic techniques and in vivo recombinant techniques (genetic recombination). Expression of nucleic acid sequences encoding a component protein, or a derivative, fragment or homolog thereof, may be regulated by a second nucleic acid sequence so that the gene or fragment thereof is expressed in a host transformed with the recombinant DNA molecule(s). For example, expression of the proteins may be controlled by any promoter/enhancer known in the art. In a specific embodiment, the promoter is not native to the genes for the component protein. In certain embodiments, a promoter that may be used is a constitutive promoter. In certain embodiments, a promoter that may be used is a inducible promoter. In certain embodiments, a promoter that may be used is a tissue-specific promoter. Promoters that may be used include but are not limited to the SV40 early promoter (Bernoist and Chambon, 1981, Nature 290:304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. USA 78:1441-1445), the regulatory sequences of the metallothionein gene (Brinster et al., 1982, Nature 296:39-42); prokaryotic expression vectors such as the β-lactamase promoter (VIIIa-Kamaroff et al., 1978, Proc. Natl. Acad. Sci. USA 75:3727-3731) or the tac promoter (DeBoer et al., 1983, Proc. Natl. Acad. Sci. USA 80:21-25; Gilbert et al., 1980, Scientific American 242:79-94); plant expression vectors comprising the nopaline synthetase promoter (Herrar-Estrella et al., 1984, Nature 303:209-213) or the cauliflower mosaic virus 35S RNA promoter (Garder et al., 1981, Nucleic Acids Res. 9:2871), and the promoter of the photosynthetic enzyme ribulose bisphosphate carboxylase (Herrera-Estrella et al., 1984, Nature 310:115-120); promoter elements from yeast and other fungi such as the Ga14 promoter (Johnston et al., 1987, Microbiol. Rev. 51:458-476), the alcohol dehydrogenase promoter (Schibler et al., 1987, Annual Review Genetics 21:237-257), the phosphoglycerol kinase promoter (Struhl et al., 1995, Annual Review Genetics 29:651-674-257; Guarente 1987, Annual Review Genetics 21:425-452), the alkaline phosphatase promoter (Struhl et al., 1995, Annual Review Genetics 29:651-674-257; Guarente 1987, Annual Review Genetics 21:425-452), and the following animal transcriptional control regions that exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald 1987, Hepatology 7:425-515); insulin gene control region which is active in pancreatic beta cells (Hanahan et al., 1985, Nature 315:115-122), immunoglobulin gene control region which is active in lymphoid cells (Grosschedl et al., 1984, Cell 38:647-658; Adams et al., 1985, Nature 318: 533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinckert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58), alpha-1 antitrypsin gene control region which is active in liver (Kelsey et al., 1987, Genes and Devel. 1:161-171), beta globin gene control region which is active in myeloid cells (Mogram et al., 1985, Nature 315:338-340; Kollias et al., 1986, Cell 46:89-94), myelin basic protein gene control region which is active in oligodendrocyte cells of the brain (Readhead et al., 1987, Cell 48:703-712), myosin light chain-2 gene control region which is active in skeletal muscle (Sani 1985, Nature 314:283-286), and gonadotrophic releasing hormone gene control region which is active in gonadotrophs of the hypothalamus (Mason et al., 1986, Science 234: 1372-1378).

In a specific embodiment, a vector is used that comprises a promoter operably linked to nucleic acid sequences encoding a component protein, or a fragment, derivative or homolog thereof, one or more origins of replication, and optionally, one or more selectable markers (e.g., an antibiotic resistance gene). In accordance with this embodiment, a promoter can be any promoter known to the skilled artisan. The promoter can be, but is not limited to be, a constitutive promoter, a tissue-specific promoter or an inducible promoter.

In another specific embodiment, an expression vector containing the coding sequence, or a portion thereof, of a component protein, either together or separately, is made by subcloning the gene sequences into the multiple cloning site of one of the three pGEX vectors (glutathione S-transferase expression vectors; Smith and Johnson, 1988, Gene 7:31-40). Care should be taken that the nucleotide sequence encoding the protein component is in the same reading frame as the nucleotide sequence encoding the GST such that the protein component and the GST are expressed as one fusion protein.

Expression vectors containing the sequences of interest can be identified by three general approaches: (1) nucleic acid hybridization, (2) presence or absence of "marker" gene function, and (3) expression of the inserted sequences. In the first approach, coding sequences can be detected by nucleic acid hybridization to probes comprising sequences homologous and complementary to the inserted sequences. In the second approach, the recombinant vector/host system can be identified and selected based upon the presence or absence of certain "marker" functions (e.g., resistance to antibiotics, occlusion body formation in baculovirus, etc.) caused by insertion of the sequences of interest in the vector. For example, if a component protein gene, or portion thereof, is inserted within the marker gene sequence of the vector, recombinants containing the encoded protein or portion will be identified by the absence of the marker gene function (e.g., loss of beta-galactosidase activity). In the third approach, recombinant expression vectors can be identified by assaying for the component protein expressed by the recombinant vector. Such assays can be based, for example, on the physical or functional properties of the interacting species in in vitro assay systems, e.g., formation of a complex comprising the protein or binding to an anti-complex antibody. The expressed sequences can be detected using antibodies that are specifically directed to the expressed protein component. In certain embodiments, the expressed sequence is a fusion protein of the protein component and comprises a peptide tag, wherein the peptide tag can be visualized, such as a GFP tag.

Once recombinant component protein molecules are identified and the complexes or individual proteins purified, several methods known in the art can be used to propagate them. Using a suitable host system and growth conditions, recombinant expression vectors can be propagated and amplified in quantity. As previously described, the expression vectors or derivatives which can be used include, but are not limited to, human or animal viruses such as vaccinia virus or adenovirus; insect viruses such as baculovirus, yeast vectors; bacteriophage vectors such as lambda phage; and plasmid and cosmid vectors.

In addition, a host cell strain may be chosen that modulates the expression of the inserted sequences, or modifies or processes the expressed proteins in the specific fashion desired. Expression from certain promoters can be elevated in the presence of certain inducers; thus expression of the genetically-engineered component proteins may be controlled. Furthermore, different host cells have characteristic and specific mechanisms for the translational and post-translational processing and modification (e.g., glycosylation, phosphorylation, etc.) of proteins. Appropriate cell lines or host systems can be chosen to ensure that the desired modification and processing of the foreign protein is achieved. For example, expression in a bacterial system can be used to produce an unglycosylated core protein, while expression in mammalian cells ensures "native" glycosylation of a heterologous protein. Furthermore, different vector/host expression systems may effect processing reactions to different extents.

In other specific embodiments, a component protein or a fragment, homolog or derivative thereof, may be expressed as fusion or chimeric protein product comprising the protein, fragment, homolog, or derivative joined via a peptide bond to a heterologous protein sequence. Such chimeric products can be made by ligating the appropriate nucleic acid sequences encoding the desired amino acids to each other by methods known in the art, in the proper coding frame, and expressing the chimeric products in a suitable host by methods commonly known in the art. Alternatively, such a chimeric product can be made by protein synthetic techniques, e.g., by use of a peptide synthesizer. Chimeric genes comprising a portion of a component protein fused to any heterologous protein-encoding sequences may be constructed.

In a specific embodiment, fusion proteins are provided that contain the interacting domains of the component proteins and, optionally, a peptide linker between the two domains, where such a linker promotes the interaction of the binding domains. These fusion proteins may be particularly useful where the stability of the interaction is desirable (due to the formation of the complex as an intra-molecular reaction), for example, in production of antibodies specific to the complex.

In particular, protein component derivatives can be made by altering their sequences by substitutions, additions or deletions that provide for functionally equivalent molecules. Due to the degeneracy of nucleotide coding sequences, other DNA sequences that encode substantially the same amino acid sequence as a component gene or cDNA can be used in the practice of the present invention. These include but are not limited to nucleotide sequences comprising all or portions of the component protein gene that are altered by the substitution of different codons that encode a functionally equivalent amino acid residue within the sequence, thus producing a silent change. Likewise, the derivatives of the invention include, but are not limited to, those containing, as a primary amino acid sequence, all or part of the amino acid sequence of a component protein, including altered sequences in which functionally equivalent amino acid residues are substituted for residues within the sequence resulting in a silent change. For example, one or more amino acid residues within the sequence can be substituted by another amino acid of a similar polarity that acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

The protein component derivatives and analogs of the invention can be produced by various methods known in the art. The manipulations which result in their production can occur at the gene or protein level. For example, the cloned gene sequences can be modified by any of numerous strategies known in the art (Sambrook et al., 1989, Molecular Cloning, A Laboratory Manual, 2d Ed., Cold Spring Harbor Laboratory Press, Cold Spring Harbor, N.Y.). The sequences can be cleaved at appropriate sites with restriction endonuclease(s), followed by further enzymatic modification if desired, isolated, and ligated in vitro. In the production of the gene encoding a derivative, homolog or analog of a component protein, care should be taken to ensure that the modified gene retains the original translational reading frame, uninterrupted by translational stop signals, in the gene region where the desired activity is encoded.

Additionally, the encoding nucleic acid sequence can be mutated in vitro or in vivo, to create and/or destroy translation, initiation, and/or termination sequences, or to create variations in coding regions and/or form new restriction endonuclease sites or destroy pre-existing ones, to facilitate further in vitro modification. Any technique for mutagenesis known in the art can be used, including but not limited to, chemical mutagenesis and in vitro site-directed mutagenesis (Hutchinson et al., 1978, J. Biol. Chem. 253:6551-6558), amplification with PCR primers containing a mutation, use of chimeric oligonucleotides, etc.

Once a recombinant cell expressing a component protein, or fragment or derivative thereof, is identified, the individual gene product or complex can be purified and analyzed. This is achieved by assays based on the physical and/or functional properties of the protein or complex, including, but not limited to, radioactive labeling of the product followed by analysis by gel electrophoresis, immunoassay, cross-linking to marker-labeled product, etc.

The component proteins and complexes may be purified by standard methods known in the art (either from natural sources or recombinant host cells expressing the complexes or proteins), including but not restricted to column chromatography (e.g., ion exchange, affinity, gel exclusion, reversed-phase high pressure, fast protein liquid, etc.), differential centrifugation, differential solubility, or by any other standard technique used for the purification of proteins. Functional properties may be evaluated using any suitable assay known in the art. For a more detailed description of purification procedures of the components and the complexes of the invention, see below.

Alternatively, once a component protein or its derivative, is identified, the amino acid sequence of the protein can be deduced from the nucleic acid sequence of the chimeric gene from which it was encoded. As a result, the protein or its derivative can be synthesized by standard chemical methods known in the art (e.g., Hunkapiller et al., 1984, Nature 310: 105-111).

Manipulations of component protein sequences may be made at the protein level. Included within the scope of the invention is a complex in which the component proteins or derivatives and analogs that are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc.

In specific embodiments, the amino acid sequences are modified to include a fluorescent label. In another specific embodiment, the protein sequences are modified to have a heterofunctional reagent; such heterofunctional reagents can be used to crosslink the members of the complex.

In addition, complexes of analogs and derivatives of component proteins can be chemically synthesized. For example, a peptide corresponding to a portion of a component protein, which comprises the desired domain or mediates the desired activity in vitro (e.g., complex formation) can be synthesized by use of a peptide synthesizer. Furthermore, if desired, non-classical amino acids or chemical amino acid analogs can be introduced as a substitution or addition into the protein sequence. Non-classical amino acids include but are not limited to the D-isomers of the common amino acids, α-amino isobutyric acid, 4-aminobutyric acid (4-Abu), 2-aminobutyric acid (2-Abu), 6-amino hexanoic acid (Ahx), 2-amino isobutyric acid (2-Aib), 3-amino propionoic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

In cases where natural products are suspected of being mutant or are purified from new species, the amino acid sequence of a component protein purified from the natural source, as well as those expressed in vitro, or from synthesized expression vectors in vivo or in vitro, can be determined from analysis of the DNA sequence, or alternatively, by direct sequencing of the purified protein. Such analysis can be performed by manual sequencing or through use of an automated amino acid sequenator.

The complexes can also be analyzed by hydrophilicity analysis (Hopp and Woods, 1981, Proc. Natl. Acad. Sci. USA 78:3824-3828). A hydrophilicity profile can be used to identify the hydrophobic and hydrophilic regions of the proteins, and help predict their orientation in designing substrates for experimental manipulation, such as in binding experiments, antibody synthesis, etc. Secondary structural analysis can also be done to identify regions of the component proteins, or their derivatives, that assume specific structures (Chou and Fasman, 1974, Biochemistry 13:222-23). Manipulation, translation, secondary structure prediction, hydrophilicity and hydrophobicity profile predictions, open reading frame prediction and plotting, and determination of sequence homologies, etc., can be accomplished using computer software programs available in the art.

Other methods of structural analysis including but not limited to X-ray crystallography (Engstrom, 1974 Biochem. Exp. Biol. 11:7-13), mass spectroscopy and gas chromatography (Methods in Protein Science, J. Wiley and Sons, New York, 1997), and computer modeling (Fletterick and Zoller, eds., 1986, Computer Graphics and Molecular Modeling, In: Current Communications in Molecular Biology, Cold Spring Harbor Laboratory, Cold Spring Harbor Press, New York) can also be employed.

In certain embodiments, at least one component of the complex is generated by recombinant DNA technology and is a derivative of the naturally occurring protein. In certain embodiments, the derivative is a fusion protein, wherein the amino acid sequence of the naturally occurring protein is fused to a second amino acid sequence. The second amino acid sequence can be a peptide tag that facilitates the purification, immunological detection and identification as well as visualization of the protein. A variety of peptide tags with different functions and affinities can be used in the invention to facilitate the purification of the component or the complex comprising the component by affinity chromatography. A specific peptide tag comprises the constant regions of an immunoglobulin. In other embodiments, the component is fused to a leader sequence to promote secretion of the protein component from the cell that expresses the protein component. Other peptide tags that can be used with the invention include, but are not limited to, FLAG epitope or polyHistidine tag, e.g., Hisx6 tag.

If the components of the complex are co-expressed, the complex can be purified by any method known to the skilled artisan, including immunoprecipitation, ammonium sulfate precipitation, acid extraction, anion or cation exchange chromatography, phosphocellulose chromatography, immuno affinity chromatography, hydroxyapatite chromatography, and lectin chromatography.

The methods described herein can be used to purify the individual components of the complex of the invention. The methods can also be used to purify the entire complex. Generally, the purification conditions as well as the dissociation constant of the complex will determine whether the complex remains intact during the purification procedure. Such conditions include, but are not limited to, salt concentration, detergent concentration, pH and redox-potential.

If at least one component of the complex comprises a peptide tag, the invention the invention also contemplates methods for the purification of the complexes of the invention which are based on the properties of the peptide tag. One approach is based on specific molecular interactions between a tag and its binding partner. The other approach relies on the immunospecific binding of an antibody to an epitope present on the tag. The principle of affinity chromatography well known in the art is generally applicable to both of these approaches. In another embodiment, the complex is purified using immunoprecipitation.

Described in section 4.3.5 below are several methods based on specific molecular interactions of a tag and its binding partner. The embodiments described in section 4.3.5 may be used to recover and purify protein components of the complex separately or to recover and purify the complexes of the invention. Methods that do not require lowering pH or denaturing conditions are most preferred for purification of the complexes.

In certain embodiments, the individual components of a complex of the invention are expressed separately. The components are subsequently incubated under conditions conducive to the binding of the components of the complex to each other to generate the complex. In certain, more specific embodiments, the components are purified before complex-formation. In other embodiments the supernatants of cells that express the component (if the component is secreted) or cell lysates of cells that express the component (if the component is not secreted) are combined first to give rise to the complex, and the complex is purified subsequently. Parameters affecting the ability of the components of the invention to bind to each other include, but are not limited to, salt concentration, detergent concentration, pH, and redox-potential. Once the complex has formed, the complex can be purified or concentrated by any method known to the skilled artisan. In certain embodiments, the complex is separated from the remaining individual components by filtration. The pore size of the filter should be such, that the individual components can still pass through the filter, but the complex does not pass through the filter. Other methods for enriching the complex include sucrose gradient centrifugation and chromatography.

4.3.1 Homologs, Derivatives and Fragments of the Components

In certain embodiments, at least one component of a complex of the invention is a homolog, a derivative, e.g., a functionally active derivative, a fragment, e.g., a functionally active fragment, of a protein component of a complex of the invention. In certain embodiments of the invention, a homolog, derivative or fragment of a protein component of a complex of the invention is still capable of forming a complex with the other component(s). Complex-formation can be tested by any method known to the skilled artisan. Such methods include, but are not limited to, non-denaturing PAGE, FRET, and Fluorescence Polarization Assay.

In certain embodiments, a fragment of a protein component of the complex consists of at least 6 (continuous) amino acids, of at least 10, at least 20 amino acids, at least 30 amino acids, at least 40 amino acids, at least 50 amino acids, at least 75 amino acids, at least 100 amino acids, at least 150 amino acids, at least 200 amino acids, at least 250 amino acids, at least 300 amino acids, at least 400 amino acids, or at least 500 amino acids of the protein component of the naturally occurring proteins. In specific embodiments, such fragments are not larger than 40 amino acids, 50 amino acids, 75 amino acids, 100 amino acids, 150 amino acids, 200 amino acids, 250 amino acids, 300 amino acids, 400 amino acids, or than 500 amino acids. In more specific embodiments, the functional fragment is capable of forming a complex of the invention, i.e., the fragment can still bind to at least one other protein component to form a complex of the invention.

Derivatives or analogs of component proteins include, but are not limited, to molecules comprising regions that are substantially homologous to the component proteins, in various embodiments, by at least 30%, 40%, 50%, 60%, 70%, 80%, 90% or 95% identity over an amino acid sequence of identical size or when compared to an aligned sequence in which the alignment is done by a computer homology program known in the art, or whose encoding nucleic acid is capable of hybridizing to a sequence encoding the component protein under stringent, moderately stringent, or nonstringent conditions.

Derivatives or analogs of component proteins also include, but are not limited, to molecules that (i) comprise regions that are substantially homologous to the component proteins, in various embodiments, by at least 30%, 40%, 50%, 60%, 70%, 80%, 90% or 95% identity over an amino acid sequence of identical size or when compared to an aligned sequence in which the alignment is done by a computer homology program known in the art, or whose encoding nucleic acid is capable of hybridizing to a sequence encoding the component protein under stringent, moderately stringent, or nonstringent conditions; (ii) are capable of forming a complex of the invention. Further, derivatives or analogs of component proteins also include, but are not limited, to molecules that comprise regions that are substantially homologous to the component proteins, in various embodiments, by at least 30%, 40%, 50%, 60%, 70%, 80%, 90% or 95% identity over an amino acid sequence of identical size or when compared to an aligned sequence in which the alignment is done by a computer homology program known in the art, or whose encoding nucleic acid is capable of hybridizing to a sequence encoding the component protein under stringent, moderately stringent, or nonstringent conditions and wherein a complex that comprises the derivative has RNA-nucleolytic activity (e.g., the pre-tRNA splicing endonuclease activity, the 3' end pre-mRNA endonuclease activity, the pre-tRNA cleavage activity of a complex of the invention, and/or the pre-ribosomal RNA cleavage activity of a complex of the invention).

Derivatives of a protein component include, but are not limited to, fusion proteins of a protein component of a complex of the invention to a heterologous amino acid sequence, mutant forms of a protein component of a complex of the invention, and chemically modified forms of a protein component of a complex of the invention. In a specific embodiment, the functional derivative of a protein component of a complex of the invention is capable of forming a complex of the invention, i.e., the derivative can still bind to at least one other protein component to form a complex of the invention.

Homologs (e.g., nucleic acids encoding component proteins from other species) or other related sequences (e.g., paralogs) which are members of a native cellular protein complex can be identified and obtained by low, moderate or high stringency hybridization with all or a portion of the particular nucleic acid sequence as a probe, using methods well known in the art for nucleic acid hybridization and cloning.

In certain embodiments, a homolog of a first protein binds to the same proteins to which the first protein binds. In certain, more specific embodiments, a homolog of a first protein binds to the same proteins to which the first protein binds wherein the binding affinity between the homolog and the binding partner of the first protein is at least 10%, at least 20%, at least 30%, at least 40%, at least 50%, at least 60%, at least 70%, at least 80%, at least 90%, at least 95% or at least 98% of the binding affinity between the first protein and the binding partner. Binding affinities between proteins can be determined by any method known to the skilled artisan.

It is well-known to the skilled artisan that hybridization conditions, such as, but not limited to, temperature, salt concentration, pH, formamide concentration (see, e.g., Sambrook et al., 1989, Chapters 9 to 11, Molecular Cloning, A Laboratory Manual, 2d Ed., Cold Spring Harbor Laboratory Press, Cold Spring Harbor, N.Y.). In certain embodiments, hybridization is performed in aqueous solution and the ionic strength of the solution is kept constant while the hybridization temperature is varied dependent on the degree of sequence homology between the sequences that are to be hybridized. For DNA sequences that 100% identical to each other and are longer than 200 basebairs, hybridization is carried out at approximately 15-25° C. below the melting temperature ($T_m$) of the perfect hybrid. The melting temperature ($T_m$) can be calculated using the following equation (Bolton and McCarthy, Proc. Natl. Acad. Sci. USA 84:1390 (1962)):

$$T_m = 81.5° C. - 16.6(\log_{10}[Na^+]) + (\% G+C) - 0.63(\% \text{ formamide}) - (600/l)$$

Wherein ($T_m$) is the melting temperature, [$Na^+$] is the sodium concentration, G+C is the Guanine and Cytosine content, and l is the length of the hybrid in basepairs. The effect of mismatches between the sequences can be calculated using the formula by Bonner et al. (Bonner et al., 1973, J. Mol. Biol. 81:123-135): for every 1% of mismatching of bases in the hybrid, the melting temperature is reduced by 1-1.5° C.

Thus, by determining the hybridization temperature of the hybrid of two sequences with a certain percentage of homology to each other and comparing the determined hybridization temperature with the temperature at which the perfect hybrids of the two sequences form allows to estimate the difference in sequence between the two sequences.

By way of example and not limitation, procedures using such conditions of high stringency are as follows. Prehybridization of filters containing DNA is carried out for 8 h to overnight at 65 C in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65 C in prehybridization mixture containing 100 µg/ml denatured salmon sperm DNA and 5–20×106 cpm of $^{32}$P-labeled probe. Washing of filters is done at 37 C for 1 h in a solution containing 2×SSC, 0.01% PVP, 0.01% Ficoll, and 0.01% BSA. This is followed by a wash in 0.1×SSC at 50 C for 45 min before autoradiography. Other conditions of high stringency which may be used are well known in the art. Alternatively, another system for high stringency is as follows: hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3). Other conditions of high stringency which may be used are well known in the art.

In other embodiments of the invention, hybridization is performed under moderate or low stringency conditions, such conditions are well-known to the skilled artisan (see e.g., Sambrook et al., 1989, Molecular Cloning, A Laboratory Manual, 2d Ed., Cold Spring Harbor Laboratory Press, Cold Spring Harbor, N.Y.; see also, Ausubel et al., eds., in the Current Protocols in Molecular Biology series of laboratory technique manuals, 1987-1997 Current Protocols,© 1994-1997 John Wiley and Sons, Inc.). An illustrative low stringency condition is provided by the following system of buffers: hybridization in a buffer comprising 35% formamide, 5×SSC, 50 mM Tris-HCl (pH 7.5), 5 mM EDTA, 0.02% PVP, 0.02% Ficoll, 0.2% BSA, 100 µg/ml denatured salmon sperm DNA, and 10% (wt/vol) dextran sulfate for 18-20 hours at 40° C., washing in a buffer consisting of 2×SSC, 25 mM Tris-HCl (pH 7.4), 5 mM EDTA, and 0.1% SDS for 1.5 hours at 55° C., and washing in a buffer consisting of 2×SSC, 25 mM Tris-HCl (pH 7.4), 5 mM EDTA, and 0.1% SDS for 1.5 hours at 60° C.

Exemplary moderately stringent hybridization conditions are as follows: prehybridization of filters containing DNA is carried out for 8 hours to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/mf, denatured salmon sperm DNA. Filters are hybridized for 48 hours at 65° C. in prehybridization mixture containing 100 µg/ml denatured salmon sperm DNA and 5-20×10$^6$ cpm of $^{32}$P-labeled probe. Washing of filters is done at 37° C. for 1 hour in a solution containing 2×SSC, 0.01% PVP, 0.01% Ficoll, and 0.01% BSA. This is followed by a wash in 0.1×SSC at 50° C. for 45 min before autoradiography.

4.3.2 Intersubunit Crosslinks

In certain embodiments of the invention, at least two components of a complex of the invention are linked to each other via at least one covalent bond. A covalent bond between components of a complex of the invention increases the stability of the complex of the invention because it prevents the dissociation of the components. Any method known to the skilled artisan can be used to achieve a covalent bond between at least two components of the invention.

In specific embodiments, covalent cross-links are introduced between adjacent subunits. Such cross-links can be between the sidechains of amino acids at opposing sides of the dimer interface. Any functional groups of amino acid residues at the dimer interface in combination with suitable cross-linking agents can be used to create covalent bonds between the protein components at the dimer interface. Existing amino acids at the dimer interface can be used or, alternatively, suitable amino acids can be introduced by site-directed mutagenesis.

In exemplary embodiments, cysteine residues at opposing sides of the dimer interface are oxidized to form disulfide bonds. See, e.g., Reznik et al., 1996, Nature Biotechnology 14:1007-1011, at page 1008. 1,3-dibromoacetone can also be used to create an irreversible covalent bond between two sulfhydryl groups at the dimer interface. In certain other embodiments, lysine residues at the dimer interface are used to create a covalent bond between the protein components of the complex. Crosslinkers that can be used to create covalent bonds between the epsilon amino groups of lysine residues are, e.g., but are not limited to, bis(sulfosuccinimidyl)suberate; dimethyladipimidate-2HDl; disuccinimidyl glutarate; N-hydroxysuccinimidyl 2,3-dibromoproprionate.

4.3.3 Fusion Complexes

In specific embodiments, at least two components of a complex of the invention are expressed as a fusion protein, i.e., fusion complexes. Any recombinant DNA technology known to the skilled artisan can be used to construct the DNA encoding the fusion complex. Care should be taken that the two or more open reading frames are cloned in frame with each other. Any method known to the skilled artisan can be used to express and purify the fusion protein. Exemplary methods are discussed herein. In certain, more specific embodiments, the two components that form the fusion protein are connected to each other via a linker peptide. Thus, the fusion complex is encoded by the ORF for the first component protein, the ORF encoding the linker peptide, and the ORF encoding the second component protein. Without being bound by theory, the linker peptide retains the two components of the complex in close spatial proximity, thus increasing the rate of binding of the two components to each other and thereby stabilizing the complex of the invention.

4.3.4 Peptide Tag and/or Leader Peptide Fusion

The protein components of the complexes of the invention can be fusion proteins comprising a peptide tag. In certain embodiments, a leader peptide may also be fused to a protein component thereby facilitating the transport of the protein component into the endoplasmic reticulum (ER) for secretion.

In various embodiments, such a fusion protein can be made by ligating a gene sequence encoding a protein component of a complex of the invention to the sequence encoding the peptide tag or the leader peptide in the proper reading frame. If genomic sequences are used, care should be taken to ensure that the modified gene remains within the same translational reading frame, uninterrupted by translational stop signals and/or spurious messenger RNA splicing signals.

In a specific embodiment, the peptide tag is fused at its amino terminal to the carboxyl terminal of the ORF for the protein component. The precise site at which the fusion is made in the carboxyl terminal is not critical. For example, the peptide tag may replace part of the ORF encoding the protein component. The optimal site can be determined by routine experimentation.

A variety of peptide tags known in the art may be used to generate fusion proteins of the protein components of a complex of the invention, such as but not limited to the immunoglobulin constant regions, polyhistidine sequence (Petty, 1996, Metal-chelate affinity chromatography, in Current Protocols in Molecular Biology, Vol. 2, Ed. Ausubel et al., Greene Publish. Assoc. & Wiley Interscience), glutathione S-transferase (GST; Smith, 1993, Methods Mol. Cell. Bio. 4:220-229), the E. coli maltose binding protein (Guan et al., 1987, Gene 67:21-30), and various cellulose binding domains (U.S. Pat. Nos. 5,496,934; 5,202,247; 5,137,819; Tomme et al., 1994, Protein Eng. 7:117-123), etc. Some peptide tags may afford the fusion protein novel structural properties, such as the ability to form multimers. Peptide tags that promote homodimerization or homopolymerization are usually derived from proteins that normally exist as homopolymers. Peptide tags such as the extracellular domains of CD8(Shiue et al., 1988, J. Exp. Med. 168:1993-2005), or CD28 (Lee et al., 1990, J. Immunol. 145:344-352), or portions of the immunoglobulin molecule containing sites for interchain disulfide bonds, could lead to the formation of multimers. In certain embodiments, the formation of homodimers or homomultimers can interfere with the formation of a complex of the invention. If this is the case, peptide tags that do not promote the formation of homodimers or homomultimers should be used.

Other possible peptide tags are short amino acid sequences to which monoclonal antibodies are available, such as but not limited to the following well known examples, the FLAG epitope, the myc epitope at amino acids 408-439, the influenza virus hemaglutinin (HA) epitope. Other peptide tags are recognized by specific binding partners and thus facilitate isolation by affinity binding to the binding partner, which is preferably immobilized and/or on a solid support. As will be appreciated by those skilled in the art, many methods can be used to obtain the coding region of the above-mentioned peptide tags, including but not limited to, DNA cloning, DNA amplification, and synthetic methods. Some of the peptide tags and reagents for their detection and isolation are available commercially.

In certain embodiments, a combination of different peptide tags is used for the purification of the protein components of a complex of the invention or for the purification of a complex. In certain embodiments, at least one component has at least two peptide tags, e.g., a FLAG tag and a His tag. The different tags can be fused together or can be fused in different positions to the protein component. In the purification procedure, the different peptide tags are used subsequently or concurrently for purification. In certain embodiments, at least two different components are fused to a peptide tag, wherein the peptide tags of the two components can be identical or different. Using different tagged components for the purification of the complex ensures that only complex will be purified and minimizes the amount of uncomplexed protein components, such as monomers or homodimers.

A specific peptide tag is a non-variable portion of the immunoglobulin molecule. Typically, such portions comprises at least a functionally CH2 and CH3 domains of the constant region of an immunoglobulin heavy chain. Fusions are also made using the carboxyl terminus of the Fc portion of a constant domain, or a region immediately amino-terminal to the CH1 of the heavy or light chain. Suitable immunoglobulin-based peptide tag may be obtained from IgG-1, -2, -3, or -4 subtypes, IgA, IgE, IgD, or IgM, but preferably IgG1. Preferably, a human immunoglobulin is used when the protein component is intended for in vivo use for humans. DNA sequences encoding immunoglobulin light or heavy chain constant regions are well-known or readily available from cDNA libraries. In a specific embodiment, such DNA sequences can be amplified using PCR. See, for example, Adams et al., Biochemistry, 1980, 19:2711-2719; Gough et al., 1980, Biochemistry, 19:2702-2710; Dolby et al., 1980, Proc. Natl. Acad. Sci. U.S.A., 77:6027-6031; Rice et al., 1982, Proc. Natl. Acad. Sci. U.S.A., 79:7862-7865; Falkner et al., 1982, Nature, 298:286-288; and Morrison et al., 1984, Ann. Rev. Immunol, 2:239-256. Because many immunological reagents and labeling systems are available for the detection of immunoglobulins, the fusion protein of a protein component of a complex of the invention can readily be detected and quantified by a variety of immunological techniques known in the art, such as the use of enzyme-linked immunosorbent assay (ELISA), immunoprecipitation, fluorescence activated cell sorting (FACS), etc. Similarly, if the peptide tag is an epitope with readily available antibodies, such reagents can be used with the techniques mentioned above to detect, quantitate, and isolate the fusion protein component of a complex of the invention containing the peptide tag.

In a specific embodiment, a protein component is fused to the hinge, CH2 and CH3 domains of murine immunoglobulin G-1 (IgG-1)(Bowen et al., J. Immunol. 156:442-9). This peptide contains three cysteine residues which are normally involved in disulfide bonding with other cysteines in the Ig molecule. Since none of the cysteines are required for the peptide to function as a tag, one or more of these cysteine residues may optionally be substituted by another amino acid residue, such as for example, serine.

Various leader sequences known in the art can be used for the efficient secretion of a protein component of a complex of the invention from bacterial and mammalian cells (von Heijne, 1985, J. Mol. Biol. 184:99-105). Leader peptides are selected based on the intended host cell, and may include bacterial, yeast, viral, animal, and mammalian sequences. For example, the herpes virus glycoprotein D leader peptide is suitable for use in a variety of mammalian cells. A preferred leader peptide for use in mammalian cells can be obtained from the V-J2-C region of the mouse immunoglobulin kappa chain (Bernard et al., 1981, Proc. Natl. Acad. Sci. 78:5812-5816).

DNA sequences encoding desired peptide tag or leader peptide which are known or readily available from libraries or commercial suppliers are suitable in the practice of this invention.

4.3.5 Purification of Complexes of the Invention

The complexes of the invention can be purified by any method known to the skilled artisan. The methods described for the purification of a complex may also be used to purify individual protein components. In certain embodiments, the complex is formed in the expression system itself, wherein the expression system can be, e.g., a cell or a cell-free expression system (such as a TNT® Coupled Reticulocyte Lysate System, which is commercially available from Promega Corporation, Madison Wis.). Once the protein components are expressed and the complex is formed, the complex is purified from the other components of the expression system and the individual protein components by any method known to the skilled artisan. If the expression system is a cell, the cell is lysed once the protein components are expressed and once the complex is formed, the protein complex of the invention is then purified from the lysate. In certain other embodiments, the protein components of a complex of the invention are expressed and purified individually and subsequently the purified components are combined to form the complex. The individual protein components can be purified by any method known to the skilled artisan.

In certain embodiments, the complex is purified via affinity chromatography using antibodies that are specific to the complex. In other embodiments, the complex is purified by performing subsequent purification steps wherein each step requires the presence of a different protein component in the complex to ensure that the purified complex is free of any monomeric protein components. Each individual purification step can be, e.g., based on the peptide tag of a protein component (for a more detailed description of the use of peptide tags in protein purification see below) or an affinity purification using antibodies specific to the protein component. Care should be taken that the antibodies to be used for the purification of the complex are not directed to epitopes that are located at the binding interface of the protein component.

In certain embodiments, a complex of the invention is purified via a protein tag that is fused to at least one of the protein components of the complex. In more specific embodiments, two protein components of a complex are fused to a peptide tag and one protein component is fused to a peptide tag different from the peptide tag to which the other protein component is fused. The complex is first purified via the one and subsequently via the other peptide tag to ensure that the purified complex is free from any monomeric protein components.

A method that is generally applicable to purifying a protein component that is fused to the constant regions of immunoglobulin or a complex that comprises a component that is fused to the constant regions of immunoglobulin is protein A affinity chromatography, a technique that is well known in the art. Staphylococcus protein A is a 42 kD polypeptide that binds specifically to a region located between the second and third constant regions of heavy chain immunoglobulins. Because of the Fc domains of different classes, subclasses and species of immunoglobulins, affinity of protein A for human Fc regions is strong, but may vary with other species. Subclasses that are less preferred include human IgG-3, and most rat subclasses. For certain subclasses, protein G (of Streptococci) may be used in place of protein A in the purification. Protein-A sepharose (Pharmacia or Biorad) is a commonly used solid phase for affinity purification of antibodies, and can be used essentially in the same manner for the purification of a protein component fused to an immunoglobulin Fc fragment. The protein component that is fused to the constant regions of immunoglobulin or a complex that comprises a component that is fused to the constant regions of immunoglobulin binds specifically to protein A on the solid phase, while the contaminants are washed away. Bound protein component that is fused to the constant regions of immunoglobulin or a complex that comprises a component that is fused to the constant regions of immunoglobulin can be eluted by various buffer systems known in the art, including a succession of citrate, acetate and glycine-HCl buffers which gradually lowers the pH. This method is less preferred if the recombinant cells also produce antibodies which will be copurified with the protein component that is fused to the constant regions of immunoglobulin or a complex that comprises a component that is fused to the constant regions of immunoglobulin. See, for example, Langone, 1982, J. Immunol. meth. 51:3; Wilchek et al., 1982, Biochem. Intl. 4:629; Sjobring et al., 1991, J. Biol. Chem. 26:399; page 617-618, in Antibodies A Laboratory Manual, edited by Harlow and Lane, Cold Spring Harbor laboratory, 1988.

Alternatively, a polyhistidine tag may be used, in which case, the protein component that is fused to the polyhistidine tag or a complex that comprises a component that is fused to the polyhistidine tag can be purified by metal chelate chromatography. The polyhistidine tag, usually a sequence of six histidines, has a high affinity for divalent metal ions, such as nickel ions ($Ni^{2+}$), which can be immobilized on a solid phase, such as nitrilotriacetic acid-matrices. Polyhistidine has a well characterized affinity for $Ni^{2+}$-NTA-agarose, and can be eluted with either of two mild treatments: imidazole (0.1-0.2 M) will effectively compete with the resin for binding sites; or lowering the pH just below 6.0 will protonate the histidine sidechains and disrupt the binding. The purification method comprises loading the cell culture supernatant onto the $Ni^{2+}$-NTA-agarose column, washing the contaminants through, and eluting the protein component that is fused to the polyhistidine tag or a complex that comprises a component that is fused to the polyhistidine tag with imidazole or weak acid. $Ni^{2+}$-NTA-agarose can be obtained from commercial suppliers such as Sigma (St. Louis) and Qiagen. Antibodies that recognize the polyhistidine tag are also available which can be used to detect and quantitate the protein component that is fused to the polyhistidine tag or a complex that comprises a component that is fused to the polyhistidine tag.

Another exemplary peptide tag that can be used is the glutathione-S-transferase (GST) sequence, originally cloned from the helminth, Schistosoma japonicum. In general, a protein component-GST fusion or a complex comprising a protein component-GST fusion expressed in a host cell can be purified from the cell culture supernatant by absorption with glutathione agarose beads, followed by elution in the presence of free reduced glutathione at neutral pH. Denaturing conditions are not required at any stage during purification, and therefore, it may be desirable for the purification of the complex. Moreover, since GST is known to form dimers under certain conditions, dimeric protein components may be obtained. See, Smith, 1993, Methods Mol. Cell. Bio. 4:220-229.

Another useful peptide tag that can be used is the maltose binding protein (MBP) of *E. coli*, which is encoded by the malE gene. The protein component-MBP fusion protein or the complex comprising a component-MPP fusion protein binds to amylose resin while contaminants are washed away. The bound modified protein component-MBP is eluted from the amylose resin by maltose. See, for example, Guan et al., 1987, Gene 67:21-30.

The second approach for purifying protein component fusion proteins is applicable to peptide tags that contain an epitope for which polyclonal or monoclonal antibodies are available. Various methods known in the art for purification of protein by immunospecific binding, such as immunoaffinity chromatography, and immunoprecipitation, can be used. See, for example, Chapter 13 in Antibodies A Laboratory Manual, edited by Harlow and Lane, Cold Spring Harbor laboratory, 1988; and Chapter 8, Sections I and II, in Current Protocols in Immunology, ed. by Coligan et al., John Wiley, 1991; the disclosure of which are both incorporated by reference herein.

A protein component of a complex of the invention can also be purified by immunoaffinity chromatography or immunoprecipitation using antibodies that are specific to the component. Likewise, a complex of the invention can be purified by immunoaffinity chromatography or immunoprecipitation using antibodies that bind to at least one of the components of the complex. In a specific embodiment, a complex of the invention can be purified by immunoaffinity chromatography or immunoprecipitation using antibodies that are specific to the complex.

4.4 Antibodies of the Invention

The present invention provides antibodies or fragments thereof that immunospecifically bind to a complex of the invention, to Sen2, to Sen15, to Sen34, to Sen54, or to Sen2deltaEx8.

According to the present invention, a protein complex of the present invention as described in section 4.2 or Sen2, Sen15, Sen34, Sen54, or Sen2deltaEx8 can be used as an immunogen to generate antibodies which immunospecifically bind such immunogen. In certain embodiments, the immunogen is a complex of the invention, wherein the protein components of the complex are covalently linked to each other. In certain embodiments of the invention, the affinity of an antibody that binds to a complex of the invention is higher than the affinity of the antibody to any of the components of the complex individually. In certain embodiments of the invention, the affinity of an antibody that binds to a complex of the invention is at least 2 times, at least 5 times, at least 10 times, at least 100 times, at least 1,000 times, at least 10,000 times or at least 100,000 times higher than the affinity of the antibody to any of the components of the complex individually. In certain embodiments of the invention, the affinity of an antibody that binds to a complex of the invention is at most 2 times, at most 5 times, at most 10 times, at most 100 times, at most 1,000 times, at most 10,000 times or at most 100,000 times higher than the affinity of the antibody to any of the components of the complex individually. In a specific embodiment, the antibody specific to the complex and the antibody does not bind the individual protein components of the complex. The binding affinity of an antibody to an antigen, such as the complex or a protein component, can be determined by any method described herein (e.g., the BIAcore assay) or known to the skilled artisan (see, e.g., van Cott et al., 1992, Real-time biospecific interaction analysis of antibody reactivity to peptides from the envelope glycoprotein, gp160, of HIV-1, J Immunol Methods 146(2):163-76).

According to the present invention, Sen2ΔEx8 as described in section 4.1 can be used as an immunogen to generate antibodies which immunospecifically bind such immunogen.

In a preferred embodiment, an antibody of the invention immuno-specifically binds to Sen2deltaEx8 but not to Sen2. In certain embodiments of the invention, the affinity of an antibody that binds to Sen2deltaEx8 is higher than the affinity of the antibody to Sen2. In certain embodiments of the invention, the affinity of an antibody that binds to Sen2deltaEx8 is at least 2 times, at least 5 times, at least 10 times, at least 100 times, at least 1,000 times, at least 10,000 times or at least 100,000 times higher than the affinity of the antibody to Sen2. In certain embodiments of the invention, the affinity of an antibody that binds to Sen2deltaEx8 is at most 2 times, at most 5 times, at most 10 times, at most 100 times, at most 1,000 times, at most 10,000 times or at most 100,000 times higher than the affinity of the antibody to Sen2. In accordance with these embodiments, the affinity of the antibody may be determined utilizing methods described herein or known in the art (e.g., the BIAcore Assay).

Such antibodies include, but are not limited to, polyclonal, monoclonal, chimeric, single chain, Fab fragments, and an Fab expression library. In a specific embodiment, antibodies to a complex comprising human protein components are produced. In another embodiment, a complex formed from a fragment of said first protein component and a fragment of said second protein component, which fragments contain the protein domain that interacts with the other component of the complex, are used as an immunogen for antibody production.

The antibodies that immunospecifically bind to an antigen can be produced by any method known in the art for the synthesis of antibodies, in particular, by chemical synthesis or preferably, by recombinant expression techniques.

Polyclonal antibodies immunospecific for an antigen can be produced by various procedures well-known in the art. For example, the antigen (i.e., a complex of the invention or a component of a complex of the invention) can be administered to various host animals including, but not limited to, rabbits, mice, rats, etc. to induce the production of sera containing polyclonal antibodies specific for the human antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T Cell Hybridomas 563 681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. Briefly, mice can be immunized with a non-murine antigen and once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

The present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with a non-murine antigen with myeloma cells and then screening the hybridomas resulting from the fusion for hybridoma clones that secrete an antibody able to bind to the antigen.

Antibody fragments which recognize specific particular epitopes may be generated by any technique known to those of skill in the art. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain. Further, the antibodies of the present invention can also be generated using various phage display methods known in the art.

In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with an scFv linker by PCR and cloned into a phagemid vector. The vector is electroporated in E. coli and the E. coli is infected with helper phage. Phage used in these methods are typically filamentous phage including fd and M13 and the VH and VL domains are usually recombinantly fused to either the phage gene III or gene VIII. Phage expressing an antigen binding domain that binds to a particular antigen can be selected or identified with antigen, e.g., using labeled antigen or antigen bound or captured to a solid surface or bead. Examples of phage display methods that can be used to make the antibodies of the present invention include those disclosed in Brinkman et al., 1995, J. Immunol. Methods 182:41-50; Ames et al., 1995, J. Immunol. Methods 184:177-186; Kettleborough et al., 1994, Eur. J. Immunol. 24:952-958; Persic et al., 1997, Gene 187:9-18; Burton et al., 1994, Advances in Immunology 57:191-280; International application No. PCT/GB91/O1 134; International publication Nos. WO 90/02809, WO 91/10737, WO 92/01047, WO 92/18619, WO 93/11236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce Fab, Fab' and F(ab')2 fragments can also be employed using methods known in the art such as those disclosed in PCT publication No. WO 92/22324; Mullinax et al., 1992, BioTechniques 12(6):864-869; Sawai et al., 1995, AJRI 34:26-34; and Better et al., 1988, Science 240:1041-1043 (said references incorporated by reference in their entireties).

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a VH constant region, e.g., the human gamma 4 constant region, and the PCR amplified VL domains can be cloned into vectors expressing a VL constant region, e.g., human kappa or lamba constant regions. Preferably, the vectors for expressing the VH or VL domains comprise an EF-1a promoter, a secretion signal, a cloning site for the variable domain, constant domains, and a selection marker such as neomycin. The VH and VL domains may also cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

For some uses, including in vivo use of antibodies in humans and in vitro detection assays, it may be preferable to use humanized antibodies or chimeric antibodies. Completely human antibodies and humanized antibodies are particularly desirable for therapeutic treatment of human subjects. Human antibodies can be made by a variety of methods known in the art including phage display methods described above using antibody libraries derived from human immunoglobulin sequences. See also U.S. Pat. Nos. 4,444,887 and 4,716,111; and International publication Nos. WO 98/46645, WO 98/50433, WO 98/24893, WO98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then be bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, 1995, Int. Rev. Immunol. 13:65 93. For a detailed discussion of this technology for producing human antibodies and human monoclonal antibodies and protocols for producing such antibodies, see, e.g., International publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

A chimeric antibody is a molecule in which different portions of the antibody are derived from different immunoglobulin molecules. Methods for producing chimeric antibodies are known in the art. See e.g., Morrison, 1985, Science 229: 1202; Oi et al., 1986, BioTechniques 4:214; Gillies et al., 1989, J. Immunol. Methods 125:191-202; and U.S. Pat. Nos. 5,807,715, 4,816,567, 4,816,397, and 6,311,415, which are incorporated herein by reference in their entirety.

A humanized antibody is an antibody or its variant or fragment thereof which is capable of binding to a predetermined antigen and which comprises a framework region having substantially the amino acid sequence of a human immunoglobulin and a CDR having substantially the amino acid sequence of a non-human immuoglobulin. A humanized antibody comprises substantially all of at least one, and typically two, variable domains (Fab, Fab', F(ab').sub.2, Fabc, Fv) in which all or substantially all of the CDR regions correspond to those of a non human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. Ordinarily, the antibody will contain both the light chain as well as at least the variable domain of a heavy chain. The antibody also may include the CH1, hinge, CH2, CH$_3$, and CH4 regions of the heavy chain. The humanized antibody can be selected from any class of immunoglobulins, including IgM, IgG, IgD, IgA and IgE, and any isotype, including IgG1, IgG2, IgG3 and IgG4. Usually the constant domain is a complement fixing constant domain where it is desired that the humanized antibody exhibit cytotoxic activity, and the class is typically IgG1. Where such cytotoxic activity is not desirable, the constant domain may be of the IgG2 class. The humanized antibody may comprise sequences from more than one class or isotype, and selecting particular constant domains to optimize desired effector functions is within the ordinary skill in the art. The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the import antibody. Such mutations, however, will not be extensive. Usually, at least 75% of the humanized antibody residues will correspond to those of the parental framework and CDR sequences, more often 90%, and most preferably greater than 95%. A humanized antibody can be produced using variety of techniques known in the art, including but not limited to, CDR-grafting (see e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see e.g., European Patent Nos. EP 592,106 and EP 519,596; Padlan, 1991, Molecular Immunology 28(4/5):489-498; Studnicka et al., 1994, Protein Engineering 7(6):805-814; and Roguska et al., 1994, PNAS 91:969-973, each of which is incorporated herein by its entirety by reference), chain shuffling (see e.g., U.S. Pat. No. 5,565,332, which is incorporated herein in its entirety by reference), and techniques disclosed in, e.g., U.S. Pat. No. 6,407,213, U.S. Pat. No. 5,766,886, International Publication No. WO 9317105, Tan et al., J. Immunol. 169: 1119 25 (2002), Caldas et al., Protein Eng. 13(5):353 60 (2000), Morea et al., Methods 20(3):267 79 (2000), Baca et al., J. Biol. Chem. 272(16):10678 84 (1997), Roguska et al., Protein Eng. 9(10):895 904 (1996), Couto et al., Cancer Res. 55 (23 Supp):5973s-5977s (1995), Couto et al., Cancer Res. 55(8):1717 22 (1995), Sandhu J S, Gene 150(2):409 10 (1994), and Pedersen et al., J. Mol. Biol. 235(3):959 73 (1994), each of which is incorporated herein in its entirety by reference. Often, framework residues in the framework regions will be substituted with the corresponding residue from the CDR donor antibody to alter, preferably improve, antigen binding. These framework substitutions are identified by methods well known in the art, e.g. by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature 332:323, which are incorporated herein by reference in their entireties.)

Further, the antibodies that immunospecifically bind to a complex of the invention or a component of a complex of the invention, in turn, be utilized to generate anti-idiotype antibodies that "mimic" an antigen using techniques well known to those skilled in the art. (See, e.g., Greenspan & Bona, 1989, FASEB J. 7(5):437-444; and Nissinoff, 1991, J. Immunol. 147(8):2429-2438).

4.4.1 Polynucleotide Sequences Encoding an Antibody

The invention provides polynucleotides comprising a nucleotide sequence encoding an antibody or fragment thereof that immunospecifically binds to a complex of the invention or a component of a complex of the invention. The invention also encompasses polynucleotides that hybridize under high stringency, intermediate or lower stringency hybridization conditions, e.g., as defined supra, to polynucleotides that encode an antibody of the invention.

The polynucleotides may be obtained, and the nucleotide sequence of the polynucleotides determined, by any method known in the art. The nucleotide sequence of antibodies immunospecific for a desired antigen can be obtained, e.g., from the literature or a database such as GenBank. Such a polynucleotide encoding the antibody may be assembled from chemically synthesized oligonucleotides (e.g., as described in Kutmeier et al., 1994, BioTechniques 17:242), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, one or more of the CDRs is inserted within framework regions using routine recombinant DNA techniques. The framework regions may be naturally occurring or consensus framework regions, and preferably human framework regions (see, e.g., Chothia et al., 1998, J. Mol. Biol. 278: 457-479 for a listing of human framework regions). Preferably, the polynucleotide generated by the combination of the framework regions and CDRs encodes an antibody that immunospecifically binds to a particular antigen. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

4.4.2 Recombinant Expression of an Antibody

Recombinant expression of an antibody of the invention, derivative, analog or fragement thereof, (e.g., a heavy or light chain of an antibody of the invention or a portion thereof or a single chain antibody of the invention), requires construction of an expression vector containing a polynucleotide that encodes the antibody. Once a polynucleotide encoding an antibody molecule or a heavy or light chain of an antibody, or portion thereof (preferably, but not necessarily, containing the heavy or light chain variable domain), of the invention has been obtained, the vector for the production of the antibody molecule may be produced by recombinant DNA technology using techniques well-known in the art. See, e.g., U.S. Pat. No. 6,331,415, which is incorporated herein by reference in its entirety. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, a heavy or light chain of an antibody, a heavy or light chain variable domain of an antibody or a portion thereof, or a heavy or light chain CDR, operably linked to a promoter. Such vectors may include the nucleotide sequence encoding the constant region of the antibody molecule (see, e.g., International Publication No. WO 86/05807 and WO 89/01036; and U.S. Pat. No. 5,122,464) and the variable domain of the antibody may be cloned into such a vector for expression of the entire heavy, the entire light chain, or both the entire heavy and light chains.

The expression vector is transferred to a host cell by conventional techniques and the transfected cells are then cultured by conventional techniques to produce an antibody of the invention. Thus, the invention includes host cells containing a polynucleotide encoding an antibody of the invention or fragments thereof, or a heavy or light chain thereof, or portion thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention (see, e.g., U.S. Pat. No. 5,807,715). Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., 1986, Gene 45:101; and Cockett et al., 1990, Bio/Technology 8:2).

In bacterial systems, a number of expression vectors may be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified may be desirable. Such vectors include, but are not limited to, the *E. coli* expression vector pUR278 (Ruther et al., 1983, EMBO 12:1791), in which the antibody coding sequence may be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa* californica nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, 1984, Proc. Natl. Acad. Sci. USA 8 1:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., 1987, Methods in Enzymol. 153:51-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, BT483, Hs578T, HTB2, BT2O and T47D, NS0 (a murine myeloma cell line that does not endogenously produce any immunoglobulin chains), CRL7O3O and HsS78Bst cells.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compositions that interact directly or indirectly with the antibody molecule.

A number of selection systems may be used, including but not limited to, the herpes simplex virus thymidine kinase (Wigler et al., 1977, Cell 11:223), hypoxanthineguanine phosphoribosyltransferase (Szybalska & Szyalski, 1992, Proc. Natl. Acad. Sci. USA 48:202), and adenine phosphoribosyltransferase (Lowy et al., 1980, Cell 22:8-17) genes can be employed in tk−, hgprt− or aprt− cells, respectively. Also, antimetabolite resistance can be used as the basis of selection for the following genes: dhfr, which confers resistance to methotrexate (Wigler et al., 1980, Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62: 191-217; May, 1993, TIB TECH 11(5):155-2 15); and hygro, which confers resistance to hygromycin (Santerre et al., 1984, Gene 30:147). Methods commonly known in the art of recombinant DNA technology may be routinely applied to select the desired recombinant clone, and such methods are described, for example, in Ausubel et al., (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al., (eds), Current Protocols in Human Genetics, John Wiley & Sons, NY (1994); Colberre-Garapin et al., 1981, J. Mol. Biol. 150:1, which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, 1986, Nature 322:52; and Kohler, 1980, Proc. Natl. Acad. Sci. USA 77:2 197). The coding sequences for the heavy and light chains may comprise cDNA or genomic DNA.

Once an antibody molecule of the invention has been produced by recombinant expression, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies of the present invention or fragments thereof may be fused to heterologous polypeptide sequences described herein or otherwise known in the art to facilitate purification.

4.4.3 Immunological Methods Using the Antibodies of the Invention

The antibodies of the invention can be used with any method known to the skilled artisan. In certain embodiments, an antibody of the invention is used to detect or quantify a complex of the invention or a component of a complex of the invention. To this end, Western blot analyses, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, or fluorescent immunoassays can be performed using an antibody of the invention.

The affinity of an antibody to its antigen can be measured by using, e.g, a Biacore® assay.

4.5 Screening Methods 4.5.1 Modulators of Complex Formation

A complex of the present invention, the component proteins of the complex and nucleic acids encoding the component proteins, as well as derivatives and fragments of the amino and nucleic acids, can be used to screen for compounds that bind to, or modulate the amount of, activity of, or protein component composition of, said complex, and thus, have potential use as modulators, i.e., agonists or antagonists, of complex activity, and/or complex formation, i.e., the amount of complex formed, and/or protein component composition of the complex.

Thus, the present invention is also directed to methods for screening for molecules that bind to, or modulate the amount of, activity of, or protein component composition of, a complex of the present invention. In one embodiment of the invention, the method for screening for a molecule that modulates directly or indirectly the function, activity or formation of a complex of the present invention comprises exposing said complex, or a cell or organism containing the complex machinery, to one or more compounds under conditions conducive to modulation; and determining the amount of, activity of, or identities of the protein components of said complex, wherein a change in said amount, activity, or identities relative to said amount, activity or identities in the absence of said compounds indicates that the compounds modulate function, activity or formation of said complex. Such screening assays can be carried out using cell-free and cell-based methods that are commonly known in the art.

The present invention is further directed to methods for screening for molecules that modulate the expression of a component of a complex of the present invention, such as, e.g., Sen2deltaEx8. In one embodiment of the invention, the method for screening for a molecule that modulates the expression of a component of a complex of the invention comprises exposing a cell or organism containing the nucleic acid encoding the component, to one or more compounds under conditions conducive to modulation; and determining the amount of, activity of, or identities of the protein components of said complex, wherein a change in said amount, activity, or identities relative to said amount, activity or identities in the absence of said compounds indicates that the compounds modulate expression of said complex. Such screening assays can be carried out using cell-free and cell-based methods that are commonly known in the art. If activity of the complex or component is used as read-out of the assay, subsequent assays, such as Western blot analysis or Northern blot analysis, may be performed to verify that the modulated expression levels of the component are responsible for the modulated activity.

Screening the libraries can be accomplished by any of a variety of commonly known methods. See, e.g., the following references, which disclose screening of peptide libraries: Parmley and Smith, 1989, Adv. Exp. Med. Biol. 251:215-218; Scott and Smith, 1990, Science 249:386-390; Fowlkes et al., 1992, BioTechniques 13:422-427; Oldenburg et al., 1992, Proc. Natl. Acad. Sci. USA 89:5393-5397; Yu et al., 1994, Cell 76:933-945; Staudt et al., 1988, Science 241:577-580; Bock et al., 1992, Nature 355:564-566; Tuerk et al., 1992, Proc. Natl. Acad. Sci. USA 89:6988-6992; Ellington et al., 1992, Nature 355:850-852; U.S. Pat. No. 5,096,815, U.S. Pat. No. 5,223,409, and U.S. Pat. No. 5,198,346, all to Ladner et al.; Rebar and Pabo, 1993, Science 263:671-673; and International Patent Publication No. WO 94/18318.

In a specific embodiment, fragments and/or analogs of protein components of a complex, especially peptidomimetics, are screened for activity as competitive or non-competitive inhibitors of complex formation, which thereby inhibit complex activity or formation.

Methods for screening may involve labeling the component proteins of the complex with radioligands (e.g., $^{125}$I or $^{3}$H), magnetic ligands (e.g., paramagnetic beads covalently attached to photobiotin acetate), fluorescent ligands (e.g., fluorescein or rhodamine), or enzyme ligands (e.g., luciferase or beta-galactosidase). The reactants that bind in solution can then be isolated by one of many techniques known in the art, including but not restricted to, co-immunoprecipitation of the labeled complex moiety using antisera against the unlabeled binding partner (or labeled binding partner with a distinguishable marker from that used on the second labeled complex moiety), immunoaffinity chromatography, size exclusion chromatography, and gradient density centrifugation. In a preferred embodiment, the labeled binding partner is a small fragment or peptidomimetic that is not retained by a commercially available filter. Upon binding, the labeled species is then unable to pass through the filter, providing for a simple assay of complex formation.

In certain embodiments, the protein components of a complex of the invention are labeled with different fluorophores such that binding of the components to each other results in FRET (Fluorescence Resonance Energy Transfer). If the addition of a compound results in a difference in FRET compared to FRET in the absence of the compound, the compound is identified as a modulator of complex formation. If FRET in the presence of the compound is decreased in comparison to FRET in the absence of the compound, the compound is identified as an inhibitor of complex formation. If FRET in the presence of the compound is increased in comparison to FRET in the absence of the compound, the compound is identified as an activator of complex formation.

In certain other embodiments, a protein component of a complex of the invention is labeled with a fluorophore such that binding of the component to another protein component to form a complex of the invention results in FP (Flourescence Polarization). If the addition of a compound results in a difference in FP compared to FP in the absence of the compound, the compound is identified as a modulator of complex formation.

Methods commonly known in the art are used to label at least one of the component members of the complex. Suitable labeling methods include, but are not limited to, radiolabeling by incorporation of radiolabeled amino acids, e.g., $^3$H-leucine or $^{35}$S-methionine, radiolabeling by post-translational iodination with $^{125}$I or $^{131}$I using the chloramine T method, Bolton-Hunter reagents, etc., or labeling with $^{32}$P using phosphorylase and inorganic radiolabeled phosphorous, biotin labeling with photobiotin-acetate and sunlamp exposure, etc. In cases where one of the members of the complex is immobilized, e.g., as described in section 4.5.1.1, the free species is labeled. Where neither of the interacting species is immobilized, each can be labeled with a distinguishable marker such that isolation of both moieties can be followed to provide for more accurate quantification, and to distinguish the formation of homomeric from heteromeric complexes. Methods that utilize accessory proteins that bind to one of the modified components to improve the sensitivity of detection, increase the stability of the complex, etc., are provided.

The physical parameters of complex formation can be analyzed by quantification of complex formation using assay methods specific for the label used, e.g., liquid scintillation counting for radioactivity detection, enzyme activity for enzyme-labeled moieties, etc. The reaction results are then analyzed utilizing Scatchard analysis, Hill analysis, and other methods commonly known in the arts (see, e.g., Proteins, Structures, and Molecular Principles, $2^{nd}$ Edition (1993) Creighton, Ed., W.H. Freeman and Company, New York).

Compounds to be screened can be provided as mixtures of a limited number of specified compounds, or as compound libraries, peptide libraries and the like. Agents/molecules/compounds to be screened may also include all forms of antisera, antisense nucleic acids, etc., that can modulate complex activity or formation. Exemplary compounds and libraries for screening are set forth in section 4.5.12.

In a specific embodiment of the invention, compounds are identified that promote the formation of a complex comprising Sen2ΔEx8, Clp1, Sen54, Sen15, and Sen34 instead of a complex comprising Sen2ΔEx8, Clp1, Sen54, Sen15, Send34, CPSF, CFIm, CFIIm and CstF.

In certain embodiments, compounds are identified that promote the formation of a Sen2ΔEx8 containing complex but not the formation of a Sen2 containing complex. In certain embodiments, compounds are identified that promote the formation of a Sen2 containing complex but not the formation of a Sen2ΔEx8 containing complex.

In certain embodiments, the compounds are screened in pools. Once a positive pool has been identified, the individual molecules of that pool are tested separately. In certain embodiments, the pool size is at least 2, at least 5, at least 10, at least 25, at least 50, at least 75, at least 100, at least 150, at least 200, at least 250, or at least 500 compounds.

In certain embodiments of the invention, the screening method further comprises determining the structure of the candidate molecule. The structure of a candidate molecule can be determined by any technique known to the skilled artisan. Exemplary methods are described in section 0.

4.5.1.1 Cell-Free Assays

In certain embodiments, the method for identifying a modulator of the formation or stability of a complex of the invention can be carried out in vitro, particularly in a cell-free system. In certain, more specific embodiments, the complex is purified. In certain embodiments the candidate molecule is purified.

In a specific embodiment, screening can be carried out by contacting the library members with a complex immobilized on a solid phase, and harvesting those library members that bind to the protein (or encoding nucleic acid or derivative). Examples of such screening methods, termed "panning" techniques, are described by way of example in Parmley and Smith, 1988, Gene 73:305-318; Fowlkes et al., 1992, BioTechniques 13:422-427; International Patent Publication No. WO 94/18318; and in references cited hereinabove.

In one embodiment, agents that modulate (i.e., antagonize or agonize) complex activity or formation can be screened for using a binding inhibition assay, wherein agents are screened for their ability to modulate formation of a complex under aqueous, or physiological, binding conditions in which complex formation occurs in the absence of the agent to be tested. Agents that interfere with the formation of complexes of the invention are identified as antagonists of complex formation. Agents that promote the formation of complexes are identified as agonists of complex formation. Agents that completely block the formation of complexes are identified as inhibitors of complex formation. In an exemplary embodiment, the binding conditions are, for example, but not by way of limitation, in an aqueous salt solution of 10-250 mM NaCl, 5-50 mM Tris-HCl, pH 5-8, and 0.5% Triton X-100 or other detergent that improves specificity of interaction. Metal chelators and/or divalent cations may be added to improve binding and/or reduce proteolysis. Reaction temperatures may include 4, 10, 15, 22, 25, 35, or 42 degrees Celsius, and time of incubation is typically at least 15 seconds, but longer times are preferred to allow binding equilibrium to occur. Particular complexes can be assayed using routine protein binding assays to determine optimal binding conditions for reproducible binding.

In certain embodiments, another common approach to in vitro binding assays is used. In this assay, one of the binding species is immobilized on a filter, in a microtiter plate well, in a test tube, to a chromatography matrix, etc., either covalently or non-covalently. Proteins can be covalently immobilized using any method well known in the art, for example, but not limited to the method of Kadonaga and Tjian, 1986, Proc. Natl. Acad. Sci. USA 83:5889-5893, i.e., linkage to a cyanogen-bromide derivatized substrate such as CNBr—Sepharose 4B (Pharmacia). Where needed, the use of spacers can reduce steric hindrance by the substrate. Non-covalent attachment of proteins to a substrate include, but are not limited to, attachment of a protein to a charged surface, binding with specific antibodies, binding to a third unrelated interacting protein, etc.

Assays of agents (including cell extracts or a library pool) for competition for binding of one member of a complex (or derivatives thereof) with another member of the complex labeled by any means (e.g., those means described above) are provided to screen for competitors or enhancers of complex formation. In specific embodiments, blocking agents to inhibit non-specific binding of reagents to other protein components, or absorptive losses of reagents to plastics, immobilization matrices, etc., are included in the assay mixture. Blocking agents include, but are not restricted to bovine serum albumin, beta-casein, nonfat dried milk, Denhardt's reagent, Ficoll, polyvinylpyrrolidine, nonionic detergents (NP40, Triton X-100, Tween 20, Tween 80, etc.), ionic detergents (e.g., SDS, LDS, etc.), polyethylene glycol, etc. Appropriate blocking agent concentrations allow complex formation.

After binding is performed, unbound, labeled protein is removed in the supernatant, and the immobilized protein retaining any bound, labeled protein is washed extensively. The amount of bound label is then quantified using standard methods in the art to detect the label.

In preferred embodiments, polypeptide derivatives that have superior stabilities but retain the ability to form a complex (e.g., one or more component proteins modified to be resistant to proteolytic degradation in the binding assay buffers, or to be resistant to oxidative degradation), are used to screen for modulators of complex activity or formation. Such resistant molecules can be generated, e.g., by substitution of amino acids at proteolytic cleavage sites, the use of chemically derivatized amino acids at proteolytic susceptible sites, and the replacement of amino acid residues subject to oxidation, i.e. methionine and cysteine.

4.5.1.2 Cell-Based Assays

In certain embodiments, assays can be carried out using recombinant cells expressing the protein components of a complex, to screen for molecules that bind to, or interfere with, or promote complex activity or formation. In certain embodiments, at least one of the protein components is expressed in the recombinant cell as fusion protein, wherein the protein component is fused to a peptide tag to facilitate purification and subsequent quantification and/or immunological visualization and quantification.

A particular aspect of the present invention relates to identifying molecules that inhibit or promote formation or degradation of a complex of the present invention, e.g., using the method described for isolating the complex and identifying members of the complex using the TAP assay described in WO 00/09716 and Rigaut et al., 1999, Nature Biotechnology 17:1030-1032, which are each incorporated by reference in their entireties.

In another embodiment of the invention, a modulator is identified by administering a candidate molecule to a transgenic non-human animal expressing the recombinant component proteins of a complex of the invention. In certain embodiments, the complex components are distinguishable from the homologous endogenous protein components. In certain embodiments, the recombinant component proteins are fusion proteins, wherein the protein component is fused to a peptide tag. In certain embodiments, the amino acid sequence of the recombinant protein component is different from the amino acid sequence of the endogenous protein component such that antibodies specific to the recombinant protein component can be used to determine the level of the protein component or the complex formed with the component. In certain embodiments, the recombinant protein component is expressed from promoters that are not the native promoters of the respective proteins. In a specific embodiment, the recombinant protein component is expressed in tissues where it is normally not expressed. In a specific embodiment, the compound is also recombinantly expressed in the transgenic non-human animal.

In certain embodiments, a mutant form of a protein component of a complex of the invention is expressed in a cell, wherein the mutant form of the protein component has a binding affinity that is lower than the binding affinity of the naturally occurring protein to the other protein component of a complex of the invention. In a specific embodiment, a dominant negative mutant form of a protein component is expressed in a cell. A dominant negative form can be the domain of the protein component that binds to the other protein component, i.e., the binding domain. Without being bound by theory, the binding domain will compete with the naturally occurring protein component for binding to the other protein component of the complex thereby preventing the formation of complex that contains full length protein components. Instead, with increasing level of the dominant negative form in the cell, an increasing amount of complex lacks those domains that are normally provided to the complex by the protein component which is expressed as dominant negative.

The binding domain of a protein component can be identified by any standard technique known to the skilled artisan. In a non-limiting example, alanine-scanning mutagenesis (Cunningham and Wells, Science 244:1081-1085 (1989) is conducted to identify the region(s) of the protein that is/are required for dimerization with another protein component. In other embodiments, different deletion mutants of the protein component are generated such that the combined deleted regions would span the entire protein. In a specific embodiment, the different deletions overlap with each other. Once mutant forms of a protein component are generated, they are tested for their ability to form a dimer with another protein component. If a particular mutant fails to form a dimer with another protein component or binds the other protein component with reduced affinity compared to the naturally occurring form, the mutation of this mutant form is identified as being in a region of the protein that is involved in the dimer formation. To exclude that the mutation simply interfered with proper folding of the protein, any structural analysis known to the skilled artisan can be performed to determine the 3-dimensional conformation of the protein. Such techniques include, but are not limited to, circular dichroism (CD), NMR, and x-ray cristallography.

In certain embodiments, a mutated form of a component of a complex of the invention can be expressed in a cell under an inducible promoter. Any method known to the skilled artisan can be used to mutate the nucleotide sequence encoding the component. Any inducible promoter known to the skilled artisan can be used. In particular, the mutated form of the component of a complex of the invention has reduced activity, e.g., reduced RNA-nucleolytic activity and/or reduced affinity to the other components of the complex.

In certain embodiments, the assays of the invention are performed in high-throughput format.

4.5.2 Use of Complexes to Identify New Binding Partners

In certain embodiments of the invention, a complex of the invention is used to identify new components the complex. In certain embodiments, new binding partners of a complex of the invention are identified and thereby implicated in RNA processing. Any technique known to the skilled artisan can be used to identify such new binding partners. In certain embodiments, a binding partner of a complex of the invention binds to a complex of the invention but not to an individual protein component of a complex of the invention. In a specific embodiment, immunoprecipitation is used to identify binding partners of a complex of the invention.

In certain embodiments, the assays of the invention are performed in high-throughput format.

4.5.3 Use of Complexes to Identify Pre-Mature Stop Codons and Modulators Thereof In certain embodiments of the invention, a complex of the invention is used to cleave an mRNA or pre-mRNA molecule containing a pre-mature stop codon. In certain, more specific, embodiments of the invention, a complex of the invention is used to cleave an mRNA or pre-mRNA molecule at or in the vicinity of a pre-mature stop codon. Without being bound by theory, a complex of the invention cleaves an mRNA or a pre-mRNA molecule at or in the vicinity of a pre-mature stop codon. In certain embodiments, the complex of the invention cleaves an mRNA or a pre-mRNA molecule within 500, 400, 300, 200, 100 or 50 nucleotides of the pre-mature stop codon. In certain embodiments, the complex of the invention cleaves an mRNA or a pre-mRNA molecule within 1 to 50, 1 to 100, 1 to 250, 1 to 500, 10 to 50, 10 to 100, 25 to 100, 50 to 100, 50 to 250, 50 to 500, 100 to 500, or 250 to 500 nucleotides of the pre-mature stop codon.

In certain embodiments of the invention, a complex of the invention is used to identify pre-mature stop codons in an mRNA or pre-mRNA molecule. In certain embodiments, the complex of the invention cleaves an mRNA or a pre-mRNA molecule within 500, 400, 300, 200, 100 or 50 nucleotides of the pre-mature stop codon. In certain embodiments, the complex of the invention cleaves an mRNA or a pre-mRNA molecule within 1 to 50, 1 to 100, 1 to 250, 1 to 500, 10 to 50, 10 to 100, 25 to 100, 50 to 100, 50 to 250, 50 to 500, 100 to 500, or 250 to 500 nucleotides of the pre-mature stop codon.

To identify the pre-mature stop codon, an mRNA or pre-mRNA of interest is incubated with a complex of the invention under conditions conducive to cleavage of the mRNA or pre-mRNA by the complex. Once cleavage occurred, the cleavage products are analyzed to determine the location of the cleavage site. The location of the cleavage site can be determined by any method known to the skilled artisan, such as, but not limited to Northern blot analysis.

In certain embodiments, the complexes of the invention can be used to identify modulators of cleavage of pre-mature stop codons by a complex of the invention. In certain embodiments, a complex of the invention is incubated with an mRNA or pre-mRNA of interest under conditions conducive to cleavage of the mRNA or pre-mRNA by the complex in the presence of a compound, wherein the mRNA or pre-mRNA is known to have a pre-mature stop codon. If the compound increases the amount of cleavage product generated, the compound is identified as an activator of the pre-mature stop codon cleavage activity of a complex of the invention. If the compound decreases the amount of cleavage product generated, the compound is identified as an inhibitor of the pre-mature stop codon cleavage activity of a complex of the invention.

In certain embodiments, the assays of the invention are performed in high-throughput format.

4.5.4 Modulators of Complex Function

Any method known to the skilled artisan can be used to identify compound that modulate the activity of a complex of the invention. In certain embodiments, compounds can be identified that modulate the activity of a pre-tRNA splicing endonuclease complex. In other embodiments, compounds can be identified using the methods of the invention that modulate the activity of a 3' end pre-mRNA processing complex. In even other embodiments, compounds can be identified using the methods of the invention that modulate the activity of a pre-tRNA cleavage complex. In yet other embodiments, compounds can be identified using the methods of the invention that modulate the activity of a complex involved in the biogenesis of mature ribosomal RNAs from precursor ribosomal RNA.

In certain embodiments, the substrate of the pre-tRNA splicing endonuclease complex or the 3' end pre-mRNA endonuclease complex comprises a reporter gene such that the endonuclease reaction results either in increased or decreased expression of the reporter gene. Any reporter gene can be used with the methods of the invention. Exemplary methods are set forth below. The substrate of the pre-tRNA splicing endonuclease complex, the 3' end pre-mRNA endonuclease complex, pre-tRNA cleavage complex or the complex involved in the biogenesis of mature ribosomal RNAs from precursor ribosomal RNA can be an RNA molecule that is detectably labeled and that is known to be cleaved by the complex. The complex and its substrate are then incubated under conditions conducive to the cleavage of the substrate by the complex and subsequently the activity is evaluated by measuring the amount of substrate and/or cleavage product. See, e.g., section 4.5.4.1. In certain embodiments, the assays of the invention are performed in high-throughput format.

Various in vitro assays can be used to identify and verify the ability of a compound to modulate the activity of a pre-tRNA splicing endonuclease complex or a 3' end pre-mRNA endonuclease complex. Multiple in vitro assays can be performed simultaneously or sequentially to assess the affect of a compound on the activity of a human tRNA splicing endonuclease.

In certain embodiments, the pre-tRNA splicing endonuclease complex is incubated with a detectably labeled pre-tRNA substrate under conditions conducive to the endonuclease reaction. After a period of time, the reaction is stopped and the RNA is resolved using PAGE. In certain embodiments, the RNA is precipitated from the reaction before the RNA is resolved on the gel. The amount of cleavage product can be determined based on the different length between substrate and product. In certain embodiments, the RNA substrate is radioactively labeled and can be detected using autoradiography. The more active the pre-tRNA splicing endonuclease complex is the more cleavage product relative to the substrate is detected.

In certain embodiments, the 3' end pre-mRNA endonuclease complex is incubated with a detectably labeled 3' end pre-mRNA substrate under conditions conducive to the endonuclease reaction. After a period of time, the reaction is stopped and the RNA is resolved using PAGE. In certain embodiments, the RNA is precipitated from the reaction before the RNA is resolved on the gel. The amount of cleavage product can be determined based on the different length between substrate and product. In certain embodiments, the RNA substrate is radioactively labeled and can be detected using autoradiography. The more active the 3' end pre-mRNA endonuclease complex is the more cleavage product relative to the substrate is detected. Such an assay can analogously be used to identify modulators of tRNA splicing endonuclease, rRNA endonuclease or tRNA cleavage activity. To identify compounds that modulate the 3' end pre-mRNA endonuclease activity of a complex of the invention, the complex can be incubated with its substrate, wherein the substrate is detectably labeled. In certain, more specific embodiments, the detectable label is a radioactive label, such as, but not limited to, $^{33}$P or $^{32}$P. In other embodiments, the label is a fluorescent label. The detectably labeled substrate is incubated with the 3' end pre-mRNA endonuclease under conditions conducive to the cleavage of the pre-mRNA substrate by the 3' end pre-mRNA endonuclease. The detectably labeled substrate can be microinjected into a cell or transfected into a cell. The substrate can be incubated with cell extract or the substrate can be incubated with purified 3' end pre-mRNA endonuclease complex. After a time sufficient for the cleavage reaction to take place, the substrate is resolved using PAGE and the reaction product and any remaining substrate is visualized. If the substrate is labeled radioactively, the reaction product can be visualized using autoradiography. In certain embodiments, the time for incubating is at least 1min, 5 min, 10 min, 30 min, 45 min, 1 h, 2 h, 4 h, 6 h, 8 h, 10 h, 12 h, 18 h, or at least 14 h. Such an assay can analogously be used to identify modulators of tRNA endonuclease, rRNA endonuclease or tRNA splicing endonuclease activity.

To identify compounds that modulate the tRNA cleavage activity of a complex of the invention or the activity of a complex of the invention in the biogenesis of mature ribosomal RNAs from precursor ribosomal RNA, the complex can be incubated with its substrate, wherein the substrate is detectably labeled. In certain embodiments, a complex with tRNA cleavage activity or a complex involved in the biogenesis of mature ribosomal RNAs from precursor ribosomal RNA are incubated under conditions conducive to the cleavage of the substrate by the complex and subsequently the activity is evaluated by measuring the amount of substrate and/or cleavage product. The complex and substrate can be incubated in the presence and absence of a compound and the effect of the compound on the RNA-nucleolytic activity of the complex is determined. In other embodiments, a pre-tRNA or a pre-rRNA is incubated with a complex of the invention to determine where cleavage sites are present in the RNA.

In certain specific embodiments, the assay is performed concurrently with a control, i.e., the assay is performed in the presence and the absence of a compound to determine the effect of the compound on the endonuclease reaction. The assay can include steps in the presence and the absence of a compound to determine the effect of the compound on the endonuclease reaction. In other embodiments, a historic value is used for comparison.

In certain embodiments, the invention provides a method comprising: (i) identifying a compound as a modulator of tRNA splicing activity, 3' end pre-mRNA endonuclease activity, and/or pre-tRNA cleavage activity in a cell-based assay, e.g., as described below; and (ii) testing the compound identified in step (i) for its ability to modify tRNA splicing activity, 3' end pre-mRNA endonuclease activity, and/or pre-tRNA cleavage activity in a cell-free assay using a purified complex of the invention.

Assays for tRNA endonuclease activity can be used to determine tRNA cleavage activity.

4.5.4.1 Reporter Gene Constructs, Transfected Cells and Cell Extracts

The invention provides for specific vectors comprising a reporter gene comprising a tRNA intron operably linked to one or more regulatory elements and host cells transfected with the vectors if tRNA endonuclease activity is to be tested. If 3' end pre-mRNA endonuclease activity is to be tested, the substrate comprises a 3' end pre-mRNA reporter (see section 4.5.4.1.3). The invention also provides for the in vitro translation of a reporter gene flanked by one or more regulatory elements. Techniques for practicing this specific aspect of this invention will employ, unless otherwise indicated, conventional techniques of molecular biology, microbiology, and recombinant DNA manipulation and production, which are routinely practiced by one of skill in the art. See, e.g., Sambrook, 1989, Molecular Cloning, A Laboratory Manual, Second Edition; DNA Cloning, Volumes I and II (Glover, Ed. 1985); Oligonucleotide Synthesis (Gait, Ed. 1984); Nucleic Acid Hybridization (Hames & Higgins, Eds. 1984); Transcription and Translation (Hames & Higgins, Eds. 1984); Animal Cell Culture (Freshney, Ed. 1986); Immobilized Cells and Enzymes (IRL Press, 1986); Perbal, A Practical Guide to Molecular Cloning (1984); Gene Transfer Vectors for Mammalian Cells (Miller & Calos, Eds. 1987, Cold Spring Harbor Laboratory); Methods in Enzymology, Volumes 154 and 155 (Wu & Grossman, and Wu, Eds., respectively), (Mayer & Walker, Eds., 1987); Immunochemical Methods in Cell and Molecular Biology (Academic Press, London, Scopes, 1987), Expression of Proteins in Mammalian Cells Using Vaccinia Viral Vectors in Current Protocols in Molecular Biology, Volume 2 (Ausubel et al., Eds., 1991).

4.5.4.1.1 Reporter Genes

Any reporter gene well-known to one of skill in the art may be used in reporter gene constructs to ascertain the effect of a compound on a tRNA endonuclease complex or a 3' end pre-mRNA endonuclease. Reporter genes refer to a nucleotide sequence encoding a protein that is readily detectable either by its presence or activity. Reporter genes may be obtained and the nucleotide sequence of the elements determined by any method well-known to one of skill in the art. The nucleotide sequence of a reporter gene can be obtained, e.g., from the literature or a database such as GenBank. Alternatively, a polynucleotide encoding a reporter gene may be generated from nucleic acid from a suitable source. If a clone containing a nucleic acid encoding a particular reporter gene is not available, but the sequence of the reporter gene is known, a nucleic acid encoding the reporter gene may be chemically synthesized or obtained from a suitable source (e.g., a cDNA library, or a cDNA library generated from, or nucleic acid, preferably poly A+ RNA, isolated from, any tissue or cells expressing the reporter gene) by PCR amplification. Once the nucleotide sequence of a reporter gene is determined, the nucleotide sequence of the reporter gene may be manipulated using methods well-known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate reporter genes having a different amino acid sequence, for example to create amino acid substitutions, deletions, and/or insertions.

Examples of reporter genes include, but are not limited to, luciferase (e.g., firefly luciferase, renilla luciferase, and click beetle luciferase), green fluorescent protein ("GFP") (e.g., green fluorescent protein, yellow fluorescent protein, red fluorescent protein, cyan fluorescent protein, and blue fluorescent protein), beta-galactosidase ("beta-gal"), beta-glucoronidase, beta-lactamase, chloramphenicol acetyltransferase ("CAT"), and alkaline phosphatase ("AP"). Table 2 below lists various reporter genes and the properties of the products of the reporter genes that can be assayed. In a preferred embodiment, a reporter gene utilized in the reporter constructs is easily assayed and has an activity which is not normally found in the cell or organism of interest.

TABLE 2

Reporter Genes and the Properties of the Reporter Gene Products

| Reporter Gene | Protein Activity & Measurement |
| --- | --- |
| CAT (chloramphenicol acetyltransferase) | Transfers radioactive acetyl groups to chloramphenicol or detection by thin layer chromatography and autoradiography |
| GAL (beta-galactosidase) | Hydrolyzes colorless galactosides to yield colored products. |
| GUS (beta-glucuronidase) | Hydrolyzes colorless glucuronides to yield colored products. |
| LUC (luciferase) | Oxidizes luciferin, emitting photons |
| GFP (green fluorescent protein) | Fluorescent protein without substrate |
| SEAP (secreted alkaline phosphatase) | Luminescence reaction with suitable substrates or with substrates that generate chromophores |

TABLE 2-continued

Reporter Genes and the Properties of the Reporter Gene Products

| Reporter Gene | Protein Activity & Measurement |
|---|---|
| HRP (horseradish peroxidase) | In the presence of hydrogen oxide, oxidation of 3,3',5,5'-tetramethylbenzidine to form a colored complex |
| AP (alkaline phosphatase) | Luminescence reaction with suitable substrates or with substrates that generate chromophores |

Described hereinbelow in further detailed are specific reporter genes and characteristics of those reporter genes.

Luciferase

Luciferases are enzymes that emit light in the presence of oxygen and a substrate (luciferin) and which have been used for real-time, low-light imaging of gene expression in cell cultures, individual cells, whole organisms, and transgenic organisms (reviewed by Greer & Szalay, 2002, Luminescence 17(1):43-74).

As used herein, the term "luciferase" is intended to embrace all luciferases, or recombinant enzymes derived from luciferases which have luciferase activity. The luciferase genes from fireflies have been well characterized, for example, from the *Photinus* and *Luciola* species (see, e.g., International Patent Publication No. WO 95/25798 for *Photinus pyralis*, European Patent Application No. EP 0 524 448 for *Luciola cruciata* and *Luciola lateralis*, and Devine et al., 1993, Biochim. Biophys. Acta 1173(2):121-132 for *Luciola mingrelica*). Other eukaryotic luciferase genes include, but are not limited to, the click beetle (*Photinus plagiophthalamus*, see, e.g., Wood et al., 1989, Science 244:700-702), the sea panzy (*Renilla reniformis*, see, e.g., Lorenz et al., 1991, Proc Natl Acad Sci USA 88(10):4438-4442), and the glow worm (Lampyris noctiluca, see e.g., Sula-Newby et al., 1996, Biochem J. 313:761-767). The click beetle is unusual in that different members of the species emit bioluminescence of different colors, which emit light at 546 nm (green), 560 nm (yellow-green), 578 nm (yellow) and 593 nm (orange) (see, e.g, U.S. Pat. Nos. 6,475,719; 6,342,379; and 6,217,847, the disclosures of which are incorporated by reference in their entireties). Bacterial luciferin-luciferase systems include, but are not limited to, the bacterial lux genes of terrestrial *Photorhabdus luminescens* (see, e.g., Manukhov et al., 2000, Genetika 36(3):322-30) and marine bacteria *Vibrio fischeri* and *Vibrio harveyi* (see, e.g., Miyamoto et al., 1988, J Biol Chem. 263(26):13393-9, and Cohn et al., 1983, Proc Natl Acad Sci USA., 80(1):120-3, respectively). The luciferases encompassed by the present invention also includes the mutant luciferases described in U.S. Pat. No. 6,265,177 to Squirrell et al., which is hereby incorporated by reference in its entirety.

In a preferred embodiment, the luciferase is a firefly luciferase, a renilla luciferase, or a click beetle luciferase, as described in any one of the references listed supra, the disclosures of which are incorporated by reference in their entireties.

Green Fluorescent Protein

Green fluorescent protein ("GFP") is a 238 amino acid protein with amino acid residues 65 to 67 involved in the formation of the chromophore which does not require additional substrates or cofactors to fluoresce (see, e.g., Prasher et al., 1992, Gene 111:229-233; Yang et al., 1996, Nature Biotechnol. 14:1252-1256; and Cody et al., 1993, Biochemistry 32:1212-1218).

As used herein, the term "green fluorescent protein" or "GFP" is intended to embrace all GFPs (including the various forms of GFPs which exhibit colors other than green), or recombinant enzymes derived from GFPs which have GFP activity. In a preferred embodiment, GFP includes green fluorescent protein, yellow fluorescent protein, red fluorescent protein, cyan fluorescent protein, and blue fluorescent protein. The native gene for GFP was cloned from the bioluminescent jellyfish *Aequorea victoria* (see, e.g., Morin et al., 1972, J. Cell Physiol. 77:313-318). Wild type GFP has a major excitation peak at 395 nm and a minor excitation peak at 470 nm. The absorption peak at 470 nm allows the monitoring of GFP levels using standard fluorescein isothiocyanate (FITC) filter sets. Mutants of the GFP gene have been found useful to enhance expression and to modify excitation and fluorescence. For example, mutant GFPs with alanine, glycine, isoleucine, or threonine substituted for serine at position 65 result in mutant GFPs with shifts in excitation maxima and greater fluorescence than wild type protein when excited at 488 nm (see, e.g., Heim et al., 1995, Nature 373:663-664; U.S. Pat. No. 5,625,048; Delagrave et al., 1995, Biotechnology 13:151-154; Cormack et al., 1996, Gene 173:33-38; and Cramer et al., 1996, Nature Biotechnol. 14:315-319). The ability to excite GFP at 488 nm permits the use of GFP with standard fluorescence activated cell sorting ("FACS") equipment. In another embodiment, GFPs are isolated from organisms other than the jellyfish, such as, but not limited to, the sea pansy, *Renilla reriformis*.

Techniques for labeling cells with GFP in general are described in U.S. Pat. Nos. 5,491,084 and 5,804,387, which are incorporated by reference in their entireties; Chalfie et al., 1994, Science 263:802-805; Heim et al., 1994, Proc. Natl. Acad. Sci. USA 91:12501-12504; Morise et al., 1974, Biochemistry 13:2656-2662; Ward et al., 1980, Photochem. Photobiol. 31:611-615; Rizzuto et al., 1995, Curr. Biology 5:635-642; and Kaether & Gerdes, 1995, FEBS Lett 369:267-271. The expression of GFPs in *E. coli* and *C. elegans* are described in U.S. Pat. No. 6,251,384 to Tan et al., which is incorporated by reference in its entirety. The expression of GFP in plant cells is discussed in Hu & Cheng, 1995, FEBS Lett 369:331-33, and GFP expression in *Drosophila* is described in Davis et al., 1995, Dev. Biology 170:726-729.

Beta-galactosidase

Beta galactosidase ("beta-gal") is an enzyme that catalyzes the hydrolysis of beta-galactosides, including lactose, and the galactoside analogs o-nitrophenyl-beta-D-galactopyranoside ("ONPG") and chlorophenol red-beta-D-galactopyranoside ("CPRG") (see, e.g., Nielsen et al., 1983 Proc Natl Acad Sci USA 80(17):5198-5202; Eustice et al., 1991, Biotechniques 11:739-742; and Henderson et al., 1986, Clin. Chem. 32:1637-1641). The beta-gal gene functions well as a reporter gene because the protein product is extremely stable, resistant to proteolytic degradation in cellular lysates, and easily assayed. When ONPG is used as the substrate, beta-gal activity can be quantitated with a spectrophotometer or microplate reader.

As used herein, the term "beta galactosidase" or "beta-gal" is intended to embrace all beta-gals, including lacZ gene products, or recombinant enzymes derived from beta-gals which have beta-gal activity. The beta-gal gene functions well as a reporter gene because the protein product is extremely stable, resistant to proteolytic degradation in cellular lysates, and easily assayed. In an embodiment where ONPG is the substrate, beta-gal activity can be quantitated with a spectrophotometer or microplate reader to determine the amount of ONPG converted at 420 nm. In an embodiment when CPRG is the substrate, beta-gal activity can be quantitated with a spectrophotometer or microplate reader to determine the amount of CPRG converted at 570 to 595 nm. In yet another embodiment, the beta-gal activity can be visually ascertained by plating bacterial cells transformed with a beta-gal construct onto plates containing Xgal and IPTG. Bacterial colonies that are dark blue indicate the presence of high beta-gal activity and colonies that are varying shades of blue indicate varying levels of beta-gal activity.

Beta-glucoronidase

Beta-glucuronidase ("GUS") catalyzes the hydrolysis of a very wide variety of beta-glucuronides, and, with much lower efficiency, hydrolyzes some beta-galacturonides. GUS is very stable, will tolerate many detergents and widely varying ionic conditions, has no cofactors, nor any ionic requirements, can be assayed at any physiological pH, with an optimum between 5.0 and 7.8, and is reasonably resistant to thermal inactivation (see, e.g., U.S. Pat. No. 5,268,463, which is incorporated by reference in its entirety).

In one embodiment, the GUS is derived from the *Esherichia coli* beta-glucuronidase gene. In alternate embodiments of the invention, the beta-glucuronidase encoding nucleic acid is homologous to the *E. coli* beta-glucuronidase gene and/or may be derived from another organism or species.

GUS activity can be assayed either by fluorescence or spectrometry, or any other method described in U.S. Pat. No. 5,268,463, the disclosure of which is incorporated by reference in its entirety. For a fluorescent assay, 4-trifluoromethylumbelliferyl beta-D-glucuronide is a very sensitive substrate for GUS. The fluorescence maximum is close to 500 nm—bluish green, where very few plant compounds fluoresce or absorb. 4-trifluoromethylumbelliferyl beta-D-glucuronide also fluoresces much more strongly near neutral pH, allowing continuous assays to be performed more readily than with MUG. 4-trifluoromethylumbelliferyl beta-D-glucuronide can be used as a fluorescent indicator in vivo. The spectrophotometric assay is very straightforward and moderately sensitive (Jefferson et al., 1986, Proc. Natl. Acad. Sci. USA 86:8447-8451). A preferred substrate for spectrophotometric measurement is p-nitrophenyl beta-D-glucuronide, which when cleaved by GUS releases the chromophore p-nitrophenol. At a pH greater than its $pK_a$ (around 7.15) the ionized chromophore absorbs light at 400-420 nm, giving a yellow color.

Beta-lactamase

Beta-lactamases are nearly optimal enzymes in respect to their almost diffusion-controlled catalysis of beta-lactam hydrolysis, making them suited to the task of an intracellular reporter enzyme (see, e.g., Christensen et al., 1990, Biochem. J. 266: 853-861). They cleave the beta-lactam ring of beta-lactam antibiotics, such as penicillins and cephalosporins, generating new charged moieties in the process (see, e.g., O'Callaghan et al., 1968, Antimicrob. Agents. Chemother. 8: 57-63 and Stratton, 1988, J. Antimicrob. Chemother. 22, Suppl. A: 23-35). A large number of beta-lactamases have been isolated and characterized, all of which would be suitable for use in accordance with the present invention (see, e.g., Richmond & Sykes, 1978, Adv. Microb. Physiol. 9:31-88 and Ambler, 1980, Phil. Trans. R. Soc. Lond. [Ser.B.] 289: 321-331, the disclosures of which are incorporated by reference in their entireties).

The coding region of an exemplary beta-lactamase employed has been described in U.S. Pat. No. 6,472,205, Kadonaga et al., 1984, J. Biol. Chem. 259: 2149-2154, and Sutcliffe, 1978, Proc. Natl. Acad. Sci. USA 75: 3737-3741, the disclosures of which re incorporated by reference in their entireties. As would be readily apparent to those skilled in the field, this and other comparable sequences for peptides having beta-lactamase activity would be equally suitable for use in accordance with the present invention. The combination of a fluorogenic substrate described in U.S. Pat. Nos. 6,472,205, 5,955,604, and 5,741,657, the disclosures of which are incorporated by reference in their entireties, and a suitable beta-lactamase can be employed in a wide variety of different assay systems, such as are described in U.S. Pat. No. 4,740,459, which is hereby incorporated by reference in its entirety.

Chloramphenicol Acetyltransferase

Chloramphenicol acetyl transferase ("CAT") is commonly used as a reporter gene in mammalian cell systems because mammalian cells do not have detectable levels of CAT activity. The assay for CAT involves incubating cellular extracts with radiolabeled chloramphenicol and appropriate co-factors, separating the starting materials from the product by, for example, thin layer chromatography ("TLC"), followed by scintillation counting (see, e.g., U.S. Pat. No. 5,726,041, which is hereby incorporated by reference in its entirety).

As used herein, the term "chloramphenicol acetyltransferase" or "CAT" is intended to embrace all CATs, or recombinant enzymes derived from CAT which have CAT activity. While it is preferable that a reporter system which does not require cell processing, radioisotopes, and chromatographic separations would be more amenable to high through-put screening, CAT as a reporter gene may be preferable in situations when stability of the reporter gene is important. For example, the CAT reporter protein has an in vivo half life of about 50 hours, which is advantageous when an accumulative versus a dynamic change type of result is desired.

Secreted Alkaline Phosphatase

The secreted alkaline phosphatase ("SEAP") enzyme is a truncated form of alkaline phosphatase, in which the cleavage of the transmembrane domain of the protein allows it to be secreted from the cells into the surrounding media. In a preferred embodiment, the alkaline phosphatase is isolated from human placenta.

As used herein, the term "secreted alkaline phosphatase" or "SEAP" is intended to embrace all SEAP or recombinant enzymes derived from SEAP which have alkaline phosphatase activity. SEAP activity can be detected by a variety of methods including, but not limited to, measurement of catalysis of a fluorescent substrate, immunoprecipitation, HPLC, and radiometric detection. The luminescent method is preferred due to its increased sensitivity over calorimetric detection methods. The advantages of using SEAP is that a cell lysis step is not required since the SEAP protein is secreted out of the cell, which facilitates the automation of sampling and assay procedures. A cell-based assay using SEAP for use in cell-based assessment of inhibitors of the Hepatitis C virus protease is described in U.S. Pat. No. 6,280,940 to Potts et al. which is hereby incorporated by reference in its entirety.

4.5.4.1.2 tRNA Introns

Any nucleotide sequence recognized and excised by a tRNA splicing endonuclease complex may be inserted into the coding region of a reporter gene such that the mRNA coding the reporter gene out of frame utilizing well-known molecular biology techniques. For example, a nucleotide sequence comprising a bulge-helix-bulge structure or a mature domain of a precursor tRNA may be inserted into the coding region of a reporter gene such that the mRNA coding the reporter gene out of frame. Alternatively, a nucleotide sequence recognized and excised by a tRNA splicing endonuclease complex may be inserted into the 5' untranslated region, 3' untranslated region or both the 5' and 3' untranslated regions of a reporter gene construct. A nucleotide sequence recognized and excised by a tRNA splicing endonuclease complex may comprise 10 nucleotides, 15 nucleotides, 20 nucleotides, 25 nucleotides, 25 nucleotides, 30 nucleotides, 40 nucleotides, 45 nucleotides, 50 nucleotides, 55 nucleotides, 60 nucleotides, 65 nucleotides, 75 nucleotides, 100 nucleotides, 125 nucleotides, 150 nucleotides, or more. In certain embodiments, the nucleotide sequence is at least 10 nucleotides in length.

In a specific embodiment, a tRNA intron is inserted within the open reading frame of a reporter gene. In another embodiment, two, three, four, five or more tRNA introns are inserted within the open reading frame of a reporter gene. In an alternative embodiment, a tRNA intron is inserted within the 5' untranslated region, 3' untranslated region or both the 5' and 3' untranslated region of a reporter gene construct. In an alternative embodiment, two, three, four, five or more tRNA introns are inserted within the 5' untranslated region, 3' untranslated region or both the 5' and 3' untranslated region of a reporter gene construct. The tRNA intron may comprise a bulge-helix-bulge conformation.

A reporter gene containing a tRNA intron may be produced by any method well-known to one of skill in the art. For example, the reporter gene containing a tRNA intron may be chemically synthesized using phosphoramidite or other solution or solid-phase methods. Detailed descriptions of the chemistry used to form polynucleotides by the phosphoramidite method are well known (see, e.g., Caruthers et al., U.S. Pat. Nos. 4,458,066 and 4,415,732; Caruthers et al., 1982, Genetic Engineering 4:1-17; Users Manual Model 392 and 394 Polynucleotide Synthesizers, 1990, pages 6-1 through 6-22, Applied Biosystems, Part No. 901237; Ojwang, et al., 1997, Biochemistry, 36:6033-6045). After synthesis, the reporter gene containing a tRNA intron can be purified using standard techniques known to those skilled in the art (see Hwang et al., 1999, Proc. Natl. Acad. Sci. USA 96(23): 12997-13002 and references cited therein). Depending on the length of the reporter gene containing a tRNA intron and the method of its synthesis, such purification techniques include, but are not limited to, reverse-phase high-performance liquid chromatography ("reverse-phase HPLC"), fast performance liquid chromatography ("FPLC"), and gel purification. Methods for labeling the substrate with a fluorescent acceptor moiety, a fluorescent donor moiety and/or quencher are well-known in the art (see, e.g., U.S. Pat. Nos. 6,472,156, 6,451,543, 6,348,322, 6,342,379, 6,323,039, 6,297,018, 6,291,201, 6,280,981, 5,843,658, and 5,439,797, the disclosures of which are incorporated by reference in their entirety).

4.5.4.1.3 3' End Pre-mRNA Cleavage Site

3' end pre-mRNA endonuclease cleaves pre-mRNA at the 3' end to give rise to to a 3' end of the mRNA that is subsequently polyadenylated. The cleavage and polyadenylation site is located between a conserved hexanucleotide, AAUAAA, upstream and a G/U-rich sequence element downstream. Any method known to the skilled artisan can be used to detect and quantify the activity of a 3' end pre-mRNA endonuclease.

An assay for the activity of a 3' end pre-mRNA endonuclease can be performed in a cell, using a cell extract or in vitro using a purified mammalian 3' end pre-mRNA endonuclease complex. For a description of 3' end pre-mRNA endonuclease complexes see section 4.2.2.

If the assay is performed in a cell, the cell expresses all components required for the activity of the 3' end pre-mRNA endonuclease. In certain, more specific embodiments, the cell is a mammalian cell, e.g., a human cell, that endogenously expresses all components of a 3' end pre-mRNA endonuclease complex. In other embodiments, the cell has been modified to recombinantly express one or more components of the 3' end pre-mRNA endonuclease complex. Further, the detectably labeled substrate of the 3' end pre-mRNA endonuclease reaction can be microinjected or transfected (permanently or transiently) into the cell by any method known to the skilled artisan. If a reporter gene construct is used as a substrate, the substrate can be microinjected or transfected (permanently or transiently) into the cell or the cell can be modified such that the reporter gene is integrated into the genome of the cell.

In certain embodiments, a 3' end pre-mRNA reporter gene construct is used as substrate to detect and/or quantify the activity of a 3' end pre-mRNA endonuclease (see FIG. 19). In certain embodiments, a 3' end pre-mRNA reporter gene construct encodes two open reading frames (ORF), the upstream and the downstream ORF, wherein the two ORFs are separated by a cleavage and polyadenylation signal and the 3' located ORF is preceded by an internal ribosome entry site (IRES). For an example of a 3' end pre-mRNA reporter gene construct, see FIG. 18. If the cleavage takes place at the cleavage and polyadenylation site, the downstream reporter gene at the 3' end of the construct is not transcribed. Thus, the more active the 3' end pre-mRNA endonuclease is the less of the downstream reporter gene is expressed. The less active, i.e., in the presence of an inhibitor, the 3' end pre-mRNA endonuclease is the more RNA that includes the downstream reporter gene will be transcribed. The downstream reporter gene can then be translated via the IRES. Any IRES can be used with the methods of the invention. In a specific embodiment, the IRES is an IRES of the Hepatitis C virus (HCV). The substrate can be generated by any recombinant DNA technology known to the skilled artisan.

In certain embodiments, the ratio between the upstream reporter gene and the downstream reporter gene of the 3' end pre-mRNA reporter gene construct is the read-out. Thus, an increase in 3' end pre-mRNA cleavage will result in an increase of the upstream reporter gene:downstream reporter gene ratio. A decrease in 3' end pre-mRNA cleavage will result in an decrease of the upstream reporter gene:downstream reporter gene ratio.

4.5.4.1.4 Vectors

The nucleotide sequence coding for a reporter gene and the nucleotide sequence coding for a tRNA intron, the 3' end pre-mRNA cleavage site, the pre-tRNA cleavage site or the rRNA cleavage site can be inserted into an appropriate expression vector, i.e., a vector which contains the necessary elements for the transcription and translation of the inserted protein-coding sequence. The necessary transcriptional and translational signals can also be supplied by the reporter gene. A variety of host-vector systems may be utilized to express the reporter gene. These include, but are not limited to, mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA; and stable cell lines generated by transformation using a selectable marker. The expression elements of vectors vary in their strengths and specificities. Depending on the host-vector system utilized, any one of a number of suitable transcription and translation elements may be used.

Any of the methods previously described for the insertion of DNA fragments into a vector may be used to construct expression vectors containing a chimeric nucleic acid consisting of appropriate transcriptional/translational control signals and the protein coding sequences. These methods may include in vitro recombinant DNA and synthetic techniques and in vivo recombinants (genetic recombination). Expression of the reporter gene construct may be regulated by a second nucleic acid sequence so that the reporter gene is expressed in a host transformed with the recombinant DNA molecule. For example, expression of a reporter gene construct may be controlled by any promoter/enhancer element known in the art, such as a constitutive promoter, a tissue-specific promoter, or an inducible promoter. Specific examples of promoters which may be used to control gene expression include, but are not limited to, the SV40 early promoter region (Bernoist & Chambon, 1981, Nature 290: 304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42); prokaryotic expression vectors such as the β-lactamase promoter (VIIIa-Kamaroff et al., 1978, Proc. Natl. Acad. Sci. U.S.A. 75:3727-3731), or the tac promoter (DeBoer et al., 1983, Proc. Natl. Acad. Sci. U.S.A. 80:21-25); see also "Useful proteins from recombinant bacteria" in Scientific American, 1980, 242:74-94; plant expression vectors comprising the nopaline synthetase promoter region (Herrera-Estrella et al., Nature 303:209-213) or the cauliflower mosaic virus 35S RNA promoter (Gardner, et al., 1981, Nucl. Acids Res. 9:2871), and the promoter of the photosynthetic enzyme ribulose biphosphate carboxylase (Herrera-Estrella et al., 1984, Nature 310:115-120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58; alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94; myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378).

In a specific embodiment, a vector is used that comprises a promoter operably linked to a reporter gene, one or more origins of replication, and, optionally, one or more selectable markers (e.g., an antibiotic resistance gene). In a preferred embodiment, the vectors are CMV vectors, T7 vectors, lac vectors, pCEP4 vectors, 5.0/F vectors, or vectors with a tetracycline-regulated promoter (e.g., pcDNA™5/FRT/TO from Invitrogen Expression vectors containing the reporter gene construct of the present invention can be identified by three general approaches: (a) nucleic acid hybridization, (b) presence or absence of "marker" nucleic acid functions, (c) expression of inserted sequences, and (d) sequencing. In the first approach, the presence of the reporter gene inserted in an expression vector can be detected by nucleic acid hybridization using probes comprising sequences that are homologous to the inserted reporter gene. In the second approach, the recombinant vector/host system can be identified and selected based upon the presence or absence of certain "marker" nucleic acid functions (e.g., thymidine kinase activity, resistance to antibiotics, transformation phenotype, occlusion body formation in baculovirus, etc.) caused by the insertion of the nucleic acid of interest, i.e., the reporter gene construct, in the vector. For example, if the nucleic acid of interest is inserted within the marker nucleic acid sequence of the vector, recombinants containing the insert can be identified by the absence of the marker nucleic acid function. In the third approach, recombinant expression vectors can be identified by assaying the reporter gene product expressed by the recombinant. Such assays can be based, for example, on the physical or functional properties of the particular reporter gene.

In a preferred embodiment, the reporter gene constructs are cloned into stable cell line expression vectors. In a preferred embodiment, the stable cell line expression vector contains a site specific genomic integration site. In another preferred embodiment, the reporter gene construct is cloned into an episomal mammalian expression vector.

4.5.4.1.5 Transfection

Once a vector encoding the appropriate gene has been synthesized, a host cell is transformed or transfected with the vector of interest. The use of stable transformants is preferred. In a preferred embodiment, the host cell is a mammalian cell. In a more preferred embodiment, the host cell is a human cell. In another embodiment, the host cells are primary cells isolated from a tissue or other biological sample of interest. Host cells that can be used in the methods of the present invention include, but are not limited to, hybridomas, pre-B cells, 293 cells, 293T cells, HeLa cells, HepG2 cells, K562 cells, 3T3 cells. In another preferred embodiment, the host cells are immortalized cell lines derived from a source, e.g., a tissue. Other host cells that can be used in the present invention include, but are not limited to, virally-infected cells.

Transformation may be by any known method for introducing polynucleotides into a host cell, including, for example packaging the polynucleotide in a virus and transducing a host cell with the virus, and by direct uptake of the polynucleotide. The transformation procedure used depends upon the host to be transformed. Mammalian transformations (i.e., transfections) by direct uptake may be conducted using the calcium phosphate precipitation method of Graham & Van der Eb, 1978, Virol. 52:546, or the various known modifications thereof. Other methods for introducing recombinant polynucleotides into cells, particularly into mammalian cells, include dextran-mediated transfection, calcium phosphate mediated transfection, polybrene mediated transfection, protoplast fusion, electroporation, encapsulation of the polynucleotide(s) in liposomes, and direct microinjection of the polynucleotides into nuclei. Such methods are well-known to one of skill in the art.

In a preferred embodiment, stable cell lines containing the constructs of interest are generated for high throughput screening. Such stable cells lines may be generated by introducing a reporter gene construct comprising a selectable marker, allowing the cells to grow for 1-2 days in an enriched medium, and then growing the cells on a selective medium. The selectable marker in the recombinant plasmid confers resistance to the selection and allows cells to stably integrate the plasmid into their chromosomes and grow to form foci which in turn can be cloned and expanded into cell lines.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk–, hgprt– or aprt– cells, respectively. Also, anti-metabolite resistance can be used as the basis of selection for dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147) genes.

4.5.4.1.6 Cell-Free Extracts

The invention provides for the translation of the reporter gene constructs in a cell-free system. Techniques for practicing this specific aspect of this invention will employ, unless otherwise indicated, conventional techniques of molecular biology, microbiology, and recombinant DNA manipulation and production, which are routinely practiced by one of skill in the art. See, e.g., Sambrook, 1989, Molecular Cloning, A Laboratory Manual, Second Edition; DNA Cloning, Volumes I and II (Glover, Ed. 1985); and Transcription and Translation (Hames & Higgins, Eds. 1984).

Any technique well-known to one of skill in the art may be used to generate cell-free extracts for translation in vitro. For example, the cell-free extracts for in vitro translation reactions can be generated by centrifuging cells and clarifying the supernatant. In particular, a cell extract utilized in accordance with the invention may be an S1 extract (i.e., the supernatant from a 1,000×g spin) to an S500 extract (i.e., the supernatant from a 500,000×g spin), preferably an S10 extract (i.e., the supernatant from a 10,000×g spin) to an S250 extract (i.e., the supernatant from a 250,000×g spin). In a specific embodiment, a cell extract utilized in accordance with the invention is an S50 extract (i.e., the supernatant from a 50,000×g spin) to an S100 extract (i.e., the supernatant from a 100,000×g spin).

The cell-free translation extract may be isolated from cells of any species origin. For example, the cell-free translation extract may be isolated from human cells, cultured mouse cells, cultured rat cells, Chinese hamster ovary (CHO) cells, *Xenopus* oocytes, rabbit reticulocytes, wheat germ, or rye embryo (see, e.g., Krieg & Melton, 1984, Nature 308:203 and Dignam et al., 1990 Methods Enzymol. 182:194-203). Alternatively, the cell-free translation extract, e.g., rabbit reticulocyte lysates and wheat germ extract, can be purchased from, e.g., Promega, (Madison, Wis.). In a preferred embodiment, the cell-free extract is an extract isolated from human cells. In a more preferred embodiment, the human cells are HeLa cells.

4.5.5 Reporter Gene-Based Assays 4.5.5.1 Cell-Based Assays

After a vector containing the reporter gene construct is transformed or transfected into a host cell and a compound library is synthesized or purchased or both, the cells are used to screen the library to identify compounds that modulate the activity of a mammalian tRNA splicing endonuclease, a mammalian 3' end pre-mRNA endonuclease, pre-tRNA cleavage activity, or rRNA cleavage activity.

An assay for the activity of a tRNA endonuclease can be performed in a cell, using a cell extract or in vitro using a purified mammalian tRNA endonuclease complex. If the assay is performed in a cell, the cell expresses all components required for the activity of the tRNA endonuclease. In certain, more specific embodiments, the cell is a mammalian cell, e.g., a human cell, that endogenously expresses all components of a tRNA endonuclease complex. In other embodiments, the cell has been modified to recombinantly express one or more components of the tRNA endonuclease complex. Further, the detectably labeled substrate of the tRNA endonuclease reaction can be microinjected or transfected (permanently or transiently) into the cell by any method known to the skilled artisan. If a reporter gene construct is used as a substrate, the substrate can be microinjected or transfected (permanently or transiently) into the cell or the cell can be modified such that the reporter gene is integrated into the genome of the cell.

The reporter gene-based assays for tRNA splicing endonuclease activity may be conducted by contacting a compound or a member of a library of compounds with a cell genetically engineered to contain a reporter gene construct comprising a reporter gene and a tRNA intron within the open reading frame of the reporter gene, or within the 5' untranslated region, 3' untranslated region or both the 5' and 3' untranslated regions of the reporter gene construct, or within a mRNA splice site of the reporter gene; and measuring the expression of said reporter gene if pre-tRNA splicing endonuclease activity is to be assayed.

The alteration in reporter gene expression relative to a previously determined reference range, the absence of the compound or a control in such reporter-gene based assays indicates that a particular compound modulates the activity of a tRNA splicing endonuclease. A decrease in reporter gene expression relative to a previously determined reference range, the absence of the compound or a control in such reporter-gene based assays indicates that a particular compound reduces or inhibits the activity of a tRNA splicing endonuclease (e.g., the recognition or cleavage of a tRNA intron). An increase in reporter gene expression relative to a previously determined reference range, the absence of the compound or a control in such reporter-gene based assays indicates that a particular compound enhances the activity of a tRNA splicing endonuclease. In a preferred embodiment, a negative control (e.g., PBS or another agent that is known to have no effect on the expression of the reporter gene) and a positive control (e.g., an agent that is known to have an effect on the expression of the reporter gene, preferably an agent that effects the activity of a human tRNA splicing endonuclease) are included in the cell-based assays described herein. In a particular embodiment, the pre-tRNA splicing endonuclease is a human pre-tRNA splicing endonuclease complex.

An assay for the activity of a 3' end pre-mRNA endonuclease can be performed in a cell, using a cell extract or in vitro using a purified mammalian 3' end pre-mRNA endonuclease complex. If the assay is performed in a cell, the cell expresses all components required for the activity of the 3' end pre-mRNA endonuclease. In certain, more specific embodiments, the cell is a mammalian cell, e.g., a human cell, that endogenously expresses all components of a 3' end pre-mRNA endonuclease complex. In other embodiments, the cell has been modified to recombinantly express one or more components of the 3' end pre-mRNA endonuclease complex. Further, the detectably labeled substrate of the 3' end pre-mRNA endonuclease reaction can be microinjected or transfected (permanently or transiently) into the cell by any method known to the skilled artisan. If a reporter gene construct is used as a substrate, the substrate can be microinjected or transfected (permanently or transiently) into the cell or the cell can be modified such that the reporter gene is integrated into the genome of the cell.

The reporter gene based assays for 3' end pre-mRNA endonuclease activity may be conducted by contacting a compound or a member of a library of compounds with a cell genetically engineered to contain a reporter gene construct comprising a reporter gene and a 3' end pre-mRNA cleavage site. In a particular embodiment, the 3' end pre-mRNA endonuclease is a human 3' end pre-mRNA endonuclease complex.

In certain embodiments, a 3' end pre-mRNA reporter gene construct encodes two open reading frames (ORF), the upstream and the downstream ORF, wherein the two ORFs are separated by a cleavage and polyadenylation signal and the 3' located ORF is preceded by an internal ribosome entry site (IRES). For an example of a 3' end pre-mRNA reporter gene construct, see FIG. 18. If the cleavage takes place at the cleavage and polyadenylation site, the downstream reporter gene at the 3' end of the construct is not transcribed. Thus, the more active the 3' end pre-mRNA endonuclease is the less of the downstream reporter gene is expressed. The less active, i.e., in the presence of an inhibitor, the 3' end pre-mRNA endonuclease is the more RNA that includes the downstream reporter gene will be transcribed. The downstream reporter gene can then be translated via the IRES.

In certain embodiments, the ratio between the upstream reporter gene and the downstream reporter gene of the 3' end pre-mRNA reporter gene construct is the read-out. Thus, an increase in 3' end pre-mRNA cleavage will result in an increase of the upstream reporter gene:downstream reporter gene ratio. A decrease in 3' end pre-mRNA cleavage will result in an decrease of the upstream reporter gene:downstream reporter gene ratio.

The step of contacting a compound or a member of a library of compounds with a cell genetically engineered to contain a reporter gene construct may be conducted under physiologic conditions. In specific embodiment, a compound or a member of a library of compounds is added to the cells in the presence of an aqueous solution. In accordance with this embodiment, the aqueous solution may comprise a buffer and a combination of salts, preferably approximating or mimicking physiologic conditions. Alternatively, the aqueous solution may comprise a buffer, a combination of salts, and a detergent or a surfactant. Examples of salts which may be used in the aqueous solution include, but not limited to, KCl, NaCl, and/or $MgCl_2$. The optimal concentration of each salt used in the aqueous solution is dependent on the cells and compounds used and can be determined using routine experimentation. The step of contacting a compound or a member of a library of compounds with a human cell genetically engineered to contain the reporter gene construct may be performed for at least 0.2 hours, 0.25 hours, 0.5 hours, 1 hour, 2 hours, 3 hours, 4 hours, 5 hours, 6 hours, 8 hours, 10 hours, 12 hours, 18 hours, or at least 1 day.

In one embodiment, the invention provides a method for identifying a compound that modulates tRNA splicing endonuclease activity or 3' end pre-mRNA endonuclease activity, wherein the method comprises: (a) expressing a nucleic acid comprising a reporter gene in a cell, wherein the reporter gene comprises a tRNA intron or a 3' end pre-mRNA cleavage site; (b) contacting said cell with a compound or a member of a library of compounds; and (c) detecting the expression of said reporter gene, wherein a compound that modulates tRNA splicing endonuclease activity is identified if the expression of said reporter gene in the presence of a compound is altered relative to a previously determined reference range or the expression of said reporter gene in the absence of the compound or the presence of a control. In another embodiment, the invention provides a method for identifying a compound that modulates tRNA splicing endonuclease activity or pre-tRNA splicing endonuclease activity, said method comprising: (a) contacting a member of a library of compounds with a cell containing a nucleic acid comprising a reporter gene, wherein the reporter gene comprises a tRNA intron or a 3' end pre-mRNA endonuclease cleavage site; and (b) detecting the expression of said reporter gene, wherein a compound that modulates tRNA splicing endonuclease activity or 3' end pre-mRNA endonuclease activity is identified if the expression of said reporter gene in the presence of a compound is altered relative to a previously determined reference range the expression of said reporter gene in the absence of said compound or the presence of a control.

The expression of a reporter gene and/or activity of the protein encoded by the reporter gene in the cell-based reporter-gene assays may be detected by any technique well-known to one of skill in the art. The expression of a reporter gene can be readily detected, e.g., by quantifying the protein and/or RNA encoded by said gene. Many methods standard in the art can be thus employed, including, but not limited to, immunoassays to detect and/or visualize gene expression (e.g., Western blot, immunoprecipitation followed by sodium dodecyl sulfate polyacrylamide gel electrophoresis (SDS-PAGE), immunocytochemistry, etc) and/or hybridization assays to detect gene expression by detecting and/or visualizing respectively mRNA encoding a gene (e.g., Northern assays, dot blots, in situ hybridization, etc), etc. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody which recognizes the antigen to the cell lysate, incubating for a period of time (e.g., 1 to 4 hours) at 40° C., adding protein A and/or protein G sepharose beads to the cell lysate, incubating for about an hour or more at 40° C., washing the beads in lysis buffer and resuspending the beads in SDS/sample buffer. The ability of the antibody to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody which recognizes the antigen) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}$P or $^{125}$I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding a primary antibody (which recognizes the antigen) conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the primary antibody) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

Methods for detecting the activity of a protein encoded by a reporter gene will vary with the reporter gene used. Assays for the various reporter genes are well-known to one of skill in the art. For example, as described in Section 5.2.1., luciferase, beta-galactosidase ("beta-gal"), beta-glucoronidase ("GUS"), beta-lactamase, chloramphenicol acetyltransferase ("CAT"), and alkaline phosphatase ("AP") are enzymes that can be analyzed in the presence of a substrate and could be amenable to high throughput screening. For example, the reaction products of luciferase, beta-galactosidase ("beta-gal"), and alkaline phosphatase ("AP") are assayed by changes in light imaging (e.g., luciferase), spectrophotometric absorbance (e.g., beta-gal), or fluorescence (e.g., AP). Assays for changes in light output, absorbance, and/or fluorescence are easily adapted for high throughput screening. For example, beta-gal activity can be measured with a microplate reader. Green fluorescent protein ("GFP") activity can be measured by changes in fluorescence. For example, in the case of mutant GFPs that fluoresce at 488 nm, standard fluorescence activated cell sorting ("FACS") equipment can be used to separate cells based upon GFP activity.

Alterations in the expression of a reporter gene may be determined by comparing the level of expression of the reporter gene to a negative control (e.g., PBS or another agent that is known to have no effect on the expression of the reporter gene) and optionally, a positive control (e.g., an agent that is known to have an effect on the expression of the reporter gene, preferably an agent that effects the activity of a human tRNA splicing endonuclease). Alternatively, alterations in the expression of a reporter gene may be determined by comparing the level of expression of the reporter gene to a previously determined reference range.

4.5.5.2 Cell-Free Assays

After a vector containing the reporter gene construct is produced, a cell-free translation extract is generated or purchased, and a compound library is synthesized or purchased or both, the cell-free translation extract and nucleic acid are used to screen the library to identify compounds that modulate the activity of tRNA splicing endonuclease or 3' end pre-mRNA endonuclease. The reporter gene-based assays may be conducted in a cell-free manner by contacting a compound with a cell-free extract and a reporter gene construct comprising the reporter gene construct (which, depending on whether 3' end pre-mRNA endonuclease activity or pre-tRNA splicing endonuclease activity is to be assayed, comprises a reporter gene and a pre-tRNA splice site or a 3' end pre-mRNA endonuclease site, respectively), and measuring the expression of said reporter gene. The alteration in reporter gene expression relative to a previously determined reference range, the absence of the compound or a control in such reporter-gene based assays indicates that a particular compound modulates the activity of a tRNA splicing endonuclease or a pre-tRNA splicing endonuclease.

The activity of a compound in the cell-free extract can be determined by assaying the activity of a reporter protein encoded by a reporter gene, or alternatively, by quantifying the expression of the reporter gene by, for example, labeling the in vitro translated protein (e.g., with $^{35}$S-labeled methionine), northern blot analysis, RT-PCR or by immunological methods, such as western blot analysis or immunoprecipitation. Such methods are well-known to one of skill in the art.

4.5.6 FRET Assays

Fluorescence resonance energy transfer ("FRET") can be used to detect alterations in the activity of a tRNA splicing endonuclease or a 3' end pre-mRNA endonuclease complex. In the FRET assays described herein, the subunits of a complex of the invention or a substrate for a tRNA splicing endonuclease or a 3' end pre-mRNA endonuclease complex may be labeled with fluorophores.

In order to obtain FRET between the fluorescent donor moiety and the fluorescent acceptor moiety or a quencher, the two moieties have to be in spatial proximity with each other. Thus, in certain embodiments, a substrate or subunits of a complex of the invention are labeled such that the fluorescent donor moiety and the fluorescent acceptor moiety or a quencher are at most 0.5 nm, at most 1 nm, at most 5 nm, at most 10 nm, at most 20 nm, at most 30 nm, at most 40 nm, at most 50 nm or at most 100 nm apart from each other.

Any nucleotide sequence recognized and excised by a human tRNA splicing endonuclease may be utilized as a substrate for a human tRNA splicing endonuclease in a FRET assay described herein. For example, a nucleotide sequence comprising a bulge-helix-bulge structure or a mature domain of a precursor tRNA may be utilized as a substrate for a human tRNA splicing endonuclease in a FRET assay described herein. A nucleotide sequence recognized and excised by a human tRNA splicing endonuclease may comprise 10 nucleotides, 15 nucleotides, 20 nucleotides, 25 nucleotides, 25 nucleotides, 30 nucleotides, 40 nucleotides, 45 nucleotides, 50 nucleotides, 55 nucleotides, 60 nucleotides, 65 nucleotides, 75 nucleotides, 100 nucleotides, 125 nucleotides, 150 nucleotides, or more. In a specific embodiment, the substrates for a tRNA splicing endonuclease utilized in the FRET assays described herein comprise a tRNA intron. The substrate may comprise a bulge-helix-bulge conformation. In a preferred embodiment, the substrate comprises a tRNA mature domain that contains an intron.

In certain embodiments, the substrates depicted in FIG. 1 are used in the FRET assays. In particular, the hybridized tRNA substrate and circularly permuted tRNA substrate depicted in FIGS. 1B and 1C, respectively, are used in the FRET assays. The free 5' and 3' ends of the intron of the hybridized tRNA substrate (FIG. 1B) or the free 5' and 3' ends of the intron of circularly permuted tRNA substrate (FIG. 1C) may be labeled with a fluorophore such that the close spatial proximity of the fluorophore on the 5' end with the fluorophore on the 3' end results in fluorescence resonance energy transfer. Cleavage of the substrate will then result in a spatial separation of the labeled 5' end from the labeled 3' end and thus, in reduced fluorescence resonance energy transfer. Thus, the skilled artisan can measure FRET and determine the concentration of cleaved versus uncleaved substrate. The concentration of uncleaved substrate decreases as FRET declines.

Alternatively, the 3' end or the 5' end is labeled with a fluorophore and the other end, i.e., the 5' end or the 3' end, respectively, is labeled with a quencher of the fluorophore. Upon cleavage of the intron by tRNA splicing endonuclease, the quencher and the fluorophore are separated from each other resulting in a measurable change in fluorescence. The fluorescence signal increases as the cleavage reaction proceeds.

In certain embodiments, a substrate of 3' end pre-mRNA endonuclease complex is labeled such that its cleavage would result in loss of FRET, i.e., one end is labeled with the donor fluorophore and the other end is labeled with an acceptor fluorophore. Alternatively, a substrate of 3' end pre-mRNA endonuclease complex is labeled such that its cleavage would result in emergence of a signal. In this embodiment, one end of the substrate is labeled with a fluorophore and the other end is labeled with a quencher.

In accordance with the invention, a substrate can be labeled with a single pair of fluorescent donor and acceptor moieties. A substrate can be labeled with different pairs of fluorescent donor moieties and fluorescent acceptor moieties. For example, two, three, four, five or more pairs of fluorescent donor moieties and fluorescent acceptor moieties can be used. In this situation, preferably, at least one of the pairs comprise a fluorescent acceptor moiety that has a different emission spectrum from the fluorescent acceptor moiety of at least one of the other pairs. Alternatively, when at least three pairs are used, the fluorescent acceptor moiety of the first pair, second pair and third pair has a different emission spectrum than the fluorescent acceptor moiety of the other two. Methods for labeling the substrate with a fluorescent acceptor moiety, a fluorescent donor moiety and/or quencher are well-known in the art (see, e.g., U.S. Pat. Nos. 6,472,156, 6,451,543, 6,348,322, 6,342,379, 6,323,039, 6,297,018, 6,291,201, 6,280,981, 5,843,658, and 5,439,797, the disclosures of which are incorporated by reference in their entirety). The labeled substrate can be microinjected or transfected into human cells (preferably, mammalian cells and more preferably, human cells) utilizing techniques well-known to one of skill in the art (see, e.g., Adams et al., 1991, Nature 349:694-697).

4.5.6.1 Cell-Based Assays with a Labeled Substrate

The FRET cell-based assays may be conducted by microinjecting or transfecting (e.g., using liposomes or electroporation) a substrate for a tRNA splicing endonuclease or a substrate for a 3' end pre-mRNA endonuclease into a cell and contacting the cell with a compound, wherein the substrate is labeled such that its cleavage by either 3' end pre-mRNA endonuclease complex or the pre-tRNA splicing endonuclease complex would result in the loss of FRET or the emergence of fluorescence, e.g., fluorescence microscopy or a fluorescence emission detector such as a Viewlux or Analyst.

In certain embodiments, a substrate is labeled with a fluorophore and a quencher in spatial proximity such that the quencher reduces or eliminates the signal emitted from the fluorophore. Upon cleavage of the labeled substrate the quencher and the fluorophore are no longer in spatial proximity and the signal emitted from the fluorophore increases or emerges. The labeled substrate is then microinjected or transfected into a cell for assaying the effect of a compound on 3' end pre-mRNA endonuclease activity or pre-tRNA endonuclease activity. In other embodiments, a substrate can be labeled with two different fluorophores. The FRET cell-based assays may be conducted by microinjecting or transfecting a substrate for a human tRNA splicing endonuclease into a cell and contacting the cell with a compound, wherein the substrate is labeled at the 5' end with a fluorescent donor moiety and labeled at the 3' end with a fluorescent acceptor moiety, or, alternatively, the substrate is labeled at the 5' end with a fluorescent acceptor moiety and labeled at the 3' end with a fluorescent donor moiety, and measuring the fluorescence of the substrate by, e.g., fluorescence microscopy or a fluorescence emission detector such as a Viewlux or Analyst. The endogenous tRNA splicing endonuclease will cleave the substrate and result in the production of a detectable fluorescent signal by the fluorescent donor moiety and fluorescent acceptor moiety at the wavelength of the fluorescent donor moiety. A compound that inhibits or reduces the activity of the endogenous tRNA splicing endonuclease will inhibit or reduce cleavage of the substrate and thus, increase the fluorescence emission of the fluorescent acceptor moiety at the wavelength of the fluorescent donor moiety relative to a negative control (e.g., PBS). A compound that enhances the activity of the endogenous tRNA splicing endonuclease will enhance the cleavage of the substrate and thus, reduce the fluorescence emission of the fluorescent acceptor moiety at the wavelength of the fluorescent donor moiety relative to a negative control (e.g., PBS). In a preferred embodiment, a negative control (e.g., PBS or another agent that is known to have no effect on the cleavage of the substrate) and a positive control (e.g., an agent that is known to have an effect on the cleavage of the substrate) are included in the FRET cell-based assays described herein.

Alternatively, the FRET cell-based assays may be conducted by microinjecting or transfecting a substrate for a human tRNA splicing endonuclease into a cell and contacting the cell with a compound, wherein the substrate is labeled at the 5' end with a fluorescent donor moiety and labeled at the 3' end with a fluorescent acceptor moiety, or, alternatively, the substrate is labeled at the 5' end with a fluorescent acceptor moiety and labeled at the 3' end with a fluorescent donor moiety, and measuring the fluorescence of the substrate by, e.g., fluorescence microscopy or a fluorescence emission detector such as a Viewlux or Analyst. The endogenous tRNA splicing endonuclease will cleave the substrate and result in the production of a detectable fluorescent signal by the fluorescent donor moiety and fluorescent acceptor moiety at the wavelength of the fluorescent donor moiety. A compound that inhibits or reduces the activity of the endogenous tRNA splicing endonuclease will inhibit or reduce cleavage of the substrate and thus, increase the fluorescence emission of the fluorescent acceptor moiety at the wavelength of the fluorescent donor moiety relative to a negative control (e.g., PBS). A compound that enhances the activity of the endogenous tRNA splicing endonuclease will enhance the cleavage of the substrate and thus, reduce the fluorescence emission of the fluorescent acceptor moiety at the wavelength of the fluorescent donor moiety relative to a negative control (e.g., PBS). In a preferred embodiment, a negative control (e.g., PBS or another agent that is known to have no effect on the cleavage of the substrate) and a positive control (e.g., an agent that is known to have an effect on the cleavage of the substrate) are included in the FRET cell-based assays described herein.

The assay can be conducted in any buffer system that provides conditions conducive to the tRNA endonuclease reaction. Such buffer systems are well known to the skilled artisan. In a specific embodiment, the buffer is the medium in which the cell culture is kept.

Care should be taken that Magnesium ions are present in the medium.

In certain embodiments, the assay is conducted for at least 0.2 hours, 0.25 hours, 0.5 hours, 1 hour, 2 hours, 3 hours, 4 hours, 5 hours, 6 hours, 8 hours, 10 hours, 12 hours, 18 hours, or at least 1 day.

In a specific embodiment, the invention provides a method of identifying an antiproliferative compound that inhibits or reduces human tRNA splicing endonuclease activity, said method comprising: (a) microinjecting or transfecting a substrate of a tRNA splicing endonuclease into a human cell, wherein the substrate is labeled at the 5' end with a fluorophore and labeled at the 3' end with a quencher, or alternatively, the substrate is labeled at the 5' end with a quencher and labeled at the 3' end with a fluorophore; (b) contacting the cell with a compound or a member of a library of compounds; and (c) measuring the activity of the tRNA splicing endonuclease, wherein an antiproliferative compound that inhibits or reduces tRNA splicing endonuclease activity is identified if a fluorescent signal is not detectable in the presence of the compound relative to the absence of the compound or the presence of a control. In another embodiment, the invention provides a method of identifying an antiproliferative compound that inhibits or reduces human tRNA splicing endonuclease activity, said method comprising: (a) contacting a human cell containing a substrate of a tRNA splicing endonuclease with a compound or a member of a library of compounds, wherein the substrate is labeled at the 5' end with a fluorophore and at the 3' end with a quencher, or alternatively, the substrate is labeled at the 5' end with a quencher and labeled at the 3' end with a fluorophore; and (b) measuring the activity of the tRNA splicing endonuclease, wherein an antiproliferative compound that inhibits or reduces tRNA splicing endonuclease activity is identified if a fluorescent signal is not detectable in the presence of the compound relative to the absence of the compound or the presence of a control.

In another embodiment, the invention provides a method of identifying an antiproliferative compound that inhibits or reduces human tRNA splicing endonuclease activity, said method comprising: (a) microinjecting or transfecting a substrate of a tRNA splicing endonuclease into a human cell, wherein the substrate is labeled at the 5' end with a fluorescent donor moiety and labeled at the 3' end with a fluorescent acceptor moiety, or alternatively, the substrate is labeled at the 5' end with a fluorescent acceptor moiety and labeled at the 3' end with a fluorescent donor moiety; (b) contacting the cell with a compound or a member of a library of compounds; and (c) measuring the activity of the tRNA splicing endonuclease, wherein an antiproliferative compound that inhibits or reduces tRNA splicing endonuclease activity is identified if the fluorescent signal detected in the presence of the compound is altered relative to the absence of the compound or the presence of a control. In another embodiment, the invention provides a method of identifying an antiproliferative compound that inhibits or reduces human tRNA splicing endonuclease activity, said method comprising: (a) contacting a human cell containing substrate of a tRNA splicing endonuclease with a compound or a member of a library of compounds, wherein the substrate is labeled at the 5' end with a fluorescent donor moiety and labeled at the 3' end with a fluorescent acceptor moiety, or alternatively, the substrate is labeled at the 5' end with a fluorescent acceptor moiety and labeled at the 3' end with a fluorescent donor moiety; and (b) measuring the activity of the tRNA splicing endonuclease, wherein an antiproliferative compound that inhibits or reduces tRNA splicing endonuclease activity is identified if the fluorescence emission of the fluorescent acceptor moiety at the wavelength of the fluorescent donor moiety in the presence of the compound is increased relative to the absence of the compound or the presence of a control.

The activity of a compound on a human tRNA splicing endonuclease or a 3' end pre-mRNA endonuclease in the FRET cell-based assays can be determined by measuring the fluorescent emission spectra of the substrate utilizing techniques well-known to one of skill in the art. The fluorescent emission spectra measured depends, in part, on the fluorophore used.

4.5.6.2 Cell-Free Assays with a Labeled Substrate

The FRET cell-free assays for human tRNA splicing endonuclease may be conducted by contacting a substrate for a human tRNA splicing endonuclease with a cell-free extract (see Section 4.4.1.2 supra regarding cell-free extracts, preferably, a tRNA splicing endonuclease extract) or a purified human tRNA splicing endonuclease and a compound, wherein the substrate is labeled at the 5' end with a fluorophore and labeled at the 3' end with a quencher or, alternatively, the substrate is labeled at the 3' end with a fluorophore and labeled at the 5' end with a quencher, and measuring the fluorescence of the substrate in, e.g., a fluorescence emission detector such as a Viewlux or Analyst. The tRNA splicing endonuclease in the cell-free extract will cleave the substrate and result in the production of a detectable fluorescent signal. A compound that inhibits or reduces the activity of the tRNA splicing endonuclease will inhibit or reduce the cleavage of the substrate and thus, inhibit or reduce the production of a detectable fluorescent signal relative to a negative control (e.g., PBS). A compound that enhances the activity of the tRNA splicing endonuclease will enhance the cleavage of the substrate and thus, increase the production of a detectable signal relative to a negative control (e.g., PBS).

Alternatively, the FRET cell-free-based assays for human tRNA splicing endonuclease may be conducted by contacting a substrate for a human tRNA splicing endonuclease with a cell-free extract (preferably, a tRNA splicing endonuclease extract) or a purified human tRNA splicing endonuclease and a compound, wherein the substrate is labeled at the 5' end with a fluorescent donor moiety and labeled at the 3' end with a fluorescent acceptor moiety, or alternatively, the substrate is labeled at the 5' end with a fluorescent acceptor moiety and labeled at the 3' end with a fluorescent donor moiety, and measuring the fluorescence of the substrate by, e.g., a fluorescence emission detector such as a Viewlux or Analyst. The tRNA splicing endonuclease will cleave the substrate and result in the production of a detectable fluorescent signal by the fluorescent donor moiety and fluorescent acceptor moiety at the wavelength of the fluorescent donor moiety. A compound that inhibits or reduces the activity of the tRNA splicing endonuclease will inhibit or reduce cleavage of the substrate and thus, increase the fluorescence emission of the fluorescent acceptor moiety at the wavelength of the fluorescent donor moiety relative to a negative control (e.g., PBS). A compound that enhances the activity of the tRNA splicing endonuclease will enhance the cleavage of the substrate and thus, reduce the fluorescence emission of the fluorescent acceptor moiety at the wavelength of the fluorescent donor moiety relative to a negative control (e.g., PBS). In a preferred embodiment, a negative control (e.g., PBS or another agent that is known to have no effect on the cleavage of the substrate) and a positive control (e.g., an agent that is known to have an effect on the cleavage of the substrate) are included in the FRET cell-free assays described herein.

The FRET cell-free assays for human 3' end mRNA endonuclease may be conducted by contacting a substrate for a human 3' end pre-mRNA endonuclease with a cell-free extract (see Section 4.4.1.2 supra regarding cell-free extracts, preferably, a tRNA splicing endonuclease extract) or a purified human 3' end pre-mRNA endonuclease and a compound, wherein the substrate is labeled at the 5' end with a fluorophore and labeled at the 3' end with a quencher or, alternatively, the substrate is labeled at the 3' end with a fluorophore and labeled at the 5' end with a quencher, and measuring the fluorescence of the substrate in, e.g., a fluorescence emission detector such as a Viewlux or Analyst. The 3' end pre-mRNA endonuclease in the cell-free extract will cleave the substrate and result in the production of a detectable fluorescent signal. A compound that inhibits or reduces the activity of the 3' end pre-mRNA endonuclease will inhibit or reduce the cleavage of the substrate and thus, inhibit or reduce the production of a detectable fluorescent signal relative to a negative control (e.g., PBS). A compound that enhances the activity of the 3' end pre-mRNA endonuclease will enhance the cleavage of the substrate and thus, increase the production of a detectable signal relative to a negative control (e.g., PBS).

The FRET cell-free assays for human 3' end mRNA endonuclease may be conducted by contacting a substrate for a human 3' end pre-mRNA endonuclease with a cell-free extract (see Section 4.4.1.2 supra regarding cell-free extracts, preferably, a tRNA splicing endonuclease extract) or a purified human 3' end pre-mRNA endonuclease and a compound, wherein the substrate is labeled at the 5' end with a fluorophore donor and labeled at the 3' end with a fluorophore acceptor or, alternatively, the substrate is labeled at the 3' end with a fluorophore donor and labeled at the 5' end with a fluorophore acceptor, and measuring the fluorescence of the substrate in, e.g., a fluorescence emission detector such as a Viewlux or Analyst. The 3' end pre-mRNA endonuclease or tRNA splicing endonuclease in the cell-free extract will cleave the substrate and result in the production of a detectable fluorescent signal. A compound that inhibits or reduces the activity of the 3' end pre-mRNA endonuclease or tRNA splicing endonuclease will inhibit or reduce the cleavage of the substrate and thus, increase the production of a detectable signal relative to a negative control (e.g., PBS). A compound that enhances the activity of the 3' end pre-mRNA endonuclease or tRNA splicing endonuclease will enhance the cleavage of the substrate and thus, inhibit or reduce the production of a detectable fluorescent signal relative to a negative control (e.g., PBS).

A FRET assay can be conducted in any buffer system that provides conditions conducive to the tRNA endonuclease reaction. Such buffer systems are well known to the skilled artisan. In a specific embodiment, the buffer comprises 20 mM Tris at a pH of 7.0, 50 mM KCl, 0.1 mM DTT, 5 mM $MgCl_2$, and 0.4% Triton X100. Care should be taken that pH, salt concentration, detergent concentration etc. of the buffer system do not interfere with FRET.

In certain embodiments, the assay is conducted for at least 0.2 hours, 0.25 hours, 0.5 hours, 1 hour, 2 hours, 3 hours, 4 hours, 5 hours, 6 hours, 8 hours, 10 hours, 12 hours, 18 hours, or at least 1 day.

In one embodiment, the invention provides a method of identifying an antiproliferative compound that inhibits or reduces human tRNA splicing endonuclease activity, said method comprising: (a) contacting a human cell-free extract (preferably, a tRNA splicing endonuclease extract) or a purified human tRNA splicing endonuclease with a substrate of a tRNA splicing endonuclease and a member of a library of compounds, wherein the substrate is labeled at the 5' end with a fluorophore and labeled at the 3' end with a quencher, or alternatively, the substrate is labeled at the 5' end with a quencher and labeled at the 3' end with a fluorophore; and (b) measuring the activity of the tRNA splicing endonuclease, wherein an antiproliferative compound that inhibits or reduces tRNA splicing endonuclease activity is identified if a fluorescent signal is not detectable in the presence of the compound relative to the absence of the compound or the presence of a control. In another embodiment, the invention provides a method of identifying an antiproliferative compound that inhibits or reduces human tRNA splicing endonuclease activity, said method comprising: (a) contacting a human cell-free extract (preferably, a tRNA splicing endonuclease extract) or a purified human tRNA splicing endonuclease with a substrate of a tRNA splicing endonuclease and a member of a library of compounds, wherein said substrate is labeled at the 5' end with a fluorescent donor moiety and labeled at the 3' end with a fluorescent acceptor moiety, or alternatively, the substrate is labeled at the 5' end with a fluorescent acceptor moiety and labeled at the 3' end with a fluorescent donor moiety; and (b) measuring the activity of the tRNA splicing endonuclease, wherein an antiproliferative compound that inhibits tRNA splicing endonuclease activity is identified if the fluorescence emission of the fluorescent acceptor moiety at the wavelength of the fluorescent donor moiety detected in the presence of the compound is increased relative to the absence of the compound or the presence of a control.

In one embodiment, the invention provides a method of identifying an antiproliferative compound that inhibits or reduces human 3' pre-mRNA endonuclease activity, said method comprising: (a) contacting a human cell-free extract (preferably, a 3' pre-mRNA endonuclease extract) or a purified human 3' pre-mRNA endonuclease with a substrate of a 3' pre-mRNA endonuclease and a member of a library of compounds, wherein the substrate is labeled at the 5' end with a fluorophore and labeled at the 3' end with a quencher, or alternatively, the substrate is labeled at the 5' end with a quencher and labeled at the 3' end with a fluorophore; and (b) measuring the activity of the 3' pre-mRNA endonuclease, wherein an antiproliferative compound that inhibits or reduces 3' pre-mRNA endonuclease activity is identified if a fluorescent signal is not detectable in the presence of the compound relative to the absence of the compound or the presence of a control. In another embodiment, the invention provides a method of identifying an antiproliferative compound that inhibits or reduces human 3' pre-mRNA endonuclease activity, said method comprising: (a) contacting a human cell-free extract (preferably, a 3' pre-mRNA endonuclease extract) or a purified human 3' pre-mRNA endonuclease with a substrate of a tRNA splicing endonuclease and a member of a library of compounds, wherein said substrate is labeled at the 5' end with a fluorescent donor moiety and labeled at the 3' end with a fluorescent acceptor moiety, or alternatively, the substrate is labeled at the 5' end with a fluorescent acceptor moiety and labeled at the 3' end with a fluorescent donor moiety; and (b) measuring the activity of the 3' pre-mRNA endonuclease, wherein an antiproliferative compound that inhibits 3' pre-mRNA endonuclease activity is identified if the fluorescence emission of the fluorescent acceptor moiety at the wavelength of the fluorescent donor moiety detected in the presence of the compound is increased relative to the absence of the compound or the presence of a control.

The activity of a compound on a human tRNA splicing endonuclease or 3' pre-mRNA endonuclease in the FRET cell-free assays can be determined by measuring the fluorescent emission spectra of the substrate utilizing techniques well-known to one of skill in the art. The fluorescent emission spectra measured depends, in part, on the fluorophore used.

4.5.6.3 Cell-Based Assays with Labeled Enzyme

A FRET cell-based assay may be conducted by microinjecting or transfecting a first subunit of a human tRNA splicing endonuclease (see Table 1 for the components of the complex) labeled with a fluorophore and a second, different subunit of a human tRNA splicing endonuclease (see Table 1 for the components of the complex) labeled with a quencher into a cell and contacting the cell with a compound, and measuring the fluorescence of the human tRNA splicing endonuclease by, e.g., fluorescence microscopy or a fluorescence emission detector such as a Viewlux or Analyst. Preferably, the cell microinjected or transfected is deficient in one or more of the subunits of the human tRNA splicing endonuclease. Any methods known to the skilled artisan can be used to remove the expression and/or function of one or more subunits of the human tRNA splicing endonuclease from the cell. In a specific embodiment, RNAi is used to transiently remove one or more of the subunits of the human tRNA splicing endonuclease. The formation of the human tRNA splicing endonuclease from the labeled subunits will result in a reduction in the fluorescence detectable. A compound that inhibits or reduces the formation of the human tRNA splicing endonuclease will reduce or inhibit the production of a detectable fluorescent signal relative to a negative control (e.g., PBS). A compound that enhances the formation of the human tRNA splicing endonuclease will increase the fluorescence detectable relative to a negative control (e.g., PBS).

Alternatively, a FRET cell-based assay may be conducted by microinjecting a first subunit of a human tRNA splicing endonuclease (e.g., SEN2) labeled with a fluorescent donor moiety and a second, different subunit of a human tRNA splicing endonuclease (e.g., SEN34) labeled with a fluorescent acceptor moiety into a cell and contacting the cell with a compound, and measuring the fluorescence of the human tRNA splicing endonuclease by, e.g., fluorescence microscopy or a fluorescence emission detector such as a Viewlux or Analyst. The formation of the human tRNA splicing endonuclease will result in the production of a detectable fluorescent signal by the fluorescent donor moiety and fluorescent acceptor moiety at the wavelength of the fluorescent donor moiety. A compound that inhibits or reduces the formation of the human tRNA splicing endonuclease will reduce the fluorescence emission of the fluorescent acceptor moiety at the wavelength of the fluorescent donor moiety relative to a negative control (e.g., PBS). A compound that enhances the formation of the human tRNA splicing endonuclease will increase the fluorescence emission of the fluorescent acceptor moiety at the wavelength of the fluorescent donor moiety relative to a negative control (e.g., PBS). In a preferred embodiment, a negative control (e.g., PBS or another agent that is known to have no effect on the cleavage of the substrate) and a positive control (e.g., an agent that is known to have an effect on the cleavage of the substrate) are included in the FRET cell-based assays described herein.

In certain embodiments, the compound and the cell are incubated for at least 0.2 hours, 0.25 hours, 0.5 hours, 1 hour, 2 hours, 3 hours, 4 hours, 5 hours, 6 hours, 8 hours, 10 hours, 12 hours, 18 hours, or at least 1 day.

Methods for labeling a subunit of a human tRNA splicing endonuclease with a fluorescent acceptor moiety, a fluorescent donor moiety and/or quencher are well-known in the art (see, e.g., U.S. Pat. Nos. 6,472,156, 6,451,543, 6,348,322, 6,342,379, 6,323,039, 6,297,018, 6,291,201, 6,280,981, 5,843,658, and 5,439,797, the disclosures of which are incorporated by reference in their entirety).

Such an assay can analogously be used to identify modulators of 3' end pre-mRNA processing, rRNA endonuclease or tRNA endonuclease activity.

4.5.6.4 Cell-Free Assays with Labeled Enzyme

A FRET cell-free assay may be conducted by contacting a first subunit of a human tRNA splicing endonuclease (see Table 1 for the components of the complex) labeled with a fluorophore and a second subunit of a human tRNA splicing endonuclease (see Table 1 for the components of the complex) labeled with a quencher with a compound in vitro under conditions conducive to the formation of the endonuclease, and measuring the fluorescence of the human tRNA splicing endonuclease by, e.g., a fluorescence emission detector such as a Viewlux or Analyst. The formation of the human tRNA splicing endonuclease from the labeled subunits will result in a reduction in the fluorescence detectable. A compound that inhibits or reduces the formation of the human tRNA splicing endonuclease will enhance the production of detectable fluorescent signal relative to the absence of the compound or the presence of a negative control (e.g., PBS). A compound that enhances the formation of the human tRNA splicing endonuclease will reduce or inhibit the fluorescence detectable relative to the absence of the compound or a negative control (e.g., PBS).

Alternatively, a FRET cell-free assay may be conducted by contacting a first subunit of a human tRNA splicing endonuclease (e.g., SEN2) labeled with a fluorescent donor moiety and a second, different subunit of a human tRNA splicing endonuclease (e.g., SEN34) labeled with a fluorescent acceptor moiety with a compound in vitro under conditions conducive to the formation of the endonuclease, and measuring the fluorescence of the human tRNA splicing endonuclease by, e.g., a fluorescence emission detector such as a Viewlux or Analyst. The formation of the human tRNA splicing endonuclease will result in the production of a detectable fluorescent signal by the fluorescent donor moiety and fluorescent acceptor moiety at the wavelength of the fluorescent donor. A compound that inhibits or reduces the formation of the human tRNA splicing endonuclease will reduce the fluorescence emission of the fluorescent acceptor moiety at the wavelength of the fluorescent donor moiety relative to the absence of the compound or the presence of a negative control (e.g., PBS). A compound that enhances the formation of the human tRNA splicing endonuclease will increase the fluorescence emission of the fluorescent acceptor moiety at the wavelength of the fluorescent donor moiety relative to the absence of the compound or the presence of a negative control (e.g., PBS). In a preferred embodiment, a negative control (e.g., PBS or another agent that is known to have no effect on the cleavage of the substrate) and a positive control (e.g., an agent that is known to have an effect on the cleavage of the substrate) are included in the FRET cell-free assays described herein.

Such an assay can analogously be used to identify modulators of 3' end pre-mRNA processing, rRNA endonuclease or tRNA endonuclease activity.

4.5.7 Direct Binding Assays

Compounds that modulate the activity of pre-tRNA splicing endonuclease, 3' end pre-mRNA endonuclease, pre-tRNA cleavage or pre-rRNA cleavage can be identified by direct binding assays. In particular, compounds that inhibit the activity of a human pre-tRNA splicing endonuclease, 3' end pre-mRNA endonuclease, pre-tRNA cleavage or pre-rRNA cleavage by directly or indirectly reducing or inhibiting the interaction between a substrate and a complex of the invention. The pre-tRNA splicing endonuclease, a 3' end pre-mRNA endonuclease, a pre-tRNA cleavage complex or a pre-rRNA cleavage complex can be purified. Such assays are described in International Patent Publication Nos. WO 02/083837 and WO 02/083953, the disclosures of which are hereby incorporated by reference in their entireties. Briefly, direct binding assays may be conducted by attaching a library of compounds to solid supports, e.g., polymer beads, with each solid support having substantially one type of compound attached to its surface. The plurality of solid supports of the library is exposed in aqueous solution to a substrate for a pre-tRNA splicing endonuclease, a 3' end pre-mRNA endonuclease, a pre-tRNA cleavage complex or a pre-rRNA cleavage complex having a detectable label, forming a dye-labeled substrate:support-attached compound complex. Binding of a substrate to a particular compound labels the solid support, e.g., bead, comprising the compound, which can be physically separated from other, unlabeled solid supports. Once labeled solid supports are identified, the chemical structures of the compounds thereon can be determined by, e.g., reading a code on the solid support that correlates with the structure of the attached compound.

Alternatively, direct binding assays may be conducted by contacting a substrate for a pre-tRNA splicing endonuclease, a 3' end pre-mRNA endonuclease, a pre-tRNA cleavage complex or a pre-rRNA cleavage complex having a detectable label with a compound or a member of a library of compounds free in solution, in labeled tubes or microtiter wells, or a microarray. Compounds in the library that bind to the labeled substrate of a pre-tRNA splicing endonuclease, a 3' end pre-mRNA endonuclease, a pre-tRNA cleavage complex or a pre-rRNA cleavage complex will form a detectably labeled complex that can be identified and removed from the uncomplexed, unlabeled compounds in the library, and from uncomplexed, labeled substrate of a pre-tRNA splicing endonuclease, a 3' end pre-mRNA endonuclease, a pre-tRNA cleavage complex or a pre-rRNA cleavage complex, by a variety of methods including, but not limited to, methods that differentiate changes in the electrophoretic, chromatographic, or thermostable properties of the complexed substrate.

4.5.8 Fluorescence Polarization Assay

The effect of a compound on the activity of a pre-tRNA splicing endonuclease, a 3' end pre-mRNA endonuclease, a pre-tRNA cleavage complex or a pre-rRNA cleavage complex may be determined utilizing a fluorescence polarization-based assay. In such an assay, a fluorescently labeled substrate for pre-tRNA splicing endonuclease, a 3' end pre-mRNA endonuclease, a pre-tRNA cleavage complex or a pre-rRNA cleavage complex is contacted with a cell-free extract (preferably, human tRNA splicing endonuclease extract or a human 3' end pre-mRNA processing extract) or a purified pre-tRNA splicing endonuclease, a purified 3' end pre-mRNA endonuclease, a purified pre-tRNA cleavage complex or a purified pre-rRNA cleavage complex and a compound or a member of a library of compounds; and the fluorescently polarized light emitted is measured. An important aspect of this assay is that the size of the substrate used in the assay is large enough to distinguish a change in fluorescent polarized light emitted following cleavage of the substrate.

In certain embodiments, substrates for the FP assay can be labeled with a fluorophore by any method known to the skilled artisan.

The pre-tRNA splicing endonuclease, a 3' end pre-mRNA endonuclease, a pre-tRNA cleavage complex or a pre-rRNA cleavage complex will cleave the substrate and result in a change in intensity of emitted polarized light. Fluorescently labeled substrates when excited with plane polarized light will emit light in a fixed plane only if they do not rotate during the period between excitation and emission. The extent of depolarization of the emitted light depends upon the amount of rotation of the substrate, which is dependent on the size of the substrate. Small substrates rotate more than larger substrates between the time they are excited and the time they emit fluorescent light. A small fluorescently labeled substrate rotates rapidly and the emitted light is depolarized. A large fluorescently labeled substrate rotates more slowly and results in the emitted light remaining polarized. A compound that inhibits the activity of the pre-tRNA splicing endonuclease, a 3' end pre-mRNA endonuclease, a pre-tRNA cleavage complex or a pre-rRNA cleavage complex will inhibit or reduce the cleavage of the substrate and thus, decrease the rotation of the substrate relative to a negative control (e.g., PBS) or the absence of the compound, which will result in the emitted light remaining polarized. A compound that enhances the activity of the pre-tRNA splicing endonuclease, a 3' end pre-mRNA endonuclease, a pre-tRNA cleavage complex or a pre-rRNA cleavage complex will enhance the cleavage of the substrate and thus, increase the rotation of the substrate relative to a negative control (e.g., PBS) or the absence of the compound, which will result in more of the emitted light being depolarized.

The intensities of the light are measured in planes 90° apart and are many times designated the horizontal and vertical intensities. In some instruments the excitation filter is moveable while the emission filter is fixed. In certain other machines the horizontal and vertical intensities are measured simultaneously via fiber optics. Research grade fluorescence polarization instruments are commercially available from, e.g., Pan Vera, BMG Lab Technologies, and LJL Biosystems. Abott provides clinical laboratory instrumentation. The value of fluorescence polarization is determined by the following equation:

$$\text{polarization} = \frac{\text{intensity}_{vertical} - \text{intensity}_{horizontal}}{\text{intensity}_{veritcal} + \text{intensity}_{horizontal}}.$$

Fluorescence polarization values are most often divided by 1000 and expressed as millipolarization units (mP).

In a specific embodiment, the hybridized tRNA or circularly permuted tRNA depicted in FIG. 1 are used as a substrate for the pre-tRNA splicing endonuclease complex. In accordance with this embodiment, the 5' end in the intron of the hybridized tRNA or the circularly permuted tRNA, or the 3' end in the intron of the hybridized tRNA or the circularly permuted tRNA or both are labeled with a fluorophore. Upon cleavage, the size of the molecule to which the fluorophore is attached changes because the intron is released from the substrate. The decrease in molecular weight of the labeled molecule results in an increase of depolarization of light that is emitted from the fluorophore. Measuring the amount of depolarization allows the skilled artisan to determine the amount of cleaved substrate.

4.5.9 tRNA Endonuclease Suppression Assay

The effect of a compound or a member of a library of compounds on the activity of a human tRNA splicing endonuclease may be determined using a tRNA endonuclease suppression assay. In such an assay, a host cell is engineered to contain a first reporter gene construct and a suppressor tRNA; the expression of the suppressor tRNA is induced; the host cell is contacted with a compound or a member of a library of compounds; and the expression of the reporter gene and/or the activity of the protein encoded by the reporter gene is measured. The first reporter gene construct comprises a reporter gene with a nonsense codon in its open reading frame such that the open reading frame is interrupted. Standard mutagenesis techniques described, e.g., in Sambrook (Sambrook, 1989, Molecular Cloning, A Laboratory Manual, Second Edition; DNA Cloning, Volumes I and II (Glover, Ed. 1985)) may be used to introduce a nonsense codon into the open reading frame of any reporter gene well-known to one of skill in the art. The first reporter gene construct is transfected into a host cell engineered to contain a suppressor tRNA. Alternatively, the first reporter gene is cotransfected into a host cell with a suppressor tRNA. The suppressor tRNA's expression is regulated by a controllable regulatory element; such as by a tetracycline regulated regulatory element (see, e.g., Buvoli et al, 2000, Molecular and Cellular Biology 20:3116-3124; Park and Bhandary, 1998, Molecular and Cellular Biology 18:4418-4425) and the suppressor tRNA contains a tRNA intron in the anticodon stem such that only properly spliced suppressor tRNA is functional. Expression of functional suppressor tRNA is dependent on (i) the transcription of the suppressor tRNA, and (ii) tRNA splicing. The expression of functional suppressor tRNA suppresses the nonsense codon in the reporter gene and results in full length, functional reporter gene expression. Accordingly, the expression of full length, functional reporter gene correlates with the expression of functional suppressor tRNA, which in turn correlates with the level of transcription of the suppressor tRNA and tRNA splicing. The expression of full-length reporter gene and the activity of the protein encoded by the reporter gene can be assayed by any method well known to the skilled artisan or as described herein.

A compound that inhibits or reduces the activity of a human tRNA splicing endonuclease will inhibit or reduce the production of functional suppressor tRNA and thus, reduce the expression of the reporter gene relative to a previously determined reference range or a control. A compound that enhances the activity of a human tRNA splicing endonuclease will enhance the production of functional suppressor tRNA and thus, enhance the production of the reporter gene relative to a previously determined reference range or a control.

The step of inducing the expression of the suppressor tRNA may be conducted simultaneously with the step of contacting the host cell with a compound or at least 5 minutes, at least 15 minutes, at least 0.5 hours, at least 1 hour, at least 1.5 hours, at least 2 hours, at least 3 hours, at least 4 hours, at least 5 hours, at least 6 hours, at least 8 hours, at least 10 hours or at least 12 hours before the step of contacting the compound with the host cell. In certain embodiments, the expression of the suppressor tRNA is induced by incubating the host cell with an agent such as, e.g., tetracycline, for approximately 5 minutes, approximately 15 minutes, approximately 0.5 hours, approximately 1 hour, approximately 1.5 hours, approximately 2 hours, approximately 3 hours, approximately 4 hours, approximately 5 hours, 6 approximately hours, 8 approximately hours, approximately 10 hours or approximately 12 hours. In other embodiments, the host cell is contacted with the compound for approximately 5 minutes, approximately 15 minutes, approximately 0.5 hours, approximately 1 hour, approximately 1.5 hours, approximately 2 hours, approximately 3 hours, approximately 4 hours, approximately 5 hours, 6 approximately hours, 8 approximately hours, approximately 10 hours or approximately 12 hours.

Optionally, the host cell is engineered to contain a second reporter gene construct comprising a reporter gene different from the first reporter gene that does not contain a nonsense codon. In a specific embodiment, the reporter genes used in the tRNA endonuclease suppression assay are Red and Green Click Beetle luciferase, wherein the Red luciferase contains the nonsense codon. A host cell may be engineered to stably express the two luciferase genes and the suppressor tRNA whose expression is regulated by a controlled regulatory element (such as a tetracycline controlled regulatory element). In the absence of an agent such as tetracycline, the suppressor tRNA is not expressed and thus the red-to-green ratio is low. In the presence of an agent such as tetracycline, the suppressor tRNA is expressed and thus the red-to-green ratio increases. For a high throughput screening, cells are plated in the presence of a compound. After a certain time-period media containing an agent such as tetracycline is added to induce suppressor tRNA expression.

Compounds that inhibit tRNA splicing endonuclease will decrease the red-to-green ration compared to a control without the compound. Once compounds are identified in this assay that modulate the activity of human tRNA splicing endonuclease, they may be tested using one or more of the assays described above to confirm their activity.

4.5.10 FISH Assay

The activity of a tRNA splicing endonuclease may be determined in an assay in which the persistence and quantity of tRNA intron is detected in a human cell. The amount of tRNA intron is quantified at different time points after or during the incubation of the cell with the compound. The tRNA intron can be detected by means of Fluorescence in situ hybridization (FISH) using a tRNA intron-specific probe. In certain embodiments, a control experiment is conducted in parallel wherein the human cell is not contacted with a compound.

In the absence of an inhibitor of human tRNA splicing endonuclease, the splicing reaction is fast and the concentration of intron in the cell is low. Without being bound by theory, because the spliced intron is normally degraded the concentration of tRNA intron in the human cell is below the detection threshold. In the presence of an inhibitor of human tRNA splicing endonuclease, the splicing reaction is slowed down and the amount of tRNA intron increases. Thus, a compound that inhibits human tRNA splicing endonuclease can be identified by its ability to increase the level of tRNA intron in the human cell.

Similarly, the activity of 3' end pre-mRNA endonuclease complex can be determined using FISH via measuring the amount of polyadenylated mRNA. An increased level of polyadenylated mRNA indicates increased activity of 3' end pre-mRNA endonuclease complex. Thus, if the assay is performed in the presence of a compound and the level of polyadenylated mRNA is increased the compound is an activator of 3' end pre-mRNA endonuclease complex. If the level of polyadenylated mRNA is decreased in the presence of a compound, the compound is an antagonist of 3' end pre-mRNA endonuclease complex. Alternatively, the part of the pre-mRNA that is 3' of the cleavage site can be detected; increased level of the part of the pre-mRNA that is 3' of the cleavage site indicates a decreased activity of 3' end pre-mRNA endonuclease complex. Thus, if the assay is performed in the presence of a compound and the level of polyadenylated mRNA is increased the compound is an antagonist of 3' end pre-mRNA endonuclease complex. If the level of polyadenylated mRNA is decreased in the presence of a compound, the compound is an activator of 3' end pre-mRNA endonuclease complex.

Methods for conducting FISH are well-known to the skilled artisan and can be used with the invention. Exemplary methods for FISH are described in Sarkar and Hopper, 1998 (Mol. Biol. Cell 9:3041-3055), which is incorporated herein in its entirety.

In certain embodiments, a FISH assay is used to determine the effect of a compound on the activity of a human tRNA splicing endonuclease or 3' end pre-mRNA endonuclease in a high-throughput screen. In particular a 96-lens microscope can be used for a high-throughput screen based on FISH. In a specific embodiment, 96 cell cultures are incubated in a 96-well plate with different compounds. Subsequently, the cells are subjected to a FISH analysis using a tRNA intron specific probe or a 3' end pre-mRNA specific probe and analyzed using the 96-lens microscope. The presence of a signal or the presence of a significantly stronger signal demonstrates that tRNA intron or 3' end pre-mRNA, respectively, was present in the cells at elevated levels and thus the compound is a candidate inhibitor of tRNA splicing endonuclease or pre-mRNA endonuclease activity, respectively.

Without being bound by theory, the FISH assay identifies the compound as inhibitor of the tRNA splicing endonuclease or 3' end pre-mRNA endonuclease directly. Thus, in certain embodiments, a compound that was identified in a FISH assay as an inhibitor of tRNA splicing or 3' end pre-mRNA endonuclease activity, respectively, is a prima facie candidate for an inhibitor of tRNA splicing endonuclease.

4.5.11 Other Screening Assays

The activity of a human tRNA splicing endonuclease, 3' end pre-mRNA endoncuclease, pre-tRNA cleavage endonuclease or ribosomal RNA endonuclease may be determined in an assay in which the amount of substrate for a tRNA splicing endonuclease, 3' end pre-mRNA endoncuclease, pre-tRNA cleavage endonuclease or ribosomal RNA endonuclease, respectively, cleaved by the endonuclease in the presence of a compound relative to a control (preferably, a negative control and more preferably, a negative control and a positive control) is detected. Such an assay may be conducted by contacting or incubating a compound with a labeled substrate for an tRNA splicing endonuclease, 3' end pre-mRNA endoncuclease, pre-tRNA cleavage endonuclease or ribosomal RNA endonuclease, respectively and a cell-free extract or purified tRNA splicing endonuclease, 3' end pre-mRNA endoncuclease, pre-tRNA cleavage endonuclease or ribosomal RNA endonuclease under conditions conducive for endonuclease activity, and measuring the amount of cleaved substrate. The substrate can be labeled with any detectable agent. Useful labels in the present invention can include, but are not limited to, spectroscopic labels such as fluorescent dyes (e.g., fluorescein and derivatives such as fluorescein isothiocyanate (FITC) and Oregon Green™, rhodamine and derivatives (e.g., Texas red, tetramethylrhodimine isothiocynate (TRITC), bora-3a,4a-diaza-s-indacene (BODIPY®) and derivatives, etc.), digoxigenin, biotin, phycoerythrin, AMCA, CyDye™, and the like), radiolabels (e.g., $^3H$, $^{125}I$, $^{35}S$, $^{14}C$, $^{32}P$, $^{33}P$, etc.), enzymes (e.g., horse radish peroxidase, alkaline phosphatase etc.), spectroscopic colorimetric labels such as colloidal gold or colored glass or plastic (e.g., polystyrene, polypropylene, latex, etc.) beads, or nanoparticles—nanoclusters of inorganic ions with defined dimension from 0.1 to 1000 nm) utilizing techniques known to one of skill in the art.

For example, a substrate can be labeled by any method known to the skilled artisan. In certain embodiments, a substrate can be labeled using site-specific labeling of RNA with fluorophores. In more specific embodiments, a substrate is labeled using the methods described in Qin and Pyle, 1999 (Methods 18(1):60-70), which is incorporated in its entirety herein. The optimal method for labeling of a substrate can be determined by the skilled artisan using routine experimentation. In a specific embodiment, a substrate is labeled using different methods, different labels and/or different positions in the substrate. The differently labeled substrates are then subjected separately to a splicing assay in the presence and absence, respectively of an inhibitor or an activator of an endonuclease. The optimal label for the screening assays is the label that allows for the most easily detectable and most reproducible detection of the effect of the inhibitor or the activater. Other labeling procedures, however, may also be used that, for example, provide other desirable advantages.

In certain embodiments, a compound is contacted or incubated with a labeled substrate and a cell-free extract or purified endonuclease complex of the invention for at least 5 minutes, at least 10 minutes, at least 15 minutes, at least 30 minutes, at least 1 hour, at least 2 hours, or more. The amount of cleaved substrate is proportional to the activity of the endonuclease. The amount of cleavage product can be measured by any technique known to one skilled in the art.

In certain embodiments, the cleaved product is separated from the uncleaved RNA substrate by gel-electrophoresis. The amount of cleaved product can be quantified by measuring the intensity of the signal of the cleaved substrate. The stronger the signal produced by the cleaved product relative to the uncleaved substrate the more active is the endonuclease. The signal intensity can be quantified using autoradiography or a phosphoimager. If the activity of the endonuclease is decreased in the presence of a compound, i.e., if the signal of the cleaved product relative to the uncleaved substrate is decreased compared to the reaction without the compound or in the presence of a negative control, the compound is identified as an inhibitor of the endonuclease.

In other embodiments, the amount of cleaved product is determined using mass spectrometry.

4.5.12 Compounds

Any molecule known in the art can be tested for its ability to modulate (increase or decrease) the amount of, activity of, or protein component composition of a complex of the present invention as detected by a change in the amount of, activity of, or protein component composition of, said complex. By way of example, a change in the amount of the complex can be detected by detecting a change in the amount of the complex that can be isolated from a cell expressing the complex machinery. In other embodiments, a change in signal intensity (e.g., when using FRET or FP) in the presence of a compound compare to the absence of the compound indicates that the compound is a modulator of complex formation. For identifying a molecule that modulates complex activity, candidate molecules can be directly provided to a cell expressing the complex, or, in the case of candidate proteins, can be provided by providing their encoding nucleic acids under conditions in which the nucleic acids are recombinantly expressed to produce the candidate proteins within the cell expressing the complex machinery, the complex is then purified from the cell and the purified complex is assayed for activity using methods well known in the art, not limited to those described, supra.

In certain embodiments, the invention provides screening assays using chemical libraries for molecules which modulate, e.g., inhibit, antagonize, or agonize, the amount of, activity of, or protein component composition of the complex. The chemical libraries can be peptide libraries, peptidomimetic libraries, chemically synthesized libraries, recombinant, e.g., phage display libraries, and in vitro translation-based libraries, other non-peptide synthetic organic libraries, etc.

Exemplary libraries are commercially available from several sources (ArQule, Tripos/PanLabs, ChemDesign, Pharmacopoeia). In some cases, these chemical libraries are generated using combinatorial strategies that encode the identity of each member of the library on a substrate to which the member compound is attached, thus allowing direct and immediate identification of a molecule that is an effective modulator. Thus, in many combinatorial approaches, the position on a plate of a compound specifies that compound's composition. Also, in one example, a single plate position may have from 1-20 chemicals that can be screened by administration to a well containing the interactions of interest. Thus, if modulation is detected, smaller and smaller pools of interacting pairs can be assayed for the modulation activity. By such methods, many candidate molecules can be screened.

Many diversity libraries suitable for use are known in the art and can be used to provide compounds to be tested according to the present invention. Alternatively, libraries can be constructed using standard methods. Chemical (synthetic) libraries, recombinant expression libraries, or polysome-based libraries are exemplary types of libraries that can be used.

The libraries can be constrained or semirigid (having some degree of structural rigidity), or linear or non-constrained. The library can be a cDNA or genomic expression library, random peptide expression library or a chemically synthesized random peptide library, or non-peptide library. Expression libraries are introduced into the cells in which the assay occurs, where the nucleic acids of the library are expressed to produce their encoded proteins.

In one embodiment, peptide libraries that can be used in the present invention may be libraries that are chemically synthesized in vitro. Examples of such libraries are given in Houghten et al., 1991, Nature 354:84-86, which describes mixtures of free hexapeptides in which the first and second residues in each peptide were individually and specifically defined; Lam et al., 1991, Nature 354:82-84, which describes a "one bead, one peptide" approach in which a solid phase split synthesis scheme produced a library of peptides in which each bead in the collection had immobilized thereon a single, random sequence of amino acid residues; Medynski, 1994, Bio/Technology 12:709-710, which describes split synthesis and T-bag synthesis methods; and Gallop et al., 1994, J. Medicinal Chemistry 37(9):1233-1251. Simply by way of other examples, a combinatorial library may be prepared for use, according to the methods of Ohlmeyer et al., 1993, Proc. Natl. Acad. Sci. USA 90:10922-10926; Erb et al., 1994, Proc. Natl. Acad. Sci. USA 91:11422-11426; Houghten et al., 1992, Biotechniques 13:412; Jayawickreme et al., 1994, Proc. Natl. Acad. Sci. USA 91:1614-1618; or Salmon et al., 1993, Proc. Natl. Acad. Sci. USA 90:11708-11712. PCT Publication No. WO 93/20242 and Brenner and Lerner, 1992, Proc. Natl. Acad. Sci. USA 89:5381-5383 describe "encoded combinatorial chemical libraries," that contain oligonucleotide identifiers for each chemical polymer library member.

In a preferred embodiment, the library screened is a biological expression library that is a random peptide phage display library, where the random peptides are constrained (e.g., by virtue of having disulfide bonding).

Further, more general, structurally constrained, organic diversity (e.g., nonpeptide) libraries, can also be used.

Conformationally constrained libraries that can be used include but are not limited to those containing invariant cysteine residues which, in an oxidizing environment, cross-link by disulfide bonds to form cystines, modified peptides (e.g., incorporating fluorine, metals, isotopic labels, are phosphorylated, etc.), peptides containing one or more non-naturally occurring amino acids, non-peptide structures, and peptides containing a significant fraction of γ-carboxyglutamic acid.

Libraries of non-peptides, e.g., peptide derivatives (for example, that contain one or more non-naturally occurring amino acids) can also be used. One example of these are peptoid libraries (Simon et al., 1992, Proc. Natl. Acad. Sci. USA 89:9367-9371). Peptoids are polymers of non-natural amino acids that have naturally occurring side chains attached not to the alpha carbon but to the backbone amino nitrogen. Since peptoids are not easily degraded by human digestive enzymes, they are advantageously more easily adaptable to drug use. Another example of a library that can be used, in which the amide functionalities in peptides have been permethylated to generate a chemically transformed combinatorial library, is described by Ostresh et al., 1994, Proc. Natl. Acad. Sci. USA 91:11138-11142).

The members of the peptide libraries that can be screened according to the invention are not limited to containing the 20 naturally occurring amino acids. In particular, chemically synthesized libraries and polysome based libraries allow the use of amino acids in addition to the 20 naturally occurring amino acids (by their inclusion in the precursor pool of amino acids used in library production). In specific embodiments, the library members contain one or more non-natural or non-classical amino acids or cyclic peptides. Non-classical amino acids include but are not limited to the D-isomers of the common amino acids, α-amino isobutyric acid, 4-aminobutyric acid, Abu, 2-amino butyric acid; γ-Abu, ε-Ahx, 6-amino hexanoic acid; Aib, 2-amino isobutyric acid; 3-amino propionic acid; ornithine; norleucine; norvaline, hydroxyproline, sarcosine, citrulline, cysteic acid, t-butylglycine, t-butylalanine, phenylglycine, cyclohexylalanine, β-alanine, designer amino acids such as β-methyl amino acids, Ca-methyl amino acids, Na-methyl amino acids, fluoro-amino acids and amino acid analogs in general. Furthermore, the amino acid can be D (dextrorotary) or L (levorotary).

In a specific embodiment, fragments and/or analogs of complexes of the invention, or protein components thereof, especially peptidomimetics, are screened for activity as competitive or non-competitive inhibitors of complex activity or formation.

In another embodiment of the present invention, combinatorial chemistry can be used to identify modulators of a the complexes. Combinatorial chemistry is capable of creating libraries containing hundreds of thousands of compounds, many of which may be structurally similar. While high throughput screening programs are capable of screening these vast libraries for affinity for known targets, new approaches have been developed that achieve libraries of smaller dimension but which provide maximum chemical diversity. (See, e.g., Matter, 1997, Journal of Medicinal Chemistry 40:1219-1229).

One method of combinatorial chemistry, affinity fingerprinting, has previously been used to test a discrete library of small molecules for binding affinities for a defined panel of proteins. The fingerprints obtained by the screen are used to predict the affinity of the individual library members for other proteins or receptors of interest (in the instant invention, the protein complexes of the present invention and protein components thereof) The fingerprints are compared with fingerprints obtained from other compounds known to react with the protein of interest to predict whether the library compound might similarly react. For example, rather than testing every ligand in a large library for interaction with a complex or protein component, only those ligands having a fingerprint similar to other compounds known to have that activity could be tested. (See, e.g., Kauvar et al., 1995, Chemistry and Biology 2:107-118; Kauvar, 1995, Affinity fingerprinting, Pharmaceutical Manufacturing International. 8:25-28; and Kauvar, Toxic-Chemical Detection by Pattern Recognition in New Frontiers in Agrochemical Immunoassay, D. Kurtz. L. Stanker and J. H. Skerritt. Editors, 1995, AOAC: Washington, D.C., 305-312).

Kay et al., 1993, Gene 128:59-65 (Kay) discloses a method of constructing peptide libraries that encode peptides of totally random sequence that are longer than those of any prior conventional libraries. The libraries disclosed in Kay encode totally synthetic random peptides of greater than about 20 amino acids in length. Such libraries can be advantageously screened to identify complex modulators. (See also U.S. Pat. No. 5,498,538 dated Mar. 12, 1996; and PCT Publication No. WO 94/18318 dated Aug. 18, 1994).

A comprehensive review of various types of peptide libraries can be found in Gallop et al., 1994, J. Med. Chem. 37:1233-1251.

Libraries screened using the methods of the present invention can comprise a variety of types of compounds. Examples of libraries that can be screened in accordance with the methods of the invention include, but are not limited to, peptoids; random biooligomers; diversomers such as hydantoins, benzodiazepines and dipeptides; vinylogous polypeptides; non-peptidal peptidomimetics; oligocarbamates; peptidyl phosphonates; peptide nucleic acid libraries; antibody libraries; carbohydrate libraries; and small molecule libraries (preferably, small organic molecule libraries). In some embodiments, the compounds in the libraries screened are nucleic acid or peptide molecules. In a non-limiting example, peptide molecules can exist in a phage display library. In other embodiments, the types of compounds include, but are not limited to, peptide analogs including peptides comprising non-naturally occurring amino acids, e.g., D-amino acids, phosphorous analogs of amino acids, such as α-amino phosphoric acids and α-amino phosphoric acids, or amino acids having non-peptide linkages, nucleic acid analogs such as phosphorothioates and PNAs, hormones, antigens, synthetic or naturally occurring drugs, opiates, dopamine, serotonin, catecholamines, thrombin, acetylcholine, prostaglandins, organic molecules, pheromones, adenosine, sucrose, glucose, lactose and galactose. Libraries of polypeptides or proteins can also be used in the assays of the invention.

In a preferred embodiment, the combinatorial libraries are small organic molecule libraries including, but not limited to, benzodiazepines, isoprenoids, thiazolidinones, metathiazanones, pyrrolidines, morpholino compounds, and benzodiazepines. In another embodiment, the combinatorial libraries comprise peptoids; random bio-oligomers; benzodiazepines; diversomers such as hydantoins, benzodiazepines and dipeptides; vinylogous polypeptides; nonpeptidal peptidomimetics; oligocarbamates; peptidyl phosphonates; peptide nucleic acid libraries; antibody libraries; or carbohydrate libraries. Combinatorial libraries are themselves commercially available (see, e.g., ComGenex, Princeton, N.J.; Asinex, Moscow, Ru, Tripos, Inc., St. Louis, Mo.; ChemStar, Ltd, Moscow, Russia; 3D Pharmaceuticals, Exton, Pennsylvania; Martek Biosciences, Columbia, Md.; etc.).

In a preferred embodiment, the library is preselected so that the compounds of the library are more amenable for cellular uptake. For example, compounds are selected based on specific parameters such as, but not limited to, size, lipophilicity, hydrophilicity, and hydrogen bonding, which enhance the likelihood of compounds getting into the cells. In another embodiment, the compounds are analyzed by three-dimensional or four-dimensional computer computation programs.

The combinatorial compound library for use in accordance with the methods of the present invention may be synthesized. There is a great interest in synthetic methods directed toward the creation of large collections of small organic compounds, or libraries, which could be screened for pharmacological, biological or other activity. The synthetic methods applied to create vast combinatorial libraries are performed in solution or in the solid phase, i.e., on a solid support. Solid-phase synthesis makes it easier to conduct multi-step reactions and to drive reactions to completion with high yields because excess reagents can be easily added and washed away after each reaction step. Solid-phase combinatorial synthesis also tends to improve isolation, purification and screening. However, the more traditional solution phase chemistry supports a wider variety of organic reactions than solid-phase chemistry.

Combinatorial compound libraries of the present invention may be synthesized using the apparatus described in U.S. Pat. No. 6,190,619 to Kilcoin et al., which is hereby incorporated by reference in its entirety. U.S. Pat. No. 6,190,619 discloses a synthesis apparatus capable of holding a plurality of reaction vessels for parallel synthesis of multiple discrete compounds or for combinatorial libraries of compounds.

In one embodiment, the combinatorial compound library can be synthesized in solution. The method disclosed in U.S. Pat. No. 6,194,612 to Boger et al., which is hereby incorporated by reference in its entirety, features compounds useful as templates for solution phase synthesis of combinatorial libraries. The template is designed to permit reaction products to be easily purified from unreacted reactants using liquid/liquid or solid/liquid extractions. The compounds produced by combinatorial synthesis using the template will preferably be small organic molecules. Some compounds in the library may mimic the effects of non-peptides or peptides. In contrast to solid phase synthesize of combinatorial compound libraries, liquid phase synthesis does not require the use of specialized protocols for monitoring the individual steps of a multi-step solid phase synthesis (Egner et al., 1995, J. Org. Chem. 60:2652; Anderson et al., 1995, J. Org. Chem. 60:2650; Fitch et al., 1994, J. Org. Chem. 59:7955; Look et al., 1994, J. Org. Chem. 49:7588; Metzger et al., 1993, Angew. Chem., Int. Ed. Engl. 32:894; Youngquist et al., 1994, Rapid Commun. Mass Spect. 8:77; Chu et al., 1995, J. Am. Chem. Soc. 117:5419; Brummel et al., 1994, Science 264:399; and Stevanovic et al., 1993, Bioorg. Med. Chem. Lett. 3:431). Combinatorial compound libraries useful for the methods of the present invention can be synthesized on solid supports. In one embodiment, a split synthesis method, a protocol of separating and mixing solid supports during the synthesis, is used to synthesize a library of compounds on solid supports (see e.g., Lam et al., 1997, Chem. Rev. 97:41-448; Ohlmeyer et al., 1993, Proc. Natl. Acad. Sci. USA 90:10922-10926 and references cited therein). Each solid support in the final library has substantially one type of compound attached to its surface. Other methods for synthesizing combinatorial libraries on solid supports, wherein one product is attached to each support, will be known to those of skill in the art (see, e.g., Nefzi et al., 1997, Chem. Rev. 97:449-472).

As used herein, the term "solid support" is not limited to a specific type of solid support. Rather a large number of supports are available and are known to one skilled in the art. Solid supports include silica gels, resins, derivatized plastic films, glass beads, cotton, plastic beads, polystyrene beads, alumina gels, and polysaccharides. A suitable solid support may be selected on the basis of desired end use and suitability for various synthetic protocols. For example, for peptide synthesis, a solid support can be a resin such as p-methylbenzhydrylamine (pMBHA) resin (Peptides International, Louisville, Ky.), polystyrenes (e.g., PAM-resin obtained from Bachem Inc., Peninsula Laboratories, etc.), including chloromethylpolystyrene, hydroxymethylpolystyrene and aminomethylpolystyrene, poly(dimethylacrylamide)-grafted styrene co-divinyl-benzene (e.g., POLYHIPE resin, obtained from Aminotech, Canada), polyamide resin (obtained from Peninsula Laboratories), polystyrene resin grafted with polyethylene glycol (e.g., TENTAGEL or ARGOGEL, Bayer, Tubingen, Germany) polydimethylacrylamide resin (obtained from Milligen/Biosearch, California), or Sepharose (Pharmacia, Sweden).

In some embodiments of the present invention, compounds can be attached to solid supports via linkers. Linkers can be integral and part of the solid support, or they may be nonintegral that are either synthesized on the solid support or attached thereto after synthesis. Linkers are useful not only for providing points of compound attachment to the solid support, but also for allowing different groups of molecules to be cleaved from the solid support under different conditions, depending on the nature of the linker. For example, linkers can be, inter alia, electrophilically cleaved, nucleophilically cleaved, photocleavable, enzymatically cleaved, cleaved by metals, cleaved under reductive conditions or cleaved under oxidative conditions. In a preferred embodiment, the compounds are cleaved from the solid support prior to high throughput screening of the compounds.

In certain embodiments of the invention, the compound is a small molecule.

4.5.13 Characterization of the Structure of Compounds

If the library comprises arrays or microarrays of compounds, wherein each compound has an address or identifier, the compound can be deconvoluted, e.g., by cross-referencing the positive sample to original compound list that was applied to the individual test assays.

If the library is a peptide or nucleic acid library, the sequence of the compound can be determined by direct sequencing of the peptide or nucleic acid. Such methods are well known to one of skill in the art.

A number of physico-chemical techniques can be used for the de novo characterization of compounds identified by the screening methods of the invention. Examples of such techniques include, but are not limited to, mass spectrometry, NMR spectroscopy, X-ray crytallography and vibrational spectroscopy.

4.5.13.1 Mass Spectrometry

Mass spectrometry (e.g., electrospray ionization ("ESI"), matrix-assisted laser desorption-ionization ("MALDI"), and Fourier-transformation cyclotron resonance ("FT-ICR") can be used for elucidating the structure of a compound.

ESI mass spectrometry ("ESI-MS") has been of greater utility for studying non-covalent molecular interactions because, unlike the MALDI process, ESI-MS generates molecular ions with little to no fragmentation (Xavier et al., 2000, Trends Biotechnol. 18(8):349-356). ESI-MS has been used to study the complexes formed by HIV Tat peptide and protein with the TAR RNA (Sannes-Lowery et al., 1997, Anal. Chem. 69:5130-5135).

Fourier-transformation cyclotron resonance ("FT-ICR") mass spectrometry provides high-resolution spectra, isotope-resolved precursor ion selection, and accurate mass assignments (Xavier et al., 2000, Trends Biotechnol. 18(8):349-356). FT-ICR has been used to study the interaction of aminoglycoside antibiotics with cognate and non-cognate RNAs (Hofstadler et al., 1999, Anal. Chem. 71:3436-3440; and Griffey et al., 1999, Proc. Natl. Acad. Sci. USA 96:10129-10133). As true for all of the mass spectrometry methods discussed herein, FT-ICR does not require labeling a compound.

4.5.13.2 NMR Spectroscopy

NMR spectroscopy is a valuable technique for determining the structure of a compound by qualitatively determining changes in chemical shift, specifically from distances measured using relaxation effects. SAR by NMR can be used to elucidate the structure of a compound.

Examples of NMR that can be used for the invention include, but are not limited to, one-dimentional NMR, two-dimentional NMR, correlation spectroscopy ("COSY"), and nuclear Overhauser effect ("NOE") spectroscopy. Such methods of structure determination of compounds are well-known to one of skill in the art.

4.5.13.3 X ray Crystallography

X-ray crystallography can be used to elucidate the structure of a compound. For a review of x-ray crystallography see, e.g., Blundell et al. 2002, Nat Rev Drug Discov 1(1):45-54. The first step in x-ray crystallography is the formation of crystals. The formation of crystals begins with the preparation of highly purified and soluble samples. The conditions for crystallization is then determined by optimizing several solution variables known to induce nucleation, such as pH, ionic strength, temperature, and specific concentrations of organic additives, salts and detergent. Techniques for automating the crystallization process have been developed to automate the production of high-quality protein crystals. Once crystals have been formed, the crystals are harvested and prepared for data collection. The crystals are then analyzed by diffraction (such as multi-circle diffractometers, high-speed CCD detectors, and detector off-set). Generally, multiple crystals must be screened for structure determinations.

4.5.13.4 Vibrational Spectroscopy

Vibrational spectroscopy (e.g. infrared (IR) spectroscopy or Raman spectroscopy) can be used for elucidating the structure of a compound. Infrared spectroscopy measures the frequencies of infrared light (wavelengths from 100 to 10,000 nm) absorbed by the compound as a result of excitation of vibrational modes according to quantum mechanical selection rules which require that absorption of light cause a change in the electric dipole moment of the molecule. The infrared spectrum of any molecule is a unique pattern of absorption wavelengths of varying intensity that can be considered as a molecular fingerprint to identify any compound.

Infrared spectra can be measured in a scanning mode by measuring the absorption of individual frequencies of light, produced by a grating which separates frequencies from a mixed-frequency infrared light source, by the compound relative to a standard intensity (double-beam instrument) or pre-measured (blank') intensity (single-beam instrument). In a preferred embodiment, infrared spectra are measured in a pulsed mode ("FT-IR") where a mixed beam, produced by an interferometer, of all infrared light frequencies is passed through or reflected off the compound. The resulting interferogram, which may or may not be added with the resulting interferograms from subsequent pulses to increase the signal strength while averaging random noise in the electronic signal, is mathematically transformed into a spectrum using Fourier Transform or Fast Fourier Transform algorithms.

Raman spectroscopy measures the difference in frequency due to absorption of infrared frequencies of scattered visible or ultraviolet light relative to the incident beam. The incident monochromatic light beam, usually a single laser frequency, is not truly absorbed by the compound but interacts with the electric field transiently. Most of the light scattered off the sample will be unchanged (Rayleigh scattering) but a portion of the scatter light will have frequencies that are the sum or difference of the incident and molecular vibrational frequencies. The selection rules for Raman (inelastic) scattering require a change in polarizability of the molecule. While some vibrational transitions are observable in both infrared and Raman spectrometry, must are observable only with one or the other technique. The Raman spectrum of any molecule is a unique pattern of absorption wavelengths of varying intensity that can be considered as a molecular fingerprint to identify any compound.

Raman spectra are measured by submitting monochromatic light to the sample, either passed through or preferably reflected off, filtering the Rayleigh scattered light, and detecting the frequency of the Raman scattered light. An improved Raman spectrometer is described in U.S. Pat. No. 5,786,893 to Fink et al., which is hereby incorporated by reference.

Vibrational microscopy can be measured in a spatially resolved fashion to address single beads by integration of a visible microscope and spectrometer. A microscopic infrared spectrometer is described in U.S. Pat. No. 5,581,085 to Reffner et al., which is hereby incorporated by reference in its entirety. An instrument that simultaneously performs a microscopic infrared and microscopic Raman analysis on a sample is described in U.S. Pat. No. 5,841,139 to Sostek et al., which is hereby incorporated by reference in its entirety.

4.6 Secondary Assays

The compounds identified in the assays described supra that modulate the activity or stability of a pre-tRNA splicing endonuclease, a 3' end pre-mRNA endonuclease, a pre-tRNA cleavage complex, rRNA endonuclease or a pre-rRNA cleavage complex (for convenience referred to herein as a "lead" compound) can be further tested for both direct binding to RNA and biological activity. In one embodiment, the compounds are tested for biological activity in further assays and/or animal models. In another embodiment, the lead compound is used to design congeners or analogs. In another embodiment, mutagenesis studies can be conducted to assess the mechanism by which a lead compound is modulating the activity of a human pre-tRNA splicing endonuclease, a human 3' end pre-mRNA endonuclease, a human pre-tRNA cleavage complex, rRNA endonuclease or a human pre-rRNA cleavage complex. In yet another embodiment, a lead compound is tested for its ability to affect wound healing in a model system.

4.6.1 Phenotypic or Physiological Readout

The compounds identified in the assays described supra (for convenience referred to herein as a "lead" compound) can be tested for biological activity using host cells containing or engineered to contain a human tRNA splicing endonuclease or a 3' end pre-mRNA endonuclease coupled to a functional readout system.

In one embodiment, the effect of a lead compound can be assayed by measuring the cell growth or viability of the target cell. Such assays can be carried out with representative cells of cell types involved in a particular proliferative disorder. A lower level of proliferation or survival of the contacted cells indicates that the lead compound is effective to treat a condition in the patient characterized by uncontrolled cell growth. Alternatively, instead of culturing cells from a patient, a lead compound may be screened using cells of a tumor or malignant cell line or an endothelial cell line. Specific examples of cell culture models include, but are not limited to, for lung cancer, primary rat lung tumor cells (Swafford et al., 1997, Mol. Cell. Biol., 17:1366-1374) and large-cell undifferentiated cancer cell lines (Mabry et al., 1991, Cancer Cells, 3:53-58); colorectal cell lines for colon cancer (Park and Gazdar, 1996, J. Cell Biochem. Suppl. 24:131-141); multiple established cell lines for breast cancer (Hambly et al., 1997, Breast Cancer Res. Treat. 43:247-258; Gierthy et al., 1997, Chemosphere 34:1495-1505; Prasad and Church, 1997, Biochem. Biophys. Res. Commun. 232:14-19); a number of well-characterized cell models for prostate cancer (Webber et al., 1996, Prostate, Part 1, 29:386-394; Part 2, 30:58-64; and Part 3, 30:136-142; Boulikas, 1997, Anticancer Res. 17:1471-1505); for genitourinary cancers, continuous human bladder cancer cell lines (Ribeiro et al., 1997, Int. J. Radiat. Biol. 72:11-20); organ cultures of transitional cell carcinomas (Booth et al., 1997, Lab Invest. 76:843-857) and rat progression models (Vet et al., 1997, Biochim. Biophys Acta 1360:39-44); and established cell lines for leukemias and lymphomas (Drexler, 1994, Leuk. Res. 18:919-927, Tohyama, 1997, Int. J. Hematol. 65:309-317). More specific examples of cell lines include the cancer cell line Huh7 (human hepatocellular carcinoma cell line) and the cancer cell line Caco-2 (a colon-cancer cell line). In certain embodiments, the effect of a lead compound on the growth and/or viability of a cancerous cell of a transformed cell is compared to the effect of such a compound on the growth and/or viability of non-cancerous, normal cells. Preferably, compounds that differentially affect the growth and/or viability of cancerous cells or transformed cells are chosen as anti-proliferative agents.

Many assays well-known in the art can be used to assess the survival and/or growth of a patient cell or cell line following exposure to a lead compound; for example, cell proliferation can be assayed by measuring Bromodeoxyuridine (BrdU) incorporation (see, e.g., Hoshino et al., 1986, Int. J. Cancer 38, 369; Campana et al., 1988, J. Immunol. Meth. 107:79) or ($^3$H)-thymidine incorporation (see, e.g., Chen, J., 1996, Oncogene 13:1395-403; Jeoung, J., 1995, J. Biol. Chem. 270:18367-73), by direct cell count, by detecting changes in transcription, translation or activity of known genes such as proto-oncogenes (e.g., fos, myc) or cell cycle markers (Rb, cdc2, cyclin A, D1, D2, D3, E, etc). The levels of such protein and mRNA and activity can be determined by any method well known in the art. For example, protein can be quantitated by known immunodiagnostic methods such as Western blotting or immunoprecipitation using commercially available antibodies. mRNA can be quantitated using methods that are well known and routine in the art, for example, using northern analysis, RNase protection, the polymerase chain reaction in connection with the reverse transcription. Cell viability can be assessed by using trypan-blue staining or other cell death or viability markers known in the art. In a specific embodiment, the level of cellular ATP is measured to determined cell viability. Differentiation can be assessed, for example, visually based on changes in morphology.

The lead compound can also be assessed for its ability to inhibit cell transformation (or progression to malignant phenotype) in vitro. In this embodiment, cells with a transformed cell phenotype are contacted with a lead compound, and examined for change in characteristics associated with a transformed phenotype (a set of in vitro characteristics associated with a tumorigenic ability in vivo), for example, but not limited to, colony formation in soft agar, a more rounded cell morphology, looser substratum attachment, loss of contact inhibition, loss of anchorage dependence, release of proteases such as plasminogen activator, increased sugar transport, decreased serum requirement, or expression of fetal antigens, etc. (see Luria et al., 1978, General Virology, 3d Ed., John Wiley & Sons, New York, pp. 436-446).

Loss of invasiveness or decreased adhesion can also be assessed to demonstrate the anti-cancer effects of a lead compound. For example, an aspect of the formation of a metastatic cancer is the ability of a precancerous or cancerous cell to detach from primary site of disease and establish a novel colony of growth at a secondary site. The ability of a cell to invade peripheral sites reflects its potential for a cancerous state. Loss of invasiveness can be measured by a variety of techniques known in the art including, for example, induction of E-cadherin-mediated cell-cell adhesion. Such E-cadherin-mediated adhesion can result in phenotypic reversion and loss of invasiveness (Hordijk et al., 1997, Science 278:1464-66).

Loss of invasiveness can further be examined by inhibition of cell migration. A variety of 2-dimensional and 3-dimensional cellular matrices are commercially available (Calbiochem-Novabiochem Corp. San Diego, Calif.). Cell migration across or into a matrix can be examined using microscopy, time-lapsed photography or videography, or by any method in the art allowing measurement of cellular migration. In a related embodiment, loss of invasiveness is examined by response to hepatocyte growth factor (HGF). HGF-induced cell scattering is correlated with invasiveness of cells such as Madin-Darby canine kidney (MDCK) cells. This assay identifies a cell population that has lost cell scattering activity in response to HGF (Hordijk et al., 1997, Science 278:1464-66).

Alternatively, loss of invasiveness can be measured by cell migration through a chemotaxis chamber (Neuroprobe/Precision Biochemicals Inc. Vancouver, BC). In such assay, a chemo-attractant agent is incubated on one side of the chamber (e.g., the bottom chamber) and cells are plated on a filter separating the opposite side (e.g., the top chamber). In order for cells to pass from the top chamber to the bottom chamber, the cells must actively migrate through small pores in the filter. Checkerboard analysis of the number of cells that have migrated can then be correlated with invasiveness (see e.g., Ohnishi, T., 1993, Biochem. Biophys. Res. Commun. 193: 518-25).

In certain embodiments, a lead compound is tested for its effects, such as, but not limited to, cytotoxicity, altered gene expression, and altered morphology, on PBMCs (Peripheral Blood Mononuclear Cells).

4.6.2 Animal Models

The lead compounds identified in the assays described herein can be tested for biological activity using animal models for a proliferative disorder. These include animals engineered to contain a tRNA splicing endonuclease or a 3' end pre-mRNA endonuclease coupled to a functional readout system, such as a transgenic mouse. Such animal model systems include, but are not limited to, rats, mice, chicken, cows, monkeys, pigs, dogs, rabbits, etc. In a specific embodiment of the invention, a compound identified in accordance with the methods of the invention is tested in a mouse model system. Such model systems are widely used and well-known to the skilled artisan such as the SCID mouse model or transgenic mice.

The anti-angiogenic activity of a compound identified in accordance with the invention can be determined by using various experimental animal models of vascularized tumors. The anti-tumor activity of a compound identified in accordance with the invention can be determined by administering the compound to an animal model and verifying that the compound is effective in reducing the proliferation or spread of cancer cells in said animal model. An example of an animal model for human cancer in general includes, but is not limited to, spontaneously occurring tumors of companion animals (see, e.g., Vail & MacEwen, 2000, Cancer Invest 18(8):781-92).

Examples of animal models for lung cancer include, but are not limited to, lung cancer animal models described by Zhang & Roth (1994, In Vivo 8(5):755-69) and a transgenic mouse model with disrupted p53 function (see, e.g., Morris et al., 1998, J La State Med Soc 150(4):179-85). An example of an animal model for breast cancer includes, but is not limited to, a transgenic mouse that overexpresses cyclin D1 (see, e.g., Hosokawa et al., 2001, Transgenic Res 10(5):471-8). An example of an animal model for colon cancer includes, but is not limited to, a TCRbeta and p53 double knockout mouse (see, e.g., Kado et al., 2001, Cancer Res 61(6):2395-8). Examples of animal models for pancreatic cancer include, but are not limited to, a metastatic model of Panc02 murine pancreatic adenocarcinoma (see, e.g., Wang et al., 2001, Int J Pancreatol 29(1):37-46) and nu-nu mice generated in subcutaneous pancreatic tumours (see, e.g., Ghaneh et al., 2001, Gene Ther 8(3):199-208). Examples of animal models for non-Hodgkin's lymphoma include, but are not limited to, a severe combined immunodeficiency ("SCID") mouse (see, e.g., Bryant et al., 2000, Lab Invest 80(4):553-73) and an IgHmu-HOX11 transgenic mouse (see, e.g., Hough et al., 1998, Proc Natl Acad Sci USA 95(23):13853-8). An example of an animal model for esophageal cancer includes, but is not limited to, a mouse transgenic for the human papillomavirus type 16 E7 oncogene (see, e.g., Herber et al., 1996, J Virol 70(3):1873-81). Examples of animal models for colorectal carcinomas include, but are not limited to, Apc mouse models (see, e.g., Fodde & Smits, 2001, Trends Mol Med 7(8):369-73 and Kuraguchi et al., 2000, Oncogene 19(50):5755-63).

In certain embodiments, the animal model is a model system for vascular wound healing, for degenerated, leisured or insured tissue. Models for wound healing include sores, lesions, ulcers and bedsores. The lead compounds of the invention can be tested for their ability to facilitate, promote and/or enhance the process of wound healing.

4.6.3 Toxicity

The toxicity and/or efficacy of a compound identified in accordance with the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). Cells and cell lines that can be used to assess the cytotoxicity of a compound identified in accordance with the invention include, but are not limited to, peripheral blood mononuclear cells (PBMCs), Caco-2 cells, and Huh7 cells. The dose ratio between toxic and therapeutic effects is the therapeutic index and it can be expressed as the ratio $LD_{50}/ED_{50}$. A compound identified in accordance with the invention that exhibits large therapeutic indices is preferred. While a compound identified in accordance with the invention that exhibits toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of a compound identified in accordance with the invention for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the compound that achieves a half-maximal inhibition of symptoms) as determined in cell culture. Such information can be used to more accurately determine useful doses in humans. Levels in plasma may be measured, for example, by high performance liquid chromatography.

4.6.4 Design of Congeners or Analogs

The compounds which display the desired biological activity can be used as lead compounds for the development or design of congeners or analogs having useful pharmacological activity. For example, once a lead compound is identified, molecular modeling techniques can be used to design variants of the compound that can be more effective. Examples of molecular modeling systems are the CHARM and QUANTA programs (Polygen Corporation, Waltham, Mass.). CHARM performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modeling of drugs interactive with specific proteins, such as Rotivinen et al., 1988, Acta Pharmaceutical Fennica 97:159-166; Ripka, 1998, New Scientist 54-57; McKinaly & Rossmann, 1989, Annu Rev. Pharmacol. Toxiciol. 29:111-122; Perry & Davies, OSAR: Quantitative Structure-Activity Relationships in Drug Design pp. 189-193 (Alan R. Liss, Inc. 1989); Lewis & Dean, 1989, Proc. R. Soc. Lond. 236:125-140 and 141-162; Askew et al., 1989, J. Am. Chem. Soc. 111:1082-1090. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to any identified region. The analogs and congeners can be tested for binding to a human tRNA splicing endonuclease using the above-described screens for biologic activity. Alternatively, lead compounds with little or no biologic activity, as ascertained in the screen, can also be used to design analogs and congeners of the compound that have biologic activity.

4.7 Pharmaceutical Compositions of the Invention

In certain embodiments, the invention provides compositions comprising a carrier and one the following or a combination of two or more of the following: (i) a component of a complex of the invention (e.g., human Sen2, human Sen15, human Sen34, human Sen54, human Sen2deltaEx8, or functionally active derivatives of functionally active fragments thereof; (ii) a complex of the invention, (iii) an antibody or a fragment thereof that immunospecifically binds to a component of a complex of the invention, or a complex of the invention, (iv) a compound that modulates the expression of a component of a complex of the invention, (v) a compound that modulates the formation of a complex of the invention, (vi) a compound that modulates the endonuclease activity (e.g., tRNA splicing endonuclease activity and/or 3' end pre-mRNA endonuclease activity) of a complex of the invention, (vii) a compound that modulates the pre-tRNA cleavage activity of a complex of the invention, and/or (viii) a compound that modulates pre-ribosomal RNA cleavage activity of a complex of the invention. The compositions may further comprise one or more other prophylatic or therapeutic agents. In a preferred embodiment, the compositions are pharmaceutical compositions. In accordance with this embodiment, the pharmaceutical compositions are preferably sterile and in suitable form for the intended method of administration or use. The invention encompasses the use of the compositions of the invention in the prevention, treatment, management or amelioration of a disorder described herein or a symptom thereof.

In certain embodiments of the invention, a pharmaceutical composition of the invention comprises Sen2, Clp1, Sen54, Sen15, and Sen34. In certain embodiments of the invention, a pharmaceutical composition of the invention comprises Sen2, Sen54, Sen15, and Sen34. In certain embodiments of the invention, a pharmaceutical composition of the invention comprises Sen2deltaEx8. In certain embodiments of the invention, a pharmaceutical composition of the invention comprises Sen2deltaEx8 and Sen54. In certain embodiments of the invention, a pharmaceutical composition of the invention comprises Sen2deltaEx8, Sen54, Sen15 and Sen34. In accordance with these embodiments, a pharmaceutical composition of the invention may further comprise: (i) human CPSF160; (ii) human CPSF30; (iii) human CstF64; and/or (iv) human symplekin.

The different protein components can be present in the form of a complex or not in the form of a complex. In other embodiments, a pharmaceutical composition comprises Sen2, Clp1, Sen54, Sen15, Send34, CPSF, CFIm, CFIIm and CstF. The different protein components can be present in the form of a complex or not in the form of a complex. In even other embodiments, a pharmaceutical composition comprises Sen2ΔEx8, Clp1, Sen54, Sen15, Send34, CPSF, CFIm, CFIIm and CstF. The different protein components can be present in the form of a complex or not in the form of a complex.

In even other embodiments, a pharmaceutical composition comprises an antibody that binds specifically to Sen2ΔEx8. In even more specific embodiments, the antibody does not bind to Sen2. In yet other embodiments, a pharmaceutical composition comprises an oligonucleotide that hybridizes specifically to a nucleic acid encoding Sen2ΔEx8.

In even other embodiments, a pharmaceutical composition comprises an antibody that binds specifically to a component of a complex of the invention. In yet other embodiments, a pharmaceutical composition comprises an oligonucleotide that hybridizes specifically to a nucleic acid encoding a component of a complex of the invention. In even other embodiments, a pharmaceutical composition comprises an antibody that binds immunospecifically to a complex of the invention. In a more specific embodiments, the antibody does not bind to an individual component of a complex of the invention.

In certain embodiments, a pharmaceutical composition of the invention also comprises a pharmaceutically acceptable carrier.

The compositions of the invention include, but are not limited to, bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. Such compositions comprise a prophylactically or therapeutically effective amount of a prophylactic and/or therapeutic agent disclosed herein or a combination of those agents and a pharmaceutically acceptable carrier.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which the therapeutic is contained in or administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

For routes of administration see section 4.9.

4.8 Prophylactic and Therapeutic Uses

A compound identified in assays described herein that modulates the expression of a component of a complex of the invention, the formation of a complex of the invention, the RNA-nucleolytic activity of a complex of the invention (e.g., the pre-tRNA splicing endonuclease activity, the 3' end pre-mRNA endonuclease activity, the pre-tRNA cleavage activity of a complex of the invention, and/or the pre-ribosomal RNA cleavage activity of a complex of the invention) may be tested in in vitro assays (e.g., cell-based assays or cell-free assays) or in vivo assays well-known to one of skill in the art or described herein for the effect of the compound a disorder described herein (e.g., a proliferative disorder or a disorder characterized by, associated with or caused by abnormal RNA-nucleolytic activity) or on cells from a patient with a particular disorder.

The present invention provides methods of preventing, treating, managing or ameliorating a proliferative disorder or a disorder characterized by, associated with or caused by abnormal RNA-nucleolytic activity or one or more symptoms thereof, said methods comprising administering to a subject in need thereof one or more compounds identified in accordance with the methods of the invention. In one embodiment, the invention provides a method of preventing, treating, managing or ameliorating a proliferative disorder or a disorder characterized by, associated with or caused by abnormal RNA-nucleolytic activity or one or more symptoms thereof, said method comprising administering to a subject in need thereof a dose of a prophylactically or therapeutically effective amount of one or more compounds identified in accordance with the methods of the invention. In another embodiment, a compound identified in accordance with the methods of the invention is not administered to prevent, treat, or ameliorate a proliferative disorder or a disorder characterized by, associated with or caused by abnormal RNA-nucleolytic activity or one or more symptoms thereof, if such compound has been used previously to prevent, treat, manage or ameliorate said proliferative disorder. In a specific embodiment, a therapeutic method of the invention comprises administering an effective amount of a compound that has been identified using the methods of the invention as an antagonist of a pre-tRNA splicing endonuclease complex or a 3' end pre-mRNA endonuclease complex. An antagonist can be a compound that destabilizes the complex, prevents its formation or decreases its catalytic activity.

In certain other embodiments, a therapeutically effective amount of a compound identified using the methods of the invention as an agonist of 3' end pre-mRNA endonuclease or pre-tRNA splicing endonuclease is administered to promote wound healing. An agonist may act by stabilizing the complex or by activating the catalytic activity of the complex.

In certain embodiments, a therapeutic method of the invention comprises administering a pharmaceutically effective amount of two or more of the following: Sen2, Clp1, Sen54, Sen15, and Sen34. In certain embodiments, a therapeutic method of the invention comprises administering a pharmaceutically effective amount of Sen2, Clp1, Sen54, Sen15, and Sen34. In accordance with these embodiments, a pharmaceutical composition of the invention may further comprise: (i) human CPSF160; (ii) human CPSF30; (iii) human CstF64; and/or (iv) human symplekin. In other embodiments, a therapeutic method of the invention comprises administering a pharmaceutically effective amount of Sen2, Clp1, Sen54, Sen15, Send34, CPSF, CFIm, CFIIm and CstF. In other embodiments, a therapeutic method comprises administering Sen2deltaEx8 and optionally Sen15, Sen34, Sen54 and Clp1. In accordance with these embodiments, a pharmaceutical composition of the invention may further comprise: (i) human CPSF160; (ii) human CPSF30; (iii) human CstF64; and/or (iv) human symplekin. In even other embodiments, a therapeutic method of the invention comprises administering a pharmaceutically effective amount of Sen2ΔEx8, Clp1, Sen54, Sen15, Send34, CPSF, CFIm, CFIIm and CstF. The different protein components can be present in the form of a complex or not in the form of a complex.

In even other embodiments, a therapeutic method of the invention comprises administering a pharmaceutically effective amount of an antibody that binds specifically to Sen2ΔEx8. In even more specific embodiments, the antibody does not bind to Sen2.

In yet other embodiments, a therapeutic method of the invention comprises administering a pharmaceutically effective amount of an oligonucleotide that hybridizes specifically to a nucleic acid encoding Sen2ΔEx8.

The invention also provides methods of preventing, treating, managing or ameliorating a proliferative disorder or a disorder characterized by, associated with or caused by abnormal RNA-nucleolytic activity (e.g., the pre-tRNA splicing endonuclease activity, the 3' end pre-mRNA endonuclease activity, the pre-tRNA cleavage activity of a complex of the invention, and/or the pre-ribosomal RNA cleavage activity of a complex of the invention) or one or more symptoms thereof, said methods comprising administering to a subject in need thereof one or more of the compounds identified utilizing the screening methods described herein, and one or more other therapies (e.g., prophylactic or therapeutic agents), which therapies are currently being used, have been used or are known to be useful in the prevention, treatment, management or amelioration of one or more symptoms associated with said proliferative disorder (including, but not limited to the prophylactic or therapeutic agents listed in Section 4.8.3 hereinbelow). The therapies (e.g., prophylactic or therapeutic agents) of the combination therapies of the invention can be administered sequentially or concurrently. In a specific embodiment, the combination therapies of the invention comprise a compound identified in accordance with the invention and at least one other therapy that has the same mechanism of action as said compound. In another specific embodiment, the combination therapies of the invention comprise a compound identified in accordance with the methods of the invention and at least one other therapy (e.g., prophylactic or therapeutic agent) which has a different mechanism of action than said compound. The combination therapies of the present invention improve the prophylactic or therapeutic effect of a compound of the invention by functioning together with the compound to have an additive or synergistic effect. The combination therapies of the present invention reduce the side effects associated with the therapies (e.g., prophylactic or therapeutic agents).

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

In specific embodiment, a pharmaceutical composition comprising one or more compounds identified in a screening assay described herein is administered to a subject, preferably a human, to prevent, treat, manage or ameliorate a proliferative disorder or one or more symptoms thereof. In accordance with the invention, the pharmaceutical composition may also comprise one or more prophylactic or therapeutic agents which are currently being used, have been used or are known to be useful in the prevention, treatment, management or amelioration of a proliferative disorder or one or more symptoms thereof.

A compound identified in accordance with the methods of the invention may be used as a first, second, third, fourth or fifth line of therapy for a proliferative disorder or a disorder characterized by, associated with or caused by abnormal RNA-nucleolytic activity (e.g., the pre-tRNA splicing endonuclease activity, the 3' end pre-mRNA endonuclease activity, the pre-tRNA cleavage activity of a complex of the invention, and/or the pre-ribosomal RNA cleavage activity of a complex of the invention). The invention provides methods for treating, managing or ameliorating a proliferative disorder or a disorder characterized by, associated with or caused by abnormal RNA-nucleolytic activity (e.g., the pre-tRNA splicing endonuclease activity, the 3' end pre-mRNA endonuclease activity, the pre-tRNA cleavage activity of a complex of the invention, and/or the pre-ribosomal RNA cleavage activity of a complex of the invention) or one or more symptoms thereof in a subject refractory to conventional therapies for such proliferative disorder, said methods comprising administering to said subject a dose of a prophylactically or therapeutically effective amount of a compound identified in accordance with the methods of the invention. In particular, a cancer or a disorder characterized by, associated with or caused by abnormal RNA-nucleolytic activity (e.g., the pre-tRNA splicing endonuclease activity, the 3' end pre-mRNA endonuclease activity, the pre-tRNA cleavage activity of a complex of the invention, and/or the pre-ribosomal RNA cleavage activity of a complex of the invention) may be determined to be refractory to a therapy means when at least some significant portion of the cancer cells or cells characterized by, associated with or caused by abnormal RNA-nucleolytic activity (e.g., the pre-tRNA splicing endonuclease activity, the 3' end pre-mRNA endonuclease activity, the pre-tRNA cleavage activity of a complex of the invention, and/or the pre-ribosomal RNA cleavage activity of a complex of the invention) are not killed or their cell division arrested in response to the therapy. Such a determination can be made either in vivo or in vitro by any method known in the art for assaying the effectiveness of treatment on cancer cells, using the art-accepted meanings of "refractory" in such a context. In a specific embodiment, a cancer is refractory where the number of cancer cells has not been significantly reduced, or has increased.

In more specific embodiments, the invention provides methods for treating, managing or ameliorating one or more symptoms of a proliferative disorder in a subject refractory to existing single agent therapies for such proliferative disorder, said methods comprising administering to said subject a dose of a prophylactically or therapeutically effective amount of a compound identified in accordance with the methods of the invention and a dose of a prophylactically or therapeutically effective amount of one or more other therapies (e.g., prophylactic or therapeutic agents). The invention also provides methods for treating or managing a proliferative disorder by administering a compound identified in accordance with the methods of the invention in combination with any other therapy (e.g., radiation therapy, chemotherapy or surgery) to patients who have proven refractory to other therapies but are no longer on these therapies. The invention also provides methods for the treatment or management of a patient having a proliferative disorder and immunosuppressed by reason of having previously undergone other therapies. The invention also provides alternative methods for the treatment or management of a proliferative disorder such as cancer where chemotherapy, radiation therapy, hormonal therapy, and/or biological therapy/immunotherapy has proven or may prove too toxic, i.e., results in unacceptable or unbearable side effects, for the subject being treated or managed. Further, the invention provides methods for preventing the recurrence of a proliferative disorder such as cancer in patients that have been treated and have no disease activity by administering a compound identified in accordance with the methods of the invention.

Proliferative disorders that can be treated by the methods encompassed by the invention include, but are not limited to, neoplasms, tumors, metastases, or any disease or disorder characterized by uncontrolled cell growth (e.g., psoriasis and pulmonary fibrosis). The cancer may be a primary or metastatic cancer.

Specific examples of cancers that can be treated by the methods encompassed by the invention include, but are not limited to, cancer of the head, neck, eye, mouth, throat, esophagus, chest, bone, lung, colon, rectum, stomach, prostate, breast, ovaries, kidney, liver, pancreas, and brain. Additional cancers include, but are not limited to, the following: leukemias such as but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenström's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but not limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungaling (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma, gallbladder cancers such as adenocarcinoma; cholangiocarcinomas such as but not limited to pappillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell cancer, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, *Medicine*, 2d Ed., J.B. Lippincott Co., Philadelphia and Murphy et al., 1997, *Informed Decisions: The Complete Book of Cancer Diagnosis, Treatment, and Recovery*, Viking Penguin, Penguin Books U.S.A., Inc., United States of America). It is also contemplated that cancers caused by aberrations in apoptosis can also be treated by the methods and compositions of the invention. Such cancers may include, but not be limited to, follicular lymphomas, carcinomas with p53 mutations, hormone dependent tumors of the breast, prostate and ovary, and precancerous lesions such as familial adenomatous polyposis, and myelodysplastic syndromes.

Wounds that can be treated by the methods encompassed by the invention include, but are not limited to, sores, lesions, ulcers and bedsores.

4.8.1 Use of Antisense Oligonucleotides for Suppression of Protein Complex Activity Or Formation In a specific embodiment of the present invention, the activity and formation of a complex of the invention is inhibited by use of antisense nucleic acids specific to a protein component of the complex that is up-regulated in a subject. The present invention provides the therapeutic or prophylactic use of nucleic acids of at least six nucleotides that are antisense to a gene or cDNA encoding a component protein, or a portion thereof. An "antisense" nucleic acid as used herein refers to a nucleic acid capable of hybridizing to a portion of a component protein RNA (preferably mRNA) by virtue of some sequence complementarity. The antisense nucleic acid may be complementary to a coding and/or non-coding region of a component protein mRNA. Such antisense nucleic acids that inhibit complex formation or activity have utility as Therapeutics, and can be used in the treatment or prevention of disorders as described supra.

The antisense nucleic acids of the invention can be oligonucleotides that are double-stranded or single-stranded, RNA or DNA, or a modification or derivative thereof, which can be directly administered to a cell, or which can be produced intracellularly by transcription of exogenous, introduced sequences.

In another embodiment, the present invention is directed to a method for inhibiting the expression of component protein nucleic acid sequences, in a prokaryotic or eukaryotic cell, comprising providing the cell with an effective amount of a composition comprising an antisense nucleic acid of the component protein, or a derivative thereof, of the invention.

The antisense nucleic acids are of at least six nucleotides and are preferably oligonucleotides, ranging from 6 to about 200 nucleotides. In specific aspects, the oligonucleotide is at least 10 nucleotides, at least 15 nucleotides, at least 100 nucleotides, or at least 200 nucleotides. The oligonucleotides can be DNA or RNA or chimeric mixtures, or derivatives or modified versions thereof, and either single-stranded or double-stranded. The oligonucleotide can be modified at the base moiety, sugar moiety, or phosphate backbone. The oligonucleotide may include other appending groups such as peptides, agents facilitating transport across the cell membrane (see, e.g., Letsinger et al., 1989, Proc. Natl. Acad. Sci.

U.S.A. 86:6553-6556; Lemaitre et al., 1987, Proc. Natl. Acad. Sci. 84:648-652; International Patent Publication No. WO 88/09810) or blood-brain barrier (see, e.g., International Patent Publication No. WO 89/10134), hybridization-triggered cleavage agents (see, e.g., Krol et al., 1988, BioTechniques 6:958-976), or intercalating agents (see, e.g., Zon, 1988, Pharm. Res. 5:539-549).

In a preferred aspect of the invention, an antisense oligonucleotide is provided, preferably as single-stranded DNA. The oligonucleotide may be modified at any position in its structure with constituents generally known in the art.

The antisense oligonucleotides may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thio-uridine, 5-carboxymethylaminomethyluracil, dihydrouracil, beta-D-galactosylqueosine, inosine, N6-isopentyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5N-methoxycarboxymethyluracil, 5-methoxyuracil, 2-methyl-thio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

In another embodiment, the oligonucleotide comprises at least one modified sugar moiety selected from the group including, but not limited to, arabinose, 2-fluoroarabinose, xylulose, and hexose.

In yet another embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal, or an analog of the foregoing.

In yet another embodiment, the oligonucleotide is a 2-a-anomeric oligonucleotide. An a-anomeric oligonucleotide forms specific double-stranded hybrids with complementary RNA in which, contrary to the usual β-units, the strands run parallel to each other (Gautier et al., 1987, Nucl. Acids Res. 15:6625-6641).

The oligonucleotide may be conjugated to another molecule, e.g., a peptide, hybridization-triggered cross-linking agent, transport agent, hybridization-triggered cleavage agent, etc.

Oligonucleotides of the invention may be synthesized by standard methods known in the art, e.g., by use of an automated DNA synthesizer (such as are commercially avail-able from Biosearch, Applied Biosystems, etc.). As examples, phosphorothioate oligo-nucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448-7451), etc.

In a specific embodiment, the antisense oligonucleotides comprise catalytic RNAs, or ribozymes (see, e.g., International Patent Publication No. WO 90/11364; Sarver et al., 1990, Science 247:1222-1225). In another embodiment, the oligonucleotide is a 2'-O-methylribonucleotide (Inoue et al., 1987, Nucl. Acids Res. 15:6131-6148), or a chimeric RNA-DNA analog (Inoue et al., 1987, FEBS Lett. 215:327-330).

In an alternative embodiment, the antisense nucleic acids of the invention are produced intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the component protein. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art to be capable of replication and expression in mammalian cells. Expression of the sequences encoding the antisense RNAs can be by any promoter known in the art to act in mammalian, preferably human, cells. Such promoters can be inducible or constitutive. Such promoters include, but are not limited to, the SV40 early promoter region (Bernoist and Chambon, 1981, Nature 290:304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42), etc.

The antisense nucleic acids of the invention comprise a sequence complementary to at least a portion of an RNA transcript of a component protein gene, preferably a human gene. However, absolute complementarity, although preferred, is not required. A sequence "complementary to at least a portion of an RNA," as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a component protein RNA it may contain and still form a stable duplex (or triplex, as the case may be). One skilled in the art can ascertain a tolerable degree of mismatch by use of standard procedures to determine the melting point of the hybridized complex.

The component protein antisense nucleic acids can be used to treat (or prevent) disorders of a cell type that expresses, or preferably overexpresses, a protein complex.

Cell types that express or overexpress component protein RNA can be identified by various methods known in the art. Such methods include, but are not limited to, hybridization with component protein-specific nucleic acids (e.g., by Northern blot hybridization, dot blot hybridization, or in situ hybridization), or by observing the ability of RNA from the cell type to be translated in vitro into the component protein by immunohistochemistry, Western blot analysis, ELISA, etc. In a preferred aspect, primary tissue from a patient can be assayed for protein expression prior to treatment, e.g., by immunocytochemistry, in situ hybridization, or any number of methods to detect protein or mRNA expression.

Pharmaceutical compositions of the invention (see section 4.7), comprising an effective amount of a protein component antisense nucleic acid in a pharmaceutically acceptable carrier can be administered to a patient having a disease or disorder that is of a type that expresses or overexpresses a protein complex of the present invention.

The amount of antisense nucleic acid that will be effective in the treatment of a particular disorder or condition will depend on the nature of the disorder or condition, and can be determined by standard clinical techniques. Where possible, it is desirable to determine the antisense cytotoxicity in vitro, and then in useful animal model systems, prior to testing and use in humans.

In a specific embodiment, pharmaceutical compositions comprising antisense nucleic acids are administered via liposomes, microparticles, or microcapsules. In various embodiments of the invention, it may be useful to use such compositions to achieve sustained release of the antisense nucleic acids. In a specific embodiment, it may be desirable to utilize liposomes targeted via antibodies to specific identifiable central nervous system cell types (Leonetti et al., 1990, Proc. Natl. Acad. Sci. U.S.A. 87:2448-2451; Renneisen et al., 1990, J. Biol. Chem. 265:16337-16342).

4.8.2 RNA Interference

In certain embodiments, an RNA interference (RNAi) molecule is used to decrease the expression of a component of a complex of the invention. RNA interference (RNAi) is the ability of double-stranded RNA (dsRNA) to suppress the expression of a gene corresponding to its own sequence (see, e.g., Cogoni and Macino, 2000, Genes Dev 10: 638-643, Guru, 2000, Nature 404, 804-808, Hammond et al., 2001, Nature Rev Gen 2: 110-119, Shi, 2003, Trends Genet. 19:9-12, U.S. Pat. No. 6,506,559, each incorporated by reference in their entireties herein). RNAi is also called post-transcriptional gene silencing or PTGS. Without being bound by theory, since the only RNA molecules normally found in the cytoplasm of a cell are molecules of single-stranded mRNA, the cell has enzymes that recognize and cut dsRNA into fragments containing 21-25 base pairs (approximately two turns of a double helix). The antisense strand of the fragment separates enough from the sense strand so that it hybridizes with the complementary sense sequence on a molecule of endogenous cellular mRNA. This hybridization triggers cutting of the mRNA in the double-stranded region, thus destroying its ability to be translated into a polypeptide. Introducing dsRNA corresponding to a particular gene thus knocks out the cell's own expression of that gene in particular tissues and/or at a chosen time.

The current models of the RNAi mechanism includes both initiation and effector steps (Hutvagner and Zamore, 2002, Curr Opin Genetics & wDevelopment 12:225-32; Hammond et al., 2001, Nature Rev Gen 2: 110-9, each incorporated by reference in their entireties herein). In the initiation step, input dsRNA is digested into 21-23 nucleotide small interfering RNAs (siRNAs), which have also been called "guide RNAs" (Sharp, 2001, Genes Dev 15: 485-490). Evidence indicates that siRNAs are produced when the enzyme Dicer, a member of the RNase III family of dsRNA-specific ribonucleases, processively cleaves dsRNA (introduced directly or via a transgene or virus) in an ATP-dependent, processive manner. Successive cleavage events degrade the RNA to 19-21 base pair duplexes (siRNAs), each with 2-nucleotide 3' overhangs (Bernstein et al., 2001, Nature 409:363-366; Hutvagner and Zamore, 2002, Curr Opin Genetics & Development 12:225-232). In the effector step, the siRNA duplexes bind to a nuclease complex to form what is known as the RNA-induced silencing complex, or RISC. An ATP-depending unwinding of the siRNA duplex is required for activation of the RISC. The active RISC then targets the homologous transcript by base pairing interactions and cleaves the mRNA ~12 nucleotides from the 3' terminus of the siRNA. Although the mechanism of cleavage is at this date unclear, research indicates that each RISC contains a single siRNA and an RNase that appears to be distinct from Dicer (Hutvagner and Zamore, 2002, Curr Opin Genetics & Development 12:225-232). Because of the remarkable potency of RNAi in some organisms, an amplification step within the RNAi pathway has also been proposed. Amplification could occur by copying of the input dsRNAs, which would generate more siRNAs, or by replication of the siRNAs themselves.

Alternatively or in addition, amplification could be effected by multiple turnover events of the RISC. Elbashir and colleagues (Elbashir et al., 2001, Nature 411:494-498; Elbashir et al., 2001, EMBO 20:6877-6888) have suggested a procedure for designing siRNAs for inducing RNAi in mammalian cells. Briefly, find a 21 nucleotide sequence in the mRNA of interest that begins with an adenine-adenine (AA) dinucleotide as a potential siRNA target site. This strategy for choosing siRNA target sites is based on the observation that siRNAs with 3' overhanging UU dinucleotides are the most effective. This is also compatible with using RNA pol III to transcribe hairpin siRNAs because RNA pol III terminates transcription at 4-6 nucleotide poly(T) tracts creating RNA molecules with a short poly(U) tail. Although siRNAs with other 3' terminal dinucleotide overhangs have been shown to effectively induce RNAi, siRNAs with guanine residues in the overhang are not recommended because of the potential for the siRNA to be cleaved by RNase at single-stranded guanine residues. In addition to beginning with an AA dinucleotide, the siRNA target site should have a guanosine and cytidine residue percentage within the range of 30-70%. The chosen siRNA target sequence should then be subjected to a BLAST search against the EST database to ensure that only the desired gene is targeted. Various products are commercially available to aid in the preparation and use of siRNA (e.g., Ambion, Inc., Austin, Tex.).

Double-stranded (ds) RNA can be used to interfere with gene expression in mammals (Brummelkamp et al., Science 296:550-3, Krichevsky and Kosik, 2002, PNAS 99:11926-9, Paddison et al., 2002, PNAS 99:1443-8, Wianny & Zernicka-Goetz, 2000, Nature Cell Biology 2:70-75, European Patent 1144623, International Patent Publication Nos. WO 02/055693, WO 02/44321, WO 03/006,477; each incorporated by reference in their entireties herein).

4.8.3 Other Anti-Cancer and Wound Healing Therapies

The present invention provides methods of preventing, treating, managing or ameliorating cancer or one or more symptoms thereof, said methods comprising administering to a subject in need thereof one or more compounds identified in accordance with the methods of the invention and one or more therapies (e.g., prophylactic or therapeutic agents). Therapeutic or prophylactic agents include, but are not limited to, peptides, polypeptides, fusion proteins, nucleic acid molecules, small molecules, mimetic agents, synthetic drugs, inorganic molecules, and organic molecules.

Any therapy (e.g., chemotherapies, radiation therapies, hormonal therapies, and/or biological therapies/immunotherapies) which is known to be useful, or which has been used or is currently being used for the prevention, treatment, management or amelioration of cancer or one or more symptoms thereof can be used in combination with a compound identified in accordance with the methods of the invention. Examples of such agents (i.e., anti-cancer agents) include, but are not limited to, angiogenesis inhibitors, topoisomerase inhibitors and immunomodulatory agents (such as chemotherapeutic agents). Angiogenesis inhibitors (i.e., anti-angiogenic agents) include, but are not limited to, angiostatin (plasminogen fragment); antiangiogenic antithrombin III; angiozyme; ABT-627; Bay 12-9566; Benefin; Bevacizumab; BMS-275291; cartilage-derived inhibitor (CDI); CAI; CD59 complement fragment; CEP-7055; Col 3; combretastatin A-4; endostatin (collagen XVIII fragment); fibronectin fragment; Gro-beta; Halofuginone; Heparinases; Heparin hexasaccharide fragment; HMV833; human chorionic gonadotropin (hCG); IM-862; Interferon alpha/beta/gamma; Interferon inducible protein (IP-10); Interleukin-12; Kringle 5 (plasminogen fragment); Marimastat; Metalloproteinase inhibitors (TIMPs); 2-methoxyestradiol; MMI 270 (CGS 27023A); MoAb IMC-1C11; Neovastat; NM-3; Panzem; PI-88; Placental ribonuclease inhibitor; plasminogen activator inhibitor; platelet factor-4 (PF4); Prinomastat; Prolactin 16 kD fragment; Proliferin-related protein (PRP); PTK 787/ZK 222594; retinoids; solimastat; squalamine; SS 3304; SU 5416; SU6668; SU11248;

tetrahydrocortisol-S; tetrathiomolybdate; thalidomide; thrombospondin-1 (TSP-1); TNP-470; transforming growth factor-beta; vasculostatin; vasostatin (calreticulin fragment); ZD6126; ZD 6474; farnesyl transferase inhibitors (FTI); and bisphosphonates. In a specific embodiment, anti-angiogenic agents do not include antibodies or fragments thereof that immunospecifically bind to integrin $\alpha_v\beta_3$.

Specific examples of anti-cancer agents which can be used in accordance with the methods of the invention include, but not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alpha-2a; interferon alpha-2b; interferon alpha-n1; interferon alpha-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; 5-fluorouracil; leucovorin; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; thalidomide; velaresol; veramine; verdins; verteporfin; vinorelbine; vinxaltine; vorozole; zanoterone; zeniplatin; zilascorb; and zinostatin stimalamer.

The invention also encompasses the administration of one or more compounds identified in accordance with the methods of the invention in combination with radiation therapy comprising the use of x-rays, gamma rays and other sources of radiation to destroy the cancer cells. In preferred embodiments, the radiation treatment is administered as external beam radiation or teletherapy wherein the radiation is directed from a remote source. In other preferred embodiments, the radiation treatment is administered as internal therapy or brachytherapy wherein a radiaoactive source is placed inside the body close to cancer cells or a tumor mass.

Cancer therapies and their dosages, routes of administration and recommended usage are known in the art and have been described in such literature as the *Physician's Desk Reference* (56$^{th}$ ed., 2002).

4.9 Compositions and Methods of Administering Compounds

Compounds identified using the methods of the invention or a pharmaceutically acceptable salt thereof, complexes of the invention, components of complexes of the invention or nucleic acids encoding components of a complex of the invention, antibodies or fragment thereof that immunospecifically bind to a complex of the invention or a component of a complex of the invention or antisense oligonucleotides that interfere with the expression of a component of a complex of the invention can be administered to a patient, preferably a mammal, more preferably a human, suffering from a proliferative disorder, a disorder characterized by, associated with or caused by abnormal RNA-nucleolytic activity or a condition associated with wound healing (e.g., sores, lesions, ulcers and bedsores). In this section, compounds identified using the methods of the invention or a pharmaceutically acceptable salt thereof, complexes of the invention, components of complexes of the invention or nucleic acids encoding components of a complex of the invention, antibodies or fragment thereof that immunospecifically bind to a complex of the invention or a component of a complex of the invention or antisense oligonucleotides that interfere with the expression of a component of a complex of the invention are collectively referred to as compound to be used with the therapeutic and prophylactic methods of the invention. In a specific embodiment, a compound to be used with the therapeutic and prophylactic methods of the invention is administered to a patient, preferably a mammal, more preferably a human, as a preventative measure against a proliferative disorder, a disorder characterized by, associated with or caused by abnormal RNA-nucleolytic activity or a condition associated with wound healing.

When administered to a patient, the compound to be used with the therapeutic and prophylactic methods of the invention is preferably administered as component of a composition that optionally comprises a pharmaceutically acceptable vehicle. The composition can be administered orally, or by any other convenient route, for example, by infusion or bolus injection, by absorption through epithelial or mucocutaneous linings (e.g., oral mucosa, rectal, and intestinal mucosa, etc.) and may be administered together with another biologically active agent. Administration can be systemic or local. Various delivery systems are known, e.g., encapsulation in liposomes, microparticles, microcapsules, capsules, etc., and can be used to administer the compound and pharmaceutically acceptable salts thereof.

Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The mode of administration is left to the discretion of the practitioner. In most instances, administration will result in the release of the compound or a pharmaceutically acceptable salt thereof into the bloodstream.

In specific embodiments, it may be desirable to administer the compound to be used with the therapeutic and prophylactic methods of the invention locally. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

In certain embodiments, it may be desirable to introduce the compound to be used with the therapeutic and prophylactic methods of the invention into the central nervous system by any suitable route, including intraventricular, intrathecal and epidural injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compound to be used with the therapeutic and prophylactic methods of the invention can be formulated as a suppository, with traditional binders and vehicles such as triglycerides.

In another embodiment, the compound to be used with the therapeutic and prophylactic methods of the invention can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In yet another embodiment, the compound to be used with the therapeutic and prophylactic methods of the invention can be delivered in a controlled release system (see, e.g., Goodson, in Medical Applications of Controlled Release, supra, vol. 2, pp. 115-138 (1984)). Other controlled-release systems discussed in the review by Langer, 1990, Science 249:1527-1533 may be used. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled-release system can be placed in proximity of a target RNA of the compound or a pharmaceutically acceptable salt thereof, thus requiring only a fraction of the systemic dose.

Compositions comprising the compound to be used with the therapeutic and prophylactic methods of the invention ("compound compositions") can additionally comprise a suitable amount of a pharmaceutically acceptable vehicle so as to provide the form for proper administration to the patient.

In a specific embodiment, the term "pharmaceutically acceptable" means approved by a regulatory agency of the Federal or a state government or listed in the U.S. Pharmacopeia or other generally recognized pharmacopeia for use in animals, mammals, and more particularly in humans. The term "vehicle" refers to a diluent, adjuvant, excipient, or carrier with which a compound of the invention is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a patient, the pharmaceutically acceptable vehicles are preferably sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Compound compositions, if desired, can also contain minor amounts of wetting or emulsifying agents, or pH buffering agents.

Compound compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155). Other examples of suitable pharmaceutical vehicles are described in Remington's Pharmaceutical Sciences, Alfonso R. Gennaro, ed., Mack Publishing Co. Easton, Pa., 19th ed., 1995, pp. 1447 to 1676, incorporated herein by reference.

In a preferred embodiment, the compound to be used with the therapeutic and prophylactic methods of the invention is formulated in accordance with routine procedures as a pharmaceutical composition adapted for oral administration to human beings. Compositions for oral delivery may be in the form of tablets, lozenges, aqueous or oily suspensions, granules, powders, emulsions, capsules, syrups, or elixirs, for example. Orally administered compositions may contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, and the like. Such vehicles are preferably of pharmaceutical grade. Typically, compositions for intravenous administration comprise sterile isotonic aqueous buffer. Where necessary, the compositions may also include a solubilizing agent.

In another embodiment, the compound to be used with the therapeutic and prophylactic methods of the invention can be formulated for intravenous administration. Compositions for intravenous administration may optionally include a local anesthetic such as lignocaine to lessen pain at the site of the injection. Generally, the ingredients are supplied either separately or mixed together in unit dosage form, for example, as a dry lyophilized powder or water-free concentrate in a hermetically sealed container such as an ampoule or sachette indicating the quantity of active agent. Where the compound to be used with the therapeutic and prophylactic methods of the invention is to be administered by infusion, it can be dispensed, for example, with an infusion bottle containing sterile pharmaceutical grade water or saline. Where the compound to be used with the therapeutic and prophylactic methods of the invention is administered by injection, an ampoule of sterile water for injection or saline can be provided so that the ingredients may be mixed prior to administration.

The amount of a compound to be used with the therapeutic and prophylactic methods of the invention that will be effective in the treatment of a particular disease will depend on the nature of the disease, and can be determined by standard clinical techniques. In addition, in vitro or in vivo assays may optionally be employed to help identify optimal dosage ranges. The precise dose to be employed will also depend on the route of administration, and the seriousness of the disease, and should be decided according to the judgment of the practitioner and each patient's circumstances. However, suitable dosage ranges for oral administration are generally about 0.001 milligram to about 500 milligrams of a compound or a pharmaceutically acceptable salt thereof per kilogram body weight per day. In specific preferred embodiments of the invention, the oral dose is about 0.01 milligram to about 100 milligrams per kilogram body weight per day, more preferably about 0.1 milligram to about 75 milligrams per kilogram body weight per day, more preferably about 0.5 milligram to 5 milligrams per kilogram body weight per day. The dosage amounts described herein refer to total amounts administered; that is, if more than one compound is administered, or if a compound is administered with a therapeutic agent, then the preferred dosages correspond to the total amount administered. Oral compositions preferably contain about 10% to about 95% active ingredient by weight.

Suitable dosage ranges for intravenous (i.v.) administration are about 0.01 milligram to about 100 milligrams per kilogram body weight per day, about 0.1 milligram to about 35 milligrams per kilogram body weight per day, and about 1 milligram to about 10 milligrams per kilogram body weight per day. Suitable dosage ranges for intranasal administration are generally about 0.01 pg/kg body weight per day to about 1 mg/kg body weight per day. Suppositories generally contain about 0.01 milligram to about 50 milligrams of a compound of the invention per kilogram body weight per day and comprise active ingredient in the range of about 0.5% to about 10% by weight.

Recommended dosages for intradermal, intramuscular, intraperitoneal, subcutaneous, epidural, sublingual, intracerebral, intravaginal, transdermal administration or administration by inhalation are in the range of about 0.001 milligram to about 200 milligrams per kilogram of body weight per day. Suitable doses for topical administration are in the range of about 0.001 milligram to about 1 milligram, depending on the area of administration. Effective doses may be extrapolated from dose-response curves derived from in vitro or animal model test systems. Such animal models and systems are well known in the art.

The compound and pharmaceutically acceptable salts thereof are preferably assayed in vitro and in vivo, for the desired therapeutic or prophylactic activity, prior to use in humans. For example, in vitro assays can be used to determine whether it is preferable to administer the compound, a pharmaceutically acceptable salt thereof, and/or another therapeutic agent. Animal model systems can be used to demonstrate safety and efficacy.

An exemplary doses of proteins, polypeptides, peptides, fusion proteins and complexes encompassed by the invention is 0.0001 mg/kg to 100 mg/kg of the patient's body weight. Preferably, the dosage administered to a patient is between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg and 0.25 mg/kg, 0.0001 and 0.15 mg/kg, 0.0001 and 0.10 mg/kg, 0.001 and 0.5 mg/kg, 0.01 and 0.25 mg/kg, 0.01 and 0.10 mg/kg or 0.1 and 10 mg/kg of the patient's body weight.

4.10 Diagnostic Methods of the Invention

In certain embodiments, the invention provides methods for diagnosing the presence of a proliferative disorder in a subject. In certain embodiments, a diagnostic method of the invention comprises determining the amount of a complex of the invention in a subject, wherein a decreased level of a complex of the invention in the subject indicates the presence of a proliferative disorder or an increased risk of developing a proliferative disorder. In other embodiments, a diagnostic method of the invention comprises determining the amount of a component of a complex (or a nucleic acid encoding the component) of the invention in a subject, wherein a decreased level of the component in the subject indicates the presence of a proliferative disorder or an increased risk of developing a proliferative disorder. In yet other embodiments, a diagnostic method of the invention comprises determining the amount of a component of a complex of the invention in the nuclei of cells in a subject, wherein a increased level of the component in the subject indicates the presence of a proliferative disorder or an increased risk of developing a proliferative disorder.

A component of a complex, a nucleic acid encoding a component of a complex of the invention can be detected and quantified by any method known to the skilled artisan. Exemplary methods include, but are not limited to, Western blot analysis, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays for proteins and PCR (particularly RT-PCR) or Northern blot analysis for nucleic acids.

The invention also provides methods for detecting, diagnosing or monitoring a proliferative disorder or a disorder associated with, characterized by or caused by abnormal pre-tRNA processing and/or 3' end pre-mRNA processing utilizing an antibody that immunospecifically binds to a complex of the invention or a component thereof, or a compound identified in accordance with the methods of the invention that specifically binds to a complex of the invention or a component thereof. In a specific embodiment, the invention provides a method for detecting, diagnosing or monitoring a proliferative disorder or a disorder associated with, characterized by or caused by increased pre-tRNA processing and/or 3' end pre-mRNA processing, said method comprising: (a) measuring the level of a complex of the invention or a component thereof in cells or a tissue sample of a subject (e.g., a subject with such a disorder or suspected of having such disorder) using one or more antibodies or fragments thereof that immunospecifically bind to the complex or a component thereof, or a compound identified in accordance with the methods of the invention that specifically binds to the complex or a component thereof; and (b) comparing the level of the complex or a component thereof with a control level, e.g., levels in normal, noncancerous cells or tissue samples, wherein an increase in the measured complex or component level in measured in (a) relative to the control level of the complex or component is indicates that the subject has a proliferative disorder or a disorder associated with, characterized by or caused by abnormal pre-tRNA processing and/or 3' end pre-mRNA processing.

The invention provides methods for detecting, diagnosing or monitoring a proliferative disorder or a disorder associated with, characterized by or caused by abnormal pre-tRNA processing and/or 3' end pre-mRNA processing by comparing the RNA-nucleolytic activity of a complex purified from cells or a tissue sample from a subject with such a disorder or suspected of having such disorder to the RNA-nucleolytic activity of a control, e.g., a complex purified from normal, non-cancerous cells or a tissue sample, using an assay well-known to one of skill in the art or described herein. In a specific embodiment, the invention provides a method for detecting, diagnosing or monitoring a proliferative disorder or a disorder associated with, characterized by or caused by increased RNA-nucleolytic activity (e.g., the pre-tRNA splicing endonuclease activity, the 3' end pre-mRNA endonuclease activity, the pre-tRNA cleavage activity of a complex of the invention, and/or the pre-ribosomal RNA cleavage activity of a complex of the invention), the method comprising (a) measuring the RNA-nucleolytic activity of a complex of the invention purified from cells or a tissue sample from a subject with such a disorder or suspected of having such disorder to the RNA-nucleolytic activity of a control, e.g., a complex purified from normal, non-cancerous, cells or a tissue sample using an assay well-known to one of skill in the art or described herein; and (b) comparing the RNA-nucleolytic activity of the complex measured in (a) with the RNA-nucleolytic activity of the complex of a control, e.g., a complex of the invention purified from normal, non-cancerous, cells or a tissue sample, wherein an increase in the RNA-nucleolytic activity in measured in (a) relative to the control indicates that the subject has a proliferative disorder or a disorder associated with, characterized by or caused by increased pre-tRNA processing and/or 3' end pre-mRNA processing. In another embodiment, the invention provides a method for detecting, diagnosing or monitoring a disorder associated with, characterized by or caused by decreased RNA-nucleolytic activity (e.g., the pre-tRNA splicing endonuclease activity, the 3' end pre-mRNA endonuclease activity, the pre-tRNA cleavage activity of a complex of the invention, and/or the pre-ribosomal RNA cleavage activity of a complex of the invention), the method comprising measuring the RNA-nucleolytic activity of a complex of the invention purified from cells or a tissue sample from a subject with such a disorder or suspected of having such disorder to the RNA-nucleolytic activity of a control, e.g., a complex of the invention purified from normal, non-cancerous, cells or a tissue sample using an assay well-known to one of skill in the art or described herein; (b) comparing the RNA-nucleolytic activity of the complex measured in (a) with the RNA-nucleolytic activity of a control, e.g., a complex purified from normal, non-cancerous, cells or a tissue sample, wherein a decrease in the RNA-nucleolytic activity in measured in (a) relative to the control indicates that the subject has a disorder associated with, characterized by or caused by decreased pre-tRNA processing and/or 3' end pre-mRNA processing.

The invention provides methods for detecting, diagnosing or monitoring a proliferative disorder or a disorder associated with, characterized by or caused by abnormal pre-tRNA processing and/or 3' end pre-mRNA processing by comparing the structure of a complex of the invention purified from cells or a tissue sample from a subject (e.g., a subject with such a disorder or suspected of having such a disorder) to the structure of a control, e.g., a complex of the invention purified from normal, non-cancerous cells or a tissue sample, using an assay well-known to one of skill in the art (e.g., circular circular dichroism and nuclear magnetic resonance).

5. EXAMPLE

The Example below describes a human endonuclease complex and demonstrates a molecular connection between tRNA splicing and pre-mRNA 3'-end formation.

Introduction

Maturation of cellular RNAs is critical for regulation of normal cell growth and division. Mature eukaryotic RNAs are generated from large precursors via a series of processing steps. For example, nascent pre-mRNAs undergo splicing, capping, and generation of 3' ends by endonucleolytic cleavage and polyadenylation. The maturation of precursor transfer RNA (pre-tRNA) requires several steps that include: 1) removal of both the 5' leader by RNase P (Xiao et al., 2002; Frank and Pace, 1998) and the 3' trailer by ELAC2 (Takaku et al., 2003); 2) addition of the CCA trinucleotide to the 3' end; 3) numerous nucleotide modifications (reviewed in Hopper and Phizicky, 2003). In addition, several tRNAs contain introns that must be removed to produce a mature tRNA molecule.

Intron-containing pre-tRNAs are found in a variety of organisms from all three domains of life. In lower eukaryotes, approximately 25% of all tRNA genes contain introns (Trotta et al., 1997), whereas in humans only 6% of tRNA genes contain introns (Lowe and Eddy, 1997). All eukaryotic tRNA introns are 14-60 nucleotides in length and interrupt the anti-codon loop one nucleotide 3' to the anticodon (Ogden et al., 1984). Among all yeast pre-tRNAs, there is no sequence conservation at the splice junctions, but the 3' splice site is invariably located in a bulged loop (Baldi et al., 1992).

The removal of introns from pre-tRNA is an enzymatic reaction that requires the activity of several different proteins (reviewed in Abelson et al., 1998). These enzymes have been most intensively investigated in Archaea and yeast. The first step is carried out by an evolutionarily conserved tRNA splicing endonuclease that recognizes and cleaves precursor tRNA at the 5' and 3' splice sites (Trotta et al., 1997). In yeast, the 5' and 3' exons are ligated by a tRNA ligase through a series of enzymatic reactions that lead to joining of the two exons with a 2' phosphate at the splice junction (Westaway et al., 1988; Phizicky et al., 1986). This unusual tRNA intermediate is then processed by a 2' phosphotransferase yielding a mature tRNA (Culver et al., 1997).

Yeast tRNA splicing endonuclease is a heteromeric complex of four subunits encoded by the SEN2, SEN34, SEN54 and SEN15 genes (Rauhut et al., 1990; Trotta et al., 1997). All four subunits are present at low levels and are essential for cell viability (Trotta et al., 1997). The structure and function of the factors of the yeast tRNA endonuclease complex has been suggested from a number of experimental results. First, strong sequence conservation of the yeast Sen2p and Sen34p to the homotetrameric archaeal enzyme suggested that these two subunits each contained a distinct active site for cleavage at the 5' and 3' sites. Consistent with this view, a mutation in Sen2p resulted in a defect in cleavage of the 5' splice site (Ho et al., 1990), whereas a mutation in a conserved histidine residue in Sen34p resulted in a defect in cleavage of the 3' splice site (Trotta et al., 1997). Second, two-hybrid analysis demonstrated strong interaction between Sen2p and Sen54p and between Sen34p and Sen15p (Trotta et al., 1997). Structural studies with the homotetrameric archaeal tRNA endonuclease suggested that the strong interaction between Sen2p-Sen54p and Sen34p-Sen15p are mediated by a conserved carboxyl-terminal beta-sheet interaction (Lykke-Andersen and Garrett, 1997; Li et al., 1998). Finally, sequence alignment of heterologous subunits Sen54p and Sen15p to the archaeal endonuclease revealed a conserved structural element near the carboxyl-terminus required for dimerization of the two yeast heterodimers, Sen54p-Sen2p and Sen15p-Sen34p (Lykke-Andersen and Garrett, 1997; Li et al., 1998). Together, these results led to a model for the configuration of the yeast tRNA splicing endonuclease (Li et al., 1998; Abelson et al., 1998).

Preliminary studies suggest a common mechanism for tRNA splicing throughout evolution. For example, extracts derived from human cell lines were reported to carry out accurate tRNA splicing under conditions in which the yeast tRNA splicing endonuclease is active (Laski et al., 1983; Standring et al., 1981). Furthermore, partially purified tRNA splicing endonuclease from *Xenopus laevis* germinal vesicles was shown to recognize and accurately cleave yeast pre-tRNA, forming two half-molecules and an intron (Gandini-Attardi et al., 1990; Baldi et al., 1986; Otsuka et al., 1981). Additionally, *Xenopus* and yeast enzymes appear to fix the sites of cleavage by recognition of local structures at the intron-exon boundaries (Baldi et al., 1992; Fabbri et al., 1998).

Although there is evidence that the mechanism of tRNA splicing is well conserved between yeast, archaea and higher eukaryotes, the enzymes responsible for the maturation of pre-tRNA in humans are unknown. The present example describes present the isolation and characterization of human tRNA splicing endonuclease. In addition, the present example describes the identification a distinct endonuclease complex resulting from alternative splicing of the SEN2 subunit. This complex differs from tRNA endonuclease complex by protein composition and the ability to process pre-tRNA. Furthermore, the endonuclease complex associates with factors required for cleavage/polyadenylation of mRNAs, suggesting a previously undiscovered biochemical link between pre-tRNA splicing and formation of the 3' end of messenger RNAs.

5.1 Subunits of the Human Endonuclease Complex 5.1.1 Materials and Methods 5.1.1.1 Generation of Stable Cell Lines that Express HIS-FLAG-Tagged Endonuclease Complex Subunits Endonuclease complex subunits include the proteins Sen2 (80746), Sen34 (79042), Sen54 (283989), Sen15 (116461), and Clp1 (10978). The open reading frame of Sen2 was generated by PCR amplification using specific primers (Forward: cgggatcccgcagaagcagttttccatgccccaaagagg (SEQ ID NO:21); Reverse: gctctagattaaagatcgtcttggtcactcctctctcg (SEQ ID NO:22)) and was cloned into the HIS-FLAG-pcDNA3.1/Hygro vector containing a gene that provides resistance to hygromycin. 293T cells that contain other necessary components of the endonuclease complex were transfected with HIS-FLAG-pcDNA3.1/Hygro plasmid encoding His-Flag-Sen2 (His-Flag-Sen2 vector), and stable clones were selected by resistance to hygromycin to generate cell lines expressing His-Flag-Sen2. 293 cell lines expressing His-Flag-Sen34 and His-Flag-Sen15 were generated similarly. The open reading frame of Sen34 was generated by PCR amplification using primers specific for Sen34 (Forward: cgggatcccctggtggtggaggtggcgaacggccgctcc (SEQ ID NO:23); Reverse: gctctagatgcaggctggcccattgcagggaggtgtag (SEQ ID NO:24)) and was cloned into the HIS-FLAG-pcDNA3.1/Hygro vector to create HIS-FLAG-Sen34 vector. 293T cells were transfected with the HIS-FLAG-Sen34 vector, and stable clones were selected by resistance to hygromycin to generate cell lines expressing His-Flag-Sen34. The open reading frame of Sen15 was generated by PCR amplification using primers specific for Sen15 (Forward: cgggatccgaggagcgcggcgattccgagccga (SEQ ID NO:25); Reverse: cgcgctagctcatcttctaagagaaatattctgagggtctggcag (SEQ ID NO:26)) and was cloned into the HIS-FLAG-pcDNA3.1/Hygro vector to create HIS-FLAG-Sen15 vector. 293T cells were transfected with the HIS-FLAG-Sen15 vector, and stable clones were selected by resistance to hygromycin to generate cell lines expressing His-Flag-Sen15. The open reading frame of Sen54 was generated by PCR amplification using primers specific for Sen54 (Forward: atcgggatcccgagcccgagcccgagcccg (SEQ ID NO:27); Reverse: gctctagatcagtgccccacatcctggggc (SEQ ID NO:28)) and was cloned into the HIS-FLAG-pcDNA3.1/Hygro vector to create HIS-FLAG-Sen54 vector. 293T cells are transfected with the HIS-FLAG-Sen54 vector, and stable clones are selected by resistance to hygromycin to generate cell lines expressing His-Flag-Sen54. The open reading frame of Clp1 was generated by PCR amplification using primers specific for Clp1 (Forward: cgggatcccggagaagaggctaatgatgatgacaagaag (SEQ ID NO:29); Reverse: gctctagactacttcagatccatgaaccggatatcc (SEQ ID NO:30)) and was cloned into the HIS-FLAG-pcDNA3.1/Hygro vector to create HIS-FLAG-Clp1 vector. 293T cells were transfected with the HIS-FLAG-Clp1 vector, and stable clones were selected by resistance to hygromycin to generate cell lines expressing His-Flag-Clp1.

5.1.1.2 Purification of the Endonuclease Complex from a Total Cell Extract Containing His-Flag-Tagged Proteins.

Total cell extracts were prepared by resuspending cell pellets in buffer B (250 mM NaCl; 30 mM Tris-HCl, pH 7.0; 1 mM EDTA; 5% glycerol; 0.1% Triton X-100; Protease inhibitors (Roche, Complete Protease Inhibitor Cocktail Tablets)). Cells were sonicated 3 times for 10 seconds, followed by centrifugation at 15,000 g for 15 minutes. Supernatants were passed through a 0.2 µm filter and added to anti-Flag beads (Sigma) pre-washed with buffer B. Extracts were incubated with anti-Flag beads for 2 hours at 4° C. Supernatants were discarded and beads were washed 3 times for 10 minutes at 4° C. with ten bed volumes of buffer W (400 mM NaCl; 30 mM Tris-HCl, pH 7.0; 1 mM EDTA; 5% glycerol; 0.04% Triton X-100). Following two washes with ten bed volumes of buffer N (200 mM NaCl; 40 mM Tris-HCl, pH 7.0; 2 mM $MgCl_2$; 5% glycerol; 0.05% triton X-100), bound proteins were eluted with three bed volumes of buffer N containing 0.25 mg/ml 3×FLAG peptide (Sigma) for 1 h at 4° C. Following addition of NaCl (final concentration of 480 mM), eluted proteins were added to Ni-beads pre-washed with buffer NBW (500 mM NaCl; 40 mM Tris-HCl, pH 7.0; 2 mM $MgCl_2$; 5% glycerol; 0.05% triton X-100) and incubated for 1 hour at 4° C. Supernatants were discarded and Ni-beads were washed three times with ten bed volumes of buffer NB (200 mM NaCl; 40 mM Tris-HCl, pH 7.0; 2 mM $MgCl_2$; 5% glycerol; 0.05% triton X-100, 15 mM imidazole) for 10 minutes at 4° C. Bound proteins were eluted with three bed volumes of buffer NE (200 mM NaCl; 40 mM Tris-HCl, pH 7.0; 2 mM MgCl$_2$; 5% glycerol; 0.05% triton X-100, 250 mM imidazole), and equal amount of 80% glycerol was added to eluted proteins. The proteins were stored at −20° C.

5.1.2 Results 5.1.2.1 Identification of Subunits of the Pre-tRNA Human Endonuclease Complex.

Figure 6:
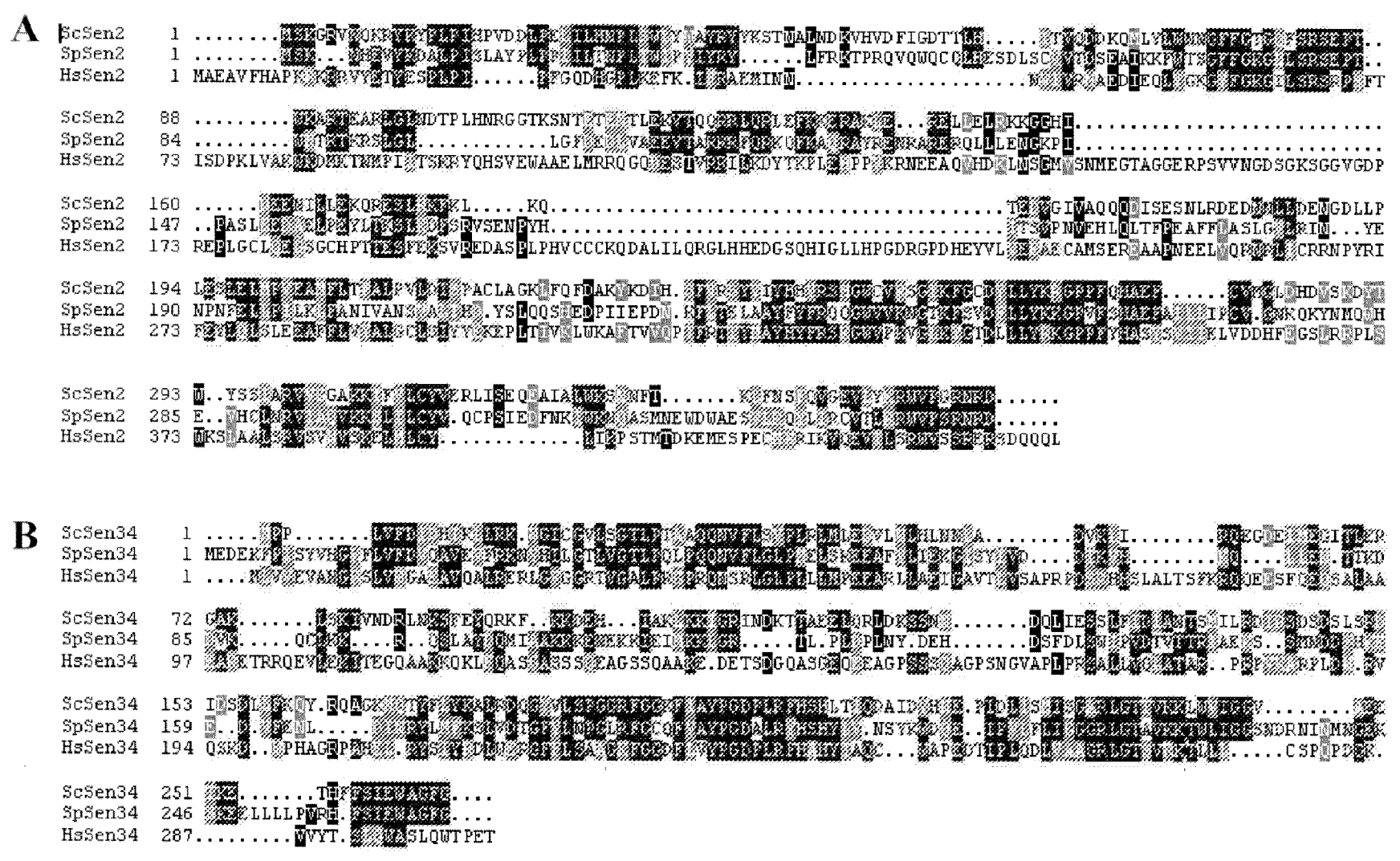
Figure 7:
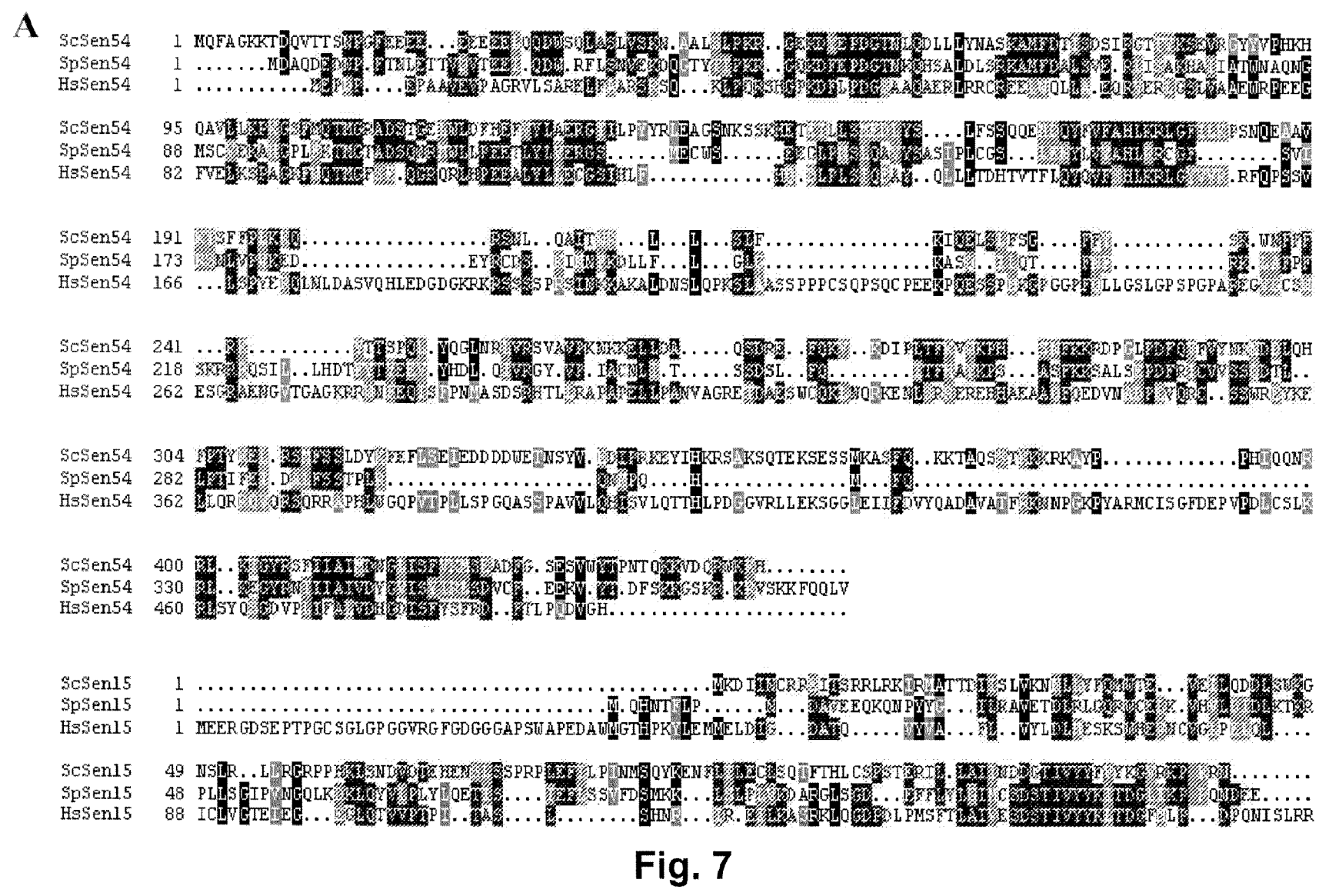

Yeast Sen2, Sen54 and Sen34 were blasted against the human protein database. Alignments of the amino acid sequences of the respective proteins are shown in FIG. 5, FIG. 6, and FIG. 7. To identify new components of the human tRNA splicing complex, stable cell lines expressing human His-Flag-Sen2 and His-Flag-Sen34 fusion proteins were generated as described above. Polypeptides that co-purify with His-Flag-Sen2 and His-Flag-Sen34 were isolated and identified by gel electrophoresis. Extracts from untransfected 293T cells were used as a negative control. As shown in FIG. 9, two new proteins were found to be co-purifed with His-Flag-Sen2 and His-Flag-Sen34. These were Sen15 and Clp1. To confirm that Sen15 and Clp1 are the subunits of the endonuclease complex, stable cell lines expressing His-Flag-Sen15 and His-Flag-Clp1 proteins were generated as described above. Proteins co-purified with His-Flag-Sen15 and His-Flag-Clp1 were analyzed by SDS-PAGE followed by a silver staining. As shown in FIG. 9, components of the endonuclease complex, Sen2, Sen34, and Sen54 were co-purified with His-Flag-Sen15 and His-Flag-Clp1, demonstrating that Cpll and Sen15 are the subunits of the human endonuclease complex.

5.1.2.2 Proteins Co-Purifying with Sen2, Sen34, Sen15 and Clp1 have Pre-tRNA Splicing Endonuclease Activity The endonuclease complex was purified from stable cell lines expressing His-Flag-Sen2 or His-Flag-Sen34 as described supra. Yeast endonuclease was used as a positive control for endonuclease activity (Trotta et al., 1997, Cell 89, 849-858). Cell extract fractions that co-purify with His-Flag-Sen2 and His-Flag-Sen34 show endonuclease activity, as demonstrated by cleavage of labeled phenylalanine pre-tRNA at intron/exon borders (FIG. 10). The generation of pre-tRNA substrate was performed according to Trotta et al., 1997, Cell 89, 849-859. Similarly, fractions that co-purify with His-Flag-Sen15 and His-Flag-Clp1 also show endonuclease activity and pre-tRNA cleavage (FIG. 10), demonstrating that Sen2, Sen34, Sen54, Sen15 and Clp1 are components of the pre-tRNA splicing endonuclease complex.

5.1.2.3 Human tRNA Splicing Endonuclease Subunits are Localized in the Nucleus

The open reading frame of Sen2 was generated by PCR amplification using specific primers (cgggatccgcagaagcagttttccatgccccaaagagg (SEQ ID NO:21), agaatagcggccgct-taaagatcgtcttggtcactcc (SEQ ID NO:31)) and was cloned into the myc-pcDNA3 vector to create myc-Sen2 vector. The open reading frame of Sen34 was generated by PCR amplification using primers specific for Sen34 (cgggatccctggtggtggaggtg-gcgaacggccgctcc (SEQ ID NO:23), gctctagatgcaggctggc-ccattgcagggaggtgtag (SEQ ID NO:24)) and was cloned into the GFP-pcDNA3 vector to create GFP-Sen34 vector. To examine the cellular distribution of tRNA splicing endonuclease components, myc-Sen2 and GFP-Sen34 vectors were transiently trasfected into Hela cells and immunofluorecence was performed as described previously (Choi and Dreyfuss, 1984, J. Cell. Biol. 99, 1997-2004). It was found that both myc-Sen2p and GFP-Sen34p localize to the nucleus (FIG. 11). This nuclear localization demonstrates that pre-tRNA splicing takes place in the nucleus.

5.1.2.4 Sen2 Splice Variant is Expressed in Different Tissues and Cell Lines.

It was found that human Sen2 is spliced into two different variants (FIG. 12). The first splice form, Sen2WT, contains all 13 exons of the Sen2 gene. The second splice form contains an alternate splicing of Exon 7 to Exon 9, bypassing Exon 8, to form the novel splice variant Sen2ΔEx8. In order to determine the presence of alternatively spliced variant of Sen2 in different tissues, cDNA libraries obtained from different tissues (Clontech) are examined by PCR using the primers located outside of exon 8: (gagtacgtgctggtcgaggaagcg (SEQ ID NO:32), gagtcccactttgggctcccagcc (SEQ ID NO:33)). As shown in FIG. 13, all examined tissues contain both, Sen2WT and Sen2ΔEx8 variant. To further determine a profile of Sen2ΔEx8 expression over a range of human tissues and cancer cell lines, "BD MTE Human Multiple Tissue Expression Array" (BD, Clontech) was hybridized with an oligonucleotide specific for Exon 8 of Sen2 (gctctgggatgtttaagtatt-tac (SEQ ID NO:34)). Hybridazation procedure was carried out according to the manufacture's instruction (BD, Clontech, user manual PT3307-1)

5.1.2.5 Fidelity and Accuracy of Pre-tRNA Cleavage Activity of Complexes Containing Sen2ΔEx8 is Compromised A purified complex from a stable cell line expressing His-Flag-Sen2ΔEx8 was obtained as described, e.g., in section 5.1.1.2. Extracts from untransfected 293T cells were used as a negative control, whereas 293T cells stably expressing His-Flag-Sen2 or His-Flag-Sen34 were used as a positive control. Yeast endonuclease was used as additional positive control for endonuclease activity (Trotta et al., 1997, Cell 89:849-858). The generation of pre-tRNA substrate was performed according to Trotta et al., 1997, Cell 89:849-859. Cell extract fractions that co-purify with His-Flag-Sen2ΔEx8 show reduced endonuclease activity compared to fractions that co-purify with His-Flag-Sen2 or His-Flag-Sen34 (FIG. 15), demonstrating that the fidelity and accuracy of pre-tRNA cleavage activity complex containing Sen2ΔEx8 is compromised. Fractions co-purifying with His-Flag-Sen2ΔEx8 contain reduced levels of Sen34 and Sen15 proteins compared with levels of Sen34 and Sen15 proteins in fractions that co-purify with His-Flag-Sen2 or His-Flag-Sen34 (FIG. 14), demonstrating that His-Flag-Sen2ΔEx8 has decreased ability to bind Sen15 and Sen34.

5.1.2.6 The Endonuclease Complexes are Associated with 3' End Pre-mRNA Processing Machinery.

Complexes from stable cell lines expressing His-Flag-Sen2, His-Flag-Sen2ΔEx8, His-Flag-Sen34, His-Flag-Clp1, His-Flag-Sen15 were purified as described above (see, e.g., section 5.1.1.2). Proteins co-purified with His-Flag-Sen2, His-Flag-Sen2ΔEx8, His-Flag-Sen34, His-Flag-Clp1, His-Flag-Sen15 were analyzed by SDS-PAGE followed by a Western blotting with antibodies against components of 3' end pre-mRNA processing complex, such as CPSF30, Symplekin, CstF64. Y12 antibody that recognizes pre-mRNA splicing SmB/B' proteins was used a a negative control. As shown in FIG. 17 all the examined components of 3' end processing complex are associated with pre-tRNA endonuclease complexes. His-Flag-Sen2ΔEx8 is strongly associated with CPSF30, Symplekin, CstF64 suggsting that Flag-Sen2ΔEx8 is largely involved in pre-mRNA processing, whereas His-Flag-Sen2WT is weakly associated with 3' end processing factors indicating that the wild type of Sen2 is mostly involved in pre-tRNA splicing.

5.2 Link Between Human tRNA Splicing and pre-mRNA 3'-End Formation

5.2.1 Materials and Methods

5.2.1.1 Generation of Stable Cell Lines Expressing His-Flag-Tagged tRNA Splicing Endonuclease Complex Subunits The open reading frames of HsSen2, HsSen2deltaEx8 and HsSen34 were modified by the addition of a sequence encoding an amino-terminal peptide tag consisting of eight histidine residues and the Flag epitope. 293 cells were transfected with a plasmid encoding His-Flag-HsSen2, His-Flag-HsSen2deltaEx8 or His-Flag-HsSen34. Clones expressing the protein were selected by hygromycin-resistance.

Human tRNA splicing endonuclease complex subunits include the proteins HsSen2 (accession number NP_079541; FIG. 20 (SEQ ID NO: 2)), HsSen34 (ACCESSION NO.:NP_076980; FIG. 23 (SEQ ID NO: 6)), HsSen54 (ACCESSION NO.:XP_208944; FIG. 24 (SEQ ID NO: 8)), HsSen15 (ACCESSION NO.:NP_443197; FIG. 22 (SEQ ID NO: 4), and HsClp1 (accession number NP_006822; FIG. 25 (SEQ ID NO: 10)). The open reading frames of HsSen2, HsSen2deltaEx8, HsSen34, HsSen54, HsSen15, and HsClp1 were generated by PCR amplification using specific primers and cloned into His-Flag-pcDNA3.1/Hygro vector. 293 cells were transfected with His-Flag-pcDNA3.1/Hygro plasmid containing the various tRNA splicing endonuclease complex subunit cDNAs in frame with the histidine and flag epitopes, and stable clones were selected by hygromycin-resistance.

5.2.1.2 Purification of the Human Endonuclease Complex from Total Cell Extract Containing His-Flag-Tagged Complex Subunits Total cell extracts were prepared by resuspending cell pellets in buffer B (250 mM NaCl; 30 mM Tris-HCl, pH 7.0; 1 mM EDTA; 5% glycerol; 0.1% Triton X-100; protease inhibitors (Roche, Complete Protease Inhibitor Cocktail Tablets)). Cells were sonicated 3 times for 10 seconds, followed by centrifugation at 15,000 g for 15 minutes. Supernatants were passed through a 0.2 micrometer filter and added to anti-Flag beads (Sigma) pre-washed with buffer B. Extracts were incubated with anti-Flag beads for 2 hours at 4° C. Supernatants were discarded and beads were washed 3 times for 10 minutes at 4° C. with ten bed volumes of buffer W (400 mM NaCl; 30 mM Tris-HCl, pH 7.0; 1 mM EDTA; 5% glycerol; 0.04% Triton X-100). Following two washes with ten bed volumes of buffer N (200 mM NaCl; 40 mM Tris-HCl, pH 7.0; 2 mM MgCl$_2$; 5% glycerol; 0.05% Triton X-100), bound proteins were eluted with three bed volumes of buffer N containing 0.25 mg/ml 3×Flag peptide (Sigma) for 1 h at 4° C. Following addition of NaCl (final concentration of 480 mM), eluted proteins were added to Ni-beads pre-washed with buffer NBW (500 mM NaCl; 40 mM Tris-HCl, pH 7.0; 2 mM MgCl$_2$; 5% glycerol; 0.05% triton X-100) and incubated for 1 hour at 4° C. Supernatants were discarded and Ni-beads were washed three times with ten bed volumes of buffer NB (200 mM NaCl; 40 mM Tris-HCl, pH 7.0; 2 mM MgCl$_2$; 5% glycerol; 0.05% Triton X-100, 15 mM imidazole) for 10 minutes at 4° C. Bound proteins were eluted with three bed volumes of buffer NE (200 mM NaCl; 40 mM Tris-HCl, pH 7.0; 2 mM MgCl$_2$; 5% glycerol; 0.05% Triton X-100, 250 mM imidazole), and equal amount of 80% glycerol was added to eluted proteins. The purified proteins were stored at −20° C.

5.2.1.3 Immunofluorescence Microscopy

HeLa cells were grown on glass coverslips, then were briefly washed with PBS, fixed in 2% formaldehyde/PBS for 20 minutes at room temperature and permeabilized in 0.5% Triton X-100/PBS for 5 minutes at room temperature. Fixed cells were blocked in 3% bovine serum albumin for 1 hour at room temperature. Immunofluorescence staining was performed by incubating with anti-myc antibody diluted in PBS containing 3% bovine serum albumin, followed by the specific secondary antibody coupled to fluorescein isothiocyanate. All incubations were carried out at room temperature. Images were obtained using a Zeiss Axiovert 200 epi-fluorescence microscope and captured using IPLab for windows v3.6 software.

5.2.1.4 Mammalian Cell Culture, Antibodies

HeLa and 293 cells were cultured in Dulbecco's modified Eagle's medium supplemented with 10% fetal bovine serum (Invitrogen).

Antibodies used in these experiments were as follows: anti—CstF64 (kindly provided by Dr. Wilusz), anti-myc (9E10) (BD-Pharmigen), anti-Symplekin (BD-Pharmigen), Y12 (Abcam), anti-Flag (Sigma), and anti-beta-actin (Oncogene).

5.2.1.5 Analysis of Expression Profile of HsSen2deltaEx8

In order to determine the presence of the alternatively spliced form of HsSen2 in different tissues, cDNA libraries obtained from different tissues (Clontech) were examined by PCR using the primers located outside of exon 8: (5'-gagtacgtgctggtcgaggaagcg-3' (SEQ ID NO:35), 5'-gagtcccactttgggctcccagcc-3' (SEQ ID NO:36). To determine a profile of HsSen2deltaEx8 expression over a range of human tissues and cancer cell lines, "BD MTE Human Multiple Tissue Expression Array" (BD, Clontech) was hybridized with an oligonucleotide specific for Exon 8 of HsSen2 (5'-gctctgggatgtttaagtatttac-3' (SEQ ID NO:37). Hybridization was carried out according to the manufacturers' instruction (BD, Clontech).

5.2.1.6 Endonuclease Assay

Yeast endonuclease was used as a positive control for endonuclease activity. Purification of *S. cerevisiae* endonuclease was performed according to Trotta et al., 1997. RNA products were extracted with phenol/chloroform, separated on a 12% polyacrylamide gel containing 8M urea, dried and exposed to film.

5.2.1.7 Protein Sequencing

Bands of interest were excised from 10-14.5% SDS-PAGE gradient gel and submitted to the protein sequencing facility at the City of Hope (Duarte, Calif.) for in-gel trypsin digestion, followed by peptide sequencing according to facility protocols.

5.2.1.8 Depletion of HsSen2 with Small Interfering RNAs (siRNA), Quantitative RT-PCR Analysis and Ribonuclease Protection Assays (RPA).

Two 19-base oligonucleotides (sense and antisense) corresponding to either exon 8 (siRNA-A) or exon 9 (siRNA-B) of the open reading frame of SEN2 were designed using "siRNA Design Guidelines" (Ambion). The oligonucleotides were annealed and cloned into the pSilencer 2.0-U6 vector (Ambion). 293 cells were transfected using Fugene 6 (Roche) with this vector encoding either the SEN2 specific sequence (siRNA-A or siRNA-B) or an irregular control sequence (Ambion). Five separate transfections were carried out for each siRNA species. Pools of stably expressing cell lines (designated A1-5 or B1-5) were selected using 200 microgram/ml hygromycin for thirty days followed by passage into 6-well dishes for either: (a) transfection of His-Flag-HsSen2 or His-Flag-HsSen2deltaEx8 followed in 3 days by addition of 2×SDS load-dye, fractionation by SDS-PAGE, and western blot detection using anti-Flag Ab (Sigma; 1:500) or anti-actin Ab (Oncogene; 1:2000); or (b) extraction of total RNA using Trizol (Sigma) according to the manufacturers' protocol. Total RNA was used for quantitative RT-PCR analysis.

RNA (5-10 micrograms) was treated with DnaseI followed by reverse transcription performed using a RETROscript kit (Ambion). Quantative PCR was carried out using a DNA Engine Opticon 2 (MJ Research) with the following oligonucleotides: precursor tRNA$^{Leu}$ (5'-gtcaggatggccgagtggtc-3' (SEQ ID NO:13); 5'-ccgaacacaggaagcagtaa-3' (SEQ ID NO:14)); tRNA$^{Leu}$ (5'-cggtacttataagacagtgc-3' (SEQ ID NO:15), 5'-gctccaggtgaggcttgaac-3' (SEQ ID NO:16)), 3' UTR of GAPDH (5'-ccagcaagagcacaagag-3' (SEQ ID NO:17); 5'-tgaggaggggagattcagt-3' (SEQ ID NO:18)); sequence downstream of the AAUAAA cleavage and polyadenylation signal of GAPDH (5'-caggtggaggaagtcagg-3' (SEQ ID NO:19); 5'-ctaaccagtcagcgtcagag3'-(SEQ ID NO:20)). Quantitation was based on normalization to 18s rRNA Amplicon.

Ten micrograms of total RNA from above was utilized in an RPA assay using RPA III kit (Ambion) as per manufacturers' protocol. Antisense riboprobe was derived from +1 to +204 downstream of the AAUAAA cleavage and polyadenylation site of the GAPDH genomic DNA sequence and +4 to +247 of EFla genomic DNA sequences. Hybridization temperature for EFTA was 44° C. and for GAPDH was 42° C.

5.2.2 Results 5.2.2.1 Human Homologs of the Yeast tRNA Splicing Endonuclease Subunits To identify human homologs of the tRNA splicing endonuclease subunits, a BLAST search of the human protein database was performed using protein sequences of all four subunits of the *S. cerevisiae* tRNA splicing endonuclease. Human homologs for three subunits, SEN54, SEN2 and SEN34 (FIGS. 7A, 6A and B) were identified, but a human homolog of yeast SEN15 was not able to be identified. Human Sen54 (HsSen54) has a predicted molecular mass of 58 kDa and amino acid conservation between the yeast and human Sen54p was restricted to the amino- and carboxyl-terminal regions of the protein (FIG. 7A). Human Sen2 (HsSen2) is predicted to be 51 kDa, larger than its yeast counterpart, and shows a high degree of similarity only in the active-site domain (FIG. 6A). Conversely, the yeast and human Sen34 (FIG. 6B) are highly homologous throughout the entire protein. Importantly, sequence alignments between yeast and human Sen2 and Sen34, the two subunits harboring the endonuclease active sites (Trotta et al., 1997), demonstrate the highest degree of similarity in the region corresponding to the active sites of Sen2 and Sen34. These findings indicate a remarkable conservation between the yeast and human tRNA splicing endonuclease active-site subunits.

5.2.2.2 The Human Sen2 Transcript is Alternatively Spliced to Form at Least Two Distinct Protein Products To demonstrate that the putative human SEN2 and SEN34 genes encode subunits of the tRNA splicing endonuclease complex the human SEN2 and SEN34 cDNAs were isolated. Surprisingly, sequencing of SEN2 clones produced by PCR amplification from human cDNA libraries identified a variant that lacked 57 nucleotides. This deletion corresponds precisely to exon 8 of the SEN2 genomic DNA sequence (FIG. 12), demonstrating that this was an alternatively spliced form of SEN2.

PCR analysis of cDNA libraries obtained from different human tissues using oligonucleotides flanking exon 8 and monitored the presence of either full-length SEN2 or SEN2 lacking exon 8 (HsSen2deltaEx8) was performed. All tissues examined harbored both isoforms of SEN2 (data not shown). Using a human multiple tissue expression array, we profiled the expression of HsSen2 and HsSen2deltaEx8 RNAs in human tissues and cancer cell lines. Northern blot analysis was performed with oligonucleotides specific for either SEN2 or SEN2deltaEx8. The results demonstrated that both mRNAs are ubiquitously expressed at very low levels in all tissue types (data not shown).

5.2.2.3 The Human Endonuclease Forms Two Functionally Distinct Isoforms

To determine whether the human homologs of the yeast endonuclease subunits function as part of a tRNA splicing complex, a method was developed for the purification of the endonuclease complex from human cells (see Experimental Procedures). A stable 293 cell lines expressing His-Flag-tagged human homologs of the active-site subunits, HsSen2 or HsSen34, as well as the alternatively spliced subunit, HsSendeltaEx8 was generated. Proteins from total cell extracts of the stable cell lines were purified by affinity chromatography using anti-FLAG M2 affinity resin followed by Ni-NTA agarose resin. Bound proteins were eluted with imidazole and tested for ability to cleave yeast pre-tRNA$^{Phe}$. The results demonstrated that protein complexes isolated from cells expressing either His-Flag-HsSen2 or His-Flag-HsSen34 accurately cleaved pre-tRNA$^{Phe}$ to yield 5' exon, 3' exon and intron (FIG. 15, lanes 4 and 5). The efficiency of cleavage was similar to that of yeast tRNA splicing endonuclease (FIG. 15, compare lane 4 and 5 with lane 2). Purification of cleavage activity was dependent upon expression of an epitope-tagged subunit, as proteins purified from untransfected 293 cells did not cleave pre-tRNA (FIG. 15, lane 1). Taken together, these results clearly demonstrate that HsSen2 and HsSen34 are orthologs of the yeast tRNA splicing endonuclease subunits and that the enzyme for cleavage of pre-tRNA is evolutionarily conserved.

The endonuclease complex harboring the His-Flag-HsSen2deltaEx8 subunit was also purified from human cells as described above. Surprisingly, the His-Flag-HsSen2deltaEx8-containing complex retained the ability to cleave precursor tRNA, but the fidelity and accuracy of cleavage was severely compromised resulting in cleavage at only the 3' splice site. Moreover, the HsSen2deltaEx8-containing complex was unable to release the intron from the pre-tRNA (FIG. 15, lane 3). In addition, there was a minor cleavage event within the intron of tRNA$^{Phe}$ resulting in two products migrating at approximately 53 and 42 nucleotide position (FIG. 15, lane 3, asterisks). This minor cleavage product is not detected with other precursor tRNAs (data not shown). Thus, pre-tRNA is the endogenous substrate for the HsSen2-containing complex, but not for the HsSen2deltaEx8-containing complex. This important observation suggests that the gene for the human endonuclease subunit SEN2 can encode two distinct active-site-containing proteins, each with different RNA cleavage specificities.

5.2.2.4 Localization of the Human Trna Splicing Endonuclease Subunits

The subcellular localization of the human tRNA splicing endonuclease subunits was determined by microscopy. Constructs encoding various epitope-tagged subunits of the human endonuclease were transiently transfected into HeLa cells and analyzed by immunofluorescence. The results demonstrated that both active-site subunits, HsSen2 and HsSen34, as well as HsSen2deltaEx8, were exclusively localized in the nucleus (FIG. 26). Interestingly, both HsSen2deltaEx8 and HsSen34 were frequently found in nucleoli in dot-like structures (FIG. 26, arrowheads).

5.2.2.5 Identification of the Components of the Human Endonuclease Complexes

The results described above identified two endonuclease complexes with distinct RNA substrate specificities. To demonstrate that these complexes may also have distinct subunits with different functions the composition of both endonuclease isoforms was analyzed by SDS-PAGE and silver staining This analysis identified an 18 kDa protein present in a similar stoichiometry to other components in HsSen2 and HsSen34 complexes (FIGS. 27A and 27B, band 1). The level of this protein was drastically reduced in HsSen2deltaEx8 purified complexes (FIG. 27B). Peptides derived from this band matched an 18 kDa protein encoded by a gene located on chromosome 1 (NP 443197). Amino acid sequence alignment to yeast Sen15 revealed a previously unobserved high degree of similarity to yeast Sen15p, strongly suggesting that the protein is a human homolog of yeast Sen15p (FIG. 7B).

To confirm that HsSenl5 is a subunit of the human tRNA splicing endonuclease, stable cell lines expressing epitope-tagged HsSenl5 were generated and purified complexes were tested for endonucleolytic activity as described above. As shown in FIG. 4D, the results demonstrated that the His-Flag-HsSenl5 complex accurately cleaved precursor-tRNA$^{Phe}$ releasing the intron and the 5' and 3' exons. The efficiency of cleavage was similar to that of endonuclease purified from His-Flag-HsSen2 and His-Flag-HsSen34 cell lines (FIG. 15), demonstrating that HsSenl5 is a component of human tRNA splicing endonuclease. Taken together, these results indicate that the human tRNA splicing endonuclease complex containing HsSen2 has a simple protein composition comprised of homologs to yeast tRNA splicing endonuclease.

Analysis of the protein composition of the three complexes, HsSen2, HsSen34 and HsSen2deltaEx8, revealed two proteins in common (FIGS. 27A and 27B). As determined by mass spectrometry, one of these proteins co-migrates with tagged HsSen2 and HsSen2deltaEx8 and represents the human homolog of the yeast Sen54 protein (FIG. 6A). The deletion of exon 8 did not effect the association of HsSen2deltaEx8 with the HsSen54 subunit (FIG. 27B). A protein complex purified via tagged HsSen54 (FIG. 27D) contains HsSen2, HsSen34 and HsSenl5 endonuclease subunits in stoichiometric amounts. The His-Flag-HsSen54 complex accurately cleaves pre-tRNA releasing intron and two exons. These results demonstrate that HsSen54 is an intrinsic subunit of the human tRNA splicing endonuclease.

In addition to the bands described above, it is evident from silver-stained gel in FIG. 27D, that there is an excess of protein found in band 2. This band, present in endonuclease complexes purified from all four tagged subunits (FIG. 27 panel A, B and D), was identified by mass spectrometry. The results identified this as the human Clp1 protein (HsClp1). This result was surprising since HsClp1 was originally isolated as a component of the cleavage factor II$_m$ (CF II$_m$) known to be involved in the cleavage of pre-mRNA in the cleavage/polyadenylation reaction (de Vries et al., 2000).

5.2.2.6 Endonuclease Complexes are Associated with Pre-mRNA 3'-End Processing Machinery Identification of a pre-mRNA cleavage/polyadenylation protein associated with the tRNA splicing endonuclease demonstrated that the endonuclease complex are involved in multiple RNA processing events. To show that HsClp 1 is a bona fide component of the human tRNA splicing endonuclease, proteins purified with His-Flag-HsClp1 were isolated and analyzed by SDS-PAGE and silver staining Remarkably, a protein pattern that was almost identical to that of complexes purified by the tagged versions of HsSen2, HsSen34 and HsSenl5 was observed (FIG. 28A). This result clearly demonstrates that HsClp1 is an integral component of the human tRNA splicing endonuclease complex.

The complex purified with tagged-HsClp1 for tRNA endonucleolytic activity was analyzed. As shown in FIG. 28B, the purified complex accurately cleaved precursor-tRNA$^{Phe}$ releasing the intron, and the 5' and 3' exons. The efficiency of cleavage was similar to that of complexes purified with His-FlagHsSen2 and His-Flag-HsSen34 (FIG. 15). Therefore, in addition to its role in pre-mRNA 3'-end formation, HsClp1 is associated with the human tRNA splicing endonuclease.

The results described above demonstrate that an endonuclease that forms distinct complexes with diverse RNA endonuclease activities had been identified. To identify the complexe(s) that are involved in mRNA 3'-end formation, the presence of additional components of pre-mRNA 3'-end processing machinery in the complexes was demonstrated. Complexes purified using the different epitope-tagged subunits of the endonuclease complexes were analyzed by Western blotting using antibodies specific for Symplekin and CstF64, components of the human pre-mRNA 3'-end processing complex. Y12 antibody (known to recognize pre-mRNA splicing snRNP SmB/B' proteins) was used as a negative control. Remarkably, the results (FIG. 29) demonstrate that all examined components of the pre-mRNA 3'-end processing complex were associated with pre-tRNA endonuclease complexes. Similar amounts of 3'-end complexes were purified from all His-Flag-tagged tRNA endonuclease subunits. Since the purification conditions were very stringent and utilized two affinity chromatography steps (see experimental procedures), the interaction between tRNA splicing endonuclease and pre-mRNA 3'-end processing factors is quite robust. Immunoprecipitation under standard salt conditions to more accurately determine the amount of 3'-end factors associated with the tRNA endonuclease was also performed. It was shown that as much as 1% of the 3'-end processing factors are associated with the tRNA endonuclease. Since endonuclease is a very low abundance protein, this suggests that a large portion of the tRNA splicing endonuclease is associated with pre-mRNA 3'-end formation complexes within human cells. Furthermore, His-Flag-HsSen2deltaEx8 and His-Flag-HsClp1 were able to associate with a larger proportion of the 3'-end formation complexes (FIG. 29, compare lane 8 and 11 to 7, 9, 10).

5.2.2.7 Depletion of Sen2 Causes Defects in tRNA Splicing and Pre-mRNA 3' End Formation The results described above demonstrate a biochemical link between tRNA splicing and pre-mRNA cleavage and polyadenylation. One theory is that if one of the endonuclease complexes were involved in mRNA 3' processing, then reduction in the amount of the endonuclease would result in defects in both pre-tRNA splicing and pre-mRNA 3'-end processing. To test this hypothesis the intracellular level of HsSen2 and HsSen2deltaEx8 were depleted by siRNA targeting. It was found that depletion of the SEN2 gene products by approximately 50% (FIG. 30A) caused an increase in the level of pre-tRNA$^{Leu}$ and pre-tRNA$^{Ile}$ in comparison to a control siRNA (FIG. 30B). This result is consistent with a role for HsSen2 in processing of pre-tRNA. Furthermore, using two independent methods, quantitative RT-PCR and ribonuclease protection (RPA), a dramatic increase in the level of GAPDH RNA containing extended sequence 3' of the cleavage and polyadenylation signal was observed (FIGS. 30B-C). In addition, a similar increase in the level of EFTA RNA containing 3'-extended sequence was observed (FIG. 30C, top panel). These results were observed with several siRNAs that targeted different regions of HsSen2/HsSen2deltaEx8, and thus are attributable to knockdown of the SEN2 gene products and not an off-target siRNA effect (FIG. 30; data not shown). Taken together, this is strong evidence that the active-site subunit HsSen2 or its spliced-variant HsSen2deltaEx8 are involved in processing of pre-tRNA and pre-mRNA, linking two fundamental processes of RNA maturation. Primers that were used in connection with the siRNA experiments are shown in FIG. 30D.

5.2.3 Discussion

All living organisms contain a population of precursor tRNAs which are interrupted by introns. Therefore, intron removal from pre-tRNAs (i.e. endonuclease cleavage) is a fundamental biological process. Although intron removal from pre-tRNA has been studied in detail in the yeast *Saccharomyces cerevisiae*, the machinery for human pre-tRNA intron removal was previously unknown. The results presented here define the components of the human tRNA endonuclease complex and raise the exciting possibility that the catalytic subunits of the tRNA endonuclease can function in distinct RNA processing events.

5.2.3.1 Identification of the Human tRNA Splicing Endonuclease Subunits

The protein composition, localization and function of the human tRNA splicing endonuclease has been determined as described herein. The enzyme was initially isolated using epitope-tagged human homologs of the two active-site subunits of yeast tRNA endonuclease. These purified complexes were demonstrated herein to accurately processed precursor tRNA, cleaving at the 5' and 3' splice sites to release the intron. This result strongly suggests that HsSen2 and HsSen34 are the orthologs of the active-site subunits of tRNA splicing endonuclease. The protein composition of the tRNA splicing endonuclease was also identified as described herein. The complex is comprised of orthologs of the yeast enzyme subunits, Sen2p, Sen34p, Sen15p, and Sen54p. An unanticipated result was the finding that HsClp1, a protein involved in pre-mRNA 3'-end processing, is also an integral member of the human tRNA endonuclease complex.

5.2.3.2 Model for the Human tRNA Splicing Endonuclease

A model of the architecture of yeast tRNA endonuclease was based on the structure of archaeal endonuclease from *M. jannaschii* (Li et al., 1998). The yeast enzyme was proposed to be a heterotetramer composed of two dimers, Sen54p-Sen2p and Sen34p-Sen15p, each containing a distinct active site. Tetramerization is thought to occur by interaction of the acidic residues within loop L10 of the Sen54p and Sen15p subunits, with a polar groove formed between the amino- and carboxyl-terminal domain of the active-site endonuclease subunits (Li et al., 1998). FIGS. 1C and 4C show that the most conserved regions of HsSen54 and HsSen15 are located in the carboxyl-terminal region of the proteins and correspond exactly to yeast loop L10 and beta 9 sequences.

5.2.3.3 Identification of an Alternatively Spliced Isoform of HsSen2

Our investigation of the human endonuclease complex resulted in the discovery of an alternatively spliced isoform of the SEN2 active-site subunit lacking exon 8. The amino acid sequence of exon 8 corresponds to a conserved alpha2-helix found in archaeal and yeast endonucleases (FIG. 6A) and is a key structural element in the formation of the tetrameric enzyme. The alpha2-helix serves to orient the amino- and carboxyl-terminal domains of the active-site subunit to allow formation of the polar groove into which the conserved loop L10 from a heterologous subunit can interact (FIG. 6A; Li et al., 1998; Bujnicki and Rychlewski, 2000; Lykke-Andersen and Garrett, 1997). Thus, one theory is that omission of this alpha2-helix in HsSen2deltaEx8 would alter the structure of this active-site subunit resulting in an inability to stably interact with loop L10 of the HsSen15/HsSen34 heterodimer. Consistent with this theory, analysis of the composition of the HsSen2deltaEx8 complex revealed a significant reduction in the level of HsSen15 and HsSen34 protein compared to the purified HsSen2 complex (FIG. 27B). This observation provides additional support for the structural model of the human and yeast tRNA splicing endonucleases.

Furthermore, these results raise the intriguing possibility that alteration of subunit interactions through alternative splicing is a strategy used by higher eukaryotes to generate multiple endonuclease complexes capable of different RNA processing events. This theory is supported by the result that HsSen2deltaEx8-containing endonuclease complex does not properly cleave pre-tRNAs, although it does retain endonucleolytic activity (FIG. 15, lane 3). Thus, it is likely that the HsSen2deltaEx8 complex is not a tRNA splicing endonuclease, but is responsible for processing as yet unknown RNA substrates.

5.2.3.4 Localization of the tRNA Splicing Endonuclease

In this study, it was shown that the active-site subunits HsSen2 and HsSen34 localize exclusively to the nucleus, consistent with previous results suggesting that tRNA maturation occurs in the nucleus in higher eukaryotes. For example, RNase P was shown to localize to the nucleoplasm with transient association in the nucleolus in HeLa cells (Jacobson et al., 1997). Additionally, human tRNA splicing endonuclease activity behaves a soluble nuclear protein in HeLa cells (Laski et al., 1983; Standring et al., 1981). Finally, in *Xenopus laevis*, intron-containing tRNAs are matured and modified in the nucleus and the endonuclease is a soluble protein found in the germinal vesicle of the oocyte (De Robertis and Olson, 1979; Otsuka et al., 1981; Mattoccia et al., 1979). In addition to the localization of the endonuclease subunits, a large portion of the tRNA splicing endonuclease is found associated with the nuclear-localized proteins of the mRNA 3'-end formation machinery. Taken together these data strongly support a model whereby tRNA splicing occurs in the nucleus of higher eukaryotes. This is consistent with the model for yeast tRNA splicing supported by localization of the endonuclease to the nuclear membrane fraction (Peebles et al., 1983; Rauhut et al., 1990) and immuno-localization of the yeast tRNA splicing ligase, which joins the 5' and 3' exons of tRNA after endonucleolytic cleavage, to the inner membrane of the nuclear envelope (Clark and Abelson, 1987).

Recently two pieces of evidence have emerged suggesting that tRNA splicing in yeast occurs in the cytoplasm. Yoshihisa and colleagues demonstrated that a fraction of tRNA endonuclease is found associated with the mitochondrial surface and that temperature-sensitive mutations of the tRNA splicing endonuclease accumulated intron-containing tRNA in the cytosol (Yoshihisa et al., 2003). Furthermore, analysis of a genome-wide GFP-fusion localization study indicated that GFP-tagged subunits of the endonuclease, ySen2, ySen54 and ySen15 localize exclusively to the mitochondria (Huh et al., 2003). In addition, a GFP-tagged fusion to tRNA splicing ligase localizes throughout the cytoplasm. Taken together, these observations are consistent with a model whereby tRNA splicing occurs within the cytoplasm in yeast. This model contrasts with the nuclear localization of the human enzyme that we have presented in this paper. Thus, it appears as though tRNA splicing localization may be regulated differently in yeast and humans. Consistent with our findings in HeLa cells we also found that GFP-tagged HsSen2 and HsSen34 localized to the nucleus in primary neurons (data not shown).

The active-site subunits can localize in dot-like structures within the nucleolus (FIG. 26, arrowheads). This suggests the possibility that the tRNA splicing endonuclease may be transiently localized in the nucleolus. In preliminary experiments, treatment of HeLa cells with Actinomycin D altered the localization of GFP-tagged HsSen2 or HsSen34 within the nucleus, leading to diffuse localization in both the nucleoplasm and the nucleolus (data not shown). This suggests that tRNA splicing endonuclease can cycle between the nucleoplasm and the nucleolus. This observation may have important implications for the regulation of the tRNA splicing in higher eukaryotes.

5.2.3.5 The Endonuclease Provides a Biochemical Link Between Trna Splicing and Pre-mRNA 3'-End Formation The demonstration of a role for HsClp1 in splicing of tRNA precursors is surprising and suggests a link between the processes of tRNA splicing and mRNA 3'-end formation. Keller and co-workers originally identified the HsClp1 protein as a component of CF II$_m$ known to be involved in 3'-end processing of pre-mRNA (de Vries et al., 2000). Generation of the 3' end of pre-mRNA is thought to be a two-step reaction, whereby pre-mRNA is endonucleolytically cleaved and subsequently polyadenylated to yield a mature mRNA. The pre-mRNA 3'-end processing complex consists of cleavage and polyadenylation specificity factor (CPSF), cleavage stimulation factor (CstF), two cleavage factors, CF I$_m$ and CF II$_m$, and poly(A) polymerase (PAP) (reviewed in Wahle and Ruegsegger, 1999; Calvo and Manley, 2003; Zhao et al., 1999a). HsClp1 has been shown to be a subunit of CF II$_m$ and is thought to act as a bridge, as it interacts with CF I$_m$ and CPSF (de Vries et al 2000). In yeast, Clp1 has also been shown to be involved in 3'-end processing (Minvielle-Sebastia and Keller, 1999).

Several pieces of evidence have been previously reported that are consistent with a link between tRNA processing and pre-mRNA 3'-end formation. O'Connor and Peebles demonstrated that yeast containing a conditional pta1 allele were defective in the processing of precursor tRNAs (O'Connor and Peebles, 1992). Subsequently, Pta1p was identified as a component of the yeast pre-mRNA 3'-end processing machinery (Preker et al., 1997; Zhao et al., 1999b). The human homolog of PTA1, symplekin, was found to be associated with cleavage stimulation factor (CstF) (Takagaki and Manley, 2000; Zhao et al., 1999b). Additionally, pre-tRNA 3'-end processing and pre-mRNA 3'-end formation have been genetically linked in humans. Takaku et al., have shown that ELAC2 is the enzyme responsible for 3'-end processing of precursor tRNA transcripts (Takaku et al., 2003; Zhao et al., 1999b; Takaku et al., 2003). Prior work showed that ELAC2 has a high degree of similarity with CPSF73, a protein belonging to the pre-mRNA cleavage and polyadenylation specificity factor (Simard et al., 2002; Tavtigian et al., 2001), suggesting that CPSF73 may be an endonuclease involved in pre-mRNA 3'-end processing. Thus, it is possible that the machinery (ie., endonuclease) for these disparate RNA processes, pre-tRNA splicing, pre-tRNA 3'-end maturation and pre-mRNA 3'-end formation, all arose from a common ancestor. This paradigm is supported by the notion that the tRNA splicing endonuclease is an ancient RNA processing enzyme (Belfort and Weiner, 1997; Trotta and Abelson, 1998).

This is the first demonstration of a biochemical link between pre-tRNA processing and pre-mRNA 3'-end processing. It has been shown herein that HsClp1 is a subunit of two distinct human endonuclease complexes: an HsSen2 tRNA splicing endonuclease complex and an endonuclease complex formed by the alternatively spliced form of SEN2, HsSen2deltaEx8. Remarkably, the tRNA endonuclease that co-purified with tagged-HsClp1 cleaves precursor tRNA specifically at the 5' and 3' splice sites to release the intron, suggesting that the HsClp1 protein is strongly associated with the machinery for cleavage of precursor tRNAs in human cells.

In addition, that the human endonuclease complexes was found to associate with a subset of 3'-end processing factors that include CPSF160, CPSF30, CstF64, symplekin, but not PAP and Sm proteins (FIG. 29 and data not shown). This specific set of protein components suggests that endonuclease complexes may be involved in the cleavage of pre-mRNA, as opposed to splicing or polyadenylation. Interestingly, the HsSen2deltaEx8 complex more strongly associated with Symplekin, and CstF64 than the HsSen2 complex. The significance of the tighter association between alternatively spliced SEN2 and pre-mRNA 3'-end processing is unknown, but the altered substrate specificity in cleavage reactions and the presence of pre-mRNA 3'-end processing factors in purified fractions suggest that HsSen2deltaEx8 may be primarily involved in processing of pre-mRNA. Consistent with this theory, siRNA depletion of the products of the SEN2 gene resulted in defects in 3'-end processing of endogenous mRNA transcripts, causing the accumulation of end-extended products, as detected by both quantitative RT-PCR and ribonuclease protection assays for several different mRNA transcripts (FIGS. 30A-C). As shown in FIG. 30, an attempt was made to distinguish the roles of wild-type Sen2 versus HsSen2deltaEx8 in processing pre-tRNA and pre-mRNA 3' ends by specifically targeting wild-type HsSen2 with siRNA-A, but for unknown reasons this siRNA caused the depletion of both versions of SEN2.

Taken together, the SEN2 siRNA targeting results and the evidence of a physical association between the two machineries described above, support a model whereby tRNA splicing and pre-mRNA 3'-end formation are catalyzed by the same components of an endonuclease complex in mammalian cells. This suggests that this endonuclease complex functions in the formation of mRNA, tRNA, and potentially other RNA substrates. The concept of coupling pre-tRNA splicing to the formation of the 3' end of mRNAs is interesting because it could allow cells to modulate the level of mature mRNA by sensing the amount of pre-tRNA that is produced in response to various growth conditions. This is the first example of regulating translation efficiency by a complex that controls multiple RNA processing activities in the cell.

REFERENCES

Abelson, J., Trona, C. R., and Li, H. (1998). tRNA splicing. J Biol Chem 273, 12685-12688.

Baldi, M. I., Mattoccia, E., Bufardeci, E., Fabbri, S., and Tocchini-Valentini, G. P. (1992). Participation of the intron in the reaction catalyzed by the *Xenopus* tRNA splicing endonuclease. Science 255, 1404-1408.

Baldi, M. I., Mattoccia, E., Clafre, S., Attardi, D. G., and Tocchini-Valentini, G. P. (1986). Binding and cleavage of pre-tRNA by the *Xenopus* splicing endonuclease: two separable steps of the intron excision reaction. Cell 47, 965-971.

Belfort, M., and Weiner, A. (1997). Another bridge between kingdoms: tRNA splicing in archaea and eukaryotes. Cell 89, 1003-1006.

Bujnicki, J. M., and Rychlewski, L. (2000). Prediction of a common fold for all four subunits of the yeast tRNA splicing endonuclease: implications for the evolution of the EndA/Sen family. FEBS Lett 486, 328-329.

Calvo, O., and Manley, J. L. (2003). Strange bedfellows: polyadenylation factors at the promoter. Genes Dev 17, 1321-1327.

Clark, M. W., and Abelson, J. (1987). The subnuclear localization of tRNA ligase in yeast. J Cell Biol 105, 1515-1526.

Culver, G. M., McCraith, S. M., Consaul, S. A., Stanford, D. R., and Phizicky, E. M. (1997). A 2'-phosphotransferase implicated in tRNA splicing is essential in *Saccharomyces cerevisiae*. J Biol Chem 272, 13203-13210.

De Robertis, E. M., and Olson, M. V. (1979). Transcription and processing of cloned yeast tyrosine tRNA genes microinjected into frog oocytes. Nature 278, 137-143.

de Vries, H., Ruegsegger, U., Hubner, W., Friedlein, A., Langen, H., and Keller, W. (2000). Human pre-mRNA cleavage factor II(m) contains homologs of yeast proteins and bridges two other cleavage factors. EMBO J. 19, 5895-5904.

Fabbri, S., Fruscoloni, P., Bufardeci, E., Di Nicola, N. E., Baldi, M. I., Attardi, D. G., Mattoccia, E., and Tocchini-Valentini, G. P. (1998). Conservation of substrate recognition mechanisms by tRNA splicing endonucleases. Science 280, 284-286.

Frank, D. N., and Pace, N. R. (1998). Ribonuclease P: unity and diversity in a tRNA processing ribozyme. Annu Rev Biochem 67, 153-180.

Gandini-Attardi, D., Baldi, I. M., Mattoccia, E., and Tocchini-Valentini, G. P. (1990). Transfer RNA splicing endonuclease from *Xenopus laevis*. Methods Enzymol 181, 510-517.

Ho, C. K., Rauhut, R., Vijayraghavan, U., and Abelson, J. (1990). Accumulation of pre-tRNA splicing '2/3' intermediates in a *Saccharomyces cerevisiae* mutant. EMBO J. 9, 1245-1252.

Hopper, A. K., and Phizicky, E. M. (2003). tRNA transfers to the limelight. Genes Dev 17, 162-180.

Hu, P., Wu, S., and Hernandez, N. (2003). A minimal RNA polymerase III transcription system from human cells reveals positive and negative regulatory roles for CK2. Mol Cell 12, 699-709.

Huh, W. K., Falvo, J. V., Gerke, L. C., Carroll, A. S., Howson, R. W., Weissman, J. S., and O'Shea, E. K. (2003). Global analysis of protein localization in budding yeast. Nature 425, 686-691.

Jacobson, M. R., Cao, L. G., Taneja, K., Singer, R. H., Wang, Y. L., and Pederson, T. (1997). Nuclear domains of the RNA subunit of RNase P. J Cell Sci 110 (Pt 7), 829-837.

Laski, F. A., Fire, A. Z., RajBhandary, U. L., and Sharp, P. A. (1983). Characterization of tRNA precursor splicing in mammalian extracts. J Biol Chem 258, 11974-11980.

Li, H., Trotta, C. R., and Abelson, J. (1998). Crystal structure and evolution of a transfer RNA splicing enzyme. Science 280, 279-284.

Lowe, T. M., and Eddy, S. R. (1997). tRNAscan-SE: a program for improved detection of transfer RNA genes in genomic sequence. Nucleic Acids Res 25, 955-964.

Lykke-Andersen, J., and Garrett, R. A. (1997). RNA-protein interactions of an archaeal homotetrameric splicing endoribonuclease with an exceptional evolutionary history. EMBO J. 16, 6290-6300.

Mattoccia, E., Baldi, M. I., Carrara, G., Fruscoloni, P., Benedetti, P., and Tocchini-Valentini, G. P. (1979). Separation of RNA transcription and processing activities from *X. laevis* germinal vesicles. Cell 18, 643-648.

Minvielle-Sebastia, L., and Keller, W. (1999). mRNA polyadenylation and its coupling to other RNA processing reactions and to transcription. Curr Opin Cell Biol 11, 352-357.

O'Connor, J. P., and Peebles, C. L. (1992). PTA1, an essential gene of *Saccharomyces cerevisiae* affecting pre-tRNA processing. Mol Cell Biol 12, 3843-3856.

Ogden, R. C., Lee, M. C., and Knapp, G. (1984). Transfer RNA splicing in *Saccharomyces cerevisiae*: defining the substrates. Nucleic Acids Res 12, 9367-9382.

Otsuka, A., De Paolis, A., and Tocchini-Valentini, G. P. (1981). Ribonuclease "XlaI," an activity from *Xenopus laevis* oocytes that excises intervening sequences from yeast transfer ribonucleic acid precursors. Mol Cell Biol 1, 269-280.

Peebles, C. L., Gegenheimer, P., and Abelson, J. (1983). Precise excision of intervening sequences from precursor tRNAs by a membrane-associated yeast endonuclease. Cell 32, 525-536.

Phizicky, E. M., Schwartz, R. C., and Abelson, J. (1986). *Saccharomyces cerevisiae* tRNA ligase. Purification of the protein and isolation of the structural gene. J Biol Chem 261, 2978-2986.

Preker, P. J., Ohnacker, M., Minvielle-Sebastia, L., and Keller, W. (1997). A multisubunit 3'-end processing factor from yeast containing poly(A) polymerase and homologues of the subunits of mammalian cleavage and polyadenylation specificity factor. EMBO J. 16, 4727-4737.

Rauhut, R., Green, P. R., and Abelson, J. (1990). Yeast tRNA-splicing endonuclease is a heterotrimeric enzyme. J Biol Chem 265, 18180-18184.

Sampson, J. R., and Saks, M. E. (1993). Contributions of discrete tRNA(Ser) domains to aminoacylation by *E. coli* seryl-tRNA synthetase: a kinetic analysis using model RNA substrates. Nucleic Acids Res 21, 4467-4475.

Simard, J., Dumont, M., Soucy, P., and Labrie, F. (2002). Perspective: prostate cancer susceptibility genes. Endocrinology 143, 2029-2040.

Standring, D. N., Venegas, A., and Rutter, W. J. (1981). Yeast tRNA3Leu gene transcribed and spliced in a HeLa cell extract. Proc Natl Acad Sci USA 78, 5963-5967.

Takagaki, Y., and Manley, J. L. (2000). Complex protein interactions within the human polyadenylation machinery identify a novel component. Mol Cell Biol 20, 1515-1525.

Takaku, H., Minagawa, A., Takagi, M., and Nashimoto, M. (2003). A candidate prostate cancer susceptibility gene encodes tRNA 3' processing endoribonuclease. Nucleic Acids Res 31, 2272-2278.

Tavtigian, S. V., Simard, J., Teng, D. H., Abtin, V., Baumgard, M., Beck, A., Camp, N. J., Carillo, A. R., Chen, Y., Dayananth, P., Desrochers, M., Dumont, M., Farnham, J. M., Frank, D., Frye, C., Ghaffari, S., Gupte, J. S., Hu, R., Iliev, D., Janecki, T., Kort, E. N., Laity, K. E., Leavitt, A., Leblanc, G., McArthur-Morrison, J., Pederson, A., Penn, B., Peterson, K. T., Reid, J. E., Richards, S., Schroeder, M., Smith, R., Snyder, S. C., Swedlund, B., Swensen, J., Thomas, A., Tranchant, M., Woodland, A. M., Labrie, F., Skolnick, M. H., Neuhausen, S., Rommens, J., and Cannon-Albright, L. A. (2001). A candidate prostate cancer susceptibility gene at chromosome 17p. Nat Genet. 27, 172-180.

Trotta, C. R. and Abelson, J. (1998). tRNA Splicing: An RNA world add-on or an ancient reaction? In RNA World II, R. F. Gesteland, T. R. Cech, and J. F. Atkins, eds. Cold Spring Harbor Laboratory Press), pp. 561-584.

Trotta, C. R., Miao, F., Arn, E. A., Stevens, S. W., Ho, C. K., Rauhut, R., and Abelson, J. N. (1997). The yeast tRNA splicing endonuclease: a tetrameric enzyme with two active site subunits homologous to the archaeal tRNA endonucleases. Cell 89, 849-858.

Wahle, E., and Ruegsegger, U. (1999). 3'-End processing of pre-mRNA in eukaryotes. FEMS Microbiol Rev 23, 277-295.

Wallace, A. M., Dass, B., Ravnik, S. E., Tonk, V., Jenkins, N. A., Gilbert, D. J., Copeland, N. G., and MacDonald, C. C. (1999). Two distinct forms of the 64,000 Mr protein of the cleavage stimulation factor are expressed in mouse male germ cells. Proc Natl Acad Sci U S A 96, 6763-6768.

Westaway, S. K., Phizicky, E. M., and Abelson, J. (1988). Structure and function of the yeast tRNA ligase gene. J Biol Chem 263, 3171-3176.

Xiao, S., Scott, F., Fierke, C. A., and Engelke, D. R. (2002). Eukaryotic ribonuclease P: a plurality of ribonucleoprotein enzymes. Annu Rev Biochem 71, 165-189.

Yoshihisa, T., Yunoki-Esaki, K., Ohshima, C., Tanaka, N., and Endo, T. (2003). Possibility of cytoplasmic pre-tRNA splicing: the yeast tRNA splicing endonuclease mainly localizes on the mitochondria. Mol Biol Cell 14, 3266-3279.

Zhao, J., Hyman, L., and Moore, C. (1999a). Formation of mRNA 3' ends in eukaryotes: mechanism, regulation, and interrelationships with other steps in mRNA synthesis. Microbiol. Mol Biol Rev 63, 405-445.

Zhao, J., Kessler, M., Helmling, S., O'Connor, J. P., and Moore, C. (1999b). Pta1, a component of yeast CF II, is required for both cleavage and poly(A) addition of mRNA precursor. Mol Cell Biol 19, 7733-7740.

EQUIVALENTS

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A purified complex, wherein the complex comprises:
   (i) a protein comprising the amino acid sequence of SEQ ID NO: 2 (Sen2);
   (ii) a protein comprising the amino acid sequence of SEQ ID NO: 4 (Sen15);
   (iii) a protein comprising the amino acid sequence of SEQ ID NO: 6 (Sen34); and
   (iv) a protein comprising the amino acid sequence of SEQ ID NO: 8 (Sen54).

2. The complex of claim 1, further comprising a protein comprising the amino acid sequence of SEQ ID NO: 10 (Clp1).

3. A purified complex having tRNA splicing endonuclease activity, wherein the complex comprises:
   (i) a protein comprising the amino acid sequence of SEQ ID NO: 2 (Sen2), or a fusion protein comprising SEQ ID NO: 2 (Sen2) and a heterologous amino acid sequence;
   (ii) a protein comprising the amino acid sequence of SEQ ID NO: 4 (Sen15), or a fusion protein comprising SEQ ID NO: 4 (Sen15) and a heterologous amino acid sequence;
   (iii) a protein comprising the amino acid sequence of SEQ ID NO: 6 (Sen34), or a fusion protein comprising SEQ ID NO:6 (Sen34) and a heterologous amino acid sequence; and
   (iv) a protein comprising the amino acid sequence of SEQ ID NO:8 (Sen54), or a fusion protein comprising SEQ ID NO:8 (Sen54) and a heterologous amino acid sequence.

4. The complex of claim 3, wherein the complex further comprises a protein comprising the amino acid sequence of SEQ ID NO: 10 (Clp1), or a fusion protein comprising SEQ ID NO: 10 (Clp1) and a heterologous amino acid sequence.

5. The complex of claim 3 which comprises a protein comprising the amino acid sequence of SEQ ID NO: 2 (Sen2).

6. The complex of claim 3 which comprises a protein comprising the amino acid sequence of SEQ ID NO: 4 (Sen15).

7. The complex of claim 3 which comprises a protein comprising the amino acid sequence of SEQ ID NO: 6 (Sen34).

8. The complex of claim 3 which comprises a protein comprising the amino acid sequence of SEQ ID NO:8 (Sen54).

9. The complex of claim 4 which comprises a protein comprising the amino acid sequence of SEQ ID NO: 10 (Clp1).

10. The complex of claim 3, wherein the complex comprises:
    (i) a fusion protein comprising SEQ ID NO: 2 (Sen2) and a heterologous amino acid sequence;
    (ii) a fusion protein comprising SEQ ID NO: 4 (Sen15) and a heterologous amino acid sequence;
    (iii) a fusion protein comprising SEQ ID NO:6 (Sen34) and a heterologous amino acid sequence; and
    (iv) a fusion protein comprising SEQ ID NO:8 (Sen54) and a heterologous amino acid sequence.

11. The complex of claim 10, wherein the complex further comprises a fusion protein comprising SEQ ID NO: 10 (Clp1), and a heterologous amino acid sequence.

12. A composition comprising the complex of claim 1 and a carrier.

13. A composition comprising the complex of claim 2 and a carrier.

14. A composition comprising the complex of claim 3 and a carrier.

15. A composition comprising the complex of claim 4 and a carrier.

* * * * *

SEQUENCE LISTING

```
<160> NUMBER OF SEQ ID NOS: 93

<210> SEQ ID NO 1
<211> LENGTH: 2373
<212> TYPE: DNA
<213> ORGANISM: Homo sapiens
<220> FEATURE:
<223> OTHER INFORMATION: HsSen2

<400> SEQUENCE: 1
gggcgaggaa agcgcggccc tttccgagtt tggtgttttg cagcgaaagg aaatctcgct      60
cttccgaaag tcctccaggg cgagagagga aagggcctag gtactgtgct ggggtcgcac     120
agccggccga gacagtgccg ggacggggag ccaggcttcc gagtgcgccc ggtcactgac     180
tcctccgcgc tttcctcgtg cgcctgcagc ccttggttct tggaaacgcc ggcgccttgt     240
tcagggctgg tggggctggg gcgcaaggtg cagctgacaa tgcccgagag gagccgcagc     300
ctctggtgga gttcggtcgg gtgtgggggt agtcaaggaa agaagcaaag ggaataccto     360 ctctgaaaaa tggcagaagc agttttccat gccccaaaga ggaaagaag agtgtatgag      420 acttacgagt ctccattgcc aatccctttt ggtcaggacc atggtcctct gaaagaattc     480
aagatattcc gtgctgaaat gattaacaac aatgtgattg tgaggaatgc ggaggacatt     540
gagcagctct atgggaaagg ttattttgga aaaggtattc tttcaagaag ccgtccaagc     600
ttcacaattt cagatcctaa actggttgct aaatggaaag atatgaagac aaacatgcct     660
atcatcacat caaagaggta tcagcatagt gttgagtggg cagcagagct gatgcgtaga     720
caggggcagg atgagagtac agtgcgcaga atcctcaagg attacacgaa accgcttgag     780
catcctcctg tgaaaaggaa tgaagaggct caagtgcatg acaagcttaa ctctggaatg     840
gtttccaaca tggaaggcac agcaggggga gagagacctt ctgtggtaaa cggggactct     900
ggaaagtcag gtggtgtggg tgatcccgt gagccattag gctgcctgca ggagggctct      960
ggctgccacc caacaacaga gagctttgag aaaagcgtgc gagaggatgc ctcacctctg    1020
ccccatgtct gttgctgcaa acaagatgct ctcatcctcc agcgtggcct tcatcatgaa    1080
gacggcagcc agcacatcgg cctcctgcat cctgggggaca gagggcctga ccatgagtac    1140
gtgctggtcg aggaagcgga gtgtgccatg agcgagaggg aggctgcccc aaatgaggaa    1200
ttggtgcaaa gaaacaggtt aatatgcaga agaaatccat ataggatctt tgagtatttg    1260
caactcagcc tagaagaggc cttttctctg gtctatgctc tgggatgttt aagtatttac    1320
```

```
tatgagaagg agcctttaac gatagtgaag ctctggaaag ctttcactgt agttcagccc   1380
acgttcagaa ccacctacat ggcctaccat tactttcgaa gcaagggctg ggtgcccaaa   1440
gtgggactca agtacgggac agatttactg ctatatcgga aaggccctcc attttaccat   1500
gcaagttatt ctgtcattat cgagctagtt gatgaccatt ttgaaggctc tctccgcagg   1560
cctctcagtt ggaagtccct ggctgccttg agcagagttt ccgttaatgt ctctaaggaa   1620
cttatgctgt gctatttgat taaaccctct actatgactg acaaggaaat ggagtcacca   1680
gaatgtatga aaaggattaa agttcaggag gtgattctga gtcgatgggt ttcttcacga   1740
gagaggagtg accaagacga tctttaacaa ttcaacctca aatttctaat ttcaccaaca   1800
actatttatt gagggctagg taaaaagttc tttttgttgt aatcgtccat taattcataa   1860
gttttaaagg gcatggtgct cccagcacca gaaaactatc agtgttttta aagataaatt   1920
acacaaggga ggagaaagat ccctgtgcta ggacaacaga ttctatactt gcgttggcct   1980
ctaactcccc catccagagc ctcctgcctc tggcgtcagt ttttttccctc atccactcac   2040 tggggagatt ggactagagg agtcctgaga ggacacttcc aacaagagac atttattctc   2100
tgatttaacc tgaaaatggt agtagtttac atttatacag tacagtttat gaagcacttt   2160
catacgcagg catctcttgt tacctacatc taagctgttc ccgaaagagt gttacagaac   2220
acaacagtat tgtacaatat tcgataagca tatcttcact gcacttgtta taaaaatgag   2280
tggtgaaata atgtttggag acataatgaa agcgattaac atttggcaaa atataataaa   2340 gccttttttgt aattggtgaa aaaaaaaaaa aaa                                2373
```

<210> SEQ ID NO 2
<211> LENGTH: 465
<212> TYPE: PRT
<213> ORGANISM: Homo sapiens
<220> FEATURE:
<223> OTHER INFORMATION: HsSen2

<400> SEQUENCE: 2

```
Met Ala Glu Ala Val Phe His Ala Pro Lys Arg Lys Arg Val Tyr
 1               5                  10                  15

Glu Thr Tyr Glu Ser Pro Leu Pro Ile Pro Phe Gly Gln Asp His Gly
                20                  25                  30

Pro Leu Lys Glu Phe Lys Ile Phe Arg Ala Glu Met Ile Asn Asn Asn
            35                  40                  45

Val Ile Val Arg Asn Ala Glu Asp Ile Glu Gln Leu Tyr Gly Lys Gly
        50                  55                  60

Tyr Phe Gly Lys Gly Ile Leu Ser Arg Ser Arg Pro Ser Phe Thr Ile
65                  70                  75                  80

Ser Asp Pro Lys Leu Val Ala Lys Trp Lys Asp Met Lys Thr Asn Met
                85                  90                  95

Pro Ile Ile Thr Ser Lys Arg Tyr Gln His Ser Val Glu Trp Ala Ala
            100                 105                 110

Glu Leu Met Arg Arg Gln Gly Gln Asp Glu Ser Thr Val Arg Arg Ile
        115                 120                 125

Leu Lys Asp Tyr Thr Lys Pro Leu Glu His Pro Val Lys Arg Asn
    130                 135                 140

Glu Glu Ala Gln Val His Asp Lys Leu Asn Ser Gly Met Val Ser Asn
145                 150                 155                 160

Met Glu Gly Thr Ala Gly Gly Glu Arg Pro Ser Val Val Asn Gly Asp
                165                 170                 175

Ser Gly Lys Ser Gly Gly Val Gly Asp Pro Arg Glu Pro Leu Gly Cys
```

```
                   180                 185                 190
Leu Gln Glu Gly Ser Gly Cys His Pro Thr Thr Glu Ser Phe Glu Lys
            195                 200                 205
Ser Val Arg Glu Asp Ala Ser Pro Leu Pro His Val Cys Cys Cys Lys
        210                 215                 220
Gln Asp Ala Leu Ile Leu Gln Arg Gly Leu His His Glu Asp Gly Ser
225                 230                 235                 240
Gln His Ile Gly Leu Leu His Pro Gly Asp Arg Gly Pro Asp His Glu
                245                 250                 255
Tyr Val Leu Val Glu Glu Ala Glu Cys Ala Met Ser Glu Arg Glu Ala
            260                 265                 270
Ala Pro Asn Glu Glu Leu Val Gln Arg Asn Arg Leu Ile Cys Arg Arg
        275                 280                 285
Asn Pro Tyr Arg Ile Phe Glu Tyr Leu Gln Leu Ser Leu Glu Glu Ala
290                 295                 300
Phe Phe Leu Val Tyr Ala Leu Gly Cys Leu Ser Ile Tyr Tyr Glu Lys
305                 310                 315                 320
Glu Pro Leu Thr Ile Val Lys Leu Trp Lys Ala Phe Thr Val Val Gln
                325                 330                 335
Pro Thr Phe Arg Thr Thr Tyr Met Ala Tyr His Tyr Phe Arg Ser Lys
            340                 345                 350
Gly Trp Val Pro Lys Val Gly Leu Lys Tyr Gly Thr Asp Leu Leu Leu
        355                 360                 365
Tyr Arg Lys Gly Pro Pro Phe Tyr His Ala Ser Tyr Ser Val Ile Ile
        370                 375                 380
Glu Leu Val Asp Asp His Phe Glu Gly Ser Leu Arg Arg Pro Leu Ser
385                 390                 395                 400
Trp Lys Ser Leu Ala Ala Leu Ser Arg Val Ser Val Asn Val Ser Lys
                405                 410                 415
Glu Leu Met Leu Cys Tyr Leu Ile Lys Pro Ser Thr Met Thr Asp Lys
            420                 425                 430
Glu Met Glu Ser Pro Glu Cys Met Lys Arg Ile Lys Val Gln Glu Val
        435                 440                 445
Ile Leu Ser Arg Trp Val Ser Ser Arg Glu Arg Ser Asp Gln Asp Asp
        450                 455                 460
Leu
465

<210> SEQ ID NO 3
<211> LENGTH: 1943
<212> TYPE: DNA
<213> ORGANISM: Homo sapiens
<220> FEATURE:
<223> OTHER INFORMATION: HsSen15

<400> SEQUENCE: 3
agcgtggggt gcgggtcgtg gtgcaccacg ggagcgccgc accggccggc atggaggagc      60
gcggcgattc cgagccgacc cccggctgca gcggcctggg tccgggcggt gttcgcggct     120
ttggcgacgg cggtggagct ccttcgtggg ccctgaggac gcctggatg ggcactcacc     180 ctaagtatct agaaatgatg gaattagata taggagatgc cacccaagtt tatgtagcgt     240
tcttggttta cctggacctc atggaaagca aaagctggca tgaagtaaac tgtgtaggat     300
taccagaact ccagctcatc tgccttgttg gtactgagat agaagggag gggttacaga     360 ctgtggtgcc taccccatc actgcttccc tcagccataa caggataagg gagatcttga     420
```

```
aggcatctcg aaagttgcaa ggtgatccag atttgccgat gtctttact ttggccatag    480 tggagtctga ttctacaata gtctattata aacttactga tggatttatg ctgccagacc    540
ctcagaatat ttctcttaga agatgacatc catgtttcct gatgcttgtt ttattcatac    600
aagattggat ttgagaccca tcagactgct tcatctttta tctcagaaat agggttgacg    660
tacatagtga gggttgactt ccccattcca taaggttttc attctgaaga gtaaaacttc    720
cccaggtaga agactttctc cttcttaaaa aatatagggt gatttcttta aaactttgtt    780
atctagagac agtttaatta cagttatata caggtttatg cctaggatgt attcagatgg    840
gtgggacctg tgtgctgctt ttgtcatccc acactcaaag ttgtctcttt gtttcttgct    900
gccactgcca gctcattgtt gagactgcca tttctttctc ttactcagct ctccccagtg    960 cctttggcc actgcagcta ccgtagaatg gcattttata tgtaccttgt cacccacttc   1020
tgtttacttt ttcctctcca gtaaaaagta aaagatttct ttcaattggt cttcccattg   1080
cagttactgt tatttctctt ttttggttaa ctttaaatca aaactcaaaa tatgttcatc   1140
cagagtgtgt cttaagtaac ttacgtgtct taagtaacag ggaccagaga catgttacct   1200
acaagagttc tgggctatcc ttttcattct tatcacatat catagcttga atattacaac   1260
agtgtgggag agaatcaacc gtaaaaatgt cttcattaat tagacccagt tattccactt   1320
ttgttaatgt ctctcaaatt gtacaaagta taaaaatta tatgcacaaa gatgttccaa   1380
gtgacattac ttttagtagc ccaaattata aaccacttta aagtttgggg taaagattgg   1440
caaacttttt ctataaaggg ccagaaagta actattttag gttttaaaac ctactgtctc   1500
tgtcataact tgtcaacact gctgtatgaa gcacaaaagc agccatagac aatacataaa   1560
caatacgggc gtggctttgt tccagtaaaa ctttgtttac aaatgtggtg ccatagtttg   1620
tcatccctgg gtctaggaaa tagtcaataa acagatatat acaaatgata cataatgtac   1680
ttattaaaaa ttagtaatga atattattaa aaacatgaaa atattacctt aagtaaaaat   1740
tgcaagacgg aaaagtgtat aagtgggtgt aatcatggct gaaataacag accaagcata   1800
tgataaaaag ataacaaagt aaatcaaatt actaactggt tatagtggga taggaggcag   1860
aaaatggatg actttgtctt ttctcaatgt ttttatttgt attttataat aaaaatgttt   1920
taaaattaaa aaaaaaaaaa aaa                                          1943
```

<210> SEQ ID NO 4
<211> LENGTH: 171
<212> TYPE: PRT
<213> ORGANISM: Homo sapiens
<220> FEATURE:
<223> OTHER INFORMATION: HsSen15

<400> SEQUENCE: 4

```
Met Glu Glu Arg Gly Asp Ser Glu Pro Thr Pro Gly Cys Ser Gly Leu
1               5                   10                  15

Gly Pro Gly Gly Val Arg Gly Phe Gly Asp Gly Gly Ala Pro Ser
            20                  25                  30

Trp Ala Pro Glu Asp Ala Trp Met Gly Thr His Pro Lys Tyr Leu Glu
        35                  40                  45

Met Met Glu Leu Asp Ile Gly Asp Ala Thr Gln Val Tyr Val Ala Phe
    50                  55                  60

Leu Val Tyr Leu Asp Leu Met Glu Ser Lys Ser Trp His Glu Val Asn
65                  70                  75                  80

Cys Val Gly Leu Pro Glu Leu Gln Leu Ile Cys Leu Val Gly Thr Glu
                85                  90                  95
```

-continued

Ile Glu Gly Glu Gly Leu Gln Thr Val Val Pro Thr Pro Ile Thr Ala
            100                 105                 110

Ser Leu Ser His Asn Arg Ile Arg Glu Ile Leu Lys Ala Ser Arg Lys
        115                 120                 125

Leu Gln Gly Asp Pro Asp Leu Pro Met Ser Phe Thr Leu Ala Ile Val
130                 135                 140

Glu Ser Asp Ser Thr Ile Val Tyr Tyr Lys Leu Thr Asp Gly Phe Met
145                 150                 155                 160

Leu Pro Asp Pro Gln Asn Ile Ser Leu Arg Arg
                165                 170

<210> SEQ ID NO 5
<211> LENGTH: 1364
<212> TYPE: DNA
<213> ORGANISM: Homo sapiens
<220> FEATURE:
<223> OTHER INFORMATION: HsSen34

<400> SEQUENCE: 5

| | | | | | | |
|---|---|---|---|---|---|---|
| cacctcgact | gcgaattact | gtttatgagg | tgactcgctg | gttctatcgg | tggacagtgg | 60 |
| gacattctga | agggaggcaa | ggaggcggac | tgagcgctcc | caattgggga | ggatgctggt | 120 |
| ggtggaggtg | gcgaacggcc | gctccctggt | gtggggagcc | gaggcggtgc | aggccctccg | 180 |
| ggagcgcctg | ggtgtggggg | gccgcacggt | aggcgccctg | ccccgcgggc | cccgccagaa | 240 |
| ctcgcgcctg | ggcctcccgc | tgctgctgat | gcccgaagag | gcgcggctct | tggccgagat | 300 |
| cggcgccgtg | actctggtca | gcgccccgcg | tccagactct | cggcaccaca | gcctggccct | 360 |
| gacatccttc | aagcgccagc | aagaggagag | cttccaggag | cagagcgcct | tggcagctga | 420 |
| ggcccgggag | acccgtcgtc | aggaggtcct | ggagaagatt | acggagggcc | aggctgctaa | 480 |
| gaagcagaaa | ctagaacagg | cttcaggggc | cagctcaagc | caggaggccg | gctcgagcca | 540 |
| ggctgccaaa | gaggatgaga | ccagtgatgg | ccaggcttcg | ggagagcagg | aggaagctgg | 600 |
| cccctcgtct | tcccaagcag | gaccctcaaa | tggggtagcc | cccttgccca | gatctgctct | 660 |
| ccttgtccag | ctggccactg | ccaggcctcg | accggtcaag | gccaggcccc | tggactggcg | 720 |
| tgtccagtct | aaagactggc | cccacgccgg | ccgccctgcc | cacgagctgc | gctacagtat | 780 |
| ctacagagac | ctgtgggagc | gaggcttctt | cctcagtgcg | gctggcaagt | tcggaggtga | 840 |
| cttcctggtc | tatcctggtg | accccctccg | cttccacgcc | cattatatcg | ctcagtgctg | 900 |
| ggcccctgag | gacacctccc | actccaagac | ctggttgctg | ctgggcgcct | tggaaccagc | 960 |
| gtcagaaaga | ccctgctcct | ctgttctccg | cagcctgatg | gtaaggtggt | ctacacctcc | 1020 |
| ctgcaatggg | ccagcctgca | gtgaactcca | gagacctagg | ggatgtggct | gtgtcggcag | 1080 |
| caagagcctt | tctggatgtt | ccccagctct | tctctgggag | tctagaacat | cctcctacct | 1140 |
| ttctccgcgg | ttagtttttg | attccaggtt | ttcgaacact | acatcttttt | tatgttcttc | 1200 |
| cttgtttcaa | agcacttatt | ggctgtgttt | ttgtagttac | ctattttcac | actgtgagct | 1260 |
| tcccagaaat | ggggcctggg | tttgattcat | ctgttttcta | cagggtttaa | gtctcaggag | 1320 |
| gtctcaataa | acttggtata | taaatgttaa | aaaaaaaaa | aaaa | | 1364 |

<210> SEQ ID NO 6
<211> LENGTH: 390
<212> TYPE: PRT
<213> ORGANISM: Homo sapiens
<220> FEATURE:
<223> OTHER INFORMATION: HsSen34

<400> SEQUENCE: 6

Met Leu Val Val Glu Val Ala Asn Gly Arg Ser Leu Val Trp Gly Ala
1               5                   10                  15

Glu Ala Val Gln Ala Leu Arg Glu Arg Leu Gly Val Gly Gly Arg Thr
            20                  25                  30

Val Gly Ala Leu Pro Arg Gly Pro Arg Gln Asn Ser Arg Leu Gly Leu
        35                  40                  45

Pro Leu Leu Leu Met Pro Glu Glu Ala Arg Leu Leu Ala Glu Ile Gly
    50                  55                  60

Ala Val Thr Leu Val Ser Ala Pro Arg Pro Asp Ser Arg His His Ser
65                  70                  75                  80

Leu Ala Leu Thr Ser Phe Lys Arg Gln Gln Glu Ser Phe Gln Glu
                85                  90                  95

Gln Ser Ala Leu Ala Ala Glu Ala Arg Glu Thr Arg Arg Gln Glu Val
                100                 105                 110

Leu Glu Lys Ile Thr Glu Gly Gln Ala Ala Lys Lys Gln Lys Leu Glu
            115                 120                 125

Gln Ala Ser Gly Ala Ser Ser Gln Glu Ala Gly Ser Ser Gln Ala
                130                 135                 140

Ala Lys Glu Asp Glu Thr Ser Asp Gly Gln Ala Ser Gly Glu Gln Glu
145                 150                 155                 160

Glu Ala Gly Pro Ser Ser Gln Ala Gly Pro Ser Asn Gly Val Ala
                165                 170                 175

Pro Leu Pro Arg Ser Ala Leu Leu Val Gln Leu Ala Thr Ala Arg Pro
            180                 185                 190

Arg Pro Val Lys Ala Arg Pro Leu Asp Trp Arg Val Gln Ser Lys Asp
        195                 200                 205

Trp Pro His Ala Gly Arg Pro Ala His Glu Leu Arg Tyr Ser Ile Tyr
    210                 215                 220

Arg Asp Leu Trp Glu Arg Gly Phe Phe Leu Ser Ala Ala Gly Lys Phe
225                 230                 235                 240

Gly Gly Asp Phe Leu Val Tyr Pro Gly Asp Pro Leu Arg Phe His Ala
                245                 250                 255

His Tyr Ile Ala Gln Cys Trp Ala Pro Glu Asp Thr Ser His Ser Lys
                260                 265                 270

Thr Trp Leu Leu Leu Gly Ala Leu Glu Pro Ala Ser Glu Arg Pro Cys
            275                 280                 285

Ser Ser Val Leu Arg Ser Leu Met Val Arg Trp Ser Thr Pro Pro Cys
        290                 295                 300

Asn Gly Pro Ala Cys Ser Glu Leu Gln Arg Pro Arg Gly Cys Gly Cys
305                 310                 315                 320

Val Gly Ser Lys Ser Leu Ser Gly Cys Ser Pro Ala Leu Leu Trp Glu
                325                 330                 335

Ser Arg Thr Ser Ser Tyr Leu Ser Pro Arg Leu Val Phe Asp Ser Arg
            340                 345                 350

Phe Ser Asn Thr Thr Ser Phe Leu Cys Ser Ser Leu Phe Gln Ser Thr
        355                 360                 365

Tyr Trp Leu Cys Phe Cys Ser Tyr Leu Phe Ser His Cys Glu Leu Pro
    370                 375                 380

Glu Asn Gly Ala Trp Val
385                 390

<210> SEQ ID NO 7
<211> LENGTH: 1932
<212> TYPE: DNA

-continued

<213> ORGANISM: Homo sapiens
<220> FEATURE:
<223> OTHER INFORMATION: HsSen54

<400> SEQUENCE: 7

| | | | | | | |
|---|---|---|---|---|---|---|
| gcggcgcgcg | cagcggcagg | cggcggcggg | atggagcccg | agcccgagcc | cgcggccgtg | 60 |
| gaggttcccg | cggggcgcgt | gctcagcgcc | cgggagctct | tcgccgcccg | ctcgcggtcg | 120 |
| cagaagctgc | cccagcgctc | gcatggcccc | aaggactttc | tgcccgacgg | ctcggcagct | 180 |
| caggccgagc | ggctgcgccg | gtgccgggaa | gagctctggc | agctgctggc | agagcagcgc | 240 |
| gtggagcgct | gggcagcttt | ggtggctgcc | gagtggaggc | cagaagaggg | cttcgtggag | 300 |
| ttgaagtctc | ccgcgggcaa | attctggcag | accatgggct | tctcagagca | gggccggcag | 360 |
| cgccttcacc | cggaagaggc | cttgtatctt | ctggagtgtg | gctccatcca | cctcttccac | 420 |
| caagacctgc | cactgtctat | ccaggaagct | taccagctgc | tgctgaccga | ccacactgtg | 480 |
| accttcctgc | agtaccaggt | cttcagccac | ctgaagaggt | tgggttatgt | ggttcgacga | 540 |
| ttccaaccaa | gctctgtcct | gtccccgtat | gagaggcagc | ttaacctgga | tgccagcgtg | 600 |
| cagcacttgg | aggatggaga | tgcaagagaa | aagaggagca | gctccagccc | tcggtccatt | 660 |
| aataagaagg | ccaaggccct | ggacaactcc | ctgcaaccca | agagtctggc | agcctccagc | 720 |
| ccacctccct | gcagccagcc | cagccaatgc | ccagaggaga | accccagga | gtcaagcccc | 780 |
| atgaagggcc | caggggggccc | cttttcagctt | ctggggtccc | tgggcccag | ccctggcccg | 840 |
| gccagggagg | gggtggggtg | cagctgggag | agtggcagag | ccgagaacgg | agtcacggga | 900 |
| gccggtaagc | ggcgctggaa | cttcgagcag | atctccttcc | ccaacatggc | ttcagacagc | 960 |
| cgccacaccc | ttctgcgcgc | cccagcccca | gagctgctcc | cggccaacgt | ggctgggcgg | 1020 |
| gagacagacg | ctgagtcctg | gtgccagaag | ctgaaccagc | gcaaggagaa | gctctccagg | 1080 |
| cgggaacggg | agcaccacgc | ggaggccgcg | cagttccagg | aagatgtcaa | cgccgatccc | 1140 |
| gaggtgcagc | ggtgctccag | ctggcgggag | tacaaggagc | tgctgcagcg | gcggcaggtg | 1200 |
| cagaggagcc | agcgccgggc | ccctcacctg | tggggccagc | ccgtcacccc | gctgctgagt | 1260 |
| cctggccagg | ccagctcccc | agccgtggtc | cttcagcata | tctctgtgct | gcagacaaca | 1320 |
| caccttcctg | atggaggtgc | ccggctgttg | gagaagtctg | ggggcttgga | aatcatcttt | 1380 |
| gatgtttacc | aggccgacgc | tgtggccaca | ttccgaaaga | ataaccctgg | caaaccctat | 1440 |
| gcccggatgt | gcattagtgg | atttgatgag | cctgtcccag | acctctgcag | cctcaagcgg | 1500 |
| ttgtcttacc | agagtgggga | tgtccctctg | atctttgccc | tggtggatca | tggtgacatc | 1560 |
| tccttctaca | gcttcaggga | cttcacgttg | ccccaggatg | tggggcactg | acctcacagc | 1620 |
| tctgcagagg | atggagcttg | ctccggggga | ccgggactgt | ctgttctcag | ggaccatctc | 1680 |
| ggctgcctcc | tgtacccaga | ctctaacctg | tagcttcaga | ggccagtctg | gccttggcc | 1740 |
| ctgggtgtct | gatactcaca | gagtgaaact | gtgaccctct | cccttccctg | ctgccttgca | 1800 |
| gtgacccctc | tggaactcag | gactcgattt | taaggaccca | ggaggtgggg | cagaagagag | 1860 |
| gactgtgtgc | ctttaacgag | agggtgcctg | cttcgtgcta | taaagccaaa | gccattaaaa | 1920 |
| atagatttct | tt | | | | | 1932 |

<210> SEQ ID NO 8
<211> LENGTH: 526
<212> TYPE: PRT
<213> ORGANISM: Homo sapiens
<220> FEATURE:
<223> OTHER INFORMATION: HsSen54

-continued

```
<400> SEQUENCE: 8

Met Glu Pro Glu Pro Glu Pro Ala Ala Val Glu Val Pro Ala Gly Arg
1               5                   10                  15

Val Leu Ser Ala Arg Glu Leu Phe Ala Ala Arg Ser Arg Ser Gln Lys
            20                  25                  30

Leu Pro Gln Arg Ser His Gly Pro Lys Asp Phe Leu Pro Asp Gly Ser
        35                  40                  45

Ala Ala Gln Ala Glu Arg Leu Arg Arg Cys Arg Glu Glu Leu Trp Gln
    50                  55                  60

Leu Leu Ala Glu Gln Arg Val Glu Arg Leu Gly Ser Leu Val Ala Ala
65                  70                  75                  80

Glu Trp Arg Pro Glu Glu Gly Phe Val Glu Leu Lys Ser Pro Ala Gly
                85                  90                  95

Lys Phe Trp Gln Thr Met Gly Phe Ser Glu Gln Gly Arg Gln Arg Leu
            100                 105                 110

His Pro Glu Glu Ala Leu Tyr Leu Leu Glu Cys Gly Ser Ile His Leu
        115                 120                 125

Phe His Gln Asp Leu Pro Leu Ser Ile Gln Glu Ala Tyr Gln Leu Leu
    130                 135                 140

Leu Thr Asp His Thr Val Thr Phe Leu Gln Tyr Gln Val Phe Ser His
145                 150                 155                 160

Leu Lys Arg Leu Gly Tyr Val Val Arg Arg Phe Gln Pro Ser Ser Val
                165                 170                 175

Leu Ser Pro Tyr Glu Arg Gln Leu Asn Leu Asp Ala Ser Val Gln His
            180                 185                 190

Leu Glu Asp Gly Asp Gly Lys Arg Lys Arg Ser Ser Ser Pro Arg
        195                 200                 205

Ser Ile Asn Lys Lys Ala Lys Ala Leu Asp Asn Ser Leu Gln Pro Lys
    210                 215                 220

Ser Leu Ala Ala Ser Ser Pro Pro Cys Ser Gln Pro Ser Gln Cys
225                 230                 235                 240

Pro Glu Glu Lys Pro Gln Glu Ser Ser Pro Met Lys Gly Pro Gly Gly
                245                 250                 255

Pro Phe Gln Leu Leu Gly Ser Leu Gly Pro Ser Pro Gly Pro Ala Arg
            260                 265                 270

Glu Gly Val Gly Cys Ser Trp Glu Ser Gly Arg Ala Glu Asn Gly Val
        275                 280                 285

Thr Gly Ala Gly Lys Arg Arg Trp Asn Phe Glu Gln Ile Ser Phe Pro
    290                 295                 300

Asn Met Ala Ser Asp Ser Arg His Thr Leu Leu Arg Ala Pro Ala Pro
305                 310                 315                 320

Glu Leu Leu Pro Ala Asn Val Ala Gly Arg Glu Thr Asp Ala Glu Ser
                325                 330                 335

Trp Cys Gln Lys Leu Asn Gln Arg Lys Glu Lys Leu Ser Arg Arg Glu
            340                 345                 350

Arg Glu His His Ala Glu Ala Ala Gln Phe Gln Glu Asp Val Asn Ala
        355                 360                 365

Asp Pro Glu Val Gln Arg Cys Ser Ser Trp Arg Glu Tyr Lys Glu Leu
    370                 375                 380

Leu Gln Arg Arg Gln Val Gln Arg Ser Gln Arg Arg Ala Pro His Leu
385                 390                 395                 400

Trp Gly Gln Pro Val Thr Pro Leu Leu Ser Pro Gly Gln Ala Ser Ser
                405                 410                 415
```

```
        Pro Ala Val Val Leu Gln His Ile Ser Val Leu Gln Thr Thr His Leu
                    420                 425                 430

Pro Asp Gly Gly Ala Arg Leu Leu Glu Lys Ser Gly Gly Leu Glu Ile
                    435                 440                 445

Ile Phe Asp Val Tyr Gln Ala Asp Ala Val Ala Thr Phe Arg Lys Asn
                    450                 455                 460

Asn Pro Gly Lys Pro Tyr Ala Arg Met Cys Ile Ser Gly Phe Asp Glu
        465                 470                 475                 480

Pro Val Pro Asp Leu Cys Ser Leu Lys Arg Leu Ser Tyr Gln Ser Gly
                        485                 490                 495

Asp Val Pro Leu Ile Phe Ala Leu Val Asp His Gly Asp Ile Ser Phe
                        500                 505                 510

Tyr Ser Phe Arg Asp Phe Thr Leu Pro Gln Asp Val Gly His
                        515                 520                 525

<210> SEQ ID NO 9
        <211> LENGTH: 2437
        <212> TYPE: DNA
        <213> ORGANISM: Homo sapiens
        <220> FEATURE:
        <223> OTHER INFORMATION: HsClp1

<400> SEQUENCE: 9
atgactgact tgtagctgga agaaatcatc ggatttttat tcttttatta aagaaaaaaa       60
atttgaaatg ccttccatgt gccaagcact gtgtcaggtg ggagatgaca gcttggtgaa      120
acctctgtca ggctgtcttc ctccgctttc tctatccctg ggtttccccc tgcctaaaaa      180
ggattttgtg cttcgtggct tgtccaggca agcaggccgt cgcgggacct agaccgagac      240
agtgagtctc tctttctccc gggcctccct tctgttccct gggctgcagg ggagcaggaa      300
atctggggcg agattcccgc cgcggacgcg cactgccgaa gcctggtccc tcgacctgtc      360
cctgcccagc gcgggggcgc aaccgccacg cctcctcacc cctccctccg gctgcacgaa      420
taatgacaac agccgcccct cccaccttttg gcgtcacgtt caaaacaatc ctttgactac      480
aactcccaga aggccgagcg gcttagcgag tgcaccccgc tcggctgct ccggcaaact       540 acacatccca agggcagcg ccgaccgcgt gtccttttcac agcaaagtgc ggaactgcgt       600
ttgtttccgg cgtgggtccg ggcaagaacc gcttgtagtt tggtttaaat tctgcacggg      660
aggaccttct gagtttacct gttgggctcc tggctgcgca ggcacagcag ctacacagaa      720
gagatgggag aagaggctaa tgatgacaag aagccaacca ctaaatttga actagagcga      780
gaaacagaac ttcgctttga ggtggaggca tctcagtcag ttcagttgga gttgttgact      840
ggcatggcag agatctttgg cacagagctg acccgaaaca agaaattcac ctttgatgct      900
ggtgccaagg tggctgtttt cacttggcat ggctgttctg tgcaactgag cggccgcact      960
gaggtggctt atgtctccaa ggacactcct atgttgcttt acctcaacac tcacacagcc     1020
ttggaacaga tgcggaggca agcggaaaag gaagaagagc gaggtccccg agtgatggta     1080
gtgggcccca ctgatgtggg caagtctaca gtgtgtcgcc ttctgctcaa ctacgcagtg     1140
cgtttgggcc gccgtcccac ttatgtggag ctggatgtgg gccagggttc tgtgtccatc     1200
cctggtacca tgggggccct ctacatcgag cggcctgcag atgtcgaaga gggtttctct     1260
atccaggccc ctctggtgta tcattttggt tccaccactc ctggcactaa catcaagctt     1320
tataataaga ttcatctccg tttagcagat gtgttcaacc aaaggtgtga ggtgaaccga     1380
agggcatctg tgagtggctg tgtcattaac acctgtggct gggtcaaggg ctctggttac     1440
caggctctgg tgcatgcagc ctcagctttt gaggtggatg tcgttgttgt tctggatcaa     1500
```

```
gaacgactgt acaatgaact gaaacgggac ctcccccact ttgtacgcac tgtgctgctc    1560
cctaaatctg ggggtgtggt ggagcgctcc aaggacttcc ggcgggaatg tagggatgag    1620
cgtatccgtg agtatttta tggattccga ggctgtttct atccccatgc cttcaatgtc     1680
aaattttcag atgtgaaaat ctacaaagtt ggggcaccca ccatcccaga ctcctgttta    1740
cctttgggca tgtctcaaga ggataatcag ctcaagctag tacctgtcac tcctgggcga    1800
gatatggtgc accacctact gagtgttagc actgccgagg gtacagagga gaacctgtcc    1860
gagacaagtg tagctggctt cattgtggtg accagtgtgg acctggagca tcaggtgttt    1920
actgttctgt ctccagcccc tcgcccactg cctaagaact tccttctcat catggatatc    1980
cggttcatgg atctgaagta gagatcagca ggaagccttg ctgcctggga catagagatc    2040
atctggccac ccctagaggc agatgggctg agataaaaga ctgttggggc cacctgacca    2100
gtaaactgtg gactagtaga aagttcatat tctacctcta aaacaggta gtggtaacct     2160 gactcttcta atcttgaacc aaaaggaaaa ccatgagact gtaattggtt tcttagacca    2220
cctaagatgc cactttgaat tctctaagac cctggagaat tgcatttctt tcactgtgct    2280
actatgtggt ttttaaaaaa tcaatgcttt atattccata tgtggttctt acccatttat    2340
catggatgaa agtgtgaatt agagggactc cttccaataa agttcaaact gaaaaaaaat    2400
cattttaata aatattttg ccatatcata aaaaaa                               2437

<210> SEQ ID NO 10
<211> LENGTH: 425
<212> TYPE: PRT
<213> ORGANISM: Homo sapiens
<220> FEATURE:
<223> OTHER INFORMATION: HsClp1

<400> SEQUENCE: 10

Met Gly Glu Glu Ala Asn Asp Asp Lys Lys Pro Thr Thr Lys Phe Glu
1               5                   10                  15

Leu Glu Arg Glu Thr Glu Leu Arg Phe Glu Val Glu Ala Ser Gln Ser
            20                  25                  30

Val Gln Leu Glu Leu Leu Thr Gly Met Ala Glu Ile Phe Gly Thr Glu
        35                  40                  45

Leu Thr Arg Asn Lys Lys Phe Thr Phe Asp Ala Gly Ala Lys Val Ala
    50                  55                  60

Val Phe Thr Trp His Gly Cys Ser Val Gln Leu Ser Gly Arg Thr Glu
65                  70                  75                  80

Val Ala Tyr Val Ser Lys Asp Thr Pro Met Leu Leu Tyr Leu Asn Thr
                85                  90                  95

His Thr Ala Leu Glu Gln Met Arg Arg Gln Ala Glu Lys Glu Glu Glu
            100                 105                 110

Arg Gly Pro Arg Val Met Val Val Gly Pro Thr Asp Val Gly Lys Ser
        115                 120                 125

Thr Val Cys Arg Leu Leu Leu Asn Tyr Ala Val Arg Leu Gly Arg Arg
    130                 135                 140

Pro Thr Tyr Val Glu Leu Asp Val Gly Gln Gly Ser Val Ser Ile Pro
145                 150                 155                 160

Gly Thr Met Gly Ala Leu Tyr Ile Glu Arg Pro Ala Asp Val Glu Glu
                165                 170                 175

Gly Phe Ser Ile Gln Ala Pro Leu Val Tyr His Phe Gly Ser Thr Thr
            180                 185                 190

Pro Gly Thr Asn Ile Lys Leu Tyr Asn Lys Ile Thr Ser Arg Leu Ala
```

| | | 195 | | | 200 | | | 205 | | | |
|---|---|---|---|---|---|---|---|---|---|---|---|

Asp Val Phe Asn Gln Arg Cys Glu Val Asn Arg Ala Ser Val Ser
210                     215                     220

Gly Cys Val Ile Asn Thr Cys Gly Trp Val Lys Gly Ser Gly Tyr Gln
225                     230                     235                     240

Ala Leu Val His Ala Ala Ser Ala Phe Glu Val Asp Val Val Val
                        245                     250                     255

Leu Asp Gln Glu Arg Leu Tyr Asn Glu Leu Lys Arg Asp Leu Pro His
                260                     265                     270

Phe Val Arg Thr Val Leu Leu Pro Lys Ser Gly Gly Val Val Glu Arg
        275                     280                     285

Ser Lys Asp Phe Arg Arg Glu Cys Arg Asp Glu Arg Ile Arg Glu Tyr
290                     295                     300

Phe Tyr Gly Phe Arg Gly Cys Phe Tyr Pro His Ala Phe Asn Val Lys
305                     310                     315                     320

Phe Ser Asp Val Lys Ile Tyr Lys Val Gly Ala Pro Thr Ile Pro Asp
                        325                     330                     335

Ser Cys Leu Pro Leu Gly Met Ser Gln Glu Asp Asn Gln Leu Lys Leu
                340                     345                     350

Val Pro Val Thr Pro Gly Arg Asp Met Val His Leu Leu Ser Val
        355                     360                     365

Ser Thr Ala Glu Gly Thr Glu Glu Asn Leu Ser Glu Thr Ser Val Ala
370                     375                     380

Gly Phe Ile Val Val Thr Ser Val Asp Leu Glu His Gln Val Phe Thr
385                     390                     395                     400

Val Leu Ser Pro Ala Pro Arg Pro Leu Pro Lys Asn Phe Leu Leu Ile
                        405                     410                     415

Met Asp Ile Arg Phe Met Asp Leu Lys
                420                     425

<210> SEQ ID NO 11
<211> LENGTH: 1347
<212> TYPE: DNA
<213> ORGANISM: Homo sapiens
<220> FEATURE:
<223> OTHER INFORMATION: HsSen2deltaEx8

<400> SEQUENCE: 11

| | | |
|---|---|---|
| atggcagaag cagttttcca tgccccaaag aggaaaagaa gagtgtatga gacttacgag | 60 |
| tctccattgc caatccctt tggtcaggac catggtcctc tgaaagaatt caagatattc | 120 |
| cgtgctgaaa tgattaacaa caatgtgatt gtgaggaatg cggaggacat tgagcagctc | 180 |
| tatgggaaag gttattttgg aaaaggtatt ctttcaagaa gccgtccaag cttcacaatt | 240 |
| tcagatccta aactggttgc taaatggaaa gatatgaaga caaacatgcc tatcatcaca | 300 |
| tcaaagaggt atcagcatag tgttgagtgg gcagcagagc tgatgcgtag acaggggcag | 360 |
| gatgagagta cagtgcgcag aatcctcaag gattacacga accgcttga gcatcctcct | 420 |
| gtgaaaagga atgaagaggc tcaagtgcat gacaagctta actctggaat ggtttccaac | 480 |
| atggaaggca cagcaggggg agagagacct tctgtggtaa acggggactc tggaaagtca | 540 |
| ggtggtgtgg gtgatccccg tgagccatta ggctgcctgc aggagggctc tggctgccac | 600 |
| ccaacaacag agagctttga gaaaagcgtg cgagaggatg cctcacctct gccccatgtc | 660 |
| tgttgctgca acaagatgc tctcatcctc cagcgtggcc ttcatcatga agacggcagc | 720 |
| cagcacatcg gcctcctgca tcctggggac agagggcctg accatgagta cgtgctggtc | 780 |

| | |
|---|---|
| gaggaagcgg agtgtgccat gagcgagagg gaggctgccc caaatgagga attggtgcaa | 840 |
| agaaacaggt taatatgcag aagaaatcca tataggatct ttgagtattt gcaactcagc | 900 |
| ctagaagagg agcctttaac gatagtgaag ctctggaaag ctttcactgt agttcagccc | 960 |
| acgttcagaa ccacctacat ggcctaccat tactttcgaa gcaagggctg ggtgccaaa | 1020 |
| gtgggactca agtacgggac agatttactg ctatatcgga aaggccctcc attttaccat | 1080 |
| gcaagttatt ctgtcattat cgagctagtt gatgaccatt ttgaaggctc tctccgcagg | 1140 |
| cctctcagtt ggaagtccct ggctgccttg agcagagttt ccgttaatgt ctctaaggaa | 1200 |
| cttatgctgt gctatttgat taaaccctct actatgactg acaaggaaat ggagtcacca | 1260 |
| gaatgtatga aaaggattaa agttcaggag gtgattctga gtcgatgggt ttcttcacga | 1320 |
| gagaggagtg accaagacga tctttaa | 1347 |

<210> SEQ ID NO 12
<211> LENGTH: 448
<212> TYPE: PRT
<213> ORGANISM: Homo sapiens
<220> FEATURE:
<223> OTHER INFORMATION: HsSen2deltaEx8

<400> SEQUENCE: 12

```
Met Ala Glu Ala Val Phe His Ala Pro Lys Arg Lys Arg Arg Val Tyr
1               5                   10                  15

Glu Thr Tyr Glu Ser Pro Leu Pro Ile Pro Phe Gly Gln Asp His Gly
            20                  25                  30

Pro Leu Lys Glu Phe Lys Ile Phe Arg Ala Glu Met Ile Asn Asn Asn
        35                  40                  45

Val Ile Val Arg Asn Ala Glu Asp Ile Glu Gln Leu Tyr Gly Lys Gly
    50                  55                  60

Tyr Phe Gly Lys Gly Ile Leu Ser Arg Ser Arg Pro Ser Phe Thr Ile
65                  70                  75                  80

Ser Asp Pro Lys Leu Val Ala Lys Trp Lys Asp Met Lys Thr Asn Met
                85                  90                  95

Pro Ile Ile Thr Ser Lys Arg Tyr Gln His Ser Val Glu Trp Ala Ala
            100                 105                 110

Glu Leu Met Arg Arg Gln Gly Gln Asp Glu Ser Thr Val Arg Arg Ile
        115                 120                 125

Leu Lys Asp Tyr Thr Lys Pro Leu Glu His Pro Pro Val Lys Arg Asn
    130                 135                 140

Glu Glu Ala Gln Val His Asp Lys Leu Asn Ser Gly Met Val Ser Asn
145                 150                 155                 160

Met Glu Gly Thr Ala Gly Gly Glu Arg Pro Ser Val Val Asn Gly Asp
                165                 170                 175

Ser Gly Lys Ser Gly Gly Val Gly Asp Pro Arg Glu Pro Leu Gly Cys
            180                 185                 190

Leu Gln Glu Gly Ser Gly Cys His Pro Thr Thr Glu Ser Phe Glu Lys
        195                 200                 205

Ser Val Arg Glu Asp Ala Ser Pro Leu Pro His Val Cys Cys Cys Lys
    210                 215                 220

Gln Asp Ala Leu Ile Leu Gln Arg Gly Leu His His Glu Asp Gly Ser
225                 230                 235                 240

Gln His Ile Gly Leu Leu His Pro Gly Asp Arg Gly Pro Asp His Glu
                245                 250                 255

Tyr Val Leu Val Glu Glu Ala Glu Cys Ala Met Ser Glu Arg Glu Ala
            260                 265                 270
```

```
Ala Pro Asn Glu Glu Leu Val Gln Arg Asn Arg Leu Ile Cys Arg Arg
        275                 280                 285

Asn Pro Tyr Arg Ile Phe Glu Tyr Leu Gln Leu Ser Leu Glu Glu Glu
        290                 295                 300

Pro Leu Thr Ile Val Lys Leu Trp Lys Ala Phe Thr Val Val Gln Pro
305                 310                 315                 320

Thr Phe Arg Thr Thr Tyr Met Ala Tyr His Tyr Phe Arg Ser Lys Gly
                325                 330                 335

Trp Val Pro Lys Val Gly Leu Lys Tyr Gly Thr Asp Leu Leu Leu Tyr
            340                 345                 350

Arg Lys Gly Pro Pro Phe Tyr His Ala Ser Tyr Ser Val Ile Ile Glu
        355                 360                 365

Leu Val Asp Asp His Phe Glu Gly Ser Leu Arg Arg Pro Leu Ser Trp
        370                 375                 380

Lys Ser Leu Ala Ala Leu Ser Arg Val Ser Val Asn Val Ser Lys Glu
385                 390                 395                 400

Leu Met Leu Cys Tyr Leu Ile Lys Pro Ser Thr Met Thr Asp Lys Glu
                405                 410                 415

Met Glu Ser Pro Glu Cys Met Lys Arg Ile Lys Val Gln Glu Val Ile
            420                 425                 430

Leu Ser Arg Trp Val Ser Ser Arg Glu Arg Ser Asp Gln Asp Asp Leu
        435                 440                 445

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
gtcaggatgg ccgagtggtc                                              20

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
ccgaacacag gaagcagtaa                                              20

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
cggtacttat aagacagtgc                                              20

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
```

```
gctccaggtg aggcttgaac                                                    20

<210> SEQ ID NO 17
<211> LENGTH: 18
<212> TYPE: DNA
<213> ORGANISM: Artificial Sequence
<220> FEATURE:
<223> OTHER INFORMATION: primer

<400> SEQUENCE: 17
ccagcaagag cacaagag                                                      18

<210> SEQ ID NO 18
<211> LENGTH: 19
<212> TYPE: DNA
<213> ORGANISM: Artificial Sequence
<220> FEATURE:
<223> OTHER INFORMATION: primer

<400> SEQUENCE: 18
tgaggagggg agattcagt                                                     19

<210> SEQ ID NO 19
<211> LENGTH: 18
<212> TYPE: DNA
<213> ORGANISM: Artificial Sequence
<220> FEATURE:
<223> OTHER INFORMATION: primer

<400> SEQUENCE: 19
caggtggagg aagtcagg                                                      18

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
ctaaccagtc agcgtcagag                                                    20

<210> SEQ ID NO 21
<211> LENGTH: 39
<212> TYPE: DNA
<213> ORGANISM: Artificial Sequence
<220> FEATURE:
<223> OTHER INFORMATION: primer

<400> SEQUENCE: 21
cgggatcccg cagaagcagt tttccatgcc ccaaagagg                               39

<210> SEQ ID NO 22
<211> LENGTH: 38
<212> TYPE: DNA
<213> ORGANISM: Artificial Sequence
<220> FEATURE:
<223> OTHER INFORMATION: primer

<400> SEQUENCE: 22
gctctagatt aaagatcgtc ttggtcactc ctctctcg                                38

<210> SEQ ID NO 23
<211> LENGTH: 39
<212> TYPE: DNA
<213> ORGANISM: Artificial Sequence
<220> FEATURE:
```

<223> OTHER INFORMATION: primer

<400> SEQUENCE: 23
cgggatcccc tggtggtgga ggtggcgaac ggccgctcc                                    39

<210> SEQ ID NO 24
<211> LENGTH: 38
<212> TYPE: DNA
<213> ORGANISM: Artificial Sequence
<220> FEATURE:
<223> OTHER INFORMATION: primer

<400> SEQUENCE: 24
gctctagatg caggctggcc cattgcaggg aggtgtag                                     38

<210> SEQ ID NO 25
<211> LENGTH: 34
<212> TYPE: DNA
<213> ORGANISM: Artificial Sequence
<220> FEATURE:
<223> OTHER INFORMATION: primer

<400> SEQUENCE: 25
cgggatcccg aggagcgcgg cgattccgag ccga                                         34

<210> SEQ ID NO 26
<211> LENGTH: 45
<212> TYPE: DNA
<213> ORGANISM: Artificial Sequence
<220> FEATURE:
<223> OTHER INFORMATION: primer

<400> SEQUENCE: 26
cgcgctagct catcttctaa gagaaatatt ctgagggtct ggcag                             45

<210> SEQ ID NO 27
<211> LENGTH: 30
<212> TYPE: DNA
<213> ORGANISM: Artificial Sequence
<220> FEATURE:
<223> OTHER INFORMATION: primer

<400> SEQUENCE: 27
atcgggatcc cgagcccgag cccgagcccg                                              30

<210> SEQ ID NO 28
<211> LENGTH: 30
<212> TYPE: DNA
<213> ORGANISM: Artificial Sequence
<220> FEATURE:
<223> OTHER INFORMATION: primer

<400> SEQUENCE: 28
gctctagatc agtgccccac atcctggggc                                              30

<210> SEQ ID NO 29
<211> LENGTH: 39
<212> TYPE: DNA
<213> ORGANISM: Artificial Sequence
<220> FEATURE:
<223> OTHER INFORMATION: primer

<400> SEQUENCE: 29
cgggatcccg gagaagaggc taatgatgat gacaagaag                                    39

<210> SEQ ID NO 30

```
<211> LENGTH: 36
<212> TYPE: DNA
<213> ORGANISM: Artificial Sequence
<220> FEATURE:
<223> OTHER INFORMATION: primer

<400> SEQUENCE: 30
gctctagact acttcagatc catgaaccgg atatcc                              36

<210> SEQ ID NO 31
<211> LENGTH: 37
<212> TYPE: DNA
<213> ORGANISM: Artificial Sequence
<220> FEATURE:
<223> OTHER INFORMATION: primer

<400> SEQUENCE: 31
agaatagcgg ccgcttaaag atcgtcttgg tcactcc                             37

<210> SEQ ID NO 32
<211> LENGTH: 24
<212> TYPE: DNA
<213> ORGANISM: Artificial Sequence
<220> FEATURE:
<223> OTHER INFORMATION: primer

<400> SEQUENCE: 32
gagtacgtgc tggtcgagga agcg                                           24

<210> SEQ ID NO 33
<211> LENGTH: 24
<212> TYPE: DNA
<213> ORGANISM: Artificial Sequence
<220> FEATURE:
<223> OTHER INFORMATION: primer

<400> SEQUENCE: 33
gagtcccact ttgggctccc agcc                                           24

<210> SEQ ID NO 34
<211> LENGTH: 24
<212> TYPE: DNA
<213> ORGANISM: Artificial Sequence
<220> FEATURE:
<223> OTHER INFORMATION: primer

<400> SEQUENCE: 34
gctctgggat gtttaagtat ttac                                           24

<210> SEQ ID NO 35
<211> LENGTH: 24
<212> TYPE: DNA
<213> ORGANISM: Artificial Sequence
<220> FEATURE:
<223> OTHER INFORMATION: primer

<400> SEQUENCE: 35
gagtacgtgc tggtcgagga agcg                                           24

<210> SEQ ID NO 36
<211> LENGTH: 24
<212> TYPE: DNA
<213> ORGANISM: Artificial Sequence
<220> FEATURE:
<223> OTHER INFORMATION: primer

<400> SEQUENCE: 36
```

-continued

```
gagtcccact ttgggctccc agcc                                            24
```

<210> SEQ ID NO 37
<211> LENGTH: 24
<212> TYPE: DNA
<213> ORGANISM: Artificial Sequence
<220> FEATURE:
<223> OTHER INFORMATION: primer

<400> SEQUENCE: 37

```
gctctgggat gtttaagtat ttac                                            24
```

<210> SEQ ID NO 38
<211> LENGTH: 465
<212> TYPE: PRT
<213> ORGANISM: Homo Sapiens
<220> FEATURE:
<223> OTHER INFORMATION: HsSen2p

<400> SEQUENCE: 38

```
Met Ala Glu Ala Val Phe His Ala Pro Lys Arg Lys Arg Arg Val Tyr
  1               5                  10                  15
Glu Thr Tyr Glu Ser Pro Leu Pro Ile Pro Phe Gly Gln Asp His Gly
             20                  25                  30
Pro Leu Lys Glu Phe Lys Ile Phe Arg Ala Glu Met Ile Asn Asn Asn
         35                  40                  45
Val Ile Val Arg Asn Ala Glu Asp Ile Glu Gln Leu Tyr Gly Lys Gly
     50                  55                  60
Tyr Phe Gly Lys Gly Ile Leu Ser Arg Ser Arg Pro Ser Phe Thr Ile
 65                  70                  75                  80
Ser Asp Pro Lys Leu Val Ala Lys Trp Lys Asp Met Lys Thr Asn Met
                 85                  90                  95
Pro Ile Ile Thr Ser Lys Arg Tyr Gln His Ser Val Glu Trp Ala Ala
            100                 105                 110
Glu Leu Met Arg Arg Gln Gly Gln Asp Glu Ser Thr Val Arg Arg Ile
        115                 120                 125
Leu Lys Asp Tyr Thr Lys Pro Leu Glu His Pro Val Lys Arg Asn
    130                 135                 140
Glu Glu Ala Gln Val His Asp Lys Leu Asn Ser Gly Met Val Ser Asn
145                 150                 155                 160
Met Glu Gly Thr Ala Gly Gly Glu Arg Pro Ser Val Val Asn Gly Asp
                165                 170                 175
Ser Gly Lys Ser Gly Gly Val Gly Asp Pro Arg Glu Pro Leu Gly Cys
            180                 185                 190
Leu Gln Glu Gly Ser Gly Cys His Pro Thr Thr Glu Ser Phe Glu Lys
        195                 200                 205
Ser Val Arg Glu Asp Ala Ser Pro Leu Pro His Val Cys Cys Cys Lys
    210                 215                 220
Gln Asp Ala Leu Ile Leu Gln Arg Gly Leu His His Glu Asp Gly Ser
225                 230                 235                 240
Gln His Ile Gly Leu Leu His Pro Gly Asp Arg Gly Pro Asp His Glu
                245                 250                 255
Tyr Val Leu Val Glu Glu Ala Glu Cys Ala Met Ser Glu Arg Glu Ala
            260                 265                 270
Ala Pro Asn Glu Glu Leu Val Gln Arg Asn Arg Leu Ile Cys Arg Arg
        275                 280                 285
Asn Pro Tyr Arg Ile Phe Glu Tyr Leu Gln Leu Ser Leu Glu Glu Ala
    290                 295                 300
```

```
Phe Phe Leu Val Tyr Ala Leu Gly Cys Leu Ser Ile Tyr Tyr Glu Lys
305                 310                 315                 320

Glu Pro Leu Thr Ile Val Lys Leu Trp Lys Ala Phe Thr Val Val Gln
                325                 330                 335

Pro Thr Phe Arg Thr Thr Tyr Met Ala Tyr His Tyr Phe Arg Ser Lys
            340                 345                 350

Gly Trp Val Pro Lys Val Gly Leu Lys Tyr Gly Thr Asp Leu Leu Leu
        355                 360                 365

Tyr Arg Lys Gly Pro Pro Phe Tyr His Ala Ser Tyr Ser Val Ile Ile
370                 375                 380

Glu Leu Val Asp Asp His Phe Glu Gly Ser Leu Arg Arg Pro Leu Ser
385                 390                 395                 400

Trp Lys Ser Leu Ala Ala Leu Ser Arg Val Ser Val Asn Val Ser Lys
                405                 410                 415

Glu Leu Met Leu Cys Tyr Leu Ile Lys Pro Ser Thr Met Thr Asp Lys
                420                 425                 430

Glu Met Glu Ser Pro Glu Cys Met Lys Arg Ile Lys Val Gln Glu Val
            435                 440                 445

Ile Leu Ser Arg Trp Val Ser Ser Arg Glu Arg Ser Asp Gln Asp Asp
450                 455                 460

Leu
465

<210> SEQ ID NO 39
<211> LENGTH: 448
<212> TYPE: PRT
<213> ORGANISM: Homo Sapiens
<220> FEATURE:
<223> OTHER INFORMATION: HsSen2 variant

<400> SEQUENCE: 39

Met Ala Glu Ala Val Phe His Ala Pro Lys Arg Lys Arg Arg Val Tyr
1               5                   10                  15

Glu Thr Tyr Glu Ser Pro Leu Pro Ile Pro Phe Gly Gln Asp His Gly
                20                  25                  30

Pro Leu Lys Glu Phe Lys Ile Phe Arg Ala Glu Met Ile Asn Asn Asn
            35                  40                  45

Val Ile Val Arg Asn Ala Glu Asp Ile Glu Gln Leu Tyr Gly Lys Gly
        50                  55                  60

Tyr Phe Gly Lys Gly Ile Leu Ser Arg Ser Arg Pro Ser Phe Thr Ile
65                  70                  75                  80

Ser Asp Pro Lys Leu Val Ala Lys Trp Lys Asp Met Lys Thr Asn Met
                85                  90                  95

Pro Ile Ile Thr Ser Lys Arg Tyr Gln His Ser Val Glu Trp Ala Ala
                100                 105                 110

Glu Leu Met Arg Arg Gln Gly Gln Asp Glu Ser Thr Val Arg Arg Ile
            115                 120                 125

Leu Lys Asp Tyr Thr Lys Pro Leu Glu His Pro Val Lys Arg Asn
130                 135                 140

Glu Glu Ala Gln Val His Asp Lys Leu Asn Ser Gly Met Val Ser Asn
145                 150                 155                 160

Met Glu Gly Thr Ala Gly Gly Glu Arg Pro Ser Val Val Asn Gly Asp
                165                 170                 175

Ser Gly Lys Ser Gly Val Gly Asp Pro Arg Glu Pro Leu Gly Cys
            180                 185                 190
```

-continued

```
Leu Gln Glu Gly Ser Gly Cys His Pro Thr Thr Glu Ser Phe Glu Lys
        195                 200                 205
Ser Val Arg Glu Asp Ala Ser Pro Leu Pro His Val Cys Cys Cys Lys
210                 215                 220
Gln Asp Ala Leu Ile Leu Gln Arg Gly Leu His His Glu Asp Gly Ser
225                 230                 235                 240
Gln His Ile Gly Leu Leu His Pro Gly Asp Arg Gly Pro Asp His Glu
                245                 250                 255
Tyr Val Leu Val Glu Glu Ala Glu Cys Ala Met Ser Glu Arg Glu Ala
                260                 265                 270
Ala Pro Asn Glu Glu Leu Val Gln Arg Asn Arg Leu Ile Cys Arg Arg
            275                 280                 285
Asn Pro Tyr Arg Ile Phe Glu Tyr Leu Gln Leu Ser Leu Glu Glu Glu
        290                 295                 300
Pro Leu Thr Ile Val Lys Leu Trp Lys Ala Phe Thr Val Val Gln Pro
305                 310                 315                 320
Thr Phe Arg Thr Thr Tyr Met Ala Tyr His Tyr Phe Arg Ser Lys Gly
                325                 330                 335
Trp Val Pro Lys Val Gly Leu Lys Tyr Gly Thr Asp Leu Leu Leu Tyr
            340                 345                 350
Arg Lys Gly Pro Pro Phe Tyr His Ala Ser Tyr Ser Val Ile Ile Glu
        355                 360                 365
Leu Val Asp Asp His Phe Glu Gly Ser Leu Arg Arg Pro Leu Ser Trp
    370                 375                 380
Lys Ser Leu Ala Ala Leu Ser Arg Val Ser Val Asn Val Ser Lys Glu
385                 390                 395                 400
Leu Met Leu Cys Tyr Leu Ile Lys Pro Ser Thr Met Thr Asp Lys Glu
                405                 410                 415
Met Glu Ser Pro Glu Cys Met Lys Arg Ile Lys Val Gln Glu Val Ile
            420                 425                 430
Leu Ser Arg Trp Val Ser Ser Arg Glu Arg Ser Asp Gln Asp Asp Leu
        435                 440                 445
```

<210> SEQ ID NO 40
<211> LENGTH: 377
<212> TYPE: PRT
<213> ORGANISM: Saccharomyces cerevisiae
<220> FEATURE:
<223> OTHER INFORMATION: ScSen2p

<400> SEQUENCE: 40

```
Met Ser Lys Gly Arg Val Asn Gln Lys Arg Tyr Lys Tyr Pro Leu Pro
1               5                   10                  15
Ile His Pro Val Asp Asp Leu Pro Glu Leu Ile Leu His Asn Pro Leu
            20                  25                  30
Ser Trp Leu Tyr Trp Ala Tyr Arg Tyr Tyr Lys Ser Thr Asn Ala Leu
        35                  40                  45
Asn Asp Lys Val His Val Asp Phe Ile Gly Asp Thr Thr Leu His Ile
    50                  55                  60
Thr Val Gln Asp Asp Lys Gln Met Leu Tyr Leu Trp Asn Asn Gly Phe
65                  70                  75                  80
Phe Gly Thr Gly Gln Phe Ser Arg Ser Glu Pro Thr Trp Lys Ala Arg
                85                  90                  95
Thr Glu Ala Arg Leu Gly Leu Asn Asp Thr Pro Leu His Asn Arg Gly
            100                 105                 110
Gly Thr Lys Ser Asn Thr Glu Thr Glu Met Thr Leu Glu Lys Val Thr
```

```
                     115                 120                 125
Gln Gln Arg Arg Leu Gln Arg Leu Glu Phe Lys Lys Glu Arg Ala Lys
            130                 135                 140

Leu Glu Arg Glu Leu Leu Glu Leu Arg Lys Lys Gly Gly His Ile Asp
145                 150                 155                 160

Glu Glu Asn Ile Leu Leu Glu Lys Gln Arg Glu Ser Leu Arg Lys Phe
                165                 170                 175

Lys Leu Lys Gln Thr Glu Asp Val Gly Ile Val Ala Gln Gln Gln Asp
            180                 185                 190

Ile Ser Glu Ser Asn Leu Arg Asp Glu Asp Asn Asn Leu Leu Asp Glu
        195                 200                 205

Asn Gly Asp Leu Leu Pro Leu Glu Ser Leu Glu Leu Met Pro Val Glu
    210                 215                 220

Ala Met Phe Leu Thr Phe Ala Leu Pro Val Leu Asp Ile Ser Pro Ala
225                 230                 235                 240

Cys Leu Ala Gly Lys Leu Phe Gln Phe Asp Ala Lys Tyr Lys Asp Ile
                245                 250                 255

His Ser Phe Val Arg Ser Tyr Val Ile Tyr His His Tyr Arg Ser His
            260                 265                 270

Gly Trp Cys Val Arg Ser Gly Ile Lys Phe Gly Cys Asp Tyr Leu Leu
        275                 280                 285

Tyr Lys Arg Gly Pro Pro Phe Gln His Ala Glu Phe Cys Val Met Gly
    290                 295                 300

Leu Asp His Asp Val Ser Lys Asp Tyr Thr Trp Tyr Ser Ser Ile Ala
305                 310                 315                 320

Arg Val Val Gly Gly Ala Lys Lys Thr Phe Val Leu Cys Tyr Val Glu
                325                 330                 335

Arg Leu Ile Ser Glu Gln Glu Ala Ile Ala Leu Trp Lys Ser Asn Asn
            340                 345                 350

Phe Thr Lys Leu Phe Asn Ser Phe Gln Val Gly Glu Val Leu Tyr Lys
        355                 360                 365

Arg Trp Val Pro Gly Arg Asn Arg Asp
    370                 375

<210> SEQ ID NO 41
<211> LENGTH: 377
<212> TYPE: PRT
<213> ORGANISM: Saccharomyces cerevisiae
<220> FEATURE:
<223> OTHER INFORMATION: ScSen2

<400> SEQUENCE: 41

Met Ser Lys Gly Arg Val Asn Gln Lys Arg Tyr Lys Tyr Pro Leu Pro
1               5                   10                  15

Ile His Pro Val Asp Asp Leu Pro Glu Leu Ile Leu His Asn Pro Leu
            20                  25                  30

Ser Trp Leu Tyr Trp Ala Tyr Arg Tyr Tyr Lys Ser Thr Asn Ala Leu
        35                  40                  45

Asn Asp Lys Val His Val Asp Phe Ile Gly Asp Thr Thr Leu His Ile
    50                  55                  60

Thr Val Gln Asp Asp Lys Gln Met Leu Tyr Leu Trp Asn Asn Gly Phe
65                  70                  75                  80

Phe Gly Thr Gly Gln Phe Ser Arg Ser Glu Pro Thr Trp Lys Ala Arg
                85                  90                  95

Thr Glu Ala Arg Leu Gly Leu Asn Asp Thr Pro Leu His Asn Arg Gly
            100                 105                 110
```

```
Gly Thr Lys Ser Asn Thr Glu Thr Glu Met Thr Leu Glu Lys Val Thr
            115                 120                 125

Gln Gln Arg Arg Leu Gln Arg Leu Glu Phe Lys Lys Glu Arg Ala Lys
        130                 135                 140

Leu Glu Arg Glu Leu Leu Glu Leu Arg Lys Lys Gly Gly His Ile Asp
145                 150                 155                 160

Glu Glu Asn Ile Leu Leu Glu Lys Gln Arg Glu Ser Leu Arg Lys Phe
                165                 170                 175

Lys Leu Lys Gln Thr Glu Asp Val Gly Ile Val Ala Gln Gln Gln Asp
            180                 185                 190

Ile Ser Glu Ser Asn Leu Arg Asp Glu Asp Asn Asn Leu Leu Asp Glu
        195                 200                 205

Asn Gly Asp Leu Leu Pro Leu Glu Ser Leu Glu Leu Met Pro Val Glu
210                 215                 220

Ala Met Phe Leu Thr Phe Ala Leu Pro Val Leu Asp Ile Ser Pro Ala
225                 230                 235                 240

Cys Leu Ala Gly Lys Leu Phe Gln Phe Asp Ala Lys Tyr Lys Asp Ile
                245                 250                 255

His Ser Phe Val Arg Ser Tyr Val Ile Tyr His His Tyr Arg Ser His
            260                 265                 270

Gly Trp Cys Val Arg Ser Gly Ile Lys Phe Gly Cys Asp Tyr Leu Leu
        275                 280                 285

Tyr Lys Arg Gly Pro Pro Phe Gln His Ala Glu Phe Cys Val Met Gly
290                 295                 300

Leu Asp His Asp Val Ser Lys Asp Tyr Thr Trp Tyr Ser Ser Ile Ala
305                 310                 315                 320

Arg Val Val Gly Gly Ala Lys Lys Thr Phe Val Leu Cys Tyr Val Glu
                325                 330                 335

Arg Leu Ile Ser Glu Gln Glu Ala Ile Ala Leu Trp Lys Ser Asn Asn
            340                 345                 350

Phe Thr Lys Leu Phe Asn Ser Phe Gln Val Gly Glu Val Leu Tyr Lys
        355                 360                 365

Arg Trp Val Pro Gly Arg Asn Arg Asp
370                 375

<210> SEQ ID NO 42
<211> LENGTH: 380
<212> TYPE: PRT
<213> ORGANISM: Schizosaccaromyces pombe
<220> FEATURE:
<223> OTHER INFORMATION: SpSen2

<400> SEQUENCE: 42

Met Ser Lys Asn His Glu Val Tyr Lys Asp Ala Leu Pro Ile Ser Leu
1               5                   10                  15

Ala Tyr Pro Leu Pro Pro Ile Ile Leu Thr Asn Pro Leu Thr Trp Ile
            20                  25                  30

Pro Tyr Ile Tyr Arg Tyr Leu Phe Arg Lys Thr Pro Arg Gln Val Gln
        35                  40                  45

Trp Gln Cys Gln Leu His Glu Ser Asp Leu Ser Cys Val Val Thr Asp
    50                  55                  60

Ser Glu Ala Ile Lys Lys Phe Trp Thr Ser Gly Phe Phe Gly Lys Gly
65                  70                  75                  80

Asn Leu Ser Arg Ser Glu Pro Thr Trp His Thr Arg Thr Lys Arg Ser
                85                  90                  95
```

-continued

```
Leu Gly Leu Leu Gly Phe Asp Glu Asp Leu Val Ala Glu Val Thr
            100                 105                 110

Ala Arg Arg Arg Phe Gln Arg Gln Phe Lys Ala Gln Arg Ala Tyr
        115                 120                 125

Arg Glu Asn Arg Ala Arg Glu Arg Gln Leu Leu Leu Glu Asn Gly Lys
    130                 135                 140

Pro Ile Pro Ala Ser Leu Glu Glu Asp Ala Glu Leu Pro Glu Tyr Leu
145                 150                 155                 160

Thr Lys Ser Leu Lys Asp Phe Ser Arg Val Ser Glu Asn Pro Tyr His
                165                 170                 175

Ile Thr Ser Val Pro Asn Val Glu His Leu Gln Leu Thr Phe Pro Glu
            180                 185                 190

Ala Phe Phe Leu Ala Ser Leu Gly Val Leu Arg Ile Asn Tyr Glu Asn
        195                 200                 205

Pro Asn Phe Glu Leu Leu Pro Ile Leu Lys Leu Phe Ala Asn Ile Val
    210                 215                 220

Ala Asn Ser Val Ala Leu Thr His Asp Tyr Ser Leu Gln Gln Ser His
225                 230                 235                 240

Glu Asp Pro Ile Ile Glu Pro Asp Asn Lys Phe Leu Thr Glu Leu Ala
                245                 250                 255

Ala Tyr Phe Tyr Phe Arg Gln Gln Gly Trp Val Val Lys Asn Gly Thr
            260                 265                 270

Lys Phe Ser Val Asp Phe Leu Leu Tyr Lys Lys Gly Pro Val Phe Ser
        275                 280                 285

His Ala Glu Phe Ala Ile Leu Leu Ile Pro Cys Val Gly Asn Lys Gln
    290                 295                 300

Lys Tyr Asn Met Gln Trp His Glu Val His Cys Leu Asn Arg Val Ile
305                 310                 315                 320

Ala Gln Val Lys Lys Ser Leu Ile Leu Cys Tyr Val Gln Cys Pro Ser
                325                 330                 335

Ile Glu Asp Phe Asn Lys Ile Trp Lys Asn Gln Ala Ser Met Asn Glu
            340                 345                 350

Trp Asp Trp Ala Glu Ser Val Leu Arg Gln Tyr Leu Ile Arg Cys Val
        355                 360                 365

Thr Leu Arg Arg Trp Val Pro Ser Arg Asn Arg Asp
    370                 375                 380

<210> SEQ ID NO 43
<211> LENGTH: 275
<212> TYPE: PRT
<213> ORGANISM: Saccaromyces cerevisiae
<220> FEATURE:
<223> OTHER INFORMATION: ScSen34

<400> SEQUENCE: 43

Met Pro Pro Leu Val Phe Asp Ile Asp His Ile Lys Leu Leu Arg Lys
1               5                   10                  15

Trp Gly Ile Cys Gly Val Leu Ser Gly Thr Leu Pro Thr Ala Ala Gln
            20                  25                  30

Gln Asn Val Phe Leu Ser Val Pro Leu Arg Leu Met Leu Glu Asp Val
        35                  40                  45

Leu Trp Leu His Leu Asn Asn Leu Ala Asp Val Lys Leu Ile Arg Gln
    50                  55                  60

Glu Gly Asp Glu Ile Met Glu Gly Ile Thr Leu Glu Arg Gly Ala Lys
65                  70                  75                  80

Leu Ser Lys Ile Val Asn Asp Arg Leu Asn Lys Ser Phe Glu Tyr Gln
```

```
                    85                  90                  95
Arg Lys Phe Lys Lys Asp Glu His Ile Ala Lys Leu Lys Lys Ile Gly
                100                 105                 110

Arg Ile Asn Asp Lys Thr Thr Ala Glu Glu Leu Gln Arg Leu Asp Lys
            115                 120                 125

Ser Ser Asn Asn Asp Gln Leu Ile Glu Ser Ser Leu Phe Ile Asp Ile
        130                 135                 140

Ala Asn Thr Ser Met Ile Leu Arg Asp Ile Arg Ser Asp Ser Asp Ser
145                 150                 155                 160

Leu Ser Arg Asp Asp Ile Ser Asp Leu Leu Phe Lys Gln Tyr Arg Gln
                165                 170                 175

Ala Gly Lys Met Gln Thr Tyr Phe Leu Tyr Lys Ala Leu Arg Asp Gln
            180                 185                 190

Gly Tyr Val Leu Ser Pro Gly Arg Phe Gly Lys Phe Ile Ala
        195                 200                 205

Tyr Pro Gly Asp Pro Leu Arg Phe His Ser His Leu Thr Ile Gln Asp
    210                 215                 220

Ala Ile Asp Tyr His Asn Glu Pro Ile Asp Leu Ile Ser Met Ile Ser
225                 230                 235                 240

Gly Ala Arg Leu Gly Thr Thr Val Lys Lys Leu Trp Val Ile Gly Gly
                245                 250                 255

Val Ala Glu Glu Thr Lys Glu Thr His Phe Phe Ser Ile Glu Trp Ala
            260                 265                 270

Gly Phe Gly
        275

<210> SEQ ID NO 44
<211> LENGTH: 284
<212> TYPE: PRT
<213> ORGANISM: Schizosaccaromyces pombe
<220> FEATURE:
<223> OTHER INFORMATION: SpSen34

<400> SEQUENCE: 44

Met Glu Asp Glu Lys Phe Pro Ile Ser Tyr Val His Gly Lys Phe Leu
1               5                   10                  15

Val Phe Asp Val Gln Ala Val Glu Val Phe Arg Lys Asn Tyr His Ile
            20                  25                  30

Leu Gly Thr Leu Val Gly Thr Leu Pro Gln Leu Pro Gln Gln Asn Val
        35                  40                  45

Phe Leu Gly Leu Pro Met Glu Leu Ser Lys Glu Ala Phe Tyr Leu
    50                  55                  60

Ile Glu Lys Gly Ile Ser Tyr Ile Val Asp Asp Thr Lys Val His Lys
65                  70                  75                  80

Gln Leu Leu Glu Asn Thr Thr Lys Asp Asp Val Lys Gln Cys Leu Lys
                85                  90                  95

Lys Arg Gln Ser Leu Ala Tyr Asp Gln Met Ile Ala Ala Lys Lys Lys
            100                 105                 110

Glu Asn Glu Lys Lys Ile Glu Ile Met Lys Lys Leu Gly Arg Thr Leu
        115                 120                 125

Pro Leu Asp Pro Leu Asn Tyr Asp Glu His Asp Ser Phe Asp Leu Ser
    130                 135                 140

Trp Ile Pro Val Asp Thr Val Thr Thr Arg Ile Ala Glu Lys Ser Ser
145                 150                 155                 160

Met Asn Asp Asp Phe His Lys Glu Glu Asp Val Phe Glu Asn Leu Asp
                165                 170                 175
```

```
Ile Asn Arg Tyr Leu Met Phe Lys Ser Leu Val Asp Thr Gly Phe Tyr
            180                 185                 190

Leu Asn Pro Gly Leu Arg Phe Gly Cys Gln Phe Val Ala Tyr Pro Gly
            195                 200                 205

Asp Ala Leu Arg Tyr His Ser His Tyr Leu Val Asn Ser Tyr Lys Trp
210                 215                 220

Asp Gln Glu Ile Pro Val Leu Phe Leu Ile Gly Gly Arg Leu Gly
225                 230                 235                 240

Thr Ala Val Lys Lys Thr Trp Leu Ile Gly Gly Ser Asn Asp Arg Asn
            245                 250                 255

Ile Asn Met Asn Gly Glu Lys Ser Lys Glu Leu Leu Leu Leu Pro
            260                 265                 270

Val Arg His Phe Ser Ile Glu Trp Ala Gly Phe Gly
            275                 280
```

<210> SEQ ID NO 45
<211> LENGTH: 467
<212> TYPE: PRT
<213> ORGANISM: Saccaromyces cerevisiae
<220> FEATURE:
<223> OTHER INFORMATION: ScSen54

<400> SEQUENCE: 45

```
Met Gln Phe Ala Gly Lys Lys Thr Asp Gln Val Thr Thr Ser Asn Pro
1               5                   10                  15

Gly Phe Glu Glu Glu Glu Glu Glu Glu Leu Gln Gln Asp Trp
            20                  25                  30

Ser Gln Leu Ala Ser Leu Val Ser Lys Asn Ala Ala Leu Ser Leu Pro
            35                  40                  45

Lys Arg Gly Glu Lys Asp Tyr Glu Pro Asp Gly Thr Asn Leu Gln Asp
        50                  55                  60

Leu Leu Leu Tyr Asn Ala Ser Lys Ala Met Phe Asp Thr Ile Ser Asp
65                  70                  75                  80

Ser Ile Arg Gly Thr Thr Val Lys Ser Glu Val Arg Gly Tyr Tyr Val
                85                  90                  95

Pro His Lys His Gln Ala Val Leu Leu Lys Pro Lys Gly Ser Phe Met
            100                 105                 110

Gln Thr Met Gly Arg Ala Asp Ser Thr Gly Glu Leu Trp Leu Asp Phe
            115                 120                 125

His Glu Phe Val Tyr Leu Ala Glu Arg Gly Thr Ile Leu Pro Tyr Tyr
        130                 135                 140

Arg Leu Glu Ala Gly Ser Asn Lys Ser Ser Lys His Glu Thr Glu Ile
145                 150                 155                 160

Leu Leu Ser Met Glu Asp Leu Tyr Ser Leu Phe Ser Ser Gln Gln Glu
                165                 170                 175

Met Asp Gln Tyr Phe Val Phe Ala His Leu Lys Arg Leu Gly Phe Ile
            180                 185                 190

Leu Lys Pro Ser Asn Gln Glu Ala Ala Val Lys Thr Ser Phe Phe Pro
            195                 200                 205

Leu Lys Lys Gln Arg Ser Asn Leu Gln Ala Ile Thr Trp Arg Leu Leu
        210                 215                 220

Ser Leu Phe Lys Ile Gln Glu Leu Ser Leu Phe Ser Gly Phe Phe Tyr
225                 230                 235                 240

Ser Lys Trp Asn Phe Phe Phe Arg Lys Tyr Thr Thr Ser Pro Gln Leu
                245                 250                 255
```

```
Tyr Gln Gly Leu Asn Arg Leu Val Arg Ser Val Ala Val Pro Lys Asn
                260                 265                 270

Lys Lys Glu Leu Leu Asp Ala Gln Ser Asp Arg Glu Phe Gln Lys Val
        275                 280                 285

Lys Asp Ile Pro Leu Thr Phe Lys Val Trp Lys Pro His Ser Asn Phe
    290                 295                 300

Lys Lys Arg Asp Pro Gly Leu Pro Asp Phe Gln Val Phe Val Tyr Asn
305                 310                 315                 320

Lys Asn Asp Asp Leu Gln His Phe Pro Thr Tyr Lys Glu Leu Arg Ser
                325                 330                 335

Met Phe Ser Ser Leu Asp Tyr Lys Phe Glu Phe Leu Ser Glu Ile Glu
        340                 345                 350

Asp Asp Asp Asp Trp Glu Thr Asn Ser Tyr Val Glu Asp Ile Pro Arg
    355                 360                 365

Lys Glu Tyr Ile His Lys Arg Ser Ala Lys Ser Gln Thr Glu Lys Ser
370                 375                 380

Glu Ser Ser Met Lys Ala Ser Phe Gln Lys Thr Ala Gln Ser Ser
385                 390                 395                 400

Thr Lys Lys Lys Arg Lys Ala Tyr Pro Pro His Ile Gln Gln Asn Arg
                405                 410                 415

Arg Leu Lys Thr Gly Tyr Arg Ser Phe Ile Ala Ile Met Asp Asn
        420                 425                 430

Gly Leu Ile Ser Phe Val Lys Met Ser Glu Ala Asp Phe Gly Ser Glu
    435                 440                 445

Ser Val Trp Tyr Thr Pro Asn Thr Gln Lys Lys Val Asp Gln Arg Trp
    450                 455                 460

Lys Lys His
465

<210> SEQ ID NO 46
<211> LENGTH: 384
<212> TYPE: PRT
<213> ORGANISM: Schizosaccaromyces pombe
<220> FEATURE:
<223> OTHER INFORMATION: SpSen54

<400> SEQUENCE: 46

Met Asp Ala Gln Asp Glu Asp Asn Pro Phe Thr Asn Leu Glu Thr Thr
1               5                   10                  15

Val Asp Val Thr Glu Glu Ile Gln Asp Trp Arg Phe Leu Ser Asn Val
                20                  25                  30

Glu Lys Asp Gln Gly Thr Tyr Thr Ile Pro Lys Arg Gly Gln Lys Asp
        35                  40                  45

Phe Glu Pro Asp Gly Thr Asn Lys Gln His Ser Ala Leu Asp Leu Ser
    50                  55                  60

Arg Lys Ala Met Phe Asp Ala Leu Ser Val Glu Arg Leu Ile Ser Ala
65                  70                  75                  80

Lys His Ala Ile Ile Ala Thr Trp Asn Ala Gln Asn Gly Met Ser Cys
                85                  90                  95

Val Glu Lys Ala His Gly Pro Leu Phe Lys Thr Met Gly Thr Ala Asp
            100                 105                 110

Ser Gln Asn Arg Met Trp Leu Leu Pro Glu Glu Thr Leu Tyr Leu Val
        115                 120                 125

Glu Arg Gly Ser Met Glu Cys Trp Ser Glu Gly Leu Pro Met Ser
    130                 135                 140

Leu Gln Ala Val Tyr Ser Ala Ser Ile Pro Leu Cys Gly Ser Leu Glu
```

```
                145                 150                 155                 160
Asn Tyr Leu Val Tyr Ala His Leu Arg Arg Cys Gly Phe Ser Val Ile
                    165                 170                 175

Arg Ser Asn Leu Val Pro Val Lys Glu Asp Glu Tyr Arg Cys Asp Ser
                180                 185                 190

Lys Ile Met Asn Phe Lys Asp Leu Leu Phe Leu Gly Leu Gly Lys Ala
                195                 200                 205

Ser Gln Ile Leu Gln Thr Phe Asn Phe Arg Lys Leu Ala Phe Pro Phe
            210                 215                 220

Ser Lys Arg Arg Gln Ser Ile Leu Leu His Asp Thr Phe Tyr Thr
225                 230                 235                 240

Tyr Glu Glu Val Tyr His Asp Leu Gln Ile Val Arg Gly Tyr Val Pro
                    245                 250                 255

Ile Ala Cys Asn Leu Ile Thr Ser Ser Asp Ser Leu Phe Gln Ile Thr
                260                 265                 270

Phe His Ala Tyr Lys Pro Ser Ala Ser Phe Lys Ser Ala Leu Ser
                275                 280                 285

Glu Pro Asp Phe Arg Ile Cys Val Val Ser Ser Gln Asp Thr Leu Leu
            290                 295                 300

Pro Thr Ile Phe Glu Ile Asp Ala Leu Phe Ser Ser Thr Pro Leu Arg
305                 310                 315                 320

Gln Asn Met Pro Gln His Met Phe Gln Arg Leu Lys Glu Gly Tyr Arg
                    325                 330                 335

Asn Ile Ile Ile Ala Ile Val Asp Tyr Gly Val Ile Ser Tyr Ile Arg
                340                 345                 350

Leu Ser Asp Val Cys Phe Glu Glu Lys Val Tyr Thr Asp Phe Ser Lys
                355                 360                 365

Lys Gly Ser Lys Arg Lys Arg Val Ser Lys Phe Gln Gln Leu Val
                    370                 375                 380

<210> SEQ ID NO 47
<211> LENGTH: 148
<212> TYPE: PRT
<213> ORGANISM: Saccaromyces cerevisiae
<220> FEATURE:
<223> OTHER INFORMATION: ScSen15

<400> SEQUENCE: 47

Met Lys Asp Ile Ile Asn Cys Arg Arg Glu Ile Thr Ser Arg Arg Leu
1               5                   10                  15

Arg Lys Ile Arg Met Ala Thr Thr Asp Ile Ile Ser Leu Val Lys Asn
                20                  25                  30

Asn Leu Leu Tyr Phe Gln Met Trp Thr Glu Val Glu Ile Leu Gln Asp
            35                  40                  45

Asp Leu Ser Trp Lys Gly Asn Ser Leu Arg Leu Leu Arg Gly Arg Pro
        50                  55                  60

Pro His Lys Leu Ser Asn Asp Val Asp Thr Glu His Glu Asn Ser Leu
65                  70                  75                  80

Ser Ser Pro Arg Pro Leu Glu Phe Ile Leu Pro Ile Asn Met Ser Gln
                85                  90                  95

Tyr Lys Glu Asn Phe Leu Thr Leu Glu Cys Leu Ser Gln Thr Phe Thr
                100                 105                 110

His Leu Cys Ser Pro Ser Thr Glu Arg Ile Leu Leu Ala Ile Ile Asn
            115                 120                 125

Asp Asp Gly Thr Ile Val Tyr Tyr Phe Val Tyr Lys Gly Val Arg Lys
        130                 135                 140
```

Pro Lys Arg Asn
           145

<210> SEQ ID NO 48
<211> LENGTH: 143
<212> TYPE: PRT
<213> ORGANISM: Schizosaccaromyces pombe
<220> FEATURE:
<223> OTHER INFORMATION: SpSen15

<400> SEQUENCE: 48

Met Gln His Asn Thr Phe Leu Pro Asn Asp Ala Val Glu Gln Lys
1               5                   10                  15

Gln Asn Pro Tyr Tyr Gly Ile Leu Arg Ala Val Glu Thr Asp Leu Arg
                20                  25                  30

Leu Gly Gln Arg Trp Cys Glu Leu Lys Val His Val Leu Asp Ile Asp
                35                  40                  45

Leu Lys Thr Lys Arg Pro Leu Leu Ser Gly Ile Pro Val Asn Gly Gln
        50                  55                  60

Leu Lys Asp Lys Leu Gln Tyr Val Leu Pro Leu Tyr Leu Gln Glu Thr
65                  70                  75                  80

Ile Ser Ile Glu Phe Leu Ser Ser Val Phe Asp Ser Met Lys Lys Leu
                85                  90                  95

Ser Leu Pro Leu Val Lys Asp Ala Arg Gly Leu Ser Gly Asp Glu Phe
                100                 105                 110

Phe Leu Tyr Leu Gly Ile Met Cys Ser Asp Ser Thr Ile Val Tyr Tyr
                115                 120                 125

Lys Ile Thr Asp Gly Leu Ile Lys Pro Arg Gln Asn Asp Glu Glu
        130                 135                 140

<210> SEQ ID NO 49
<211> LENGTH: 423
<212> TYPE: PRT
<213> ORGANISM: Drosophilia melanogaster
<220> FEATURE:
<223> OTHER INFORMATION: D.m. Clp1

<400> SEQUENCE: 49

Met Ser Glu Asp Gln Gly Lys Asp Tyr Thr Leu Glu Ser Asp Ser Glu
1               5                   10                  15

Leu Arg Phe Glu Ile Glu Gln Lys Asp Ala Lys Val Leu Val Ser Leu
                20                  25                  30

Val Ser Gly Phe Ala Glu Leu Phe Gly Thr Glu Leu Val Lys Lys Lys
                35                  40                  45

Gln Tyr Glu Phe Gly Val Gly Ala Lys Val Ala Ile Phe Thr Tyr Gln
        50                  55                  60

Gly Cys Val Leu His Val Ser Gly Lys Met Asp Val Cys Tyr Ile Ser
65                  70                  75                  80

Lys Glu Thr Pro Met Val Gln Tyr Val Asn Cys His Ala Ala Leu Glu
                85                  90                  95

Gln Phe Arg Met Glu Ala Glu Lys Asp Arg Tyr Gly Pro Val Ala
                100                 105                 110

Met Val Val Gly Pro Met Asp Val Gly Lys Ser Thr Leu Cys Arg Ile
                115                 120                 125

Leu Leu Asn Tyr Ala Val Arg Val Gly Arg Arg Pro Leu Tyr Ala Asp
        130                 135                 140

Asp Asp Val Cys Gln Gly Ser Ile Ala Ile Ser Gly Ser Val Ala Thr
145                 150                 155                 160

```
Ile Leu Ile Glu Arg Pro Ala Asn Val Glu Glu Gly Phe Ala Lys Thr
            165                 170                 175
Ala Pro Leu Val Tyr His Phe Gly His Lys Ser Pro Ser Gly Asn Ser
            180                 185                 190
Val Leu Tyr Asn Ala Val Val Ser Lys Met Ala Glu Val Thr Leu Gln
            195                 200                 205
Ser Leu Asn Ser Asn Lys Arg Thr Lys Ser Ser Gly Ile Thr Thr Asn
210                 215                 220
Thr Cys Gly Trp Val Lys Gly Ser Gly Tyr Ala His Leu Leu His Ala
225                 230                 235                 240
Ala Lys Ala Tyr Gly Ala Cys Ala Ile Phe Val Leu Asp Gln Glu Arg
            245                 250                 255
Leu Tyr Asn Glu Leu Leu Arg Asp Val Pro Lys Gly Val His Val Val
            260                 265                 270
Leu Leu Pro Lys Ser Gly Gly Val Val Glu Arg Ser Lys Glu Leu Arg
            275                 280                 285
His Glu Ala Arg Asp Gln Arg Ile Lys Glu Tyr Phe Tyr Gly Asn Thr
            290                 295                 300
Arg Ala Pro Phe Tyr Pro Phe Ser Phe Glu Val Lys Phe Gln Asp Leu
305                 310                 315                 320
Arg Leu Tyr Lys Ile Gly Ala Pro Pro Leu Pro Asp Ser Cys Met Pro
            325                 330                 335
Ile Gly Met Lys Ala Glu Asp Asn Lys Thr Lys Val Val Ala Val Thr
            340                 345                 350
Pro Thr Pro Ala Leu Ile His His Val Leu Ala Leu Ser Phe Ala Glu
            355                 360                 365
Ser Val Glu Asp Asp Val Ile Gly Thr Asn Val Ala Gly Phe Cys Cys
            370                 375                 380
Val Thr Glu Val Asp Met Glu Arg Gln Ala Val Met Leu Leu Ser Pro
385                 390                 395                 400
Gln Pro Arg Pro Leu Pro Pro Asn Ala Leu Leu Leu Trp Ser Glu Leu
            405                 410                 415
Gln Phe Met Asp Asn His Thr

<210> SEQ ID NO 50
<211> LENGTH: 428
<212> TYPE: PRT
<213> ORGANISM: Caenorhabditis elegans
<220> FEATURE:
<223> OTHER INFORMATION: C.e. Clp1

<400> SEQUENCE: 50

Met Ser Glu Glu Asn Val Gln Glu Phe Val Leu Lys Glu Asp Cys Glu
1               5                   10                  15
Leu Arg Phe Ala Ala Gly Asp Asp Ser Asp Val Cys Leu Glu Leu Val
            20                  25                  30
Lys Gly Tyr Ala Glu Ile Phe Gly Thr Glu Leu Leu Leu Asn Lys Lys
            35                  40                  45
Tyr Thr Phe Pro Ala Lys Ser Arg Val Ala Ala Phe Thr Trp Lys Gly
        50                  55                  60
Ala Thr Ile Glu Leu Val Gly Thr Thr Glu Ser Ala Tyr Val Ala Glu
65                  70                  75                  80
Ser Thr Pro Met Val Ile Tyr Leu Asn Ile His Ala Ala Met Glu Glu
            85                  90                  95
Val Arg Lys Lys Arg Glu Glu Gln Ala Ala Gly Asn Ser Asn Lys Ala
```

```
                100                 105                 110
Lys Gly Pro Arg Leu Leu Val Gly Pro Thr Asp Val Gly Lys Thr
        115                 120                 125

Thr Val Ser Arg Ile Leu Cys Asn Tyr Ser Val Arg Gln Gly Arg Thr
        130                 135                 140

Pro Ile Phe Val Glu Leu Asp Val Gly Gln Asn Ser Val Ser Val Pro
145                 150                 155                 160

Gly Thr Val Ala Ala Val Leu Val Gln Lys Thr Ala Asp Val Ile Asp
                165                 170                 175

Gly Phe Glu Arg Asn Gln Pro Ile Val Phe Asn Phe Gly His Thr Ser
        180                 185                 190

Pro Ser Ala Asn Leu Ser Leu Tyr Glu Ala Leu Phe Lys Glu Met Ala
        195                 200                 205

Thr Thr Leu Asn Ala Gln Ile Gln Glu Asn Asp Glu Ala Lys Ile Gly
        210                 215                 220

Gly Met Ile Ile Asn Thr Cys Gly Trp Val Asp Gly Glu Gly Tyr Lys
225                 230                 235                 240

Cys Ile Val Lys Ala Ala Ser Ala Phe Glu Val Asp Val Ile Val
                245                 250                 255

Leu Asp His Glu Arg Leu Tyr Ser Asp Leu Ser Lys Glu Leu Pro Glu
                260                 265                 270

Phe Val Arg Leu Thr His Val Pro Lys Ser Gly Val Glu Gln Arg
        275                 280                 285

Thr Gly Gln Ile Arg Ser Lys Met Arg Gly Glu Asn Val His Arg Tyr
        290                 295                 300

Phe Tyr Gly Thr Arg Ala Asn Asn Leu Tyr Pro Phe Thr Phe Asp Val
305                 310                 315                 320

Ser Phe Asp Asp Val Thr Leu Cys Lys Ile Gly Ala Glu Gln Leu Pro
                325                 330                 335

Asp Ser Cys Leu Pro Phe Gly Met Glu Val Glu Asn His Glu Thr Lys
                340                 345                 350

Leu Val Ile Met Glu Pro Ser Ala Asp Ile Lys His His Leu Phe Ala
        355                 360                 365

Phe Ser Arg Ser Thr Lys Ala Asp Glu Asn Val Leu Lys Ser Pro Val
        370                 375                 380

Phe Gly Phe Cys Leu Val Thr Glu Val Asp Leu Glu Lys Arg Thr Met
385                 390                 395                 400

Ser Ile Leu Cys Pro Gln Arg Thr Leu Pro Ser Lys Val Leu Val Phe
                405                 410                 415

Ser Asp Ile Thr His Leu Asp Asp Gln Ile Lys Arg
                420                 425

<210> SEQ ID NO 51
<211> LENGTH: 423
<212> TYPE: PRT
<213> ORGANISM: Arabidopsis thaliana
<220> FEATURE:
<223> OTHER INFORMATION: A.t.1. Clp1

<400> SEQUENCE: 51

Met Phe Gly Pro Gln Ile Arg Arg Val Lys Leu Glu Lys Gln Ser Glu
1               5                   10                  15

Leu Arg Ile Glu Leu Gln Pro Thr Ser Pro Leu Arg Leu Arg Leu Leu
            20                  25                  30

Asp Gly Lys Ala Glu Ile Phe Gly Tyr Glu Leu Pro His Glu Val Trp
        35                  40                  45
```

Ile Thr Phe Pro Pro Leu Met Thr Phe Ala Val Phe Thr Trp Tyr Gly
     50                  55                  60

Ala Thr Ile Glu Ile Asp Gly Ile Thr Gly Asn Glu Tyr Ile Ser Cys
 65                  70                  75                  80

Glu Thr Pro Met Val Asn Tyr Leu Gly Leu His Asn Ser Leu Gln Val
                 85                  90                  95

Gln Arg His Arg Val Thr Ser Ser Thr Arg Asp Ser Ala Ser Ser Gln
            100                 105                 110

Glu Gly Pro Arg Val Ile Ile Val Gly Asp Ile Asp Ser Gly Lys Ser
            115                 120                 125

Thr Leu Ala Lys Met Leu Leu Asn Trp Ala Val Lys Asp Gly Trp Lys
        130                 135                 140

Pro Thr Phe Val Asp Leu Asn Val Gly Gln Ser Ser Ile Thr Ile Pro
145                 150                 155                 160

Gly Thr Ile Ala Ala Pro Ile Lys Met Leu Val Asp Pro Val Glu
            165                 170                 175

Gly Phe Pro Leu Asp Lys Ala Leu Ile His Tyr Phe Gly Leu Thr Asn
            180                 185                 190

Pro Ser Val Asn Leu Arg Leu Tyr Arg Thr Leu Val Glu Glu Leu Ala
            195                 200                 205

Arg Glu Leu Lys Glu Glu Phe Ser Ala Asn Ala Glu Ser Arg Ala Ser
210                 215                 220

Gly Met Val Ile Asp Thr Met Gly Phe Ile Val Arg Glu Gly Tyr Thr
225                 230                 235                 240

Leu Leu Leu His Ala Ile Arg Thr Phe Asn Ala Ser Leu Val Ile Val
                245                 250                 255

Val Gly Gln Glu Lys Leu Val Tyr Asp Leu Lys Lys Asn Leu Lys Phe
            260                 265                 270

Lys Lys Asn Leu Gln Val Leu Asn Leu Glu Lys Ser Glu Gly Val Phe
        275                 280                 285

Ser Arg Ser Ser Asp Phe Arg Lys Thr Leu Arg Asn Ser Asn Ile Gln
        290                 295                 300

Asn Tyr Phe Tyr Gly Val Thr Asn Asp Leu Thr Val Tyr Thr Lys Thr
305                 310                 315                 320

Val Lys Phe Ser Asp Val Gln Val Tyr Arg Ile Gly Asp Phe Arg Val
                325                 330                 335

Ser Gly Ser Thr Ser Ala His Gln Arg Gly Asn Asp Pro Leu Lys Ile
            340                 345                 350

Thr Leu Val Thr Ile Asp Glu His Leu Val Asn Lys Val Leu Ala Ile
        355                 360                 365

Ser Tyr Ala Ile Lys Pro Asp Gln Ile Ile Ser Ile Val Ala Gly
    370                 375                 380

Phe Val Cys Ile Lys Asn Val Asp Ile Ser Glu Glu Arg Ile Thr Tyr
385                 390                 395                 400

Val Ser Pro Ser Ala Ala Glu Leu Pro Ser Lys Ile Leu Ile Leu Gly
            405                 410                 415

Thr Leu Thr Trp His Val Thr
            420

<210> SEQ ID NO 52
<211> LENGTH: 444
<212> TYPE: PRT
<213> ORGANISM: Arabidopsis thaliana
<220> FEATURE:
<223> OTHER INFORMATION: A.t.2 Clp1

```
<400> SEQUENCE: 52

Met Ala Tyr Gly Gly Pro Ser Met Asn Pro Ala Leu Ser Gly Ala
1               5                   10                  15

Val Pro Gly Ser Ala Asn Leu Lys Gln Val Lys Leu Glu Arg Glu Ser
            20                  25                  30

Glu Leu Arg Ile Glu Val Ser Glu Glu Pro Leu Arg Leu Arg Val Val
        35                  40                  45

Asn Gly Thr Ala Glu Ile Phe Gly Ser Glu Leu Pro Pro Glu Ile Trp
    50                  55                  60

Arg Thr Phe Pro Pro Arg Met Lys Phe Ala Val Phe Thr Trp Tyr Gly
65                  70                  75                  80

Ala Thr Ile Glu Met Asp Gly Val Thr Glu Thr Asp Tyr Thr Ala Asp
                85                  90                  95

Glu Thr Pro Met Val Ser Tyr Ile Asn Val His Ala Ile Leu Asp Ala
            100                 105                 110

Arg Arg Arg Phe Ala Lys Ala Ser Thr Ser Asn Asp Pro Glu Ser Ser
        115                 120                 125

Gln Gly Pro Arg Val Ile Val Gly Pro Thr Asp Ser Gly Lys Ser
    130                 135                 140

Thr Leu Thr Lys Met Leu Leu Ser Trp Ala Ala Lys Gln Gly Trp Arg
145                 150                 155                 160

Pro Thr Phe Val Asp Leu Asp Val Gly Gln Gly Ser Ile Thr Ile Pro
                165                 170                 175

Gly Ser Ile Ala Ala Ala Pro Ile Glu Met Pro Leu Asp Pro Val Glu
            180                 185                 190

Gly Phe Pro Leu Asp Met Ala Leu Val Tyr Tyr Tyr Gly His Ala Ser
        195                 200                 205

Pro Asn Met Asn Val Glu Leu Tyr Lys Ala Leu Val Lys Glu Leu Ala
    210                 215                 220

Gln Val Leu Glu Lys Gln Phe Val Gly Asn Pro Glu Ser Arg Ala Ala
225                 230                 235                 240

Gly Met Val Ile Asn Thr Met Gly Trp Ile Glu Gly Ile Gly Tyr Glu
                245                 250                 255

Leu Leu Leu His Ala Ile Asp Thr Phe Asn Ala Ser Val Val Leu Val
            260                 265                 270

Leu Gly Gln Glu Lys Leu Phe Ser Arg Leu Lys Asp Val Leu Arg Ser
        275                 280                 285

Lys Ser Asn Val Asp Val Val Lys Leu His Lys Ser Gly Gly Val Val
    290                 295                 300

Ala Arg Val Lys Glu Val Arg Lys Arg Ser Arg Asn Phe Lys Ile Gln
305                 310                 315                 320

Glu Tyr Phe Tyr Gly Leu Ser Lys Glu Leu Ser Pro Tyr Ala Asn Thr
                325                 330                 335

Ser Ser Phe Ser Asp Leu Gln Val Phe Arg Ile Gly Gly Pro Gln
            340                 345                 350

Ala Pro Lys Ser Ala Leu Pro Ala Gly Ser Thr Ser Val Ser Asn Pro
        355                 360                 365

Leu Arg Val Thr Pro Val Asn Ile Asp Asp Arg Asp Leu Leu His Ser
    370                 375                 380

Val Leu Ala Val Ser Tyr Ala Glu Glu Pro Asp Gln Ile Ile Ser Ser
385                 390                 395                 400

Asn Val Ser Gly Phe Val Tyr Val Thr Glu Val Asn Val Gln Lys Lys
                405                 410                 415
```

```
Lys Ile Thr Tyr Leu Ala Pro Ser Pro Gly Thr Leu Pro Ser Lys Leu
            420                 425                 430

Leu Val Ala Gly Ser Leu Ala Trp Leu Glu Ser Val
            435                 440

<210> SEQ ID NO 53
<211> LENGTH: 456
<212> TYPE: PRT
<213> ORGANISM: Schizosaccaromyces pombe
<220> FEATURE:
<223> OTHER INFORMATION: S.p.Clp1

<400> SEQUENCE: 53

Met Lys Glu Ile Phe Ile Pro Lys Glu Cys Glu Trp Arg Phe Glu Val
1               5                   10                  15

Asp Glu Pro Ala Ile Gln Ile Arg Leu Val Ser Gly Asn Ala Glu Tyr
            20                  25                  30

Phe Gly Thr Glu Leu Ala Leu Gly Pro Pro Tyr His Phe Thr Arg Val
        35                  40                  45

Lys Gly Ala Ile Tyr Thr Trp Gln Gly Cys Thr Leu Glu Val Glu Gly
    50                  55                  60

Glu Pro Ser Val Glu Tyr Val Ala Glu Thr Pro Met Ser Thr Tyr
65                  70                  75                  80

Leu Asn Leu His Phe Ala Leu Gly Leu Arg Leu Gln Ala Glu Asn
                85                  90                  95

Ala Ala Ala Asn Asp Glu Ser Tyr Gly Pro Cys Val Cys Leu Ile
            100                 105                 110

Gly Pro Arg Ser Cys Gly Lys Thr Ser Val Leu Lys Ile Leu Glu Ser
        115                 120                 125

Tyr Ala Leu Lys Gln Ser Arg Glu Pro Ile Cys Val Asn Leu Gln Pro
    130                 135                 140

Thr Gln Pro Met Leu Ala Leu Pro Gly Ser Ile Ser Ala Phe His Asn
145                 150                 155                 160

Ala Thr Ile Leu Asp Ile Gln Asp Ala Asp Gly Phe Gly Ala Ser Thr
                165                 170                 175

Ser Thr Gly Pro Thr His Val Leu Ala Lys Val Pro Leu Val Tyr Asn
            180                 185                 190

Phe Gly Leu Asp Ser Pro Leu Asp Asn Pro Lys Leu Tyr Lys Leu Ser
        195                 200                 205

Leu Ser Arg Leu Ala Leu Ala Val His Ser Arg Met Ser Gln Ser Lys
    210                 215                 220

Asp Ala Arg Val Ser Gly Cys Leu Val Asp Thr Ser Ser Ile Gln Glu
225                 230                 235                 240

Asn Ala Glu Lys Tyr Gln Asp Ile Leu His Ser Ile Ile Thr Asp Phe
                245                 250                 255

Arg Ile Asn Ile Ile Val Leu Gly Ser Arg Leu Tyr Ser Ser
            260                 265                 270

Met Lys Arg Lys Tyr Ala Asp Ala Thr Trp Leu Ser Val Val Lys Val
        275                 280                 285

Ser Ser Ser Gly Gly Cys Ile Asp Arg Glu Glu Trp Ile Gln Gln
    290                 295                 300

Phe Gln Ala Arg Cys Ile Lys Gln Tyr Phe Tyr Gly Asp Asp Arg Met
305                 310                 315                 320

Pro Leu Ser Pro Leu Ser Met Ile Val Asp Ser Thr Gln Leu Val Val
                325                 330                 335
```

```
Tyr Arg Val Leu Glu Ala Ser Glu Ser Gly Pro Lys Ser Val Leu
            340                 345                 350

Pro Leu Gly Phe Glu Glu Asn Thr Gln Ser Glu Lys Gln Asp Gly
            355                 360                 365

Asn Thr Ser Leu Arg Leu His Gly Lys Gly Glu Phe Leu Glu Arg Ile
            370                 375                 380

Ser Thr Glu Ala Met Thr Ile Leu Gln Asn Ser Ile Leu Ala Val Ser
385                 390                 395                 400

Ser Val Gly Glu Asp Glu Asp Glu Ala Thr Val Asp Ser Cys Ile
                405                 410                 415

Ile Gly Tyr Val Phe Val Ser Asp Val Asp Val Lys Asn Arg Met
            420                 425                 430

Thr Leu Leu Ser Pro Val Pro Glu Gln Leu Pro Ser Asn Ala Leu Ile
            435                 440                 445

Met Gly Thr Cys Lys Trp Gln Glu
            450                 455

<210> SEQ ID NO 54
<211> LENGTH: 445
<212> TYPE: PRT
<213> ORGANISM: Saccaromyces cerevisiae
<220> FEATURE:
<223> OTHER INFORMATION: S.c. Clp1

<400> SEQUENCE: 54

Met Ala Ser Leu Pro Gly Ile Asp Glu His Thr Thr Ser Glu Glu Leu
1               5                   10                  15

Ile Thr Gly Asp Asn Glu Trp His Lys Leu Val Ile Pro Lys Gly Ser
            20                  25                  30

Asp Trp Gln Ile Asp Leu Lys Ala Glu Gly Lys Leu Ile Val Lys Val
        35                  40                  45

Asn Ser Gly Ile Val Glu Ile Phe Gly Thr Glu Leu Ala Val Asp Asp
    50                  55                  60

Glu Tyr Thr Phe Gln Asn Trp Lys Phe Pro Ile Tyr Ala Val Glu Glu
65                  70                  75                  80

Thr Glu Leu Leu Trp Lys Cys Pro Asp Leu Thr Thr Asn Thr Ile Thr
                85                  90                  95

Val Lys Pro Asn His Thr Met Lys Tyr Ile Tyr Asn Leu His Phe Met
            100                 105                 110

Leu Glu Lys Ile Arg Met Ser Asn Phe Glu Gly Pro Arg Val Ile
        115                 120                 125

Val Gly Gly Ser Gln Thr Gly Lys Thr Ser Leu Ser Arg Thr Leu Cys
130                 135                 140

Ser Tyr Ala Leu Lys Phe Asn Ala Tyr Gln Pro Leu Tyr Ile Asn Leu
145                 150                 155                 160

Asp Pro Gln Gln Pro Ile Phe Thr Val Pro Gly Cys Ile Ser Ala Thr
                165                 170                 175

Pro Ile Ser Asp Ile Leu Asp Ala Gln Leu Pro Thr Trp Gly Gln Ser
            180                 185                 190

Leu Thr Ser Gly Ala Thr Leu Leu His Asn Lys Gln Pro Met Val Lys
        195                 200                 205

Asn Phe Gly Leu Glu Arg Ile Asn Glu Asn Lys Asp Leu Tyr Leu Glu
    210                 215                 220

Cys Ile Ser Gln Leu Gly Gln Val Val Gly Gln Arg Leu His Leu Asp
225                 230                 235                 240

Pro Gln Val Arg Arg Ser Gly Cys Ile Val Asp Thr Pro Ser Ile Ser
```

```
                        245                 250                 255
Gln Leu Asp Glu Asn Leu Ala Glu Leu His His Ile Ile Glu Lys Leu
            260                 265                 270

Asn Val Asn Ile Met Leu Val Leu Cys Ser Glu Thr Asp Pro Leu Trp
            275                 280                 285

Glu Lys Val Lys Lys Thr Phe Gly Pro Glu Leu Gly Asn Asn Asn Ile
            290                 295                 300

Phe Phe Ile Pro Lys Leu Asp Gly Val Ser Ala Val Asp Val Tyr
305                 310                 315                 320

Lys Arg Ser Leu Gln Arg Thr Ser Ile Arg Glu Tyr Phe Tyr Gly Ser
            325                 330                 335

Leu Asp Thr Ala Leu Ser Pro Tyr Ala Ile Gly Val Asp Tyr Glu Asp
            340                 345                 350

Leu Thr Ile Trp Lys Pro Ser Asn Val Phe Asp Asn Glu Val Gly Arg
            355                 360                 365

Val Glu Leu Phe Pro Val Thr Ile Thr Pro Ser Asn Leu Gln His Ala
            370                 375                 380

Ile Ile Ala Ile Thr Phe Ala Glu Arg Arg Ala Asp Gln Ala Thr Val
385                 390                 395                 400

Ile Lys Ser Pro Ile Leu Gly Phe Ala Leu Ile Thr Glu Val Asn Glu
            405                 410                 415

Lys Arg Arg Lys Leu Arg Val Leu Pro Val Pro Gly Arg Leu Pro
            420                 425                 430

Ser Lys Ala Met Ile Leu Thr Ser Tyr Arg Tyr Leu Glu
            435                 440                 445

<210> SEQ ID NO 55
<211> LENGTH: 465
<212> TYPE: PRT
<213> ORGANISM: Homo sapiens
<220> FEATURE:
<223> OTHER INFORMATION: HsSen2 (See Fig 6)

<400> SEQUENCE: 55

Met Ala Glu Ala Val Phe His Ala Pro Lys Arg Lys Arg Val Tyr
1               5                   10                  15

Glu Thr Tyr Glu Ser Pro Leu Pro Ile Pro Phe Gly Gln Asp His Gly
            20                  25                  30

Pro Leu Lys Glu Phe Lys Ile Phe Arg Ala Glu Met Ile Asn Asn Asn
            35                  40                  45

Val Ile Val Arg Asn Ala Glu Asp Ile Glu Gln Leu Tyr Gly Lys Gly
        50                  55                  60

Tyr Phe Gly Lys Gly Ile Leu Ser Arg Ser Arg Pro Ser Phe Thr Ile
65                  70                  75                  80

Ser Asp Pro Lys Leu Val Ala Lys Trp Lys Asp Met Lys Thr Asn Met
            85                  90                  95

Pro Ile Ile Thr Ser Lys Arg Tyr Gln His Ser Val Glu Trp Ala Ala
            100                 105                 110

Glu Leu Met Arg Arg Gln Gly Gln Asp Glu Ser Thr Val Arg Arg Ile
            115                 120                 125

Leu Lys Asp Tyr Thr Lys Pro Leu Glu His Pro Val Lys Arg Asn
            130                 135                 140

Glu Glu Ala Gln Val His Asp Lys Leu Asn Ser Gly Met Val Ser Asn
145                 150                 155                 160

Met Glu Gly Thr Ala Gly Gly Glu Arg Pro Ser Val Val Asn Gly Asp
            165                 170                 175
```

Ser Gly Lys Ser Gly Gly Val Gly Asp Pro Arg Glu Pro Leu Gly Cys
            180                 185                 190

Leu Gln Glu Gly Ser Gly Cys His Pro Thr Thr Glu Ser Phe Glu Lys
        195                 200                 205

Ser Val Arg Glu Asp Ala Ser Pro Leu Pro His Val Cys Cys Cys Lys
    210                 215                 220

Gln Asp Ala Leu Ile Leu Gln Arg Gly Leu His His Glu Asp Gly Ser
225                 230                 235                 240

Gln His Ile Gly Leu Leu His Pro Gly Asp Arg Gly Pro Asp His Glu
            245                 250                 255

Tyr Val Leu Val Glu Glu Ala Glu Cys Ala Met Ser Glu Arg Glu Ala
        260                 265                 270

Ala Pro Asn Glu Glu Leu Val Gln Arg Asn Arg Leu Ile Cys Arg Arg
    275                 280                 285

Asn Pro Tyr Arg Ile Phe Glu Tyr Leu Gln Leu Ser Leu Glu Glu Ala
290                 295                 300

Phe Phe Leu Val Tyr Ala Leu Gly Cys Leu Ser Ile Tyr Tyr Glu Lys
305                 310                 315                 320

Glu Pro Leu Thr Ile Val Lys Leu Trp Lys Ala Phe Thr Val Val Gln
            325                 330                 335

Pro Thr Phe Arg Thr Thr Tyr Met Ala Tyr His Tyr Phe Arg Ser Lys
        340                 345                 350

Gly Trp Val Pro Lys Val Gly Leu Lys Tyr Gly Thr Asp Leu Leu Leu
    355                 360                 365

Tyr Arg Lys Gly Pro Pro Phe Tyr His Ala Ser Tyr Ser Val Ile Ile
    370                 375                 380

Glu Leu Val Asp Asp His Phe Glu Gly Ser Leu Arg Arg Pro Leu Ser
385                 390                 395                 400

Trp Lys Ser Leu Ala Ala Leu Ser Arg Val Ser Val Asn Val Ser Lys
            405                 410                 415

Glu Leu Met Leu Cys Tyr Leu Ile Lys Pro Ser Thr Met Thr Asp Lys
        420                 425                 430

Glu Met Glu Ser Pro Glu Cys Met Lys Arg Ile Lys Val Gln Glu Val
    435                 440                 445

Ile Leu Ser Arg Trp Val Ser Ser Arg Glu Arg Ser Asp Gln Gln Gln
    450                 455                 460

Leu
465

<210> SEQ ID NO 56
<211> LENGTH: 5
<212> TYPE: PRT
<213> ORGANISM: Saccaromyces cerevisiae
<220> FEATURE:
<223> OTHER INFORMATION: active site motif of tRNA splicing endonuclease
      Sen2 subunit

<400> SEQUENCE: 56

Tyr Arg Gly Gly Tyr
1               5

<210> SEQ ID NO 57
<211> LENGTH: 526
<212> TYPE: PRT
<213> ORGANISM: Homo sapiens
<220> FEATURE:
<223> OTHER INFORMATION: HsSen54

<400> SEQUENCE: 57

```
Met Glu Pro Asp Pro Glu Pro Ala Ala Val Glu Val Pro Ala Gly Arg
1               5                   10                  15

Val Leu Ser Ala Arg Glu Leu Phe Ala Ala Arg Ser Arg Ser Gln Lys
            20                  25                  30

Leu Pro Gln Arg Ser His Gly Pro Lys Asp Phe Leu Pro Asp Gly Ser
        35                  40                  45

Ala Ala Gln Ala Glu Arg Leu Arg Cys Arg Glu Glu Leu Trp Gln
    50                  55                  60

Leu Leu Ala Glu Gln Arg Val Glu Arg Leu Gly Ser Leu Val Ala Ala
65                  70                  75                  80

Glu Trp Arg Pro Glu Glu Gly Phe Val Glu Leu Lys Ser Pro Ala Gly
                85                  90                  95

Lys Phe Trp Gln Thr Met Gly Phe Ser Glu Gln Gly Arg Gln Arg Leu
            100                 105                 110

His Pro Glu Glu Ala Leu Tyr Leu Leu Glu Cys Gly Ser Ile His Leu
        115                 120                 125

Phe His Gln Asp Leu Pro Leu Ser Ile Gln Glu Ala Tyr Gln Leu Leu
    130                 135                 140

Leu Thr Asp His Thr Val Thr Phe Leu Gln Tyr Gln Val Phe Ser His
145                 150                 155                 160

Leu Lys Arg Leu Gly Tyr Val Val Arg Arg Phe Gln Pro Ser Ser Val
                165                 170                 175

Leu Ser Pro Tyr Glu Arg Gln Leu Asn Leu Asp Ala Ser Val Gln His
            180                 185                 190

Leu Glu Asp Gly Asp Gly Lys Arg Lys Arg Ser Ser Ser Pro Arg
        195                 200                 205

Ser Ile Asn Lys Lys Ala Lys Ala Leu Asp Asn Ser Leu Gln Pro Lys
    210                 215                 220

Ser Leu Ala Ala Ser Ser Pro Pro Cys Ser Gln Pro Ser Gln Cys
225                 230                 235                 240

Pro Glu Glu Lys Pro Gln Glu Ser Ser Pro Met Lys Gly Pro Gly Gly
                245                 250                 255

Pro Phe Gln Leu Leu Gly Ser Leu Gly Pro Ser Pro Gly Pro Ala Arg
            260                 265                 270

Glu Gly Val Gly Cys Ser Trp Glu Ser Gly Arg Ala Glu Asn Gly Val
        275                 280                 285

Thr Gly Ala Gly Lys Arg Arg Trp Asn Phe Glu Gln Ile Ser Phe Pro
    290                 295                 300

Asn Met Ala Ser Asp Ser Arg His Thr Leu Leu Arg Ala Pro Ala Pro
305                 310                 315                 320

Glu Leu Leu Pro Ala Asn Val Ala Gly Arg Glu Thr Asp Ala Glu Ser
                325                 330                 335

Trp Cys Gln Lys Leu Asn Gln Arg Lys Glu Asn Leu Ser Arg Arg Glu
            340                 345                 350

Arg Glu His His Ala Glu Ala Ala Gln Phe Gln Glu Asp Val Asn Ala
        355                 360                 365

Asp Pro Glu Val Gln Arg Cys Ser Ser Trp Arg Glu Tyr Lys Glu Leu
    370                 375                 380

Leu Gln Arg Arg Gln Val Gln Arg Ser Gln Arg Ala Pro His Leu
385                 390                 395                 400

Trp Gly Gln Pro Val Thr Pro Leu Leu Ser Pro Gly Gln Ala Ser Ser
                405                 410                 415
```

```
Pro Ala Val Val Leu Gln His Ile Ser Val Leu Gln Thr Thr His Leu
            420                 425                 430

Pro Asp Gly Val Arg Leu Leu Glu Lys Ser Gly Leu Glu Ile
            435                 440             445

Ile Phe Asp Val Tyr Gln Ala Asp Ala Val Ala Thr Phe Arg Lys Asn
450                 455                 460

Asn Pro Gly Lys Pro Tyr Ala Arg Met Cys Ile Ser Gly Phe Asp Glu
465                 470                 475                 480

Pro Val Pro Asp Leu Cys Ser Leu Lys Arg Leu Ser Tyr Gln Ser Gly
                485                 490                 495

Asp Val Pro Leu Ile Phe Ala Leu Val Asp His Gly Asp Ile Ser Phe
                500                 505                 510

Tyr Ser Phe Arg Asp Phe Thr Leu Pro Gln Asp Val Gly His

<210> SEQ ID NO 58
<211> LENGTH: 315
<212> TYPE: PRT
<213> ORGANISM: Homo sapiens
<220> FEATURE:
<223> OTHER INFORMATION: HsSen34 (See Fig 6)

<400> SEQUENCE: 58

Met Leu Val Val Glu Val Ala Asn Gly Arg Ser Leu Val Trp Gly Ala
1               5                   10                  15

Glu Ala Val Gln Ala Leu Arg Glu Arg Leu Gly Val Gly Gly Arg Thr
                20                  25                  30

Val Gly Ala Leu Pro Arg Gly Pro Arg Gln Asn Ser Arg Leu Gly Leu
            35                  40                  45

Pro Leu Leu Leu Met Pro Glu Glu Ala Arg Leu Leu Ala Glu Ile Gly
        50                  55                  60

Ala Val Thr Leu Val Ser Ala Pro Arg Pro Asp Ser Arg His His Ser
65                  70                  75                  80

Leu Ala Leu Thr Ser Phe Lys Arg Gln Gln Glu Ser Phe Gln Glu
                85                  90                  95

Gln Ser Ala Leu Ala Glu Ala Arg Glu Thr Arg Arg Gln Glu Val
            100                 105                 110

Leu Glu Lys Ile Thr Glu Gly Gln Ala Ala Lys Lys Gln Lys Leu Glu
        115                 120                 125

Gln Ala Ser Gly Ala Ser Ser Gln Glu Ala Gly Ser Ser Gln Ala
    130                 135                 140

Ala Lys Glu Asp Glu Thr Ser Asp Gly Gln Ala Ser Gly Glu Gln Glu
145                 150                 155                 160

Glu Ala Gly Pro Ser Ser Gln Ala Gly Pro Ser Asn Gly Val Ala
                165                 170                 175

Pro Leu Pro Arg Ser Ala Leu Leu Val Gln Leu Ala Thr Ala Arg Pro
                180                 185                 190

Arg Pro Val Lys Ala Arg Pro Leu Asp Trp Arg Val Gln Ser Lys Asp
        195                 200                 205

Trp Pro His Ala Gly Arg Pro Ala His Glu Leu Arg Tyr Ser Ile Tyr
    210                 215                 220

Arg Asp Leu Trp Glu Arg Gly Phe Phe Leu Ser Ala Ala Gly Lys Phe
225                 230                 235                 240

Gly Gly Asp Phe Leu Val Tyr Pro Gly Asp Pro Leu Arg Phe His Ala
                245                 250                 255

His Tyr Ile Ala Gln Cys Trp Ala Pro Glu Asp Thr Ile Pro Leu Gln
            260                 265                 270
```

```
Asp Leu Val Ala Ala Gly Arg Leu Gly Thr Ser Val Arg Lys Thr Leu
        275                 280                 285

Leu Leu Cys Ser Pro Gln Pro Asp Gly Lys Val Val Tyr Thr Ser Leu
        290                 295                 300

Gln Trp Ala Ser Leu Gln Trp Thr Pro Glu Thr
305                 310                 315

<210> SEQ ID NO 59
<211> LENGTH: 5834
<212> TYPE: DNA
<213> ORGANISM: Homo sapiens
<220> FEATURE:
<223> OTHER INFORMATION: CFIIm subunit hPcf11

<400> SEQUENCE: 59
```

| | | | | | |
|---|---|---|---|---|---|
| ggagccgcca | ctgccgccgc | cattttgtgt | ctgtggagaa | agaagcttct | gtggcggctg | 60 |
| gaagtggacg | gagatcaccc | gcgagacggc | ggcgtttcat | acccgaggtt | ccccctgtgt | 120 |
| cgtcccccat | ccccccctccg | cggtcagcat | gtggtgaagc | cggagccgcg | agagagccgg | 180 |
| ggagaggaag | aggagtcgga | agggaggcgg | ggtatccaga | gcggcttcag | cttcagctgc | 240 |
| agcggacctc | ggagggggggc | cgcggcgcaa | tgtcagagca | gacgccggcc | gaggccggtg | 300 |
| ctgcgggggc | cgggaggac | gcctgtcggg | attatcagtc | atcgctcgaa | gacctgacct | 360 |
| tcaatagcaa | gccgcacatc | aatatgctga | ccattctagc | cgaggagaac | ctgcccttcg | 420 |
| ccaaggagat | cgtctctctc | atcgaggccc | aaaccgccaa | ggctccttcc | tcagagaagc | 480 |
| ttcctgttat | gtaccttatg | gattctattg | tgaaaaacgt | tggaagagag | tatctcactg | 540 |
| cctttactaa | aaatctagtt | gcaacattta | tttgtgtgtt | tgaaaaggtg | gatgaaaata | 600 |
| ctaggaaaag | tttatttaag | ttacgttcta | catgggatga | aatattccct | ttgaagaaac | 660 |
| tttatgccct | ggatgtcaga | gtcaattcat | tagatcctgc | ttggcctatt | aaacctctac | 720 |
| cccccaatgt | gaatacgtct | agcatccatg | tgaatcctaa | attttttaaat | aaatcgcccg | 780 |
| aggagccttc | aacacctggt | acagtggtca | gttcccctag | catctccact | cctccaattg | 840 |
| ttcctgatat | acaaaagaat | cttacacaag | aacaactaat | aaggcagcag | ttactggcaa | 900 |
| agcaaaaaca | gttgttagaa | cttcagcaga | aaaagctgga | gcttgagcta | gagcaagcta | 960 |
| aggcacagtt | ggcagtttct | cttagtgttc | agcaggaaac | atccaattta | ggtcctggat | 1020 |
| ctgcaccatc | caaattacat | gtttcacaga | ttccccctat | ggcagttaaa | gctcctcatc | 1080 |
| aggttcctgt | gcaatctgag | aaaagccgtc | caggaccatc | cttacaaatt | caggatttaa | 1140 |
| aaggaactaa | ccgggatcct | cgtctgaaca | ggataagcca | acattctcat | ggaaaagatc | 1200 |
| agagtcacag | gaaagaattt | ctaatgaaca | cattaaacca | gtctgatact | aagacaagta | 1260 |
| aaactatacc | ctctgaaaaa | ctaaattcat | ccaagcaaga | aaaagtaaa | tcaggtgaaa | 1320 |
| aaataaccaa | gaaagaactt | gaccaattag | attctaaatc | gaaatcgaaa | tcgaaatcac | 1380 |
| cctcacctt | gaaaaacaaa | ttatctcaca | caaaagactt | gaaaaatcaa | gaatcggaaa | 1440 |
| gtatgaggtt | gtctgatatg | aacaagagag | atccaagatt | aaaaaaacat | cttcaggata | 1500 |
| agaccgatgg | caaagatgat | gatgtgaaag | agaagagaaa | aactgcagaa | aaaaaggata | 1560 |
| aagatgagca | catgaagtca | tccgaacaca | gactggctgg | aagtagaaat | aaaatcataa | 1620 |
| atggcattgt | acaaaaacag | gatacaataa | cagaagagtc | agaaaaacag | gggacaaaac | 1680 |
| cagggagatc | gagtactaga | aagcgatcaa | gatctcgatc | acccaagtct | aggtcaccaa | 1740 |
| ttatacattc | cccaaagaga | agagataggc | ggtcacccaa | acgaaggcaa | agaagtatgt | 1800 |

```
ctccaacatc gacacctaaa gctggaagaa ttcgccaatc tggagctaag cagtcacata    1860
tggaagagtt tacaccacct tctagggaag acagaaatgc taagagaagt actaaacagg    1920
atattcggga tccaaggcga atgaaaaaga ctgaagagga gcgaccacaa gaaactacaa    1980
atcagcattc tacaaagtca ggcactgaac caaaggagaa tgtagaaaac tggcaaagtt    2040
ccaagtctgc caaaagatgg aaatctggtt gggaagaaaa taaaagctta caacaggttg    2100
atgaacatag taaacctcct catctgaggc atagggagag ctggtcaagc actaaaggaa    2160
ttttatcacc tcgagcccca aagcagcaac agcatcgatt aagtgtagat gccaatcttc    2220
agattcctaa agagttaact cttgcaagca aaagagaatt acttcaaaag acgagtgaac    2280
gtttagcatc tggtgaaatt acacaggatg acttccttgt tgttgtgcat caaattcgac    2340
agctatttca gtatcaagaa ggtgtgcgag aagagcagag atctccattc aatgatcgtt    2400
ttccacttaa gcgacctcga tatgaagatt cagataaacc atttgtagat agtccagcat    2460
caagattcgc cggcctggat acaaatcagc gacttacagc tttagctgaa gacagaccgt    2520
tatttgatgg acctagtagg ccatcagtag caagagatgg cccaacgaag atgattttg     2580 aaggacccaa taaattaagc cctcgaattg atggacctcc cacaccagct tctcttcggt    2640
ttgatgggtc accaggacaa atgggggag gaggcccttt gagatttgag gggccacaag     2700
gtcagctagg aggtgggtgt cctttgagat ttgaaggtcc tccaggacca gtggggacac    2760
ctctgcggtt tgagggccca attggtcaag caggaggagg tggttttcgg tttgaaggtt    2820
cccctggtct gaggtttgag ggatctccag gtggtttgag atttgaggga ccaggaggcc    2880
agcctgtggg tggtctgagg tttgagggac atcgtggtca acctgtgggt ggtctaaggt    2940
ttgagggacc tcatggtcag cctgtgggtg gacttagatt tgataatccc cgaggtcagc    3000
ctgtaggtgg acttagattt gagggggtc atggtccatc aggggctgcg attaggtttg     3060
atggacctca tggtcagcca ggaggtggaa tcagatttga gggccctttg ctacagcaag    3120
gggttggaat gaggtttgag ggccccatg gtcagtcagt agctggtctg agatttgagg      3180
gacaacataa tcaacttggt gggaacctta ggtttgaggg tccacatggt cagccagggg    3240
ttggtatcag gtttgaaggc cctttagtcc aacaaggagg tggaatgagg tttgagggtc    3300
cttctgtacc aggaggtggc ctgagaattg aagggcctct gggtcaaggt ggtccaagat    3360
ttgaaggttg tcatgcttta aggtttgatg ggcagccagg tcagccgtca ctcttgccaa    3420
gatttgatgg attacatggt cagccaggtc ctagatttga aaggactcct ggtcagccag    3480
gccctcagag gttgatggaa ccacctggac agcaggttca acccagattt gacggtgtac    3540
ctcaaagatt tgatggtcca caacatcagc aagcatcaag gtttgatatt cctcttggtc    3600
ttcaaggcac aagatttgac aatcatcctt cacaaaggct tgaatcagta tctttcaatc    3660
agactggtcc atataatgat ccacctggca atgcttttaa tgccccatcc caaggactac    3720
agttccaaag acatgaacaa atatttgatt caccctcaagg accaaatttt aatgaccac    3780 atggccctgg aaaccagagt ttctctaatc cacttaacag agcttctgga cactattttg    3840
atgaaaaaaa tcttcagagt ctcaatttg gaaactttgg caatataacc tgctccaatga    3900 cagtaggaaa tattcaggca tctcaacagg ttctgagtgg tgttgctcag ccagtagctt    3960
ttggtcaagg acaacagttt ttaccagttc atccacaaaa tcctggattt gttcagaatc    4020
cttcaggagc cctccctaag gcatatcctg ataatcatct cagtcaggtg gatgtaaatg    4080
aattgttttc aaaattgcta aaaacaggaa ttctcaaatt gtcccaaact gattcagcta    4140
caacacaagt aagtgaagta actgctcagc ctccccctga agaggaggaa gatcaaaatg    4200
```

| | | |
|---|---|---|
| aagatcaaga tgttccagat cttactaatt ttacagttga agaattgaaa caacgttatg | 4260 | |
| acagtgttat aaatcgactg tacactggta ttcagtgtta ctcttgtgga atgaggttta | 4320 | |
| caacatcaca gacagatgtt tatgcagatc atttggactg gcattatcgg caaaatagaa | 4380 | |
| ctgaaaagga tgttagccga aaagtcactc atagacgttg gtactacagt ttaacagact | 4440 | |
| ggatagaatt tgaggagata gctgatctgg aagaacgggc aaagagccag ttttttgaaa | 4500 | |
| aggtgcatga agaagttgtg ctcaaaactc aagaggctgc taaagaaaaa gagttccaaa | 4560 | |
| gtgtacctgc tggaccagct ggagcagttg agagttgtga atctgtcaa gaacaatttg | 4620 | |
| aacaatactg ggatgaagaa gaggaggaat ggcatttgaa aaatgctatt agagtagatg | 4680 | |
| gaaagattta tcatccatca tgttatgaag attatcaaaa tacatcttca tttgattgta | 4740 | |
| caccatctcc cagcaagaca ccagttgaaa accccttgaa tattatgttg aacattgtca | 4800 | |
| aaaacgaatt gcaggaaccc tgtgacagtc ccaaagttaa ggaagaacga attgatacac | 4860 | |
| caccagcttg tacagaggaa agcatagcaa caccctctga aattaaaaca gaaaatgaca | 4920 | |
| cagtcgagtc agtttaaata aaatgagaaa ggtatgtttt tctttttaa aaaagctgct | 4980 | |
| gttggatcta gaaggtgaag aatttttta tgtatatata gacatatcta tataaattgt | 5040 | |
| ctggctgagg cagggccttc agctatcatt tggttaataa atacattta gtatttgcat | 5100 | |
| ttcctactgc ctgcagagtt tcaggtgctt gttgtgtgaa agttctgtag atgtgtgcaa | 5160 | |
| atttaacgaa atgaaattgt atgtgtaaaa atgtacgatt tttcactgtg caactgtaaa | 5220 | |
| ttataaataa aaaatatttt tgctattcat ggagtgtaat atttatgcac accatcaaat | 5280 | |
| agtttctgta cttttttattg ggtaaaaatg gaattgaaca gcaaccctcaa cataagattt | 5340 | |
| tttttctagt agcctcccac tgattaaaga agcaagtttg aggtttcatc cttcaaaagg | 5400 | |
| gggttccgag agagcaccgt agggcttttc tcaaatagaa aagccagatt ttgaaaaaat | 5460 | |
| tttaaagata aaataggaca tattttgcag atatatatat atatatacac aaacacatct | 5520 | |
| ccaggtatag agaaccatcc agatgttcac ttttgaaaat atctaatgat gcaaagtttt | 5580 | |
| attcttgaac ttggacactg atgccatcaa acaattaaca aatatattta agtactaaag | 5640 | |
| gtgattttt ttttaaagac ttttttcaaat tgtcaaatga tttaatgcag atgaacatat | 5700 | |
| ttctattta agtaacggga atctgtaaga atgtttgctt gagatatggt taactttttt | 5760 | |
| cttttgttgg ttttgactta gatggacacc atgagatgtt aatattcata catgtaataa | 5820 | |
| atagaatgat gaag | 5834 | |

<210> SEQ ID NO 60
<211> LENGTH: 1555
<212> TYPE: PRT
<213> ORGANISM: Homo Sapiens
<220> FEATURE:
<223> OTHER INFORMATION: CFIIm subunit hPcf11

<400> SEQUENCE: 60

```
Met Ser Glu Gln Thr Pro Ala Glu Ala Gly Ala Ala Gly Ala Arg Glu
1               5                   10                  15

Asp Ala Cys Arg Asp Tyr Gln Ser Ser Leu Glu Asp Leu Thr Phe Asn
            20                  25                  30

Ser Lys Pro His Ile Asn Met Leu Thr Ile Leu Ala Glu Glu Asn Leu
        35                  40                  45

Pro Phe Ala Lys Glu Ile Val Ser Leu Ile Glu Ala Gln Thr Ala Lys
    50                  55                  60

Ala Pro Ser Ser Glu Lys Leu Pro Val Met Tyr Leu Met Asp Ser Ile
65                  70                  75                  80
```

```
Val Lys Asn Val Gly Arg Glu Tyr Leu Thr Ala Phe Thr Lys Asn Leu
            85                  90                  95

Val Ala Thr Phe Ile Cys Val Phe Glu Lys Val Asp Glu Asn Thr Arg
            100                 105                 110

Lys Ser Leu Phe Lys Leu Arg Ser Thr Trp Asp Glu Ile Phe Pro Leu
            115                 120                 125

Lys Lys Leu Tyr Ala Leu Asp Val Arg Val Asn Ser Leu Asp Pro Ala
            130                 135                 140

Trp Pro Ile Lys Pro Leu Pro Pro Asn Val Asn Thr Ser Ser Ile His
145                 150                 155                 160

Val Asn Pro Lys Phe Leu Asn Lys Ser Pro Glu Glu Pro Ser Thr Pro
            165                 170                 175

Gly Thr Val Val Ser Ser Pro Ser Ile Ser Thr Pro Pro Ile Val Pro
            180                 185                 190

Asp Ile Gln Lys Asn Leu Thr Gln Glu Gln Leu Ile Arg Gln Gln Leu
            195                 200                 205

Leu Ala Lys Gln Lys Gln Leu Leu Glu Leu Gln Gln Lys Lys Leu Glu
            210                 215                 220

Leu Glu Leu Glu Gln Ala Lys Ala Gln Leu Ala Val Ser Leu Ser Val
225                 230                 235                 240

Gln Gln Glu Thr Ser Asn Leu Gly Pro Gly Ser Ala Pro Ser Lys Leu
            245                 250                 255

His Val Ser Gln Ile Pro Pro Met Ala Val Lys Ala Pro His Gln Val
            260                 265                 270

Pro Val Gln Ser Glu Lys Ser Arg Pro Gly Pro Ser Leu Gln Ile Gln
            275                 280                 285

Asp Leu Lys Gly Thr Asn Arg Asp Pro Arg Leu Asn Arg Ile Ser Gln
            290                 295                 300

His Ser His Gly Lys Asp Gln Ser His Arg Lys Glu Phe Leu Met Asn
305                 310                 315                 320

Thr Leu Asn Gln Ser Asp Thr Lys Thr Ser Lys Thr Ile Pro Ser Glu
            325                 330                 335

Lys Leu Asn Ser Ser Lys Gln Glu Lys Ser Lys Ser Gly Glu Lys Ile
            340                 345                 350

Thr Lys Lys Glu Leu Asp Gln Leu Asp Ser Lys Ser Lys Ser Lys Ser
            355                 360                 365

Lys Ser Pro Ser Pro Leu Lys Asn Lys Leu Ser His Thr Lys Asp Leu
            370                 375                 380

Lys Asn Gln Glu Ser Glu Ser Met Arg Leu Ser Asp Met Asn Lys Arg
385                 390                 395                 400

Asp Pro Arg Leu Lys Lys His Leu Gln Asp Lys Thr Asp Gly Lys Asp
            405                 410                 415

Asp Asp Val Lys Glu Lys Arg Lys Thr Ala Glu Lys Lys Asp Lys Asp
            420                 425                 430

Glu His Met Lys Ser Ser Glu His Arg Leu Ala Gly Ser Arg Asn Lys
            435                 440                 445

Ile Ile Asn Gly Ile Val Gln Lys Gln Asp Thr Ile Thr Glu Glu Ser
            450                 455                 460

Glu Lys Gln Gly Thr Lys Pro Gly Arg Ser Ser Thr Arg Lys Arg Ser
465                 470                 475                 480

Arg Ser Arg Ser Pro Lys Ser Arg Ser Pro Ile Ile His Ser Pro Lys
            485                 490                 495

Arg Arg Asp Arg Arg Ser Pro Lys Arg Arg Gln Arg Ser Met Ser Pro
```

```
                500             505             510
Thr Ser Thr Pro Lys Ala Gly Lys Ile Arg Gln Ser Gly Ala Lys Gln
        515             520             525

Ser His Met Glu Glu Phe Thr Pro Pro Ser Arg Glu Asp Arg Asn Ala
    530             535             540

Lys Arg Ser Thr Lys Gln Asp Ile Arg Asp Pro Arg Arg Met Lys Lys
545             550             555             560

Thr Glu Glu Glu Arg Pro Gln Glu Thr Thr Asn Gln His Ser Thr Lys
                565             570             575

Ser Gly Thr Glu Pro Lys Glu Asn Val Glu Asn Trp Gln Ser Ser Lys
            580             585             590

Ser Ala Lys Arg Trp Lys Ser Gly Glu Glu Asn Lys Ser Leu Gln
        595             600             605

Gln Val Asp Glu His Ser Lys Pro Pro His Leu Arg His Arg Glu Ser
    610             615             620

Trp Ser Ser Thr Lys Gly Ile Leu Ser Pro Arg Ala Pro Lys Gln Gln
625             630             635             640

Gln His Arg Leu Ser Val Asp Ala Asn Leu Gln Ile Pro Lys Glu Leu
                645             650             655

Thr Leu Ala Ser Lys Arg Glu Leu Leu Gln Lys Thr Ser Glu Arg Leu
            660             665             670

Ala Ser Gly Glu Ile Thr Gln Asp Asp Phe Leu Val Val Val His Gln
        675             680             685

Ile Arg Gln Leu Phe Gln Tyr Gln Glu Gly Val Arg Glu Gly Gln Arg
    690             695             700

Ser Pro Phe Asn Asp Arg Phe Pro Leu Lys Arg Pro Arg Tyr Glu Asp
705             710             715             720

Ser Asp Lys Pro Phe Val Asp Ser Pro Ala Ser Arg Phe Ala Gly Leu
                725             730             735

Asp Thr Asn Gln Arg Leu Thr Ala Leu Ala Glu Asp Arg Pro Leu Phe
            740             745             750

Asp Gly Pro Ser Arg Pro Ser Val Ala Arg Asp Gly Pro Thr Lys Met
        755             760             765

Ile Phe Glu Gly Pro Asn Lys Leu Ser Pro Arg Ile Asp Gly Pro Pro
    770             775             780

Thr Pro Ala Ser Leu Arg Phe Asp Gly Ser Pro Gly Gln Met Gly Gly
785             790             795             800

Gly Gly Pro Leu Arg Phe Glu Gly Pro Gln Gly Gln Leu Gly Gly Gly
                805             810             815

Cys Pro Leu Arg Phe Glu Gly Pro Pro Gly Pro Val Gly Thr Pro Leu
            820             825             830

Arg Phe Glu Gly Pro Ile Gly Gln Ala Gly Gly Gly Phe Arg Phe
        835             840             845

Glu Gly Ser Pro Gly Leu Arg Phe Glu Gly Ser Pro Gly Gly Leu Arg
    850             855             860

Phe Glu Gly Pro Gly Gly Gln Pro Val Gly Gly Leu Arg Phe Glu Gly
865             870             875             880

His Arg Gly Gln Pro Val Gly Gly Leu Arg Phe Glu Gly Pro His Gly
                885             890             895

Gln Pro Val Gly Gly Leu Arg Phe Asp Asn Pro Arg Gly Gln Pro Val
            900             905             910

Gly Gly Leu Arg Phe Glu Gly Gly His Gly Pro Ser Gly Ala Ala Ile
        915             920             925
```

```
Arg Phe Asp Gly Pro His Gly Gln Pro Gly Gly Ile Arg Phe Glu
            930                 935                 940
Gly Pro Leu Leu Gln Gln Gly Val Gly Met Arg Phe Glu Gly Pro His
945                 950                 955                 960
Gly Gln Ser Val Ala Gly Leu Arg Phe Glu Gly Gln His Asn Gln Leu
                965                 970                 975
Gly Gly Asn Leu Arg Phe Glu Gly Pro His Gly Gln Pro Gly Val Gly
            980                 985                 990
Ile Arg Phe Glu Gly Pro Leu Val Gln Gln Gly Gly Met Arg Phe
            995                 1000                1005
Glu Gly Pro Ser Val Pro Gly Gly Leu Arg Ile Glu Gly Pro Leu
            1010                1015                1020
Gly Gln Gly Gly Pro Arg Phe Glu Gly Cys His Ala Leu Arg Phe Asp
1025                1030                1035                1040
Gly Gln Pro Gly Gln Pro Ser Leu Leu Pro Arg Phe Asp Gly Leu His
            1045                1050                1055
Gly Gln Pro Gly Pro Arg Phe Glu Arg Thr Pro Gly Gln Pro Gly Pro
            1060                1065                1070
Gln Arg Phe Asp Gly Pro Pro Gly Gln Gln Val Gln Pro Arg Phe Asp
            1075                1080                1085
Gly Val Pro Gln Arg Phe Asp Gly Pro Gln His Gln Gln Ala Ser Arg
            1090                1095                1100
Phe Asp Ile Pro Leu Gly Leu Gln Gly Thr Arg Phe Asp Asn His Pro
1105                1110                1115                1120
Ser Gln Arg Leu Glu Ser Val Ser Phe Asn Thr Gly Pro Tyr Asn
            1125                1130                1135
Asp Pro Pro Gly Asn Ala Phe Asn Ala Pro Ser Gln Gly Leu Gln Phe
            1140                1145                1150
Gln Arg His Glu Gln Ile Phe Asp Ser Pro Gln Gly Pro Asn Phe Asn
            1155                1160                1165
Gly Pro His Gly Pro Gly Asn Gln Ser Phe Ser Asn Pro Leu Asn Arg
            1170                1175                1180
Ala Ser Gly His Tyr Phe Asp Glu Lys Asn Leu Gln Ser Ser Gln Phe
1185                1190                1195                1200
Gly Asn Phe Gly Asn Ile Pro Ala Pro Met Thr Val Gly Asn Ile Gln
            1205                1210                1215
Ala Ser Gln Gln Val Leu Ser Gly Val Ala Gln Pro Val Ala Phe Gly
            1220                1225                1230
Gln Gly Gln Gln Phe Leu Pro Val His Pro Gln Asn Pro Gly Phe Val
            1235                1240                1245
Gln Asn Pro Ser Gly Ala Leu Pro Lys Ala Tyr Pro Asp Asn His Leu
            1250                1255                1260
Ser Gln Val Asp Val Asn Glu Leu Phe Ser Lys Leu Leu Lys Thr Gly
1265                1270                1275                1280
Ile Leu Lys Leu Ser Gln Thr Asp Ser Ala Thr Thr Gln Val Ser Glu
            1285                1290                1295
Val Thr Ala Gln Pro Pro Glu Glu Glu Asp Gly Asn Glu Asp
            1300                1305                1310
Gln Asp Val Pro Asp Leu Thr Asn Phe Thr Val Glu Glu Leu Lys Gln
            1315                1320                1325
Arg Tyr Asp Ser Val Ile Asn Arg Leu Tyr Thr Gly Ile Gln Cys Tyr
            1330                1335                1340
Ser Cys Gly Met Arg Phe Thr Ser Gln Thr Asp Val Tyr Ala Asp
1345                1350                1355                1360
```

His Leu Asp Trp His Tyr Arg Gln Asn Arg Thr Glu Lys Asp Val Ser
            1365                1370                1375
Arg Lys Val Thr His Arg Arg Trp Tyr Tyr Ser Leu Thr Asp Trp Ile
        1380                1385                1390
Glu Phe Glu Glu Ile Ala Asp Leu Glu Glu Arg Ala Lys Ser Gln Phe
    1395                1400                1405
Phe Glu Lys Val His Glu Glu Val Val Leu Lys Thr Gln Glu Ala Ala
1410                1415                1420
Lys Glu Lys Glu Phe Gln Ser Val Pro Ala Gly Pro Ala Gly Ala Val
1425                1430                1435                1440
Glu Ser Cys Glu Ile Cys Gln Glu Gln Phe Glu Gln Tyr Trp Asp Glu
            1445                1450                1455
Glu Glu Glu Glu Trp His Leu Lys Asn Ala Ile Arg Val Asp Gly Lys
        1460                1465                1470
Ile Tyr His Pro Ser Cys Tyr Glu Asp Tyr Gln Asn Thr Ser Ser Phe
    1475                1480                1485
Asp Cys Thr Pro Ser Pro Ser Lys Thr Pro Val Glu Asn Pro Leu Asn
    1490                1495                1500
Ile Met Leu Asn Ile Val Lys Asn Glu Leu Gln Glu Pro Cys Asp Ser
1505                1510                1515                1520
Pro Lys Val Lys Glu Glu Arg Ile Asp Thr Pro Pro Ala Cys Thr Glu
            1525                1530                1535
Glu Ser Ile Ala Thr Pro Ser Glu Ile Lys Thr Glu Asn Asp Thr Val
        1540                1545                1550
Glu Ser Val
        1555

<210> SEQ ID NO 61
<211> LENGTH: 4407
<212> TYPE: DNA
<213> ORGANISM: Homo sapiens
<220> FEATURE:
<223> OTHER INFORMATION: CFIm25kD subunit (NM_007006)

<400> SEQUENCE: 61

```
ttccggcgtg cctacgcctc ctcttgcgct gtcctgttaa tggcgggcag tagccgctga    60
ggggattgca gataaccgct tcccgcacgg ggaaagtcta ccctgcctgc cactttctgc   120
tcgccgtcag cgccggagct cgccagcatg tctgtggtac cgcccaatcg ctcgcagacc   180
ggctggcccc gggggtcac tcagttcggc aacaagtaca tccagcagac gaagcccctc   240
accctggagc gcaccatcaa cctgtaccct cttaccaatt atacttttgg tacaaaagag   300
cccctctacg agaaggacag ctctgttgca gccagatttc agcgcatgag ggaagaattt   360
gataaaattg aatgaggag gactgtagaa ggggttctga ttgtacatga gcaccggcta   420
ccccatgtgt tactgctgca gctgggaaca actttcttca aactacctgg tggtgaactt   480
aacccaggag aagatgaagt tgaaggacta aaacgcttaa tgacagagat actgggtcgt   540
caggatggag ttttgcaaga ctgggtcatt gacgattgca ttggtaactg gtggagacca   600
aattttgaac tccctcagta tccatatatt cctgcacata ttacaaagcc taggaacat    660
aagaagttgt ttctggttca gcttcaagaa aaagccttgt ttgcagtccc taaaaattac   720
aagctggtag ctgcaccatt gtttgaattg tatgacaatg caccaggata tggacccatc   780
atttctagtc tccctcagct gttgagcagg ttcaatttta tttacaactg aattcctgcg   840
cagtggagaa gtaaaagaag ccgcttgtct ctgtgagcac agctatatac agtgtagaat   900
```

```
aaatgtggta gaaaagttttt tttggttttta tctcttttgc gatccctaaa ttgccacctt      960
tctattgttt gaatagtaaa attaatatga agaactagat agtggtgtaa acaaatgtga     1020
taatgtttat ttactttcgg ttctgctcat acttttttgt acaacattaa agaaaatgga     1080
cttttttat tttaatttct cattaaactt ctaaaattct tataggtgag gatcattttt     1140
ccccccacct taggatggtg aatgttgcaa cacaatgaca ggtttaagtc agtcaagttt     1200
attggaccct tgctttgata ccattcttgg gcacatactc caagattgta ttagattttt     1260
gtgatgaaga gcttccatta cttctgaaaa ctatatttat ctgagtgagt ccaaggtgca     1320
actcctaaat gaattgtgtt gcagagaact cccagtataa ttcactgacc agtacatttt     1380
ataaccatcc aggccttggt ttgcaagcaa cagaccttaa acatacagga aactattaaa     1440
attggctcga tcagtagtca taggaattgg tataagaaga gactcattta gagctcagag     1500
ttttcttcac ataatggggg tattaattat ttgtgctgtt gcgaaattat gtgtcttatt     1560
cttaaagcca tggtaaaaat agggatctgt gaaggaaatt tctaaaattg gatgtattag     1620
gttttgaact ctgagattgc acaaatattc aattaacttg aagttgtgta catagagaag     1680
aaaatttggt tttagcaaat gacagagcct tcaaaaatat ttttggaata atgtgaatca     1740
accgaaaact gggggcaagg cagaggacag gttttctcag gttaagagaa aaacgaaatt     1800
ttaaaaactt taaaaaatac tgataaaattc ggatcaaatt tggggaata aaaaatatta     1860
gagcaaagga gtttgctggt tgtgtcatta tttaatgatc aaagtatagc atgtatgcct     1920
tattacagac ttgttgacta taggcttaat gtaaaaagga atcttgccag atgtagctac     1980
ttaaggaaaa aagggttttt aatagaaatg aacttttgat tagtatggtg ccagtcacag     2040
ggctattttc ctgaatattg ggtgatgtca aaggtatatg atacttgagg aaatcaggcc     2100
aagtgtagct gagcaattaa taaacactca agttttttta gttggggtca tgtcaaaccc     2160
tcacatggtg gttaagtagt gactaactgt gcatgtcctt catggtaggt gagcaccagt     2220
ctccatgatc aaaaatgccc cagtttcctt tgaaaaagcc actagttctg tgaattgtcc     2280
ttttccctcc tgcccctaac agtcctaccc ctctagccta cattagcata tttctcatgt     2340
aatgtatttt gctggtaagc tcatccatta gctgcgtcct tcagctattc ctttagattg     2400
gaggaagtgg atatgaagat ggattgattc agctcacctt ccatgattgc ttttgaggga     2460
aaagctacag tggccacatt tcagatgttc acttttgcaa tttgtggagg gtggagagag     2520
gtagactttt gttgtgtgtt ttataaagta ctctcagtaa ggagtgtttg agttgaagag     2580
tcatctgatt cgaggccact catgttcttt gtaacttaaa ctttgaccaa gaaattcttc     2640
acttctcact tcttcacttc ttcccaatat acagtaagta cgtgagccag tcatccatac     2700
actaaggcct agttgagaaa aacctttgat tcaggatggc tgggttacta accttgaaat     2760
gtaagagatc tggttttgaa tgtaaaagtt gcaacacaca aacggaagtc ttaaaaactt     2820
tttgctctgg tcagttacag gtggatcccc aataatctgt ttttggtttt ctgatgaaaa     2880
taatagaatt aggggaaatc aaatctggtt ggtaggtgtc tacagtatta gaagagggta     2940
taagggcact gtttaacact aagttctaat acttccagaa actgtgcatt ccagatctac     3000
atactaaatg ctccttatcat tttgaaatgg gctcttgatt aatagaccca tattttttag     3060
tggcttctat gttgtatatt tgtctaaaat gaaagctctt ttgcgttcta aaactacaat     3120
atatgtcatc ttatttccc tgagtatcca agtatagtgc agattctatg taaaactact     3180
aaatgacact ggaatatgtt tagtagatta ggggggaaaaa ctataaaggt ttatacaatt     3240
gtttgtagtt acatttagga tggacttatc cctttggaga agagtgaagt ttgtttttc     3300
```

-continued

```
gccatgtgat gaagaccact gtgatttttt aaaaaagtag ataatactta aaatggcgta   3360
ataattctgc acttgaattt gtactgttaa cagcacattt ggaagatttt aaaacttttt   3420
attgtcttat aaatagcatt cacttattat tttggatatt taagggttcc attaagttaa   3480
cactgtattt ggacaaagtg tgaccaaatt agccagtctg ttttcttcca tgtttaatta   3540
gaagtgagag gtagaagtac ttcaaattca acaggccagc aagcaatcgg cttaaaattc   3600
cctttcttaa atgttgtgct cttatgtcct cggcttttta atgactttat ttttacagta   3660
cttgttcagt cacttgagat gaaatgcttg gggtagcttt tccatcctca aacttaatgt   3720
ttttactagt tcatagtgtt tggaacagta tatgccaatc actgagactg catcagagtt   3780
tgcaattttg tatgtttcat tgccaaagaa ggcttagtgg ttgttgactg tagtataagt   3840
cagctttctg tagcataaga tttgattttc ccatacttac ttcacttgtt atacatcact   3900
gattatttgg gttaaactgg actcatttca agcagtttgc ttttgttcaa atcgtgatga   3960
gaaacctaat actgtaattt gatttgagcc ataaaacaca ttttaatatt agcttgtatt   4020
atagttatta agcttgtttt tgtggaaaaa aacttactaa aacctaggta actctagatt   4080
aggccagttc aggtgtattt tgtatcttag taatggatca tatcgtaaaa atagagataa   4140
gttgggaaga tatattgatt atgctgttct gttgagggaa aggtcatgta tttagaaatt   4200
taaacttttg gttattgtgt tcacatcata gtattcaagc atcatttata gtttggtttt   4260
gagaactttt ctggtattac gtttatggca aatgtataaa agaaacaagt tttggttata   4320
tttttatatt tgtaaagtaa gtttggttaa agtgatcact gttctttttt tatttattg    4380 tcatttcaat aaaaaatatt tgaaaga                                        4407
```

<210> SEQ ID NO 62
<211> LENGTH: 227
<212> TYPE: PRT
<213> ORGANISM: Homo Sapiens
<220> FEATURE:
<223> OTHER INFORMATION: CFIm 25kD subunit (NP_008937)

<400> SEQUENCE: 62

```
Met Ser Val Val Pro Pro Asn Arg Ser Gln Thr Gly Trp Pro Arg Gly
1               5                   10                  15

Val Thr Gln Phe Gly Asn Lys Tyr Ile Gln Gln Thr Lys Pro Leu Thr
            20                  25                  30

Leu Glu Arg Thr Ile Asn Leu Tyr Pro Leu Thr Asn Tyr Thr Phe Gly
        35                  40                  45

Thr Lys Glu Pro Leu Tyr Glu Lys Asp Ser Ser Val Ala Ala Arg Phe
    50                  55                  60

Gln Arg Met Arg Glu Glu Phe Asp Lys Ile Gly Met Arg Arg Thr Val
65                  70                  75                  80

Glu Gly Val Leu Ile Val His Glu His Arg Leu Pro His Val Leu Leu
                85                  90                  95

Leu Gln Leu Gly Thr Thr Phe Phe Lys Leu Pro Gly Gly Glu Leu Asn
            100                 105                 110

Pro Gly Glu Asp Glu Val Glu Gly Leu Lys Arg Leu Met Thr Glu Ile
        115                 120                 125

Leu Gly Arg Gln Asp Gly Val Leu Gln Asp Trp Val Ile Asp Asp Cys
    130                 135                 140

Ile Gly Asn Trp Trp Arg Pro Asn Phe Glu Pro Gln Tyr Pro Tyr
145                 150                 155                 160

Ile Pro Ala His Ile Thr Lys Pro Lys Glu His Lys Lys Leu Phe Leu
                165                 170                 175
```

```
Val Gln Leu Gln Glu Lys Ala Leu Phe Ala Val Pro Lys Asn Tyr Lys
            180                 185                 190

Leu Val Ala Ala Pro Leu Phe Glu Leu Tyr Asp Asn Ala Pro Gly Tyr
        195                 200                 205

Gly Pro Ile Ile Ser Ser Leu Pro Gln Leu Leu Ser Arg Phe Asn Phe
    210                 215                 220

Ile Tyr Asn
225

<210> SEQ ID NO 63
<211> LENGTH: 764
<212> TYPE: DNA
<213> ORGANISM: Homo Sapiens
<220> FEATURE:
<223> OTHER INFORMATION: CFIm 25kD subunit (AJ001810)

<400> SEQUENCE: 63
atgtctgtgg taccgcccaa tcgctcgcag accggctggc cccgggggt cactcagttc        60 ggcaacaagt acatccagca gacgaagccc ctcaccctgg agcgcaccat caacctgtac       120
cctcttacca attatacttt tggtacaaaa gagcccctct acgagaagga cagctctgtt       180
gcagccagat ttcagcgcat gagggaagaa tttgataaaa ttggaatgag gaggactgta       240
gaaggggttc tgattgtaca tgagcaccgg ctaccccatg tgttactgct gcagctggga       300
acaactttct tcaaactacc tggtggtgaa cttaacccag agaagatga agttgaagga        360 ctaaaacgct taatgacaga gatactgggt cgtcaggatg gagttttgca agactgggtc       420
attgacgatt gcattggtaa ctggtggaga ccaaatttg aacctcctca gtatccatat         480
attcctgcac atattacaaa gcctaaggaa cataagaagt tgtttctggt tcagcttcaa       540
gaaaaagcct tgtttgcagt ccctaaaaat tacaagctgg tagctgcacc attgtttgaa       600
ttgtatgaca atgcaccagg atatggaccc atcatttcta gtctccctca gctgttgagc       660
aggttcaatt ttatttacaa ctgaattcct gcgcagtgga gaagtaaaag aagccgcttg       720
tctctgtgag cacagctata tacagtgtag aataaatgtg gtag                        764

<210> SEQ ID NO 64
<211> LENGTH: 3524
<212> TYPE: DNA
<213> ORGANISM: Homo sapiens
<220> FEATURE:
<223> OTHER INFORMATION: KIAA0649 mRNA (NM_024811.2)

<400> SEQUENCE: 64
gagtcgcggg cctttgagg gaggaggcag agcgcgccgg gccggtggca tcttccttac         60
tttgtccatc ctccggactc gcgatcttcc ttccggagcc atgtcagaag gagtggactt       120
gattgatata tatgctgacg aggagttcaa ccaggaccca gagttcaaca atacagatca      180
gattgacctg tatgatgatg tgctgacagc cacctcacag ccctcagatg acagaagcag       240
cagcactgaa ccacctcctc ctgttcgcca ggagccatct cccaagccca caacaagac        300 ccctgcaatt ctgtatacct acagtggcct gcgtaataga cgagctgccg tttatgtggg       360
cagcttctcc tggtggacca cagaccagca gctgatccag ttattcgct ctataggagt        420 ctatgatgtg gtggagttga attttgcaga gaatcgagca aatggccagt ccaaggggta      480
tgctgaggtg gtggtagcct ctgaaaaactc tgtccacaaa ttgttggaac tcctaccagg       540
gaaagttctt aatggagaaa aagtggacgt gaggccggcc acccggcaga acctgtcaca      600
gtttgaggca caggctcgga acgtgagtg tgtccgagtc ccaagagggg gaatacctcc       660
```

```
acgggcccat tcccgagatt ctagtgattc tgctgatgga cgggccacac cctctgagaa    720
ccttgtaccc tcatctgctc gtgtggataa gccccccagt gtgctgccct acttcaatcg    780
tcctccttcg gcccttcccc tgatgggtct gcccccacca ccaattccac ccccaccacc    840
tctctcctca agctttgggg tccctcctcc tcctcctggt atccactacc agcatctcat    900
gcccccacct cctcgattac ctcctcatct tgctgtacct cccctgggg ccatcccacc    960 tgcccttcac ctcaatccag ccttcttccc cccaccaaac gctacagtgg ggcctccacc    1020
agatacttac atgaaggcct ctgccccta taaccaccat ggcagccgag attcgggccc    1080
tccaccctct acagtgagtg aagccgaatt tgaagatatc atgaagcgaa acagagcaat    1140
ttccagcagt gccatttcca aagcagtatc tggagccagt gcaggggatt acagtgacgc    1200
aattgagacg ctgctcacag ccattgcggt tatcaaacag tcccgggttg ccaatgatga    1260
gcgttgccgt gtcctcatct cctctcttaa ggactgtctt catggcattg aagccaagtc    1320
ctacagtgtg ggtgccagtg ggagctcttc caggaaaaga catcgctccc gggaaaggtc    1380
acctagccgg tcccgggaga gcagcaggag gcaccgggat ctgcttcata atgaagatcg    1440
gcatgatgat tatttccaag aaaggaaccg ggagcatgag agacaccggg atagagaacg    1500
ggaccggcac cactgagaaa ggagtctggt tggaagcaaa tgttttttta atggacttgc    1560
atctcctcac cttgatcagg actaaaggac ggaggccgcc ccaccccctt ccctttcctc    1620
caaaccccta actccctcca gacacccagg gaataccctc tgccccacag gattgaagac    1680
tgcttggcag tcctcccaat cccacacctc ctgtttgcca ggggaaagaa cctaaagact    1740
tcgtgtgatt gggagggtg gcagacagga agaaaacatg tccaggcccc tggtctccat    1800
agagaatggt gctttgtcca agaaaacgta tgagtttctg attctccggg agccgttcaa    1860
tggtgaggtt gatgggaaga cttccttccc aaagaaaata gatcctccat gcaggatcta    1920
ggagagtgac tgggtgtgcc aaaatatgcc cagggtcctg ccctcagcac tagatttaat    1980
ggggccaaga gggtccaaac cccttgctaa cataccactt cttttgtttaa ctcctttacc    2040 tttccagccc tttgaggagg accatgaga acagaaatta ccttatgaaa agctacttct    2100
gttcctgctt tccctctcac gtattgacgg tttatttctt tgacctccca gagggctgaa    2160
ctctttcaac tctgcgctgc ccagcctct cagtggactt gccctcca agcagagaag    2220 gcctatgagg ttgcttgctg ctgggaagcc tggcagagcc aattaccacc ctctgctgct    2280
tagtgcttgg gtacctcttg caataaccag ctcttagttg ttcccttttcc ctggggcttt    2340 tccatttaac acatggagcc cttccccag aaggctactt tcttgttttta gaggaaggta    2400 ctgcccattg ggagatgggg acattgggac ctcagcaatg aagaaccctt gtgaagtaac    2460
caggaggaat ggggaaagaa gcaagttggg caggatatgg cctacttcca taggcttttc    2520 tttttttcagg tttgatgtaa gcatgggctt acatccccca ggtacatact tttacttatt    2580
gtgggataac ctggcactag taggcaggta aagtcacaaa tttggtgtct tttcaccttt    2640
tgactgttga cttaatagct cctctcactc tgcctggaga tacttcctgc ctcagatgag    2700
gagccagaag aaacagagcc cgacttgaat gaactcagct cagagttcta aggaccagca    2760
ttctgggggc catttctct acaggcaaat ggaattgctt ttccataaca tccaaattgt    2820
aatgtggttg ctgctgaagg aggaggcagc agcgaggtcc tgcggtaccc atggggtgat    2880
gctacttctg catgcatcta cagggcatct gacacctaac atgagacgtg catgtgaga    2940 tgagacttgg catgtgagac ataggggtcac tagagaccct tctgggtcag aggagagaga    3000
ctgaattgga ctaaacccgt cctctgttcc cagcacgttt ctcatatagc cctcagtcac    3060
```

| | |
|---|---|
| tgagggagtc ccccgcagga ttggagaggc acattcccct gggacagagg ctacaggttg | 3120 |
| gagcttttt tccctgtcc cccaacccca tccccacctc cacttcagaa catggcaccc | 3180 |
| cacccaactg gccaagtgtt aagtgatgtg cttattgaga gcaactccgg gtgtcttta | 3240 |
| aaatgtagag aaaaggtgac agtttaagga aaaatatata tagaatacca gaaatgccgt | 3300 |
| ttacccggag aattttttc tccccatttg ttttgttttt actcaatgac accatttta | 3360 |
| gttttatttc ctgatagcaa aaggaaaaaa aacacccatc cctcaaaaag gccaaggtcc | 3420 |
| cgtcccctg ttgtcggtga tttgtttgtc tttctgatag gttgaaaatt gtgtaataaa | 3480 |
| cttgatgacg ctgtcaaaaa aaaaaaaaaa aaaaaaaaaa aaaa | 3524 |

<210> SEQ ID NO 65
<211> LENGTH: 1416
<212> TYPE: DNA
<213> ORGANISM: Homo Sapiens
<220> FEATURE:
<223> OTHER INFORMATION: CFIm 59kD subunit(AJ275970)

<400> SEQUENCE: 65

| | |
|---|---|
| atgtcagaag gagtggactt gattgatata tatgctgacg aggagttcaa ccaggaccca | 60 |
| gagttcaaca atacagatca gattgacctg tatgatgatg tgctgacagc cacctcacag | 120 |
| ccctcagatg cagaagcag cagcactgaa ccacctcctc ctgttcgcca ggagccatct | 180 |
| cccaagccca caacaagac ccctgcaatt ctgtatacct acagtggcct gcgtaataga | 240 |
| cgagctgccg tttatgtggg cagcttctcc tggtggacca cagaccagca gctgatccag | 300 |
| gttattcgct ctataggagt ctatgatgtg gtggagttga atttgcaga gaatcgagca | 360 |
| aatggccagt ccaaagggta tgctgaggtg gtggtagcc ctgaaaactc tgtccacaaa | 420 |
| ttgttggaac tcctaccagg gaaagttctt aatggagaaa agtggacgt gaggccggcc | 480 |
| acccggcaga acctgtcaca gtttgaggca caggctcgga acgtgagtg tgtccgagtc | 540 |
| ccaagagggg gaatacctcc acgggcccat tcccgagatt ctagtgattc tgctgatgga | 600 |
| cgggccacac cctctgagaa ccttgtaccc tcatctgctc gtgtggataa gccccccagt | 660 |
| gtgctgccct acttcaatcg tcctccttcg gcccttcccc tgatgggtct gccccaccca | 720 |
| ccaattccac cccaccacc tctctcctca gcttgggg tccctcctcc tcctcctggt | 780 |
| atccactacc agcatctcat gccccacct cctcgattac ctcctcatct tgctgtacct | 840 |
| cccctgggg ccatcccacc tgcccttcac ctcaatccag ccttcttccc cccaccaaac | 900 |
| gctacagtgg ggcctccacc agatacttac atgaaggcct ctgcccccta taaccaccat | 960 |
| ggcagccgag attcgggccc tccacccttct acagtgagtg aagccgaatt tgaagatatc | 1020 |
| atgaagcgaa acagagcaat ttccagcagt gccatttcca agcagtatc tggagccagt | 1080 |
| gcaggggatt acagtgacgc aattgagacg ctgctcacag ccattgcggt tatcaaacag | 1140 |
| tcccgggttg ccaatgatga gcgttgccgt gtcctcatct cctctcttaa ggactgtctt | 1200 |
| catggcatcg aagccaagtc ctacagtgtg ggtgccagtg ggagctcttc caggaaaaga | 1260 |
| catcgctccc gggaaaggtc acctagccgg tcccgggaga gcagcaggag gcaccggat | 1320 |
| ctgcttcata tgaagatcg gcatgatgat tatttccaag aaaggaaccg ggagcatgag | 1380 |
| agacaccggg atagagaacg ggaccggcac cactga | 1416 |

<210> SEQ ID NO 66
<211> LENGTH: 471
<212> TYPE: PRT
<213> ORGANISM: Homo Sapiens
<220> FEATURE:
<223> OTHER INFORMATION: CFIm 59kD subunit(NP079087)

<400> SEQUENCE: 66

```
Met Ser Glu Gly Val Asp Leu Ile Asp Ile Tyr Ala Asp Glu Glu Phe
1               5                   10                  15

Asn Gln Asp Pro Glu Phe Asn Asn Thr Asp Gln Ile Asp Leu Tyr Asp
            20                  25                  30

Asp Val Leu Thr Ala Thr Ser Gln Pro Ser Asp Arg Ser Ser Ser
        35                  40                  45

Thr Glu Pro Pro Pro Val Arg Gln Glu Pro Ser Pro Lys Pro Asn
    50                  55                  60

Asn Lys Thr Pro Ala Ile Leu Tyr Thr Tyr Ser Gly Leu Arg Asn Arg
65                  70                  75                  80

Arg Ala Ala Val Tyr Val Gly Ser Phe Ser Trp Trp Thr Thr Asp Gln
                85                  90                  95

Gln Leu Ile Gln Val Ile Arg Ser Ile Gly Val Tyr Asp Val Val Glu
                100                 105                 110

Leu Lys Phe Ala Glu Asn Arg Ala Asn Gly Gln Ser Lys Gly Tyr Ala
            115                 120                 125

Glu Val Val Ala Ser Glu Asn Ser Val His Lys Leu Leu Glu Leu
130                 135                 140

Leu Pro Gly Lys Val Leu Asn Gly Glu Lys Val Asp Val Arg Pro Ala
145                 150                 155                 160

Thr Arg Gln Asn Leu Ser Gln Phe Glu Ala Gln Ala Arg Lys Arg Glu
                165                 170                 175

Cys Val Arg Val Pro Arg Gly Gly Ile Pro Pro Arg Ala His Ser Arg
            180                 185                 190

Asp Ser Ser Asp Ser Ala Asp Gly Arg Ala Thr Pro Ser Glu Asn Leu
        195                 200                 205

Val Pro Ser Ser Ala Arg Val Asp Lys Pro Pro Ser Val Leu Pro Tyr
    210                 215                 220

Phe Asn Arg Pro Pro Ser Ala Leu Pro Leu Met Gly Leu Pro Pro Pro
225                 230                 235                 240

Pro Ile Pro Pro Pro Pro Leu Ser Ser Ser Phe Gly Val Pro Pro
                245                 250                 255

Pro Pro Pro Gly Ile His Tyr Gln His Leu Met Pro Pro Pro Pro Arg
            260                 265                 270

Leu Pro Pro His Leu Ala Val Pro Pro Gly Ala Ile Pro Pro Ala
        275                 280                 285

Leu His Leu Asn Pro Ala Phe Phe Pro Pro Asn Ala Thr Val Gly
    290                 295                 300

Pro Pro Pro Asp Thr Tyr Met Lys Ala Ser Ala Pro Tyr Asn His His
305                 310                 315                 320

Gly Ser Arg Asp Ser Gly Pro Pro Ser Thr Val Ser Glu Ala Glu
                325                 330                 335

Phe Glu Asp Ile Met Lys Arg Asn Arg Ala Ile Ser Ser Ser Ala Ile
            340                 345                 350

Ser Lys Ala Val Ser Gly Ala Ser Ala Gly Asp Tyr Ser Asp Ala Ile
        355                 360                 365

Glu Thr Leu Leu Thr Ala Ile Ala Val Ile Lys Gln Ser Arg Val Ala
    370                 375                 380

Asn Asp Glu Arg Cys Arg Val Leu Ile Ser Ser Leu Lys Asp Cys Leu
385                 390                 395                 400
```

```
                His Gly Ile Glu Ala Lys Ser Tyr Ser Val Gly Ala Ser Gly Ser Ser
                                405                 410                 415

Ser Arg Lys Arg His Arg Ser Arg Glu Arg Ser Pro Ser Arg Ser Arg
                            420                 425                 430

Glu Ser Ser Arg Arg His Arg Asp Leu Leu His Asn Glu Asp Arg His
                        435                 440                 445

Asp Asp Tyr Phe Gln Glu Arg Asn Arg Glu His Glu Arg His Arg Asp
                    450                 455                 460

Arg Glu Arg Asp Arg His His
                465                 470

<210> SEQ ID NO 67
<211> LENGTH: 3426
<212> TYPE: DNA
<213> ORGANISM: Homo Sapiens
<220> FEATURE:
<223> OTHER INFORMATION: CFIm 68kD subunit (NM_007007)

<400> SEQUENCE: 67
aattccgggc ggcggcggcc gaggctgaag gaagatggcg gacggcgtgg accacataaa      60
catttacgcg gatgtcggcg aagagttcaa ccaggaagct gaatatggtg ggcatgatca     120
gatagatttg tatgacgatg tcatatctcc atctgcaaat aatggagatg ccccagaaga     180
ccgagattac atggatactc tcccaccaac tgttggtgat gatgtgggta aggagcagc      240
accaaatgtt gtctatacat atactggaaa gagaattgca ttatatattg gaaatctaac     300
atggtggaca acagatgaag acttaactga agcagttcat tctttgggag taaatgatat     360
tttggagata aaattttttg aaaatcgagc aaatggccag tcaaaggggt tgcccttgt      420
tggtgttgga tctgaagcat cttcaaaaaa gttaatggat ctgttaccta aaagagaact     480
tcatggtcag atcctgttg taactccatg caataaacag ttcctgagtc aatttgaaat      540
gcagtccagg aaaactacac aatcaggaca aatgtctggg gaaggtaaag ctggtcctcc     600
aggaggcagt tcccgtgcag catttccaca aggtggtaga ggacggggcc gttttccagg     660
ggctgttcct ggtggggaca gatttcctgg gccagcagga ccaggagggc caccccacc      720
ttttccagct ggacagactc caccacgtcc acccttaggt cctccaggcc cacctggtcc     780
accaggtcct ccacctcctg gtcaggttct gcctcctcct ctagctgggc ctcctaatcg     840
aggagatcgc cctccaccac cagttctttt tcctggacaa ccttttgggc agcctccatt     900
gggtccactt cctcctggcc ctccacctcc agttccaggc tacggccccc ctcctggccc     960
accacctcca caacagggac cacctccacc tccaggcccc tttccacctc gtccacccgg    1020
tccacttggg ccaccccta cactagctcc tcctccgcat cttcctggac cacctccagg    1080
tgccccaccg ccagctccgc atgtgaaccc agctttcttt cctccaccaa ctaacagtgg    1140
catgcctaca tcagatagcc gaggtccacc accaacagat ccatatgggc gacctccacc    1200
atatgatagg ggtgactatg gccccccctgg aagggaaatg gatactgcaa gaacgccatt    1260
gagtgaagct gaatttgaag aaatcatgaa tagaaatagg gcaatctcaa gcagtgctat    1320
ttcgagagct gtgtctgatg ccagtgctgg tgattatggg agtgctattg agacactggt    1380
aactgcaatt tctttaatta aacaatccaa agtatctgct gatgatcgtt gcaaagttct    1440
tattagttct ttgcaagatt gccttcatgg aattgagtcc agtcttatg gttctggatc    1500
aagacgtgaa cgatcaagag agagggacca tagtagatca cgagaaaaga gtcgacgtca    1560
taatccccgt agtagagacc gtcatgacga ttattacaga gagagaagca gagaacgaga    1620
gaggcaccgg gatcgtgacc gagaccgtga ccgagagcgt gaccgagagc gcgaatatcg    1680
```

```
tcatcgttag aagctgaagg aagaggatca ccttccaaga caaaacagtc ttcatgggcc    1740
aaaaatgacg cttgtccagc agtttgcttc ttgtgattga actgaacctg taaggattca    1800
tggataaaat gaacaggaat agatctgaat aaagcaaatc tgcataaatg gtaaccagta    1860
gctctacttt tatttttat gttgcttaac tgttttattt gaaggaaacc tgtgtgattt     1920
aaaaagttat agcttttgca actttattac tggttatata catttggcca ttatgatgtg    1980
caagcaattg gaaaaaagt caagtaaatg cttgttttg tagtagtttg ttcttgttaa      2040
aaatgtttat atgataatgt ctgtaaacag catcactttg attacaatag atgtagtgtt    2100
gtaataaact gtttaatggg gctgatgtgt aaagctgttc aagttatttg atgtttacac    2160
ctcagggaaa gtcttgtgtt cagcaatatc taaagataat gttactatga caacattttt    2220
actgtccttt aaagcattgc aatagcgttt ttggatatgc ctcaatctaa tcttgcgttc    2280
agtgaattaa acatagtaat taagtgtctt ttgcccttga ttttgatatt agaataggtg    2340
attacatgga tatttaatat ttctatattc tgcttttcta gctgttttta cctagttagc    2400
ttgtgacttt gctgaatggt atgtaaactt gtaaaaatag agatttgaca gacatagcaa    2460
tctagtcaat gtgtaagggg tcaaaaaaaa cagaggtttt aacacataag taaaaacccg    2520
tacatatttg atgtgtaatg caggttaatt acaacacaga tgtaccgaaa cacttaattg    2580
tgaaccgcta acattgaaga aattttgaca attccgattt gatgctgcaa ttacttgctg    2640 ttttattga tcttatggtt tatttcttaa gccatagtca gtgtaaatac agccctgcag     2700
caggtaaatg tgagtaaaga gagccttata ttttccaatt ggtataaaat ttttgaagga    2760
tgtgatgttc attaacattc ggttgtattc cccagtatttt gtaatgggaa attacagata   2820
aaccgtgtct gcacagttta aggaatacta tgtatattca tgcaccgtat tgattcatgc    2880
tatagttact taatcaaaga tttttttcaa acctgcctta catataggcc cactttaaaa    2940
gcacctgact agcatgtgtt cttgattgca aaattggcag aggcagggtg tcaacttgat    3000
taggtgtttt tatgggaatg taatttgaaa tcactacttc agaaatttga cttaaaattc    3060
ttgagcacgt taatatgttt ttaagatctg attatctttg agagatcttc tgttaataca    3120
cattggttgt taaagagtac ccaaattcta ggacaatgct taaagtgtta aaatacccta    3180
gatactgtgt tatgtgcaac tgtagaaacc ctccagaaat ttccactgct gttcttcact    3240
ttcatcttgt ctgctatcaa accacttctg acaaaattag ctgttttgaa ttacccatat    3300
cactgccagt tttattttaa aatattttgt gtttgaagta tctgtgcatg ggatcgttga    3360
tgtttatcag aactgttcac tttcagaaat gattttttaa agcattttgt tgaaatgcgg    3420
ttgctt                                                               3426
```

<210> SEQ ID NO 68
<211> LENGTH: 551
<212> TYPE: PRT
<213> ORGANISM: Homo Sapiens
<220> FEATURE:
<223> OTHER INFORMATION: CFIm 68kD subunit (NP_008938)

<400> SEQUENCE: 68

```
Met Ala Asp Gly Val Asp His Ile Asn Ile Tyr Ala Asp Val Gly Glu
1               5                   10                  15

Glu Phe Asn Gln Glu Ala Glu Tyr Gly Gly His Asp Gln Ile Asp Leu
                20                  25                  30

Tyr Asp Asp Val Ile Ser Pro Ser Ala Asn Asn Gly Asp Ala Pro Glu
            35                  40                  45
```

```
Asp Arg Asp Tyr Met Asp Thr Leu Pro Pro Thr Val Gly Asp Asp Val
 50                  55                  60

Gly Lys Gly Ala Ala Pro Asn Val Val Tyr Tyr Thr Gly Lys Arg
 65                  70                  75                  80

Ile Ala Leu Tyr Ile Gly Asn Leu Thr Trp Trp Thr Thr Asp Glu Asp
                 85                  90                  95

Leu Thr Glu Ala Val His Ser Leu Gly Val Asn Asp Ile Leu Glu Ile
            100                 105                 110

Lys Phe Phe Glu Asn Arg Ala Asn Gly Gln Ser Lys Gly Phe Ala Leu
        115                 120                 125

Val Gly Val Gly Ser Glu Ala Ser Ser Lys Lys Leu Met Asp Leu Leu
    130                 135                 140

Pro Lys Arg Glu Leu His Gly Gln Asn Pro Val Val Thr Pro Cys Asn
145                 150                 155                 160

Lys Gln Phe Leu Ser Gln Phe Glu Met Gln Ser Arg Lys Thr Thr Gln
                165                 170                 175

Ser Gly Gln Met Ser Gly Glu Gly Lys Ala Gly Pro Pro Gly Gly Ser
            180                 185                 190

Ser Arg Ala Ala Phe Gln Gly Gly Arg Gly Arg Gly Arg Phe Pro
        195                 200                 205

Gly Ala Val Pro Gly Gly Asp Arg Phe Pro Gly Pro Ala Gly Pro Gly
    210                 215                 220

Gly Pro Pro Pro Pro Phe Pro Ala Gly Gln Thr Pro Pro Arg Pro Pro
225                 230                 235                 240

Leu Gly Pro Pro Gly Pro Pro Gly Pro Gly Pro Pro Pro Pro Pro Gly
                245                 250                 255

Gln Val Leu Pro Pro Pro Leu Ala Gly Pro Pro Asn Arg Gly Asp Arg
            260                 265                 270

Pro Pro Pro Pro Val Leu Phe Pro Gly Gln Pro Phe Gly Gln Pro Pro
        275                 280                 285

Leu Gly Pro Leu Pro Pro Gly Pro Pro Pro Val Pro Gly Tyr Gly
    290                 295                 300

Pro Pro Pro Gly Pro Pro Pro Gln Gln Gly Pro Pro Pro Pro Pro
305                 310                 315                 320

Gly Pro Phe Pro Pro Arg Pro Pro Gly Pro Leu Gly Pro Pro Leu Thr
                325                 330                 335

Leu Ala Pro Pro Pro His Leu Pro Gly Pro Pro Gly Ala Pro Pro
            340                 345                 350

Pro Ala Pro His Val Asn Pro Ala Phe Phe Pro Pro Pro Thr Asn Ser
        355                 360                 365

Gly Met Pro Thr Ser Asp Ser Arg Gly Pro Pro Thr Asp Pro Tyr
    370                 375                 380

Gly Arg Pro Pro Pro Tyr Asp Arg Gly Asp Tyr Gly Pro Pro Gly Arg
385                 390                 395                 400

Glu Met Asp Thr Ala Arg Thr Pro Leu Ser Glu Ala Phe Glu Glu
                405                 410                 415

Ile Met Asn Arg Asn Arg Ala Ile Ser Ser Ser Ala Ile Ser Arg Ala
            420                 425                 430

Val Ser Asp Ala Ser Ala Gly Asp Tyr Gly Ser Ala Ile Glu Thr Leu
        435                 440                 445

Val Thr Ala Ile Ser Leu Ile Lys Gln Ser Lys Val Ser Ala Asp Asp
    450                 455                 460

Arg Cys Lys Val Leu Ile Ser Ser Leu Gln Asp Cys Leu His Gly Ile
465                 470                 475                 480
```

```
Glu Ser Lys Ser Tyr Gly Ser Gly Ser Arg Arg Glu Arg Ser Arg Glu
            485                 490                 495

Arg Asp His Ser Arg Ser Arg Glu Lys Ser Arg Arg His Lys Ser Arg
            500                 505                 510

Ser Arg Asp Arg His Asp Asp Tyr Tyr Arg Glu Arg Ser Arg Glu Arg
            515                 520                 525

Glu Arg His Arg Asp Arg Asp Arg Asp Arg Asp Arg Glu Arg Asp Arg
            530                 535                 540

Glu Arg Glu Tyr Arg His Arg
545                 550

<210> SEQ ID NO 69
<211> LENGTH: 2323
<212> TYPE: DNA
<213> ORGANISM: Homo Sapiens
<220> FEATURE:
<223> OTHER INFORMATION: CstF50 (50 kD subunit 1) (NM_001324)

<400> SEQUENCE: 69
aactaacctt tgaacgtgcc agtaagtaag atggcgagaa aagcaagaga gagtgggacc      60
gatcgatagc gcagcggtcg gcttggcgcc ctttcagcgt gcgcagtgaa cgtgcgctcg     120
gagcggtaga ttgggcagga ttcgcgcctc cattttttcca ggagagagcg ggataccaag    180
agaaccggac cagctgctgg cagggaaact gtcttccttt tctccaagat gtacagaacc     240
aaagtgggct tgaaggaccg ccagcagctc tacaagctga tcattagcca gctgctatat    300
gacggctaca tcagcatcgc caatggcctc atcaatgaaa tcaagcctca gtctgtgtgt    360
gcaccctcgg agcagctcct gcatctcatc aaactcggaa tggaaaacga tgacaccgca    420
gttcagtatg caattggtcg ttcagatact gttgccctg gcacagggat tgacctggaa     480
tttgatgcag atgttcagac tatgtcccca gaggcttctg agtacgaaac atgctatgtc    540
acatcacata aaggaccatg ccgtgtagct acctatagta gagatggaca gttaatagct    600
actgggtctg ctgatgcttc gataaagata cttgacacag agaggatgtt ggccaaaagt    660
gccatgccaa tagaggtcat gatgaatgag accgcacaac aaaatatgga aaccaccca     720 gtgattcgaa ctctttatga ccatgtggat gaagtcacgt gccttgcttt ccacccaaca    780
gaacagatcc tggcttctgg ttcaagggat tatactctta aattatttga ttattccaaa    840
ccatcagcaa aaagagcctt caaatacatt caggaagctg aaatgttacg ttccatctct    900
tttcatcctt ctggagactt tatacttgtc ggaactcagc atcctactct tcgcctttat    960
gatatcaaca cctttcaatg ttttgtctct tgcaatcctc aagatcaaca caccgatgct   1020
atatgttccg ttaattacaa ttctagtgcc aatatgtacg taactggaag caaggacggc   1080
tgcatcaaat tatgggatgg tgtttcaaat cgatgcatca caacttttga aaagcacat    1140 gacggtgctg aagtttgttc tgccattttt tccaaaaatt ctaaatacat tctctcaagt   1200
ggaaaagact ctgtagctaa actttgggaa atatcaacgg gacgaacact ggtcagatac   1260
acgggcgcgg gtttaagtgg acgccaggtg caccggacac aggctgtgtt taaccacacc   1320
gaggactatg tgttgctgcc cgacgagagg acgatcagtc tttgctgctg ggactcgagg   1380
acagccgagc ggagaaaacct gctgtcgttg gggcacaaca atattgtacg ctgcatagtg   1440 cactcccccca ccaacccgg gttcatgacg tgcagcgatg acttcagagc gcggttttgg    1500
taccggagat cgaccactga ctgagccacc ctctccgtag ggttctttct cgaggactct   1560
accctcctcc cccacgtcct gtctcagctg cagtcgtaag tccgtgcacc atccttgacg   1620
```

```
ttttgctgcc acctctgtcc acattcttct tggatttgta taaagaatc ttttttttacc    1680 ttgatgtaga atcatggtgg aaaaagttgg aaacacagat ctgtgcagtt ctacattcac    1740
tgattattac agtgtgattt tcatcggttt tgtaagtaca ggacttgccg tttctttttga   1800 tctcttgatt gaaggaggat agggcattaa agtgcttttg acatgaggaa ttttcatttg    1860
gttcttctgt caactttctt gcttattctg ctgaaccctc tgtgtatttc ccttccaggt    1920
atatttgaac agataagcag gcatgcagct ctgagactcc tgagttttat gccattatca    1980
aaagcatttt caagaatccc tcaattctat cctgaaatga tgttattctg ataataaagc    2040
tcagatctgc aactttattg ttatatattt ttcacttctg taaaattaat ggccagtttt    2100
tcctgacaat ttataggaac agtatctttc aacatactcc ctacattatc cttcaatatc    2160
tgcaatactt gtctttagta actgtatttc tggtaagatt atgatttcat gagaaacaat    2220
tgaaaatata tccgatctaa ttaaattagg tcagcctgct attgctctca ggtgttgcct    2280
gtcttcacga atgattagta tcgattgacc tctttcttag gtg                      2323
```

<210> SEQ ID NO 70
<211> LENGTH: 431
<212> TYPE: PRT
<213> ORGANISM: Homo Sapiens
<220> FEATURE:
<223> OTHER INFORMATION: CstF50 (50 kD subunit 1) (NP_001315)

<400> SEQUENCE: 70

```
Met Tyr Arg Thr Lys Val Gly Leu Lys Asp Arg Gln Gln Leu Tyr Lys
1               5                   10                  15

Leu Ile Ile Ser Gln Leu Leu Tyr Asp Gly Tyr Ile Ser Ile Ala Asn
            20                  25                  30

Gly Leu Ile Asn Glu Ile Lys Pro Gln Ser Val Cys Ala Pro Ser Glu
        35                  40                  45

Gln Leu Leu His Leu Ile Lys Leu Gly Met Glu Asn Asp Asp Thr Ala
    50                  55                  60

Val Gln Tyr Ala Ile Gly Arg Ser Asp Thr Val Ala Pro Gly Thr Gly
65                  70                  75                  80

Ile Asp Leu Glu Phe Asp Ala Asp Val Gln Thr Met Ser Pro Glu Ala
                85                  90                  95

Ser Glu Tyr Glu Thr Cys Tyr Val Thr Ser His Lys Gly Pro Cys Arg
            100                 105                 110

Val Ala Thr Tyr Ser Arg Asp Gly Gln Leu Ile Ala Thr Gly Ser Ala
        115                 120                 125

Asp Ala Ser Ile Lys Ile Leu Asp Thr Glu Arg Met Leu Ala Lys Ser
    130                 135                 140

Ala Met Pro Ile Glu Val Met Met Asn Glu Thr Ala Gln Gln Asn Met
145                 150                 155                 160

Glu Asn His Pro Val Ile Arg Thr Leu Tyr Asp His Val Asp Glu Val
                165                 170                 175

Thr Cys Leu Ala Phe His Pro Thr Glu Gln Ile Leu Ala Ser Gly Ser
            180                 185                 190

Arg Asp Tyr Thr Leu Lys Leu Phe Asp Tyr Ser Lys Pro Ser Ala Lys
        195                 200                 205

Arg Ala Phe Lys Tyr Ile Gln Glu Ala Glu Met Leu Arg Ser Ile Ser
    210                 215                 220

Phe His Pro Ser Gly Asp Phe Ile Leu Val Gly Thr Gln His Pro Thr
225                 230                 235                 240

Leu Arg Leu Tyr Asp Ile Asn Thr Phe Gln Cys Phe Val Ser Cys Asn
```

|    |    |    |    |    |    | 245 |    |    |    | 250 |    |    |    | 255 |    |
|----|----|----|----|----|----|-----|----|----|----|-----|----|----|----|-----|----|

Pro Gln Asp Gln His Thr Asp Ala Ile Cys Ser Val Asn Tyr Asn Ser
        260                  265                  270

Ser Ala Asn Met Tyr Val Thr Gly Ser Lys Asp Gly Cys Ile Lys Leu
        275                  280                  285

Trp Asp Gly Val Ser Asn Arg Cys Ile Thr Thr Phe Glu Lys Ala His
    290                  295                  300

Asp Gly Ala Glu Val Cys Ser Ala Ile Phe Ser Lys Asn Ser Lys Tyr
305                310                  315                  320

Ile Leu Ser Ser Gly Lys Asp Ser Val Ala Lys Leu Trp Glu Ile Ser
        325                  330                  335

Thr Gly Arg Thr Leu Val Arg Tyr Thr Gly Ala Gly Leu Ser Gly Arg
        340                  345                  350

Gln Val His Arg Thr Gln Ala Val Phe Asn His Thr Glu Asp Tyr Val
        355                  360                  365

Leu Leu Pro Asp Glu Arg Thr Ile Ser Leu Cys Cys Trp Asp Ser Arg
    370                  375                  380

Thr Ala Glu Arg Arg Asn Leu Leu Ser Leu Gly His Asn Asn Ile Val
385                390                  395                  400

Arg Cys Ile Val His Ser Pro Thr Asn Pro Gly Phe Met Thr Cys Ser
                405                  410                  415

Asp Asp Phe Arg Ala Arg Phe Trp Tyr Arg Arg Ser Thr Thr Asp
        420                  425                  430

<210> SEQ ID NO 71
<211> LENGTH: 2027
<212> TYPE: DNA
<213> ORGANISM: Homo Sapiens
<220> FEATURE:
<223> OTHER INFORMATION: CstF64 (64 kD subunit 2) (NM_001325)

<400> SEQUENCE: 71

| | | | | | |
|---|---|---|---|---|---|
| ggcttgtgct | ccgtacggaa | gtgtgctttg | gcgcaccgga | agccgactca | acagagctat | 60 |
| ggcgggtttg | actgtgagag | acccagcggt | ggatcgttct | ctacgttctg | tgttcgtggg | 120 |
| gaacattcct | tatgaagcta | ctgaagagca | gttgaaggac | atcttttctg | aggttggacc | 180 |
| tgttgttagt | ttcagattgg | tatacgatag | agagacagga | aagccaaagg | gttatggctt | 240 |
| ctgtgaatac | caagaccaag | agacagcact | tagtgccatg | cggaacctga | atgggcgcga | 300 |
| attcagtggg | agagcacttc | gagtggacaa | tgctgccagt | gaaaagaaca | agaagagct | 360 |
| gaagagcctt | ggcactggtg | cccctgtcat | tgagtcacct | tatggagaga | ccatcagtcc | 420 |
| tgaggatgcc | cctgagtcca | ttagcaaagc | agttgccagc | cttccaccag | agcagatgtt | 480 |
| tgagctgatg | aaacaaatga | agctctgtgt | ccagaatagt | ccccaggagg | cacggaacat | 540 |
| gttacttcag | aaccctcaac | tggcttatgc | tttgctgcaa | gcacaggtag | tgatgagaat | 600 |
| tgtggatccg | gaaattgccc | tgaaaattct | gcatcgccag | acaaatatcc | caacgctgat | 660 |
| tgcaggcaac | cctcagccag | tccatggtgc | tgggcctggc | tcaggatcca | atgtgtcaat | 720 |
| gaaccagcag | aatcctcagg | cccctcaggc | ccagtctttg | ggtggaatgc | atgtcaatgg | 780 |
| cgcacctcct | ctgatgcaag | cttctatgca | gggtggagtt | ccagcaccag | gcaaatgcc | 840 |
| agctgctgtc | acaggacctg | gcctggttc | cttagctcct | ggaggaggaa | tgcaggctca | 900 |
| ggttggaatg | ccaggaagtg | gaccagtgtc | catggaacgg | gggcaagtgc | cgatgcaaga | 960 |
| ccccagagca | gctatgcagc | ggggatcctt | gcctgcgaat | gtcccaaccc | ctcgaggctt | 1020 |
| gttaggagat | gctccgaatg | atccacgggg | aggcactta | cttctctgtaa | ctggagaggt | 1080 |

```
agagcctaga ggttacttgg gaccacctca tcagggtcca cccatgcacc atgtccctgg   1140
ccatgagagc cgaggaccac ccccacatga actgagggga gggccattac ccgagcccag   1200
acctctaatg gcagaaccaa gaggacccat gctagatcag aggggtccac ccttggatgg   1260
cagaggtgga agggatcccc gaggaataga tgcacgaggg atggaggccc gagccatgga   1320
ggcaagaggg ttagatgcca gaggattaga ggcccgtgca atggaggccc gtgcgatgga   1380
agctcgtgca atggaggccc gagcgatgga ggcccgtgca atggaagtcc gagggatgga   1440
ggccagaggc atggatacca gaggcccagt gcctggcccc agaggaccta tacctagtgg   1500
aatgcagggt cccagtccaa ttaacatggg ggcggttgtc ccccagggat ccagacaggt   1560
cccagtcatg cagggaacag gaatgcaagg agcaagtata cagggtggaa gccagcctgg   1620
cggctttagt cccgggcaga accaagtcac tccacaggat catgagaagg ctgctttgat   1680
tatgcaggtt ctacaactga ctgcagacca gattgccatg ttgcctcctg agcaaaggca   1740
gagtatcctg atttttaaagg aacaaataca gaaatccact ggagcacctt gataggtttt   1800
caaaaatacc tggcaagaaa tctggaaatt ctataatttt gttgaaatat tgaaaaaaga   1860
tgacctgcat cctaacccct gaatgactca aatcagtgcc aggtgagga ctcccatcac   1920 cttctctcag aacaaaatca cttcatttta ttgtcttagt ttgtatattt tctgtgactt   1980
gaaataaact ttgaacacaa ttttagtaca ctgcaaaaaa aaaaaaa                  2027
```

<210> SEQ ID NO 72
<211> LENGTH: 4127
<212> TYPE: DNA
<213> ORGANISM: Homo sapiens
<220> FEATURE:
<223> OTHER INFORMATION: CstF64 (64kD subunit 2) (NM_015235)

<400> SEQUENCE: 72

```
agacgcctcg aagaatccgc tatcggctgt ctgcacaacc ggaatcatgt cgagtttggc     60
ggtgagagac ccggcaatgg atcgatcact gcgttccgtg ttcgtgggga acattccata    120
tgaggcaact gaggagcagt taaaggacat tttctcggag gttggttctg ttgtcagttt    180
ccggctggta tacgatagag agacgggaaa acccaagggc tatggcttct gcgaatacca    240
agaccaggag accgcgctta gtgccatgcg gaacctcaat gggcgggagt tcagtgggag    300
agcgcttcgg gtggacaatg ctgccagtga aaagaataag gaggagttaa agagccttgg    360
gcctgcagcg cccattattg actcacccta tggggatccc atcgatccag aagatgcccc    420
tgaatcgatt accagagcag tagccagtct ccccccggag cagatgtttg agctgatgaa    480
gcagatgaag ctctgtgtcc aaaacagcca ccaggaagct cgaaacatgt tacttcaaaa    540
tccacaactg gcttatgcac tgttgcaggc acaagtagtg atgagaatca tggatccaga    600
gattgctctg aaaattctgc atcggaagat acatgtcaca ccactgatcc caggcaaatc    660
tcagtctgtg tctgtctctg gccctggccc tgggcctggc cctgggctct gcccaggacc    720
taatgttctg ctgaaccagc agaatcctcc agctcctcag cctcagcatt tggctagaag    780
acctgtgaag gacattcctc ctctgatgca gactcctatc cagggtggaa ttccagctcc    840
agggccaata ccagctgcag ttcccggagc tggtcctggt tccttaactc ctggaggagc    900
aatgcagccc caacttggaa tgccagggt ggcccagtg cctttagagc ggggacaagt    960
gcagatgtca gatcctagag ctcctatacc tcgcggaccc gtgactcctg gtggtctgcc   1020
tcctcgagga ctgttaggag atgctccaaa tgacccacgt ggagggactt tgctttcagt   1080
cactggagaa gtggagccca gaggttatct gggtccaccc catcagggtc ccccatgca     1140
```

```
tcatgcctct ggtcatgaca ctcgtggccc ttcctcacat gagatgaggg gagggccatt     1200
aggagatccc agactgctaa ttggagagcc cagaggcccc atgatagatc aaagggtct     1260 acctatggat ggtagaggtg gtagagattc tcgagcgatg gagactcgtg ccatggaaac    1320
tgaggtctta gagacacgtg taatggagag gagaggaatg gagacctgtg cgatggaaac    1380
cagagggatg gaagcaaggg gcatggatgc aagaggattg gagatgaggg gccctgtccc    1440
cagttcaaga ggcccctatga ctggtggaat tcagggtcct ggtcccatta atatagggc    1500 aggtggccct cctcagggac ccagacaggt cccaggcatt tcaggggtgg ggaatcctgg    1560
agctggtatg cagggtacag gcatacaagg aacaggcatg cagggagcag gcatacaagg    1620 aggaggggatg caggggcag gcatacaagg agtcagtata caaggaggag gtatacaagg   1680
aggaggtata caggggcaa gcaagcaagg tggaagccag cctagcagtt ttagtcctgg    1740
gcagagccag gtcactccac aggatcagga gaaggcagct ttgatcatgc aggttcttca    1800
actgactgca gatcagattg ccatgctgcc ccctgagcaa aggcagagta tcctgatttt    1860
aaaggaacaa atccagaaat ccactggagc gtcttgaaag gttttagaaa atatttggct    1920
gtagtctcaa atttttattct gtagcatgga gaatgggtgc aaaaagctga cttctgtatc   1980
cccacacttg gattagggtt tccctcctcc tagaacctaa tcttatttt tgttcttttt     2040 ctttctttct gttttccttt tttttttaat tgagggtggg gggaggaggg agtgcgtctg    2100
ttcactttaa gttactttaa ataactctg aacatgatta tattatgcca aataagatta    2160
caaagaataa gcagcaatat tgaagcatct acagtatgtt aactcatttt tttaaatgtc   2220
gagtaaaact tcgtgaaaac tgctcataaa gactaaaagt tgacctgtta aaacgttaat   2280
gtactaagat agttttaaga tttttggttg tataacaaaa taaagtttta cccaaaagta  2340
taagatacat ttttttggtaa accatttaaa atacaaaatc ctattttgga ggcaatagga  2400
taagcattgt cttagtgttt tagaattatt tttgaaacag agttaacagg ataaggttac   2460
acttgtatta gaattgtttt tttctaaagt tatgttacct gaaaaatcaa ggagtgcacc   2520
tgatttactg ttgcttcatt tatcccatcc ttcagagacc agcaaggttc tgccaggccc   2580
caagcatctg agcatgatga ttttgctgtg acaattctaa gatcaaccag gttacttaag   2640
tccgctctga tgaaacccag tctctcaata ccttcctatt tctcaatagt ctttaagccc   2700
taaatctgag tcagtaattc tctaaaaatc cttcccaaaa atcagtgtct agggactggt   2760
tgatctagat gagttataaa tggtatttga cttttcataa gtagtggaag gtttcactaa   2820
gtaaagatct gagtttcttg gtatctgacg tttgtataca gatggtgtcc atttgctcaa   2880
ccagacagga gttaacttgt attagaattg ttttttctaa agttatgtta cctgagaaat   2940
taaggactgc acctggttta atgttgcttc acttatccca ccctacagag accagcaagg   3000
ttctgccagg cctcgagcat ccaagcatga ttttgctgtg acaaatctaa aatcaaccag   3060
gctacttaag tctgctctga tgaaacccaa taatctctca ataccttcct atttctcaat   3120
agtctttaaa ccctaaatct gagtcagtaa ttctcttaca tccttcccaa aaatcagtgt   3180
ctagggacta gttgatctgg atgagttata catgatattt gacttttcat aagtagtgga   3240
aggtttcact aagtaaaaact ctcagtttct tggtatctgg cttttcttata cagatggtgt   3300 ccatttgctc caccagacag gagttaaaaa ccttttaaaga gcatttaaca tgccttttag   3360
ttttcttatt tcataatcta cttttctatc attaatcatc ttaccaggaa taatcaaggc    3420
ccaggtaggt agaagttttt atatagcctg aatactcact tgacttactg ctcattttac   3480
tttttgcatg gaatacagcc atttagtcct aatatacata ccaatgagac aattaaaaat   3540
```

-continued

```
tggttggaag atggagctta tcacattgtg ctactacgac tttatttttt cttgaaaata      3600
aagccttgag gatgtgaaca taaatgttgg tatcataaaa caagtagtaa taaaagcata      3660
aattatcaaa tatcaggtga tcttactatg gagaagaaaa accaatatct agttacagat      3720
gaaaaaatgt taatacaaa gagctgaaaa tgtagaaatt gagttatctt cccttttgcaa      3780 aatttttaca ctttaaatta gtaattcttt gtttgcaagg ttttcatccc tatgctgttg      3840
ttttctacta cctgttttac tcttgttcat actgctactt tcccatgttt cctatatgcc      3900
tcccctatat tggagaggat aactcgcgtt tacatatgtg atagttatgc ttaatactaa      3960
ttcacagagt tggctcgatc atttttgagat tctagttgct ttatctcaaa gctttcactg      4020
aagggctgta actgaaaatt attaaatgtt agtctttagt caaatctctg cattgtttca      4080
tgcagaaaat aaagatacaa ttaaggctga aaaaaaaaaa aaaaaaa                    4127
```

<210> SEQ ID NO 73
<211> LENGTH: 577
<212> TYPE: PRT
<213> ORGANISM: Homo Sapiens
<220> FEATURE:
<223> OTHER INFORMATION: CstF64 (64 kD subunit 2) (NP_001316)

<400> SEQUENCE: 73

```
Met Ala Gly Leu Thr Val Arg Asp Pro Ala Val Asp Arg Ser Leu Arg
1               5                   10                  15

Ser Val Phe Val Gly Asn Ile Pro Tyr Glu Ala Thr Glu Glu Gln Leu
            20                  25                  30

Lys Asp Ile Phe Ser Glu Val Gly Pro Val Val Ser Phe Arg Leu Val
        35                  40                  45

Tyr Asp Arg Glu Thr Gly Lys Pro Lys Gly Tyr Gly Phe Cys Glu Tyr
    50                  55                  60

Gln Asp Gln Glu Thr Ala Leu Ser Ala Met Arg Asn Leu Asn Gly Arg
65                  70                  75                  80

Glu Phe Ser Gly Arg Ala Leu Arg Val Asp Asn Ala Ala Ser Glu Lys
                85                  90                  95

Asn Lys Glu Glu Leu Lys Ser Leu Gly Thr Gly Ala Pro Val Ile Glu
            100                 105                 110

Ser Pro Tyr Gly Glu Thr Ile Ser Pro Glu Asp Ala Pro Glu Ser Ile
        115                 120                 125

Ser Lys Ala Val Ala Ser Leu Pro Pro Glu Gln Met Phe Glu Leu Met
    130                 135                 140

Lys Gln Met Lys Leu Cys Val Gln Asn Ser Pro Gln Glu Ala Arg Asn
145                 150                 155                 160

Met Leu Leu Gln Asn Pro Gln Leu Ala Tyr Ala Leu Leu Gln Ala Gln
                165                 170                 175

Val Val Met Arg Ile Val Asp Pro Glu Ile Ala Leu Lys Ile Leu His
            180                 185                 190

Arg Gln Thr Asn Ile Pro Thr Leu Ile Ala Gly Asn Pro Gln Pro Val
        195                 200                 205

His Gly Ala Gly Pro Gly Ser Gly Ser Asn Val Ser Met Asn Gln Gln
    210                 215                 220

Asn Pro Gln Ala Pro Gln Ala Gln Ser Leu Gly Gly Met His Val Asn
225                 230                 235                 240

Gly Ala Pro Pro Leu Met Gln Ala Ser Met Gln Gly Val Pro Ala
                245                 250                 255

Pro Gly Gln Met Pro Ala Ala Val Thr Gly Pro Gly Pro Gly Ser Leu
```

-continued

```
                260                 265                 270
Ala Pro Gly Gly Gly Met Gln Ala Gln Val Gly Met Pro Gly Ser Gly
            275                 280                 285

Pro Val Ser Met Glu Arg Gly Gln Val Pro Met Gln Asp Pro Arg Ala
        290                 295                 300

Ala Met Gln Arg Gly Ser Leu Pro Ala Asn Val Pro Thr Pro Arg Gly
305                 310                 315                 320

Leu Leu Gly Asp Ala Pro Asn Asp Pro Arg Gly Thr Leu Leu Ser
            325                 330                 335

Val Thr Gly Glu Val Glu Pro Arg Gly Tyr Leu Gly Pro His Gln
            340                 345                 350

Gly Pro Pro Met His His Val Pro Gly His Glu Ser Arg Gly Pro Pro
            355                 360                 365

Pro His Glu Leu Arg Gly Gly Pro Leu Pro Glu Pro Arg Pro Leu Met
        370                 375                 380

Ala Glu Pro Arg Gly Pro Met Leu Asp Gln Arg Gly Pro Pro Leu Asp
385                 390                 395                 400

Gly Arg Gly Gly Arg Asp Pro Arg Gly Ile Asp Ala Arg Gly Met Glu
                405                 410                 415

Ala Arg Ala Met Glu Ala Arg Gly Leu Asp Ala Arg Gly Leu Glu Ala
                420                 425                 430

Arg Ala Met Glu Ala Arg Ala Met Glu Ala Arg Ala Met Glu Ala Arg
            435                 440                 445

Ala Met Glu Ala Arg Ala Met Glu Val Arg Gly Met Glu Ala Arg Gly
            450                 455                 460

Met Asp Thr Arg Gly Pro Val Pro Gly Pro Arg Gly Pro Ile Pro Ser
465                 470                 475                 480

Gly Met Gln Gly Pro Ser Pro Ile Asn Met Gly Ala Val Val Pro Gln
                485                 490                 495

Gly Ser Arg Gln Val Pro Val Met Gln Gly Thr Gly Met Gln Gly Ala
                500                 505                 510

Ser Ile Gln Gly Gly Ser Gln Pro Gly Gly Phe Ser Pro Gly Gln Asn
            515                 520                 525

Gln Val Thr Pro Gln Asp His Glu Lys Ala Ala Leu Ile Met Gln Val
            530                 535                 540

Leu Gln Leu Thr Ala Asp Gln Ile Ala Met Leu Pro Pro Glu Gln Arg
545                 550                 555                 560

Gln Ser Ile Leu Ile Leu Lys Glu Gln Ile Gln Lys Ser Thr Gly Ala
                565                 570                 575

Pro
```

<210> SEQ ID NO 74
<211> LENGTH: 616
<212> TYPE: PRT
<213> ORGANISM: Homo sapiens
<220> FEATURE:
<223> OTHER INFORMATION: CstF64(64kD subunit 2) (NP056050)

<400> SEQUENCE: 74

```
Met Ser Ser Leu Ala Val Arg Asp Pro Ala Met Asp Arg Ser Leu Arg
1               5                   10                  15

Ser Val Phe Val Gly Asn Ile Pro Tyr Glu Ala Thr Glu Glu Gln Leu
            20                  25                  30

Lys Asp Ile Phe Ser Glu Val Gly Ser Val Val Ser Phe Arg Leu Val
        35                  40                  45
```

-continued

```
Tyr Asp Arg Glu Thr Gly Lys Pro Lys Gly Tyr Gly Phe Cys Glu Tyr
 50                  55                  60

Gln Asp Gln Glu Thr Ala Leu Ser Ala Met Arg Asn Leu Asn Gly Arg
 65                  70                  75                  80

Glu Phe Ser Gly Arg Ala Leu Arg Val Asp Asn Ala Ala Ser Glu Lys
                 85                  90                  95

Asn Lys Glu Glu Leu Lys Ser Leu Gly Pro Ala Ala Pro Ile Ile Asp
            100                 105                 110

Ser Pro Tyr Gly Asp Pro Ile Asp Pro Glu Asp Ala Pro Glu Ser Ile
            115                 120                 125

Thr Arg Ala Val Ala Ser Leu Pro Pro Glu Gln Met Phe Glu Leu Met
130                 135                 140

Lys Gln Met Lys Leu Cys Val Gln Asn Ser His Gln Glu Ala Arg Asn
145                 150                 155                 160

Met Leu Leu Gln Asn Pro Gln Leu Ala Tyr Ala Leu Leu Gln Ala Gln
                165                 170                 175

Val Val Met Arg Ile Met Asp Pro Glu Ile Ala Leu Lys Ile Leu His
                180                 185                 190

Arg Lys Ile His Val Thr Pro Leu Ile Pro Gly Lys Ser Gln Ser Val
                195                 200                 205

Ser Val Ser Gly Pro Gly Pro Gly Pro Gly Leu Cys Pro Gly
            210                 215                 220

Pro Asn Val Leu Leu Asn Gln Gln Asn Pro Pro Ala Pro Gln Pro Gln
225                 230                 235                 240

His Leu Ala Arg Arg Pro Val Lys Asp Ile Pro Pro Leu Met Gln Thr
                245                 250                 255

Pro Ile Gln Gly Gly Ile Pro Ala Pro Gly Pro Ile Pro Ala Ala Val
                260                 265                 270

Pro Gly Ala Gly Pro Gly Ser Leu Thr Pro Gly Gly Ala Met Gln Pro
            275                 280                 285

Gln Leu Gly Met Pro Gly Val Gly Pro Val Pro Leu Glu Arg Gly Gln
            290                 295                 300

Val Gln Met Ser Asp Pro Arg Ala Pro Ile Pro Arg Gly Pro Val Thr
305                 310                 315                 320

Pro Gly Gly Leu Pro Pro Arg Gly Leu Leu Gly Asp Ala Pro Asn Asp
                325                 330                 335

Pro Arg Gly Gly Thr Leu Leu Ser Val Thr Gly Glu Val Glu Pro Arg
            340                 345                 350

Gly Tyr Leu Gly Pro Pro His Gln Gly Pro Pro Met His His Ala Ser
            355                 360                 365

Gly His Asp Thr Arg Gly Pro Ser Ser His Glu Met Arg Gly Gly Pro
        370                 375                 380

Leu Gly Asp Pro Arg Leu Leu Ile Gly Glu Pro Arg Gly Pro Met Ile
385                 390                 395                 400

Asp Gln Arg Gly Leu Pro Met Asp Gly Arg Gly Arg Asp Ser Arg
                405                 410                 415

Ala Met Glu Thr Arg Ala Met Glu Thr Glu Val Leu Gly Thr Arg Val
                420                 425                 430

Met Glu Arg Arg Gly Met Glu Thr Cys Ala Met Glu Thr Arg Gly Met
            435                 440                 445

Glu Ala Arg Gly Met Asp Ala Arg Gly Leu Glu Met Arg Gly Pro Val
            450                 455                 460

Pro Ser Ser Arg Gly Pro Met Thr Gly Gly Ile Gln Gly Pro Gly Pro
465                 470                 475                 480
```

```
Ile Asn Ile Gly Ala Gly Gly Pro Gln Gly Pro Arg Gln Val Pro
                485                 490                 495
Gly Ile Ser Gly Val Gly Asn Pro Gly Ala Gly Met Gln Gly Thr Gly
            500                 505                 510
Ile Gln Gly Thr Gly Met Gln Gly Ala Gly Ile Gln Gly Gly Met
        515                 520                 525
Gln Gly Ala Gly Ile Gln Gly Val Ser Ile Gln Gly Gly Ile Gln
530                 535                 540
Gly Gly Ile Gln Gly Ala Ser Lys Gln Gly Gly Ser Gln Pro Ser
545                 550                 555                 560
Ser Phe Ser Pro Gly Gln Ser Gln Val Thr Pro Gln Asp Gln Glu Lys
            565                 570                 575
Ala Ala Leu Ile Met Gln Val Leu Gln Leu Thr Ala Asp Gln Ile Ala
        580                 585                 590
Met Leu Pro Pro Glu Gln Arg Gln Ser Ile Leu Ile Leu Lys Glu Gln
    595                 600                 605
Ile Gln Lys Ser Thr Gly Ala Ser
610                 615

<210> SEQ ID NO 75
<211> LENGTH: 2846
<212> TYPE: DNA
<213> ORGANISM: Homo Sapiens
<220> FEATURE:
<223> OTHER INFORMATION: CstF77 (77 kD subunit 3) (NM_001326)

<400> SEQUENCE: 75
gcagccattt taattcatat ttgagtgggc ggtggcgatt ggtgttggcg gtctggctca    60
gctgggcagg gggtaacttt actgatttgg gggtggtttt tagtttaatt tttcttttct   120
agcttcccat cgacggtcag tgcgcacgtt gtaatcagct gaggccatgt caggagacgg   180
agccacggag caggcagctg agtatgtccc agagaaggtg aagaaagcgg aaaagaaatt   240
agaagagaat ccatatgacc ttgatgcttg gagcattctc attcgagagg cacagaatca   300
acctatagac aaagcacgga agactatgaa acgccttgtt gcccagttcc ccagttctgg   360
cagattctgg aaactgtaca ttgaagcaga gattaaagct aaaaattatg acaaggttga   420
aaagctattt cagagatgcc ttatgaaggt tttgcacatt gatttatgga agtgttatct   480
ttcatatgtc cgagaaacca agggtaaact accaagttac aaagaaaaaa tggctcaagc   540
atatgacttt gcactggata aaattggaat ggaaattatg tcctatcaga tttgggtgga   600
ttacatcaat ttcctaaaag gcgtggaagc tgtaggatct tatgcagaaa atcaaagaat   660
aacagctgtc cgaagagttt atcaacgagg ttgtgttaat ccgatgatca acattgaaca   720
gctctggaga gactataaca agtatgaaga gggtatcaat attcatttag ctaaaaaaat   780
gattgaagat cggagtagag attatatgaa tgctagacgt gtagcaaagg aatatgagac   840
agtaatgaaa ggcttggacc gtaatgctcc ctcggtgcct cctcagaata tcctcaaga   900
agctcaacaa gtagatatgt ggaagaaata tatacagtgg aaaagagca accctcttcg   960
tacagaggat cagacccctta taacaaaaag agttatgttt gcttatgaac agtgcctgct  1020
tgtgctgggc catcaccctg atatttggta tgaagctgcc cagtatcttg agcagtcaag  1080
taaactgctc gcagaaaagg gagatatgaa taatgccaaa ttatttagtg atgaagctgc  1140
taatatatat gaaagagcca taagcacttt attgaagaag aatatgcttc tttattttgc  1200
atatgcagat tatgaagaga gtcgcatgaa gtatgaaaag gttcacagta tatataacag  1260
```

-continued

```
acttctggca attgaggata ttgaccctac cttggtatat atccaatata tgaaatttgc    1320
acggagagca gaaggcatca aatctggaag aatgatattt aaaaaagcaa gagaagatac    1380
cagaacccgc caccatgtct atgttactgc agcactcatg gaatattact gtagtaagga    1440
caaatctgtt gcctttaaga ttttgagct ggggctaaaa aaatatggag acattccaga    1500
gtatgtcctg gcctatattg actatctttc tcacctcaat gaggacaata tacccgagt    1560 tttgttgaa cgagttttaa catctggaag ccttcctcct gagaagtctg gagaaatctg    1620
ggcccgattt ctagcatttg aaagtaatat tggtgatcta gctagtatac tcaaagtgga    1680
gaaaagacgg tttacagcat tcaaagaaga gtatgaaggg aaagaaacgg ctttactagt    1740
agatagatac aagttcatgg atttatatcc ttgctctgca agtgaattaa aagcacttgg    1800
ttataaggat gtctcccgtg ctaagctagc agctataatt ccggacccag ttgtagctcc    1860
ttctatagtg cctgttctga aagatgaagt ggatagaaaa ccagaatacc ctaaaccaga    1920
cactcagcag atgattccat ttcagccacg acatttagca cctccaggtt tacaccctgt    1980
acctggtgga gtgttcccag tccctcctgc agctgttgtt ttaatgaaac ttctccctcc    2040
tcctatctgt ttccagggtc cttttgtaca agtggatgaa ctgatggaaa ttttccgaag    2100
atgcaagata ccaaatactg ttgaggaagc tgtgaggatc attactggtg ggccccaga    2160 gctagctgta gaaggcaacg gccccgtgga agtaatgca gtactcacca aggccgtcaa    2220
aaggcccaac gaggattcag atgaagatga agaaaaggga gccgttgtcc ccctgttca    2280 tgacatttac agagcacggc agcagaagcg gattcggtag ggttttaaac gcctctgcag    2340
aaaactcctg tccaggattc cttttgcctc aagtggtatg tttaaaagag acaacgcttt    2400
gttacaaggt tcttggaaac aaagttgtat tgtcattggt gcctctatca catggttctt    2460
gagaaaaaac aaaccaacct gtgtgaattt tagaatacgg aacagaccta tgctctaagc    2520
aaaattaggt tttcaaaaat gtgagaacag tacaaagtgg cagaaccaca ttttgttccc    2580
tcttcaaggg tgtcttgtat gtgccgcttg aagatttgtg agttttcaa cagttttatt    2640 ttaaaaactg gatggcttat gattgtaaag cattttatca cattttctga aaacaattgt    2700
tcttggtttg cttatgtaga gtcctgcctt attgtttgtt tttatttatg gcagaatgta    2760
tgaaatccgt tttgtagttt caaattttaa aagtccttta aaaataaaa ggattcagaa    2820 acaaaaaaaa aaaaaaaaa aaaaaa                                         2846
```

<210> SEQ ID NO 76
<211> LENGTH: 717
<212> TYPE: PRT
<213> ORGANISM: Homo Sapiens
<220> FEATURE:
<223> OTHER INFORMATION: CstF77 (77 kD subunit 3) (NP_001317)

<400> SEQUENCE: 76

```
Met Ser Gly Asp Gly Ala Thr Glu Gln Ala Ala Glu Tyr Val Pro Glu
1               5                   10                  15

Lys Val Lys Lys Ala Glu Lys Lys Leu Glu Glu Asn Pro Tyr Asp Leu
            20                  25                  30

Asp Ala Trp Ser Ile Leu Ile Arg Glu Ala Gln Asn Gln Pro Ile Asp
        35                  40                  45

Lys Ala Arg Lys Thr Tyr Glu Arg Leu Val Ala Gln Phe Pro Ser Ser
    50                  55                  60

Gly Arg Phe Trp Lys Leu Tyr Ile Glu Ala Glu Ile Lys Ala Lys Asn
65                  70                  75                  80

Tyr Asp Lys Val Glu Lys Leu Phe Gln Arg Cys Leu Met Lys Val Leu
```

```
                    85                  90                  95
His Ile Asp Leu Trp Lys Cys Tyr Leu Ser Tyr Val Arg Glu Thr Lys
            100                 105                 110

Gly Lys Leu Pro Ser Tyr Lys Glu Lys Met Ala Gln Ala Tyr Asp Phe
            115                 120                 125

Ala Leu Asp Lys Ile Gly Met Glu Ile Met Ser Tyr Gln Ile Trp Val
            130                 135                 140

Asp Tyr Ile Asn Phe Leu Lys Gly Val Glu Ala Val Gly Ser Tyr Ala
145                 150                 155                 160

Glu Asn Gln Arg Ile Thr Ala Val Arg Arg Val Tyr Gln Arg Gly Cys
                165                 170                 175

Val Asn Pro Met Ile Asn Ile Glu Gln Leu Trp Arg Asp Tyr Asn Lys
            180                 185                 190

Tyr Glu Glu Gly Ile Asn Ile His Leu Ala Lys Lys Met Ile Glu Asp
            195                 200                 205

Arg Ser Arg Asp Tyr Met Asn Ala Arg Arg Val Ala Lys Glu Tyr Glu
            210                 215                 220

Thr Val Met Lys Gly Leu Asp Arg Asn Ala Pro Ser Val Pro Pro Gln
225                 230                 235                 240

Asn Thr Pro Gln Glu Ala Gln Gln Val Asp Met Trp Lys Lys Tyr Ile
                245                 250                 255

Gln Trp Glu Lys Ser Asn Pro Leu Arg Thr Glu Asp Gln Thr Leu Ile
            260                 265                 270

Thr Lys Arg Val Met Phe Ala Tyr Glu Gln Cys Leu Leu Val Leu Gly
            275                 280                 285

His His Pro Asp Ile Trp Tyr Glu Ala Ala Gln Tyr Leu Glu Gln Ser
            290                 295                 300

Ser Lys Leu Leu Ala Glu Lys Gly Asp Met Asn Asn Ala Lys Leu Phe
305                 310                 315                 320

Ser Asp Glu Ala Ala Asn Ile Tyr Glu Arg Ala Ile Ser Thr Leu Leu
                325                 330                 335

Lys Lys Asn Met Leu Leu Tyr Phe Ala Tyr Ala Asp Tyr Glu Glu Ser
            340                 345                 350

Arg Met Lys Tyr Glu Lys Val His Ser Ile Tyr Asn Arg Leu Leu Ala
            355                 360                 365

Ile Glu Asp Ile Asp Pro Thr Leu Val Tyr Ile Gln Tyr Met Lys Phe
            370                 375                 380

Ala Arg Arg Ala Glu Gly Ile Lys Ser Gly Arg Met Ile Phe Lys Lys
385                 390                 395                 400

Ala Arg Glu Asp Thr Arg Thr Arg His His Val Tyr Val Thr Ala Ala
                405                 410                 415

Leu Met Glu Tyr Tyr Cys Ser Lys Asp Lys Ser Val Ala Phe Lys Ile
            420                 425                 430

Phe Glu Leu Gly Leu Lys Lys Tyr Gly Asp Ile Pro Glu Tyr Val Leu
            435                 440                 445

Ala Tyr Ile Asp Tyr Leu Ser His Leu Asn Glu Asp Asn Asn Thr Arg
450                 455                 460

Val Leu Phe Glu Arg Val Leu Thr Ser Gly Ser Leu Pro Pro Glu Lys
465                 470                 475                 480

Ser Gly Glu Ile Trp Ala Arg Phe Leu Ala Phe Glu Ser Asn Ile Gly
                485                 490                 495

Asp Leu Ala Ser Ile Leu Lys Val Glu Lys Arg Arg Phe Thr Ala Phe
            500                 505                 510
```

```
Lys Glu Glu Tyr Glu Gly Lys Glu Thr Ala Leu Leu Val Asp Arg Tyr
        515                 520                 525

Lys Phe Met Asp Leu Tyr Pro Cys Ser Ala Ser Glu Leu Lys Ala Leu
530                 535                 540

Gly Tyr Lys Asp Val Ser Arg Ala Lys Leu Ala Ala Ile Ile Pro Asp
545                 550                 555                 560

Pro Val Val Ala Pro Ser Ile Val Pro Val Leu Lys Asp Glu Val Asp
                565                 570                 575

Arg Lys Pro Glu Tyr Pro Lys Pro Asp Thr Gln Met Ile Pro Phe
                580                 585                 590

Gln Pro Arg His Leu Ala Pro Pro Gly Leu His Pro Val Pro Gly Gly
            595                 600                 605

Val Phe Pro Val Pro Pro Ala Ala Val Val Leu Met Lys Leu Leu Pro
        610                 615                 620

Pro Pro Ile Cys Phe Gln Gly Pro Phe Val Gln Val Asp Glu Leu Met
625                 630                 635                 640

Glu Ile Phe Arg Arg Cys Lys Ile Pro Asn Thr Val Glu Glu Ala Val
                645                 650                 655

Arg Ile Ile Thr Gly Gly Ala Pro Glu Leu Ala Val Glu Gly Asn Gly
                660                 665                 670

Pro Val Glu Ser Asn Ala Val Leu Thr Lys Ala Val Lys Arg Pro Asn
            675                 680                 685

Glu Asp Ser Asp Glu Asp Glu Glu Lys Gly Ala Val Val Pro Pro Val
690                 695                 700

His Asp Ile Tyr Arg Ala Arg Gln Gln Lys Arg Ile Arg
705                 710                 715

<210> SEQ ID NO 77
<211> LENGTH: 4188
<212> TYPE: DNA
<213> ORGANISM: Homo sapiens
<220> FEATURE:
<223> OTHER INFORMATION: symplekin (SYMPK) (NM_004819)

<400> SEQUENCE: 77
ggaaatgaag ggtctgctcg ccgtagtatg gaggcgggca gaatgccgct cgcacgggac      60
gaggcatggg cggggtcggg ctgtgctctg gactccattt cccggcggcc ctgggtgtgt     120
ggcgcgtgcg caccgttccc ggcgacgaac ggaagatggc ggcggcggcg gcggcggagt     180
gtaggaagag gcactgctga gggggcgcga ggggaacgga ggccagagct gcgctgacag     240
cagccatggc gagcggcagt ggagacagcg tcacccgtcg gagcgtggca tcacagtttt     300
tcactcaaga ggaggggccg ggcatcgatg gcatgaccac ctcagagagg gtggtggatc     360
ttctgaacca ggcggcgctg atcaccaatg actcaaagat cacagtgctc aaacaggtcc     420
aggagctgat catcaacaaa gaccccacac tactggacaa cttcctggat gagatcatcg     480
cattccaagc agacaagtca atcgaagtgc gaaaatttgt catcggcttc atcgaggagg     540
catgcaagcg agacattgag ttgctgctga aactcattgc aaacctcaac atgctcttga     600
gggacgagaa tgtgaacgtg gtgaagaagg ctatcctcac catgacccag ctctacaagg     660
tggccctgca gtggatggta aagtcacggg tcattagcga gctacaggag gcctgctggg     720
acatggtatc tgccatggcg ggggacatca tcctgctatt ggactctgac aatgacggca     780
tccgcaccca cgccatcaag tttgtggagg gcctcattgt caccctgtca ccccgcatgg     840
ctgactcaga gataccccga cgccaggagc atgatatcag cctggaccgc atccctcgtg     900 accacccta catccagtac aacgtgctat gggaagaggg caaggcagcc ttggagcagc     960
```

```
tgcttaagtt catggtgcac cctgccatct cctccatcaa cctgaccaca gcgctgggct    1020
cccttgccaa tatcgcccgc cagagaccca tgttcatgtc tgaggtgatc caggcctatg    1080
aaactctgca tgccaacctg cccccgacgc tggccaaatc gcaggtgagc agtgtgcgta    1140
agaatctgaa gctgcacctg ttgagtgtgc tgaagcaccc ggcttccttg gagttccagg    1200
cccagatcac cacctgctg gtggacctgg cacacctca ggccgagatc gcccgcaaca    1260
tgccgagcag caaggacacc cgcaagcggc cccgcgatga ctcggactcc acactcaaga    1320
agatgaagct ggagcccaac ctgggggagg acgatgagga caaagacttg gagccaggcc    1380
cgtcggggac ctcgaaggcc tcagcgcaga tctccggcca gtcagacacg gacatcacag    1440
ctgagttcct gcagcctctg ctgacgcctg ataatgtggc taatctggtc ctcatcagca    1500
tggtgtacct acccgaggcc atgccagcct ccttccaggc catctacacc cccgtggagt    1560
cagcaggcac ggaagcccag atcaagcacc tggctcggct catggccaca cagatgacag    1620
ctgccggact gggaccaggt gtagagcaga ccaaacagtg caaggaggag cccaaggagg    1680
agaaggtggt gaagacagag agcgtcctga tcaagcggcg cctgtcagcc cagggccaag    1740
ccatctcggt ggtgggttcc ctgagctcca tgtcccccct ggaggaagag gcaccgcagg    1800
ccaagaggag gccagagccc attatccctg tcactcagcc ccggctggca ggcgctggtg    1860
ggcgcaagaa aattttccgt tcagcgacg tgctgaagcc ccttaccgat gcccaggtgg    1920
aagccatgaa gctgggcgct gtgaagcgga tcctgcgggc tgagaaggct gtggcctgca    1980
gcggggcagc ccaggtccgc ataaagatcc tggccagcct ggtgacacag ttcaactcgg    2040
gcctgaaggc ggaggtcctg tccttcatcc tggaggatgt gcgggcccgc ctggacctgg    2100
ccttcgcctg gctctaccag gagtacaacg cctacctggc cgcaggtgcc tcgggctccc    2160
tggacaagta tgaggactgc ctcatccgcc tgttgtctgg cctgcaggag aaaccagacc    2220
agaaggatgg gatcttcacc aaggttgtgc tggaggcgcc actcatcaca gagagtgccc    2280
tggaggtggt ccgcaagtac tgcgaggatg agagtcgcac ctatctgggc atgtccacac    2340
ttcgagacct gatcttcaag cgcccgtccc gccagttcca gtacctgcat gtcctcctcg    2400
acctcagctc ccatgagaag gacaaggtgc gctcccaggc cctgctgttc atcaaacgca    2460
tgtatgagaa ggagcagctg cgggagtatg tggagaaatt tgccctcaac tacctgcagc    2520
tcctggtgca ccccaaccca ccgtctgtgc tgtttggagc tgacaaggac acagaggtgg    2580
cagcaccctg gacggaggag acagtgaagc agtgtctgta cctctacctg gccctcctgc    2640
ctcagaacca caagctgatc cacgaactgg cggccgtgta cactgaagcc atcgccgaca    2700
tcaagcggac ggtgctgagg gtcattgagc agccgatccg aggaatgggc atgaactccc    2760
cggagctgct cctgctggtg gaaaattgtc ccaagggagc agagacactg gtcacgagat    2820
gtctgcacag cctcacagac aaagtccac cctccccaga gctggtgaag cgggtccggg    2880
atctctacca caagcgactg ccagacgtcc gcttcctcat cccggtgctc aatgggctgg    2940
agaagaaaga ggtgatccag gccctgccta aactcatcaa actcaacccc atcgtggtga    3000
aggaagtctt caaccgcctg ctgggcaccc agcatggtga gggaaactca gccttgtccc    3060
cgctgaaccc tggagagctc ctgatcgcat tacacaacat tgactccgtg aagtgcgaca    3120
tgaaatccat catcaaagcc accaacctgt gctttgcgga gcggaacgtg tacacgtcag    3180
aggtgctggc cgtggtgatg cagcagctga tggagcagag ccccctgccc atgctgctca    3240
tgaggaccgt catccagtcc ctgaccatgt accccgcct gggggcttc gtcatgaaca    3300 tcctgtcccg cctcatcatg aagcaggtgt ggaagtaccc caaggtgtgg gagggcttca    3360
```

```
tcaagtgctg ccagcgcaca aagccccaga gcttccaggt catcctgcag ctgccgcccc    3420
agcagctggg agccgtcttt gacaagtgcc cagagctccg ggagcccctg ctggcccatg    3480
tccgctcctt cacccccac cagcaagctc acatccctaa ctccatcatg accatcttgg     3540
aggccagcgg caagcaggag ccagaggcca aggaggcgcc tgcggggccc ttggaggagg    3600
atgatctgga gcccctgacc ttggccccgg ccccagcacc ccggcccct  caggacctca    3660 tcggcctgcg actggcccag gagaaggcct taaagcggca gctggaggag gaacagaagc    3720
tgaagccggg aggagtggga gcccctcct cttcctcccc ctctccctct ccgtcggccc     3780
ggccaggccc gccccgtct gaggaagcca tggatttccg ggaggagggg cctgagtgcg     3840 agacccgg catcttcatc agcatggatg acgactcggg gctgaccgag gccgcgctgt      3900
tggactctag tctcgagggc cccctaccca aggagacggc agcgggcggg ctgaccttga    3960
aggaggagcg gagcccccag accctcgcac ctgttggaga agatgctatg aagactccca    4020
gcccggctgc cgaggacgcc agggaacccg aggccaaggg gaacagctga cggggctcga    4080
gggggaaagg gggtgggaca gggactcggg gctgggggac ggggcggggc ttgacctgcg    4140
ggtgctttgc cttaaaaaga aataaaagat gtgaacttgg gcaagtta               4188
```

<210> SEQ ID NO 78
<211> LENGTH: 1274
<212> TYPE: PRT
<213> ORGANISM: Homo sapiens
<220> FEATURE:
<223> OTHER INFORMATION: symplekin (SYMPK) (NP_004810)

<400> SEQUENCE: 78

```
Met Ala Ser Gly Ser Gly Asp Ser Val Thr Arg Arg Ser Val Ala Ser
1               5                   10                  15

Gln Phe Phe Thr Gln Glu Glu Gly Pro Gly Ile Asp Gly Met Thr Thr
                20                  25                  30

Ser Glu Arg Val Val Asp Leu Leu Asn Gln Ala Ala Leu Ile Thr Asn
            35                  40                  45

Asp Ser Lys Ile Thr Val Leu Lys Gln Val Gln Glu Leu Ile Ile Asn
        50                  55                  60

Lys Asp Pro Thr Leu Leu Asp Asn Phe Leu Asp Glu Ile Ile Ala Phe
65                  70                  75                  80

Gln Ala Asp Lys Ser Ile Glu Val Arg Lys Phe Val Ile Gly Phe Ile
                85                  90                  95

Glu Glu Ala Cys Lys Arg Asp Ile Glu Leu Leu Leu Lys Leu Ile Ala
            100                 105                 110

Asn Leu Asn Met Leu Leu Arg Asp Glu Asn Val Asn Val Val Lys Lys
        115                 120                 125

Ala Ile Leu Thr Met Thr Gln Leu Tyr Lys Val Ala Leu Gln Trp Met
    130                 135                 140

Val Lys Ser Arg Val Ile Ser Glu Leu Gln Glu Ala Cys Trp Asp Met
145                 150                 155                 160

Val Ser Ala Met Ala Gly Asp Ile Ile Leu Leu Leu Asp Ser Asp Asn
                165                 170                 175

Asp Gly Ile Arg Thr His Ala Ile Lys Phe Val Glu Gly Leu Ile Val
            180                 185                 190

Thr Leu Ser Pro Arg Met Ala Asp Ser Glu Ile Pro Arg Arg Gln Glu
        195                 200                 205

His Asp Ile Ser Leu Asp Arg Ile Pro Arg Asp His Pro Tyr Ile Gln
    210                 215                 220
```

```
Tyr Asn Val Leu Trp Glu Glu Gly Lys Ala Ala Leu Glu Gln Leu Leu
225                 230                 235                 240

Lys Phe Met Val His Pro Ala Ile Ser Ser Ile Asn Leu Thr Thr Ala
                245                 250                 255

Leu Gly Ser Leu Ala Asn Ile Ala Arg Gln Arg Pro Met Phe Met Ser
            260                 265                 270

Glu Val Ile Gln Ala Tyr Glu Thr Leu His Ala Asn Leu Pro Pro Thr
        275                 280                 285

Leu Ala Lys Ser Gln Val Ser Ser Val Arg Lys Asn Leu Lys Leu His
    290                 295                 300

Leu Leu Ser Val Leu Lys His Pro Ala Ser Leu Glu Phe Gln Ala Gln
305                 310                 315                 320

Ile Thr Thr Leu Leu Val Asp Leu Gly Thr Pro Gln Ala Glu Ile Ala
                325                 330                 335

Arg Asn Met Pro Ser Ser Lys Asp Thr Arg Lys Arg Pro Arg Asp Asp
                340                 345                 350

Ser Asp Ser Thr Leu Lys Lys Met Lys Leu Glu Pro Asn Leu Gly Glu
            355                 360                 365

Asp Asp Glu Asp Lys Asp Leu Glu Pro Gly Pro Ser Gly Thr Ser Lys
        370                 375                 380

Ala Ser Ala Gln Ile Ser Gly Gln Ser Asp Thr Asp Ile Thr Ala Glu
385                 390                 395                 400

Phe Leu Gln Pro Leu Leu Thr Pro Asp Asn Val Ala Asn Leu Val Leu
                405                 410                 415

Ile Ser Met Val Tyr Leu Pro Glu Ala Met Pro Ala Ser Phe Gln Ala
                420                 425                 430

Ile Tyr Thr Pro Val Glu Ser Ala Gly Thr Glu Ala Gln Ile Lys His
            435                 440                 445

Leu Ala Arg Leu Met Ala Thr Gln Met Thr Ala Ala Gly Leu Gly Pro
    450                 455                 460

Gly Val Glu Gln Thr Lys Gln Cys Lys Glu Glu Pro Lys Glu Glu Lys
465                 470                 475                 480

Val Val Lys Thr Glu Ser Val Leu Ile Lys Arg Arg Leu Ser Ala Gln
                485                 490                 495

Gly Gln Ala Ile Ser Val Val Gly Ser Leu Ser Ser Met Ser Pro Leu
            500                 505                 510

Glu Glu Glu Ala Pro Gln Ala Lys Arg Arg Pro Glu Pro Ile Ile Pro
        515                 520                 525

Val Thr Gln Pro Arg Leu Ala Gly Ala Gly Arg Lys Lys Ile Phe
    530                 535                 540

Arg Leu Ser Asp Val Leu Lys Pro Leu Thr Asp Ala Gln Val Glu Ala
545                 550                 555                 560

Met Lys Leu Gly Ala Val Lys Arg Ile Leu Arg Ala Glu Lys Ala Val
                565                 570                 575

Ala Cys Ser Gly Ala Ala Gln Val Arg Ile Lys Ile Leu Ala Ser Leu
            580                 585                 590

Val Thr Gln Phe Asn Ser Gly Leu Lys Ala Glu Val Leu Ser Phe Ile
        595                 600                 605

Leu Glu Asp Val Arg Ala Arg Leu Asp Leu Ala Phe Ala Trp Leu Tyr
    610                 615                 620

Gln Glu Tyr Asn Ala Tyr Leu Ala Ala Gly Ala Ser Gly Ser Leu Asp
625                 630                 635                 640

Lys Tyr Glu Asp Cys Leu Ile Arg Leu Leu Ser Gly Leu Gln Glu Lys
```

```
                    645                 650                 655
Pro Asp Gln Lys Asp Gly Ile Phe Thr Lys Val Val Leu Glu Ala Pro
                660                 665                 670

Leu Ile Thr Glu Ser Ala Leu Glu Val Val Arg Lys Tyr Cys Glu Asp
            675                 680                 685

Glu Ser Arg Thr Tyr Leu Gly Met Ser Thr Leu Arg Asp Leu Ile Phe
        690                 695                 700

Lys Arg Pro Ser Arg Gln Phe Gln Tyr Leu His Val Leu Leu Asp Leu
705                 710                 715                 720

Ser Ser His Glu Lys Asp Lys Val Arg Ser Gln Ala Leu Leu Phe Ile
                725                 730                 735

Lys Arg Met Tyr Glu Lys Glu Gln Leu Arg Glu Tyr Val Glu Lys Phe
                740                 745                 750

Ala Leu Asn Tyr Leu Gln Leu Val His Pro Asn Pro Pro Ser Val
            755                 760                 765

Leu Phe Gly Ala Asp Lys Asp Thr Glu Val Ala Ala Pro Trp Thr Glu
        770                 775                 780

Glu Thr Val Lys Gln Cys Leu Tyr Leu Tyr Leu Ala Leu Leu Pro Gln
785                 790                 795                 800

Asn His Lys Leu Ile His Glu Leu Ala Ala Val Tyr Thr Glu Ala Ile
                805                 810                 815

Ala Asp Ile Lys Arg Thr Val Leu Arg Val Ile Glu Gln Pro Ile Arg
                820                 825                 830

Gly Met Gly Met Asn Ser Pro Glu Leu Leu Leu Val Glu Asn Cys
            835                 840                 845

Pro Lys Gly Ala Glu Thr Leu Val Thr Arg Cys Leu His Ser Leu Thr
        850                 855                 860

Asp Lys Val Pro Pro Ser Pro Glu Leu Val Lys Arg Val Arg Asp Leu
865                 870                 875                 880

Tyr His Lys Arg Leu Pro Asp Val Arg Phe Leu Ile Pro Val Leu Asn
                885                 890                 895

Gly Leu Glu Lys Lys Glu Val Ile Gln Ala Leu Pro Lys Leu Ile Lys
                900                 905                 910

Leu Asn Pro Ile Val Val Lys Glu Val Phe Asn Arg Leu Leu Gly Thr
            915                 920                 925

Gln His Gly Glu Gly Asn Ser Ala Leu Ser Pro Leu Asn Pro Gly Glu
        930                 935                 940

Leu Leu Ile Ala Leu His Asn Ile Asp Ser Val Lys Cys Asp Met Lys
945                 950                 955                 960

Ser Ile Ile Lys Ala Thr Asn Leu Cys Phe Ala Glu Arg Asn Val Tyr
                965                 970                 975

Thr Ser Glu Val Leu Ala Val Val Met Gln Gln Leu Met Glu Gln Ser
            980                 985                 990

Pro Leu Pro Met Leu Leu Met Arg Thr Val Ile Gln Ser Leu Thr Met
        995                 1000                1005

Tyr Pro Arg Leu Gly Gly Phe Val Met Asn Ile Leu Ser Arg Leu Ile
    1010                1015                1020

Met Lys Gln Val Trp Lys Tyr Pro Lys Val Trp Glu Gly Phe Ile Lys
1025                1030                1035                1040

Cys Cys Gln Arg Thr Lys Pro Gln Ser Phe Gln Val Ile Leu Gln Leu
                1045                1050                1055

Pro Pro Gln Gln Leu Gly Ala Val Phe Asp Lys Cys Pro Glu Leu Arg
            1060                1065                1070
```

-continued

```
Glu Pro Leu Leu Ala His Val Arg Ser Phe Thr Pro His Gln Gln Ala
        1075                1080                1085

His Ile Pro Asn Ser Ile Met Thr Ile Leu Glu Ala Ser Gly Lys Gln
    1090                1095                1100

Glu Pro Glu Ala Lys Glu Ala Pro Ala Gly Pro Leu Glu Glu Asp Asp
1105                1110                1115                1120

Leu Glu Pro Leu Thr Leu Ala Pro Ala Pro Ala Pro Arg Pro Pro Gln
            1125                1130                1135

Asp Leu Ile Gly Leu Arg Leu Ala Gln Glu Lys Ala Leu Lys Arg Gln
                1140                1145                1150

Leu Glu Glu Glu Gln Lys Leu Lys Pro Gly Gly Val Gly Ala Pro Ser
        1155                1160                1165

Ser Ser Ser Pro Ser Pro Ser Pro Ser Ala Arg Pro Gly Pro Pro Pro
    1170                1175                1180

Ser Glu Glu Ala Met Asp Phe Arg Glu Glu Gly Pro Glu Cys Glu Thr
1185                1190                1195                1200

Pro Gly Ile Phe Ile Ser Met Asp Asp Asp Ser Gly Leu Thr Glu Ala
                1205                1210                1215

Ala Leu Leu Asp Ser Ser Leu Glu Gly Pro Leu Pro Lys Glu Thr Ala
        1220                1225                1230

Ala Gly Gly Leu Thr Leu Lys Glu Glu Arg Ser Pro Gln Thr Leu Ala
    1235                1240                1245

Pro Val Gly Glu Asp Ala Met Lys Thr Pro Ser Pro Ala Ala Glu Asp
1250                1255                1260

Ala Arg Glu Pro Glu Ala Lys Gly Asn Ser
1265                1270

<210> SEQ ID NO 79
<211> LENGTH: 4494
<212> TYPE: DNA
<213> ORGANISM: Homo Sapiens
<220> FEATURE:
<223> OTHER INFORMATION: CPSF160 (160 kD factor 1) (NM_013291)

<400> SEQUENCE: 79
ggcccggccg gactgagttc gctgctgtcc cggttcctct cgagtcggct ccaactgcca      60
gcccgggttg gcgccatgta cgccgtgtac aaacaggcgc atccgcccac cggtctggag     120
ttctccatgt actgcaactt cttcaacaac agcgagcgca acctggtagt ggccgggacc     180
tcgcagctct acgtgtaccg cctcaaccgc gacgccgagg ctctgaccaa gaatgacagg     240
agcacagagg ggaaggccca ccgggagaag ctcgagcttg ctgcctcctt ctccttcttt     300
ggcaacgtca tgtccatggc cagcgtgcag ctggcaggag ccaagcggga tgccctgctc     360
ctaagcttca aggatgccaa gctgtctgtg gtggagtacg accgggcac ccatgacctg      420 aagaccctgt cactgcacta ctttgaggag cctgagcttc gggacgggtt tgtgcagaat     480
gtacacacgc gcgagtgcg ggtggacccc gacgggcgct gtgcagccat gcttgtctac      540
ggcacgcggc tggtggtcct gccctttcgc agggagagcc tggctgagga gcacgagggg     600
ctcgtgggtg aggggcagag gtccagcttc ctgcccagct acatcatcga cgtgcgggcc     660
ctagacgaga agctgctcaa catcatcgac ctgcagttcc tgcatggcta ctacgagcct     720
accctcctca tcctgtttga gcccaaccag acctggctg ggcgcgtggc cgtgcggcag      780
gacacgtgct ccattgtggc catctcactg aacatcacgc agaaggtgca ccccgtcatc     840
tggtccctca ccagcctgcc ctttgactgc acccaggctc tggctgtgcc caagcccata     900 ggtgggtgg tggtgtttgc cgtcaactcg ctgttgtacc tgaaccagag cgtcccccg      960
```

-continued

```
tatggcgtgg ctctcaacag cctcaccaca ggaaccacgg ctttcccgct tcgcacccag      1020
gagggtgtgc ggatcaccct ggactgcgcc caggccacct tcatctccta cgacaagatg      1080
gtcatctccc tcaagggcgg cgagatctac gtgctgaccc tcatcaccga cggcatgcgc      1140
agtgtccgag cgttccactt tgacaaggcg gccgccagcg tcctcaccac cagcatggtc      1200
accatggagc ccgggtacct gttcctgggt tctcgcctgg gcaattccct cctcctcaag      1260
tacacggaga agctgcagga gccccggcc agtgctgtcc gtgaggctgc cgacaaggaa       1320
gagcctccct caaagaagaa gcgagtggat gcgacggccg gctggtcagc tgcgggtaag     1380
tcggtgccgc aggatgaggt ggacgagatt gaagtgtacg gcagcgaggc ccagtcggga      1440
acacagctgg ccacctactc ctttgaggtg tgtgacagca tcctgaacat tggaccctgt      1500
gccaatgccg ccgtgggcga gcctgccttc ctctctgaag agtttcagaa cagccccgag     1560
ccggacctgg agattgtggt ttgctccggc cacgggaaga acggggcttt gtcggtgctg      1620
cagaagagca tccggcccca ggtggtgaca acctttgagc ttccggctg ctatgacatg       1680 tggacagtca tcgccccggt gcgtaaggag gaggaggaca tcccaagggg ggagggcaca     1740
gagcaggaac ccagcaccac ccctgaagca gacgacgacg ccgcagaca cggattcctg      1800 attctgagcc gggaagactc caccatgatc ctgcagacgg ggcaggagat catggagctg      1860
gacaccagtg gcttcgccac tcagggcccc acggtctttg ctgggaacat cggggacaac     1920
cgctacattg tccaagtgtc accactgggc atccgcctgc tggaaggagt gaatcagctg     1980
cacttcatcc ccgtggacct gggcgccccc atcgtgcagt gcgccgtggc cgaccctat      2040 gtggtcatca tgagtgccga gggccacgtc accatgttcc tgctgaagag tgactcctac     2100
ggtggccgcc accaccgcct ggcgctgcac aagcccccgc tgcaccatca gtccaaggtg     2160
attacgctgt gcctgtaccg agacctcagc ggcatgttca ccactgagag ccgcctgggt     2220
ggggcccgtg acgagctcgg gggccgcagt ggcccgagg ccgagggcct gggctcagag      2280
actagcccca cagtggatga cgaggaggag atgctgtatg gggattcggg ctccctcttc     2340
agccccagca aggaggaggc ccgaagaagc agccagcccc ctgctgaccg ggaccctgca     2400
cccttccggg cagagcctac ccactggtgc ctgctggtgc gggagaatgg caccatggag     2460
atctaccagc ttcccgactg gcggctggtg ttcctggtga agaacttccc tgtggggcag      2520
cgggtccttg tggacagctc ctttggacag cccactacac agggcgaggc ccgcaggag      2580 gaggccacgc gccaggggga gctgcccctc gtcaaggagg tgctgctggt ggcgctgggc     2640
agccgccaga gcaggcccta cctgctggtg catgtggacc aagagctgct tatctacgag     2700
gccttccccc acgactctca gctcggccag ggcaatctca aagtccgctt taagaaggtc     2760
cctcacaaca tcaacttccg tgagaagaag ccaaagccat ccaagaagaa agcagaaggt     2820
ggcggcgcag aggagggggc tgggcccgg ggccgcgtgg cgcgtttccg ctacttcgag      2880
gatatttatg gctactcagg ggtcttcatc tgcggcccct cccctcactg gctcttggtg     2940
accggccgag gggctctgcg gctacacccc atggccatcg acggcccggt cgactctttc     3000
gctccattcc acaatgtcaa ctgtcccgc ggcttcctgt acttcaacag acagggcgag      3060
ctgaggatca gtgtcctgcc tgcctacctg tcctatgatg cccatggcc tgtcaggaag      3120 atcccgctgc gctgcacggc ccactatgtg gcttaccacg tggagtctaa ggtgtatgct     3180
gtggccacca gcaccaacac gccgtgtgcc cgcatccac gcatgactgg cgaggagaag      3240
gagtttgaga ccatcgagag agatgagcgg tacatccacc cccagcagga ggccttctcc     3300
atccagctca tctcccccggt cagctgggag gctattccca tgccaggat cgagctgcag     3360
```

```
gagtgggagc atgtgacctg catgaagaca gtgtctctgc gcagtgagga gaccgtgtcg    3420
ggcctcaaag gctacgtggc cgccgggacc tgcctcatgc agggggagga ggtcacgtgc    3480
cgagggcgga tcttgatcat ggatgtgatt gaggtggtgc ccgagcctgg ccagcccttg    3540
accaagaaca agttcaaagt cctttacgag aaggagcaga aggggcccgt gaccgccctg    3600
tgccactgca atggccacct ggtgtcggcc atcggccaga agattttcct gtggagcctg    3660
cgggccagcg agctgacggg catggccttc atcgacacgc agctctacat acaccagatg    3720
atcagcgtca agaacttcat cctggcagcc gacgtcatga agagcatttc gctgctgcgc    3780
taccaggagg aaagcaagac gctgagcctg gtgtcgcggg atgccaagcc cctggaggtg    3840
tacagcgtgg acttcatggt ggacaatgcc cagctgggtt ttctggtgtc tgaccgcgac    3900
cgcaacctca tggtgtacat gtacctgccc gaagccaagg agagtttcgg gggcatgcgc    3960
ctgctgcgtc gggcagactt ccacgtgggt gcccacgtga acgttctg gaggaccccg    4020 tgccgggggg ccactgaagg gctcagcaaa aagtcggtcg tgtgggagaa taagcacatc    4080
acgtggtttg ccaccctgga cggcggcatc gggctgctgc tgcccatgca ggagaagacc    4140
taccggcggc tgctgatgct gcagaacgcg ctgaccacca tgctgccaca ccacgccggc    4200
ctcaaccccc gcgccttccg gatgctgcac gtggaccgcc gcaccctcca gaatgccgtg    4260
cgcaacgtgc tggatgggga gctgctcaac cgctacctgt acctgagcac catggagcgc    4320
agcgagctag ccaagaagat cggcaccaca ccagacataa tcctggacga cttgctggag    4380
acggaccgcg tcaccgccca cttctagccc cgtggatgcc gtcaccacca gcacacggaa    4440
ctacctccca cccccttttt gtacaaaaca caaggaaaaa catttttgc ttga          4494

<210> SEQ ID NO 80
<211> LENGTH: 1731
<212> TYPE: DNA
<213> ORGANISM: Homo sapiens
<220> FEATURE:
<223> OTHER INFORMATION: CPSF 160 kDa subunit (XM_209402)

<400> SEQUENCE: 80
gtggagtcca agatgtacgc tgtggccacc agcaccaaca cactgtgcac ctgcatccca      60
catgactggc gaggagaagg catttgagac cattgagaga gatgagcagt gcatccaccc     120
ccaggaggcg gccttatcta tccagttcat ctccctagtc tgctgggagg ctattcccaa     180
tgccaggatt gagctgcaga agtgggagct tgtgaccagc acgaagacag tgtcgctgca     240
gcaaggagac caggtcaggc ttcaaaggct acgcgtggcc gccgggacct gcctcatgca     300
ggaggaggag gaggtcatgt cctgagggcg gatcttgatc atggatgtga ctgaggtggt     360
gcccgagccc agccagccct tgaccaagaa caagttcaga gtcctttacg agaaggagca     420
gaagggcccc gtgactgccc tgtgcactgc aaggccacct ggtgtcggcc atcagccaga     480
agattttcct gtgaagcctg cgggccagcg agctgacggg catggccttc atggtcgaca     540
ggcagctcta catccaccag atgatcagcg tcaggaactt catcctggca gccgacctca     600
tgaagagcat ctggctgctg ttaccaggag agagcaaga cgctgagcct cgtcatgtga     660
tgccaagacc ctggaggtgt acagcgtgga cttcatggta gacaacaccc agctgggttt     720
tctggtgtct gaccacgact gcagcctcat ggtgtacatg tacctgcctg aagccaagga     780
gagttttggg ggcatgtgcc tgctgcgctg ggcagacttc catgtgggtg cccacatgaa     840
cgcattctat aggaccctgt gccagggagc cactgagggg ctcagcaaaa agtcagtggt     900
gggagaataa gcatatcgcg tggttcgcca cccaggatgg tggcatcggg ctgctgctgc     960
```

```
ccatgcagga gaaaacctac tggaggctgc tgatgctgct gaacgtgctg ccacaccaca    1020
caggcctcaa cctccgcacc ttccggatgc tgcgtgtgga cctccgcacc ctccagaatg    1080
ctgtgctgca agctgcacgg ggagctgctc aaccgctacc tgtacctgag caccatggag    1140
cagcaagctg gccaagaaga tcagcaccat atccgacatc atcctggatg acttgctgga    1200
gacagatggc gtcactgccc acttctagct ccatggatgt cgctgccacc accacaccgc    1260
actacctccc accaccttt tgaacaaaa cacaaggaat atatactttc tggaagacca     1320
tctgatacta tgtatcaaga atctcaaaaa tattcatata ctataatgca ataaggccat    1380
ttctaaaaat ttaccctgag aagataatcc agacctgtgc tacaatttcc attacagaga    1440
catctgttgt aatattgttt acggaagggg gaaacagaaa acagcctcca tgtccacaga    1500
ggaatgatta aatatgtggt acacctacag gctggagtgt aaaatggaca caaaaacaag    1560
aagaaatgct catgagaaaa cacagtgata gacgcctttt ctaaacagtt tctgctttgt    1620
ttggggtaag tgttccacct ttaccatccc taaatgctct agtatagtat agtcttaatc    1680
acatgtttat ttgtatgcat ctattattac tttataaaat ctttgaaaac c             1731
```

<210> SEQ ID NO 81
<211> LENGTH: 1443
<212> TYPE: PRT
<213> ORGANISM: Homo Sapiens
<220> FEATURE:
<223> OTHER INFORMATION: CPSF160 (160 kD factor 1) (NP_037423)

<400> SEQUENCE: 81

```
Met Tyr Ala Val Tyr Lys Gln Ala His Pro Pro Thr Gly Leu Glu Phe
1               5                   10                  15

Ser Met Tyr Cys Asn Phe Phe Asn Asn Ser Glu Arg Asn Leu Val Val
            20                  25                  30

Ala Gly Thr Ser Gln Leu Tyr Val Tyr Arg Leu Asn Arg Asp Ala Glu
        35                  40                  45

Ala Leu Thr Lys Asn Asp Arg Ser Thr Glu Gly Lys Ala His Arg Glu
    50                  55                  60

Lys Leu Glu Leu Ala Ala Ser Phe Ser Phe Phe Gly Asn Val Met Ser
65                  70                  75                  80

Met Ala Ser Val Gln Leu Ala Gly Ala Lys Arg Asp Ala Leu Leu Leu
                85                  90                  95

Ser Phe Lys Asp Ala Lys Leu Ser Val Val Glu Tyr Asp Pro Gly Thr
            100                 105                 110

His Asp Leu Lys Thr Leu Ser Leu His Tyr Phe Glu Glu Pro Glu Leu
        115                 120                 125

Arg Asp Gly Phe Val Gln Asn Val His Thr Pro Arg Val Arg Val Asp
    130                 135                 140

Pro Asp Gly Arg Cys Ala Ala Met Leu Val Tyr Gly Thr Arg Leu Val
145                 150                 155                 160

Val Leu Pro Phe Arg Arg Glu Ser Leu Ala Glu Glu His Glu Gly Leu
                165                 170                 175

Val Gly Glu Gly Gln Arg Ser Ser Phe Leu Pro Ser Tyr Ile Ile Asp
            180                 185                 190

Val Arg Ala Leu Asp Glu Lys Leu Leu Asn Ile Ile Asp Leu Gln Phe
        195                 200                 205

Leu His Gly Tyr Tyr Glu Pro Thr Leu Leu Ile Leu Phe Glu Pro Asn
    210                 215                 220

Gln Thr Trp Pro Gly Arg Val Ala Val Arg Gln Asp Thr Cys Ser Ile
```

```
              225                 230                 235                 240
Val Ala Ile Ser Leu Asn Ile Thr Gln Lys Val His Pro Val Ile Trp
            245                 250                 255

Ser Leu Thr Ser Leu Pro Phe Asp Cys Thr Gln Ala Leu Ala Val Pro
            260                 265                 270

Lys Pro Ile Gly Gly Val Val Phe Ala Val Asn Ser Leu Leu Tyr
            275                 280                 285

Leu Asn Gln Ser Val Pro Pro Tyr Gly Val Ala Leu Asn Ser Leu Thr
            290                 295                 300

Thr Gly Thr Thr Ala Phe Pro Leu Arg Thr Gln Glu Gly Val Arg Ile
305                 310                 315                 320

Thr Leu Asp Cys Ala Gln Ala Thr Phe Ile Ser Tyr Asp Lys Met Val
            325                 330                 335

Ile Ser Leu Lys Gly Gly Glu Ile Tyr Val Leu Thr Leu Ile Thr Asp
            340                 345                 350

Gly Met Arg Ser Val Arg Ala Phe His Phe Asp Lys Ala Ala Ala Ser
            355                 360                 365

Val Leu Thr Thr Ser Met Val Thr Met Glu Pro Gly Tyr Leu Phe Leu
            370                 375                 380

Gly Ser Arg Leu Gly Asn Ser Leu Leu Leu Lys Tyr Thr Glu Lys Leu
385                 390                 395                 400

Gln Glu Pro Pro Ala Ser Ala Val Arg Glu Ala Ala Asp Lys Glu Glu
            405                 410                 415

Pro Pro Ser Lys Lys Lys Arg Val Asp Ala Thr Ala Gly Trp Ser Ala
            420                 425                 430

Ala Gly Lys Ser Val Pro Gln Asp Glu Val Asp Glu Ile Glu Val Tyr
            435                 440                 445

Gly Ser Glu Ala Gln Ser Gly Thr Gln Leu Ala Thr Tyr Ser Phe Glu
            450                 455                 460

Val Cys Asp Ser Ile Leu Asn Ile Gly Pro Cys Ala Asn Ala Ala Val
465                 470                 475                 480

Gly Glu Pro Ala Phe Leu Ser Glu Glu Phe Gln Asn Ser Pro Glu Pro
            485                 490                 495

Asp Leu Glu Ile Val Val Cys Ser Gly His Gly Lys Asn Gly Ala Leu
            500                 505                 510

Ser Val Leu Gln Lys Ser Ile Arg Pro Gln Val Val Thr Thr Phe Glu
            515                 520                 525

Leu Pro Gly Cys Tyr Asp Met Trp Thr Val Ile Ala Pro Val Arg Lys
            530                 535                 540

Glu Glu Glu Asp Asn Pro Lys Gly Glu Gly Thr Glu Gln Glu Pro Ser
545                 550                 555                 560

Thr Thr Pro Glu Ala Asp Asp Gly Arg Arg His Gly Phe Leu Ile
            565                 570                 575

Leu Ser Arg Glu Asp Ser Thr Met Ile Leu Gln Thr Gly Gln Glu Ile
            580                 585                 590

Met Glu Leu Asp Thr Ser Gly Phe Ala Thr Gln Gly Pro Thr Val Phe
            595                 600                 605

Ala Gly Asn Ile Gly Asp Asn Arg Tyr Ile Val Gln Val Ser Pro Leu
            610                 615                 620

Gly Ile Arg Leu Leu Glu Gly Val Asn Gln Leu His Phe Ile Pro Val
625                 630                 635                 640

Asp Leu Gly Ala Pro Ile Val Gln Cys Ala Val Ala Asp Pro Tyr Val
            645                 650                 655
```

-continued

```
Val Ile Met Ser Ala Glu Gly His Val Thr Met Phe Leu Leu Lys Ser
            660                 665                 670

Asp Ser Tyr Gly Gly Arg His His Arg Leu Ala Leu His Lys Pro Pro
        675                 680                 685

Leu His His Gln Ser Lys Val Ile Thr Leu Cys Leu Tyr Arg Asp Leu
    690                 695                 700

Ser Gly Met Phe Thr Thr Glu Ser Arg Leu Gly Gly Ala Arg Asp Glu
705                 710                 715                 720

Leu Gly Gly Arg Ser Gly Pro Glu Ala Glu Gly Leu Gly Ser Glu Thr
                725                 730                 735

Ser Pro Thr Val Asp Asp Glu Glu Met Leu Tyr Gly Asp Ser Gly
            740                 745                 750

Ser Leu Phe Ser Pro Ser Lys Glu Glu Ala Arg Arg Ser Ser Gln Pro
        755                 760                 765

Pro Ala Asp Arg Asp Pro Ala Pro Phe Arg Ala Glu Pro Thr His Trp
    770                 775                 780

Cys Leu Leu Val Arg Glu Asn Gly Thr Met Glu Ile Tyr Gln Leu Pro
785                 790                 795                 800

Asp Trp Arg Leu Val Phe Leu Val Lys Asn Phe Pro Val Gly Gln Arg
                805                 810                 815

Val Leu Val Asp Ser Ser Phe Gly Gln Pro Thr Thr Gln Gly Glu Ala
            820                 825                 830

Arg Arg Glu Glu Ala Thr Arg Gln Gly Glu Leu Pro Leu Val Lys Glu
        835                 840                 845

Val Leu Leu Val Ala Leu Gly Ser Arg Gln Ser Arg Pro Tyr Leu Leu
    850                 855                 860

Val His Val Asp Gln Glu Leu Leu Ile Tyr Glu Ala Phe Pro His Asp
865                 870                 875                 880

Ser Gln Leu Gly Gln Gly Asn Leu Lys Val Arg Phe Lys Val Pro
                885                 890                 895

His Asn Ile Asn Phe Arg Glu Lys Lys Pro Lys Pro Ser Lys Lys Lys
            900                 905                 910

Ala Glu Gly Gly Ala Glu Glu Gly Ala Gly Ala Arg Gly Arg Val
        915                 920                 925

Ala Arg Phe Arg Tyr Phe Glu Asp Ile Tyr Gly Tyr Ser Gly Val Phe
    930                 935                 940

Ile Cys Gly Pro Ser Pro His Trp Leu Leu Val Thr Gly Arg Gly Ala
945                 950                 955                 960

Leu Arg Leu His Pro Met Ala Ile Asp Gly Pro Val Asp Ser Phe Ala
                965                 970                 975

Pro Phe His Asn Val Asn Cys Pro Arg Gly Phe Leu Tyr Phe Asn Arg
            980                 985                 990

Gln Gly Glu Leu Arg Ile Ser Val Leu Pro Ala Tyr Leu Ser Tyr Asp
        995                 1000                1005

Ala Pro Trp Pro Val Arg Lys Ile Pro Leu Arg Cys Thr Ala His Tyr
    1010                1015                1020

Val Ala Tyr His Val Glu Ser Lys Val Tyr Ala Val Ala Thr Ser Thr
1025                1030                1035                1040

Asn Thr Pro Cys Ala Arg Ile Pro Arg Met Thr Gly Glu Glu Lys Glu
                1045                1050                1055

Phe Glu Thr Ile Glu Arg Asp Glu Arg Tyr Ile His Pro Gln Gln Glu
            1060                1065                1070

Ala Phe Ser Ile Gln Leu Ile Ser Pro Val Ser Trp Glu Ala Ile Pro
        1075                1080                1085
```

Asn Ala Arg Ile Glu Leu Gln Glu Trp Glu His Val Thr Cys Met Lys
    1090                1095                1100

Thr Val Ser Leu Arg Ser Glu Glu Thr Val Ser Gly Leu Lys Gly Tyr
1105                1110                1115                1120

Val Ala Ala Gly Thr Cys Leu Met Gln Gly Glu Val Thr Cys Arg
                1125                1130                1135

Gly Arg Ile Leu Ile Met Asp Val Ile Glu Val Val Pro Glu Pro Gly
            1140                1145                1150

Gln Pro Leu Thr Lys Asn Lys Phe Lys Val Leu Tyr Glu Lys Glu Gln
        1155                1160                1165

Lys Gly Pro Val Thr Ala Leu Cys His Cys Asn Gly His Leu Val Ser
    1170                1175                1180

Ala Ile Gly Gln Lys Ile Phe Leu Trp Ser Leu Arg Ala Ser Glu Leu
1185                1190                1195                1200

Thr Gly Met Ala Phe Ile Asp Thr Gln Leu Tyr Ile His Gln Met Ile
                1205                1210                1215

Ser Val Lys Asn Phe Ile Leu Ala Ala Asp Val Met Lys Ser Ile Ser
            1220                1225                1230

Leu Leu Arg Tyr Gln Glu Glu Ser Lys Thr Leu Ser Leu Val Ser Arg
        1235                1240                1245

Asp Ala Lys Pro Leu Glu Val Tyr Ser Val Asp Phe Met Val Asp Asn
    1250                1255                1260

Ala Gln Leu Gly Phe Leu Val Ser Asp Arg Asp Arg Asn Leu Met Val
1265                1270                1275                1280

Tyr Met Tyr Leu Pro Glu Ala Lys Glu Ser Phe Gly Gly Met Arg Leu
                1285                1290                1295

Leu Arg Arg Ala Asp Phe His Val Gly Ala His Val Asn Thr Phe Trp
            1300                1305                1310

Arg Thr Pro Cys Arg Gly Ala Thr Glu Gly Leu Ser Lys Lys Ser Val
        1315                1320                1325

Val Trp Glu Asn Lys His Ile Thr Trp Phe Ala Thr Leu Asp Gly Gly
    1330                1335                1340

Ile Gly Leu Leu Leu Pro Met Gln Glu Lys Thr Tyr Arg Arg Leu Leu
1345                1350                1355                1360

Met Leu Gln Asn Ala Leu Thr Thr Met Leu Pro His His Ala Gly Leu
                1365                1370                1375

Asn Pro Arg Ala Phe Arg Met Leu His Val Asp Arg Arg Thr Leu Gln
            1380                1385                1390

Asn Ala Val Arg Asn Val Leu Asp Gly Glu Leu Leu Asn Arg Tyr Leu
        1395                1400                1405

Tyr Leu Ser Thr Met Glu Arg Ser Glu Leu Ala Lys Lys Ile Gly Thr
    1410                1415                1420

Thr Pro Asp Ile Ile Leu Asp Asp Leu Leu Glu Thr Asp Arg Val Thr
1425                1430                1435                1440

Ala His Phe

<210> SEQ ID NO 82
<211> LENGTH: 120
<212> TYPE: PRT
<213> ORGANISM: Homo sapiens
<220> FEATURE:
<223> OTHER INFORMATION: CPSF 160 kDa subunit (XP_209402)

<400> SEQUENCE: 82

Met Gln Glu Lys Thr Tyr Trp Arg Leu Leu Met Leu Leu Asn Val Leu

```
                1               5              10              15
         Pro His His Thr Gly Leu Asn Leu Arg Thr Phe Arg Met Leu Arg Val
                            20                  25                  30

Asp Leu Arg Thr Leu Gln Asn Ala Val Leu Gln Ala Ala Arg Gly Ala
                     35                  40                  45

Ala Gln Pro Leu Pro Val Pro Glu His His Gly Ala Ala Ser Trp Pro
                 50                  55                  60

Arg Arg Ser Ala Pro Tyr Pro Thr Ser Ser Trp Met Thr Cys Trp Arg
         65                  70                  75                  80

Gln Met Ala Ser Leu Pro Thr Ser Ser Met Asp Val Ala Ala Thr
                             85                  90                  95

Thr Thr Pro His Tyr Leu Pro Pro Phe Leu Asn Lys Thr Gln Gly
                         100                 105                 110

Ile Tyr Thr Phe Trp Lys Thr Ile
                         115                 120

<210> SEQ ID NO 83
<211> LENGTH: 5041
<212> TYPE: DNA
<213> ORGANISM: Homo Sapiens
<220> FEATURE:
<223> OTHER INFORMATION: CPSF100 (100 kD factor 2) (XM_029311.2)

<400> SEQUENCE: 83
aaaatggcgg ctgccactgt ggggcttctg ccggccggta gtccctggcg ctgctgaccc     60
agcatcggct tttctacgtc ttgaacctgg attcgcctag ggttgggaa gggctgtgga    120 cggcgttggg ggaggcctga cgagattaat aaagaactct tcagaattcc tggtgtttca    180
tcatatatac gactaagata tcaactcttc tagcttgctg tttctggacc aaaaaaaatg    240
acgtctatta tcaaattaac taccctttct ggggtccaag aagaatctgc cctttgctat    300
cttctccaag ttgatgagtt tagatttta ttggactgtg gctgggatga gcacttttct    360
atggatatta ttgattccct gaggaagcat gttcaccaga ttgatgcagt gctgttgtct    420
caccctgatc ctctccacct tggtgccctc ccgtatgctg tcggaaagtt gggtctgaac    480
tgtgctatct atgcaaccat tcctgtttat aaaatgggac agatgttcat gtatgatctt    540
tatcagtctc gacacaatac agaagatttt acactcttta cattagatga tgtggatgca    600
gcctttgata aaatacagca gctaaaattc tctcagattg tgaatttgaa aggtaaagga    660
catggcctgt ctatcacacc tctgccagct ggtcatatga taggtggaac aatatgggaaa   720 atagtcaaag atggagaaga agaaattgtt tatgcagttg acttcaacca caagagggag    780 atccattaa atggatgttc cctggaaatg ctaagcaggc cttccctact tatcacagat    840
tcattcaatg ctacatatgt acagcctaga agaaaacaga gagatgagca gcttctgaca    900
aatgtcctgg aaacacttcg aggtgatgga aatgtgttaa tagcagtgga cacagcaggc    960
agagttttgg aacttgctca acttcttgat cagatttgga ggactaaaga tgcaggattg   1020
ggtgtttact cattggcact cctaaataat gtcagttaca atgtggtgga gtttttctaag  1080 tcccaggtag aatggatgag tgataaattg atgagatgtt ttgaagacaa agaaataat    1140 ccgtttcagt ttcgccatct ctctttatgt catggtcttt ctgacttggc ccgtgtacct   1200
agccctaaag ttgtacttgc cagccaacct gacctggaat gcggattttc aagggatctc   1260
tttattcagt ggtgtcagga ccctaaaaac tcaatcattc taacctacag aactactcct   1320
gggactttag cacgtttcct aattgataat ccttctgaaa aaattacaga aatagagttg   1380
aggaaacgtg tgaagcttga agggaaagaa cttgaagaat acttggaaaa agagaaacta   1440
```

```
aagaaagaag ctgccaaaaa gcttgagcag tcaaaagagg cagatataga ttccagtgat    1500
gagagtgata ttgaggaaga tattgaccag ccatcagctc ataagacgaa gcatgacttg    1560
atgatgaaag gtgaaggcag tcgtaaagga agttttttca acaggcaaa  aaagtcctat    1620 cctatgtttc ctgccccaga agaaagaatt aaatgggatg aatatggaga gattatcaaa    1680
ccagaggatt tcttagtgcc agagcttcaa gctactgaag aagaaaaaag caaattagaa    1740
tctggtttga caaatggaga tgaacctatg gatcaggatt tatctgatgt tcctactaaa    1800
tgtatttcta caacagagtc tattgaaata aaagcccggg ttacctacat agactatgaa    1860
ggacgctctg atggggattc cattaaaaaa atcattaatc agatgaaacc acgacagttg    1920
atcatcgtcc atggcccacc agaggccagt caagatctgg cagagtgctg tcgcgccttt    1980
ggtgggaaag atattaaagt gtacatgcca aagctacatg aaacagttga tgccactagt    2040
gaaactcaca tctaccaggt gaggttaaaa gactcacttg tcagctctct tcagttttgt    2100
aaggcaaaag atgctgaatt agcttggata gatggtgtct tagatatgag agtttccaaa    2160
gtggacacag ggttatttt  agaagaagga gaactaaagg atgatggaga agactcagag    2220
atgcaagtgg aagctccctc agattctagc gttatagcac aacaaaaggc catgaaaagt    2280
ctgttcggag atgatgaaaa agaaacaggt gaagaaagtg agatcattcc tactttggaa    2340
cccttgccac ctcatgaggt tcctggacat cagtcagttt tatgaatga  accaaggctg    2400 tcagacttca agcaagttct cttacgggag gggattcaag ctgaatttgt aggaggtgta    2460
cttgtttgca acaatcaagt agcagtccgc agaacgaaa  ctggacgcat tggattagaa    2520
ggctgccttt gtcaagattt ttataggata agagaccttt tatatgaaca atatgccatt    2580
gtataaagga catgatgtca agaagtatct gcttgacctt tctaagaaaa agggattctt    2640
atcttactct gagcttttga tgttttgttt tgtaacatac aaaaagaatc tgccagaaaa    2700
acttacatgt atcagatttt taaaaatata aatagagaac attttgcaaa tgctcaaatg    2760
agcattctat cttttggctt tcagagtgat agagctccta acaggtgtac aggcccaaga    2820
gttgaaggtg attggttttc tttacagact ccttgttctc tagaagggct ttttacttga    2880
ataaaacaat gcaacttagc aaaccaattt atggccttag agaaacattt ttgcatgagt    2940
tcttacaaac tgtttgttat attttctgga atgataagtg agaattattt agaaaagaca    3000
tgctccaaaa aaaaaacaaa actgataaaa cagttttcg  aaacttactt ttaaaagcat    3060
acgtgctatg actctctcca gtttgaatat gcaattgttt tcacaggcag atgtctgtt    3120 ttctgcctgt atttcccagt gatttactct agggtaaggt agtacacatt tggttcagaa    3180
attaattttt atttctccta tatcttgttt tatcaagatt ttgttgtggc atttcaatgt    3240
aaattataac accatcattt gagtatacat aattcaaaag aactacttga tgcagtatag    3300
tcttaagggt tctgcataca ttttagaaac atcttagccg taagttaggt cctgtgttaa    3360
actgtttagt gctctgtttt taagaaaaca aatgttgaac ctcacacttt tatgtggtga    3420
cagtgtaatt taattaaaag gtgtaaatgt tttcatctct taggcttgct gtctcctaag    3480
gtcacccaag cagtggttgg attttataca cattactact aaaataatac tgaagttgga    3540
taaggttatc ctttctgtat ttgcgtcttt cttgtgacta accaccctga tatagtatta    3600
accactgtgt tcaagagtaa aaacaatata tgcaattttc attgaactta aagagtgaaa    3660
accatgtaaa ctattgaaac tattgtaatc cattaatgct ttttagaat  ggcagacctt    3720 gatgtttatt tctcaaatgg ttaagccctc ttctttactc ttaatttttt tttgagacag    3780
agtcacccag gctggagtgc agtggtgaga ttttggctca ctataacctc ttcctccagg    3840
```

```
gttcaagtga ttctcccacc tcagcctccc aagtagctgg gactacgggc acatgccact    3900
gcacctggct aatttttata ttttttggtag agacagggtt tcaccatgtt ggccaggctg    3960
gtctcaaact cctgacctca agcgatccac ccacctaggc ctcccaaagt gctgggatta    4020
caggcatgaa tcaccacaac tagcctaccc ttagattttt ggaaggatcg atcttattta    4080
actatgtgtg aacaaccca gtaatatcag actcgaatta ctatttcatt ctatttcaaa    4140
tgcttataaa gctactattg tagattatag tgttaatgca aagtttacag acttttgata    4200
tggaaaacca gataaaacaa tgttacaaaa ggcaaatata aagagtatgt tttctttttta    4260 gtgctttgga aaaatttcac ttaaactctt attactgtat agattaagcc ctataatgct    4320
atttatattc caggggaacg aaaatctgaa tttgttttat gatttaaagc atctggtttg    4380
catattgtat tgtaatactg atacagtttg gctgtgtccc caccaaattg aattgtgtta    4440
atagttccca taatccctac gtgttgtggg agggacccag tgggcagtaa tttaatcatg    4500
gtggtggtta ccctcatgct gttcttgtga tggtgagttc tcatgagatc tgatgggtgt    4560
ttttttttgt tttgtttttt gttttttgag atggagtttt gctcttgttg cccagactgg    4620
agtgcaatgg cacacgatct cggctcaccg caacctctgc ctcctgggtt caagcgattc    4680
tcctgcctca gcatctcgag tagctgggat tacaggcatg caccaccacg cccagctaat    4740
tttgtatttt tagtagagac ggggtttctc catgttggtt aggctggcct caaactcccg    4800
acctcaggtg atccgcccgc ctgggcctcc caaagtgctg ggattacagg cgtgagccac    4860
tgctcctggc ccaagatctg atggttttgt aagggaattt tccccctttg cttggcactt    4920
cttcctgctg ccatgtgaag aaggatgtgt ttgcttcccc ttccaccatg attgtaagtt    4980
tcatgaggcc tccccagcct gtgggactgt gagtcaatta aacgtgttta ctttataaat    5040
t                                                                      5041
```

<210> SEQ ID NO 84
<211> LENGTH: 782
<212> TYPE: PRT
<213> ORGANISM: Homo Sapiens
<220> FEATURE:
<223> OTHER INFORMATION: CPSF100 (100 kD factor 2) (XP_029311)

<400> SEQUENCE: 84

```
Met Thr Ser Ile Ile Lys Leu Thr Thr Leu Ser Gly Val Gln Glu Glu
1               5                   10                  15

Ser Ala Leu Cys Tyr Leu Leu Gln Val Asp Glu Phe Arg Phe Leu Leu
            20                  25                  30

Asp Cys Gly Trp Asp Glu His Phe Ser Met Asp Ile Ile Asp Ser Leu
        35                  40                  45

Arg Lys His Val His Gln Ile Asp Ala Val Leu Leu Ser His Pro Asp
    50                  55                  60

Pro Leu His Leu Gly Ala Leu Pro Tyr Ala Val Gly Lys Leu Gly Leu
65                  70                  75                  80

Asn Cys Ala Ile Tyr Ala Thr Ile Pro Val Tyr Lys Met Gly Gln Met
                85                  90                  95

Phe Met Tyr Asp Leu Tyr Gln Ser Arg His Asn Thr Glu Asp Phe Thr
            100                 105                 110

Leu Phe Thr Leu Asp Asp Val Asp Ala Ala Phe Asp Lys Ile Gln Gln
        115                 120                 125

Leu Lys Phe Ser Gln Ile Val Asn Leu Lys Gly Lys Gly His Gly Leu
    130                 135                 140
```

-continued

```
Ser Ile Thr Pro Leu Pro Ala Gly His Met Ile Gly Thr Ile Trp
145                 150                 155                 160

Lys Ile Val Lys Asp Gly Glu Glu Ile Val Tyr Ala Val Asp Phe
            165                 170                 175

Asn His Lys Arg Glu Ile His Leu Asn Gly Cys Ser Leu Glu Met Leu
            180                 185                 190

Ser Arg Pro Ser Leu Leu Ile Thr Asp Ser Phe Asn Ala Thr Tyr Val
            195                 200                 205

Gln Pro Arg Arg Lys Gln Arg Asp Glu Gln Leu Leu Thr Asn Val Leu
            210                 215                 220

Glu Thr Leu Arg Gly Asp Gly Asn Val Leu Ile Ala Val Asp Thr Ala
225                 230                 235                 240

Gly Arg Val Leu Glu Leu Ala Gln Leu Leu Asp Gln Ile Trp Arg Thr
                245                 250                 255

Lys Asp Ala Gly Leu Gly Val Tyr Ser Leu Ala Leu Leu Asn Asn Val
                260                 265                 270

Ser Tyr Asn Val Val Glu Phe Ser Lys Ser Gln Val Glu Trp Met Ser
            275                 280                 285

Asp Lys Leu Met Arg Cys Phe Glu Asp Lys Arg Asn Asn Pro Phe Gln
290                 295                 300

Phe Arg His Leu Ser Leu Cys His Gly Leu Ser Asp Leu Ala Arg Val
305                 310                 315                 320

Pro Ser Pro Lys Val Val Leu Ala Ser Gln Pro Asp Leu Glu Cys Gly
                325                 330                 335

Phe Ser Arg Asp Leu Phe Ile Gln Trp Cys Gln Asp Pro Lys Asn Ser
            340                 345                 350

Ile Ile Leu Thr Tyr Arg Thr Thr Pro Gly Thr Leu Ala Arg Phe Leu
            355                 360                 365

Ile Asp Asn Pro Ser Glu Lys Ile Thr Glu Ile Glu Leu Arg Lys Arg
            370                 375                 380

Val Lys Leu Glu Gly Lys Glu Leu Glu Glu Tyr Leu Glu Lys Glu Lys
385                 390                 395                 400

Leu Lys Lys Glu Ala Lys Lys Leu Glu Gln Ser Lys Glu Ala Asp
                405                 410                 415

Ile Asp Ser Ser Asp Glu Ser Asp Ile Glu Glu Asp Ile Asp Gln Pro
            420                 425                 430

Ser Ala His Lys Thr Lys His Asp Leu Met Met Lys Gly Glu Gly Ser
            435                 440                 445

Arg Lys Gly Ser Phe Phe Lys Gln Ala Lys Lys Ser Tyr Pro Met Phe
450                 455                 460

Pro Ala Pro Glu Glu Arg Ile Lys Trp Asp Glu Tyr Gly Glu Ile Ile
465                 470                 475                 480

Lys Pro Glu Asp Phe Leu Val Pro Glu Leu Gln Ala Thr Glu Glu
            485                 490                 495

Lys Ser Lys Leu Glu Ser Gly Leu Thr Asn Gly Asp Glu Pro Met Asp
            500                 505                 510

Gln Asp Leu Ser Asp Val Pro Thr Lys Cys Ile Ser Thr Thr Glu Ser
            515                 520                 525

Ile Glu Ile Lys Ala Arg Val Thr Tyr Ile Asp Tyr Glu Gly Arg Ser
            530                 535                 540

Asp Gly Asp Ser Ile Lys Lys Ile Ile Asn Gln Met Lys Pro Arg Gln
545                 550                 555                 560

Leu Ile Ile Val His Gly Pro Pro Glu Ala Ser Gln Asp Leu Ala Glu
                565                 570                 575
```

```
Cys Cys Arg Ala Phe Gly Gly Lys Asp Ile Lys Val Tyr Met Pro Lys
                580                 585                 590

Leu His Glu Thr Val Asp Ala Thr Ser Glu Thr His Ile Tyr Gln Val
                595                 600                 605

Arg Leu Lys Asp Ser Leu Val Ser Ser Leu Gln Phe Cys Lys Ala Lys
            610                 615                 620

Asp Ala Glu Leu Ala Trp Ile Asp Gly Val Leu Asp Met Arg Val Ser
625                 630                 635                 640

Lys Val Asp Thr Gly Val Ile Leu Glu Glu Gly Glu Leu Lys Asp Asp
                645                 650                 655

Gly Glu Asp Ser Glu Met Gln Val Glu Ala Pro Ser Asp Ser Ser Val
                660                 665                 670

Ile Ala Gln Gln Lys Ala Met Lys Ser Leu Phe Gly Asp Asp Glu Lys
                675                 680                 685

Glu Thr Gly Glu Glu Ser Glu Ile Ile Pro Thr Leu Glu Pro Leu Pro
            690                 695                 700

Pro His Glu Val Pro Gly His Gln Ser Val Phe Met Asn Glu Pro Arg
705                 710                 715                 720

Leu Ser Asp Phe Lys Gln Val Leu Leu Arg Glu Gly Ile Gln Ala Glu
                725                 730                 735

Phe Val Gly Gly Val Leu Val Cys Asn Asn Gln Val Ala Val Arg Arg
                740                 745                 750

Thr Glu Thr Gly Arg Ile Gly Leu Gly Cys Leu Cys Gln Asp Phe
            755                 760                 765

Tyr Arg Ile Arg Asp Leu Leu Tyr Glu Gln Tyr Ala Ile Val
                770                 775                 780

<210> SEQ ID NO 85
<211> LENGTH: 2286
<212> TYPE: DNA
<213> ORGANISM: Homo Sapiens
<220> FEATURE:
<223> OTHER INFORMATION: CPSF73 (73 kD factor 3) (NM_016207)

<400> SEQUENCE: 85
gttcctcacc cccgcttcgc cctcacactt tcgggatgtc tgcgattcct gctgaggaga      60
gcgaccagct gctgatccga ccccttggag ctgggcaaga agtaggaaga tcatgtatta     120
ttctcgagtt caaaggaaga aaaataatgc tcgactgtgg gatccaccct ggcctagaag     180
gaatggatgc tcttccttat attgatttaa ttgacccagc tgagattgat ctcctattaa     240
ttagtcattt ccatttggat cactgtggag ctctgccctg gtttctacag aagacaagtt     300
tcaaaggaag aacatttatg actcatgcca caaaagctat ttatagatgg cttctttctg     360
attatgtcaa agttagtaac atatcagcag acgacatgct gtataccgag acagatttgg     420
aagaaagcat ggacaaaatt gaaactatca actttcatga agttaaggaa gttgcgggaa     480
tcaagttttg gtgttaccat gcaggtcacg tcctaggagc cgccatgttc atgattgaga     540
tcgcaggcgt gaagcttttg tacactggtg atttctcaag acaagaagat aggcacttaa     600
tggcagctga aattcctaat attaagcctg atattcttat cattgaatct acttatggga     660
cccatatcca tgagaaacgt gaagagcgag aagcaagatt ctgtaacact gtccacgata     720
ttgtaaacag aggaggcagg ggtctcattc ctgtctttgc tcttggaagg ctcaggagc      780 tgctcttgat tctagatgag tactggcaga tcacccaga actacatgac attccaatat     840
actatgcatc atctttggcc aagaagtgta tggcagtgta ccagacatat gtaaatgcca     900
```

```
tgaatgacaa atccgcaaa cagatcaaca tcaataatcc ctttgttttc aaacacatta    960
gtaacctcaa gagcatggat cattttgatg acattggtcc cagtgttgta atggcctccc   1020
caggcatgat gcaaagtggc ttatccagag aattatttga aagctggtgt actgataaga   1080
ggaatggtgt cattatagcg ggatactgtg tagaagggac acttgccaag cacatcatgt   1140
ctgaacctga agaaatcact actatgtctg acagaagtt accactgaaa atgtctgttg    1200
attacatttc tttctcagct cacacggatt accagcaaac cagtgaattt attcgtgctt   1260
tgaaaccgcc tcatgtgatt ttagtccatg agaacagaa tgaaatggcc agattgaaag    1320
cagcactgat tcgagaatat gaagataacg atgaagttca catagaggtt cataatcctc   1380
ggaatacaga agcagtgacc ttaaacttca gaggagaaaa actagccaag gttatgggat    1440
ttttagcaga caaaaaacca gaacaaggcc agcgggtctc aggaatactt gttaaaagaa    1500
actttaatta tcacatactt tctccttgcg acctgtccaa ttatactgac ctggccatga    1560
gcacggtgaa gcagacccaa gccattccat atactggtcc ctttaatttg ctctgttacc    1620
agctgcagaa attgacaggt gatgtggaag aattagaaat tcaagaaaaa cctgctctga    1680
aagtgttcaa aaatattact gtaatacaag aaccaggcat ggtggtatta aatggctgg    1740
caaacccttc taatgatatg tatgcagata cagtaacaac tgtgatattg aagttcagt    1800
caaatcccaa aataagaaaa ggtgcagtac agaaggtttc taaaaaatta gaaatgcacg    1860
tttacagcaa gaggttggag atcatgctcc aggacatatt tggagaagac tgtgtaagtg    1920
taaggatga ctctattctt agcgtcacag tggacgggaa aactgccaac cttaacttgg     1980
agacacggac tgtagaatgt gaagagggaa gtgaagacga tgaatccctc cgagaaatgg    2040
tggagctggc tgcacagaga ctgtacgagg ccctgacgcc agttcactga gactgtgcct    2100
gtatatgaac tttgaaaaaa tacttgactc tacttttgtt acctaaaata aaatgcattc    2160
gtttctctgg gaaaaaaaaa aaaaaaaaaa aaaaaaaaaa aaaaaaaaaa aaaaaaaaaa    2220
aaaaaaaaa aaaaaaaaa aaaaaaaaa aaaaaaaaa aaaaaaaaa aaaaaaaaa          2280
aaaaaa                                                              2286
```

<210> SEQ ID NO 86
<211> LENGTH: 684
<212> TYPE: PRT
<213> ORGANISM: Homo Sapiens
<220> FEATURE:
<223> OTHER INFORMATION: CPSF73 (73 kD factor 3) (NP_057291)

<400> SEQUENCE: 86

```
Met Ser Ala Ile Pro Ala Glu Glu Ser Asp Gln Leu Leu Ile Arg Pro
1               5                   10                  15

Leu Gly Ala Gly Gln Glu Val Gly Arg Ser Cys Ile Ile Leu Glu Phe
            20                  25                  30

Lys Gly Arg Lys Ile Met Leu Asp Cys Gly Ile His Pro Gly Leu Glu
        35                  40                  45

Gly Met Asp Ala Leu Pro Tyr Ile Asp Leu Ile Asp Pro Ala Glu Ile
    50                  55                  60

Asp Leu Leu Leu Ile Ser His Phe His Leu Asp His Cys Gly Ala Leu
65                  70                  75                  80

Pro Trp Phe Leu Gln Lys Thr Ser Phe Lys Gly Arg Thr Phe Met Thr
                85                  90                  95

His Ala Thr Lys Ala Ile Tyr Arg Trp Leu Leu Ser Asp Tyr Val Lys
            100                 105                 110

Val Ser Asn Ile Ser Ala Asp Asp Met Leu Tyr Thr Glu Thr Asp Leu
```

-continued

```
            115                 120                 125
Glu Glu Ser Met Asp Lys Ile Glu Thr Ile Asn Phe His Glu Val Lys
130                 135                 140

Glu Val Ala Gly Ile Lys Phe Trp Cys Tyr His Ala Gly His Val Leu
145                 150                 155                 160

Gly Ala Ala Met Phe Met Ile Glu Ile Ala Gly Val Lys Leu Leu Tyr
                    165                 170                 175

Thr Gly Asp Phe Ser Arg Gln Glu Asp Arg His Leu Met Ala Ala Glu
                180                 185                 190

Ile Pro Asn Ile Lys Pro Asp Ile Leu Ile Glu Ser Thr Tyr Gly
                195                 200                 205

Thr His Ile His Glu Lys Arg Glu Glu Arg Glu Ala Arg Phe Cys Asn
                210                 215                 220

Thr Val His Asp Ile Val Asn Arg Gly Gly Arg Gly Leu Ile Pro Val
225                 230                 235                 240

Phe Ala Leu Gly Arg Ala Gln Glu Leu Leu Ile Leu Asp Glu Tyr
                    245                 250                 255

Trp Gln Asn His Pro Glu Leu His Asp Ile Pro Ile Tyr Tyr Ala Ser
                260                 265                 270

Ser Leu Ala Lys Lys Cys Met Ala Val Tyr Gln Thr Tyr Val Asn Ala
                275                 280                 285

Met Asn Asp Lys Ile Arg Lys Gln Ile Asn Ile Asn Asn Pro Phe Val
290                 295                 300

Phe Lys His Ile Ser Asn Leu Lys Ser Met Asp His Phe Asp Ile
305                 310                 315                 320

Gly Pro Ser Val Val Met Ala Ser Pro Gly Met Met Gln Ser Gly Leu
                    325                 330                 335

Ser Arg Glu Leu Phe Glu Ser Trp Cys Thr Asp Lys Arg Asn Gly Val
                340                 345                 350

Ile Ile Ala Gly Tyr Cys Val Glu Gly Thr Leu Ala Lys His Ile Met
                355                 360                 365

Ser Glu Pro Glu Glu Ile Thr Thr Met Ser Gly Gln Lys Leu Pro Leu
370                 375                 380

Lys Met Ser Val Asp Tyr Ile Ser Phe Ser Ala His Thr Asp Tyr Gln
385                 390                 395                 400

Gln Thr Ser Glu Phe Ile Arg Ala Leu Lys Pro Pro His Val Ile Leu
                    405                 410                 415

Val His Gly Glu Gln Asn Glu Met Ala Arg Leu Lys Ala Ala Leu Ile
                420                 425                 430

Arg Glu Tyr Glu Asp Asn Asp Glu Val His Ile Glu Val His Asn Pro
                435                 440                 445

Arg Asn Thr Glu Ala Val Thr Leu Asn Phe Arg Gly Glu Lys Leu Ala
                450                 455                 460

Lys Val Met Gly Phe Leu Ala Asp Lys Pro Glu Gln Gly Gln Arg
465                 470                 475                 480

Val Ser Gly Ile Leu Val Lys Arg Asn Phe Asn Tyr His Ile Leu Ser
                    485                 490                 495

Pro Cys Asp Leu Ser Asn Tyr Thr Asp Leu Ala Met Ser Thr Val Lys
                500                 505                 510

Gln Thr Gln Ala Ile Pro Tyr Thr Gly Pro Phe Asn Leu Leu Cys Tyr
                515                 520                 525

Gln Leu Gln Lys Leu Thr Gly Asp Val Glu Glu Leu Glu Ile Gln Glu
530                 535                 540
```

```
Lys Pro Ala Leu Lys Val Phe Lys Asn Ile Thr Val Ile Gln Glu Pro
545                 550                 555                 560

Gly Met Val Val Leu Glu Trp Leu Ala Asn Pro Ser Asn Asp Met Tyr
                565                 570                 575

Ala Asp Thr Val Thr Thr Val Ile Leu Glu Val Gln Ser Asn Pro Lys
            580                 585                 590

Ile Arg Lys Gly Ala Val Gln Lys Val Ser Lys Lys Leu Glu Met His
        595                 600                 605

Val Tyr Ser Lys Arg Leu Glu Ile Met Leu Gln Asp Ile Phe Gly Glu
    610                 615                 620

Asp Cys Val Ser Val Lys Asp Asp Ser Ile Leu Ser Thr Val Thr Asp
625                 630                 635                 640

Gly Lys Thr Ala Asn Leu Asn Leu Glu Thr Arg Thr Val Glu Cys Glu
                645                 650                 655

Glu Gly Ser Glu Asp Asp Glu Ser Leu Arg Glu Met Val Glu Leu Ala
                660                 665                 670

Ala Gln Arg Leu Tyr Glu Ala Leu Thr Pro Val His
        675                 680
```

<210> SEQ ID NO 87
<211> LENGTH: 1829
<212> TYPE: DNA
<213> ORGANISM: Homo sapiens
<220> FEATURE:
<223> OTHER INFORMATION: Human cleavage and polyadenylation specific factor 4 (30kDa CPSF4) (NM_006693)

<400> SEQUENCE: 87

```
cccggcatcc ctcgggcggc ggcggcggcg gcggcgaggc gaagcgaagg aggagtgtgt    60
gcggcgggc cggcggcggg taaaggcgag aaggctgcag gagaccgagg gggagccggg    120
ccggtggggc cgccgccgcc gccatgcagg aaatcatcgc cagcgtggac cacatcaagt    180
ttgacttgga gatcgcggtg gagcagcagc tgggggcgca gccgctgccc ttccccggca    240
tggacaagtc gggcgctgct gtctgtgaat tcttttttgaa agctgcctgc ggcaaagggg    300
gcatgtgtcc gtttcgccac atcagtggtg agaagacagt tgtgtgcaaa cactggctgc    360
gtggcctatg caagaaaggg gaccagtgtg agttcctgca tgagtatgac atgaccaaga    420
tgcccgagtg ctacttctac tccaagttcg gggagtgcag caacaaggaa tgtcccttcc    480
tgcacatcga ccccgagtcc aagatcaagg actgtccttg gtatgaccgt ggcttctgca    540
agcacggtcc cctctgcagg caccggcaca cacgagagt catctgtgtg aattacctcg    600
tgggattctg cccggagggg ccctcgtgta aattcatgca ccctcgattt gaactgccca    660
tgggaaccac cgagcagccc ccactgccgc agcagacaca gcctccagca aagcaaagta    720
acaatccgcc attacaaagg tcgtcctcct tgatccagtt aacgagtcag aactcttctc    780
ccaatcagca gagaaccccg caggtcatcg ggtcatgca gagtcaaaac agcagcgcgg    840
gcaaccgggg accccggcca ctggagcagg tcacctgtta caagtgtggc gagaaaggac    900
actacgccaa cagatgcacc aaagggcact tggcctttct cagtgggacag tgacagcagc    960
tggagccagc tccgagcagc ccgggggccc cgctgttggg agtgtgcatt taactgtttc    1020
atgcgcttgt tggcgcgact gtggctcgag ctgcccgca gacacgtggg tttcatcact    1080
ctgagggcc acgtctgtta gttttcctatc attttgcctt agtatttttt gaaaagggga    1140
catgtgtcct gtgggtccct gcagtcgaca tcatgtttgg ctgggcatcg atgcctcctt    1200
tctgggactc ccggcacaac tcccctcatc cagggaggga ggcagctgct ggggaggggc    1260
```

```
ttggctaggt agttctgtgt ggcggtggtc attcccctca ttaaacacca gttcttggtg   1320
acgccagggg ctggtaggtc attcaaagct gtggccagct cacgcctgct tcctccctcc   1380
ctgccctgct gaatcctaaa gctgtgccta tatctgtgat ttgaatgagg gagccctttg   1440
gggcaaattc aggtgccccc attgcctcag gctggccctg gtcccaggtg gcagcggttg   1500
aggaggggta cagggctctc aagcctgagg ttttcttctc tgggcttaat tttctcttgg   1560
ggtacgtgcc tgacagtgtt taaggtgtcc gttgaactgg agttgcagac ttttaaatag   1620
atgacccctt cagatcatct gtgcctacct cctgcccatc aggcgtctac actgtcactc   1680
agacacctgt ggcatgtgga ggagactgcc tgtcctgagc ctggaaaat gtgaaactgt    1740 ctcctgcaac ctgctgggca tgtgggcctg gctgtgttca attgcaagaa caattttat    1800 gaaatggatt aaagcttgtt ttttaaaaa                                     1829

<210> SEQ ID NO 88
<211> LENGTH: 516
<212> TYPE: DNA
<213> ORGANISM: Homo sapiens
<220> FEATURE:
<223> OTHER INFORMATION: CPSF30 (30kD factor 4)(XM_292584)

<400> SEQUENCE: 88
gaaatctggg gaaatcttgg ggatctcaat gtggctgagt tcctggtgga aaccctgcac     60
tctcccctga gcacccacag agaaatcagc ttccgcagcc ccagcaggag acggaagatg    120
caagaggtca ttgcggggct agagcggttc acctttgcct tcgagaagga tgtcgagatg    180
cagaagggca ctgggctcct gcctttccag ggcatggaca agtcggcctc agctgtgtgc    240
aacttcttca ctaaagggct ctgtgagaaa gggaaactct gccccttccg acatgaccga    300
ggggagaaga tggtggtatg caagcactgg ctccgggggc tctgcaagaa gggtgatcac    360
tgcaagttcc tgcaccagta tgacctcacc aggatgcctg agtgctactt ctactccaag    420
tttggcggat tgaaggctga ggtgctgctg ccacctgctg gccaggccag gaatgcagag    480
acgtgcacgc agcagaacgg caaccagtgt agatga                             516

<210> SEQ ID NO 89
<211> LENGTH: 269
<212> TYPE: PRT
<213> ORGANISM: Homo Sapiens
<220> FEATURE:
<223> OTHER INFORMATION: CPSF30 (30 kD factor 4) (XP_006684)

<400> SEQUENCE: 89

Met Gln Glu Ile Ile Ala Ser Val Asp His Ile Lys Phe Asp Leu Glu
1               5                   10                  15

Ile Ala Val Glu Gln Gln Leu Gly Ala Gln Pro Leu Pro Phe Pro Gly
            20                  25                  30

Met Asp Lys Ser Gly Ala Ala Val Cys Glu Phe Phe Leu Lys Ala Ala
        35                  40                  45

Cys Gly Lys Gly Gly Met Cys Pro Phe Arg His Ile Ser Gly Glu Lys
    50                  55                  60

Thr Val Val Cys Lys His Trp Leu Arg Gly Leu Cys Lys Lys Gly Asp
65                  70                  75                  80

Gln Cys Glu Phe Leu His Glu Tyr Asp Met Thr Lys Met Pro Glu Cys
                85                  90                  95

Tyr Phe Tyr Ser Lys Phe Gly Glu Cys Ser Asn Lys Glu Cys Pro Phe
            100                 105                 110

Leu His Ile Asp Pro Glu Ser Lys Ile Lys Asp Cys Pro Trp Tyr Asp
```

```
                115                 120                 125
Arg Gly Phe Cys Lys His Gly Pro Leu Cys Arg His Arg His Thr Arg
130                 135                 140
Arg Val Ile Cys Val Asn Tyr Leu Val Gly Phe Cys Pro Glu Gly Pro
145                 150                 155                 160
Ser Cys Lys Phe Met His Pro Arg Phe Glu Leu Pro Met Gly Thr Thr
                165                 170                 175
Glu Gln Pro Pro Leu Pro Gln Gln Thr Gln Pro Pro Ala Lys Gln Ser
            180                 185                 190
Asn Asn Pro Pro Leu Gln Arg Ser Ser Leu Ile Gln Leu Thr Ser
            195                 200                 205
Gln Asn Ser Ser Pro Asn Gln Gln Arg Thr Pro Gln Val Ile Gly Val
        210                 215                 220
Met Gln Ser Gln Asn Ser Ser Ala Gly Asn Arg Gly Pro Arg Pro Leu
225                 230                 235                 240
Glu Gln Val Thr Cys Tyr Lys Cys Gly Glu Lys Gly His Tyr Ala Asn
                245                 250                 255
Arg Cys Thr Lys Gly His Leu Ala Phe Leu Ser Gly Gln
            260                 265

<210> SEQ ID NO 90
<211> LENGTH: 132
<212> TYPE: PRT
<213> ORGANISM: Homo sapiens
<220> FEATURE:
<223> OTHER INFORMATION: CPSF30 (30 kD factor 4) (XP_292584)

<400> SEQUENCE: 90

Met Gln Glu Val Ile Ala Gly Leu Glu Arg Phe Thr Phe Ala Phe Glu
1               5                   10                  15
Lys Asp Val Glu Met Gln Lys Gly Thr Gly Leu Leu Pro Phe Gln Gly
            20                  25                  30
Met Asp Lys Ser Ala Ser Ala Val Cys Asn Phe Phe Thr Lys Gly Leu
        35                  40                  45
Cys Glu Lys Gly Lys Leu Cys Pro Phe Arg His Asp Arg Gly Glu Lys
    50                  55                  60
Met Val Val Cys Lys His Trp Leu Arg Gly Leu Cys Lys Lys Gly Asp
65                  70                  75                  80
His Cys Lys Phe Leu His Gln Tyr Asp Leu Thr Arg Met Pro Glu Cys
                85                  90                  95
Tyr Phe Tyr Ser Lys Phe Gly Gly Leu Lys Ala Glu Val Leu Leu Pro
            100                 105                 110
Pro Ala Gly Gln Ala Arg Asn Ala Glu Thr Cys Thr Gln Gln Asn Gly
        115                 120                 125
Asn Gln Cys Arg
    130

<210> SEQ ID NO 91
<211> LENGTH: 1961
<212> TYPE: DNA
<213> ORGANISM: Homo sapiens
<220> FEATURE:
<223> OTHER INFORMATION: C1orf19 mRNA

<400> SEQUENCE: 91
gggaacccac aggcgcgcgc gccgctgctt ctggccgggc gcgggtcgtg gtgcaccacg      60
ggagcgccgc accggccggc atggaggagc gcggcgattc cgagccgacc cccggctgca    120
```

```
gcggcctggg tccgggcggt gttcgcggct ttggcgacgg cggtggagct ccttcgtggg      180
cccctgagga cgcctggatg ggcactcacc ctaagtatct agaaatgatg gaattagata      240
taggagatgc cacccaagtt tatgtagcgt tcttggttta cctggacctc atggaaagca      300
aaagctggca tgaagtaaac tgtgtaggat taccagaact ccagctcatc tgccttgttg      360
gtactgagat agaaggggag gggttacaga ctgtggtgcc tacccccatc actgcttccc      420
tcagccataa caggataagg gagatcttga aggcatctcg aaagttgcaa ggtgatccag      480
atttgccgat gtcttttact ttggccatag tggagtctga ttctacaata gtctattata      540
aacttactga tggatttatg ctgccagacc ctcagaatat ttctcttaga agatgacatc      600
catgtttcct gatgcttgtt ttattcatac aagattggat ttgagaccca tcagactgct      660
tcatctttta tctcagaaat agggttgacg tacatagtga gggttgactt ccccattcca      720
taaggttttc attctgaaga gtaaaacttc cccaggtaga agactttctc cttcttaaaa      780
aatatagggt gatttcttta aaactttgtt atctagagac agtttaatta cagttatata      840
caggtttatg cctaggatgt attcagatgg gtgggacctg tgtgctgctt ttgtcatccc      900
acactcaaag ttgtctcttt gtttcttgct gccactgcca gctcattgtt gagactgcca      960
tttctttctc ttactcagct ctccccagtg ccttttggcc actgcagcta ccgtagaatg     1020
gcattttata tgtaccttgt cacccacttc tgtttacttt ttcctctcca gtaaaaagta     1080
aaagatttct ttcaattggt cttcccattg cagttactgt tatttctctt ttttggttaa     1140
ctttaaatca aaactcaaaa tatgttcatc cagagtgtgt cttaagtaac ttacgtgtct     1200
taagtaacag ggaccagaga catgttacct acaagagttc tgggctatcc ttttcattct     1260
tatcacatat catagcttga atattacaac agtgtgggag agaatcaacc gtaaaaatgt     1320
cttcattaat tagacccagt tattccactt ttgttaatgt ctctcaaatt gtacaaagta     1380
taaaaaatta tatgcacaaa gatgttccaa gtgacattac ttttagtagc ccaaattata     1440
aaccacttta aagtttgggg taaagattgg caaacttttt ctataaaggg ccagaaagta     1500
actattttag gtttttaaac ctactgtctc tgtcataact tgtcaacact gctgtatgaa     1560
gcacaaaagc agccatagac aatacataaa caatacgggc gtggctttgt tccagtaaaa     1620
ctttgtttac aaatgtggtg ccatagtttg tcatccctgg gtctaggaaa tagtcaataa     1680
acagatatat acaaatgata cataatgtac ttattaaaaa ttagtaatga atattattaa     1740
aaacatgaaa atattacctt aagtaaaaat tgcaagacgg aaaagtgtat aagtgggtgt     1800
aatcatggct gaaataacag accaagcata tgataaaaag ataacaaagt aaatcaaatt     1860
actaactggt tatagtggga taggaggcag aaaatggatg actttgtctt ttctcaatgt     1920
ttttatttgt attttataat aaaaatgttt taaaattaaa a                        1961
```

<210> SEQ ID NO 92
<211> LENGTH: 197
<212> TYPE: PRT
<213> ORGANISM: Homo sapiens
<220> FEATURE:
<223> OTHER INFORMATION: C1orf19

<400> SEQUENCE: 92

Glu Pro Thr Gly Ala Arg Ala Ala Ala Ser Gly Arg Ala Arg Val Val
1               5                   10                  15

Val His His Gly Ser Ala Ala Pro Ala Gly Met Glu Glu Arg Gly Asp
                20                  25                  30

Ser Glu Pro Thr Pro Gly Cys Ser Gly Leu Gly Pro Gly Gly Val Arg
            35                  40                  45

```
Gly Phe Gly Asp Gly Gly Ala Pro Ser Trp Ala Pro Glu Asp Ala
     50                  55                  60

Trp Met Gly Thr His Pro Lys Tyr Leu Glu Met Met Glu Leu Asp Ile
 65                  70                  75                  80

Gly Asp Ala Thr Gln Val Tyr Val Ala Phe Leu Val Tyr Leu Asp Leu
                 85                  90                  95

Met Glu Ser Lys Ser Trp His Glu Val Asn Cys Val Gly Leu Pro Glu
            100                 105                 110

Leu Gln Leu Ile Cys Leu Val Gly Thr Glu Ile Glu Gly Glu Gly Leu
        115                 120                 125

Gln Thr Val Val Pro Thr Pro Ile Thr Ala Ser Leu Ser His Asn Arg
    130                 135                 140

Ile Arg Glu Ile Leu Lys Ala Ser Arg Lys Leu Gln Gly Asp Pro Asp
145                 150                 155                 160

Leu Pro Met Ser Phe Thr Leu Ala Ile Val Glu Ser Asp Ser Thr Ile
                165                 170                 175

Val Tyr Tyr Lys Leu Thr Asp Gly Phe Met Leu Pro Asp Pro Gln Asn
            180                 185                 190

Ile Ser Leu Arg Arg
        195

<210> SEQ ID NO 93
<211> LENGTH: 310
<212> TYPE: PRT
<213> ORGANISM: Homo sapiens
<220> FEATURE:
<223> OTHER INFORMATION: tRNA-splicing endonuclease subunit Sen34
      (NP_076980, also XP_085899.4)

<400> SEQUENCE: 93

Met Leu Val Val Glu Val Ala Asn Gly Arg Ser Leu Val Trp Gly Ala
 1               5                  10                  15

Glu Ala Val Gln Ala Leu Arg Glu Arg Leu Gly Val Gly Gly Arg Thr
                20                  25                  30

Val Gly Ala Leu Pro Arg Gly Pro Arg Gln Asn Ser Arg Leu Gly Leu
            35                  40                  45

Pro Leu Leu Leu Met Pro Glu Glu Ala Arg Leu Leu Ala Glu Ile Gly
     50                  55                  60

Ala Val Thr Leu Val Ser Ala Pro Arg Pro Asp Ser Arg His His Ser
 65                  70                  75                  80

Leu Ala Leu Thr Ser Phe Lys Arg Gln Gln Glu Glu Ser Phe Gln Glu
                 85                  90                  95

Gln Ser Ala Leu Ala Ala Glu Ala Arg Glu Thr Arg Arg Gln Glu Leu
            100                 105                 110

Leu Glu Lys Ile Thr Glu Gly Gln Ala Ala Lys Lys Gln Lys Leu Glu
        115                 120                 125

Gln Ala Ser Gly Ala Ser Ser Ser Gln Glu Ala Gly Ser Ser Gln Ala
    130                 135                 140

Ala Lys Glu Asp Glu Thr Ser Asp Gly Gln Ala Ser Gly Glu Gln Glu
145                 150                 155                 160

Glu Ala Gly Pro Ser Ser Ser Gln Ala Gly Pro Ser Asn Gly Val Ala
                165                 170                 175

Pro Leu Pro Arg Ser Ala Leu Leu Val Gln Leu Ala Thr Ala Arg Pro
            180                 185                 190

Arg Pro Val Lys Ala Arg Pro Leu Asp Trp Arg Val Gln Ser Lys Asp
        195                 200                 205
```

```
Trp Pro His Ala Gly Arg Pro Ala His Glu Leu Arg Tyr Ser Ile Tyr
    210             215             220

Arg Asp Leu Trp Glu Arg Gly Phe Phe Leu Ser Ala Ala Gly Lys Phe
225             230             235             240

Gly Gly Asp Phe Leu Val Tyr Pro Gly Asp Pro Leu Arg Phe His Ala
            245             250             255

His Tyr Ile Ala Gln Cys Trp Ala Pro Glu Asp Thr Ile Pro Leu Gln
            260             265             270

Asp Leu Val Ala Ala Gly Arg Leu Gly Thr Ser Val Arg Lys Thr Leu
        275             280             285

Leu Leu Cys Ser Pro Gln Pro Asp Gly Lys Val Val Tyr Thr Ser Leu
    290             295             300

Gln Trp Ala Ser Leu Gln
305             310
```